United States Patent
Florio et al.

(10) Patent No.: US 9,133,272 B2
(45) Date of Patent: Sep. 15, 2015

(54) BISPECIFIC BINDING AGENTS

(75) Inventors: Monica Florio, Thousand Oaks, CA (US); Taruna Arora, Thousand Oaks, CA (US); Christopher J. R. Paszty, Ventura, CA (US); William G. Richards, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/409,019

(22) Filed: Feb. 29, 2012

(65) Prior Publication Data

US 2013/0164293 A1   Jun. 27, 2013

Related U.S. Application Data

(60) Provisional application No. 61/448,089, filed on Mar. 1, 2011, provisional application No. 61/482,979, filed on May 5, 2011.

(51) Int. Cl.
| | |
|---|---|
| *C07K 16/46* | (2006.01) |
| *C07K 16/18* | (2006.01) |
| *A61K 39/395* | (2006.01) |
| *C07K 16/22* | (2006.01) |
| *A61K 39/00* | (2006.01) |

(52) U.S. Cl.
CPC .............. *C07K 16/22* (2013.01); *C07K 16/18* (2013.01); *A61K 2039/505* (2013.01); *C07K 2317/31* (2013.01); *C07K 2317/64* (2013.01); *C07K 2317/76* (2013.01)

(58) Field of Classification Search
CPC .. C07K 16/22; C07K 16/468; C07K 2317/31; C07K 16/18
See application file for complete search history.

(56) References Cited

U.S. PATENT DOCUMENTS

| | | | |
|---|---|---|---|
| 4,331,647 A | 5/1982 | Goldenberg |
| 4,376,110 A | 3/1983 | David et al. |
| 4,411,993 A | 10/1983 | Gillis |
| 4,427,115 A | 1/1984 | Laipply |
| 4,543,439 A | 9/1985 | Frackelton, Jr. et al. |
| RE32,011 E | 10/1985 | Zimmerman et al. |
| 4,837,440 A | 6/1989 | Burtscher et al. |
| 4,902,614 A | 2/1990 | Wakabayashi et al. |
| 5,070,108 A | 12/1991 | Margolis |
| 5,145,684 A | 9/1992 | Liversidge et al. |
| 5,223,409 A | 6/1993 | Ladner et al. |
| 5,399,363 A | 3/1995 | Liversidge et al. |
| 5,453,492 A | 9/1995 | Butzow et al. |
| 5,466,468 A | 11/1995 | Schneider et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,571,714 A | 11/1996 | Dasch et al. |
| 5,627,052 A | 5/1997 | Schrader et al. |
| 5,641,515 A | 6/1997 | Ramtoola |
| 5,698,426 A | 12/1997 | Huse |
| 5,738,868 A | 4/1998 | Shinkarenko et al. |
| 5,780,263 A | 7/1998 | Hastings et al. |
| 5,795,587 A | 8/1998 | Gao et al. |
| 5,795,965 A | 8/1998 | Tsuchiya et al. |
| 5,811,238 A | 9/1998 | Stemmer et al. |
| 5,830,721 A | 11/1998 | Stemmer et al. |
| 5,837,458 A | 11/1998 | Minshull et al. |
| 5,877,397 A | 3/1999 | Lonberg et al. |
| 6,054,561 A | 4/2000 | Ring |
| 6,057,421 A | 5/2000 | Muller et al. |
| 6,117,911 A | 9/2000 | Grainger et al. |
| 6,133,426 A | 10/2000 | Gonzalez et al. |
| 6,180,370 B1 | 1/2001 | Queen et al. |
| 6,207,153 B1 | 3/2001 | Dan et al. |
| 6,344,541 B1 | 2/2002 | Bass et al. |
| 6,395,511 B1 | 5/2002 | Brunkow et al. |
| 6,489,445 B1 | 12/2002 | Brunkow et al. |
| 6,495,736 B1 | 12/2002 | Brunkow et al. |
| 6,703,199 B1 | 3/2004 | Koide |
| 6,803,453 B1 | 10/2004 | Brunkow et al. |
| 6,806,055 B2 | 10/2004 | Berman et al. |
| 6,815,201 B2 | 11/2004 | Pinter |
| 6,818,748 B2 | 11/2004 | Fulton et al. |
| 6,844,422 B1 | 1/2005 | Niehrs et al. |
| 7,057,017 B2 | 6/2006 | McCarthy |
| 7,192,583 B2 | 3/2007 | Brunkow et al. |
| 7,226,902 B2 | 6/2007 | Winkler et al. |
| 7,381,409 B2 | 6/2008 | Winkler et al. |
| 7,572,899 B2 | 8/2009 | Brunkow et al. |
| 7,578,999 B2 | 8/2009 | Winkler et al. |
| 7,592,429 B2 * | 9/2009 | Paszty et al. ............. 530/388.24 |

(Continued)

FOREIGN PATENT DOCUMENTS

| | | |
|---|---|---|
| JP | 4-141095 | 5/1992 |
| WO | WO-91/13152 | 9/1991 |

(Continued)

OTHER PUBLICATIONS

Paul, Fundamental Immunology, 3rd Edition, 1993, pp. 292-295.*
Wu et al. Nature Biotechnology, 2007, vol. 25, pp. 1290-1297.*
Wu et al., mAbs 2009; 1:339-47.*
A diagram of a relevant part of the human genome (D64), citation in Appeal, European Patent No. 1133558, dated Apr. 15, 2010.
Abbas et. al. (Eds.), Cellular and Molecular Immunology, Third Edition, Section II, p. 54 (1997).
Alberts et. al. (Eds.), Molecular Biology of the Cell, Third Edition, Chapter 23, p. 1212 (1994).
Albertsen et. al., A physical map and candidate genes in the BRCA1 region on chromosome 17q12-21. *Nat. Genet.*, 7:472-9 (1994).
Alting-Mees et. al., Monoclonal antibody expression libraries: A rapid alternative to hybridomas. *Strat. Molec. Biol.*, 3:1-9 (1990).
Alves et. al., Sclerosteosis: A marker of Dutch ancestry? *Rev. Bras. Genet.*, 4:825-34 (1982).

(Continued)

*Primary Examiner* — Sheela J Huff
*Assistant Examiner* — Jessica H Roark
(74) *Attorney, Agent, or Firm* — Marshall, Gerstein & Borun LLP

(57) ABSTRACT

The invention relates to bispecific anti-sclerostin/anti-DKK1 binding agents and combinations of anti-sclerostin and anti-DKK1 binding agents, and related methods of treatment.

16 Claims, 20 Drawing Sheets

(56) References Cited

U.S. PATENT DOCUMENTS

| | | | |
|---|---|---|---|
| 7,642,238 B2 | 1/2010 | Shaughnessy | |
| 7,758,858 B2 | 7/2010 | Brunkow et al. | |
| 7,868,134 B2 | 1/2011 | Winkler et al. | |
| 7,872,106 B2 | 1/2011 | Paszty et al. | |
| 8,178,099 B2 | 5/2012 | Ellies | |
| 8,192,927 B2 * | 6/2012 | Van Den Brink et al. | 435/5 |
| 2003/0165410 A1 | 9/2003 | Taylor | |
| 2003/0166247 A1 | 9/2003 | Brunkow et al. | |
| 2003/0186915 A1 | 10/2003 | Pan et al. | |
| 2003/0229041 A1 | 12/2003 | Sutherland et al. | |
| 2004/0009535 A1 | 1/2004 | Brunkow et al. | |
| 2004/0023356 A1 | 2/2004 | Krumlauf et al. | |
| 2004/0038860 A1 | 2/2004 | Allen et al. | |
| 2004/0058321 A1 | 3/2004 | Brunkow et al. | |
| 2004/0141875 A1 | 7/2004 | Doshi | |
| 2004/0146888 A1 | 7/2004 | Paszty et al. | |
| 2004/0158045 A1 | 8/2004 | Brunkow et al. | |
| 2005/0014650 A1 | 1/2005 | Seitz et al. | |
| 2005/0069915 A1 | 3/2005 | McCarthy | |
| 2005/0079173 A1 | 4/2005 | Niehrs et al. | |
| 2005/0085418 A1 | 4/2005 | Winkler et al. | |
| 2005/0106683 A1 | 5/2005 | Winkler et al. | |
| 2005/0238646 A1 | 10/2005 | Ledbetter et al. | |
| 2006/0127393 A1 | 6/2006 | Li et al. | |
| 2006/0233801 A1 | 10/2006 | Brunkow et al. | |
| 2007/0072797 A1 | 3/2007 | Robinson et al. | |
| 2007/0110747 A1 | 5/2007 | Paszty et al. | |
| 2007/0292444 A1 | 12/2007 | Krumlauf et al. | |
| 2008/0182788 A1 | 7/2008 | Brunkow et al. | |
| 2008/0234219 A1 | 9/2008 | Brunkow et al. | |
| 2009/0074763 A1 | 3/2009 | Padhi et al. | |
| 2009/0117118 A1 | 5/2009 | Winkler et al. | |
| 2009/0304713 A1 | 12/2009 | Paszty et al. | |
| 2009/0311253 A1 * | 12/2009 | Ghayur et al. | 424/133.1 |
| 2010/0015665 A1 | 1/2010 | Latham et al. | |
| 2010/0036091 A1 | 2/2010 | Robinson et al. | |
| 2010/0151524 A1 | 6/2010 | Winkler et al. | |
| 2010/0196398 A1 * | 8/2010 | Gazit-Bornstein et al. | 424/172.1 |
| 2011/0044978 A1 | 2/2011 | Ke et al. | |
| 2011/0097342 A1 | 4/2011 | Paszty et al. | |
| 2011/0150866 A1 | 6/2011 | Brunkow et al. | |
| 2013/0209475 A1 * | 8/2013 | Richards et al. | 424/139.1 |

FOREIGN PATENT DOCUMENTS

| | | |
|---|---|---|
| WO | WO-92/01047 | 1/1992 |
| WO | WO-92/02551 | 2/1992 |
| WO | WO-92/06693 | 4/1992 |
| WO | WO-95/30003 | 11/1995 |
| WO | WO-96/04375 | 2/1996 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/44777 | 8/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-02/24888 | 3/2002 |
| WO | WO-02/30463 | 4/2002 |
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2004/094477 | 11/2004 |
| WO | WO-2004/098491 | 11/2004 |
| WO | WO-2005/003158 | 1/2005 |
| WO | WO-2005/014650 | 2/2005 |
| WO | WO-2005/115356 | 12/2005 |
| WO | WO-2006/015373 | 2/2006 |
| WO | WO-2006/065746 | 6/2006 |
| WO | WO-2006/102070 | 9/2006 |
| WO | WO-2006/119062 | 11/2006 |
| WO | WO-2006/119107 | 11/2006 |
| WO | WO-2007/080129 | 7/2007 |
| WO | WO-2008/061013 | 5/2008 |
| WO | WO-2008/092894 | 8/2008 |
| WO | WO-2008/115732 | 9/2008 |
| WO | WO-2008/133722 | 11/2008 |
| WO | WO-2009/039175 | 3/2009 |
| WO | WO-2009/047356 | 4/2009 |
| WO | WO2009/047356 A1 * | 4/2009 |
| WO | WO-2009/056634 | 5/2009 |
| WO | WO-2009/079471 | 6/2009 |
| WO | WO-2009/131553 | 10/2009 |
| WO | WO-2009/149189 | 12/2009 |
| WO | WO-2010/100179 | 9/2010 |
| WO | WO-2010/100200 | 9/2010 |
| WO | WO-2010/115932 | 10/2010 |
| WO | WO-2010/130830 | 11/2010 |
| WO | WO-2012/028683 | 3/2012 |
| WO | WO-2012/058393 | 5/2012 |

OTHER PUBLICATIONS

Andersson et. al., Molecular genetics and pathophysiology of 17β-hydroxysteriod dehydrogenase 3 deficiency. *J. Clin. Endocrinol. Metab.*, 81(1): 130-6 (1996).

Angal et. al., A single amino acid substitution abolishes the heterogeneity of chimeric mouse/human (IgG4) antibody. *Mol. Immunol.*, 30(1):105-8 (1993).

Annex EW6 to Declaration filed in connection with the European Patent EP 1133558 Opposition, Expert opinion of Prof. Dr. Edgar Wingender, dated Sep. 24, 2009.

Annex regarding the purported relevance of gene/peptides mentioned by Professor Arnett, dated Apr. 2, 2010.

Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).

Anonymous, UCB on track. UCB News <http://hugin.info/133973/R/1176122/233395.pdf> (2007).

Arnett et. al., Effect of pH on bone resorption by rat osteoclasts in vitro. *Endocrinol.*, 119(1): 119-124 (1986).

Attana Application Example, cited in Opposition against European Patent No. 1721979 by Opponent: Novartis AG, dated Jun. 15, 2011.

Avsian-Kretchmer et. al., Comparative genomic analysis of the eight-membered ring cystine knot-containing bone morphogenetic protein antagonists. *Molec. Endocrinol.*, 18(1):1-12 (2004).

Babcook et. al., A novel strategy for generating monoclonal antibodies from single, isolated lymphocytes producing antibodies of defined specificities. *Proc. Natl. Acad. Sci. USA*, 93:7843-8 (1996).

Baines et. al., Purification of immunoglobulin G (IgG). *Meth. Molec. Biol.*, 10:79-104 (1992).

Balemans et. al., Extracellular regulation of BMP signaling in vertebrates: A cocktail of modulators. *Dev. Biol.*, 250:231-50 (2002).

Balemans et. al., Increased bone density in sclerosteosis is due to the deficiency of a novel secreted protein (SOST). *Hum. Mol. Genet.*, 10:537-43 (2001).

Balemans et. al., Localization of the gene for sclerosteosis to the van Buchem disease-gene region on chromosome 17q12-q21. *Am. J. Hum. Genet.*, 64:1661-9 (1999).

Balint et. al., Antibody engineering by parsimonious mutagenesis. *Gene*, 137(1):109-18 (1993).

Bateman et. al., Granulins: The structure and function of an emerging family of growth factors. *J. Endocrinol.*, 158: 145-51 (1998).

Baxevanis (Ed.) et. al., Bioinformatics: A practical guide to the analysis of genes and proteins, John Wiley & Sons, Inc. p. 234 (1998).

Beighton et. al., Heterozygous manifestations in the heritable disorders of the skeleton. *Pediatr. Radiol.*, 27: 397-401 (1997).

Beighton et. al., The clinical features of sclerosteosis. *Clin. Genet.*, 25:175-81 (1984).

Beighton et. al., The syndromic status of sclerosteosis and van Buchem disease. *Ann. Intern. Med.*, 84:393-7 (1976).

Bellows et. al., Parathyroid hormone reversibly suppresses the differentiation of osteoprogenitor cells in functional osteoblasts. *Endocrinol.*, 127(6): 3111-6 (1990).

(56) References Cited

OTHER PUBLICATIONS

Bendayan, Possibilities of false immunocytochemical results generated by the use of monoclonal antibodies: The example of the anti-proinsulin antibody. *J. Histochem. Cytochem.*, 43(9):881-6 (1995).

Bendig, Humanization of rodent monoclonal antibodies by CDR grafting. *Methods*, 8:83-93 (1995).

Bergfeld et. al., Release of ATP from human erythrocytes in response to a brief period of hypoxia and hypercapnia. *Cardiovascular Res.*, 26: 40-7 (1992).

Berman et. al., The protein data bank. *Acta. Cryst.*, 58(1):899-907 (2002).

Bigger versions of Figures from Declaration of Professor Teresa Attwood, citation in Appeal, European Patent No. 1133558, dated Apr. 13, 2010.

Bird et. al., Single-chain antigen-binding proteins. *Science*, 242:423-6 (1988).

Birren et. al., EMBL sequence database accession No. AC003098.2, Nov. 14, 1997.

Bishop (Ed.), Guide to Human Genome Computing, Second Edition, Academic Press, Chapter 1: Introduction to human genome computer via the world wide web, pp. 1-14 (2003).

Black et. al., A somatic cell hybrid map of the long arm of human chromosome 17, containing the familial breast cancer ILocus (BRCAI). *Am. J. Hum. Genet.*, 52:702-10 (1993).

Blum et. al., Study plan for German students in the summer of 1998, University Bioinformatik lecture announcement (1998).

Boden et. al., Glucocorticoid-induced differentiation of fetal rat calvarial osteoblasts is mediated by bone morphogenetic protein-6. *Endocrinology*, 138(7):2820-8 (1997).

Boerner et. al., Production of antigen-specific human monoclonal antibodies from in vitro-primed human splenocytes. *J. Immunol.*, 147:86-95 (1991).

Bonaldo et. al., EMBL Sequence Database Accession No. AI113131, Sep. 4, 1998.

Bonaldo et. al., Normalization and subtraction: Two approaches to facilitate gene discovery. *Genome Res.*, 6(9):791-806 (1996).

Bondestam, Ligands & Signaling Components of the Transforming Growth Factor, Helsinki University Biomedical Dissertations (2002).

Bork et. al., Go hunting in sequence databases by watch out for the traps. *Trends Genet.*, 12:425-7 (1996).

Bos et. al., Ras ongogenes in human cancer: A review. *Cancer Res.*, 49: 4682-9 (1989).

Bost et. al., Antibodies against a peptide sequence within the HIV envelope protein crossreacts with human interleukin-2. *Immunol. Invest.*, 17(6&7):577-86 (1988).

Bostrom et. al., Ligand and signaling components of the transforming growth factor β family. *J. Orth. Res.*, 13:357-67 (1995).

Bottcher et. al., NCBI Sequence database accession No. NM_004329, Aug. 2, 2009.

Bouffard et. al., A physical map of human chromosome 7: An integrated YAC contig map with average STS spacing of 79 kb. *Genome Res.*, 7: 673-92 (1997).

Bowie et. al., A method to identify protein sequences that fold into a known three-dimensional structure. *Science*, 253:164-70 (1991).

Bowie et. al., Deciphering the message in protein sequences: Tolerance to amino acid substitutions. *Science*, 247(4948):1306-10 (1990).

Boyden et al., High bone density due to mutation in LDL-receptor-related protein 5. *N. Eng. J. Med.*, 346:1513-1521 (2002).

Bradley et. al., Modifying the mouse: Design and desire. *Bio/Technology*, 10:534-9 (1992).

Brandao-Burch et. al., Acidosis inhibits bone formation by osteoblasts in vitro by preventing mineralization. *Calcif. Tissue Int.*, 77: 167-74 (2005).

Brenner et. al., Population statistics of protein structures: Lessons from structural classifications. *Curr. Op. Struct. Biol.*, 7(3):369-76 (1997).

Brown, Hybridization analysis of DNA blots, *Current Protocols in Protein Science*, 13:A.4H.1-A.4H.9 (1990).

Brown, Hybridization analysis of DNA blots, *Current Protocols in Protein Science*, 2.10.1-2.10.16 (2000).

Bruggemann et. al., Production of human antibody repertoires in transgenic mice. *Curr. Opin. Biotechnol.*, 8:455-8 (1997).

Brunkow et. al., Bone dysplasia sclerosteosis results from loss of the SOST gene product, a novel cysteine knot-containing protein. *Am. J. Hum. Genet.*, 68:577-89 (2001).

Burton et. al., Human antibodies from combinatorial libraries. *Adv. Immunol.*, 57:191-280 (1994).

Butcher et. al., Increased salt concentration reversibly destabilizes p53 quaternary structure and sequence-specific DNA binding. *Biochem. J.*, 298: 513-6 (1994).

Byrne et. al., CD4+CD45RBHi T cell transfer induced colitis in mice is accompanied by osteopenia which is treatable with recombinant human osteoprotegerin. *Gut.*, 54:78-86 (2005).

Campbell et. al., Totipotency or multipotentiality of cultured cells: Applications and progress. *Theriogenology*, 47:63-72 (1997).

Caverzasio et. al., Characteristics and regulation of Pi transport in osteogenic cells for bone metabolism. *Kindey Int.*, 49: 975-80 (1996).

Chan et. al., A new paradigm in the treatment of osteoporosis: Wnt pathway proteins and their antagonists. *Curr. Opin. Invest. Drugs*, 8:293-8 (2007).

Chandran et. al., Recent trends in drug delivery systems: Liposomal drug delivery system—Preparation and characterization. *Indian J. Exp. Biol.*, 35(8):801-9 (1997).

Charlier et. al., A pore mutation in a novel KQT-like potassium channel gene in an idiopathic epilepsy family. *Nat. Genet.*, 18:53-5 (1998).

Chenu et. al., Glutamate receptors are expressed by bone cells and are involved in bone resorption. *Bone*, 22(4): 295-9 (1998).

Chou et. al., Empirical predication of protein conformation. *Ann. Rev. Biochem.*, 47:251-76 (1979).

Chou et. al., Prediction of the secondary structure of proteins from their amino acid sequence. *Adv. Enzymol. Relat. Areas Mol. Biol.*, 47:145-8 (1978).

Clark, Antibody humanization: A case of the 'Emperor's New Clothes'?. *Immunology Today*, 21(8):397-402 (2000).

Cogan et. al., NCBI Sequence Database Accession No. NM_033346, Jul. 19, 2005.

Collins, Identifying human disease genes by positional cloning. The Harvey Lectures, Series 86:149-64 (1992).

Collins, Positional cloning moves from perditional to traditional. *Nat. Genet.*, 9:347-50 (1995).

Colman, Effects of amino acid sequence changes on antibody-antigen interactions. *Biomolec. Res. Inst.*, 55:33-6 (1994).

Communication from the European Patent Office providing an "Observation by a Third Party according to Article 115 EPC" submitted in connection with the Opposition to European Patent No. 1 133 558, dated Dec. 3, 2008.

Cook et. al., Structural basis for a functional antagonist in the transforming growth factor β superfamily. *J. Biol. Chem.*, 280(48):40177-86 (2005).

Cormier, Markers of bone metabolism. *Curr. Opin. in Rheu.*, 7:243-8 (1995).

Couvreur et. al., Polyalkylcyanoacrylates as colloidal drug carriers. *Crit. Rev. Ther. Drug Carrier Syst.*, 5(1):1-20 (1988).

Craig et. al., Sclerostin binds and regulates the activity of cysteine rich protein 61. *Biochem. Biophys. Res. Commun.*, 293(1): 36-40 (2010).

Craig et. al., Sclerostin-erbB-3 interactions: Modulation of erbB-3 activity by sclerostin. *Biochem. Biophys. Res. Commun.*, 402: 421-4 (2010).

Crameri et. al., DNA shuffling of a family of genes from diverse species accelerates directed evolution. *Nature*, 391:288-91 (1998).

Dall'Acqua et. al., Antibody humanization by framework shuffling. *Methods*, 36(1):43-60 (2005).

Davies, et. al., Affinity improvement of single antibody VH domains: Residues in all three hypervariable regions affect antigen binding. *Immunotechnology*, 2(3): 169-79 (1996).

de Jong et. al., Evolution of the α-crystallin/small heat-shock protein family. *Mol. Biol. Evol.*, 10(1): 103-26 (1993).

Dean et. al., Matrix vesicles produced by osteoblast-like cells in culture become significantly enriched in proteoglycan-degrading

(56) References Cited

OTHER PUBLICATIONS metalloproteinases after addition of β-glycerophosphate and ascorbic acid. *Calcif. Tissue*, 54: 399-408 (1994).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Alistair J. Henry, citation in Appeal, European Patent No. 1133558, dated Apr. 2, 2010.
Declaration of Dr. Martyn Robinson, submitted in Opposition to European Patent No. 1133558, Jan. 13, 2008.
Declaration of Dr. Mary E. Brunkow, submitted in Opposition to European Patent No. 1133558, Jan. 9, 2008.
Declaration of Dr. Raymond Dalgleish dated Dec. 8, 2011, citation in Appeal, European Patent No. 1133558.
Declaration of Prof. Edgar Wingender filed in connection with that Opposition regarding European Patent EP 1133558 B1, dated Mar. 10, 2011.
Declaration of Professor Teresa Attwood, citation in Appeal, European Patent No. 1133558, dated Apr. 13, 2010.
Declaration of Tim Arnett, citation in Appeal, European Patent No. 1133558, dated Apr. 2, 2010.
Delmas et. al., The use of biochemical markers of bone turnover in osteoporosis. *Osteoporosis International*, Suppl. 6:S2-17 (2000).
Diagram of the candidate interval, citation by Propriator in Opposition against European Patent No. 1721979 on Feb. 20, 2012.
Ducy et. al., 5-HT and bone biology. *Curr. Opin. Pharmacol.*, 11: 34-8 (2011).
Ducy et. al., Genetic control of cell differentiation in the skeleton. *Curr. Opin. Cell Biol.*, 10:614-9 (1998).
Durham et. al., Alterations in insulin-like growth factor (IGF)-dependent IGF-binding protein-4 proteolysis in transformed osteoblastic cells. *Endocrinology*, 136(4):1374-80 (1995).
Ebara et. al., Mechanism for the action of bone morphogenetic proteins and regulation of their activity. *Spine*, 27(16S):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference C193, dated Sep. 28, 2009.
Epstein et. al., Endocrine function in sclerosteosis. *S. Afr. Med. J.*, 55:1105-10 (1979).
European Patent Office Communication, Opposition to European Patent No. 1133558, dated Nov. 4, 2008.
European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], cited Jun. 15, 2011.
Expert Opinion from Dr. Catalina Lopez-Correa, submitted in Opposition to European Patent No. 1133558, dated Mar. 6, 2009.
Expert opinion of Professor Dr.-Ing Ulrich Vollrath, citation in Appeal of European Patent No. 1133558, dated Apr. 12, 2005.
Extract from Sigma Aldrich catalogue, cited in Opposition against European Patent No. 1721979 by Opponent: Laudens, dated Jun. 15, 2011.
Eyre et. al., Characterization of aromatase and 17β-hydroxysteroid dehydrogenase expression in rat osteoblastic cells. *J. Bone Miner. Res.*, 13(6): 996-1004 (1998).
Foster et. al., Establishment of interference in osteoblasts by an osteopetrosis-inducing Avian Leukosis virus. *Virology*, 205: 376-8 (1994).
Fouser et. al., Feedback regulation of collagen gene expression: A Trojan horse approach. *Proc. Natl. Acad. Sci. USA*, 88: 10158-62 (1991).
Frost et. al., On the rat model of human osteopenias and osteoporoses. *Bone and Mineral*, 18:227-36 (1992).
Fujiwara et. al., GenBank Sequence Database Accession No. D79813, Feb. 9, 1996.
Gardner et. al., Bone mineral density in sclerosteosis; Affected individuals and gene carriers. *J. Clin. Endocrinol. Metab.*, 90(12): 6392-5 (2005).
Gavarini et. al., Opposite effects of PSD-95 and MPP3 PDZ proteins on serotonin 5-hydroxytryptamine2C receptor desensitization and membrane stability. *Molec. Biol.*, 17: 4619-31 (2006).
Gavriatolpoulou et al., Dickkopf-1: a suitable target for the management of myeloma bone disease. *Expert Opin. Ther. Targets.*, 13(7):839-48 (2009).
Gazzerro et. al., Bone morphogenetic proteins induce the expression of noggin which limits their activity in cultured rat osteoblasts. *J. Clin. Invest.*, 102(12):2106-14 (1998).
Gazzerro et. al., Potential drug targets within bone morphogenetic protein signaling pathways. *Curr. Opin. Pharmacol.*, 7: 325-3 (2007).
Geissler et la., Male pseudohermaphroditism caused by mutations of testicular 17β-hydroxysteroid hehydrogenase 3. *Nat. Genetics*, 7: 34-9 (1994).
Gencic et. al., Conservative amino acid substitution in the myelin proteolipid protein of Jimpymsd mice. *J. Neurosci.*, 10(1):117-24 (1990).
Geysen et. al., Cognitive features of continuous antigenic determinants. *J. Molec. Recog.*, 1(1):32-41 (1988).
Gitelman et. al., Vgr-1/BMP-6 induces osteoblastic differentiation of pluripotential mesenchymal cells. *Cell Growth & Differentiation*, 6:827-36 (1995).
Glasky et. al., Stability of specific immunoglobulin secretion by EBV-transformed lymphoblastoid cells and human-murine heterohybridomas. *Hybridoma*, 8:377-89 (1989).
Gowen et. al., Actions of recombinant human γ-interferon and tumor necrosis factor α on the proliferation and osteoblastic characteristics of human trabecular bone cells in vitro. *Arthritis Rheumatism*, 31(12): 1500-7 (1988).
Graner et. al., Splice variants of the Drosophila PS2 integrins differentially interact with RGD-containing fragments of the extracellular proteins tiggrin, Ten-m and D-laminin α2. *J. Biol. Chem.*, 273(29): 18235-41 (1998).
Green et. al., Antigen-specific human monoclonal antibodies from mice engineered with human Ig heavy and light chain YACs. *Nat. Genet.*, 7:13 (1994).
Green et al., Cytosolic pH regulation in osteoblasts. *J. Gen. Physiol.*, 95: 121-45 (1990).
Greene et. al., Screening Recombinant DNA Libraries. *Current Protocols in Molecular Biology*, Ch. 6(1) (1990).
Gribskov et. al., Profile analysis. *Meth. Enzym.*, 183:146-59 (1990).
Gribskov et. al., Profile analysis: Detection of distantly related proteins. *Proc. Nat. Acad. Sci. USA*, 84(13):4355-8 (1987).
Groeneveld et. al., Bone morphogenetic proteins in human bone regeneration. *Eur. J. Endocrinol.*, 142:9-21 (2000).
Gronthos et. al., Integrin expression and function on human osteoblast-like cells. *J. Bone Miner. Res.*, 12(8): 1189-97 (1997).
Groppe et. al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection, 8th Ed., pp. 149, 258, 428 (1994).

(56) References Cited

OTHER PUBLICATIONS

He et. al., High-throughput dynamic light scattering method for measuring viscosity of concentrated protein solutions. *Anal. Biochem.*, 399(1): 141-3 (2010).
Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28 (1996).
Hilliker et. al., Truncation of the amino terminus of PTH alters its anabolic activity on bone in vivo. *Bone*, 19(5): 469-77 (1996).
Hirschhorn, Letter to the editor: Dominance and homozygosity in man. *Am. J. Med. Genetics*, 18: 541 (1984).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hoggard et. al., Localization of leptin receptor mRNA splice variants in murine peripheral tissues by RT-PCR and in situ hybridization. *Biochem. Biophys. Res. Commun.*, 232: 383-7 (1997).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunisation: Human antibodies from synthetic repertoires of germline VH gene segmens rearranged in vitro. *J. Molec. Biol.*, 227:381-8 (1992).
Hoogewerf et. al., Glycosaminoglycans mediate cell surface oligomerization of chemokines. *Biochemistry*, 36: 13570-8 (1997).
Horton et. al., Arg-Gly-Asp (RGD) peptides and the anti-vitronectin receptor antibody 23C6 inhibit dentine resorption and cell spreading by osteoclasts. *Exp. Cell Res.*, 195: 368-75 (1991).
Hsu et. al., The Xenopus dorsalizing factor gremlin indentified a novel family of secreted proteins that antagonize BMP activities. *Molec. Cell*, 1:673-83 (1998).
Hufner et. al., Evidence for an osteoblast-activating factor in a patient with peripheral T-cell lymphoma and osteosclerosis. *Klin. Wochenscher.*, 67: 402-7 (1989).
Hulley et. al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et. al., Generation of a large combinatorial library of the immunoglobulin repertoire in phage lambda. *Science*, 246:1275-81 (1989).
Hwang et. al., Use of human germline genes in a CDR homoloy-based approach to antibody humanization. *Methods*, 36(1):35-42 (2005).
Ide et. al., GenBank Sequence Database Accession No. BAA19765, Feb. 7, 1999.
Ide et. al., GenBank Sequence Datacase Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for stie-directed mutagenesis. *Protein Engineering*, 13(12):839-47 (2000).
Jakobovits et. al., Production of antigen-specific human antibodies from mice engineered with human heavy and light chain YACs a. *Ann. N.Y. Acad. Sci.*, 764:525-35 (1995).

Jee et. al., Overview: Animal models of osteopenia and osteoporosis. *J. Musculoskel. Neuron. Interact.*, 1:193-207 (2001).
Jilka et. al., Increased bone formation by prevention of osteoblast apoptosis with parathyroid hormone. *J. Clin. Invest.*, 104:439-46 (1999).
Jilka et. al., Osteoblast programmed cell death (apoptosis): Modulation by growth factors and cytokines. *J. Bone Miner. Res.*, 13(5): 793-802 (1998).
Jones, Progress in protein structure predication. *Curr. Opin. Struct. Biol.*, 7(3):377-387 (1997).
Kabat et. al., Sequences of proteins of immunological interest, U.S. Department of Health and Human Services, *NIH, USA* (1987) (Table of Contents).
Kalu, The ovariectomized rat model of postmenopausal bone loss. *Bone and Mineral*, 15:175-92 (1991).
Kang et. al., Linkage of recognition and replication functions by assembling combinatorial antibody Fab libraries along phage surfaces. *Proc. Natl. Acad. Sci. USA*, 88:4363-6 (1991).
Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et. al., Signal transduction by bone morphogenetic proteins. *Cytokine and Growth Factor Reviews*, 9(1):49-61 (1998).
Keller et. al., Molecular recognition of BMP-2 and BMP receptor IA. *Nat. Struct. Mol. Biol.*, 11(5):481-488 (2004).
Khalil, TGF-β: From latent to active. *Microbes and Infection*, 1(15):1255-63 (1999).
Khosla et. al., Concise review for primary-care physicians. Treatment pptions for osteoporosis. *Mayo Clin. Proc.*, 70:978-82 (1995).
Kirsch et. al., BMP-2 antagonists emerge from alterations in the low-affinity binding epitope for receptor BMPR-II, *EMBO J.*, 19(13): 3314-24 (2000).
Kohler et. al., Continuous cultures of fused cells secreting antibody of predefined specificity. *Nature*, 256:495 (1975).
Koli et. al., Latency, activation, and binding proteins of TGF-. *Microscopy Res. Tech.*, 52:354-62 (2001).
Komatsu et al., Modulation of Wnt signaling influences fracture repair. *J. Orthop. Res.*, 28(7):928-36 (2010).
Koreth et. al., Microsatellites and PCR genomic analysis. *J. Pathology*, 178:239-48 (1996).
Kramer et. al., The gapped duplex DNA approach to oligonucleotide-directed mutation construction. *Nuc. Acids Res.*, 12:9441 (1984).
Krause et. al., Distinct modes of inhibition by sclerostin on bone morphogenetic protein and Wnt signaling pathways. *J. Biol. Chem.*, 285(53): 41614-26 (2010).
Krupnik et al., Functional and structrual diversity of the human Dickkopf gene family. *Gene*, 238: 301-313 (1999).
Kunkel et. al., Rapid and efficient site-specific mutagenesis without phenoypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).
Kurahashi et. al., Regions of genomic instability on 22q11 and 11q23 as the etiology for the recurrent constitutional t(11;22). *Hum. Molec. Genet.*, 9: 1665-70 (2000).
Kusu et. al., Sclerostin is a novel secreted osteoclast-dervied bone morphogenic protein antagonist with unique ligand specificity. *J. Biol. Chem.*, 278:24113-7 (2003).
Labat et. al., Retroviral expression in mononuclear blood cells isolated from a patient with osteopetrosis (Albers-Schonberg disease). *J. Bone Miner. Res.*, 5(5): 425-35 (1989).
Labat, A new approach to the study of the origin of genetic disease: Retroviral etiology of osteopetrosis. *Biomed. Pharmacother.*, 45: 23-7 (1991).
Lasic, Novel applications of liposomes. *Trends Biotechnol.*, 16(7):307-21 (1998).
Latham, The biochemical and cellular characterization of sclerostin, The causative gene for sclerostenosis. *Calcified Tissue International*, 70(4):244 (2002).
Leppert et. al., Benign familial neonatal epilepsy with mutations in two potassium channel genes. *Curr. Opin. Neurol.*, 12: 143-7 (1999).

(56) References Cited

OTHER PUBLICATIONS

Lewiecki et. al., Sclerostin monoclonal antibody therapy with AMG 785: A potential treatment for osteoporosis. *Exp. Opin. Biol. Ther.*, 11(1): 117-27 (2011).
Li et. al., Sclerostin binds to LRP5/6 and antagonizes canonical Wnt signaling. *J. Biol. Chem.*, 280: 19883-7 (2005).
Li et. al., Treatment with an anti-sclerostin antibody directly stimulates bone formation in a dose-dependent manner in ovariectomized rats with established osteopenia. J. Bone Min. Res., 22(Suppl. S1): S65 (2007).
Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Lierop et. al., Van Buchem disease: Clinical, biochemical and densitometric features of patients and disease carriers. *J. Bone Miner. Res. Accepted Article* (2012).
Liu et. al., GenBank Sequence Database Accession No. U25110, Feb. 2, 1996.
Liu et. al., Human type II receptor for bone morphogenic proteins (BMPs): Extension of the two-kinase receptor model to the BMPs. *Molec. Cell. Biol.*, 15(7):3479-86 (1995).
Lonberg et. al., Antigen-specific human antibodies from mice comprising four distinct genetic modifications. *Nature*, 368:856 (1994).
Loots et. al., Genomic deletion of a long-range bone enhancer misregulates sclerostin in Van Buchem disease. *Genome Res.*, 15: 928-35 (2005).
Low et. al., Mimicking somatic hypermutation: Affinity maturation of antibodies displayed on bacteriophage using a bacterial mutator strain. *J. Mol. Biol.*, 250:350-68 (1996).
Lowik et. al., Wnt signaling is involved in the inhibitory action of sclerostin on BMP-stimulated bone formation. *J. Musculoskeleton Neuronal Interact.* 6: 357 (2006).
Luckman et. al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).
Luckman et. al., Nitrogen-containing bisphosphonates inhibit the mevalonate pathway and prevent post-translational prenylation of GTP-binding proteins, including Ras. *J. Bone Miner. Res.*, 13(4): 581-9 (1998).
Malone et. al., Bone anabolism achieved by reducing sclerostin bioavailability with an anti-sclerostin antibody. 37th International Sun Valley Workshop on Skeletal Tissue Biology. Aug. 5-8, 2007.
Mango et. al., Carboxy-terminal truncation activates glp-1 protein to specify vulval fates in Caenorhabditis elegans. *Lett. Nature*, 352: 811-15 (1991).
Margalit et. al., Comparative analysis of structurally defined herparin binding sequences reveals a distinct spatial distribution of basic residues. *J. Biol. Chem.*, 268 (26): 19228-31 (1993).
Margalit, Liposome-mediated drug targeting in topical and regional therapies. *Crit. Rev. Ther. Drug Carrier Syst.*, 12(2-3):233-61 (1995).
Marks et. al., By-passing immunization: Building high affinity human antibodies by chain shuffling. *Bio/Technology*, 10:779-83 (1992).
Matthews et. al., Adenovirus protein-protein interactions: Hexon and protein VI. *J. Gen. Virol.*, 75: 3365-74 (1994).
Mayer et al., Differentiation of osteogenetic cells: Systems and regulators, Z. Orthop., 130: 276-84 (1992)—Abstract Only.
McClung et. al., Inhibition of sclerostin with AMG 785 in postmenopausal women with low bone mineral density: Phase 2 trial results—Abstract presented at the 2012 meeting of the American Society for Bone and Mineral Reasearch (2012).
Memorandum C, Munich Diplomatic Conference, Sep. 1 to Oct. 6, 1973.
Minabe-Saegusa et. al., Genbank Sequence Database Accession No. AB011030, Jun. 23, 1998.
Minutes of the oral proceedings before the opposition division for Opposition against European Patent No. 1721979, dated May 10, 2013.
Miyazono et. al., Divergence and convergence of TGF-β/BMP signaling. *J. Cell. Physiol.*, 187:265-76 (2001).
Miyazono et. al., TGF-β signaling by Smad proteins. *Adv. Immunology*, 75:115-57 (2000).
Morais et. al., In vitro biomineralization by osteoblast-like cells I. Retardation of tissue mineralization by metal salts. *Biomaterials*, 19: 13-21 (1998).
Mori et. al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Morrison et. al., ATP is a potent stimulator of the activiation and formation of rodent osteoclasts. *J. Physiol.*, 511.2: 495-500 (1998).
Mosekilde et. al., Assessing bone quality—Animcal models in preclinincal osteoporosis research. *Bone*, 17 (4): 343S-52S (1995).
Moult, The current state of the art in protein structure predicion. *Curr. Opin. Biotech.*, 7(4):422-7 (1996).
Mullins et. al., Perspectives series: Molecular medicine in genetically engineered animals; Transgenesis in the rat and larger mammals. *J. Clin. Invest.*, 97(7):1557-60 (1996).
Muntoni et. al., A mutation in the dystrophin gene selectively affecting dystrophin expression in the heart. *J. Clin. Invest.*, 96: 693-9 (1995).
Nagaraja et. al., X chromosome map at 75-kb STS resolution, revealing extremes of recombination and GC content. *Genome Res.*, 7: 210-22 (1997).
Nakase et. al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et. al., The crystal structure of the BMP-2: BMPR-1A complex and the generation of BMP-2 antagonists. *J. Bone Joint Surg.*, 83-A:S1-7-S1-14 (2001).
Nicolas et. al., An age-related decrease in the concentration of insulin-like growth factor binding protein-5 in human cortical bone. *Calcif. Tissue Int.*, 57:206-12 (1995).
Nifuji et. al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et. al., Separation of univalent fragments from the bivalent rabbit antidody molecule by reduction of disulfide bonds. *Arch. Biochem. Biophys.*, 89:230-44 (1960).
Niu et. al., Sclerostin inhibition leads to increased periosteal and endocortical bone formation as well as decreased cortical porosity in aged ovariectomized rats. *J. Bone Min. Res.*, 22(Suppl. S1) S65 (2007).
Nordsletten et. al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition to European Patent No. 1 133 558, dated May 29, 2007.
Nygren et. al., Scaffolds for engineering novel binding sites in proteins. *Curr. Opin. Struct. Biol.*, 7:463-9 (1997).
Observations of Opponent: Laudens in response to summons to oral proceedings in Opposition against European Patent No. 1721979, dated Feb. 25, 2013.
Oelgeschlager et. al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et. al., Sclerostin monoclonal antibody treatment increases bone strength in aged osteopenic ovariectomozed rats. *J. Bone Min. Res.*, 21(1): S44 PRES1161 (2006). Abstract.

(56) References Cited

OTHER PUBLICATIONS

Opposition Decision for Opposition against European Patent No. 1721979, dated Aug. 2, 2013.
Opposition Statement of May 20, 2007 filed by Opponent 2 (Eli Lilly) against European Patent No. 1133558.
Oreffo et. al., Human bone marrow osteoprogenitors express estrogen receptor-alpha and bone morphogenetic proteins 2 and 4 mRNA during osteoblastic differentiation. *J. Cell Biochem.*, 75:382-92 (1999).
Orriss et al., Purinergic signaling and bone remodeling. *Curr. Opin. Pharmacol.*, 10:322-30 (2010).
Utting et al., Hypoxia stimulates osteoclast formation from human peripheral blood. *Cell Biochem. Funct.*, 28:374-80 (2010).
Oshima et. al., TGF-β receeptor type II deficiency results in defects of yolk Sac hematopoiesis and vasculogenesis. *Dev. Biol.*, 179:297-302 (1996).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padhi et al., Single-dose, placebo-controlled, randomized study of AMG 785, a sclerostin monoclonal antibody. *J. Bone Miner. Res.*, 19-26 (2011).
Padlan et. al., Structure of an antibody-antigen complex; Crystal structure of the HyHEL-10 Feb-lysozyme complex. *Proc. Natl. Acad. Sci. USA*, 86:5938-42 (1989).
Palokangas et. al., Endocytic pathway from the basal plasma membrane to the ruffled border membrane in bone-resorbing osteoclasts. *J. Cell Sci.*, 110: 1767-80 (1997).
Pandey et. al., Nucleotide sequence database: A gold mine for biologists. *TIBS.*, 24: 276-80 (1999).
Papapoulos et. al., Targeting sclerostin as potential treatment of osteoporosis. *Ann. Rheum. Dis.*, 70(Suppl. 1): I119-22 (2011).
Patel et. al., Current and potential future drug treatments for osteoporosis. *Ann. Rheumatic Dis.*, 55: 700-14 (1996).
Patel et al., Regulation of bone formation and vison by LRP5. *N. Eng. J. Med.*, 346:1572-3 (2002).
Patten et. al., Applications of DNA shuffling to pharmaceuticals and vaccines. *Curr. Opin. Biotechnol.*, 8:724-33 (1997).
Pearson et. al., Effective protein sequence comparison. Chapter 15, pp. 227-258 (1996).
Piao et. al., The proximal promotor region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-Θ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional anitbody Fv and Fab fragments in *Escherichia coli. Meth. Meth. Enzymol.*, 178:497-515 (1989).
Pockwinse et. al., Expression of cell growth and bone specific genes at single cell resolution during development of bone tissue-like organization in primary osteoblast cultures. *J. Cell. Biol.*, 49:310-23 (1992).
Poole et. al., Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).

Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et. al., Preparation techniques and mechanisms of formation of biodegradable nanoparticles from preformed polymers. *Drug Dev. Ind. Pharm.*, 24(12):1113-28 (1998).
Rachner et. al., Osteoporosis: Now and the future. *Lancet*, 377(9773): 1276-87 (2011).
Rawadi et. al., BMP-2 controls alkaline phosphatase expression and osteoblast mineralization by a Wnt autocrine loop. *J. Bone Min. Res.*, 18: 1842-53 (2003).
Reb, Antikorpergegen sclerostin, *Medical Tribune*, 39:12 (2007).
Reddi et. al., The Escherichia coli chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
RnD Systems catalogue excerpt, cited in Opposition against European Patent No. 1721979 by Opponent: Novartis AG dated Jun. 15, 2011.
Roberts et. al., Essential functional interactions of SAFA, a Saccharomyces cerevisiae complex of Spt, Ada, and Gcn5 proteins, with the Snf/Swi and Srb/Mediator complexes. *Genetics*, 147: 451-65 (1997).
Robinson et. al., The sclerostin antibody project. *Hum. Antibodies*, 16: 36 (2007).
Roitt et la., Roitt's Essential Immunology, 9th Edition, pp. 90-91 (1997).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Ruppert et. al., Human bone morphogenetic protein 2 contains a heparin-binding site which modifies its biological activity. *Eur. J. Biochem.*, 237: 295-302 (1996).
Sada et. al., Adsorption equilibirum in immuno-affinity chromatography with polyclonal and monoclonal antibodies. *Biotechnol. Bioengin.*, 28 (1986). Abstract.
Sali et. al., Comparative protein modeling by satisfaction of spatial restraints. *J. Mol. Biol.*, 234(3):779-815 (1993).
Sambrook et. al., Synthetic oligonucleotide probes, molecular cloning—A Laboratory Manual, Ch.11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in Escherichia coli for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N.Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).

(56) References Cited

OTHER PUBLICATIONS

Schmidt et. al., Retrovirus-induced osteopetrosis in mice: Effects of viral infection on osteogenic differentiation in skeletoblast cell cultures. *Am. J. Pathol.*, 129(3): 503-10 (1987).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Scully et. al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.
Serra et. al., Expression of a truncated, kinase-defective TGF-β type II receoptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc. Biol.*, 20:1425-9 (2000).
Silverman et. al., Sclerostin, *J. Osteoporosis*, 2010: 1-3 (2010).
Sippl et. al., Threading thrills and threats. *Structure*, 4(1)15-19 (1996).
Siris, Clinical Review: Paget's disease of bone. *J. Bone Miner. Res.*, 13(7): 1061-5 (1998).
Sivakumar et. al., New insights into extracellular matrix assembly and reorganization from dynamic imaging of extracellular matrix proteins in living osteoblasts. *J. Cell. Sci.*, 119(7):1350-60 (2006).
Skiple Skjerpen et. al., Binding of FGF-1 variants to protein kinase CK2 correlates with mitogenicity. *EMBO J.*, 21(15): 4058-69 (2002).
Slater et. al., Involvement of platelets in stimulating osteogenic activity. *J. Orthopaedic Res.*, 13: 655-63 (1995).
Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et. al., A range of clinical phenotypes associated with mutations in CRX, a photoreceptor transcription-factor gene. *Am. J. Hum. Genet.*, 63: 1307-15 (1998).
Spranger, International classification of osteochondrodysplasias, *Eur. J. Pediatr.*, 151: 407-15 (1992).
Staehling-Hampton et. al., A 52-kb deletion in the SOST-MEOX1 intergenic region on 17q12-q21 is associated with van Buchem disease in the Dutch population. *Am. J. Med. Gen.*, 110: 144-52 (2002).
Stanley et. al., DAN is a secreted glycopeotein related to Xenopus cerberus. *Mech. Dev.*, 77: 173-84 (1998).
Statement of Grounds of Appeal to Decision of Opposition against European Patent No. 1133558, dated Sep. 28, 2009.
Stenmark et. al., Distinct structural elements of rab5 define its functional specificity. *EMBO J.*, 13(3): 575-83 (1994).
Strachan et. al. (Eds.), Diagram from text book entitled Human Molecular Genetics, 2nd Edition (1999).
Strachan et. al. (Eds.), Human Molecular Genetics, 1st Edition, p. 420 (1996).
Strachan et. al., (Eds.), Human Molecular Genetics, 2nd Edition, Figure 15.4 (1999).
Submission in response to oral proceedings in Opposition against European Patent No. 1721979, Opponent: Eli Lilly, dated Apr. 24, 2013.
Sudo et. al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Summons to attend oral proceedings in Opposition against European Patent No. 1721979, dated Nov. 12, 2012.
Sutherland et. al., Sclerostin romotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Sverdlov et. al., Perpetually mobile footprints of ancient infections in human genome. *FEBS Lett.*, 428: 1-6 (1998).
Sylatron label, cited in Opposition against European Patent No. 1721979 by Opponent: Novartis AG, dated Jun. 15, 2011.
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.
Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61 (4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
The Merck Manual—Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
Tjaderhane et. al., A high sucrose diet decreases the mechanical strength of bones in growing rats. *J. Nutr.*, 128: 1807-10 (1998).
Tuncay et. al., Oxygen tension regulates osteoblast function. *Am. J. Orthod. Dentofac. Orthop.*, 105: 457-63 (1994).
UCB and Amgen announce positive phase 2 results of CDP7851/AMG785 in patients with post menopausal osteoporosis (PMO), dated Apr. 21, 2011—Citation in Opposition against European Patent No. 1721979.
Uitterlinden et. al., Relation of alleles of the collagen type Iα1 gene to bone density and the risk of osteoporotic fractures in postmenopausal women. *New Engl. J. Med.*, 338: 1016-21 (1998).
Valero et. al., Quaternary structure of casein kinase 2. *J. Biol. Chem.*, 27(14): 8345-52 (1995).
van Bezooijen et. al., Sclerostin is an osteocyte-expressed negative regulator of bone formation, but not a classical BMP antagonist. *J. Exp. Med.*, 199: 805-14 (2004).
van Bezooijen et. al., SOST/sclerostin, an osteocyte-derived negative regulator of bone formation, *Cytokine Growth Factor Rev.*, 16: 319-27 (2005).
van Bezooijen et. al., Wnt but not BMP signaling is involved in the inhibitory action of sclerostin on BMP-stimulated bone formation. *J. Bone. Miner. Res.*, 22:19-28 (2007).
Van Hul et. al., Van Buchem Disease (hyperostosis corticalis generalisata) maps to chromosome 17q12-a21. *Am. J. Hum. Genet.*, 2:391-9 (1998).
Vanier et. al., Recent advances in elucidating Niemann-Pick C disease. *Brain Pathol.*, 8: 163-74 (1998).
Veverka et. al., Characterization of the structural features and interactions of sclerostin. *J. Biol. Chem.*, 284(16): 10890-900 (2009).
Viter et. al., Analysis of antigenic structure of potato virus M Ukrainian strains. *Biopolimery I Kletka, Naukova Dumka, Kiev K, UK*, 16: 312-9 (2000).
Von Bubnoff et. al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang et. al., IFP 35 forms complexes with B-ATF, a member of the AP1 family of transcription factors. Biochem. Biophys. Res. *Commun.*, 229: 316-22 (1996).
Wang, Bone morphogenetic proteins (BMPs): Therapeutic potential in healing bony defects. *TIBTECH*, 11:379-83 (1993).

(56) References Cited

OTHER PUBLICATIONS

Warmington et. al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).

Warmington et. al., Sclerostin monoclonal antibody treatment of osteoporotic rats completely reverses one year of overiectomy-induced systemic bone loss, *J. Bone Min. Res.*, 20:S22 (2005).

Winkler et. al., Noggin and sclerostin bone morphogenetic protein antagonists form a mutually inhibitory complex. *J. Biol. Chem.*, 279(35): 36296-8 (2004).

Winkler et. al., Osteocyte control of bone formation via sclerostin, a novel BMP antagonist. *EMBO J.* 22: 6267-76 (2003).

Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).

Winter et. al., Making antibodies by phase display technology. *Annu. Rev. Immunol.*, 12:433-55 (1994).

Wolff et. al., Monoclonal antibody homodimers: Enhanced antitumor activity in nude mice. Cancer Res., 53:2560-5 (1993).

Wollenberger et. al. (Eds.), Analytische Biochemie, Chapter 3, pp. 47-49 (2003).

Written submission—Observation by a Third Party According to Art.115 EPC, Opposition to European Patent No. 1133558, dated Nov. 25, 2008.

Written submission in response to summons to oral proceedings in Opposition against European Patent No. 1721979, Opponent: Norvartis AG, dated Feb. 25, 2013.

Written submission in response to summons to oral proceedings in Opposition against European Patent No. 1721979, Opponent: Eli Lilly Company, dated Feb. 25, 2013.

Written submission of Eli Lilly & Company to European Patent Office, Opposition to European Patent No. 1133558, dated May 29, 2007.

Written Submission of Eli Lilly & Company, Opposition to European Patent No. 1133558, dated Mar. 9, 2009.

Written submission of UCB S.A., Proprietor's Preliminary Response to the Opponent's submission of Mar. 9, 2009, Opposition to European Patent No. 1133558, dated Mar. 20, 2009.

Written submission of UCB S.A., Proprietor's Response to Opposition against European Patent No. 1133558, dated Mar. 14, 2008.

Yanagita et. al., USAG-1: A bone morphogenetic protein antagonist abundantly expressed in the kidney. *Biochem. Biophys. Res. Comm.* ,316: 490-550 (2004).

Yang et. al., CDR walking mutagenesis for the affinity maturation of a potent human Anti-HIV-1 antibody into the picomolar range. *J. Mol. Biol.*, 254:392-403 (1995).

Yates et. al., Inhibition of bone resorption by inorganic phosphate in mediated by both reduced osteoclast formation and decreased activity of mature osteoclasts. *J. Bone Miner. Res.*, 6(5): 476-8 (1990).

Yerges et. al., NCBI Sequence Database Accession No. NM_001203, Jul. 12, 2009.

Yerges et. al., NCBI Sequence Database Accession No. NP_001194, Jul. 12, 2009.

Yoshida et. al., Osteoinduction capability of recombinant human bone morphogenetic protein-2 in intramuscular and subcutaneous sites: An experimental study. *J. Cranio-Maxillofac. Surg.*, 26: 112-5 (1998).

Zambaux et. al., Influence of experimental parameters on the characteristics of poly(lactic acid) nanoparticles prepared by a double emulsion method. *J. Controlled Rel.*, 50(1-3):31-40 (1998).

Zhang et. al., Humanization of an anti-human TNF-β antibody by variable region resurfacing with the aid of molecular modeling. *Molec. Immunol.*, 42(12):1445-51 (2005).

Zimmerman et. al., The spemann organizer signal noggin binds and inactives bone morphogenetic protein 4. *Cell*, 86(4):599-606 (1996).

Zlotogora et. al., Dominance and homozygosity, *Am. J. Med. Genet.*, 68: 412-6 (1997).

zur Muhlen et. al., Solid lipid nanoparticles (SLN) for controlled drug delivery—Drug release and release mechanism. *Eur. J. Pharm. Biopharm.*, 45(2):149-55 (1998).

\* cited by examiner

ELISA analysis of bispecific Rat-Abs binding to huDKK1 or huScl

Sost-Ab and Dkk1-Ab Combination Therapy Increase PTHR1 expression

FIG. 13
huDVD Ig increased bone mass in lumbar vertebrae in 10 week old intact mice
(in vivo DXA Analysis – at week 2)
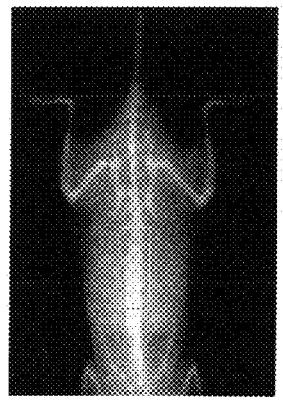
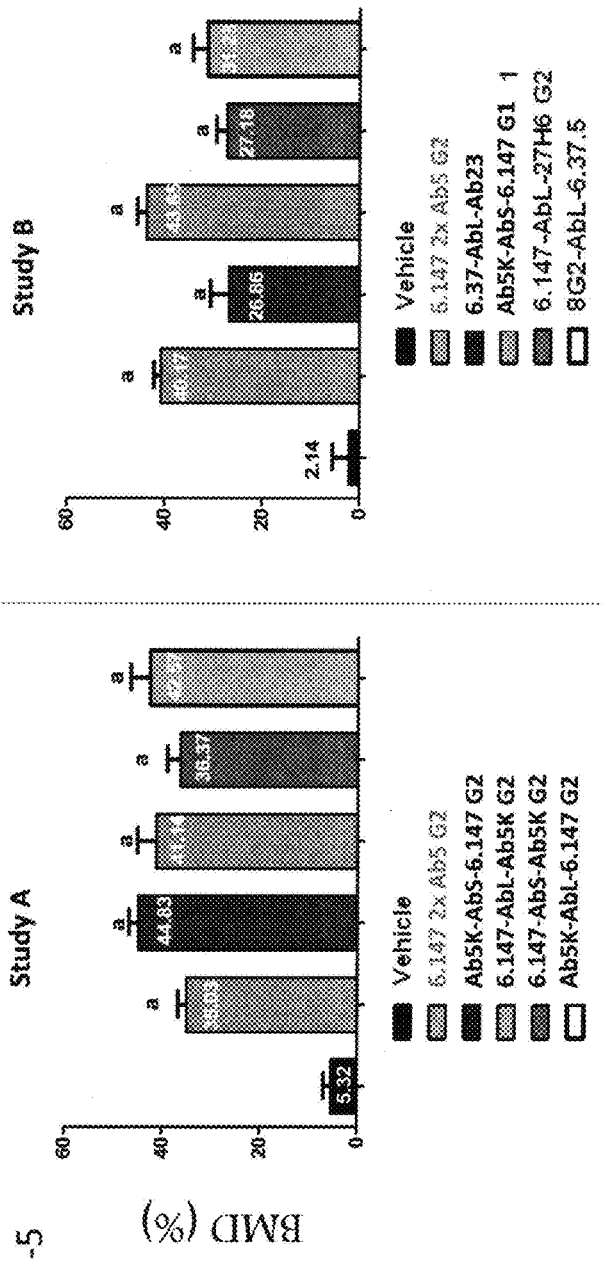

FIG. 14
huDVD Ig Increased BMD in Femur-Tibia
(In vivo Analysis – at week2)
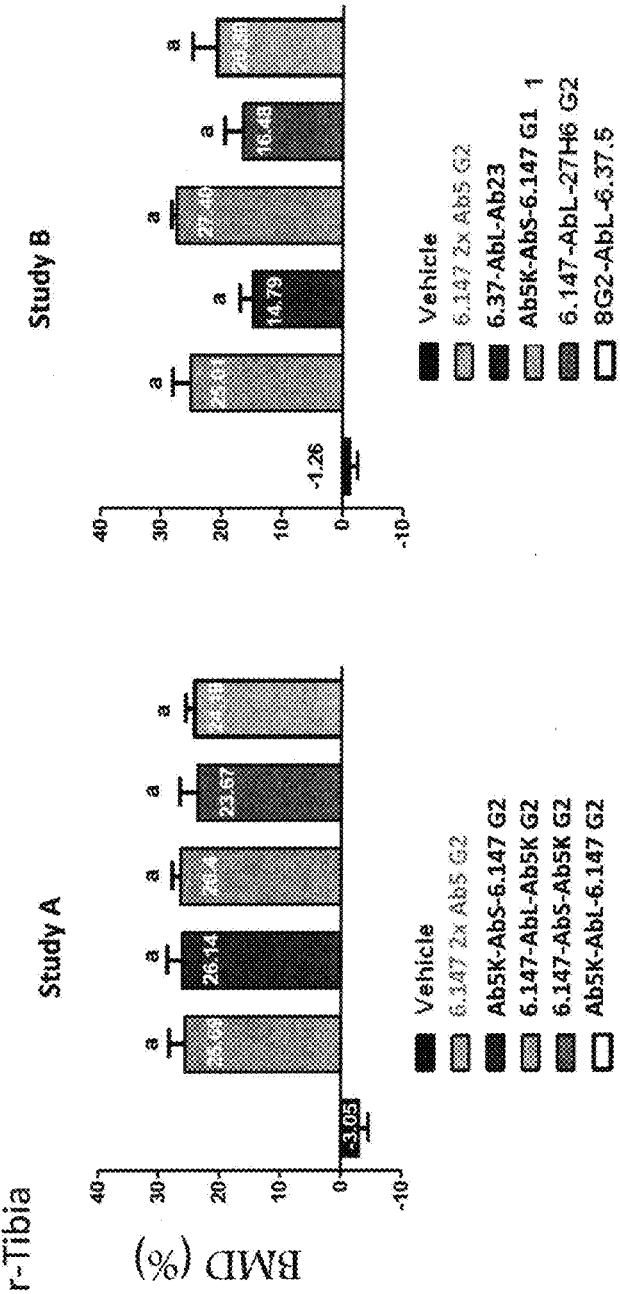
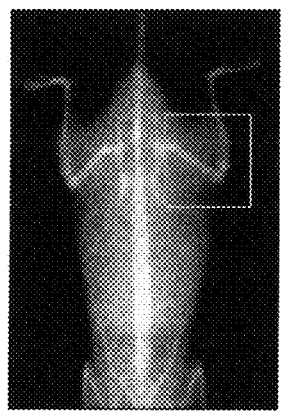

Rat 13C7-11H10 retains the neutralizing activity of parental antibodies in osteoblast MC3T3E1 cells treated with Wnt proteins.

Inhibition of Lrp6 binding to Sclerostin or Dkk1 by DVD-Igs

DVD-Ig Structure 2 tandem variable domains to encourage dual target binding

Linkers are inserted between the 2 variable domains

BISPECIFIC BINDING AGENTS

CROSS-REFERENCE TO RELATED APPLICATION

This application claims the benefit of priority to U.S. provisional application No. 61/448,089 filed Mar. 1, 2011, and to U.S. provisional application No. 61/482,979 filed May 5, 2011, each of which is hereby incorporated by reference herein.

This application contains an ASCII "txt" compliant sequence listing which serves as both the computer readable form (CRF) and the paper copy required by 37 C.F.R. Section 1.821(c) and 1.821(e), and is hereby incorporated by reference in its entirety. The name of the "txt" file created on Feb. 29, 2012 is A-1598-US -NP_SequenceListing_022912_ST25_AddedSeq485-496.txt, and is 471 KB in size.

BACKGROUND OF THE INVENTION

1. Field of the Invention

The invention relates to bispecific anti-sclerostin/anti-DKK1 binding agents and combinations of anti-sclerostin and anti-DKK1 binding agents, and related methods of treatment.

2. Background of the Invention

Two or three distinct phases of changes to bone mass occur over the life of an individual (see Riggs, West J. Med. 154:63 77 (1991)). The first phase occurs in both men and women and proceeds to attainment of a peak bone mass. This first phase is achieved through linear growth of the endochondral growth plates and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss and occurs in both men and women. In women, a third phase of bone loss also occurs, most likely due to postmenopausal estrogen deficiencies. During this phase alone, women may lose additional bone mass from the cortical bone and from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7 8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long term benefit and whether estrogen has any effect on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, Mayo Clin. Proc. 70:978982, 1995).

Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (see Khosla and Riggs, supra).

Sclerostin, the product of the SOST gene, is absent in sclerosteosis, a skeletal disease illustrated by bone overgrowth and strong dense bones (Brunkow et al., Am. J. Hum. Genet., 68:577 589, 2001; Balemans et al., Hum. Mol. Genet., 10:537 543, 2001). Inhibitors of sclerostin have been shown to increase the rate of bone mineralization, and thus bone mineral density (Padhi et al., J Bone Miner Res. 2010 June; e-published ahead of print). Likewise, Dkk-1 has been shown to be involved in the regulation of bone formation, particularly in bone fracture repair, and its role in various other diseases that are associated with bone loss (e.g., cancer and diabetes) (Komatsu et al., J. Orthop. Res. 2010 July; 28(7): 928-36; Gavriatolpoulou et al., Expert Opin. Ther. Targets. 2009 July; 13(7):839-48).

Dickkopf-1 (Dkk-1) is a secreted protein that participates in embryonic head induction and antagonizes Wnt (Glinka et al., Nature 391: 357-362 (1998)). The amino acid sequence of human Dkk-1 and nucleotides encoding it have been described (U.S. Pat. Nos. 6,344,541; 6,844,422; 7,057,017; Published Patent Application No. 20050069915; Krupnick et al., Gene 238: 301-313 (1999)). Expression of Dkk-1 in human was thought to be restricted to placenta, suggesting a role for Dkk-1 in embryonic development (Krupnick et al., supra). Allen and colleagues (U.S. Published Patent Application No. 20040038860) describe assays relating to the interaction between LRP5, HBM or LRP6 with Dkk-1. Antibodies that bind Dkk-1 have been described in the aforementioned patents and patent applications and in U.S. Published patent Application Nos. 20050079173 and 20060127393.

Human Dkk-1 is a member of a Dickkopf gene family which includes Dkk-1, Dkk-2, Dkk-3, and Dkk4 (Krupnick et al., supra). Although Dkk-1 and Dkk-4 have been shown to suppress Wnt-induced secondary axis induction in Xenopus embryos, neither block axis induction triggered by Xenopus Dishevelled or Frizzled, suggesting that their Wnt inhibitory activity is upstream of Frizzled in the Wnt signaling pathway (Krupnick et al., supra). It has been suggested that Dkk-1 might have an inhibitory effect on bone formation, making them potential targets for the prevention or treatment of osteoporosis (Patel and Karensky, N. Eng. J. Med. 346: 1572-1573 (2002); Boyden et al., N. Eng. J. Med. 346: 1513-1521 (2002)).

SUMMARY OF THE INVENTION

Provided herein are novel inhibitors that are effective in treating conditions requiring increased bone building, for example, fracture repair or bone loss associated with pathological conditions, such as multiple myeloma. In addition, provided herein are multi-specific agents that increase bone anabolism including combinations of DKK-1 and sclerostin inhibitors. These combinations can be used for treatment of, for example, osteoporosis, accelerating healing of fractures, and any number of conditions requiring an increase in the rate of bone building. In particular, the DKK-1 and sclerostin inhibitors can be two separate inhibitors, for example, an anti-sclerostin antibody and an anti-DKK-1 antibody. Alternatively, the DKK-1 and sclerostin inhibitors can be a single molecular entity. Nonlimiting examples include bispecific binding molecules such as DVD-Ig's, bispecific antibodies, and bispecific linkerbodies.

In one aspect of this embodiment, the patient suitable for treatment with the molecules of the invention is one who suffers from cancer that metastasizes to bone, and in another aspect, the patient is one who suffers from multiple myeloma. In yet another aspect, the patient is selected from patients who have osteoporosis, osteopenia, Paget's disease, periodontitis, rheumatoid arthritis, and bone loss due to immobilization. In yet other embodiments, the patient is selected from those who have bone damage that may or may not result from an underlying loss of bone mass such as that caused by osteoporosis or osteolytic lesions associated with cancer (e.g., multiple myeloma). Examples of such bone damage include but are not limited to orthopedic procedures, dental procedures, implant surgery, joint replacement (e.g., hip replacement, knee replacement, etc.), bone grafting, bone cosmetic surgery and bone repair such as fracture healing, nonunion healing, delayed union healing and facial reconstruction. One or more compositions may be administered before, during and/or after the procedure, replacement, graft, surgery or repair.

In one embodiment, provided is a binding molecule comprising a polypeptide chain, wherein said polypeptide chain comprises VH1-(X1)n-VH2-C-(X2)n, wherein: VH1 is a first heavy chain variable domain obtained from a first parent antibody or antigen binding portion thereof; VH2 is a second heavy chain variable domain obtained from a second parent antibody or antigen binding portion thereof; C is a heavy chain constant domain; (X1)n is a linker, wherein said (X1)n is either present or absent; and (X2)n is an Fc region, wherein said (X2)n is either present or absent, wherein the binding molecule specifically binds both sclerostin and DKK-1.

In another embodiment, provided is a binding molecule comprising a polypeptide chain, wherein said polypeptide chain comprises VL1-(X1)n-VL2-C-(X2)n, wherein: VL1 is a first light chain variable domain obtained from a first parent antibody or antigen binding portion thereof; VL2 is a second light chain variable domain obtained from a second parent antibody or antigen binding portion thereof; C is a light chain constant domain; (X1)n is a linker, wherein said (X1)n is either present or absent; and (X2)n is an Fc region, wherein said (X2)n is either present or absent, wherein the binding molecule specifically binds sclerostin and DKK-1.

In a further embodiment, provided is a binding molecule comprising first and second polypeptide chains, wherein said first polypeptide chain comprises a VH1-(X1)n-VH2-C-(X2) n, wherein VH1 is a first heavy chain variable domain obtained from a first parent antibody or antigen binding portion thereof; VH2 is a second heavy chain variable domain obtained from a second parent antibody or antigen binding portion thereof; C is a heavy chain constant domain; (X1)n is a linker, wherein said (X1)n is either present or absent; and (X2)n is an Fc region, wherein said (X2)n is either present or absent; and wherein said second polypeptide chain comprises a VL1-(X1)n-VL2-C-(X2)n, wherein VL1 is a first light chain variable domain obtained from a first parent antibody or antigen binding portion thereof; VL2 is a second light chain variable domain obtained from a second parent antibody or antigen binding portion thereof; C is a light chain constant domain; (X1)n is a linker, wherein said (X1)n is either present or absent; and (X2)n does not comprise an Fc region, wherein said (X2)n is either present or absent, wherein the binding molecule specifically binds sclerostin and DKK-1.

In another embodiment, provided is a binding molecule that binds both sclerostin and DKK-1 comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the VH1 and VH2 heavy chain variable domains comprise an amino acid sequence selected from the group consisting of sclerostin binders SEQ ID NOs: 95, 96, 104, 112, 120, 128, 136, 144, 152, 160, 168, 176, 184, 192, 200, 208, and 216, or DKK-1 binders SEQ ID NOs: 224, 232, 240, 248, 256, 264, 272, 280, 288, 296, 304, 312, 320, 328, 336, 344, 352, 360, 368, 376, 384, 392, 400, and 408, and wherein the VL1 and VL2 light chain variable domains comprise an amino acid sequence selected from the group consisting of sclerostin binders SEQ ID NOs: 94, 103, 111, 119, 127, 135, 143, 151, 159, 167, 175, 183, 191, 199, 207, and 215, or DKK-1 binders SEQ ID NOs: 223, 231, 239, 247, 255, 263, 271, 279, 287, 295, 303, 311, 319, 327, 335, 343, 351, 359, 367, 375, 383, 391, 399, and 407.

In yet a further embodiment, provided is a binding molecule that binds both sclerostin and DKK-1 comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the binding molecule comprises VH1-(X1)n-VH2-C-(X2)n and VL1-(X1)n-VL2-C-(X2)n pairings selected from the group consisting of:

SEQ ID NOs: 18 and 20; 22 and 24; 26 and 28; 30 and 32; 34 and 36; 38 and 40; 42 and 44; 46 and 48; 50 and 52; 54 and 76; 56 and 72; 58 and 60; 62 and 64; 66 and 68; 70 and 72; 74 and 76; 78 and 80; 82 and 84; 86 and 88; and 90 and 92.

In another embodiment, provided is a binding molecule comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the binding molecule comprises 3 VH1 CDRs, 3 VH2 CDRs, 3 VL1 CDRs and 3 VL2 CDRs, wherein the paired VH1 and VL1 CDRs, and paired VH2 and VL2 CDRs, are selected from the group consisting of SEQ ID NOs:

97-102; 105-110; 113-118; 121-126; 129-134; 137-142; 145-150; 153-158; 161-166; 169-174; 177-182; 185-190; 193-198; 201-206; 209-214; 217-222, or SEQ ID NOs:

225-230; 233-238; 241-246; 249-254; 257-262; 265-270; 273-278; 281-286; 289-294; 297-302; 305-310; 313-318; 321-326; 329-334; 337-342; 345-350; 353-358; 361-366; 369-374; 377-382; 385-390; 393-398; 401-406; 409-414.

In another embodiment, provided is a method for generating a binding molecule that binds sclerostin and DKK-1 comprising the steps of: (a) obtaining a first parent antibody, or antigen binding portion thereof, that can bind sclerostin or DKK-1; (b) obtaining a second parent antibody, or antigen binding portion thereof, that can bind sclerostin or DKK-1; (c) constructing first and third polypeptide chains comprising VH1-(X1)n-VH2-C-(X2)n, wherein: VH1 is a first heavy chain variable domain obtained from said first parent antibody or antigen binding portion thereof; VH2 is a second heavy chain variable domain obtained from said second parent antibody or antigen binding portion thereof; C is a heavy chain constant domain; (X1)n is a linker with the proviso that it is not CH1, wherein said (X1)n is either present or absent; and (X2)n is an Fc region, wherein said (X2)n is either present or absent; (d) constructing second and fourth polypeptide chains comprising VL1-(X1)n-VL2-C-(X2)n, wherein: VL1 is a first light chain variable domain obtained from said first parent antibody or antigen binding portion thereof; VL2 is a second light chain variable domain obtained from said second parent antibody or antigen binding thereof; C is a light chain constant domain; (X1)n is a linker, wherein said (X1)n is either present or absent; and (X2)n does not comprise an Fc region, wherein said (X2)n is either present or absent; and (e) expressing said first, second, third and fourth polypeptide chains such that a binding molecule that binds sclerostin and DKK-1 is generated.

In another embodiment, pharmaceutical compositions comprising binding molecules of the invention are provided. In a further embodiment, binding molecules of the invention in combination with one or more of a pharmaceutically acceptable excipient, diluent or carrier are provided.

In one embodiment, provided is a method of treating a bone disorder comprising administering to a patient in need thereof a binding molecule of the invention. In another embodiment, provided is a method of accelerating bone fracture repair comprising administering to a patient in need thereof a binding molecule of the invention. In another embodiment, provided is a method of increasing bone density comprising administering to a patient in need thereof a binding molecule of the invention. In a further embodiment, provided is a method of increasing bone strength comprising administering to a patient in need thereof a binding molecule of the invention.

These and other aspects of the present invention will become apparent upon reference to the following detailed description and attached drawings.

BRIEF DESCRIPTION OF THE DRAWINGS

FIGS. 13-14 summarize percent change in BMD in lumbar vertebrae and femur-tibia from rats treated with vehicle, 6.147-2x-Ab5 bispecific, 6.37-AbL-Ab23 bispecific, Ab5K-AbS-6.147 bispecific, 6.147-AbL-27H6 bispecific, and 8G2-AbL-6.37.5 bispecific.

DETAILED DESCRIPTION OF THE INVENTION

Figure 1:
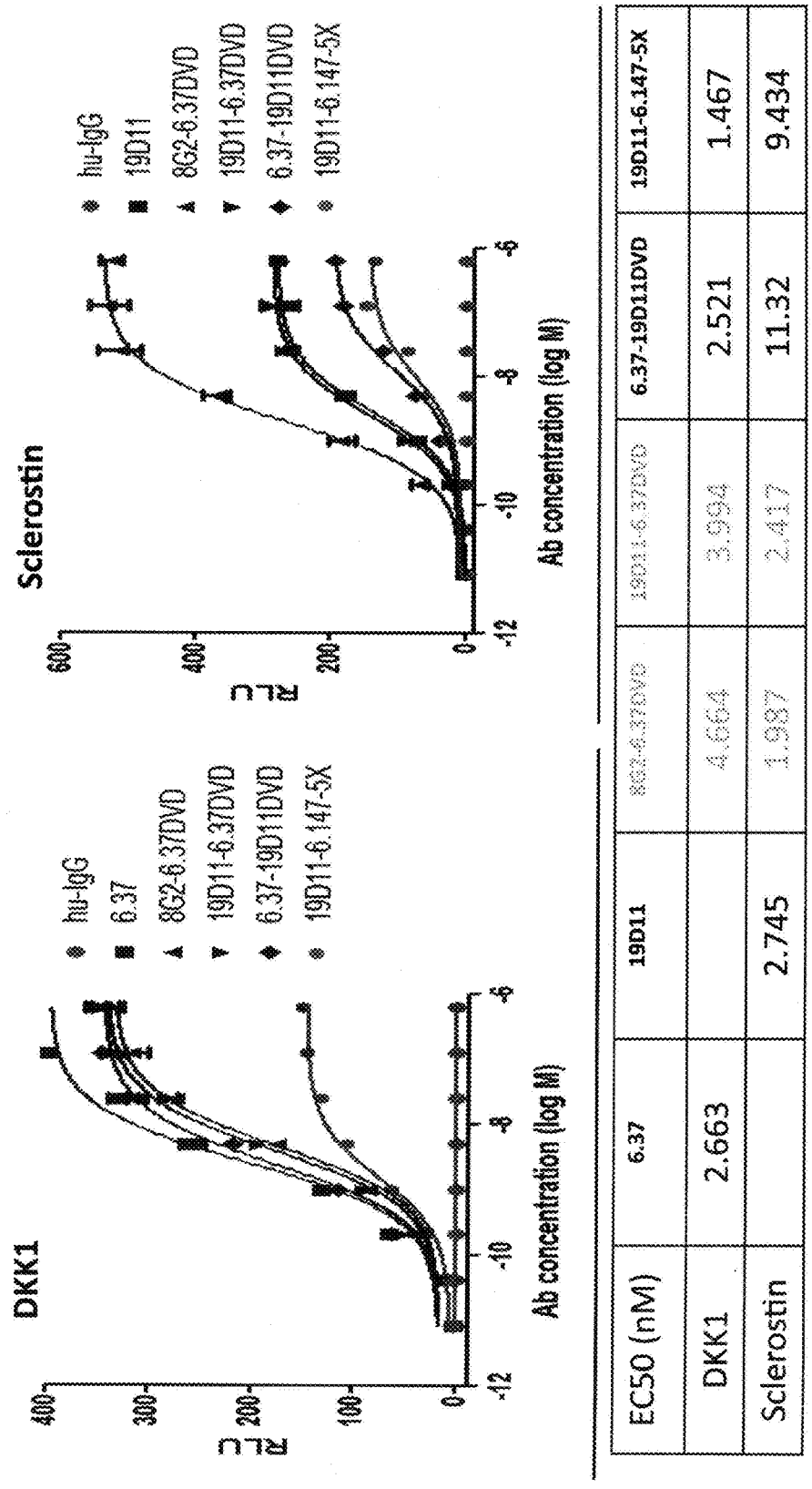
FIG. 1 summarizes ELISA analysis of bispecific huAbs binding to huDKK1 or huScl.

The section headings herein are for organizational purposes only and are not to be construed as limiting the subject matter described therein. All references cited in this application are expressly incorporated by reference herein. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

Provided herein are novel bispecific molecules that are effective in treating conditions requiring increased bone building, for example, fracture repair or bone loss associated with pathological conditions, such as multiple myeloma. In addition, provided herein are combinations of agents that increase bone anabolism including combinations of DKK-1 and sclerostin inhibitors. These combinations can be used for treatment of, for example, osteoporosis, increase the rate of fracture healing, and any number of conditions requiring an increase in the rate of bone building. The combination therapeutic can take the form of two separate inhibitors, for example, an anti-sclerostin antibody and a bispecific molecule, or can be a single molecular entity, for example, a bispecific binding molecule.

Reports indicate that Dkk-1 expression is elevated in fracture models of non-unions (Bajada, et al., 2009 Bone; 45(4): 726-35.). Likewise, healthy bone expresses lower levels of Dkk-1 helping to explain the limited effect of Dkk-1 antibodies alone on BMD in intact bone. Thus, combinations of sclerostin and Dkk-1 inhibitors to treat fractures are particularly useful given the surprisingly strong healing response including the significant increase in the peak load in a relatively short period. A bispecific molecule comprising inhibitors of both sclerostin and DKK-1 has been unexpectedly found to generate a greater biological response than either monotherapy alone.

As used herein, a bispecific molecule binds one antigen on one of its two binding regions, and binds a different antigen on its second binding region. Thus, for example, a bispecific antibody may have two distinct antigen binding regions and be monovalent for each antigen it binds. A further nonlimiting example of a bispecific molecule is a DVD-Ig, which may have two distinct antigen binding regions on each of its two arms, thus being bivalent for both distinct antigens. Bispecific and bifunctional sclerostin and DKK-1 binding molecules provided herein can include one or more CDRs or one or more variable regions as described herein. A bispecific or bifunctional antibody in some instances is an artificial hybrid antibody having two different heavy/light chain pairs and two different binding sites. These bispecific antibodies may be produced by a variety of methods including, but not limited to, fusion of hybridomas or linking of Fab' fragments. See, e.g., Songsivilai & Lachmann, 1990, Clin. Exp. Immunol. 79: 315-321; Kostelny et al., 1992, J. Immunol. 148: 1547-1553.

Bispecific molecules can also be created according to the invention by fusion. In one example, it can be linked (e.g., by expressing fused proteins, chemical linking, high affinity non-covalent association or the like) to one or more other binding molecules. Examples of such binding molecules include but are not limited to another antibody, antibody fragment, peptide or binding mimetic, such that a bispecific molecule results.

Bispecific molecules can also be created by selecting for, and/or engineering, an antibody that specifically binds to two distinct antigens, such as DKK-1 and sclerostin. See, e.g., Bostrom et al., 2009, Science 323: 1610-1614.

Bispecific molecules can also comprise a first binding specificity for sclerostin and a second binding specificity for a second target. For example, the second target can be another epitope of sclerostin different from the first epitope. Another example is a bispecific molecule comprising at least one first binding specificity for sclerostin and a second binding specificity for an epitope within Dkk-1. Another example is a bispecific molecule comprising at least one first binding specificity for sclerostin and a second binding specificity for an epitope within LRP4. Additionally, for the invention in which the bispecific molecule is multi-specific, the molecule can further include a third binding specificity, in addition to the first and second target epitope.

Formats for Bispecific Binding Agents

In one aspect, the present invention features bispecific or multispecific molecules comprising an anti-sclerostin binding agent and an anti-DKK1 binding agent, or a fragment thereof. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" or "bispecific binding molecule" or "bispecific binding protein" as used herein.

To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for sclerostin and a second binding specificity for a second target epitope. For example, the second target epitope is another epitope of sclerostin different from the first target epitope. Another example is a bispecific molecule comprising at least one first binding specificity for sclerostin and a second binding specificity for an epitope within Dkk-1. Another example is a bispecific molecule comprising at least one first binding specificity for sclerostin and a second binding specificity for an epitope within LRP4. Additionally, for the invention in which the bispecific molecule is multi-specific, the molecule can further include a third binding specificity, in addition to the first and second target epitope.

In certain embodiments, the bispecific format is a dual variable domain (DVD) Ig. In certain embodiments, the DVD-Ig format comprises two variable domains on each arm on an immunoglobulin, giving a total of four variable domains per molecule. In one embodiment the binding protein of the invention is a DVD-Ig capable of binding two antigens comprising four polypeptide chains, wherein, first and third polypeptide chains comprise VH1-(X1)n-VH2-C-(X2)n, wherein, VH1 is a first heavy chain variable domain obtained from a first parent antibody or antigen binding portion thereof; VH2 is a second heavy chain variable domain obtained from a second parent antibody or antigen binding portion thereof; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain obtained from a first parent antibody or antigen binding portion thereof; VL2 is a second light chain variable domain obtained from a second parent antibody or antigen binding portion thereof; C is a light chain constant domain. Nonlimiting examples of the combinations contemplated are provided herein in Table 1, SEQ ID NOs: 17-92, which describe nucleic acid and amino acid sequences of DVD-Ig heavy chains and light chains. However, any combination of antibodies, or fragments thereof, including CDRs, provided herein, is contemplated.

Nonlimiting examples of DVD-Ig's can be found in U.S. Pat. No. 7,612,181, U.S. Patent Appl. Publ. Nos. US20110008766A1, US20090311253A1, US20100047239A1, US20090215992A1, US20070081996A1, US20070071675A1, US20070041905A1, US20100260668A1, US20100076178A1, US20090304693A1, US20090311253A1, and US20100233079A1. Additional nonlimiting examples of DVD-Ig's can be found in International Patent Application Publ. Nos. WO2007024715A2, WO2008024188A2, WO2009134776A2, WO2009149185A2, WO2009149189A2, WO2010065882A1, WO2010127284A2, and WO2010127294A2.

The term "linker" is used to denote polypeptides comprising two or more amino acid residues joined by peptide bonds and are optionally used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). For example, X1 of the DVD-Ig can be a linker selected from any of the linker sequences set forth in Table 1 herein.

In specific embodiments, the linkers can be mutated to make amino acid substitutions to change their properties. For example, O-glycosylation may be observed with DVD-Igs that comprise the AbL linker. To address this, one or more Ser or Thr residues (underlined below) may be changed to glycine (Gly; G) or glutamine (Gln; Q) depending on which specific sites are O-glycosylated in each DVD-Ig as determined by peptide mapping.

```
A<u>S</u>TKGP<u>S</u>VFPLAP HC

<u>T</u>VAAP<u>S</u>VFIFPP LC

QPKAAP<u>SV</u><u>T</u>LFPPLC
```

Sites may be substituted in either, or in both the heavy chain and light chain linkers.

In one embodiment, the binding protein does not comprise X2. In another embodiment, X1 is a linker with the proviso that it is not CH1.

In one embodiment, both the variable heavy and variable light chain comprise the same linker. In another embodiment, the variable heavy and variable light chain comprise different linkers. In another embodiment, both the variable heavy and variable light chain comprise a short (about 6 amino acids or shorter) linker. In another embodiment, both the variable heavy and variable light chain comprise a long (greater than 6 amino acids) linker. In another embodiment, the variable heavy chain comprises a short linker and the variable light chain comprises a long linker. In another embodiment, the variable heavy chain comprises a long linker and the variable light chain comprises a short linker.

In certain embodiments, the bispecific format is an immunoglobulin further comprising a monomer domain that binds to sclerostin or DKK-1. See, for example, U.S. Pat. Nos. 7,503,907 and 7,820,790, and U.S. Patent Publ. Nos. 20040175756, 20050048512, 20050053973, and 20060223114. In one embodiment the bispecific molecule comprises multiple monomer domains, alternatively known as an avimer. Avimers comprise two or more peptide sequences of 30 to 35 amino acids each, connected by linker peptides. In certain embodiments, the individual sequences are derived from A domains of various membrane receptors and have a rigid structure, stabilized by disulfide bonds and calcium. In some embodiments, each A domain can bind to a certain epitope of the target protein. The combination of domains binding to different epitopes of the same protein increases affinity to this protein, an effect known as avidity. In one embodiment, the monomer domain or the avimer is located within the Fc region of the immunoglobulin.

In certain embodiments, the bispecific format is a linkerbody. A "linkerbody" is a bivalent, bispecific antibody. The linkerbody is constructed by joining a VL of an antibody to its respective heavy chain using a linker. Two halves representing specificity for DKK and sclerostin respectively can be brought together by introducing opposite charge pair mutations in the Fc of each heavy chain. For example, the first Fc contains 392D and 409D while the second Fc contains 356K and 359K (see, e.g., Kannan Gunasekhran et al, J. Biol Chem, June 2010).

In certain embodiments, the bispecific format comprises a peptide binding region (e.g. a peptide mimetic). Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, Adv. Drug Res. 15: 29; Veber and Freidinger, 1985, TINS p. 392; and Evans et al., 1987, J. Med. Chem. 30: 1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as here the ability to specifically bind Dkk-1 or sclerostin, but have one or more peptide linkages optionally replaced by a linkage selected from: —CH2NH—, —CH2S—, —CH2-CH.2-, —CH—CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, 1992, Ann. Rev. Biochem. 61: 387), incorporated herein by reference), for example, by adding internal cysteine residues capable of forming intramolecular disulfide bridges which cyclize the peptide.

In certain embodiments, the bispecific binding molecule is a bispecific diabody. Bispecific diabodies (Db) utilize the diabody format for expression. Diabodies are produced from scFv fragments by reducing the length of the linker connecting the VH and VL domain to approximately 5 residues (see Peipp, M. and T. Valerius (2002) Biochem. Soc. Trans. 30(4): 507-11). This reduction of linker size facilitates dimerization of two polypeptide chains by crossover pairing of the VH and VL domains. Bispecific diabodies are produced by expressing, two polypeptide chains with, either the structure VHA-VLB and VHB-VLA (VH-VL configuration), or VLA-VHB and VLB-VHA (VL-VH configuration) within the same cell. A large variety of different bispecific diabodies have been produced in the past and most of them are expressed in soluble form in bacteria. However, a recent comparative study demonstrates that the orientation of the variable domains can influence expression and formation of active binding sites (see Mack, M. et al. (1995) Proc. Natl. Acad. Sci. USA 92(15): 7021-5). Nevertheless, soluble expression in bacteria represents an important advantage over tandem scFv molecules. However, since two different polypeptide chains are expressed within a single cell inactive homodimers can be produced together with active heterodimers. This necessitates the implementation of additional purification steps in order to obtain homogenous preparations of bispecific diabodies. One approach to force the generation of bispecific diabodies is the production of knob-into-hole diabodies (see Holliger, P., T. Prospero, and G. Winter (1993) Proc. Natl. Acad. Sci. USA 90(14): 6444-8.18). This approach was demonstrated for a bispecific diabody directed against HER2 and CD3. A large knob was introduced in the VH domain by exchanging Val37 with Phe and Leu45 with Trp and a complementary hole was produced in the VL domain by mutating Phe98 to Met and Tyr87 to Ala, either in the anti-HER2 or the anti-CD3 variable domains. By using this approach the production of bispecific diabodies could be increased from 72% by the parental diabody to over 90% by the knob-into-hole diabody. Diabodies have also been fused to Fc to generate more Ig-like molecules, named di-diabodies (see Lu, D., et al. (2004) J. Biol. Chem. 279(4): 2856-65). In addition, multivalent antibody construct comprising two Fab repeats in the heavy chain of an IgG and capable of binding four antigen molecules has been described (see WO 0177342A1, and Miller, K., et al. (2003) J. Immunol. 170(9): 4854-61).

In certain embodiments, the bispecific binding molecule can be in the context of a multispecific binding molecule. A nonlimiting example of this format can be found in International Patent Application Publ. No. WO2009018386A1 and U.S. Patent Appl. Publ. No. US20090155275.

In certain embodiments, the bispecific format is a domain antibody. A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens. See for example, U.S Patent Publ. Nos. 20100234570 and 20040219643A1.

In one embodiment, the bispecific molecules of the invention comprise as a binding specificity at least one antibody, or an antibody fragment thereof, including, e.g., an Fab, Fab', F(ab')2, Fv, or a single chain Fv from a novel bispecific molecule sequence provided herein. It may also be a light chain or heavy chain dimer, or any minimal fragment such as a Fv or a single chain construct as described in Ladner et al. U.S. Pat. No. 4,946,778.

Bispecific molecules can be prepared by chemically conjugating the binding portions using methods known in the art. When the binding portions are proteins or peptides, a variety of coupling or cross-linking agents can be used for covalent conjugation. Examples include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl4-(N-maleimidomethyl) cyclohaxane-Icarboxylate (sulfo-SMCC) (see e.g., Karpovsky et a/., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-1 32; Brennan et al., 1985 Science 229:81-83, and Glennie et al., 1987 J. Immunol. 139: 2367-2375. Conjugating agents include SATA and sulfo-SMCC, both available from Pierce Chemical Co. (Rockford, Ill.). When the binding portions are antibodies, they can be conjugated by sulfhydryl bonding of the hinge regions of the two heavy chains. In one embodiment, the hinge region is modified to contain an odd number of sulfhydryl residues such that there is a free sulfhydryl group that has not formed a disulfide linkage with a corresponding heavy or light chain counterpart.

Bispecific molecules may comprise at least two single chain molecules. Non-limiting examples of methods for preparing bispecific molecules are described various patent publications including in U.S. Pat. Nos. 5,260,203; 5,455,030; 4,881,175; 5,132,405; 5,091,513; 5,476,786; 5,013,653; 5,258,498; 5,482,858; and U.S. Patent Application No. 2010/0076178.

Alternatively, both binding moieties can be encoded in the same vector and expressed and assembled in the same host cell. This method is particularly useful where the bispecific molecule is a mAb×mAb, mAb×Fab, Fab×F(abl):! or ligandx Fab fusion protein. A bispecific molecule of the invention can be a single chain molecule comprising one single chain antibody and a binding determinant, or a single chain bispecific molecule comprising two binding determinants.

Nonlimiting examples of antibodies that bind to Sclerostin and DKK-1 are disclosed herein. It will be appreciated by one skilled in the art that the antibodies described herein can be employed in the context of the bispecific molecules of the invention.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Sclerostin Binding Molecules

The invention provides sclerostin binding molecules that can be used in the bispecific molecules of the invention. In certain embodiments, the sclerostin binding molecules are antibodies, or fragments thereof. In certain embodiments, the bispecific molecule comprises the VH and/or the VL domain of an immunoglobulin described herein. In other embodiments, the bispecific molecule comprises at least one of light chain CDR1, CDR2, CDR3 and at least one heavy chain CDR1, CDR2, or CDR3. Nonlimiting examples of CDR sequences of sclerostin binding molecules are provided in Table 1 herein.

The sclerostin binding component of the bispecific molecules that are provided can include one, two, three, four, five or six of the CDRs listed in Table 1. It is contemplated that the bispecific molecule can include two or more CDRs from a single antibody, or two or more CDRs from any combination of the antibodies listed above. Some sclerostin binding components include both the light chain CDR3 and the heavy chain CDR3. Certain sclerostin binding components have variant forms of the CDRs listed in Table 1, with one or more (i.e., 2, 3, 4, 5 or 6) of the CDRs each having at least 80%, 85%, 90% or 95% sequence identity to a CDR sequence listed in Table 1. For example, the sclerostin binding components can include both a light chain CDR3 and a heavy chain CDR3 that each have at least 80%, 85%, 90% or 95% sequence identity to the light chain CDR3 sequence and the heavy chain CDR3, respectively, listed in Table 1. The CDR sequences of some of the sclerostin binding components that are provided may also differ from the CDR sequences listed in Table 1, such that the amino acid sequence for any given CDR differs from the sequence listed in Table 1 by no more than 1, 2, 3, 4 or 5 amino acid residues. Differences from the listed sequences are typically, but not limited to, conservative substitutions.

It is further contemplated that each of the light chains described herein can be combined with any of the heavy chains described herein to form the sclerostin binding component of the bispecific molecule. Certain sclerostin binding components that are provided herein comprise a light chain variable domain comprising a sequence of amino acids that differs from the sequence of a light chain variable domain provided herein at only 1, 2, 3, 4, 5, 6, 7, 8, 9, 10, 11, 12, 13, 14 or 15 amino acid residues, wherein each such sequence difference is independently either a deletion, insertion or substitution of one amino acid, or a combination thereof. The light chain variable region in certain sclerostin binding components comprises a sequence of amino acids that has at least 70%, 75%, 80%, 85%, 90%, 95%, 97% or 99% sequence identity to the amino acid sequences of the light chain variable regions provided herein.

Certain sclerostin binding components that are provided herein comprise a heavy chain variable domain comprising a sequence of amino acids that differs from the sequence of a heavy chain variable domain provided herein at only 1, 2, 3, 4, 5, 6, 7, 8, 9, 10, 11, 12, 13, 14 or 15 amino acid residues, wherein each such sequence difference is independently either a deletion, insertion or substitution of one amino acid, or a combination thereof. The heavy chain variable region in certain sclerostin binding components comprises a sequence of amino acids that has at least 70%, 75%, 80%, 85%, 90%, 95%, 97% or 99% sequence identity to the amino acid sequences of the heavy chain variable regions provided herein.

In other embodiments, the portion of the bispecific molecule that binds to sclerostin is selected from those sclerostin binding molecules disclosed in U.S. Pat. No. 7,744,874, U.S. Pat. No. 7,592,429, and U.S. Patent Appl. Publ. No. 2009/0130113. In a specific embodiment, a DVD-Ig comprising a sclerostin binding VH and VL from the antibodies disclosed in the above patents and patent applications is contemplated.

DKK-1 Binding Agents

The invention provides DKK-1 binding molecules that can be used in the bispecific molecules of the invention. In certain embodiments, the DKK-1 binding molecules are antibodies, or fragments thereof. In certain embodiments, the bispecific molecule comprises the VH and/or the VL domain of an immunoglobulin described herein. In other embodiments, the bispecific molecule comprises at least one of light chain CDR1, CDR2, CDR3 and heavy chain CDR1, CDR2, or CDR3. Nonlimiting examples of CDR sequences of DKK-1 binding molecules are provided in Table 1.

The DKK-1 binding component of the bispecific molecules that are provided can include one, two, three, four, five or six of the CDRs listed in Table 1. It is contemplated that the bispecific molecule can include two or more CDRs from a single antibody, or two or more CDRs from any combination of the antibodies listed in Table 1. Some DKK-1 binding components include both the light chain CDR3 and the heavy chain CDR3. Certain DKK-1 binding components have variant forms of the CDRs listed in Table 1, with one or more (i.e., 2, 3, 4, 5 or 6) of the CDRs each having at least 80%, 85%, 90% or 95% sequence identity to a CDR sequence listed in Table 1. For example, the DKK-1 binding components can include both a light chain CDR3 and a heavy chain CDR3 that each have at least 80%, 85%, 90% or 95% sequence identity to the light chain CDR3 sequence and the heavy chain CDR3, respectively, listed in Table 1. The CDR sequences of some of the DKK-1 binding components that are provided may also differ from the CDR sequences listed in Table 1 such that the amino acid sequence for any given CDR differs from the sequence listed in Table 1 by no more than 1, 2, 3, 4 or 5 amino acid residues. Differences from the listed sequences are typically, but not limited to, conservative substitutions.

It is further contemplated that each of the light chains described herein can be combined with any of the heavy chains described herein to form the DKK-1 binding component of the bispecific molecule. Certain DKK-1 binding components that are provided herein comprise a light chain variable domain comprising a sequence of amino acids that differs from the sequence of a light chain variable domain provided herein at only 1, 2, 3, 4, 5, 6, 7, 8, 9, 10, 11, 12, 13, 14 or 15 amino acid residues, wherein each such sequence difference is independently either a deletion, insertion or substitution of one amino acid, or a combination thereof. The light chain variable region in certain DKK-1 binding components comprises a sequence of amino acids that has at least 70%, 75%, 80%, 85%, 90%, 95%, 97% or 99% sequence identity to the amino acid sequences of the light chain variable regions provided herein.

Certain DKK-1 binding components that are provided herein comprise a heavy chain variable domain comprising a sequence of amino acids that differs from the sequence of a heavy chain variable domains provided herein at only 1, 2, 3, 4, 5, 6, 7, 8, 9, 10, 11, 12, 13, 14 or 15 amino acid residues, wherein each such sequence difference is independently either a deletion, insertion or substitution of one amino acid, or a combination thereof. The heavy chain variable region in certain DKK-1 binding components comprises a sequence of amino acids that has at least 70%, 75%, 80%, 85%, 90%, 95%, 97% or 99% sequence identity to the amino acid sequences of the heavy chain variable regions provided herein.

In other embodiments, the portion of the bispecific molecule that binds to DKK-1 is selected from those DKK-1 binding molecules disclosed in U.S. Pat. No. 7,709,611, U.S. Patent Publ. No. 2008/0193449, U.S. Pat. No. 7,642,238, U.S. Pat. No. 7,700,101, and WO 2007/084344. In a specific embodiment, a DVD-Ig comprising a sclerostin binding VH and VL from the antibodies disclosed in the above patents and patent applications is contemplated.

Antibodies and Binding Epitopes

The bispecific binding molecules of the invention can comprise the anti-sclerostin and anti-DKK-1 antibodies and fragments thereof provided herein. The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 10 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

When an antibody is said to bind an epitope within specified residues, such as within Dkk-1, for example, what is meant is that the antibody specifically binds to a polypeptide consisting of the specified residues (e.g., a specified segment of Dkk-1). Such an antibody does not necessarily contact every residue within Dkk-1. Nor does every single amino acid substitution or deletion within Dkk-1 necessarily significantly affect binding affinity. Epitope specificity of an antibody can be determined in variety of ways. One approach, for example, involves testing a collection of overlapping peptides of about 15 amino acids spanning the sequence of Dkk-1 and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. This is useful for identifying end-specific antibodies. Optionally, additional peptides can be included terminating at a particular amino acid of interest. This approach is useful for identifying end-specific antibodies to internal fragments of Dkk-1. An antibody or immunologically functional fragment is screened for specific binding to each of the various peptides. The epitope is defined as occurring with a segment of amino acids that is common to all peptides to which the antibody shows specific binding.

Antibodies and functional fragments thereof that bind to a conformational epitope that is located in the carboxy-terminal portion of Dkk-1 are also provided to be used in the bispecific molecules of the invention. The carboxy-terminus of Dkk-1 contains several cysteine residues that form a cluster of disulfide bonds which create several loops. The invention provides antibodies, for use in the bispecific molecules of the invention, that bind to two of these loops, thereby neutralizing the ability of Dkk-1 to suppress Wnt activity. Exemplary antibodies, for use in the bispecific molecules of the invention, capable of binding to the aforementioned conformational epitope are the monoclonal antibodies 11H10 and 1F11, each of which comprises a light chain and a heavy chain. Further examples for use in the bispecific molecules of the invention can be found in U.S. Patent Appl. No. 61/407,128, filed on Oct. 27, 2010, and International Patent App. No. PCT/US2011/058025, filed on Oct. 27, 2011. The epitope comprising these two loops is formed by disulfide bonds between cysteine residues 220 and 237 of SEQ ID NO: 190 and between cysteine residues 245 and 263 of SEQ ID NO: 190. The body of the two loops that form the epitope thus includes amino acids 221-236 and 246-262 of SEQ ID NO: 190. Segments within this loop that are involved in binding include amino acids 221-229 of SEQ ID NO: 190 and amino acids 246-253 of SEQ ID NO: 190. Thus, certain antibodies and fragments that are provided herein, for use in the bispecific molecules of the invention, specifically bind to the foregoing region(s). Some of the antibodies and fragments, for instance, bind to a peptide comprising or consisting of amino acids 221 to 262 of SEQ ID NO: 190.

Competing Antibodies

Antibodies and immunologically functional fragments thereof that are useful in the context of the bispecific binding molecules of the invention that compete with one of the exemplified antibodies or functional fragments for specific binding to Dkk-1 or sclerostin are also provided. Such antibodies and fragments may also bind to the same epitope as one of the exemplified antibodies. Antibodies and fragments that compete with or bind to the same epitope as the exemplified antibody or fragment are expected to show similar functional properties. The exemplified antibodies and fragment include those described herein, including those with the heavy and light chains, variable region domains and CDRs listed herein. In specific embodiments, the invention encompasses bispecific binding molecules, such as the provided DVD-Igs (e.g., SEQ ID NOs 17-92 of the present invention), that comprise the VH and VL of the provided antibodies, and binding molecules that compete for binding with these bispecific binding molecules. The binding competition can be for DKK-1 and/or sclerostin. Competition assays, such as a Biacore assay, are well known in the art.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as CH1, CH2 and CH3. The antibodies that are provided for use in the bispecific molecules of the invention can have any of these isotypes and subtypes.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The term "neutralizing antigen binding protein" or "neutralizing antibody" refers to an antigen binding protein or antibody, respectively, for use in the bispecific molecules of the invention, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In some embodiments, the neutralizing ability is characterized and/or described via a competition assay. In some embodiments, the neutralizing ability is described in terms of an $IC_{50}$ or $EC_{50}$ value.

In certain embodiments, the antibodies that are provided for use in the bispecific molecules of the invention have a binding affinity (Ka) for sclerostin or Dkk-1 of at least $10^4$ or $10^5$/M×seconds as measured by techniques well known in the art (e.g. Biacore or KinExA). Other antibodies have a Ka of at least $10^6$, $10^7$, $10^8$ or $10^9$/M×seconds. Certain antibodies that are provided have a low disassociation rate. Some antibodies, for instance, have a Koff of $1\times10^{-4}$s-1, $1\times10^{-5}$s-1 or lower.

Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and 5194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a Dkk-1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a Dkk-1 polypeptide. Such hybridoma cell lines, and anti-Dkk-1 monoclonal antibodies produced by them, are encompassed by the present invention.

Monoclonal antibodies secreted by a hybridoma cell line can be purified using any useful technique known in the antibody arts. Hybridomas or mAbs may be further screened to identify mAbs with particular properties, such as the ability to block a Wnt induced activity. Examples of such screens are provided in the examples below.

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., Proc. Natl. Acad. Sci. USA 81:6851-6855 (1985). CDR grafting is described, for example, in U.S. Pat. Nos. 6,180,370, 5,693,762, 5,693,761, 5,585,089, and 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, Nature 321:522-25; Riechmann et al., 1988, Nature 332:323-27; Verhoeyen et al., 1988, Science 239:1534-36). In certain embodiments, constant regions from species other than human can be used along with the human variable region(s) to produce hybrid antibodies.

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (MAbs) in mouse, an animal that can be immunized with any desirable antigen. Using fully human antibodies can minimize the immunogenic and allergic responses that can sometimes be caused by administering mouse or mouse-derivatized Mabs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., 1993, Proc. Natl. Acad. Sci. USA 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy (μ and gamma) and kappa light chain immunoglobulin sequences, together with targeted mutations that inactivate the endogenous μ and .kappa. chain loci (Lonberg et al., 1994, Nature 368: 856-859). Accordingly, the mice exhibit reduced expression of mouse IgM or .kappa. and in response to immunization, and the introduced human heavy and light chain transgenes undergo class switching and somatic mutation to generate high affinity human IgG .kappa. monoclonal antibodies (Lonberg et al., supra.; Lonberg and Huszar, 1995, Intern. Rev. Immunol., 13: 65-93; Harding and Lonberg, 1995, Ann. N.Y. Acad. Sci. 764: 536-546). The preparation of HuMab mice is described in detail in Taylor et al., 1992, Nucleic Acids Research, 20: 6287-6295; Chen et al., 1993, International Immunology 5: 647-656; Tuaillon et al., 1994, J. Immunol. 152: 2912-2920; Lonberg et al., 1994, Nature 368: 856-859; Lonberg, 1994, Handbook of Exp. Pharmacology 113: 49-101; Taylor et al., 1994, International Immunology 6: 579-591; Lonberg and Huszar, 1995, Intern. Rev. Immunol. 13: 65-93; Harding and Lonberg, 1995, Ann. N.Y. Acad. Sci. 764: 536-546; Fishwild et al., 1996, Nature Biotechnology 14: 845-851. See further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918. Technologies utilized for producing human antibodies in these transgenic mice are disclosed also in WO 98/24893, and Mendez et al., 1997, Nature Genetics 15: 146-156. For example, the HCO7 and HCO12 transgenic mice strains can be used to generate binding agents suitable for use herein.

Using hybridoma technology, antigen-specific human MAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, J. Mol. Biol. 227:381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT Publication No. WO99/10494, which describes the isolation of high affinity and functional agonistic antibodies for MPL- and msk-receptors using such an approach.

The bispecific molecules provided herein may also block or reduce binding between sclerostin and/or Dkk-1 and LRP5 and/or LRP6, thereby stimulating at least one activity associated with Wnt signaling.

Nucleic acids molecules, vectors, and host cells useful in the production of the antibodies and selective binding agents are also provided. Certain bispecific molecules or fragments include one, two, three, four, five or all six of the anti-sclerostin or anti-DKK-1 antibody CDRs listed in Table 1, and in certain embodiments a bispecific binding molecule will comprise a total of twelve CDRs (6 from a VH and 6 from a VL).

Pharmaceutical compositions that include any of the foregoing bispecific molecules and fragments are also provided. Such compositions typically also include a buffer, a pharmaceutically acceptable diluent, a carrier, a solubilizer, an emulsifier or a preservative. The use of the foregoing antibodies and fragments in the preparation of a pharmaceutical composition or medicament is also provided.

Variants

Some of the antibodies or fragments that are provided for use in the bispecific molecules of the invention are variant forms of the antibodies and fragments disclosed above (e.g., those having the sequences listed in Table 1). For instance, some of the antibodies or fragments are ones having one or more conservative amino acid substitutions in one or more of the heavy or light chains, variable regions or CDRs listed in Table 1.

Naturally-occurring amino acids may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe. Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions that are homologous with human corresponding sequences, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within +/−2 is included. In some aspects of the invention, those which are within +/−1 are included, and in other aspects of the invention, those within +/−0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0+/−1); glutamate (+3.0+/−1); serine (+0.3); asparagine (+0.2); glutamine (+0.2); glycine (0); threonine (−0.4); proline (−0.5+/−1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +/−2 is included, in other embodiments, those which are within +/−1 are included, and in still other embodiments, those within +/−0.5 are included. In some instances, one may also identify epitopes from primary amino acid sequences on the basis of hydrophilicity. These regions are also referred to as "epitopic core regions."

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

A number of scientific publications have been devoted to the prediction of secondary structure. See Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol. Relat. Areas Mol. Biol. 47:45-148; Chou et al., 1979, Ann. Rev. Biochem. 47:251-276; and Chou et al., 1979, Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et at., 1991, Nature 354: 105, which are each incorporated herein by reference.

The invention also encompasses glycosylation variants of the bispecific molecules of the invention wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Additional variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

Mimetics (e.g., peptide mimetics" or "peptidomimetics") based upon the variable region domains and CDRs that are described herein are also provided. These analogs can be peptides, non-peptides or combinations of peptide and non-peptide regions. Fauchere, 1986, Adv. Drug Res. 15: 29; Veber and Freidinger, 1985, TINS p. 392; and Evans et al., 1987, J. Med. Chem. 30: 1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as here the ability to specifically bind Dkk-1, but have one or more peptide linkages optionally replaced by a linkage selected from: —CH2NH—, —CH2S—, —CH2-CH.2-, —CH—CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, 1992, Ann. Rev. Biochem. 61: 387), incorporated herein by reference), for example, by adding internal cysteine residues capable of forming intramolecular disulfide bridges which cyclize the peptide.

Derivatives of the antibodies and fragments for use in the bispecific molecules of the invention that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of bispecific molecules, or fragments thereof, with other proteins or polypeptides, such as by expression of recombinant fusion proteins comprising heterologous polypeptides fused to the N-terminus or C-terminus of a bispecific molecule polypeptide. For example, the conjugated peptide may be a heterologous signal (or leader) polypeptide, e.g., the yeast alpha-factor leader, or a peptide such as an epitope tag. Bispecific molecule-containing fusion proteins can comprise peptides added to facilitate purification or identification of the molecule (e.g., poly-His). A bispecific molecule polypeptide also can be linked to the FLAG peptide as described in Hopp et al., Bio/Technology 6:1204, 1988, and U.S. Pat. No. 5,011, 912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. Nos. 5,426,048 and 5,262,522 (each of which is hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a bispecific molecule such as disclosed herein may be substituted for the variable portion of an antibody heavy and/or light chain.

Alternatively, the oligomer is a fusion protein comprising multiple bispecific molecule polypeptides, with or without peptide linkers (spacer peptides). Among the suitable peptide linkers are those described in U.S. Pat. Nos. 4,751,180 and 4,935,233.

Another method for preparing oligomeric bispecific molecule derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344: 191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising a bispecific molecule fragment or derivative fused to a leucine zipper peptide are expressed in suitable host cells, and the soluble oligomeric bispecific molecule fragments or derivatives that form are recovered from the culture supernatant.

In another aspect, the present invention provides a bispecific molecule having a half-life of at least one day in vitro or in vivo (e.g., when administered to a human subject). In one embodiment, the antibody has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antibody contains point mutations to increase serum half life, such as described in WO 00/09560.

Nucleic acids that encode the polypeptide chains of a bispecific molecule of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

DNA encoding antibody polypeptides (e.g., heavy or light chain, variable domain only, or full length) may be isolated from B-cells of mice that have been immunized with Dkk-1 or sclerostin or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

The invention further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5.times. sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide that it encodes. Mutations can be introduced using any technique known in the art. In one embodiment, one or more particular amino acid residues are changed using, for example, a site-directed mutagenesis protocol. In another embodiment, one or more randomly selected residue is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

Conservative modifications may be made to the heavy and light chains described in (and corresponding modifications to the encoding nucleic acids) to produce a bispecific molecule having functional and biochemical characteristics. Methods for achieving such modifications are described above.

The single chain antibodies that are contemplated for use with the bispecific molecules of the invention may be formed by linking heavy and light chain variable domain (Fv region) fragments provided herein via an amino acid bridge (short peptide linker), resulting in a single polypeptide chain. Such single-chain Fvs (scFvs) may be prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

Proteins and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies or bispecific molecules of the invention provided herein, or to increase or decrease the affinity of these antibodies or bispecific molecules of the invention for human Dkk-1 or sclerostin or for modifying the binding affinity of other bispecific molecules described herein.

Expression

The bispecific molecules and functional fragments can be prepared by any of a number of conventional techniques to express the nucleic acid sequences provided in Table 1, or to express an nucleic acid sequence that encodes any of the amino acid sequences provided in Table 1.

For example, bispecific molecules may be produced by recombinant expression systems, using any technique known in the art. See, for example, Monoclonal Antibodies, Hybridomas: A New Dimension in Biological Analyses, Kennet et al. (eds.) Plenum Press, New York (1980): and Antibodies: A Laboratory Manual, Harlow and Lane (eds.), Cold Spring Harbor Laboratory Press, Cold Spring Harbor, N.Y. (1988).

Bispecific molecules of the present invention can be expressed in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region (e.g., CH1, CH2 and/or CH3); a heavy chain variable region, and optionally, at least two or more heavy chain variable regions; a light chain constant region; a light chain variable region, and optionally, at least two or more light chain variable regions; one or more CDRs of the light or heavy chain of the bispecific molecule; and optionally a linker sequence between multiple variable regions. These nucleic acid sequences are inserted into an appropriate expression vector using standard ligation techniques. In some embodiments, vectors are used that employ protein-fragment complementation assays using protein reporters, such as dihydrofolate reductase (see, for example, U.S. Pat. No. 6,270,964). Suitable expression vectors can be purchased, for example, from Invitrogen Life Technologies or BD Biosciences (formerly "Clontech"). Other useful vectors for cloning and expressing the antibodies and fragments of the invention include those described in Bianchi and McGrew, Biotech Biotechnol Bioeng 84(4):439-44 (2003). Additional suitable expression vectors are discussed, for example, in Methods Enzymol, vol. 185 (D. V. Goeddel, ed.), 1990, New York: Academic Press, which is hereby incorporated by reference.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as FLAG©, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the bispecific molecule or immunologically functional fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding bispecific molecule by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and—most preferably Simian Virus 40 (5V40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bemoist and Chambon, 1981, Nature 290: 304-10); the CMV promoter; the promoter contained in the 3' long terminal repeat of Rous sarcoma virus (Yamamoto, et al., 1980, Cell 22: 787-97); the herpes thymidine kinase promoter (Wagner et al., 1981, Proc. Natl. Acad. Sci. U.S.A. 78: 1444-45); the regulatory sequences of the metallothionine gene (Brinster et al., 1982, Nature 296: 39-42); prokaryotic expression vectors such as the beta-lactamase promoter (VIIIa-Kamaroff et al., 1978, Proc. Natl. Acad. Sci. U.S.A., 75: 3727-31); or the tac promoter (DeBoer et al., 1983, Proc. Natl. Acad. Sci. U.S.A. 80: 21-25). Also available for use are the following animal transcriptional control regions, which exhibit tissue specificity and have been utilized in transgenic animals: the elastase I gene control region that is active in pancreatic acinar cells (Swift et al., 1984, Cell 38: 63946; Ornitz et al., 1986, Cold Spring Harbor Symp. Quant. Biol. 50: 399409; MacDonald, 1987, Hepatology 7: 425-515); the insulin gene control region that is active in pancreatic beta cells (Hanahan, 1985, Nature 315: 115-22); the mouse mammary tumor virus control region that is active in testicular, breast, lymphoid and mast cells (Leder et al., 1986, Cell 45: 485-95); the albumin gene control region that is active in liver (Pinkert et al., 1987, Genes and Devel. 1: 268-76); the alpha-feto-protein gene control region that is active in liver (Krumlauf et al., 1985, Mol. Cell. Biol. 5: 1639-48; Hammer et al., 1987, Science 235: 53-58); the alpha 1-antitrypsin gene control region that is active in the liver (Kelsey et al., 1987, Genes and Devel. 1: 161-71); the beta-globin gene control region that is active in myeloid cells (Mogram et al., 1985, Nature 315: 338-40; Kollias et al., 1986, Cell 46: 89-94); the myelin basic protein gene control region that is active in oligodendrocyte cells in the brain (Readhead et al., 1987, Cell 48: 703-12); the myosin light chain-2 gene control region that is active in skeletal muscle (Sani, 1985, Nature 314: 283-86); the gonadotropic releasing hormone gene control region that is active in the hypothalamus (Mason et al., 1986, Science 234: 1372-78); and most particularly the immunoglobulin gene control region that is active in lymphoid cells (Grosschedl et al., 1984, Cell 38: 647-58; Adames et al., 1985, Nature 318: 533-38; Alexander et al., 1987, Mol. Cell Biol. 7: 1436-44).

An enhancer sequence may be inserted into the vector to increase the transcription in higher eukaryotes of a nucleic acid encoding a bispecific molecule or immunologically functional fragment thereof of the present invention. Enhancers are cis-acting elements of DNA, usually about 10-300 bp in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding a bispecific molecule of the invention, is co-amplified with the selection gene.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding a bispecific molecule or immunologically functional fragment thereof is inserted into the proper site of the vector.

The completed vector containing sequences encoding the inventive antibody or immunologically functional fragment thereof is inserted into a suitable host cell for amplification and/or polypeptide expression. The transformation of an expression vector for a bispecific molecule immunologically functional fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes a bispecific molecule or functional fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive Dkk-1 binding properties.

Formulation

In certain embodiments, the invention also provides compositions comprising the subject bispecific molecules or fragments thereof together with one or more of the following: a pharmaceutically acceptable diluent; a carrier; a solubilizer; an emulsifier; a preservative; and/or an adjuvant. Such compositions may contain an effective amount of the bispecific molecule or immunologically functional fragment thereof. Thus, the use of the antibodies and fragments that are provided herein in the preparation of a pharmaceutical composition or medicament is also included. Such compositions can be used in the treatment of a variety of diseases such as listed below in the section on exemplary utilities.

Acceptable formulation components for pharmaceutical preparations are nontoxic to recipients at the dosages and concentrations employed. In addition to the bispecific molecules, the antibodies, and the fragments that are provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see Remington's Pharmaceutical Sciences, 18th Edition, (A. R. Gennaro, ed.), 1990, Mack Publishing Company), hereby incorporated by reference.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising bispecific molecules or fragments thereof may be prepared for storage by mixing the selected composition having the desired degree of purity with optional formulation agents in the form of a lyophilized cake or an aqueous solution. Further, the bispecific molecules or fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of bispecific molecules or fragments thereof in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bio-erodible microparticles or porous beads and depot injections can be used (see, for e.g., PCT/US93/00829, which describes the controlled release of porous polymeric microparticles for the delivery of pharmaceutical compositions). Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, Biopolymers 22: 547-556), poly (2-hydroxyethyl-methacrylate) (Langer et al., 1981, J Biomed Mater Res 15: 167-277) and Langer, 1982, Chem Tech 12: 98-105), ethylene vinyl acetate (Langer et al., ibid.) or poly-D(−) -3-hydroxybutyric acid (EP 133,988). Sustained release compositions may also include liposomes, which can be prepared by any of several methods known in the art. See e.g., Eppstein et al., 1985, Proc. Natl. Acad. Sci. USA 82: 3688-3692; EP 036,676; EP 088,046 and EP 143, 949.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing a multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the antibodies may be administered in a pyrogen-free, parenterally acceptable aqueous solution comprising the desired bispecific molecules or fragments thereof in a pharmaceutically acceptable vehicle. A particularly suitable vehicle for parenteral injection is sterile distilled water in which the bispecific molecules or fragments thereof are formulated as a sterile, isotonic solution, properly preserved.

Pharmaceutical compositions comprising the subject bispecific molecules and functional fragments thereof may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising a bispecific molecule or functional fragment thereof may be formulated for inhalation. In these embodiments, a bispecific molecule is formulated as a dry powder for inhalation, or bispecific molecule inhalation solutions may also be formulated with a propellant for aerosol delivery, such as by nebulization. Pulmonary administration is further described in PCT/US94/001875, which describes pulmonary delivery of chemically modified proteins, and which is hereby incorporated by reference.

Certain pharmaceutical compositions of the invention can be delivered through the digestive tract, such as orally. The subject bispecific molecules or fragments thereof that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the bispecific molecule or functional fragment thereof. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising bispecific molecules or fragments thereof also may be used ex vivo. In such instances, cells, tissues or organs that have been removed from the patient are exposed to or cultured with the bispecific molecule. The cultured cells may then be implanted back into the patient or a different patient or used for other purposes.

In certain embodiments, bispecific molecules or fragments thereof can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

Dosage

The pharmaceutical compositions that are provided can be administered for prophylactic and/or therapeutic treatments. An "effective amount" refers generally to an amount that is a sufficient, but non-toxic, amount of the active ingredient (i.e., a bispecific molecule or immunologically functional fragment thereof) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from cell culture and/or animal studies can be used in formulating a range of dosages for humans. The dosage of the active ingredient typically lines within a range of circulating concentrations that include the ED50 with little or no toxicity. The dosage can vary within this range depending upon the dosage form employed and the route of administration utilized.

The effective amount of a pharmaceutical composition comprising bispecific molecules or fragments thereof to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the bispecific molecule is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 150 mg/kg; or 1 µg/kg up to about 100 mg/kg; or 5 µg/kg up to about 50 mg/kg. In certain embodiments, the dose is at least 0.1 µg/kg. In certain embodiments, the dose is at least 1 µg/kg. In certain embodiments, the dose is at least 5 µg/kg. In certain embodiments, the dose is at least 5 mg/kg. In certain embodiments, the dose is at least 10 mg/kg. In certain embodiments, the dose is at least 50 mg/kg. In certain embodiments, the dose is at least 100 mg/kg.

The dosing frequency will depend upon the pharmacokinetic parameters of the bispecific molecule or immunologically functional fragment thereof in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a medical disorder by targeting Sclerostin and/or Dkk-1, a composition comprising the subject bispecific molecules or fragments thereof may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of the skilled physician to determine the appropriate interval for determining whether the improvement is sustained. The degree of improvement is determined based on signs or symptoms, and may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of antibody. Preferably, the baseline examination is done within about 60 days of administering the first dose. If the antibody is being administered to treat acute symptoms, such as for example to treat a broken bone, the first dose is administered as soon as practically possible after the injury has occurred.

Improvement is induced by administering the subject bispecific molecules or fragments thereof until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

The subject bispecific molecules and fragments thereof can be used to detect sclerostin and/or Dkk-1 in biological samples. Such uses allow the identification of cells or tissues that produce the protein or serve as a diagnostic for detecting pathological conditions in which sclerostin and/or Dkk-1 is overproduced or underproduced. The antibodies and fragments that are provided can also be used in methods to screen for a molecule that binds to sclerostin and/or Dkk-1. A variety of competitive screening methods, for example, can be used. In some methods, a sclerostin and/or Dkk-1 molecule or fragment thereof to which a bispecific molecule binds, is contacted with an antibody or fragment disclosed herein together with another molecule (i.e., a candidate molecule). A reduction in binding between the bispecific molecule or fragment and sclerostin and/or Dkk-1 is an indication that the molecule binds the target. Binding of the bispecific molecule or fragment can be detected using a variety of methods, e.g., an ELISA. Detection of binding between the bispecific molecule or fragment to the target can be simplified by detectably labeling the antibody. In some methods, a molecule that exhibits binding in the initial screen is further analyzed to determine whether it inhibits a sclerostin and/or Dkk-1 activity (e.g., whether the molecule activates Wnt signaling).

Methods of Treatment and Uses

In another aspect, the use of the foregoing antibodies or fragments in the treatment of a variety of diseases is disclosed. Certain methods, for instance, involve administering to a patient in need thereof an effective amount of a bispecific molecules of the invention or fragment as described herein to treat arthritis, diseases responsive to stem cell renewal, inflammatory diseases, neurological diseases, ocular diseases, renal diseases, pulmonary diseases, and skin diseases. Some treatment methods involve treating rheumatoid arthritis, psoriatic arthritis or osteoarthritis. Certain antibodies and fragments are used to treat a disease that: (a) is responsive to stem cell renewal and is selected from the group consisting of diabetes, chronic heart failure and diseases of the muscle; (b) is an inflammatory disease selected from the group consisting of Crohn's disease, colitis, and inflammatory bowel disease; (c) is a neurological disease selected from the group consisting of Alzheimer's disease, Parkinson's disease, and Huntington's disease; (d) is an ocular disease selected from the group consisting of macular degeneration and retinopathies; (e) is a renal disease selected from the group consisting of end stage renal disease, chronic renal disease, glomerulonephritis, tubulointerstitial nephritis, and IgA nephropathy; (f) is a pulmonary disease selected from the group consisting of chronic obstructive pulmonary disease, idiopathic pulmonary fibrosis, and cystic fibrosis; or (g) is a skin disease resulting from chemotherapy-induced damage to the intestinal epithelium.

Further provided herein are methods of treating or preventing loss of bone mass comprising administering to a patient in need thereof a therapeutically effective amount of a bispecific molecule of the invention. In one embodiment, the bispecific molecule of the invention comprises a variable region selected from an antibody described in any of U.S. Pat. No. 7,744,874, US 2009/0130113, U.S. Pat. No. 7,592,429, US 2008/0193449, U.S. Pat. No. 7,642,238 and U.S. Pat. No. 7,700,101, or immunologically functional fragment thereof as described herein. In one aspect of this embodiment, the patient is one who suffers from cancer that metastasizes to bone, and in another aspect, the patient is one who suffers from multiple myeloma.

Particular conditions which may be treated by the compositions of the present invention include dysplasias, wherein growth or development of bone is abnormal. Representative examples of such conditions include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, and pyogenic osteomyelitis.

Other conditions that may be treated or prevented include a wide variety of causes of osteopenia, osteoporosis and bone loss. Representative examples of such conditions include periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, idiopathic osteopenia or osteoporosis, congenital osteopenia or osteoporosis, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, fibrous dysplasia, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, and bone loss associated with space travel. Further conditions relate to bone loss associated with aging, including facial bone loss associated with aging, cranial bone loss associated with aging, jaw bone loss associated with aging, and skull bone loss associated with aging.

Compositions of the present invention may also be useful for improving outcomes in orthopedic procedures, dental procedures, implant surgery, joint replacement (e.g., hip or knee), bone grafting, bone cosmetic surgery and bone repair such as fracture healing, nonunion healing, delayed union healing and facial reconstruction. One or more compositions may be administered before, during and/or after the procedure, replacement, graft, surgery or repair.

In certain embodiments, local delivery of the binding molecules of the invention is envisioned, such as, but not limited to, fracture sites, spinal fusion or dentistry related indications. In one embodiment, the binding molecule is delivered via a local injection to the site of therapy. In another embodiment, an additional binding sequence is added to the binding molecules of the invention to direct the binding molecules against proteins restricted to the bone extracellular matrix, which can improve retention time at the therapeutic site and the PK of the binding molecule, thereby improving efficacy. Nonlimiting examples of these proteins include, but are not limited to, type 1 collagen, bone sialoprotein, and dentin matrix protein. In certain embodiments, the additional binding sequence is a binding peptide or an avimer sequence that binds the proteins restricted to the bone extracellular matrix.

The following is a nonlimiting list of specific embodiments contemplated by the present invention:

It is contemplated that when a VH1, or CDRs from a VH1, is selected from the sclerostin binders, the VH2, or CDRs from a VH2, is selected from the DKK-1 binders. Conversely, when a VH1, or CDRs from a VH1, is selected from DKK-1 binders, the VH2, or CDRs from a VH2, is selected from sclerostin binders. It is further contemplated that when a VL1, or CDRs from a VL1, is selected from the sclerostin binders, the VL2, or CDRs from a VL2, is selected from the DKK-1 binders. Conversely, when a VL1, or CDRs from a VL1, is selected from DKK-1 binders, the VL2, or CDRs from a VL2, is selected from sclerostin binders.

1. A binding molecule comprising a polypeptide chain, wherein said polypeptide chain comprises VH1-(X1)n-VH2-C-(X2)n, wherein: VH1 is a first heavy chain variable domain obtained from a first parent antibody or antigen binding portion thereof; VH2 is a second heavy chain variable domain obtained from a second parent antibody or antigen binding portion thereof; C is a heavy chain constant domain; (X1)n is a linker, wherein said (X1)n is either present or absent; and (X2)n is an Fc region, wherein said (X2)n is either present or absent, wherein the binding molecule specifically binds both sclerostin and DKK-1.

2. The binding molecule of embodiment 1, wherein VH1 and VH2 comprise an amino acid sequence selected from the group consisting of sclerostin binders SEQ ID NOs: 95, 96, 104, 112, 120, 128, 136, 144, 152, 160, 168, 176, 184, 192, 200, 208, and 216, or DKK-1 binders SEQ ID NOs: 224, 232, 240, 248, 256, 264, 272, 280, 288, 296, 304, 312, 320, 328, 336, 344, 352, 360, 368, 376, 384, 392, 400, and 408.

3. A binding molecule comprising a polypeptide chain, wherein said polypeptide chain comprises VL1-(X1)n-VL2-C-(X2)n, wherein: VL1 is a first light chain variable domain obtained from a first parent antibody or antigen binding portion thereof; VL2 is a second light chain variable domain obtained from a second parent antibody or antigen binding portion thereof; C is a light chain constant domain; (X1)n is a linker, wherein said (X1)n is either present or absent; and (X2)n is an Fc region, wherein said (X2)n is either present or absent, wherein the binding molecule specifically binds both sclerostin and DKK-1.

4. The binding molecule of embodiment 3, wherein VL1 and VL2 comprise an amino acid sequence selected from the group consisting of sclerostin binders SEQ ID NOs: 94, 103, 111, 119, 127, 135, 143, 151, 159, 167, 175, 183, 191, 199, 207, and 215, or DKK-1 binders SEQ ID NOs: 223, 231, 239, 247, 255, 263, 271, 279, 287, 295, 303, 311, 319, 327, 335, 343, 351, 359, 367, 375, 383, 391, 399, and 407.

5. The binding molecule of embodiment 1 or 3, wherein (X2)n is absent.

6. A binding molecule comprising first and second polypeptide chains, wherein said first polypeptide chain comprises a VH1-(X1)n-VH2-C-(X2)n, wherein VH1 is a first heavy chain variable domain obtained from a first parent antibody or antigen binding portion thereof; VH2 is a second heavy chain variable domain obtained from a second parent antibody or antigen binding portion thereof; C is a heavy chain constant domain; (X1)n is a linker, wherein said (X1)n is either present or absent; and (X2)n is an Fc region, wherein said (X2)n is either present or absent; and wherein said second polypeptide chain comprises a VL1-(X1)n-VL2-C-(X2)n, wherein VL1 is a first light chain variable domain obtained from a first parent antibody or antigen binding portion thereof; VL2 is a second light chain variable domain obtained from a second parent antibody or antigen binding portion thereof; C is a light chain constant domain; (X1)n is a linker, wherein said (X1)n is either present or absent; and (X2)n does not comprise an Fc region, wherein said (X2)n is either present or absent, wherein the binding molecule specifically binds sclerostin and DKK-1.

7. The binding molecule of embodiment 6, wherein the VH1 and VH2 heavy chain variable domains comprise an amino acid sequence selected from the group consisting of sclerostin binders SEQ ID NOs: 95, 96, 104, 112, 120, 128, 136, 144, 152, 160, 168, 176, 184, 192, 200, 208, and 216, or DKK-1 binders SEQ ID NOs: 224, 232, 240, 248, 256, 264, 272, 280, 288, 296, 304, 312, 320, 328, 336, 344, 352, 360, 368, 376, 384, 392, 400, and 408, and wherein the VL1 and VL2 light chain variable domains comprise an amino acid sequence selected from the group consisting of sclerostin binders SEQ ID NOs: 94, 103, 111, 119, 127, 135, 143, 151, 159, 167, 175, 183, 191, 199, 207, and 215, or DKK-1 binders SEQ ID NOs: 223, 231, 239, 247, 255, 263, 271, 279, 287, 295, 303, 311, 319, 327, 335, 343, 351, 359, 367, 375, 383, 391, 399, and 407.

8. The binding molecule of embodiment 1, 3, or 6, wherein (X1)n is an amino acid sequence selected from the group consisting of SEQ ID NOs: 415-482.

9. The binding molecule of embodiments 6, wherein the binding molecule comprises two first polypeptide chains and two second polypeptide chains.

10. The binding molecule of embodiment 1, 3, or 6, wherein the Fc region is selected from the group consisting of native sequence Fc region and a variant sequence Fc region.

11. The binding molecule of embodiment 10, wherein the Fc region is selected from the group consisting of an Fc region from an IgG1, IgG2, IgG3, IgG4, IgA, IgM, IgE, and IgD.

12. The binding molecule of embodiment 1, 3, or 6, wherein said VH1 of the first polypeptide chain and said VL1 of the second polypeptide chain are obtained from the same parent antibody or antigen binding portion thereof.

13. The binding molecule of embodiment 1, 3, or 6, wherein said VH1 of the first polypeptide chain and said VL1 of the second polypeptide chain are obtained from different parent antibody or antigen binding portion thereof.

14. The binding molecule of embodiment 1, 3, or 6, wherein said VH2 of the first polypeptide chain and said VL2 of the second polypeptide chain are obtained from the same parent antibody or antigen binding portion thereof.

15. The binding molecule of embodiment 1, 3, or 6, wherein said VH2 of the first polypeptide chain and said VL2 of the second polypeptide chain are obtained from different parent antibody or antigen binding portion thereof.

16. The binding molecule of embodiment 1, 3, or 6 with the proviso that said linker (X1)n is not CH1.

17. The binding molecule of embodiment 1, 3, or 6, wherein said first parent antibody, or antigen binding portion thereof, binds said first antigen with a potency different from the potency with which said second parent antibody, or antigen binding portion thereof, binds said second antigen.

18. The binding molecule of embodiment 1, 3, or 6, wherein said first parent antibody, or antigen binding portion thereof, binds said first antigen with an affinity different from the affinity with which said second parent antibody, or antigen binding portion thereof, binds said second antigen.

19. The binding molecule of embodiment 1, 3, or 6, wherein said first parent antibody, or antigen binding portion thereof, and said second parent antibody, or antigen binding portion thereof, are selected from the group consisting of a human antibody, a CDR grafted antibody, and a humanized antibody.

20. The binding molecule of embodiment 1, 3, or 6, wherein said first parent antibody, or antigen binding portion thereof, and said second parent antibody, or antigen binding portion thereof, are selected from the group consisting of a Fab fragment; a F(ab')₂ fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment; an isolated complementarity determining region (CDR); a single chain antibody; and a diabody.

21. The binding molecule of embodiment 1, 3, or 6, wherein said binding molecule possesses at least one desired property exhibited by said first parent antibody, or antigen binding portion thereof, or said second parent antibody, or antigen binding portion thereof.

22. The binding molecule of embodiment 21, wherein said desired property is selected from one or more antibody parameters.

23. The binding molecule of embodiment 21, wherein said antibody parameters are selected from the group consisting of antigen specificity, affinity to antigen, potency, biological function, epitope recognition, stability, solubility, production efficiency, immunogenicity, pharmacokinetics, bioavailability, tissue cross reactivity, and orthologous antigen binding.

24. A binding molecule that binds both sclerostin and DKK-1 comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the VH1 and VH2 heavy chain variable domains comprise an amino acid sequence selected from the group consisting of sclerostin binders SEQ ID NOs: 95, 96, 104, 112, 120, 128, 136, 144, 152, 160, 168, 176, 184, 192, 200, 208, and 216, or DKK-1 binders SEQ ID NOs: 224, 232, 240, 248, 256, 264, 272, 280, 288, 296, 304, 312, 320, 328, 336, 344, 352, 360, 368, 376, 384, 392, 400, and 408, and wherein the VL1 and VL2 light chain variable domains comprise an amino acid sequence selected from the group consisting of sclerostin binders SEQ ID NOs: 94, 103, 111, 119, 127, 135, 143, 151, 159, 167, 175, 183, 191, 199, 207, and 215, or DKK-1 binders SEQ ID NOs: 223, 231, 239, 247, 255, 263, 271, 279, 287, 295, 303, 311, 319, 327, 335, 343, 351, 359, 367, 375, 383, 391, 399, and 407.

25. The binding molecule of embodiment 24 with the proviso that said linker (X1)n is not CH1.

26. A binding molecule that binds both sclerostin and DKK-1 comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the binding molecule comprises VH1-(X1)n-VH2-C-(X2)n and VL1-(X1)n-VL2-C-(X2)n pairings selected from the group consisting of:

SEQ ID NOs: 18 and 20; 22 and 24; 26 and 28; 30 and 32; 34 and 36; 38 and 40; 42 and 44; 46 and 48; 50 and 52; 54 and 76; 56 and 72; 58 and 60; 62 and 64; 66 and 68; 70 and 72; 74 and 76; 78 and 80; 82 and 84; 86 and 88; 90 and 92; 486 and 488; 490 and 492; and 494 and 496.

27. The binding molecule of embodiment 26, wherein the VH1-(X1)n-VH2-C-(X2)n and VL1-(X1)n-VL2-C-(X2)n pairing is SEQ ID NOs: 18 and 20.

28. The binding molecule of embodiment 26, wherein the VH1-(X1)n-VH2-C-(X2)n and VL1-(X1)n-VL2-C-(X2)n pairing is SEQ ID NOs: 22 and 24.

29. The binding molecule of embodiment 26, wherein the VH1-(X1)n-VH2-C-(X2)n and VL1-(X1)n-VL2-C-(X2)n pairing is SEQ ID NOs: 26 and 28.

30. The binding molecule of embodiment 26, wherein the VH1-(X1)n-VH2-C-(X2)n and VL1-(X1)n-VL2-C-(X2)n pairing is SEQ ID NOs: 30 and 32.

31. The binding molecule of embodiment 26, wherein the VH1-(X1)n-VH2-C-(X2)n and VL1-(X1)n-VL2-C-(X2)n pairing is SEQ ID NOs: 34 and 36.

32. The binding molecule of embodiment 26, wherein the VH1-(X1)n-VH2-C-(X2)n and VL1-(X1)n-VL2-C-(X2)n pairing is SEQ ID NOs: 38 and 40.

33. The binding molecule of embodiment 26, wherein the VH1-(X1)n-VH2-C-(X2)n and VL1-(X1)n-VL2-C-(X2)n pairing is SEQ ID NOs: 42 and 44.

34. The binding molecule of embodiment 26, wherein the VH1-(X1)n-VH2-C-(X2)n and VL1-(X1)n-VL2-C-(X2)n pairing is SEQ ID NOs: 46 and 48.

35. The binding molecule of embodiment 26, wherein the VH1-(X1)n-VH2-C-(X2)n and VL1-(X1)n-VL2-C-(X2)n pairing is SEQ ID NOs: 50 and 52.

36. The binding molecule of embodiment 26, wherein the VH1-(X1)n-VH2-C-(X2)n and VL1-(X1)n-VL2-C-(X2)n pairing is SEQ ID NOs: 54 and 76.

37. The binding molecule of embodiment 26, wherein the VH1-(X1)n-VH2-C-(X2)n and VL1-(X1)n-VL2-C-(X2)n pairing is SEQ ID NOs: 56 and 72.

38. The binding molecule of embodiment 26, wherein the VH1-(X1)n-VH2-C-(X2)n and VL1-(X1)n-VL2-C-(X2)n pairing is SEQ ID NOs: 58 and 60.

39. The binding molecule of embodiment 26, wherein the VH1-(X1)n-VH2-C-(X2)n and VL1-(X1)n-VL2-C-(X2)n pairing is SEQ ID NOs: 62 and 64.

40. The binding molecule of embodiment 26, wherein the VH1-(X1)n-VH2-C-(X2)n and VL1-(X1)n-VL2-C-(X2)n pairing is SEQ ID NOs: 66 and 68.

41. The binding molecule of embodiment 26, wherein the VH1-(X1)n-VH2-C-(X2)n and VL1-(X1)n-VL2-C-(X2)n pairing is SEQ ID NOs: 70 and 72.

42. The binding molecule of embodiment 26, wherein the VH1-(X1)n-VH2-C-(X2)n and VL1-(X1)n-VL2-C-(X2)n pairing is SEQ ID NOs: 74 and 76.

43. The binding molecule of embodiment 26, wherein the VH1-(X1)n-VH2-C-(X2)n and VL1-(X1)n-VL2-C-(X2)n pairing is SEQ ID NOs: 78 and 80.

44. The binding molecule of embodiment 26, wherein the VH1-(X1)n-VH2-C-(X2)n and VL1-(X1)n-VL2-C-(X2)n pairing is SEQ ID NOs: 82 and 84.

45. The binding molecule of embodiment 26, wherein the VH1-(X1)n-VH2-C-(X2)n and VL1-(X1)n-VL2-C-(X2)n pairing is SEQ ID NOs: 86 and 88.

46. The binding molecule of embodiment 26, wherein the VH1-(X1)n-VH2-C-(X2)n and VL1-(X1)n-VL2-C-(X2)n pairing is SEQ ID NOs: 90 and 92.

47. The binding molecule of embodiments 1, 3 and 6, wherein the sclerostin binder VH comprises 3 CDRs selected from the group consisting of SEQ ID NOs, where each group member has 3 CDRs (CDR1, CDR2, CDR3):

100, 101, 102; 108, 109, 110; 116, 117, 118; 124, 125, 126; 132, 133, 134; 140, 141, 142; 148, 149, 150; 156, 157, 158; 164, 165, 166; 172, 173, 174; 180, 181, 182; 188, 189, 190; 196, 197, 198; 204, 205, 206; 212, 213, 214; and 220, 221, 222, and wherein the DKK1 binder VH comprises 3 CDRs selected from the group consisting of SEQ ID NOs where each group member has 3 CDRs (CDR1, CDR2, CDR3):

228, 229, 230; 236, 237, 238; 244, 245, 246; 252, 253, 254; 260, 261, 262; 268, 269, 270; 276, 277, 278; 284, 285, 286; 292, 293, 294; 300, 301, 302; 308, 309, 310; 316, 317, 318; 324, 325, 326; 332, 333, 334; 340, 341, 342; 348, 349, 350; 356, 357, 358; 364, 365, 366; 372, 373, 374; 380, 381, 382; 388, 389, 390; 396, 397, 398; 404, 405, 406; and 412, 413, 414.

48. The binding molecule of embodiments 1, 3 and 6, wherein the sclerostin binder VL comprises 3 CDRs selected from the group consisting of SEQ ID NOs where each group member has 3 CDRs (CDR1, CDR2, CDR3):

97, 98, 99; 105, 106, 107; 113, 114, 115; 121, 122, 123; 129, 130, 131; 137, 138, 139; 145, 146, 147; 153, 154, 155; 161, 162, 163; 169, 170, 171; 177, 178, 179; 185, 186, 187; 193, 194, 195; 201, 202, 203; 209, 210, 211; and 217, 218, 219, and wherein the DKK1 binder VL comprises 3 CDRs selected from the group consisting of SEQ ID NOs where each group member has 3 CDRs (CDR1, CDR2, CDR3):

a) 225, 226, 227; 233, 234, 235; 241, 242, 243; 249, 250, 251; 257, 258, 259; 265, 266, 267; 273, 274, 275; 281, 282, 283; 289, 290, 291; 297, 298, 299; 305, 306, 307; 313, 314, 315; 321, 322, 323; 329, 330, 331; 337, 338, 339; 345, 346, 347; 353, 354, 355; 361, 362, 363; 369, 370, 371; 377, 378, 379; 385, 386, 387; 393, 394, 395; 401, 402, 403; and 409, 410, 411.

49. The binding molecule of embodiments 1, 3, and 6, wherein the sclerostin binder VH comprises 3 CDRs selected from the group consisting of SEQ ID NOs where each group member has 3 CDRs (CDR1, CDR2, CDR3):

100, 101, 102; 108, 109, 110; 116, 117, 118; 124, 125, 126; 132, 133, 134; 140, 141, 142; 148, 149, 150; 156, 157, 158; 164, 165, 166; 172, 173, 174; 180, 181, 182; 188, 189, 190; 196, 197, 198; 204, 205, 206; 212, 213, 214; and 220, 221, 222, and wherein the DKK1 binder VH comprises 3 CDRs selected from the group consisting of SEQ ID NOs where each group member has 3 CDRs (CDR1, CDR2, CDR3):

228, 229, 230; 236, 237, 238; 244, 245, 246; 252, 253, 254; 260, 261, 262; 268, 269, 270; 276, 277, 278; 284, 285, 286; 292, 293, 294; 300, 301, 302; 308, 309, 310; 316, 317, 318; 324, 325, 326; 332, 333, 334; 340, 341, 342; 348, 349, 350; 356, 357, 358; 364, 365, 366; 372, 373, 374; 380, 381, 382; 388, 389, 390; 396, 397, 398; 404, 405, 406; and 412, 413, 414.

and wherein the sclerostin binder VL comprises 3 CDRs selected from the group consisting of SEQ ID NOs where each group member has 3 CDRs (CDR1, CDR2, CDR3):

97, 98, 99; 105, 106, 107; 113, 114, 115; 121, 122, 123; 129, 130, 131; 137, 138, 139; 145, 146, 147; 153, 154, 155; 161, 162, 163; 169, 170, 171; 177, 178, 179; 185, 186, 187; 193, 194, 195; 201, 202, 203; 209, 210, 211; and 217, 218, 219, and wherein the DKK1 binder VL comprises 3 CDRs selected from the group consisting of SEQ ID NOs where each group member has 3 CDRs (CDR1, CDR2, CDR3):

225, 226, 227; 233, 234, 235; 241, 242, 243; 249, 250, 251; 257, 258, 259; 265, 266, 267; 273, 274, 275; 281, 282, 283; 289, 290, 291; 297, 298, 299; 305, 306, 307; 313, 314, 315; 321, 322, 323; 329, 330, 331; 337, 338, 339; 345, 346, 347; 353, 354, 355; 361, 362, 363; 369, 370, 371; 377, 378, 379; 385, 386, 387; 393, 394, 395; 401, 402, 403; and 409, 410, 411.

50. A binding molecule comprising four polypeptide chains, wherein first and third polypeptide chains comprise VH1-(X1)n-VH2-C-(X2)n, wherein: VH1 is a first heavy chain variable domain; VH2 is a second heavy chain variable domain; C is a heavy chain constant domain; (X1)n is a linker, wherein said (X1)n is either present or absent; and (X2)n is an Fc region, wherein said (X2)n is either present or absent; and wherein second and fourth polypeptide chains comprise VL1-(X1)n-VL2-C-(X2)n, wherein VL1 is a first light chain variable domain; VL2 is a second light chain variable domain; C is a light chain constant domain; (X1)n is a linker, wherein said (X1)n is either present or absent; and (X2)n does not comprise an Fc region, wherein said (X2)n is either present or absent, wherein the binding molecule comprises 3 VH1 CDRs, 3 VH2 CDRs, 3 VL1 CDRs and 3 VL2 CDRs, wherein the paired VH1 and VL1 CDRs, and paired VH2 and VL2 CDRs, are selected from the group consisting of SEQ ID NOs:

97-102; 105-110; 113-118; 121-126; 129-134; 137-142; 145-150; 153-158; 161-166; 169-174; 177-182; 185-190; 193-198; 201-206; 209-214; 217-222, or SEQ ID NOs:

a) 225-230; 233-238; 241-246; 249-254; 257-262; 265-270; 273-278; 281-286; 289-294; 297-302; 305-310; 313-318; 321-326; 329-334; 337-342; 345-350; 353-358; 361-366; 369-374; 377-382; 385-390; 393-398; 401-406; 409-414.

51. The binding molecule of embodiment 50, wherein said VL1 CDRs are SEQ ID NOs: 161-163, said VH1 CDRs are SEQ ID NOs: 164-166, said VL2 CDRs are SEQ ID NOs: 385-387, and said VH2 CDRs are SEQ ID NOs: 388-390.

52. The binding molecule of embodiment 50, wherein said VL1 CDRs are SEQ ID NOs: 385-387, said VH1 CDRs are SEQ ID NOs: 388-390, said VL2 CDRs are SEQ ID NOs: 161-163, and said VH2 CDRs are SEQ ID NOs: 164-166.

53. The binding molecule of embodiment 50, wherein said VL1 CDRs are SEQ ID NOs: 153-155, said VH1 CDRs are SEQ ID NOs: 156-158, said VL2 CDRs are SEQ ID NOs: 385-387, and said VH2 CDRs are SEQ ID NOs: 388-390.

54. The binding molecule of embodiment 50, wherein said VL1 CDRs are SEQ ID NOs: 385-387, said VH1 CDRs are SEQ ID NOs: 388-390, said VL2 CDRs are SEQ ID NOs: 153-155, and said VH2 CDRs are SEQ ID NOs: 156-158.

55. The binding molecule of embodiment 50, wherein said VL1 CDRs are SEQ ID NOs: 409-411, said VH1 CDRs are SEQ ID NOs: 412-414, said VL2 CDRs are SEQ ID NOs: 121-123, and said VH2 CDRs are SEQ ID NOs: 124-126.

56. The binding molecule of embodiment 50, wherein said VL1 CDRs are SEQ ID NOs: 409-411, said VH1 CDRs are SEQ ID NOs: 412-414, said VL2 CDRs are SEQ ID NOs: 177-179, and said VH2 CDRs are SEQ ID NOs: 180-182.

57. The binding molecule of embodiment 50, wherein said VL1 CDRs are SEQ ID NOs: 409-411, said VH1 CDRs are SEQ ID NOs: 412-414, said VL2 CDRs are SEQ ID NOs: 97-99, and said VH2 CDRs are SEQ ID NOs: 100-102.

58. The binding molecule of embodiment 50, wherein said VL1 CDRs are SEQ ID NOs: 385-387, said VH1 CDRs are SEQ ID NOs: 388-390, said VL2 CDRs are SEQ ID NOs: 105-107, and said VH2 CDRs are SEQ ID NOs: 108-110.

59. The binding molecule of embodiment 50, wherein said VL1 CDRs are SEQ ID NOs: 97-99, said VH1 CDRs are SEQ ID NOs: 100-102, said VL2 CDRs are SEQ ID NOs: 409-411, and said VH2 CDRs are SEQ ID NOs: 412-414.

60. The binding molecule of embodiment 50, wherein said VL1 CDRs are SEQ ID NOs: 385-387, said VH1 CDRs are SEQ ID NOs: 388-390, said VL2 CDRs are SEQ ID NOs: 105-107, and said VH2 CDRs are SEQ ID NOs: 108-110.

61. The binding molecule of embodiment 50, wherein said VL1 CDRs are SEQ ID NOs: 409-411, said VH1 CDRs are SEQ ID NOs: 412-414, said VL2 CDRs are SEQ ID NOs: 105-107, and said VH2 CDRs are SEQ ID NOs: 108-110.

62. The binding molecule of embodiment 50, wherein said VL1 CDRs are SEQ ID NOs: 105-107, said VH1 CDRs are SEQ ID NOs: 108-110, said VL2 CDRs are SEQ ID NOs: 385-387, and said VH2 CDRs are SEQ ID NOs: 388-390.

63. The binding molecule of embodiment 50, wherein said VL1 CDRs are SEQ ID NOs: 105-107, said VH1 CDRs are SEQ ID NOs: 108-110, said VL2 CDRs are SEQ ID NOs: 409-411, and said VH2 CDRs are SEQ ID NOs: 412-414.

64. The binding molecule of embodiment 50, wherein said VL1 CDRs are SEQ ID NOs: 369-371, said VH1 CDRs are SEQ ID NOs: 372-374, said VL2 CDRs are SEQ ID NOs: 105-107, and said VH2 CDRs are SEQ ID NOs: 108-110.

65. The binding molecule of embodiments 50-64, wherein said (X1)n is selected from the group consisting of SEQ ID NOs: 415-484.

66. The binding molecule of embodiments 50-64, wherein said (X1)n is selected from the group consisting of SEQ ID NOs: 440, 441, 437, 438, 431, 432, 483, and 484.

67. The binding molecule of embodiments 50-64, wherein said (X1)n of the VH1-(X1)n-VH2-C-(X2)n chain is SEQ ID NO: 440.

68. The binding molecule of embodiments 50-64, wherein said (X1)n of the VH1-(X1)n-VH2-C-(X2)n chain is SEQ ID NO: 441.

69. The binding molecule of embodiments 50-64, wherein said (X1)n of the VH1-(X1)n-VH2-C-(X2)n chain is SEQ ID NO: 437.

70. The binding molecule of embodiments 50-64, wherein said (X1)n of the VH1-(X1)n-VH2-C-(X2)n chain is SEQ ID NO: 438.

71. The binding molecule of embodiments 50-64, wherein said (X1)n of the VL1-(X1)n-VL2-C-(X2)n is SEQ ID NO: 440.

72. The binding molecule of embodiments 50-64, wherein said (X1)n of the VL1-(X1)n-VL2-C-(X2)n is SEQ ID NO: 441.

73. The binding molecule of embodiments 50-64, wherein said (X1)n of the VL1-(X1)n-VL2-C-(X2)n is SEQ ID NO: 483.

74. The binding molecule of embodiments 50-64, wherein said (X1)n of the VL1-(X1)n-VL2-C-(X2)n is SEQ ID NO: 484.

75. The binding molecule of embodiments 50-64, wherein said (X1)n of the VL1-(X1)n-VL2-C-(X2)n is SEQ ID NO: 431.

76. The binding molecule of embodiments 50-64, wherein said (X1)n of the VL1-(X1)n-VL2-C-(X2)n is SEQ ID NO: 432.

77. The binding molecule of embodiments 1, 3, 6, 24, 26 and 50, wherein said (X1)n is the different on the VH1-(X1)n-VH2-C-(X2)n and VL1-(X1)n-VL2-C-(X2)n chains.

78. A method for generating a binding molecule that binds sclerostin and DKK-1 comprising the steps of: (a) obtaining a first parent antibody, or antigen binding portion thereof, that can bind sclerostin or DKK-1; (b) obtaining a second parent antibody, or antigen binding portion thereof, that can bind sclerostin or DKK-1; (c) constructing first and third polypeptide chains comprising VH1-(X1)n-VH2-C-(X2)n, wherein: VH1 is a first heavy chain variable domain obtained from said first parent antibody or antigen binding portion thereof; VH2 is a second heavy chain variable domain obtained from said second parent antibody or antigen binding portion thereof; C is a heavy chain constant domain; (X1)n is a linker with the proviso that it is not CH1, wherein said (X1)n is either present or absent; and (X2)n is an Fc region, wherein said (X2)n is either present or absent; (d) constructing second and fourth polypeptide chains comprising VL1-(X1)n-VL2-C-(X2)n, wherein: VL1 is a first light chain variable domain obtained from said first parent antibody or antigen binding portion thereof; VL2 is a second light chain variable domain obtained from said second parent antibody or antigen binding thereof; C is a light chain constant domain; (X1)n is a linker, wherein said (X1)n is either present or absent; and (X2)n does not comprise an Fc region, wherein said (X2)n is either present or absent; and (e) expressing said first, second, third and fourth polypeptide chains such that a binding molecule that binds sclerostin and DKK-1 is generated.

79. The method of embodiment 78, wherein the VH1 and VH2 heavy chain variable domains comprise an amino acid sequence selected from the group consisting of sclerostin binders SEQ ID NOs: 95, 96, 104, 112, 120, 128, 136, 144, 152, 160, 168, 176, 184, 192, 200, 208, and 216, or DKK-1 binders SEQ ID NOs: 224, 232, 240, 248, 256, 264, 272, 280, 288, 296, 304, 312, 320, 328, 336, 344, 352, 360, 368, 376, 384, 392, 400, and 408, and wherein the VL1 and VL2 light chain variable domains comprise an amino acid sequence selected from the group consisting of sclerostin binders SEQ ID NOs: 94, 103, 111, 119, 127, 135, 143, 151, 159, 167, 175, 183, 191, 199, 207, and 215, or DKK-1 binders SEQ ID NOs: 223, 231, 239, 247, 255, 263, 271, 279, 287, 295, 303, 311, 319, 327, 335, 343, 351, 359, 367, 375, 383, 391, 399, and 407.

80. The method of embodiment 78, wherein each of said first parent antibody, or antigen binding portion thereof, and each of said second parent antibody, or antigen binding portion thereof, are separately selected from the group consisting of a human antibody, a CDR grafted antibody, and a humanized antibody.

81. The method of embodiment 78, wherein each of said first parent antibody, or antigen binding portion thereof, and each of said second parent antibody, or antigen binding portion thereof, are separately selected from the group consisting of a Fab fragment, a F(ab')$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody, a dAb fragment, an isolated complementarity determining region (CDR), a single chain antibody, and diabodies.

82. The method of embodiment 78, wherein said first parent antibody, or antigen binding portion thereof, possesses at least one desired property exhibited by the binding molecule.

83. The method of embodiment 78, wherein said second parent antibody, or antigen binding portion thereof, possesses at least one desired property exhibited by the binding molecule.

84. The method of embodiment 78, wherein the Fc region is selected from the group consisting of a native sequence Fc region and a variant sequence Fc region.

85. The method of embodiment 78, wherein the Fc region is selected from the group consisting of an Fc region from an IgG1, IgG2, IgG3, IgG4, IgA, IgM, IgE, and IgD.

86. The method of embodiment 78, wherein said desired property is selected from one or more antibody parameters.

87. The method of embodiment 78, wherein said desired property is selected from one or more antibody parameters.

88. The method of embodiment 78, wherein said antibody parameters are selected from the group consisting of antigen specificity, affinity to antigen, potency, biological function, epitope recognition, stability, solubility, production efficiency, immunogenicity, pharmacokinetics, bioavailability, tissue cross reactivity, and orthologous antigen binding.

89. The method of embodiment 78, wherein said antibody parameters are selected from the group consisting of antigen specificity, affinity to antigen, potency, biological function, epitope recognition, stability, solubility, production efficiency, immunogenicity, pharmacokinetics, bioavailability, tissue cross reactivity, and orthologous antigen binding.

90. The method of embodiment 78, wherein said first parent antibody, or antigen binding portion thereof, binds said first antigen with a different affinity than the affinity with which said second parent antibody, or antigen binding portion thereof, binds said second antigen.

91. The method of embodiment 78, wherein said first parent antibody, or antigen binding portion thereof, binds said first antigen with a different potency than the potency with which said second parent antibody, or antigen binding portion thereof, binds said second antigen.

92. The method of embodiment 78, with the proviso that said linker is not CH1.

93. A pharmaceutical composition comprising the binding molecule of any of embodiments 1-77.

94. The binding molecule of any of embodiments 1-77 in combination with one or more of a pharmaceutically acceptable excipient, diluent or carrier.

95. A method of treating a bone disorder comprising administering to a patient in need thereof the binding molecule of any of embodiments 1-77.

96. A method of accelerating bone fracture repair comprising administering to a patient in need thereof the binding molecule of any of embodiments 1-77.

97. A method of increasing bone density comprising administering to a patient in need thereof the binding molecule of any of embodiments 1-77.

98. A method of increasing bone strength comprising administering to a patient in need thereof the binding molecule of any of embodiments 1-77.

99. The method of embodiments 96-98, wherein BMC is increased by at least 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 percent as compared to an untreated patient.

100. The method of embodiments 96-98, wherein BMD is increased by at least 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 percent as compared to an untreated patient.

101. A polynucleotide encoding the binding molecule of any of embodiments 1-77.

102. The binding molecule of embodiment 26, wherein the VH1-(X1)n-VH2-C-(X2)n and VL1-(X1)n-VL2-C-(X2)n pairing is SEQ ID NOs: 486 and 488.

103. The binding molecule of embodiment 26, wherein the VH1-(X1)n-VH2-C-(X2)n and VL1-(X1)n-VL2-C-(X2)n pairing is SEQ ID NOs: 490 and 492.

104. The binding molecule of embodiment 26, wherein the VH1-(X1)n-VH2-C-(X2)n and VL1-(X1)n-VL2-C-(X2)n pairing is SEQ ID NOs: 494 and 496.

105. The binding molecule of embodiment 50, wherein said VL1 CDRs are SEQ ID NOs: 225-227, said VH1 CDRs are SEQ ID NOs: 228-230, said VL2 CDRs are SEQ ID NOs: 105-107, and said VH2 CDRs are SEQ ID NOs: 108-110.

As permitted in certain national jurisdictions, all references disclosed herein are hereby incorporated by reference in their entireties as if each was incorporated individually, for any purpose including enabling and describing the invention. The following examples are provided solely to illustrate certain aspects of the antibodies, fragments and compositions that are provided herein and thus should not be construed to limit the scope of the claimed invention.

TABLE 1

| SEQ ID NO: | DESCRIPTION | SEQUENCE |
|---|---|---|
| | | Target Protein Sequences |
| 1 | Human DKK-1 | ATGATGGCTCTGGGCGCAGCGGGAGCTACCCGGGTCTTTGTCGCGATG |
| | NA | GTAGCGGCGGCTCTCGGCGGCCACCCTCTGCTGGGAGTGAGCGCCAC |
| | | CTTGAACTCGGTTCTCAATTCCAACGCTATCAAGAACCTGCCCCCACC |
| | | GCTGGGCGGCGCTGCGGGGCACCCAGGCTCTGCAGTCAGCGCCGCGC |
| | | CGGGAATCCTGTACCCGGGCGGGAATAAGTACCAGACCATTGACAAC |
| | | TACCAGCCGTACCCGTGCGCAGAGGACGAGGAGTGCGGCACTGATGA |
| | | GTACTGCGCTAGTCCCACCCGCGGAGGGGACGCAGGCGTGCAAATCT |
| | | GTCTCGCCTGCAGGAAGCGCCGAAAACGCTGCATGCGTCACGCTATGT |
| | | GCTGCCCCGGGAATTACTGCAAAAATGGAATATGTGTGTCTTCTGATC |
| | | AAAATCATTTCCGAGGAGAAATTGAGGAAACCATCACTGAAAGCTTT |

TABLE 1-continued

| SEQ ID NO: | DESCRIPTION | SEQUENCE |
|---|---|---|
| | | GGTAATGATCATAGCACCTTGGATGGGTATTCCAGAAGAACCACCTTG |
| | | TCTTCAAAAATGTATCACACCAAAGGACAAGAAGGTTCTGTTTGTCTC |
| | | AGGTCATCAGACTGTGCCTCAGGATTGTGTTGTGATAGACACTTCTGG |
| | | TCCAAGATCTGTAAACCTGTCCTGAAAGAAGGTCAAGTGTGTACCAAG |
| | | CATAGGAGAAAAGGCTCTCATGGACTAGAAATATTCCAGCGTTGTTAC |
| | | TGTGGAGAAGGTCTGTCTTGCCGGATACAGAAAGATCACCATCAAGC |
| | | CAGTAATTCTTCTAGGCTTCACACTTGTCAGAGACAC |
| 2 | Human DKK-1 AA | MMALGAAGATRVFVAMVAAALGGHPLLGVSATLNSVLNSNAIKNLPPP |
| | | LGGAAGHPGSAVSAAPGILYPGGNKYQTIDNYQPYPCAEDEECGTDEYC |
| | | ASPTRGGDAGVQICLACRKRRKRCMRHAMCCPGNYCKNGICVSSDQNH |
| | | FRGEIEETITESFGNDHSTLDGYSRRTTLSSKMYHTKGQEGSVCLRSSDCA |
| | | SGLCCDRHFWSKICKPVLKEGQVCTKHRRKGSHGLEIFQRCYCGEGLSCR |
| | | IQKDHHQASNSSRLHTCQRH |
| 3 | Mouse DKK-1 NA | ATGATGGTTGTGTGTGCAGCGGCAGCTGTCCGGTTCTTGGCCGTGTTT |
| | | ACAATGATGGCTCTCTGCAGCCTCCCTCTGCTAGGAGCCAGTGCCACC |
| | | TTGAACTCAGTTCTCATCAATTCCAACGCGATCAAGAACCTGCCCCCA |
| | | CCGCTGGGTGGTGCTGGGGGGCAGCCGGGCTCTGCTGTCAGTGTGGCG |
| | | CCGGGAGTTCTCTATGAGGGCGGGAACAAGTACCAGACTCTTGACAA |
| | | CTACCAGCCCTACCCTTGCGCTGAAGATGAGGAGTGCGGCTCTGACGA |
| | | GTACTGCTCCAGCCCCAGCCGCGGGGCAGCCGGCGTCGGAGGTGTAC |
| | | AGATCTGTCTGGCTTGCCGAAAGCGCAGGAAGCGCTGCATGAGGCAC |
| | | GCTATGTGCTGCCCCGGGAACTACTGCAAAAATGGAATATGCATGCCC |
| | | TCTGACCACAGCCATTTTCCTCGAGGGGAGATTGAGGAAAGCATCATT |
| | | GAAAACCTTGGTAATGACCACAACGCCGCCGCGGGGGATGGATATCC |
| | | CAGAAGAACCACACTGACTTCAAAAATATATCACACCAAAGGACAAG |
| | | AAGGCTCCGTCTGCCTCCGATCATCAGACTGTGCCGCAGGGCTGTGTT |
| | | GTGCAAGACACTTCTGGTCCAAGATCTGTAAACCTGTCCTTAAAGAAG |
| | | GTCAGGTGTGCACCAAGCACAAACGGAAAGGCTCCCACGGGCTGGAG |
| | | ATATTCCAGCGCTGTTACTGCGGGGAAGGCCTGGCTTGCAGGATACAG |
| | | AAAGATCACCATCAAGCCAGCAATTCTTCTAGGCTCCACACCTGCCAG |
| | | AGACAC |
| 4 | Mouse DKK-1 AA | MMVVCAAAAVRFLAVFTMMALCSLPLLGASATLNSVLINSNAIKNLPPP |
| | | LGGAGGQPGSAVSVAPGVLYEGGNKYQTLDNYQPYPCAEDEECGSDEY |
| | | CSSPSRGAAGVGGVQICLACRKRRKRCMRHAMCCPGNYCKNGICMPSD |
| | | HSHFPRGEIEESIIENLGNDHNAAAGDGYPRRTTLTSKIYHTKGQEGSVCL |
| | | RSSDCAAGLCCARHFWSKICKPVLKEGQVCTKHKRKGSHGLEIFQRCYC |
| | | GEGLACRIQKDHHQASNSSRLHTCQRH |

TABLE 1-continued

| SEQ ID NO: | DESCRIPTION | SEQUENCE |
|---|---|---|
| 5 | Rat DKK-1 NA | ATGACGGTTGTGCGTGCAGTGGCAGCTGTCCGGTTCTTGGTCGTGCTT ACAACGATGGCTCTCTGCAGCCTCCCTCCGCTCGGAGTCAGCGCCACT TTGAACTCAGTTCTCATCAATTCCAACGCGATCAAGAACCTGCCCCCA CCGCTGGGTGGTGCTGGGGGGCAGCCGGGCTCTGCTGTCAGCGTGGC GCCCGGAGTCCTCTATGAGGGCGGGAACAAGTACCAGACTCTTGACA ACTACCAGCCCTACCCTTGCGCGGAGGATGAGGAGTGCGGCACTGAC GAGTACTGCTCCAGTCCCAGCCGCGGGGCAGCCGGCGTGGGAGGTGT ACAAATCTGCCTGGCTTGCCGAAAGCGCAGGAAACGCTGCATGAGGC ACGCTATGTGCTGCCCCGGGAATTACTGCAAAAACGGAATATGCATGC CCTCTGACCACAGCCATTTACCTCGAGGGGAAATCGAGGAAGGCATC ATTGAAAACCTTGGCAATGACCACGGTGCCGGGGATGGATATCCCAG AAGAACCACACTGACTTCAAAAATATATCACACCAAAGGGCAAGAAG GCTCTGTCTGCCTCCGATCATCAGACTGCGCCACAGGGCTGTGTTGTG CAAGACATTTCTGGTCCAAGATCTGTAAACCTGTCCTTAAAGAAGGTC AGGTATGCACCAAGCACAGAAGGAAAGGCTCCCACGGGCTGGAGATA TTCCAGCGCTGTTACTGTGGGGAAGGTCTGGCTTGCAGGATACAGAAA GATCACCATCAAACCAGCAATTCTTCCAGGCTCCACACCTGCCAGAGA CAC |
| 6 | Rat DKK-1 AA | MTVVRAVAAVRFLVVLTTMALCSLPPLGVSATLNSVLINSNAIKNLPPPL GGAGGQPGSAVSVAPGVLYEGGNKYQTLDNYQPYPCAEDEECGTDEYC SSPSRGAAGVGGVQICLACRKRRKRCMRHAMCCPGNYCKNGICMPSDH SHLPRGEIEEGIIENLGNDHGAGDGYPRRTTLTSKIYHTKGQEGSVCIRSS DCATGLCCARHFWSKICKPVLKEGQVCTKHRRKGSHGLEIFQRCYCGEG LACRIQKDHHQTSNSSRLHTCQRH |
| 7 | Cyno DKK-1 NA | ATGATGGCTCTGGGCGCAGCAGGAGCTGCCCGGGTCTTGGTCGCGCTG GTAGCGGCGGCTCTTGGCGGCCACCCTCTGCTGGGAGTGAGCGCCACC TTGAACTCGGTTCTCAATTCCAACGCGATCAAGAACCTGCCCCCACCG CTGGGCGGCGCTGCGGGGCACCCAGGCTCTGCAGTCAGCGCCGCGCC AGGAATTCTGTACCCGGGCGGGAATAAGTACCAGACCATTGACAACT ACCAGCCGTACCCTTGCGCAGAGGATGAGGAGTGCGGCACTGATGAG TACTGCGCTAGTCCCACCCGCGGAGGGGACGCGGGCGTGCAAATCTG TCTCGCCTGCAGGAAGCGCCGAAAACGCTGCATGCGTCACGCTATGTG CTGCCCCGGGAATTACTGCAAAAATGGAATATGTGTGTCTTCTGATCA AAATAATTTCCGAGGGGAAATTGAGGAAACCATTACTGAAAGCTTTG GTAATGATCATAGCACTTTGGATGGGTATTCCAGAAGAACAACATTGT CTTCAAAAATGTATCACAGCAAAGGACAAGAAGGTTCTGTGTGTCTCC GGTCATCAGACTGTGCCACAGGACTGTGTTGTGCTAGACACTTCTGGT CCAAGATCTGTAAACCTGTCCTCAAAGAAGGTCAAGTGTGTACCAAGC |

TABLE 1-continued

| SEQ ID NO: | DESCRIPTION | SEQUENCE |
|---|---|---|
| | | ATAGAAGAAAAGGCTCTCATGGGCTAGAAATATTCCAGCGTTGTTACT |
| | | GCGGAGAAGGTCTGTCTTGCCGGATACAGAAAGATCACCATCAAGCC |
| | | AGTAATTCTTCTAGGCTTCACACTTGTCAGAGACAC |
| 8 | Cyno DKK-1 AA | MMALGAAGAARVLVALVAAALGGHPLLGVSATLNSVLNSNAIKNLPPPL |
| | | GGAAGHPGSAVSAAPGILYPGGNKYQTIDNYQPYPCAEDEECGTDEYCA |
| | | SPTRGGDAGVQICLACRKRRKRCMRHAMCCPGNYCKNGICVSSDQNNF |
| | | RGEIEETITESFGNDHSTLDGYSRRTTLSSKMYHSKGQEGSVCLRSSDCAT |
| | | GLCCARHFWSKICKPVLKEGQVCTKHRRKGSHGLEIFQRCYCGEGLSCRI |
| | | QKDHHQASNSSRLHTCQRH |
| 9 | Human Sclerostin NA | ATGCAGCTCCCACTGGCCCTGTGTCTCGTCTGCCTGCTGGTACACACA |
| | | GCCTTCCGTGTAGTGGAGGGCCAGGGGTGGCAGGCGTTCAAGAATGA |
| | | TGCCACGGAAATCATCCCCGAGCTCGGAGAGTACCCCGAGCCTCCAC |
| | | CGGAGCTGGAGAACAACAAGACCATGAACCGGGCGGAGAACGGAGG |
| | | GCGGCCTCCCCACCACCCCTTTGAGACCAAAGACGTGTCCGAGTACAG |
| | | CTGCCGCGAGCTGCACTTCACCCGCTACGTGACCGATGGGCCGTGCCG |
| | | CAGCGCCAAGCCGGTCACCGAGCTGGTGTGCTCCGGCCAGTGCGGCC |
| | | CGGCGCGCCTGCTGCCCAACGCCATCGGCCGCGGCAAGTGGTGGCGA |
| | | CCTAGTGGGCCCGACTTCCGCTGCATCCCCGACCGCTACCGCGCGCAG |
| | | CGCGTGCAGCTGCTGTGTCCCGGTGGTGAGGCGCCGCGCGCGCGCAA |
| | | GGTGCGCCTGGTGGCCTCGTGCAAGTGCAAGCGCCTCACCCGCTTCCA |
| | | CAACCAGTCGGAGCTCAAGGACTTCGGGACCGAGGCCGCTCGGCCGC |
| | | AGAAGGGCCGGAAGCCGCGGCCCCGCGCCCGGAGCGCCAAAGCCAA |
| | | CCAGGCCGAGCTGGAGAACGCCTACTAG |
| 10 | Human Sclerostin AA (signal peptide underlined) | <u>MQLPLALCLVCLLVHTAFRVVEG</u>QGWQAFKNDATEIIPELGEYPEPPPEL |
| | | ENNKTMNRAENGGRPPHHPF |
| | | ETKDVSEYSCRELHFTRYVTDGPCRSAKPVTELVCSGQCGPARLLPNAIG |
| | | RGKWWRPSGPDFRCIPDRYR |
| | | AQRVQLLCPGGEAPRARKVRLVASCKCKRLTRFHNQSELKDFGTEAARP |
| | | QKGRKPRPRARSAKANQAELE |
| | | NAY |
| 11 | Mouse Sclerostin NA | ATGCAGCCCTCACTAGCCCCGTGCCTCATCTGCCTACTTGTGCACGCT |
| | | GCCTTCTGTGCTGTGGAGGGCCAGGGGTGGCAAGCCTTCAGGAATGAT |
| | | GCCACAGAGGTCATCCCCAGGGCTTGGAGAGTACCCCGAGCCTCCTCCT |
| | | GAGAACAACCAGACCATGAACCGGGCGGAGAATGGAGGCAGACCTC |
| | | CCCACCATCCCTATGACGCCAAAGATGTGTCCGAGTACAGCTGCCGCG |
| | | AGCTGCACTACACCCGCTTCCTGACAGACGGCCATGCCGCAGCGCCA |
| | | AGCCGGTCACCGAGTTGGTGTGCTCCGGCCAGTGCGGCCCCGCGCGG |
| | | CTGCTGCCCAACGCCATCGGCGCGTGAAGTGGTGGCGCCCGAACGG |
| | | ACCGGATTTCCGCTGCATCCCGGATCGCTACCGCGCGCAGCGGGTGCA |

TABLE 1-continued

| SEQ ID NO: | DESCRIPTION | SEQUENCE |
|---|---|---|
| | | GCTGCTGTGCCCCGGGGCGCGGCGCCGCGCTCGCGCAAGGTGCGTC |
| | | TGGTGGCCTCGTGCAAGTGCAAGCGCCTCACCCGCTTCCACAACCAGT |
| | | CGGAGCTCAAGGACTTCGGGCCGGAGACCGCGCGGCCGCAGAAGGGT |
| | | CGCAAGCCGCGGCCCGGCGCCCGGGGAGCCAAAGCCAACCAGGCGG |
| | | AGCTGGAGAACGCCTACTAG |
| 12 | Mouse Sclerostin AA (signal peptide underlined) | MQPSLAPCLICLLVHAAFCAVEGQGWQAFRNDATEVIPGLGEYPEPPPEN NQTMNRAENGGRPPHHPYDAKDVSEYSCRELHYTRFLTDGPCRSAKPVT ELVCSGQCGPARLLPNAIGRVKWWRPNGPDFRCIPDRYRAQRVQLLCPG GAAPRSRKVRLVASCKCKRLTRFHNQSELKDFGPETARPQKGRKPRPGA RGAKANQAELENAY |
| 13 | Rat Sclerostin NA | ATGCAGCTCTCACTAGCCCCTTGCCTTGCCTGCCTGCTTGTACATGCAG CCTTCGTTGCTGTGGAGAGCCAGGGGTGGCAAGCCTTCAAGAATGATG CCACAGAAATCATCCCGGGACTCAGAGAGTACCCAGAGCCTCCTCAG GAACTAGAGAACAACCAGACCATGAACCGGGCCGAGAACGGAGGCA GACCCCCCCACCATCCTTATGACACCAAAGACGTGTCCGAGTACAGCT GCCGCGAGCTGCACTACACCCGCTTCGTGACCGACGGCCCGTGCCGCA GTGCCAAGCCGGTCACCGAGTTGGTGTGCTCGGGCCAGTGCGGCCCC GCGCGGCTGCTGCCCAACGCCATCGGGCGCGTGAAGTGGTGGCGCCC GAACGGACCCGACTTCCGCTGCATCCCGGATCGCTACCGCGCGCAGC GGGTGCAGCTGCTGTGCCCCGGCGGCGCGGCGCCCGCGCTCGCGCAAG GTGCGTCTGGTGGCCTCGTGCAAGTGCAAGCGCCTCACCCGCTTCCAC AACCAGTCGGAGCTCAAGGACTTCGGACCTGAGACCGCGCGGCCGCA GAAGGGTCGCAAGCCGCGGCCCCGCGCCCGGGGAGCCAAAGCCAACC AGGCGGAGCTGGAGAACGCCTACTAG |
| 14 | Rat Sclerostin AA (signal peptide underlined) | MQLSLAPCLACLLVHAAFVAVESQGWQAFKNDATEIIPGLREYPEPPQEL ENNQTMNRAENGGRPPHHPYDTKDVSEYSCRELHYTRFVTDGPCRSAKP VTELVCSGQCGPARLLPNAIGRVKWWRPNGPDFRCIPDRYRAQRVQLLC PGGAAPRSRKVRLVASCKCKRLTRFHNQSELKDFGPETARPQKGRKPRP RARGAKANQAELENAY |
| 15 | Cyno Sclerostin NA | ATGCAGCTCCCACTAGCCCTGTGTCTTGTCTGCCTGCTGGTACACGCA GCCTTCCGTGTAGTGGAGGGCCAGGGGTGGCAGGCCTTCAAGAATGA TGCCACGGAAATCATCCCCGAGCTCGGAGAGTACCCCGAGCCTCCAC CGGAGCTGGAGAACAACAAGACCATGAACCGGGCGGAGAACGGAGG GCGGCCTCCCCACCACCCCTTTGAGACCAAAGACGTGTCCGAGTACAG CTGCCGAGAGCTGCACTTCACCCGCTACGTGACCGACGGGCAGTGCC GCAGCGCCAAGCCAGTCACCGAGTTGGTGTGCTCCGGCCAGTGCGGC CCGGCACGCCTGCTGCCCAACGCCATCGGCCGCGGCAAGTGGTGGCG CCCGAGTGGGCCCGACTTTCGCTGCATCCCCGACCGCTACCGCGCGCA |

TABLE 1-continued

| SEQ ID NO: | DESCRIPTION | SEQUENCE |
|---|---|---|
| | | GCGTGTGCAGCTGCTGTGTCCCGGTGGTGCCGCGCCGCGCGCGCAA |
| | | GGTGCGCCTGGTGGCCTCGTGCAAGTGCAAGCGCCTCACCCGCTTCCA |
| | | CAACCAGTCGGAGCTCAAGGACTTCGGTCCCGAGGCCGCTCGGCCGC |
| | | AGAAGGGCCGGAAGCCGCGGCCCCGCGCCCGGGGGGCCAAAGCCAA |
| | | TCAGGCTGAGCTGGAGAACGCCTACTAG |
| 16 | Cyno Sclerostin AA (signal peptide underlined) | MQLPLALCLVCLLVHAAFRVVEGQGWQAFKNDATEIIPELGEYPEPPPEL ENNKTMNRAENGGRPPHHPFETKDVSEYSCRELHFTRYVTDGQCRSAKP VTELVCSGQCGPARLLPNAIGRKWWRPSGPDFRCIPDRYRAQRVQLLC PGGAAPRARKVRLVASCKCKRLTRFHNQSELKDFGPEAARPQKGRKPRP RARGAKANQAELENAY |

DVD-Ig Sequences

| 17 | 19D11-6.37 G2 NA | ATGGACATGAGGGTGCCCGCTCAGCTCCTGGGGCTCCTGCTGCTGTGG CT |
| | | GAGAGGTGCGCGCTGTGAGGTGCAGCTGGTGGAGTCTGGGGGAGGCT TGG |
| | | TACAGCCTGGGGGGTCCCTGAGACTCTCCTGTGCAGCCTCTGGATTCA CC |
| | | TTCAGTAGCTACGACATGCACTGGGTCCGCCAAGCTACAGGAAAAGG TCT |
| | | GGAGTGGGTCTCAGCTATTGGTACTGCTGGTGACACATACTATGCAGG CT |
| | | CCGTGAAGGGCCGATTCACCATCTCCAGAGAAAATGCCAAGAACTCC TTG |
| | | TATCTTCAAATGAACAGCCTGAGAGTCGGGGACACGGCTGTGTATTAC TG |
| | | TGCAAGGTCCTGGGGAGAGGGGAATTACTACTTCTACTACGGTATGGA CG |
| | | TCTGGGGCCAAGGGACCACGGTCACCGTCTCTAGTGCCTCCACCAAGG GC |
| | | CCATCGGTCTTCCCCCTGGCGCCCCAGGTGCAGCTGGTGGAGTCTGGG GG |
| | | AGGCGTGGTCCAGCCTGGGAGGTCCCTGAGACTCTCCTGTGCAGCCTC TG |
| | | GATTCACCTTCAGTGGCTATGGCATGCACTGGGTCCGCCAGGCTCCAG GC |
| | | AAGGGGCTGGAGTGGGTGGCAGTTATATCATATGATGGAAATGATAA ATA |
| | | CTATGCAGACTCCGTGAAGGGCCGATTCACCATCTCCAGAGACAATGC CA |

TABLE 1-continued

| SEQ ID NO: | DESCRIPTION | SEQUENCE |
|---|---|---|
| | | AGAACACGCTGTATCTGCAAATGAACAGCCTGAGAGCTGAGGACACGGCT |
| | | GTGTATTACTGTGCGAGAGAGCTACGGGTCCTCTGGGGCCAGGGAACCCT |
| | | GGTCACCGTCTCTAGTGCCTCCACCAAGGGCCCATCGGTCTTCCCCCTGG |
| | | CGCCCTGCTCCAGGAGCACCTCCGAGAGCACAGCGGCCCTGGGCTGCCTG |
| | | GTCAAGGACTACTTCCCCGAACCGGTGACGGTGTCGTGGAACTCAGGCGC |
| | | TCTGACCAGCGGCGTGCACACCTTCCCAGCTGTCCTACAGTCCTCAGGAC |
| | | TCTACTCCCTCAGCAGCGTGGTGACCGTGCCCTCCAGCAACTTCGGCACC |
| | | CAGACCTACACCTGCAACGTAGATCACAAGCCCAGCAACACCAAGGTGGA |
| | | CAAGACAGTTGAGCGCAAATGTTGTGTCGAGTGCCCACCGTGCCCAGCAC |
| | | CACCTGTGGCAGGACCGTCAGTCTTCCTCTTCCCCCCAAAACCCAAGGAC |
| | | ACCCTCATGATCTCCCGGACCCCTGAGGTCACGTGCGTGGTGGTGGACGT |
| | | GAGCCACGAAGACCCCGAGGTCCAGTTCAACTGGTACGTGGACGGCGTGG |
| | | AGGTGCATAATGCCAAGACAAAGCCACGGGAGGAGCAGTTCAACAGCACG |
| | | TTCCGTGTGGTCAGCGTCCTCACCGTTGTGCACCAGGACTGGCTGAACGG |
| | | CAAGGAGTACAAGTGCAAGGTCTCCAACAAAGGCCTCCCAGCCCCCATCG |
| | | AGAAAACCATCTCCAAAACCAAAGGGCAGCCCCGAGAACCACAGGTGTAC |
| | | ACCCTGCCCCCATCCCGGGAGGAGATGACCAAGAACCAGGTCAGCCTGAC |
| | | CTGCCTGGTCAAAGGCTTCTACCCCAGCGACATCGCCGTGGAGTGGGAGA |
| | | GCAATGGGCAGCCGGAGAACAACTACAAGACCACACCTCCCATGCTGG |
| | | ACTCCGACGGCTCCTTCTTCCTCTACAGCAAGCTCACCGTGGACAAGA |

TABLE 1-continued

| SEQ ID NO: | DESCRIPTION | SEQUENCE |
|---|---|---|
| | | GCAGGTGGCAGCAGGGGAACGTCTTCTCATGCTCCGTGATGCATGAGG |
| | | CTCTGCACAACCACTACACGCAGAAGAGCCTCTCCCTGTCTCCGGGTAA |
| | | A |
| 18 | 19D11-6.37 G2 AA | EVQLVESGGGLVQPGGSLRLSCAASGFTFSSYDMHWVRQATGKGLEWVSA |
| | | IGTAGDTYYAGSVKGRFTISRENAKNSLYLQMNSLRVGDTAVYYCARSWG |
| | | EGNYYFYYGMDVWGQGTTVTVSSASTKGPSVFPLAPQVQLVESGGGVVQP |
| | | GRSLRLSCAASGFTFSGYGMHWVRQAPGKGLEWVAVISYDGNDKYYADSV |
| | | KGRFTISRDNAKNTLYLQMNSLRAEDTAVYYCARELRVLWGQGTLVTVSS |
| | | ASTKGPSVFPLAPCSRSTSESTAALGCLVKDYFPEPVTVSWNSGALTSGV |
| | | HTFPAVLQSSGLYSLSSVVTVPSSNFGTQTYTCNVDHKPSNTKVDKTVER |
| | | KCCVECPPCPAPPVAGPSVFLFPPKPKDTLMISRTPEVTCVVVDVSHEDP |
| | | EVQFNWYVDGVEVHNAKTKPREEQFNSTFRVVSVLTVVHQDWLNGKEYKC |
| | | KVSNKGLPAPIEKTISKTKGQPREPQVYTLPPSREEMTKNQVSLTCLVKG |
| | | FYPSDIAVEWESNGQPENNYKTTPPMLDSDGSFFLYSKLTVDKSRWQQGN |
| | | VFSCSVMHEALHNHYTQKSLSLSPGK |
| 19 | 19D11-6.37 LC NA | ATGGACATGAGGGTGCCCGCTCAGCTCCTGGGGCTCCTGCTGCTGTGGCT |
| | | GAGAGGTGCGCGCTGTTCCTATGTGCTGACTCAGCCACCCTCGGTGTCAG |
| | | TGGCCCCAGGACAGACGGCCAGGATTACCTGTGGGGGAGACAACATTGGA |
| | | AGTATAAGTGTGCATTGGTACCAGCAGAAGCCAGGCCAGGCCCCTGTGCT |
| | | GGTCGTCTATGATGATAGCGACCGGCCCTCAGGGATCCCTGAGCGATTCT |
| | | CTGGCTCCAACTCTGGGAACACGGCCACCCTGACCATCAGCTGGGTCGAA |
| | | GCCGGGGATGAGGCCGACTATTACTGTCAGGTGTGGGATAGTAGTATTGA |
| | | TCATCCTGTGTTATTCGGCGGAGGGACCAAGCTGACCGTCCTAGGTCAGC |

TABLE 1-continued

| SEQ ID NO: | DESCRIPTION | SEQUENCE |
|---|---|---|
| | | CCAAGGCTGCCCCCTCGGTCACTCTGTTCGATATTGTGATGACCCAGACT |
| | | CCACTCTCTCTGTCCGTCACCCCTGGACAGCCGGCCTCCATCTCCTGCAA |
| | | GTCTGGTCAGAGCCTCCTGCATAGTGATGGAAAGACCTATTTGTATTGGT |
| | | ACCTGCAGAAGCCAGGCCAGCCTCCACAGTTCCTGATCTATGAAGTTTCC |
| | | AACCGGTTCTCTAGAGTGCCAGATAGGTTCAGTGGCAGCGGGTCAGGGAC |
| | | AGATTTCACACTGAGAATCAGCCGGGTGGAGGCTGAGGATGTTGGAATTT |
| | | ATTACTGCATGCAAAGTATACAGCTTCCGTGGACGTTCGGCCAAGGGACC |
| | | CAGGTGGAAATCAAACGAACTGTGGCTGCACCATCTGTCTTCATCTTCCC |
| | | GCCATCTGATGAGCAGTTGAAATCTGGAACTGCCTCTGTTGTGTGCCTGC |
| | | TGAATAACTTCTATCCCAGAGAGGCCAAAGTACAGTGGAAGGTGGATAAC |
| | | GCCCTCCAATCGGGTAACTCCCAGGAGAGTGTCACAGAGCAGGACAGCAA |
| | | GGACAGCACCTACAGCCTCAGCAGCACCCTGACGCTGAGCAAAGCAGACT |
| | | ACGAGAAACACAAAGTCTACGCCTGCGAAGTCACCCATCAGGGCCTGAGC |
| | | TCGCCCGTCACAAAGAGCTTCAACAGGGGAGAGTGT |
| 20 | 19D11-6.37 LC AA | SYVLTQPPSVSVAPGQTARITCGGDNIGSISVHWYQQKPGQAPVLVVYDD |
| | | SDRPSGIPERFSGSNSGNTATLTISWVEAGDEADYYCQVWDSSIDHPVLF |
| | | GGGTKLTVLGQPKAAPSVTLFDIVMTQTPLSLSVTPGQPASISCKSGQSL |
| | | LHSDGKTYLYWYLQKPGQPPQFLIYEVSNRFSRVPDRFSGSGSGTDFTLR |
| | | ISRVEAEDVGIYYCMQSIQLPWTFGQGTQVEIKRTVAAPSVFIFPPSDEQ |
| | | LKSGTASVVCLLNNFYPREAKVQWKVDNALQSGNSQESVTEQDSKDSTYS |
| | | LSSTLTLSKADYEKHKVYACEVTHQGLSSPVTKSFNRGEC |

TABLE 1-continued

| SEQ ID NO: | DESCRIPTION | SEQUENCE |
|---|---|---|
| 21 | 6.37.5-19D11 G2 NA | ATGGACATGAGGGTGCCCGCTCAGCTCCTGGGGCTCCTGCTGCTGTGGCTGAGAGGTGCGCGCTGTCAGGTGCAGCTGGTGGAGTCTGGGGGAGGCGTGGTCCAGCCTGGGAGGTCCCTGAGACTCTCCTGTGCAGCCTCTGGATTCACCTTCAGTGGCTATGGCATGCACTGGGTCCGCCAGGCTCCAGGCAAGGGGCTGGAGTGGGTGGCAGTTATATCATATGATGGAAATGATAAATACTATGCAGACTCCGTGAAGGGCCGATTCACCATCTCCAGAGACAATGCCAAGAACACGCTGTATCTGCAAATGAACAGCCTGAGAGCTGAGGACACGGCTGTGTATTACTGTGCGAGAGAGCTACGGGTCCTCTGGGGCCAGGGAACCCTGGTCACCGTCTCTAGTGCCTCCACCAAGGGCCCATCGGTCTTCCCCCTGGCGCCCGAGGTGCAGCTGGTGGAGTCTGGGGGAGGCTTGGTACAGCCTGGGGGGTCCCTGAGACTCTCCTGTGCAGCCTCTGGATTCACCTTCAGTAGCTACGACATGCACTGGGTCCGCCAAGCTACAGGAAAAGGTCTGGAGTGGGTCTCAGCTATTGGTACTGCTGGTGACACATACTATGCAGGCTCCGTGAAGGGCCGATTCACCATCTCCAGAGAAAATGCCAAGAACTCCTTGTATCTTCAAATGAACAGCCTGAGAGTCGGGGACACGGCTGTGTATTACTGTGCAAGGTCCTGGGGAGAGGGGAATTACTACTTCTACTACGGTATGGACGTCTGGGGCCAAGGGACCACGGTCACCGTCTCTAGTGCCTCCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGC |

TABLE 1-continued

| SEQ ID NO: | DESCRIPTION | SEQUENCE |
|---|---|---|
| | | TCTGACCAGCGGCGTGCACACCTTCCCAGCTGTCCTACAGTCCTCAGGAC |
| | | TCTACTCCCTCAGCAGCGTGGTGACCGTGCCCTCCAGCAACTTCGGCACC |
| | | CAGACCTACACCTGCAACGTAGATCACAAGCCCAGCAACACCAAGGTGGA |
| | | CAAGACAGTTGAGCGCAAATGTTGTGTCGAGTGCCCACCGTGCCCAGCAC |
| | | CACCTGTGGCAGGACCGTCAGTCTTCCTCTTCCCCCCAAAACCCAAGGAC |
| | | ACCCTCATGATCTCCCGGACCCCTGAGGTCACGTGCGTGGTGGTGGACGT |
| | | GAGCCACGAAGACCCCGAGGTCCAGTTCAACTGGTACGTGGACGGCGTGG |
| | | AGGTGCATAATGCCAAGACAAAGCCACGGGAGGAGCAGTTCAACAGCACG |
| | | TTCCGTGTGGTCAGCGTCCTCACCGTTGTGCACCAGGACTGGCTGAACGG |
| | | CAAGGAGTACAAGTGCAAGGTCTCCAACAAAGGCCTCCCAGCCCCCATCG |
| | | AGAAAACCATCTCCAAAACCAAAGGGCAGCCCCGAGAACCACAGGTGTAC |
| | | ACCCTGCCCCCATCCCGGGAGGAGATGACCAAGAACCAGGTCAGCCTGAC |
| | | CTGCCTGGTCAAAGGCTTCTACCCCAGCGACATCGCCGTGGAGTGGGAGA |
| | | GCAATGGGCAGCCGGAGAACAACTACAAGACCACACCTCCCATGCTG |
| | | GACTCCGACGGCTCCTTCTTCCTCTACAGCAAGCTCACCGTGGACAA |
| | | GAGCAGGTGGCAGCAGGGGAACGTCTTCTCATGCTCCGTGATGCATG |
| | | AGGCTCTGCACAACCACTACACGCAGAAGAGCCTCTCCCTGTCTCCG |
| | | GGTAAA |
| 22 | 6.37.5-19D11 G2 AA | QVQLVESGGGVVQPGRSLRLSCAASGFTFSGYGMHWVRQAPGKGLEWVAV |
| | | ISYDGNDKYYADSVKGRFTISRDNAKNTLYLQMNSLRAEDTAVYYCAREL |
| | | RVLWGQGTLVTVSSASTKGPSVFPLAPEVQLVESGGGLVQPGGSLRLSCA |
| | | ASGFTFSSYDMHWVRQATGKGLEWVSAIGTAGDTYYAGSVKGRFTISREN |

TABLE 1-continued

| SEQ ID NO: | DESCRIPTION | SEQUENCE |
|---|---|---|
| | | AKNSLYLQMNSLRVGDTAVYYCARSWGEGNYYFYYGMDVWGQGTTV |
| | | TVSS |
| | | ASTKGPSVFPLAPCSRSTSESTAALGCLVKDYFPEPVTVSWNSGALTSGV |
| | | HTFPAVLQSSGLYSLSSVVTVPSSNFGTQTYTCNVDHKPSNTKVDKTVER |
| | | KCCVECPPCPAPPVAGPSVFLFPPKPKDTLMISRTPEVTCVVVDVSHEDP |
| | | EVQFNWYVDGVEVHNAKTKPREEQFNSTFRVVSVLTVVHQDWLNGKEY |
| | | KC |
| | | KVSNKGLPAPIEKTISKTKGQPREPQVYTLPPSREEMTKNQVSLTCLVKG |
| | | FYPSDIAVEWESNGQPENNYKTTPPMLDSDGSFFLYSKLTVDKSRWQQG |
| | | N |
| | | VFSCSVMHEALHNHYTQKSLSLSPGK |
| 23 | 6.37.5-19D11 LC NA | ATGGACATGAGGGTGCCCGCTCAGCTCCTGGGGCTCCTGCTGCTGTGG |
| | | CT |
| | | GAGAGGTGCGCGCTGTGATATTGTGATGACCCAGACTCCACTCTCTCT |
| | | GT |
| | | CCGTCACCCCTGGACAGCCGGCCTCCATCTCCTGCAAGTCTGGTCAGA |
| | | GC |
| | | CTCCTGCATAGTGATGGAAAGACCTATTTGTATTGGTACCTGCAGAAG |
| | | CC |
| | | AGGCCAGCCTCCACAGTTCCTGATCTATGAAGTTTCCAACCGGTTCTC |
| | | TA |
| | | GAGTGCCAGATAGGTTCAGTGGCAGCGGGTCAGGGACAGATTTCACA |
| | | CTG |
| | | AGAATCAGCCGGGTGGAGGCTGAGGATGTTGGAATTTATTACTGCATG |
| | | CA |
| | | AAGTATACAGCTTCCGTGGACGTTCGGCCAAGGGACCCAGGTGGAAA |
| | | TCA |
| | | AACGAACGGTGGCTGCACCATCTGTCTTCATCTTCCCGTCCTATGTGCT |
| | | G |
| | | ACTCAGCCACCCTCGGTGTCAGTGGCCCCAGGACAGACGGCCAGGAT |
| | | TAC |
| | | CTGTGGGGAGACAACATTGGAAGTATAAGTGTGCATTGGTACCAGC |
| | | AGA |
| | | AGCCAGGCCAGGCCCCTGTGCTGGTCGTCTATGATGATAGCGACCGGC |
| | | CC |
| | | TCAGGGATCCCTGAGCGATTCTCTGGCTCCAACTCTGGGAACACGGCC |
| | | AC |

| SEQ ID NO: | DESCRIPTION | SEQUENCE |
|---|---|---|
| | | CCTGACCATCAGCTGGGTCGAAGCCGGGGATGAGGCCGACTATTACT |
| | | GTC |
| | | AGGTGTGGGATAGTAGTATTGATCATCCTGTGTTATTCGGCGGAGGGA |
| | | CC |
| | | AAGCTGACCGTCCTAGGTCAGCCCAAGGCCAACCCCACTGTCACTCTG |
| | | TT |
| | | CCCGCCCTCCTCTGAGGAGCTCCAAGCCAACAAGGCCACACTAGTGTG |
| | | TC |
| | | TGATCAGTGACTTCTACCCGGGAGCTGTGACAGTGGCCTGGAAGGCA |
| | | GAT |
| | | GGCAGCCCCGTCAAGGCGGGAGTGGAGACCACCAAACCCTCCAAACA |
| | | GAG |
| | | CAACAACAAGTACGCGGCCAGCAGCTACCTGAGCCTGACGCCCGAGC |
| | | AGT |
| | | GGAAGTCCCACAGAAGCTACAGCTGCCAGGTCACGCATGAAGGGAGC |
| | | ACC |
| | | GTGGAGAAGACAGTGGCCCCTACAGAATGTTCA |
| 24 | 6.37.5-19D11 LC AA | DIVMTQTPLSLSVTPGQPASISCKSGQSLLHSDGKTYLYWYLQKPGQPPQ |
| | | FLIYEVSNRFSRVPDRFSGSGSGTDFTLRISRVEAEDVGIYYCMQSIQLP |
| | | WTFGQGTQVEIKRTVAAPSVFIFPSYVLTQPPSVSVAPGQTARITCGGDN |
| | | IGSISVHWYQQKPGQAPVLVVYDDSDRPSGIPERFSGSNSGNTATLTISW |
| | | VEAGDEADYYCQVWDSSIDHPVLFGGGTKLTVLGQPKANPTVTLFPPSSE |
| | | ELQANKATLVCLISDFYPGAVTVAWKADGSPVKAGVETTKPSKQSNNKY |
| | | A |
| | | ASSYLSLTPEQWKSHRSYSCQVTHEGSTVEKTVAPTECS |
| 25 | 8G2-6.37 G2 NA | ATGGACATGAGGGTGCCCGCTCAGCTCCTGGGGCTCCTGCTGCTGTGG |
| | | CT |
| | | GAGAGGTGCGCGCTGTCAGGTGCAGCTGGTGCAGTCTGGGGCTGAGG |
| | | TGA |
| | | AGAAGCCTGGGGCCTCAGTGAAGGTCTCCTGCAAGGCTTCTGGATACA |
| | | CC |
| | | TTCACCAGTTATGATATCAACTGGGTGCGACAGGCCACTGGACAAGG |
| | | GCT |
| | | TGAGTGGATGGGATGGATGAACCCTAACAGTGGTAAAACAGGGTATG |
| | | CAC |
| | | AGAAGTTCCAGGGCAGAGTCACCATGACCAGGGACACCTCCATAAGC |
| | | ACA |

TABLE 1-continued

| SEQ ID NO: | DESCRIPTION | SEQUENCE |
|---|---|---|
| | | GCCTACATGGAGCTGAGCAGCCTGAGATCTGAGGACACGGCCGTGTATTA |
| | | CTGTGCGAGAGAGGAGGAATACTATGAATCGGGGAGCCTCTTCTACTACT |
| | | ACGGTTTGGACGTCTGGGGCCAAGGGACCACGGTCACCGTCTCTAGTGCC |
| | | TCCACCAAGGGCCCATCGGTCTTCCCCCTGGCGCCCCAGGTGCAGCTGGT |
| | | GGAGTCTGGGGGAGGCGTGGTCCAGCCTGGGAGGTCCCTGAGACTCTCCT |
| | | GTGCAGCCTCTGGATTCACCTTCAGTGGCTATGGCATGCACTGGGTCCGC |
| | | CAGGCTCCAGGCAAGGGGCTGGAGTGGGTGGCAGTTATATCATATGATGG |
| | | AAATGATAAATACTATGCAGACTCCGTGAAGGGCCGATTCACCATCTCCA |
| | | GAGACAATGCCAAGAACACGCTGTATCTGCAAATGAACAGCCTGAGAGCT |
| | | GAGGACACGGCTGTGTATTACTGTGCGAGAGAGCTACGGGTCCTCTGGGG |
| | | CCAGGGAACCCTGGTCACCGTCTCTAGTGCCTCCACCAAGGGCCCATCGG |
| | | TCTTCCCCCTGGCGCCCTGCTCCAGGAGCACCTCCGAGAGCACAGCGGCC |
| | | CTGGGCTGCCTGGTCAAGGACTACTTCCCCGAACCGGTGACGGTGTCGTG |
| | | GAACTCAGGCGCTCTGACCAGCGGCGTGCACACCTTCCCAGCTGTCCTAC |
| | | AGTCCTCAGGACTCTACTCCCTCAGCAGCGTGGTGACCGTGCCCTCCAGC |
| | | AACTTCGGCACCCAGACCTACACCTGCAACGTAGATCACAAGCCCAGCAA |
| | | CACCAAGGTGGACAAGACAGTTGAGCGCAAATGTTGTGTCGAGTGCCCAC |
| | | CGTGCCCAGCACCACCTGTGGCAGGACCGTCAGTCTTCCTCTTCCCCCCA |
| | | AAACCCAAGGACACCCTCATGATCTCCCGGACCCCTGAGGTCACGTGCGT |

TABLE 1-continued

| SEQ ID NO: | DESCRIPTION | SEQUENCE |
|---|---|---|
| | | GGTGGTGGACGTGAGCCACGAAGACCCCGAGGTCCAGTTCAACTGGTACG |
| | | TGGACGGCGTGGAGGTGCATAATGCCAAGACAAAGCCACGGGAGGAGCAG |
| | | TTCAACAGCACGTTCCGTGTGGTCAGCGTCCTCACCGTTGTGCACCAGGA |
| | | CTGGCTGAACGGCAAGGAGTACAAGTGCAAGGTCTCCAACAAAGGCCTCC |
| | | CAGCCCCCATCGAGAAAACCATCTCCAAAACCAAAGGGCAGCCCCGAGAA |
| | | CCACAGGTGTACACCCTGCCCCCATCCCGGGAGGAGATGACCAAGAACCA |
| | | GGTCAGCCTGACCTGCCTGGTCAAAGGCTTCTACCCCAGCGACATCGCCG |
| | | TGGAGTGGGAGAGCAATGGGCAGCCGGAGAACAACTACAAGACCAC |
| | | ACCTCCCATGCTGGACTCCGACGGCTCCTTCTTCCTCTACAGCAAG |
| | | CTCACCGTGGACAAGAGCAGGTGGCAGCAGGGGAACGTCTTCTCAT |
| | | GCTCCGTGATGCATGAGGCTCTGCACAACCACTACACGCAGAAGAG |
| | | CCTCTCCCTGTCTCCGGGTAAA |
| 26 | 8G2-6.37 G2 AA | QVQLVQSGAEVKKPGASVKVSCKASGYTFTSYDINWVRQATGQGLEWMGW |
| | | MNPNSGKTGYAQKFQGRVTMTRDTSISTAYMELSSLRSEDTAVYYCAREE |
| | | EYYESGSLFYYYGLDVWGQGTTVTVSSASTKGPSVFPLAPQVQLVESGGG |
| | | VVQPGRSLRLSCAASGFTFSGYGMHWVRQAPGKGLEWVAVISYDGNDKYY |
| | | ADSVKGRFTISRDNAKNTLYLQMNSLRAEDTAVYYCARELRVLWGQGTLV |
| | | TVSSASTKGPSVFPLAPCSRSTSESTAALGCLVKDYFPEPVTVSWNSGAL |
| | | TSGVHTFPAVLQSSGLYSLSSVVTVPSSNFGTQTYTCNVDHKPSNTKVDK |
| | | TVERKCCVECPPCPAPPVAGPSVFLFPPKPKDTLMISRTPEVTCVVVDVS |
| | | HEDPEVQFNWYVDGVEVHNAKTKPREEQFNSTFRVVSVLTVVHQDWLNGK |
| | | EYKCKVSNKGLPAPIEKTISKTKGQPREPQVYTLPPSREEMTKNQVSLTC |
| | | LVKGFYPSDIAVEWESNGQPENNYKTTPPMLDSDGSFFLYSKLTVDKSRW |
| | | QQGNVFSCSVMHEALHNHYTQKSLSLSPGK |

TABLE 1-continued

| SEQ ID NO: | DESCRIPTION | SEQUENCE |
|---|---|---|
| 27 | 8G2-6.37 LC NA | ATGGACATGAGGGTGCCCGCTCAGCTCCTGGGGCTCCTGCTGCTGTGGCT<br>GAGAGGTGCGCGCTGTGACATCCAGATGACCCAGTCTCCATCTTCCGTGT<br>CTGCGTCTGTAGGAGACAGAGTCACCATCACTTGTCGGGCGAGTCAGGAT<br>ATTAGCAACTGGTTAGCCTGGTATCAGCAGAAACCAGGGAAAGTCCCCAA<br>GCTCCTGATCTATGCTGCGTCCTATTTACAAAGTGGGGTCCCATCAAGGT<br>TCAGCGGCAGTGGATCTGGGACAGATTTCACTCTCACCATCAGCAGCCTG<br>CAGCCTGAAGATTTTGCAACTTACTCTTGTCAACAGGCTAACAGTTTCCC<br>ATTCACTTTCGGCCCTGGGACCAAAGTGGATATCAAACGTACTGTGGCTG<br>CACCATCTGTCTTCATCTTCCCGCCAGATATTGTGATGACCCAGACTCCA<br>CTCTCTCTGTCCGTCACCCCTGGACAGCCGGCCTCCATCTCCTGCAAGTC<br>TGGTCAGAGCCTCCTGCATAGTGATGGAAAGACCTATTTGTATTGGTACC<br>TGCAGAAGCCAGGCCAGCCTCCACAGTTCCTGATCTATGAAGTTTCCAAC<br>CGGTTCTCTAGAGTGCCAGATAGGTTCAGTGGCAGCGGGTCAGGGACAGA<br>TTTCACACTGAGAATCAGCCGGGTGGAGGCTGAGGATGTTGGAATTTATT<br>ACTGCATGCAAAGTATACAGCTTCCGTGGACGTTCGGCCAAGGGACCCAG<br>GTGGAAATCAAACGAACTGTGGCTGCACCATCTGTCTTCATCTTCCCGCC<br>ATCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGA |

TABLE 1-continued

| SEQ ID NO: | DESCRIPTION | SEQUENCE |
|---|---|---|
| | | CAGCACCTACAGCCTCAGCAGCACCCTGACGCTGAGCAAAGCAGACT |
| | | ACG |
| | | AGAAACACAAAGTCTACGCCTGCGAAGTCACCCATCAGGGCCTGAGC |
| | | TCG |
| | | CCCGTCACAAAGAGCTTCAACAGGGGAGAGTGT |
| 28 | 8G2-6.37 LC AA | DIQMTQSPSSVSASVGDRVTITCRASQDISNWLAWYQQKPGKVPKLLIYA |
| | | ASYLQSGVPSRFSGSGSGTDFTLTISSLQPEDFATYSCQQANSFPFTFGP |
| | | GTKVDIKRTVAAPSVFIFPPDIVMTQTPLSLSVTPGQPASISCKSGQSLL |
| | | HSDGKTYLYWYLQKPGQPPQFLIYEVSNRFSRVPDRFSGSGSGTDFTLRI |
| | | SRVEAEDVGIYYCMQSIQLPWTFGQGTQVEIKRTVAAPSVFIFPPSDEQL |
| | | KSGTASVVCLLNNFYPREAKVQWKVDNALQSGNSQESVTEQDSKDSTYS |
| | | L |
| | | SSTLTLSKADYEKHKVYACEVTHQGLSSPVTKSFNRGEC |
| 29 | 6.37-8G2 G2 NA | ATGGACATGAGGGTGCCCGCTCAGCTCCTGGGGCTCCTGCTGCTGTGG |
| | | CT |
| | | GAGAGGTGCGCGCTGTCAGGTGCAGCTGGTGGAGTCTGGGGGAGGCG |
| | | TGG |
| | | TCCAGCCTGGGAGGTCCCTGAGACTCTCCTGTGCAGCCTCTGGATTCA |
| | | CC |
| | | TTCAGTGGCTATGGCATGCACTGGGTCCGCCAGGCTCCAGGCAAGGG |
| | | GCT |
| | | GGAGTGGGTGGCAGTTATATCATATGATGGAAATGATAAATACTATGC |
| | | AG |
| | | ACTCCGTGAAGGGCCGATTCACCATCTCCAGAGACAATGCCAAGAAC |
| | | ACG |
| | | CTGTATCTGCAAATGAACAGCCTGAGAGCTGAGGACACGGCTGTGTAT |
| | | TA |
| | | CTGTGCGAGAGAGCTACGGGTCCTCTGGGGCCAGGGAACCCTGGTCA |
| | | CCG |
| | | TCTCTAGTGCCTCCACCAAGGGCCCATCGGTCTTCCCCCTGGCGCCCC |
| | | AG |
| | | GTGCAGCTGGTGCAGTCTGGGGCTGAGGTGAAGAAGCCTGGGGCCTC |
| | | AGT |
| | | GAAGGTCTCCTGCAAGGCTTCTGGATACACCTTCACCAGTTATGATAT |
| | | CA |
| | | ACTGGGTGCGACAGGCCACTGGACAAGGGCTTGAGTGGATGGGATGG |
| | | ATG |
| | | AACCCTAACAGTGGTAAAACAGGGTATGCACAGAAGTTCCAGGGCAG |
| | | AGT |

TABLE 1-continued

| SEQ ID NO: | DESCRIPTION | SEQUENCE |
|---|---|---|
| | | CACCATGACCAGGGACACCTCCATAAGCACAGCCTACATGGAGCTGAGCA |
| | | GCCTGAGATCTGAGGACACGGCCGTGTATTACTGTGCGAGAGAGGAGGAA |
| | | TACTATGAATCGGGGAGCCTCTTCTACTACTACGGTTTGGACGTCTGGGG |
| | | CCAAGGGACCACGGTCACCGTCTCTAGTGCCTCCACCAAGGGCCCATCGG |
| | | TCTTCCCCCTGGCGCCCTGCTCCAGGAGCACCTCCGAGAGCACAGCGGCC |
| | | CTGGGCTGCCTGGTCAAGGACTACTTCCCCGAACCGGTGACGGTGTCGTG |
| | | GAACTCAGGCGCTCTGACCAGCGGCGTGCACACCTTCCCAGCTGTCCTAC |
| | | AGTCCTCAGGACTCTACTCCCTCAGCAGCGTGGTGACCGTGCCCTCCAGC |
| | | AACTTCGGCACCCAGACCTACACCTGCAACGTAGATCACAAGCCCAGCAA |
| | | CACCAAGGTGGACAAGACAGTTGAGCGCAAATGTTGTGTCGAGTGCCCAC |
| | | CGTGCCCAGCACCACCTGTGGCAGGACCGTCAGTCTTCCTCTTCCCCCCA |
| | | AAACCCAAGGACACCCTCATGATCTCCCGGACCCCTGAGGTCACGTGCGT |
| | | GGTGGTGGACGTGAGCCACGAAGACCCCGAGGTCCAGTTCAACTGGTACG |
| | | TGGACGGCGTGGAGGTGCATAATGCCAAGACAAAGCCACGGGAGGAGCAG |
| | | TTCAACAGCACGTTCCGTGTGGTCAGCGTCCTCACCGTTGTGCACCAGGA |
| | | CTGGCTGAACGGCAAGGAGTACAAGTGCAAGGTCTCCAACAAAGGCCTCC |
| | | CAGCCCCCATCGAGAAAACCATCTCCAAAACCAAAGGGCAGCCCCGAGAA |
| | | CCACAGGTGTACACCCTGCCCCCATCCCGGGAGGAGATGACCAAGAACCA |
| | | GGTCAGCCTGACCTGCCTGGTCAAAGGCTTCTACCCCAGCGACATCGCCG |

TABLE 1-continued

| SEQ ID NO: | DESCRIPTION | SEQUENCE |
|---|---|---|
| | | TGGAGTGGGAGAGCAATGGGCAGCCGGAGAACAACTACAAGACCAC |
| | | ACCTCCCATGCTGGACTCCGACGGCTCCTTCTTCCTCTACAGCAAG |
| | | CTCACCGTGGACAAGAGCAGGTGGCAGCAGGGGAACGTCTTCTCAT |
| | | GCTCCGTGATGCATGAGGCTCTGCACAACCACTACACGCAGAAGAG |
| | | CCTCTCCCTGTCTCTCCGGGTAAA |
| 30 | 6.37-8G2 G2 AA | QVQLVESGGGVVQPGRSLRLSCAASGFTFSGYGMHWVRQAPGKGLEWVAV |
| | | ISYDGNDKYYADSVKGRFTISRDNAKNTLYLQMNSLRAEDTAVYYCAREL |
| | | RVLWGQGTLVTVSSASTKGPSVFPLAPQVQLVQSGAEVKKPGASVKVSCK |
| | | ASGYTFTSYDINWVRQATGQGLEWMGWMNPNSGKTGYAQKFQGRVTMTRD |
| | | TSISTAYMELSSLRSEDTAVYYCAREEEYYESGSLFYYYGLDVWGQGTTV |
| | | TVSSASTKGPSVFPLAPCSRSTSESTAALGCLVKDYFPEPVTVSWNSGAL |
| | | TSGVHTFPAVLQSSGLYSLSSVVTVPSSNFGTQTYTCNVDHKPSNTKVDK |
| | | TVERKCCVECPPCPAPPVAGPSVFLFPPKPKDTLMISRTPEVTCVVVDVS |
| | | HEDPEVQFNWYVDGVEVHNAKTKPREEQFNSTFRVVSVLTVVHQDWLNGK |
| | | EYKCKVSNKGLPAPIEKTISKTKGQPREPQVYTLPPSREEMTKNQVSLTC |
| | | LVKGFYPSDIAVEWESNGQPENNYKTTPPMLDSDGSFFLYSKLTVDKSRW |
| | | QQGNVFSCSVMHEALHNHYTQKSLSLSPGK |
| 31 | 6.37-8G2 LC NA | ATGGACATGAGGGTGCCCGCTCAGCTCCTGGGGCTCCTGCTGCTGTGGCT |
| | | GAGAGGTGCGCGCTGTGATATTGTGATGACCCAGACTCCACTCTCTCTGT |
| | | CCGTCACCCCTGGACAGCCGGCCTCCATCTCCTGCAAGTCTGGTCAGAGC |
| | | CTCCTGCATAGTGATGGAAAGACCTATTTGTATTGGTACCTGCAGAAGCC |
| | | AGGCCAGCCTCCACAGTTCCTGATCTATGAAGTTTCCAACCGGTTCTCTA |
| | | GAGTGCCAGATAGGTTCAGTGGCAGCGGGTCAGGGACAGATTTCACACTG |
| | | AGAATCAGCCGGGTGGAGGCTGAGGATGTTGGAATTTATTACTGCATGCA |

TABLE 1-continued

| SEQ ID NO: | DESCRIPTION | SEQUENCE |
|---|---|---|
| | | AAGTATACAGCTTCCGTGGACGTTCGGCCAAGGGACCCAGGTGGAAA |
| | | TCA |
| | | AACGAACGGTGGCTGCACCATCTGTCTTCATCTTCCCGGACATCCAGA |
| | | TG |
| | | ACCCAGTCTCCATCTTCCGTGTCTGCGTCTGTAGGAGACAGAGTCACC |
| | | AT |
| | | CACTTGTCGGGCGAGTCAGGATATTAGCAACTGGTTAGCCTGGTATCA |
| | | GC |
| | | AGAAACCAGGGAAAGTCCCCAAGCTCCTGATCTATGCTGCGTCCTATT |
| | | TA |
| | | CAAAGTGGGGTCCCATCAAGGTTCAGCGGCAGTGGATCTGGGACAGA |
| | | TTT |
| | | CACTCTCACCATCAGCAGCCTGCAGCCTGAAGATTTTGCAACTTACTC |
| | | TT |
| | | GTCAACAGGCTAACAGTTTCCCATTCACTTTCGGCCCTGGGACCAAAG |
| | | TG |
| | | GATATCAAACGTACGGTGGCTGCACCATCTGTCTTCATCTTCCCGCCA |
| | | TC |
| | | TGATGAGCAGTTGAAATCTGGAACTGCCTCTGTTGTGTGCCTGCTGAA |
| | | TA |
| | | ACTTCTATCCCAGAGAGGCCAAAGTACAGTGGAAGGTGGATAACGCC |
| | | CTC |
| | | CAATCGGGTAACTCCCAGGAGAGTGTCACAGAGCAGGACAGCAAGGA |
| | | CAG |
| | | CACCTACAGCCTCAGCAGCACCCTGACGCTGAGCAAAGCAGACTACG |
| | | AGA |
| | | AACACAAAGTCTACGCCTGCGAAGTCACCCATCAGGGCCTGAGCTCG |
| | | CCC |
| | | GTCACAAAGAGCTTCAACAGGGGAGAGTGT |
| 32 | 6.37-8G2 LC AA | DIVMTQTPLSLSVTPGQPASISCKSGQSLLHSDGKTYLYWYLQKPGQPPQ |
| | | FLIYEVSNRFSRVPDRFSGSGSGTDFTLRISRVEAEDVGIYYCMQSIQLP |
| | | WTFGQGTQVEIKRTVAAPSVFIFPDIQMTQSPSSVSASVGDRVTITCRAS |
| | | QDISNWLAWYQQKPGKVPKLLIYAASYLQSGVPSRFSGSGSGTDFTLTIS |
| | | SLQPEDFATYSCQQANSFPFTFGPGTKVDIKRTVAAPSVFIFPPSDEQLK |
| | | SGTASVVCLLNNFYPREAKVQWKVDNALQSGNSQESVTEQDSKDSTYSL |
| | | S |
| | | STLTLSKADYEKHKVYACEVTHQGLSSPVTKSFNRGEC |

TABLE 1-continued

| SEQ ID NO: | DESCRIPTION | SEQUENCE |
|---|---|---|
| 33 | 6.147-AbL-20c3.1 G2 NA | CAGGTGCAGCTTGTCGAGAGCGGTGGAGGGGTGGTACAACCCGGAAG ATCACTCCGGCTTTCATGCGCAGCATCCGGTTTTACATTTTCGCGGTAT GACATGCACTGGGTGAGACAGGCACCAGGAAAAGGGCTGGAGTGGGT GGCCATCATCTTCTATGATGGGTCCAATAAGTACTACGCCGACCCGGT AAAAGGGAGGTTCACTATTAGCCGCGACAACTCGAAGAATACGCTGT ACCTGCAGATGAACTCGTTGCGAGCCGAAGATACCGCGGTCTACTATT GTGCGACGCTCGCGGCTGCGTTCGATTACTGGGGCCAAGGAACATTGG TCACGGTCTCCTCAGCGTCAACGAAAGGACCGTCGGTGTTCCCCTTGG CCCCTCAGGTCCAACTGCAAGAGTCAGGACCCGGCCTTGTGAAACCTT CGGAAACTCTTAGCTTGACGTGTACTGTGTCGGGAGGATCAATCTCGT CATACTATTGGTCGTGGATTCGGCAGCCGCCTGGTAAAGGCTTGGAGT GGATTGGGTATATCTCCGACTCCGGGTCCACGAATTACAACCCCTCCC TCAAGTCGAGAATTCCGATCAGCGTGGATACCTCGAAGAACCAGTTTA GCCTCAAGCTGTCGTCAGTGACAGCGGCCGACACCGCCGTCTATTACT GCGCACGCTGGCAGCTCGCTCACGATGCGTTCGACATCTGGGGTCAGG GGACAATGGTAACCGTCTCTAGTGCCTCCACCAAGGGCCCATCGGTCT TCCCCCTGGCGCCCTGCTCCAGGAGCACCTCCGAGAGCACAGCGGCCC TGGGCTGCCTGGTCAAGGACTACTTCCCCGAACCGGTGACGGTGTCGT GGAACTCAGGCGCTCTGACCAGCGGCGTGCACACCTTCCCAGCTGTCC TACAGTCCTCAGGACTCTACTCCCTCAGCAGCGTGGTGACCGTGCCCT CCAGCAACTTCGGCACCCAGACCTACACCTGCAACGTAGATCACAAG CCCAGCAACACCAAGGTGGACAAGACAGTTGAGCGCAAATGTTGTGT CGAGTGCCCACCGTGCCCAGCACCACCTGTGGCAGGACCGTCAGTCTT CCTCTTCCCCCCAAAACCCAAGGACACCCTCATGATCTCCCGGACCCC TGAGGTCACGTGCGTGGTGGTGGACGTGAGCCACGAAGACCCCGAGG TCCAGTTCAACTGGTACGTGGACGGCGTGGAGGTGCATAATGCCAAG ACAAAGCCACGGGAGGAGCAGTTCAACAGCACGTTCCGTGTGGTCAG CGTCCTCACCGTTGTGCACCAGGACTGGCTGAACGGCAAGGAGTACA AGTGCAAGGTCTCCAACAAAGGCCTCCCAGCCCCCATCGAGAAAACC ATCTCCAAAACCAAAGGGCAGCCCCGAGAACCACAGGTGTACACCCT GCCCCCATCCCGGGAGGAGATGACCAAGAACCAGGTCAGCCTGACCT GCCTGGTCAAAGGCTTCTACCCCAGCGACATCGCCGTGGAGTGGGAG AGCAATGGGCAGCCGGAGAACAACTACAAGACCACACCTCCCATGCT GGACTCCGACGGCTCCTTCTTCCTCTACAGCAAGCTCACCGTGGACAA GAGCAGGTGGCAGCAGGGGAACGTCTTCTCATGCTCCGTGATGCATG AGGCTCTGCACAACCACTACACGCAGAAGAGCCTCTCCCTGTCTCCGG GTAAA |

TABLE 1-continued

| SEQ ID NO: | DESCRIPTION | SEQUENCE |
|---|---|---|
| 34 | 6.147-AbL-20C3.1 G2 AA | QVQLVESGGGVVQPGRSLRLSCAASGFTFSRYDMHWVRQAPGKGLEWVAIIFYDGSNKYYADPVKGRFTISRDNSKNTLYLQMNSLRAEDTAVYYCATLAAAFDYWGQGTLVTVSS<u>ASTKGPSVFPLAP</u>QVQLQESGPGLVKPSETLSLTCTVSGGSISSYYWSWIRQPPGKGLEWIGYISDSGSTNYNPSLKSRIPISVDTSKNQFSLKLSSVTAADTAVYYCARWQLAHDAFDIWGQGTMVTVSS*ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK* |
| 35 | 6.147-AbL-20C3.1 LC NA | TCATACGTGCTCACTCAGCCGCCCAGCGTATCGGTGGCTCCCGGACAGACGGCGCGAATCACGTGCGGTGGGAACAATATCGGCTCCAAGTCAGTCCATTGGTATCAACAGAAACCTGGTCAGGCACCAGTCCTGGTGGTATACGATGACTCGGACAGGCCCTCGGAGATTCCGGAACGCTTCTCCGGATCGAATTCGGGGAACACAGCGACCTTGACGATCAGCAGAGTGGAGGCCGGAGATGAAGCCGACTACTATTGTCAGGTGTGGGATTCCAGCTCCGACCACGTCGTATTTGGAGGTGGGACACGGCTTACCGTCCTCGGGCAGCCCAAGGCTGCGCCATCGGTCACTCTGTTCCCACCTCAGAGCGCCCTGACCCAACCGGCGTCCGTGTCGGGTTCACCAGGCCAGTCAATCACTATTTCATGTACGGGACGTCGTCCGACGTGGGAGGGTACAACTACGTATCATGGTATCAACAGCACCCCGGTAAAGCGCCGAAGCTGATGATCTACGAGGTCAGCTATAGGCCTTCCGGAGTGTCAAATCGGTTCTCCGGGTCGAAATCGGGTTCGACGGCATCGTTGACAATCAGCGGGCTCCAGCCCGAAGATGAGGCCGACTACTATTGCTCCTCGTATGCGATTTCCAGCACTCTTGTCTTTGGCGGAGGAACAAAGATGACCGTCCTAGGTCAGCCCAAGGCCAACCCCACTGTCACTCTGTTCCCGCCCTCCTCTGAGGAGCTCCAAGCCAACAAGGCCACACTAGTGTGTCTGATCAGTGACTTCTACCCGGGAGCTGTGACAGTGGCCTGGAAGGCAGATGGCAGCCCCGTCAAGGCGGGAGTGGAGACCACCAAACCCTCCAAACAGAGCAACAACAAGTACGCGGCCAGCAGCTACCTGAGCCTGACGCCCGAGCAGTGGAAGTCCCACAGAAGCTACAGCTGCCAGGTCACGCATGAAGGGAGCACCGTGGAGAAGACAGTGGCCCCTACAGAATGTTCA |

TABLE 1-continued

| SEQ ID NO: | DESCRIPTION | SEQUENCE |
|---|---|---|
| 36 | 6.147-AbL-20C3.1 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVLG*QPKAAPSVTLFPP*QSALTQPASVSGSPGQSITISCTGTSSD VGGYNYVSWYQQHPGKAPKLMIYEVSYRPSGVSNRFSGSKSGSTASLTI SGLQPEDEADYYCSSYAISSTLVFGGGTKMTVLG*QPKANPTVTLFPPSSE ELQANKATLVCLISDFYPGAVTVAWKADGSPVKAGVETTKPSKQSNNKYA ASSYLSLTPEQWKSHRSYSCQVTHEGSTVEKTVAPTECS* |
| 37 | 6.147-AbL-27H6 G2 NA | CAGGTGCAGCTTGTCGAGAGCGGTGGAGGGGTGGTACAACCCGGAAG ATCACTCCGGCTTTCATGCGCAGCATCCGGTTTTACATTTTCGCGGTAT GACATGCACTGGGTGAGACAGGCACCAGGAAAAGGGCTGGAGTGGGT GGCCATCATCTTCTATGATGGGTCCAATAAGTACTACGCCGACCCGGT AAAAGGGAGGTTCACTATTAGCCGCGACAACTCGAAGAATACGCTGT ACCTGCAGATGAACTCGTTGCGAGCCGAAGATACCGCGGTCTACTATT GTGCGACGCTCGCGGCTGCGTTCGATTACTGGGGCCAAGGAACATTGG TCACGGTCTCCTCAGCGTCAACGAAAGGACCGTCGGTGTTCCCCTTGG CCCCTGAGGTGCAGCTCGTCGAAAGCGGAGGAGGCCTGGTCCAACCT GGTGGTTCCCTCCGACTGTCATGTGCCGCATCCGGTTTCACGTTTTCAT CGTACTCGATGAACTGGGTCCGCCAGGCACCGGGGAAAGGGTTGGAA TGGGTATCCTACATTTCGTCCAGCGGGTCAAGCATCTACTATGCGGAT AGCGTAAAGGGCCGGTTCACGATCTCGAGAGACAACGCGAAGAATTC GTTGTATCTTCAGATGAATTCGCTCAGGGATGAGGACACAGCGGTGTA TTACTGCGCTCGCGAAAGATACTATGGAGACACCCCCTTTGATTACTG GGGACAGGGAACTCTTGTGACCGTCTCTAGTGCCTCCACCAAGGGCCC ATCGGTCTTCCCCCTGGCGCCCTGCTCCAGGAGCACCTCCGAGAGCAC AGCGGCCCTGGGCTGCCTGGTCAAGGACTACTTCCCCGAACCGGTGAC GGTGTCGTGGAACTCAGGCGCTCTGACCAGCGGCGTGCACACCTTCCC AGCTGTCCTACAGTCCTCAGGACTCTACTCCCTCAGCAGCGTGGTGAC CGTGCCCTCCAGCAACTTCGGCACCCAGACCTACACCTGCAACGTAGA TCACAAGCCCAGCAACACCAAGGTGGACAAGACAGTTGAGCGCAAAT GTTGTGTCGAGTGCCCACCGTGCCCAGCACCACCTGTGGCAGGACCGT CAGTCTTCCTCTTCCCCCCAAAACCCAAGGACACCCTCATGATCTCCC GGACCCCTGAGGTCACGTGCGTGGTGGTGGACGTGAGCCACGAAGAC CCCGAGGTCCAGTTCAACTGGTACGTGGACGGCGTGGAGGTGCATAA TGCCAAGACAAAGCCACGGGAGGAGCAGTTCAACAGCACGTTCCGTG TGGTCAGCGTCCTCACCGTTGTGCACCAGGACTGGCTGAACGGCAAGG AGTACAAGTGCAAGGTCTCCAACAAAGGCCTCCCAGCCCCCATCGAG AAAACCATCTCCAAAACCAAAGGGCAGCCCCGAGAACCACAGGTGTA |

TABLE 1-continued

| SEQ ID NO: | DESCRIPTION | SEQUENCE |
|---|---|---|
| | | CACCCTGCCCCCATCCCGGGAGGAGATGACCAAGAACCAGGTCAGCC |
| | | TGACCTGCCTGGTCAAAGGCTTCTACCCCAGCGACATCGCCGTGGAGT |
| | | GGGAGAGCAATGGGCAGCCGGAGAACAACTACAAGACCACACCTCCC |
| | | ATGCTGGACTCCGACGGCTCCTTCTTCCTCTACAGCAAGCTCACCGTG |
| | | GACAAGAGCAGGTGGCAGCAGGGGAACGTCTTCTCATGCTCCGTGAT |
| | | GCATGAGGCTCTGCACAACCACTACACGCAGAAGAGCCTCTCCCTGTC |
| | | TCCGGGTAAA |
| 38 | 6.147-AbL-27H6 G2 AA | QVQLVESGGGVVQPGRSLRLSCAASGFTFSRYDMHWVRQAPGKGLEW VAIIFYDGSNKYYADPVKGRFTISRDNSKNTLYLQMNSLRAEDTAVYYC ATLAAAFDYWGQGTLVTVSSASTKGPSVFPLAPEVQLVESGGGLVQPGG SLRLSCAASGFTFSSYSMNWVRQAPGKGLEWVSYISSSGSSIYYADSVK GRFTISRDNAKNSLYLQMNSLRDEDTAVYYCARERYYGDTPFDYWGQG TLVTVSS*ASTKGPSVFPLAPCSRSTSESTAALGCLVKDYFPEPVTVSWNSG ALTSGVHTFPAVLQSSGLYSLSSVVTVPSSNFGTQTYTCNVDHKPSNTKV DKTVERKCCVECPPCPAPPVAGPSVFLFPPKPKDTLMISRTPEVTCVVVD VSHEDPEVQFNWYVDGVEVHNAKTKPREEQFNSTFRVVSVLTVVHQDW LNGKEYKCKVSNKGLPAPIEKTISKTKGQPREPQVYTLPPSREEMTKNQV SLTCLVKGFYPSDIAVEWESNGQPENNYKTTPPMLDSDGSFFLYSKLTVD KSRWQQGNVFSCSVMHEALHNHYTQKSLSLSPGK* |
| 39 | 6.147-AbL-27H6 LC NA | TCATACGTGCTCACTCAGCCGCCCAGCGTATCGGTGGCTCCCGGACAG ACGGCGCGAATCACGTGCGGTGGGAACAATATCGGCTCCAAGTCAGT CCATTGGTATCAACAGAAACCTGGTCAGGCACCAGTCCTGGTGGTATA CGATGACTCGGACAGGCCCTCGGAGATTCCGGAACGCTTCTCCGGATC GAATTCGGGGAACACAGCGACCTTGACGATCAGCAGAGTGGAGGCCG GAGATGAAGCCGACTACTATTGTCAGGTGTGGGATTCCAGCTCCGACC ACGTCGTATTTGGAGGTGGGACACGGCTTACCGTCCTCGGGCAGCCCA AGGCTGCGCCATCGGTCACTCTGTTCCCACCTGATATCGTAATGACAC AGACACCCCTCTCCCTCCCCGTGACCCCAGGGGAGCCTGCATCAATCT CCTGCCGCTCATCGCAGTCGCTTCTGAATTCGGTGGACGGATCGACTA ACCTTGACTGGTATTTGCAAAAACCGGGACAGTCACCTCAACTCCTGA TCTACACTCTGAGCTATCGGGCGTCAGGCGTCCCCGACAGGTTTAGCG GTTCCGGGTCCGGCACGGATTTCACGCTTAAGATTTCGCGAGTCGAGG CCGAAGATGTGGGTGTATACTACTGTATGCAGAGAATCGAATTCCCGT TGACATTTGGGGGAGGGACCAAAGTGGAGATTAAGCGTACGGTGGCT GCACCATCTGTCTTCATCTTCCCGCCATCTGATGAGCAGTTGAAATCTG GAACTGCCTCTGTTGTGTGCCTGCTGAATAACTTCTATCCCAGAGAGG CCAAAGTACAGTGGAAGGTGGATAACGCCCTCCAATCGGGTAACTCC CAGGAGAGTGTCACAGAGCAGGACAGCAAGGACAGCACCTACAGCCT |

| SEQ ID NO: | DESCRIPTION | SEQUENCE |
|---|---|---|
| | | CAGCAGCACCCTGACGCTGAGCAAAGCAGACTACGAGAAACACAAAG |
| | | TCTACGCCTGCGAAGTCACCCATCAGGGCCTGAGCTCGCCCGTCACAA |
| | | AGAGCTTCAACAGGGGAGAGTGT |
| 40 | 6.147-AbL-27H6 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVLGQPKAAPSVTLFPPDIVMTQTPLSLPVTPGEPASISCRSSQSL LNSVDGSTNLDWYLQKPGQSPQLLIYTLSYRASGVPDRFSGSGSGTDFTL KISRVEAEDVGVYYCMQRIEFPLTFGGGTKVEIKR*TVAAPSVFIFPPSDE QLKSGTASVVCLLNNFYPREAKVQWKVDNALQSGNSQESVTEQDSKDST YSLSSTLTLSKADYEKHKVYACEVTHQGLSSPVTKSFNRGEC* |
| 41 | 6.147-AbL-Ab5K G2 NA | CAGGTGCAGCTTGTCGAGAGCGGTGGAGGGGTGGTACAACCCGGAAG ATCACTCCGGCTTTCATGCGCAGCATCCGGTTTTACATTTTCGCGGTAT GACATGCACTGGGTGAGACAGGCACCAGGAAAAGGGCTGGAGTGGGT GGCCATCATCTTCTATGATGGGTCCAATAAGTACTACGCCGACCCGGT AAAAGGGAGGTTCACTATTAGCCGCGACAACTCGAAGAATACGCTGT ACCTGCAGATGAACTCGTTGCGAGCCGAAGATACCGCGGTCTACTATT GTGCGACGCTCGCGGCTGCGTTCGATTACTGGGGCCAAGGAACATTGG TCACGGTCTCCTCAGCGTCAACGAAAGGACCGTCGGTGTTCCCCTTGG CCCCTGAGGTGCAGCTCGTGCAGTCCGGAGCCGAGGTGGTGCAGCCT GGGGCATCCGTCAAAGTCTCGTGCGCCGCGTCAGGGTACACATTCACC GACTATAACATGCATTGGGTCCGGCAGGCTCCCGGTCAGGGGCTGGA GTGGATGGGGGAAATCAATCCGAACTCCGGAGGGGCAGGATACAATC AAAAGTTTAAGGGACGCGTAACGATGACCACTGACACGTCAACCTCC ACGGCGTATATGGAGCTCAGAAGCCTCCGAAGCGACGACACTGCTGT CTATTACTGTGCGAGACTGGGATATGATGATATCTACGACGATTGGTA CTTCGATGTATGGGGACAAGGGACGACGGTCACCGTCTCTAGTGCCTC CACCAAGGGCCCATCGGTCTTCCCCCTGGCGCCCTGCTCCAGGAGCAC CTCCGAGAGCACAGCGGCCCTGGGCTGCCTGGTCAAGGACTACTTCCC CGAACCGGTGACGGTGTCGTGGAACTCAGGCGCTCTGACCAGCGGCG TGCACACCTTCCCAGCTGTCCTACAGTCCTCAGGACTCTACTCCCTCA GCAGCGTGGTGACCGTGCCCTCCAGCAACTTCGGCACCCAGACCTACA CCTGCAACGTAGATCACAAGCCCAGCAACACCAAGGTGGACAAGACA GTTGAGCGCAAATGTTGTGTCGAGTGCCCACCGTGCCCAGCACCACCT GTGGCAGGACCGTCAGTCTTCCTCTTCCCCCCAAAACCCAAGGACACC CTCATGATCTCCCGGACCCCTGAGGTCACGTGCGTGGTGGTGGACGTG AGCCACGAAGACCCCGAGGTCCAGTTCAACTGGTACGTGGACGGCGT GGAGGTGCATAATGCCAAGACAAAGCCACGGGAGGAGCAGTTCAACA |

TABLE 1-continued

| SEQ ID NO: | DESCRIPTION | SEQUENCE |
|---|---|---|
| | | GCACGTTCCGTGTGGTCAGCGTCCTCACCGTTGTGCACCAGGACTGGC |
| | | TGAACGGCAAGGAGTACAAGTGCAAGGTCTCCAACAAAGGCCTCCCA |
| | | GCCCCCATCGAGAAAACCATCTCCAAAACCAAAGGGCAGCCCCGAGA |
| | | ACCACAGGTGTACACCCTGCCCCCATCCCGGGAGGAGATGACCAAGA |
| | | ACCAGGTCAGCCTGACCTGCCTGGTCAAAGGCTTCTACCCCAGCGACA |
| | | TCGCCGTGGAGTGGGAGAGCAATGGGCAGCCGGAGAACAACTACAAG |
| | | ACCACACCTCCCATGCTGGACTCCGACGGCTCCTTCTTCCTCTACAGC |
| | | AAGCTCACCGTGGACAAGAGCAGGTGGCAGCAGGGGAACGTCTTCTC |
| | | ATGCTCCGTGATGCATGAGGCTCTGCACAACCACTACACGCAGAAGA |
| | | GCCTCTCCCTGTCTCCGGGTAAA |
| 42 | 6.147-AbL-Ab5K G2 AA | QVQLVESGGGVVQPGRSLRLSCAASGFTFSRYDMHWVRQAPGKGLEW VAIIPYDGSNKYYADPVKGRFTISRDNSKNTLYLQMNSLRAEDTAVYYC ATLAAAFDYWGQGTLVTVSS<u>ASTKGPSVFPLAP</u>EVQLVQSGAEVVQPGA SVKVSCAASGYTFTDYNMHWVRQAPGQGLEWMGEINPNSGGAGYNQ KFKGRVTMTTDTSTSTAYMELRSLRSDDTAVYYCARLGYDDIYDDWYF DVWGQGTTVTVSS*ASTKGPSVFPLAPCSRSTSESTAALGCLVKDYFPEPV TVSWNSGALTSGVHTFPAVLQSSGLYSLSSVVTVPSSNFGTQTYTCNVDH KPSNTKVDKTVERKCCVECPPCPAPPVAGPSVFLFPPKPKDTLMISRTPE VTCVVVDVSHEDPEVQFNWYVDGVEVHNAKTKPREEQFNSTFRVVSVLT VVHQDWLNGKEYKCKVSNKGLPAPIEKTISKTKGQPREPQVYTLPPSREE MTKNQVSLTCLVKGFYPSDIAVEWESNGQPENNYKTTPPMLDSDGSFFL YSKLTVDKSRWQQGNVFSCSVMHEALHNHYTQKSLSLSPGK* |
| 43 | 6.147-AbL-Ab5 LC NA | TCATACGTGCTCACTCAGCCGCCCAGCGTATCGGTGGCTCCCGGACAG ACGGCGCGAATCACGTGCGGTGGGAACAATATCGGCTCCAAGTCAGT CCATTGGTATCAACAGAAACCTGGTCAGGCACCAGTCCTGGTGGTATA CGATGACTCGGACAGGCCCTCGGAGATTCCGGAACGCTTCTCCGGATC GAATTCGGGGAACACAGCGACCTTGACGATCAGCAGAGTGGAGGCCG GAGATGAAGCCGACTACTATTGTCAGGTGTGGGATTCCAGCTCCGACC ACGTCGTATTTGGAGGTGGGACACGGCTTACCGTCCTCGGGCAGCCCA AGGCTGCGCCATCGGTCACTCTGTTCCCACCTGACATTCAGATGACTC AGTCGCCTTCGTCATTGAGCGCGTCGGTGGGAGATCGGGTCACGATTA CTTGTCGGGCATCGCAAGACATCTCGAACTATTTGAATTGGTACCAGC AAAAGCCTGGTAAAGCGCCCAAACTTCTTATCTACTATACGTCCCGCC TCCTCTCGGGCGTCCCGTCAAGGTTTAGCGGATCGGGAAGCGGGACG GATTTCACACTGACGATTTCATCACTTCAGCCCGAAGATTTCGCCACC TATTACTGTCAGCAAGGAGACACCCTGCCATACACTTTTGGCGGTGGG ACAAAGGTCGAAATCAAGCGTACGGTGGCTGCACCATCTGTCTTCATC TTCCCGCCATCTGATGAGCAGTTGAAATCTGGAACTGCCTCTGTTGTG |

TABLE 1-continued

| SEQ ID NO: | DESCRIPTION | SEQUENCE |
|---|---|---|
| | | TGCCTGCTGAATAACTTCTATCCCAGAGAGGCCAAAGTACAGTGGAA |
| | | GGTGGATAACGCCCTCCAATCGGGTAACTCCCAGGAGAGTGTCACAG |
| | | AGCAGGACAGCAAGGACAGCACCTACAGCCTCAGCAGCACCCTGACG |
| | | CTGAGCAAAGCAGACTACGAGAAACACAAAGTCTACGCCTGCGAAGT |
| | | CACCCATCAGGGCCTGAGCTCGCCCGTCACAAAGAGCTTCAACAGGG |
| | | GAGAGTGT |
| 44 | 6.147-AbL-Ab5 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVLGQPKAAPSVTLFPPDIQMTQSPSSLSASVGDRVTITCRASQD ISNYLNWYQQKPGKAPKLLIYYTSRLLSGVPSRFSGSGSGTDFTLTISSLQ PEDFATYYCQQGDTLPYTFGGGTKVEIKR*TVAAPSVFIFPPSDEQLKSGT ASVVCLLNNFYPREAKVQWKVDNALQSGNSQESVTEQDSKDSTYSLSSTL TLSKADYEKHKVYACEVTHQGLSSPVTKSFNRGEC* |
| 45 | 6.147-AbS-Ab5K G2 NA | CAGGTGCAGCTTGTCGAGAGCGGTGGAGGGGTGGTACAACCCGGAAG ATCACTCCGGCTTTCATGCGCAGCATCCGGTTTTACATTTTCGCGGTAT GACATGCACTGGGTGAGACAGGCACCAGGAAAAGGGCTGGAGTGGGT GGCCATCATCTTCTATGATGGGTCCAATAAGTACTACGCCGACCCGGT AAAAGGGAGGTTCACTATTAGCCGCGACAACTCGAAGAATACGCTGT ACCTGCAGATGAACTCGTTGCGAGCCGAAGATACCGCGGTCTACTATT GTGCGACGCTCGCGGCTGCGTTCGATTACTGGGGCCAAGGAACATTGG TCACGGTCTCCTCAGCGTCAACGAAAGGACCGGAGGTGCAGCTCGTG CAGTCCGGAGCCGAGGTGGTGCAGCCTGGGGCATCCGTCAAAGTCTC GTGCGCCGCGTCAGGGTACACATTCACCGACTATAACATGCATTGGGT CCGGCAGGCTCCCGGTCAGGGGCTGGAGTGGATGGGGGAAATCAATC CGAACTCCGGAGGGGCAGGATACAATCAAAAGTTTAAGGGACGCGTA ACGATGACCACTGACACGTCAACCTCCACGGCGTATATGGAGCTCAG AAGCCTCCGAAGCGACGACACTGCTGTCTATTACTGTGCGAGACTGGG ATATGATGATATCTACGACGATTGGTACTTCGATGTATGGGGACAAGG GACGACGGTCACCGTCTCTAGTGCCTCCACCAAGGGCCCATCGGTCTT CCCCCTGGCGCCCTGCTCCAGGAGCACCTCCGAGAGCACAGCGGCCCT GGGCTGCCTGGTCAAGGACTACTTCCCCGAACCGGTGACGGTGTCGTG GAACTCAGGCGCTCTGACCAGCGGCGTGCACACCTTCCCAGCTGTCCT ACAGTCCTCAGGACTCTACTCCCTCAGCAGCGTGGTGACCGTGCCCTC CAGCAACTTCGGCACCCAGACCTACACCTGCAACGTAGATCACAAGC CCAGCAACACCAAGGTGGACAAGACAGTTGAGCGCAAATGTTGTGTC GAGTGCCCACCGTGCCCAGCACCACCTGTGGCAGGACCGTCAGTCTTC CTCTTCCCCCCAAAACCCAAGGACACCCTCATGATCTCCCGGACCCCT |

| SEQ ID NO: | DESCRIPTION | SEQUENCE |
|---|---|---|
| | | GAGGTCACGTGCGTGGTGGTGGACGTGAGCCACGAAGACCCCGAGGT |
| | | CCAGTTCAACTGGTACGTGGACGGCGTGGAGGTGCATAATGCCAAGA |
| | | CAAAGCCACGGGAGGAGCAGTTCAACAGCACGTTCCGTGTGGTCAGC |
| | | GTCCTCACCGTTGTGCACCAGGACTGGCTGAACGGCAAGGAGTACAA |
| | | GTGCAAGGTCTCCAACAAAGGCCTCCCAGCCCCCATCGAGAAAACCA |
| | | TCTCCAAAACCAAAGGGCAGCCCCGAGAACCACAGGTGTACACCCTG |
| | | CCCCCATCCCGGGAGGAGATGACCAAGAACCAGGTCAGCCTGACCTG |
| | | CCTGGTCAAAGGCTTCTACCCCAGCGACATCGCCGTGGAGTGGGAGA |
| | | GCAATGGGCAGCCGGAGAACAACTACAAGACCACACCTCCCATGCTG |
| | | GACTCCGACGGCTCCTTCTTCCTCTACAGCAAGCTCACCGTGGACAAG |
| | | AGCAGGTGGCAGCAGGGGAACGTCTTCTCATGCTCCGTGATGCATGA |
| | | GGCTCTGCACAACCACTACACGCAGAAGAGCCTCTCCCTGTCTCCGGG |
| | | TAAA |
| 46 | 6.147-AbS-Ab5K G2 AA | QVQLVESGGGVVQPGRSLRLSCAASGFTFSRYDMHWVRQAPGKGLEW |
| | | VAIIFYDGSNKYYADPVKGRFTISRDNSKNTLYLQMNSLRAEDTAVYYC |
| | | ATLAAAFDYWGQGTLVTVSSASTKGPEVQLVQSGAEVVQPGASVKVSC |
| | | AASGYTFTDYNMHWVRQAPGQGLEWMGEINPNSGGAGYNQKFKGRV |
| | | TMTTDTSTSTAYMELRSLRSDDTAVYYCARLGYDDIYDDWYFDVWGQ |
| | | GTTVTVSS*ASTKGPSVFPLAPCSRSTSESTAALGCLVKDYFPEPVTVSWNS* |
| | | *GALTSGVHTFPAVLQSSGLYSLSSVVTVPSSNFGTQTYTCNVDHKPSNTK* |
| | | *VDKTVERKCCVECPPCPAPPVAGPSVFLFPPKPKDTLMISRTPEVTCVVV* |
| | | *DVSHEDPEVQFNWYVDGVEVHNAKTKPREEQFNSTFRVVSVLTVVHQD* |
| | | *WLNGKEYKCKVSNKGLPAPIEKTISKTKGQPREPQVYTLPPSREEMTKNQ* |
| | | *VSLTCLVKGFYPSDIAVEWESNGQPENNYKTTPPMLDSDGSFFLYSKLTV* |
| | | *DKSRWQQGNVFSCSVMHEALHNHYTQKSLSLSPGK* |
| 47 | 6.147-AbS-Ab5 LC NA | TCATACGTGCTCACTCAGCCGCCCAGCGTATCGGTGGCTCCCGGACAG |
| | | ACGGCGCGAATCACGTGCGGTGGGAACAATATCGGCTCCAAGTCAGT |
| | | CCATTGGTATCAACAGAAACCTGGTCAGGCACCAGTCCTGGTGGTATA |
| | | CGATGACTCGGACAGGCCCTCGGAGATTCCGGAACGCTTCTCCGGATC |
| | | GAATTCGGGGAACACAGCGACCTTGACGATCAGCAGAGTGGAGGCCG |
| | | GAGATGAAGCCGACTACTATTGTCAGGTGTGGGATTCCAGCTCCGACC |
| | | ACGTCGTATTTGGAGGTGGGACACGGCTTACCGTCCTCGGGCAGCCCA |
| | | AGGCTGCGCCAGACATTCAGATGACTCAGTCGCCTTCGTCATTGAGCG |
| | | CGTCGGTGGGAGATCGGGTCACGATTACTTGTCGGGCATCGCAAGAC |
| | | ATCTCGAACTATTTGAATTGGTACCAGCAAAAGCCTGGTAAAGCGCCC |
| | | AAACTTCTTATCTACTATACGTCCCGCCTCCTCTCGGGCGTCCCGTCAA |
| | | GGTTTAGCGGATCGGGAAGCGGGACGGATTTCACACTGACGATTTCAT |
| | | CACTTCAGCCCGAAGATTTCGCCACCTATTACTGTCAGCAAGGAGACA |

TABLE 1-continued

| SEQ ID NO: | DESCRIPTION | SEQUENCE |
|---|---|---|
| | | CCCTGCCATACACTTTTGGCGGTGGGACAAAGGTCGAAATCAAGCGTA |
| | | CGGTGGCTGCACCATCTGTCTTCATCTTCCCGCCATCTGATGAGCAGTT |
| | | GAAATCTGGAACTGCCTCTGTTGTGTGCCTGCTGAATAACTTCTATCCC |
| | | AGAGAGGCCAAAGTACAGTGGAAGGTGGATAACGCCCTCCAATCGGG |
| | | TAACTCCCAGGAGAGTGTCACAGAGCAGGACAGCAAGGACAGCACCT |
| | | ACAGCCTCAGCAGCACCCTGACGCTGAGCAAAGCAGACTACGAGAAA |
| | | CACAAAGTCTACGCCTGCGAAGTCACCCATCAGGGCCTGAGCTCGCCC |
| | | GTCACAAAGAGCTTCAACAGGGGAGAGTGT |
| 48 | 6.147-AbS-Ab5 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVLGQPKAAPDIQMTQSPSSLSASVGDRVTITCRASQDISNYLN WYQQKPGKAPKLLIYYTSRLLSGVPSRFSGSGSGTDFTLTISSLQPEDFAT YYCQQGDTLPYTFGGGTKVEIKR*TVAAPSVFIFPPSDEQLKSGTASVVCL* *LNNFYPREAKVQWKVDNALQSGNSQESVTEQDSKDSTYSLSSTLTLSKAD* *YEKHKVYACEVTHQGLSSPVTKSFNRGEC* |
| 49 | 6.37-AbL-Ab23 G2 NA | CAGGTACAACTGGTCGAGTCAGGTGGAGGCGTGGTCCAGCCCGGACG GTCGCTCAGGCTCAGCTGTGCTGCGTCAGGGTTCACCTTTTCGGGGTA TGGGATGCACTGGGTGCGCCAAGCACCGGGAAAAGGGCTTGAATGGG TCGCGGTCATTTCCTACGACGGGAACGACAAATACTACGCGGACTCCG TAAAGGGAAGGTTCACAATCAGCCGGGATAACGCCAAGAATACGTTG TATCTCCAGATGAATTCGTTGCGAGCAGAAGATACGGCCGTGTACTAT TGCGCGAGAGAGCTTCGCGTGTTGTGGGGACAGGGTACTCTGGTGAC GGTCTCCTCAGCGTCAACGAAAGGACCGTCGGTGTTCCCCTTGGCCCC TGAGGTGCAGCTCGTACAGTCGGGTGCGGAAGTAAAGAAACCCGGCT CATCCGTGAAAGTCTCGTGTAAAGCCTCCGGGTTCACCTTCACAGACT ACATTATGCACTGGGTGCGGCAGGCCCCTGGGCAGGGCCTTGAATGG ATGGGGTATATCAACCCCTACAATGATGACACGGAGTATAACGAAAA GTTTAAGGGAAGGGTGACAATCACGGCGGATAAGAGCACCAGCACTG CATACATGGAGCTCTCGTCATTGCGCTCGGAGGACACTGCAGTCTACT ATTGCGCGAGATCCATCTACTATTACGATGCGCCGTTTGCTTATTGGG GACAAGGAACGCTGGTCACCGTCTCTAGTGCCTCCACCAAGGGCCCAT CGGTCTTCCCCCTGGCGCCCTGCTCCAGGAGCACCTCCGAGAGCACAG CGGCCCTGGGCTGCCTGGTCAAGGACTACTTCCCCGAACCGGTGACGG TGTCGTGGAACTCAGGCGCTCTGACCAGCGGCGTGCACACCTTCCCAG CTGTCCTACAGTCCTCAGGACTCTACTCCCTCAGCAGCGTGGTGACCG TGCCCTCCAGCAACTTCGGCACCCAGACCTACACCTGCAACGTAGATC ACAAGCCCAGCAACACCAAGGTGGACAAGACAGTTGAGCGCAAATGT |

TABLE 1-continued

| SEQ ID NO: | DESCRIPTION | SEQUENCE |
|---|---|---|
| | | TGTGTCGAGTGCCCACCGTGCCCAGCACCACCTGTGGCAGGACCGTCA |
| | | GTCTTCCTCTTCCCCCCAAAACCCAAGGACACCCTCATGATCTCCCGG |
| | | ACCCCTGAGGTCACGTGCGTGGTGGTGGACGTGAGCCACGAAGACCC |
| | | CGAGGTCCAGTTCAACTGGTACGTGGACGGCGTGGAGGTGCATAATG |
| | | CCAAGACAAAGCCACGGGAGGAGCAGTTCAACAGCACGTTCCGTGTG |
| | | GTCAGCGTCCTCACCGTTGTGCACCAGGACTGGCTGAACGGCAAGGA |
| | | GTACAAGTGCAAGGTCTCCAACAAAGGCCTCCCAGCCCCCATCGAGA |
| | | AAACCATCTCCAAAACCAAAGGGCAGCCCCGAGAACCACAGGTGTAC |
| | | ACCCTGCCCCCATCCCGGGAGGAGATGACCAAGAACCAGGTCAGCCT |
| | | GACCTGCCTGGTCAAAGGCTTCTACCCCAGCGACATCGCCGTGGAGTG |
| | | GGAGAGCAATGGGCAGCCGGAGAACAACTACAAGACCACACCTCCCA |
| | | TGCTGGACTCCGACGGCTCCTTCTTCCTCTACAGCAAGCTCACCGTGG |
| | | ACAAGAGCAGGTGGCAGCAGGGGAACGTCTTCTCATGCTCCGTGATG |
| | | CATGAGGCTCTGCACAACCACTACACGCAGAAGAGCCTCTCCCTGTCT |
| | | CCGGGTAAA |
| 50 | 6.37-AbL-Ab23 G2 AA | QVQLVESGGGVVQPGRSLRLSCAASGFTFSGYGMHWVRQAPGKGLEWVAVISYDGNDKYYADSVKGRFTISRDNAKNTLYLQMNSLRAEDTAVYYCARELRVLWGQGTLVTVSSASTKGPSVFLAPEVQLVQSGAEVKKPGSSVKVSCKASGFTFTDYIMHWVRQAPGQGLEWMGYINPYNDDTEYNEKF KGRVTITADKSTSTAYMELSSLRSEDTAVYYCARSIYYYDAPFAYWGQGTLVTVSS*ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK* |
| 51 | 6.37-AbL-Ab23 LC NA | GATATTGTGATGACCCAGACGCCGTTGTCACTGAGCGTCACACCCGGACAGCCCGCGTCGATTAGCTGCAAATCGGGACAATCGCTTCTCCACTCGGACGGGAAAACGTATCTTTACTGGTATTTGCAAAAGCCAGGGCAGCCTCCCCAGTTTCTTATCTACGAAGTGTCGAACAGGTTTTCCAGAGTACCTGACCGATTCTCCGGATCAGGTAGCGGAACGGACTTCACTCTGCGCATCTCACGGGTCGAAGCCGAGGATGTGGGCATCTACTACTGTATGCAGTCAATTCAGCTCCCGTGGACATTCGGTCAGGGGACCCAAGTAGAGATCAAGCGCACAGTGGCTGCTCCATCCGTCTTTATCTTCCCTCCAGACATTCAAATGACACAGTCGCCCTCCTCGCTCTCGGCGTCAGTCGGGGATCGCGTGACAATCACGTGTCGGGCCAGCCAGGACATTTCGAGCTACCTCAACTGGTATCAGCAGAAACCGGGGAAAGCGCCGAAGCTGCTTATCTACTCCAC

TABLE 1-continued

| SEQ ID NO: | DESCRIPTION | SEQUENCE |
|---|---|---|
| | | CTCAAGGTTGAATTCCGGAGTACCCTCAAGATTTTCGGGTAGCGGATC |
| | | AGGAACCGACTTCACACTTACGATCTCGTCGTTGCAGCCAGAAGATTT |
| | | CGCAACGTACTATTGCCAGCAAGATATCAAGCACCCTACGTTTGGTCA |
| | | GGGCACTAAAGTGGAGATTAAGCGTACGGTGGCTGCACCATCTGTCTT |
| | | CATCTTCCCGCCATCTGATGAGCAGTTGAAATCTGGAACTGCCTCTGT |
| | | TGTGTGCCTGCTGAATAACTTCTATCCCAGAGAGGCCAAAGTACAGTG |
| | | GAAGGTGGATAACGCCCTCCAATCGGGTAACTCCCAGGAGAGTGTCA |
| | | CAGAGCAGGACAGCAAGGACAGCACCTACAGCCTCAGCAGCACCCTG |
| | | ACGCTGAGCAAAGCAGACTACGAGAAACACAAAGTCTACGCCTGCGA |
| | | AGTCACCCATCAGGGCCTGAGCTCGCCCGTCACAAAGAGCTTCAACA |
| | | GGGGAGAGTGT |
| 52 | 6.37-AbL-Ab23 LC AA | DIVMTQTPLSLSVTPGQPASISCKSGQSLLHSDGKTYLYWYLQKPGQPP |
| | | QFLIYEVSNRFSRVPDRFSGSGSGTDFTLRISRVEAEDVGIYYCMQSIQLP |
| | | WTFGQGTQVEIKR*TVAAPSVFIFPPP*DIQMTQSPSSLSASVGDRVTITCRAS |
| | | QDISSYLNWYQQKPGKAPKLLIYSTSRLNSGVPSRFSGSGSGTDFTLTISS |
| | | LQPEDFATYYCQQDIKHPTFGQGTKVEIKR*TVAAPSVFIFPPSDEQLKSG* |
| | | *TASVVCLLNNFYPREAKVQWKVDNALQSGNSQESVTEQDSKDSTYSLSST* |
| | | *LTLSKADYEKHKVYACEVTHQGLSSPVTKSFNRGEC* |
| 53 | Ab5K-AbL-6.147 G2 NA | GAGGTGCAGCTCGTGCAGTCCGGAGCCGAGGTGGTGCAGCCTGGGGC |
| | | ATCCGTCAAAGTCTCGTGCGCCGCGTCAGGGTACACATTCACCGACTA |
| | | TAACATGCATTGGGTCCGGCAGGCTCCCGGTCAGGGCTGGAGTGGA |
| | | TGGGGGAAATCAATCCGAACTCCGGAGGGGCAGGATACAATCAAAAG |
| | | TTTAAGGGACGCGTAACGATGACCACTGACACGTCAACCTCCACGGC |
| | | GTATATGGAGCTCAGAAGCCTCCGAAGCGACGACACTGCTGTCTATTA |
| | | CTGTGCGAGACTGGGATATGATGATATCTACGACGATTGGTACTTCGA |
| | | TGTATGGGGACAAGGGACGACGGTCACGGTCTCCTCAGCGTCAACGA |
| | | AAGGACCGTCGGTGTTCCCCTTGGCCCCTCAGGTGCAGCTTGTCGAGA |
| | | GCGGTGGAGGGGTGGTACAACCCGGAAGATCACTCCGGCTTTCATGC |
| | | GCAGCATCCGGTTTTACATTTTCGCGGTATGACATGCACTGGGTGAGA |
| | | CAGGCACCAGGAAAGGGCTGGAGTGGGTGGCCATCATCTTCTATGA |
| | | TGGGTCCAATAAGTACTACGCCGACCCGGTAAAAGGGAGGTTCACTA |
| | | TTAGCCGCGACAACTCGAAGAATACGCTGTACCTGCAGATGAACTCGT |
| | | TGCGAGCCGAAGATACCGCGGTCTACTATTGTGCGACGCTCGCGGCTG |
| | | CGTTCGATTACTGGGGCCAAGGAACATTGGTCACCGTCTCTAGTGCCT |
| | | CCACCAAGGGCCCATCGGTCTTCCCCCTGGCGCCCTGCTCCAGGAGCA |
| | | CCTCCGAGAGCACAGCGGCCCTGGGCTGCCTGGTCAAGGACTACTTCC |
| | | CCGAACCGGTGACGGTGTCGTGGAACTCAGGCGCTCTGACCAGCGGC |

TABLE 1-continued

| SEQ ID NO: | DESCRIPTION | SEQUENCE |
|---|---|---|
| | | GTGCACACCTTCCCAGCTGTCCTACAGTCCTCAGGACTCTACTCCCTC |
| | | AGCAGCGTGGTGACCGTGCCCTCCAGCAACTTCGGCACCCAGACCTAC |
| | | ACCTGCAACGTAGATCACAAGCCCAGCAACACCAAGGTGGACAAGAC |
| | | AGTTGAGCGCAAATGTTGTGTCGAGTGCCCACCGTGCCCAGCACCACC |
| | | TGTGGCAGGACCGTCAGTCTTCCTCTTCCCCCCAAAACCCAAGGACAC |
| | | CCTCATGATCTCCCGGACCCCTGAGGTCACGTGCGTGGTGGTGGACGT |
| | | GAGCCACGAAGACCCCGAGGTCCAGTTCAACTGGTACGTGGACGGCG |
| | | TGGAGGTGCATAATGCCAAGACAAAGCCACGGGAGGAGCAGTTCAAC |
| | | AGCACGTTCCGTGTGGTCAGCGTCCTCACCGTTGTGCACCAGGACTGG |
| | | CTGAACGGCAAGGAGTACAAGTGCAAGGTCTCCAACAAAGGCCTCCC |
| | | AGCCCCCATCGAGAAAACCATCTCCAAAACCAAAGGGCAGCCCCGAG |
| | | AACCACAGGTGTACACCCTGCCCCCATCCCGGGAGGAGATGACCAAG |
| | | AACCAGGTCAGCCTGACCTGCCTGGTCAAAGGCTTCTACCCCAGCGAC |
| | | ATCGCCGTGGAGTGGGAGAGCAATGGGCAGCCGGAGAACAACTACAA |
| | | GACCACACCTCCCATGCTGGACTCCGACGGCTCCTTCTTCCTCTACAG |
| | | CAAGCTCACCGTGGACAAGAGCAGGTGGCAGCAGGGGAACGTCTTCT |
| | | CATGCTCCGTGATGCATGAGGCTCTGCACAACCACTACACGCAGAAG |
| | | AGCCTCTCCCTGTCTCCGGGTAAA |
| 54 | Ab5K-AbL-6.147 G2 AA | EVQLVQSGAEVVQPGASVKVSCAASGYTFTDYNMHWRQAPGQGLEW MGEINPNSGGAGYNQKFKGRVTMTTDTSTSTAYMELRSLRSDDTAVYY CARLGYDDIYDDWYFDVWGQGTTVTVSSASTKGPSVFPLAPQVQLVES GGGVVQPGRSLRLSCAASGFTFSRYDMHWVRQAPGKGLEWVAIIFYDG SNKYYADPVKGRFTISRDNSKNTLYLQMNSLRAEDTAVYYCATLAAAF DYWGQGTLVTVSS*ASTKGPSVFPLAPCSRSTSESTAALGCLVKDYFPEPV TVSWNSGALTSGVHTFPAVLQSSGLYSLSSVVTVPSSNFGTQTYTCNVDH KPSNTKVDKTVERKCCVECPPCPAPPVAGPSVFLFPPKPKDTLMISRTPE VTCVVVDVSHEDPEVQFNWYVDGVEVHNAKTKPREEQFNSTFRVVSVLT VVHQDWLNGKEYKCKVSNKGLPAPIEKTISKTKGQPREPQVYTLPPSREE MTKNQVSLTCLVKGFYPSDIAVEWESNGQPENNYKTTPPMLDSDGSFFL YSKLTVDKSRWQQGNVFSCSVMHEALHNHYTQKSLSLSPGK* |
| 55 | Ab5K-AbS-6.147 G2 NA | GAGGTGCAGCTCGTGCAGTCCGGAGCCGAGGTGGTGCAGCCTGGGGC ATCCGTCAAAGTCTCGTGCGCCGCGTCAGGGTACACATTCACCGACTA TAACATGCATTGGGTCCGGCAGGCTCCCGGTCAGGGCTGGAGTGGA TGGGGGAAATCAATCCGAACTCCGGAGGGGCAGGATACAATCAAAAG TTTAAGGGACGCGTAACGATGACCACTGACACGTCAACCTCCACGGC GTATATGGAGCTCAGAAGCCTCCGAAGCGACGACACTGCTGTCTATTA CTGTGCGAGACTGGGATATGATGATATCTACGACGATTGGTACTTCGA TGTATGGGGACAAGGGACGACGGTCACGGTCTCCTCAGCGTCAACGA |

TABLE 1-continued

| SEQ ID NO: | DESCRIPTION | SEQUENCE |
|---|---|---|
| | | AAGGACCGCAGGTGCAGCTTGTCGAGAGCGGTGGAGGGGTGGTACAA |
| | | CCCGGAAGATCACTCCGGCTTTCATGCGCAGCATCCGGTTTTACATTTT |
| | | CGCGGTATGACATGCACTGGGTGAGACAGGCACCAGGAAAAGGGCTG |
| | | GAGTGGGTGGCCATCATCTTCTATGATGGGTCCAATAAGTACTACGCC |
| | | GACCCGGTAAAAGGGAGGTTCACTATTAGCCGCGACAACTCGAAGAA |
| | | TACGCTGTACCTGCAGATGAACTCGTTGCGAGCCGAAGATACCGCGGT |
| | | CTACTATTGTGCGACGCTCGCGGCTGCGTTCGATTACTGGGGCCAAGG |
| | | AACATTGGTCACCGTCTCTAGTGCCTCCACCAAGGGCCCATCGGTCTT |
| | | CCCCCTGGCGCCCTGCTCCAGGAGCACCTCCGAGAGCACAGCGGCCCT |
| | | GGGCTGCCTGGTCAAGGACTACTTCCCCGAACCGGTGACGGTGTCGTG |
| | | GAACTCAGGCGCTCTGACCAGCGGCGTGCACACCTTCCCAGCTGTCTT |
| | | ACAGTCCTCAGGACTCTACTCCCTCAGCAGCGTGGTGACCGTGCCCTC |
| | | CAGCAACTTCGGCACCCAGACCTACACCTGCAACGTAGATCACAAGC |
| | | CCAGCAACACCAAGGTGGACAAGACAGTTGAGCGCAAATGTTGTGTC |
| | | GAGTGCCCACCGTGCCCAGCACCACCTGTGGCAGGACCGTCAGTCTTC |
| | | CTCTTCCCCCCAAAACCCAAGGACACCCTCATGATCTCCCGGACCCCT |
| | | GAGGTCACGTGCGTGGTGGTGGACGTGAGCCACGAAGACCCCGAGGT |
| | | CCAGTTCAACTGGTACGTGGACGGCGTGGAGGTGCATAATGCCAAGA |
| | | CAAAGCCACGGGAGGAGCAGTTCAACAGCACGTTCCGTGTGGTCAGC |
| | | GTCCTCACCGTTGTGCACCAGGACTGGCTGAACGGCAAGGAGTACAA |
| | | GTGCAAGGTCTCCAACAAAGGCCTCCCAGCCCCCATCGAGAAAACCA |
| | | TCTCCAAAACCAAAGGGCAGCCCCGAGAACCACAGGTGTACACCCTG |
| | | CCCCCATCCCGGGAGGAGATGACCAAGAACCAGGTCAGCCTGACCTG |
| | | CCTGGTCAAAGGCTTCTACCCCAGCGACATCGCCGTGGAGTGGGAGA |
| | | GCAATGGGCAGCCGGAGAACAACTACAAGACCACACCTCCCATGCTG |
| | | GACTCCGACGGCTCCTTCTTCCTCTACAGCAAGCTCACCGTGGACAAG |
| | | AGCAGGTGGCAGCAGGGGAACGTCTTCTCATGCTCCGTGATGCATGA |
| | | GGCTCTGCACAACCACTACACGCAGAAGAGCCTCTCCCTGTCTCCGGG |
| | | TAAA |

TABLE 1-continued

| SEQ ID NO: | DESCRIPTION | SEQUENCE |
|---|---|---|
| 56 | Ab5K-AbS-6.147 G2 AA | EVQLVQSGAEVVQPGASVKVSCAASGYTFTDYNMHWVRQAPGQGLEW MGEINPNSGGAGYNQKFKGRVTMTTDTSTSTAYMELRSLRSDDTAVYY CARLGYDDIYDDWYFDVWGQGTTVTVSS<u>ASTKGP</u>QLQLVESGGGVVQP GRSLRLSCAASGFTFSRYDMHWVRQAPGKGLEWVAIIFYDGSNKYYAD PVKGRFTISRDNSKNTLYLQMNSLRAEDTAVYYCATLAAAFDYWGQGT LVTVSS*ASTKGPSVFPLAPCSRSTSESTAALGCLVKDYFPEPVTVSWNSGA LTSGVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVVDV SHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDK SRWQQGNVFSCSVMHEALHNHYTQKSLSLSPGK* |
| 57 | 6.37-3x-Ab23 G2 NA | CAGGTACAACTGGTCGAGTCAGGTGGAGGCGTGGTCCAGCCCGGACG GTCGCTCAGGCTCAGCTGTGCTGCGTCAGGGTTCACCTTTTCGGGGTA TGGGATGCACTGGGTGCGCCAAGCACCGGGAAAGGGCTTGAATGGG TCGCGGTCATTTCCTACGACGGGAACGACAAATACTACGCGGACTCCG TAAAGGGAAGGTTCACAATCAGCCGGGATAACGCCAAGAATACGTTG TATCTCCAGATGAATTCGTTGCGAGCAGAAGATACGGCCGTGTACTAT TGCGCGAGAGAGCTTCGCGTGTTGTGGGGACAGGGTACTCTGGTGAC AGTGAGCTCAGGGGGTGGCGGTTCGGGCGGTGGAGGCTCGGGAGGTG GTGGATCCGAGGTGCAGCTCGTACAGTCGGGTGCGGAAGTAAAGAAA CCCGGCTCATCCGTGAAAGTCTCGTGTAAAGCCTCCGGGTTCACCTTC ACAGACTACATTATGCACTGGGTGCGGCAGGCCCCTGGGCAGGGCCTT GAATGGATGGGGTATATCAACCCCTACAATGATGACACGGAGTATAA CGAAAAGTTTAAGGGAAGGGTGACAATCACGGCGGATAAGAGCACCA GCACTGCATACATGGAGCTCTCGTCATTGCGCTCGGAGGACACTGCAG TCTACTATTGCGCGAGATCCATCTACTATTACGATGCGCCGTTTGCTTA TTGGGGACAAGGAACGCTGGTCACCGTCTCTAGTGCCTCCACCAAGGG CCCATCGGTCTTCCCCCTGGCGCCCTGCTCCAGGAGCACCTCCGAGAG CACAGCGGCCCTGGGCTGCCTGGTCAAGGACTACTTCCCCGAACCGGT GACGGTGTCGTGGAACTCAGGCGCTCTGACCAGCGGCGTGCACACCTT CCCAGCTGTCCTACAGTCCTCAGGACTCTACTCCCTCAGCAGCGTGGT GACCGTGCCCTCCAGCAACTTCGGCACCCAGACCTACACCTGCAACGT AGATCACAAGCCCAGCAACACCAAGGTGGACAAGACAGTTGAGCGCA AATGTTGTGTCGAGTGCCCACCGTGCCCAGCACCACCTGTGGCAGGAC CGTCAGTCTTCCTCTTCCCCCCAAAACCCAAGGACACCCTCATGATCT CCCGGACCCCTGAGGTCACGTGCGTGGTGGTGGACGTGAGCCACGAA |

| SEQ ID NO: | DESCRIPTION | SEQUENCE |
|---|---|---|
| | | GACCCCGAGGTCCAGTTCAACTGGTACGTGGACGGCGTGGAGGTGCA |
| | | TAATGCCAAGACAAAGCCACGGGAGGAGCAGTTCAACAGCACGTTCC |
| | | GTGTGGTCAGCGTCCTCACCGTTGTGCACCAGGACTGGCTGAACGGCA |
| | | AGGAGTACAAGTGCAAGGTCTCCAACAAAGGCCTCCCAGCCCCCATC |
| | | GAGAAAACCATCTCCAAAACCAAAGGGCAGCCCCGAGAACCACAGGT |
| | | GTACACCCTGCCCCCATCCCGGGAGGAGATGACCAAGAACCAGGTCA |
| | | GCCTGACCTGCCTGGTCAAAGGCTTCTACCCCAGCGACATCGCCGTGG |
| | | AGTGGGAGAGCAATGGGCAGCCGGAGAACAACTACAAGACCACACCT |
| | | CCCATGCTGGACTCCGACGGCTCCTTCTTCCTCTACAGCAAGCTCACC |
| | | GTGGACAAGAGCAGGTGGCAGCAGGGGAACGTCTTCTCATGCTCCGT |
| | | GATGCATGAGGCTCTGCACAACCACTACACGCAGAAGAGCCTCTCCCT |
| | | GTCTCCGGGTAAA |
| 58 | 6.37-3x-Ab23 G2 AA | QVQLVESGGGVVQPGRSLRLSCAASGFTFSGYGMHWVRQAPGKGLEWVAVISYDGNDKYYADSVKGRFTISRDNAKNTLYLQMNSLRAEDTAVYYCARELRVLWGQGTLVTVSSGGGGSGGGGSGGGGSEVQLVQSGAEVKKPGSSVKVSCKASGFTFTDYIMHWVRQAPGQGLEWMGYINPYNDDTEYNEKFKGRVTITADKSTSTAYMELSSLRSEDTAVYYCARSIYYYDAPFAYWGQGTLVTVSS*ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK* |
| 59 | 6.37-3x-Ab23 LC NA | GATATTGTGATGACCCAGACGCCGTTGTCACTGAGCGTCACACCCGGA |
| | | CAGCCCGCGTCGATTAGCTGCAAATCGGGACAATCGCTTCTCCACTCG |
| | | GACGGGAAAACGTATCTTTACTGGTATTTGCAAAAGCCAGGGCAGCCT |
| | | CCCCAGTTTCTTATCTACGAAGTGTCGAACAGGTTTTCCAGAGTACCT |
| | | GACCGATTCTCCGGATCAGGTAGCGGAACGGACTTCACTCTGCGCATC |
| | | TCACGGGTCGAAGCCGAGGATGTGGGCATCTACTACTGTATGCAGTCA |
| | | ATTCAGCTCCCGTGGACATTCGGTCAGGGGACCCAAGTAGAGATCAA |
| | | GGGGGGTGGCGGTTCGGGCGGTGGAGGCTCGGAGGTGGTGGATCCG |
| | | ACATTCAAATGACACAGTCGCCCTCCTCGCTCTCGGCGTCAGTCGGGG |
| | | ATCGCGTGACAATCACGTGTCGGGCCAGCCAGGACATTTCGAGCTACC |
| | | TCAACTGGTATCAGCAGAAACCGGGGAAAGCGCCGAAGCTGCTTATC |
| | | TACTCCACCTCAAGGTTGAATTCCGGAGTACCCTCAAGATTTTCGGGT |
| | | AGCGGATCAGGAACCGACTTCACACTTACGATCTCGTCGTTGCAGCCA |
| | | GAAGATTTCGCAACGTACTATTGCCAGCAAGATATCAAGCACCCTACG |

TABLE 1-continued

| SEQ ID NO: | DESCRIPTION | SEQUENCE |
|---|---|---|
| | | TTTGGTCAGGGCACTAAAGTGGAGATTAAGCGTACGGTGGCTGCACC |
| | | ATCTGTCTTCATCTTCCCGCCATCTGATGAGCAGTTGAAATCTGGAACT |
| | | GCCTCTGTTGTGTGCCTGCTGAATAACTTCTATCCCAGAGAGGCCAAA |
| | | GTACAGTGGAAGGTGGATAACGCCCTCCAATCGGGTAACTCCCAGGA |
| | | GAGTGTCACAGAGCAGGACAGCAAGGACAGCACCTACAGCCTCAGCA |
| | | GCACCCTGACGCTGAGCAAAGCAGACTACGAGAAACACAAAGTCTAC |
| | | GCCTGCGAAGTCACCCATCAGGGCCTGAGCTCGCCCGTCACAAAGAG |
| | | CTTCAACAGGGGAGAGTGT |
| 60 | 6.37-3x-Ab23 LC AA | DIVMTQTPLSLSVTPGQPASISKSGQSLLHSDGKTYLYWYLQKPGQPP |
| | | QFLIYEVSNRFSRVPDRFSGSGSGTDFTLRISRVEAEDVGIYYMQSIQLP |
| | | WTFGQGTQVEIKGGGGSGGGGSGGGGSDIQMTQSPSSLSASVGDRVTIT |
| | | CRASQDISSYLNWYQQKPGKAPKLLIYSTSRLNSGVPSRFSGSGSGTDFT |
| | | LTISSLQPEDFATYYCQQDIKHPTFGQGTKVEIKR*TVAAPSVFIFPPSDEQ* |
| | | *LKSGTASVVCLLNNFYPREAKVQWKVDNALQSGNSQESVTEQDSKDSTYS* |
| | | *LSSTLTLSKADYEKHKVYACEVTHQGLSSPVTKSFNRGEC* |
| 61 | 6.147-2x-Ab5 G2 NA | CAGGTGCAGCTTGTCGAGAGCGGTGGAGGGGTGGTACAACCCGGAAG |
| | | ATCACTCCGGCTTTCATGCGCAGCATCCGGTTTTACATTTTCGCGGTAT |
| | | GACATGCACTGGGTGAGACAGGCACCAGGAAAAGGGCTGGAGTGGGT |
| | | GGCCATCATCTTCTATGATGGGTCCAATAAGTACTACGCCGACCCGGT |
| | | AAAAGGGAGGTTCACTATTAGCCGCGACAACTCGAAGAATACGCTGT |
| | | ACCTGCAGATGAACTCGTTGCGAGCCGAAGATACCGCGGTCTACTATT |
| | | GTGCGACGCTCGCGGCTGCGTTCGATTACTGGGGCCAAGGAACATTGG |
| | | TCACAGTGAGCTCAGGCGGTGGAGGCTCGGAGGTGGTGGATCCGAG |
| | | GTGCAGCTCGTGCAGTCCGGAGCCGAGGTGAAGAAGCCTGGGGCATC |
| | | CGTCAAAGTCTCGTGCAAGGCGTCAGGGTACACATTCACCGACTATAA |
| | | CATGCATTGGGTCCGGCAGGCTCCCGGTCAGGGGCTGGAGTGGATGG |
| | | GGGAAATCAATCCGAACTCCGGAGGGGCAGGATACAATCAAAAGTTT |
| | | AAGGGACGCGTAACGATGACCACTGACACGTCAACCTCCACGGCGTA |
| | | TATGGAGCTCAGAAGCCTCCGAAGCGACGACACTGCTGTCTATTACTG |
| | | TGCGAGACTGGGATATGATGATATCTACGACGATTGGTACTTCGATGT |
| | | ATGGGGACAAGGGACGACGGTCACCGTCTCTAGTGCCTCCACCAAGG |
| | | GCCCATCGGTCTTCCCCCTGGCGCCCTGCTCCAGGAGCACCTCCGAGA |
| | | GCACAGCGGCCCTGGGCTGCCTGGTCAAGGACTACTTCCCCGAACCG |
| | | GTGACGGTGTCGTGGAACTCAGGCGCTCTGACCAGCGGCGTGCACAC |
| | | CTTCCCAGCTGTCCTACAGTCCTCAGGACTCTACTCCCTCAGCAGCGT |
| | | GGTGACCGTGCCCTCCAGCAACTTCGGCACCCAGACCTACACCTGCAA |
| | | CGTAGATCACAAGCCCAGCAACACCAAGGTGGACAAGACAGTTGAGC |

TABLE 1-continued

| SEQ ID NO: | DESCRIPTION | SEQUENCE |
|---|---|---|
| | | GCAAATGTTGTGTCGAGTGCCCACCGTGCCCAGCACCACCTGTGGCAG |
| | | GACCGTCAGTCTTCCTCTTCCCCCCAAAACCCAAGGACACCCTCATGA |
| | | TCTCCCGGACCCCTGAGGTCACGTGCGTGGTGGTGGACGTGAGCCACG |
| | | AAGACCCCGAGGTCCAGTTCAACTGGTACGTGGACGGCGTGGAGGTG |
| | | CATAATGCCAAGACAAAGCCACGGGAGGAGCAGTTCAACAGCACGTT |
| | | CCGTGTGGTCAGCGTCCTCACCGTTGTGCACCAGGACTGGCTGAACGG |
| | | CAAGGAGTACAAGTGCAAGGTCTCCAACAAAGGCCTCCCAGCCCCCA |
| | | TCGAGAAAACCATCTCCAAAACCAAAGGGCAGCCCCGAGAACCACAG |
| | | GTGTACACCCTGCCCCCATCCCGGGAGGAGATGACCAAGAACCAGGT |
| | | CAGCCTGACCTGCCTGGTCAAAGGCTTCTACCCCAGCGACATCGCCGT |
| | | GGAGTGGGAGAGCAATGGGCAGCCGGAGAACAACTACAAGACCACA |
| | | CCTCCCATGCTGGACTCCGACGGCTCCTTCTTCCTCTACAGCAAGCTC |
| | | ACCGTGGACAAGAGCAGGTGGCAGCAGGGGAACGTCTTCTCATGCTC |
| | | CGTGATGCATGAGGCTCTGCACAACCACTACACGCAGAAGAGCCTCT |
| | | CCCTGTCTCCGGGTAAA |
| 62 | 6.147-2x-Ab5 G2 AA | QVQLVESGGGVVQPGRSLRLSCAASGFTFSRYDMHWVRQAPGKGLEW |
| | | VAIIFYDGSNKYYADPVKGRFTISRDNSKNTLYLQMNSLRAEDTAVYYC |
| | | ATLAAAFDYWGQGTLVTVSSGGGGSGGGGSEVQLVQSGAEVKKPGASV |
| | | KVSCKASGYTFTDYNMHWVRQAPGQGLEWMGEINPNSGGAGYNQKF |
| | | KGRVTMTTDTSTSTAYMELRSLRSDDTAVYYCARLGYDDIYDDWYFDV |
| | | WGQGTTVTVSS*ASTKGPSVFPLAPCSRSTSESTAALGCLVKDYFPEPVTVS* |
| | | *WNSGALTSGVHTFPAVLQSSGLYSLSSVVTVPSSNFGTQTYTCNVDHKPS* |
| | | *NTNKVDKTVERKCCVECPPCPAPPVAGPSVFLFPPKPKDTLMISRTPEVTC* |
| | | *VVVDVSHEDPEVQFNWYVDGVEVHNAKTKPREEQFNSTFRVVSVLTVV* |
| | | *HQDWLNGKEYKCKVSNKGLPAPIEKTISKTKGQPREPQVYTLPPSREEMT* |
| | | *KNQVSLTCLVKGFYPSDIAVEWESNGQPENNYKTTPPMLDSDGSFFLYSK* |
| | | *LTVDKSRWQQGNVFSCSVMHEALHNHYTQKSLSLSPGK* |
| 63 | 6.147-2x-Ab5 LC NA | TCATACGTGCTCACTCAGCCGCCCAGCGTATCGGTGGCTCCCGGACAG |
| | | ACGGCGCGAATCACGTGCGGTGGGAACAATATCGGCTCCAAGTCAGT |
| | | CCATTGGTATCAACAGAAACCTGGTCAGGCACCAGTCCTGGTGGTATA |
| | | CGATGACTCGGACAGGCCCTCGGAGATTCCGGAACGCTTCTCCGGATC |
| | | GAATTCGGGGAACACAGCGACCTTGACGATCAGCAGAGTGGAGGCCG |
| | | GAGATGAAGCCGACTACTATTGTCAGGTGTGGGATTCCAGCTCCGACC |
| | | ACGTCGTATTTGGAGGTGGGACACGGCTTACCGTCTTGGGCGGTGGAG |
| | | GCTCGGGAGGTGGTGGATCCGACATTCAGATGACTCAGTCGCCTTCGT |
| | | CATTGAGCGCGTCGGTGGGAGATCGGGTCACGATTACTTGTCGGGCAT |
| | | CGCAAGACATCTCGAACTATTTGAATTGGTACCAGCAAAAGCCTGGTA |
| | | AAGCGCCCAAACTTCTTATCTACTATACGTCCCGCCTCCTCTCGGGCG |

| SEQ ID NO: | DESCRIPTION | SEQUENCE |
|---|---|---|
| | | TCCCGTCAAGGTTTAGCGGATCGGGAAGCGGGACGGATTTCACACTG |
| | | ACGATTTCATCACTTCAGCCCGAAGATTTCGCCACCTATTACTGTCAG |
| | | CAAGGAGACACCCTGCCATACACTTTTGGCGGTGGGACAAAGGTCGA |
| | | AATCAAGCGTACGGTGGCTGCACCATCTGTCTTCATCTTCCCGCCATCT |
| | | GATGAGCAGTTGAAATCTGGAACTGCCTCTGTTGTGTGCCTGCTGAAT |
| | | AACTTCTATCCCAGAGAGGCCAAAGTACAGTGGAAGGTGGATAACGC |
| | | CCTCCAATCGGGTAACTCCCAGGAGAGTGTCACAGAGCAGGACAGCA |
| | | AGGACAGCACCTACAGCCTCAGCAGCACCCTGACGCTGAGCAAAGCA |
| | | GACTACGAGAAACACAAAGTCTACGCCTGCGAAGTCACCCATCAGGG |
| | | CCTGAGCTCGCCCGTCACAAAGAGCTTCAACAGGGGAGAGTGT |
| 64 | 6.147-2x-Ab5 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVL<u>GGGGSGGGGS</u>DIQMTQSPSSLSASVGDRVTITCRASQDISN YLNWYQQKPGKAPKLLIYYTSRLLSGVPSRFGSGSGTDFTLTISSLQPED FATYYCQQGDTLPYTFGGGTKVEIKR*TVAAPSVFIFPPSDEQLKSGTASV* *VCLLNNFYPREAKVQWKVDNALQSGNSQESVTEQDSKDSTYSLSSTLTLS* *KADYEKHKVYACEVTHQGLSSPVTKSFNRGEC* |
| 65 | 6.147-AbL-Ab23 G2 NA | CAGGTGCAGCTTGTCGAGAGCGGTGGAGGGGTGGTACAACCCGGAAG ATCACTCCGGCTTTCATGCGCAGCATCCGGTTTTACATTTTCGCGGTAT GACATGCACTGGGTGAGACAGGCACCAGGAAAAGGGCTGGAGTGGGT GGCCATCATCTTCTATGATGGGTCCAATAAGTACTACGCCGACCCGGT AAAAGGGAGGTTCACTATTAGCCGCGACAACTCGAAGAATACGCTGT ACCTGCAGATGAACTCGTTGCGAGCCGAAGATACCGCGGTCTACTATT GTGCGACGCTCGCGGCTGCGTTCGATTACTGGGGCCAAGGAACATTGG TCACGGTCTCCTCAGCGTCAACGAAAGGACCGTCGGTGTTCCCCTTGG CCCCTGAGGTGCAGCTCGTACAGTCGGGTGCGGAAGTAAAGAAACCC GGCTCATCCGTGAAAGTCTCGTGTAAAGCCTCCGGGTTCACCTTCACA GACTACATTATGCACTGGGTGCGGCAGGCCCCTGGGCAGGGCCTTGA ATGGATGGGGTATATCAACCCCTACAATGATGACACGGAGTATAACG AAAAGTTTAAGGGAAGGGTGACAATCACGGCGGATAAGAGCACCAGC ACTGCATACATGGAGCTCTCGTCATTGCGCTCGGAGGACACTGCAGTC TACTATTGCGCGAGATCCATCTACTATTACGATGCGCCGTTTGCTTATT GGGGACAAGGAACGCTGGTCACCGTCTCTAGTGCCTCCACCAAGGGC CCATCGGTCTTCCCCCTGGCGCCCTGCTCCAGGAGCACCTCCGAGAGC ACAGCGGCCCTGGGCTGCCTGGTCAAGGACTACTTCCCCGAACCGGTG ACGGTGTCGTGGAACTCAGGCGCTCTGACCAGCGGCGTGCACACCTTC CCAGCTGTCCTACAGTCCTCAGGACTCTACTCCCTCAGCAGCGTGGTG |

TABLE 1-continued

| SEQ ID NO: | DESCRIPTION | SEQUENCE |
|---|---|---|
| | | ACCGTGCCCTCCAGCAACTTCGGCACCCAGACCTACACCTGCAACGTA |
| | | GATCACAAGCCCAGCAACACCAAGGTGGACAAGACAGTTGAGCGCAA |
| | | ATGTTGTGTCGAGTGCCCACCGTGCCCAGCACCACCTGTGGCAGGACC |
| | | GTCAGTCTTCCTCTTCCCCCCAAAACCCAAGGACACCCTCATGATCTC |
| | | CCGGACCCCTGAGGTCACGTGCGTGGTGGTGGACGTGAGCCACGAAG |
| | | ACCCCGAGGTCCAGTTCAACTGGTACGTGGACGGCGTGGAGGTGCAT |
| | | AATGCCAAGACAAAGCCACGGGAGGAGCAGTTCAACAGCACGTTCCG |
| | | TGTGGTCAGCGTCCTCACCGTTGTGCACCAGGACTGGCTGAACGGCAA |
| | | GGAGTACAAGTGCAAGGTCTCCAACAAAGGCCTCCCAGCCCCCATCG |
| | | AGAAAACCATCTCCAAAACCAAAGGGCAGCCCCGAGAACCACAGGTG |
| | | TACACCCTGCCCCCATCCCGGGAGGAGATGACCAAGAACCAGGTCAG |
| | | CCTGACCTGCCTGGTCAAAGGCTTCTACCCCAGCGACATCGCCGTGGA |
| | | GTGGGAGAGCAATGGGCAGCCGGAGAACAACTACAAGACCACACCTC |
| | | CCATGCTGGACTCCGACGGCTCCTTCTTCCTCTACAGCAAGCTCACCG |
| | | TGGACAAGAGCAGGTGGCAGCAGGGGAACGTCTTCTCATGCTCCGTG |
| | | ATGCATGAGGCTCTGCACAACCACTACACGCAGAAGAGCCTCTCCCTG |
| | | TCTCCGGGTAAA |
| 66 | 6.147-AbL-Ab23 G2 AA | QVQLVESGGGVVQPGRSLRLSCAASGFTFSRYDMHWVRQAPGKGLEW |
| | | VAIIFYDGSNKYYADPVKGRFTISRDNSKNTLYLQMNSLRAEDTAVYYC |
| | | ATLAAAFDYWGQGTLVTVSSASTKGPSVFPLAPEVQLVQSGAEVKKPGS |
| | | SVKVSCKASGFTFTDYIMHWVRQAPGQGLEWMGYINPYNDDTEYNEK |
| | | FKGRVTITADKSTSTAYMELSSLRSEDTAVYYCARSIYYYDAPFAYWGQ |
| | | GTLVTVSS*ASTKGPSVFPLAPCSRSTSESTAALGCLVKDYFPEPVTVSWNS* |
| | | *GALTSGVHTFPAVLQSSGLYSLSSVVTVPSSNFGTQTYTCNVDHKPSNTK* |
| | | *VDKTVERKCCVECPPCPAPPVAGPSVFLFPPKPKDTLMISRTPEVTCVVV* |
| | | *DVSHEDPEVQFNWYVDGVEVHNAKTKPREEQFNSTFRVVSVLTVVHQD* |
| | | *WLNGKEYKCKVSNKGLPAPIEKTISKTKGQPREPQVYTLPPSREEMTKNQ* |
| | | *VSLTCLVKGFYPSDIAVEWESNGQPENNYKTTPPMLDSDGSFFLYSKLTV* |
| | | *DKSRWQQGNVFSCSVMHEALHNHYTQKSLSLSPGK* |
| 67 | 6.147-AbL-Ab23 LC NA | TCATACGTGCTCACTCAGCCGCCCAGCGTATCGGTGGCTCCCGGACAG |
| | | ACGGCGCGAATCACGTGCGGTGGGAACAATATCGGCTCCAAGTCAGT |
| | | CCATTGGTATCAACAGAAACCTGGTCAGGCACCAGTCCTGGTGGTATA |
| | | CGATGACTCGGACAGGCCCTCGGAGATTCCGGAACGCTTCTCCGGATC |
| | | GAATTCGGGGAACACAGCGACCTTGACGATCAGCAGAGTGGAGGCCG |
| | | GAGATGAAGCCGACTACTATTGTCAGGTGTGGGATTCCAGCTCCGACC |
| | | ACGTCGTATTTGGAGGTGGGACACGGCTTACCGTCCTCGGGCAGCCCA |
| | | AGGCTGCGCCATCGGTCACTCTGTTCCCACCTGACATTCAAATGACAC |
| | | AGTCGCCCTCCTCGCTCTCGGCGTCAGTCGGGGATCGCGTGACAATCA |

TABLE 1-continued

| SEQ ID NO: | DESCRIPTION | SEQUENCE |
|---|---|---|
| | | CGTGTCGGGCCAGCCAGGACATTTCGAGCTACCTCAACTGGTATCAGC |
| | | AGAAACCGGGGAAAGCGCCGAAGCTGCTTATCTACTCCACCTCAAGG |
| | | TTGAATTCCGGAGTACCCTCAAGATTTTCGGGTAGCGGATCAGGAACC |
| | | GACTTCACACTTACGATCTCGTCGTTGCAGCCAGAAGATTTCGCAACG |
| | | TACTATTGCCAGCAAGATATCAAGCACCCTACGTTTGGTCAGGGCACT |
| | | AAAGTGGAGATTAAGCGTACGGTGGCTGCACCATCTGTCTTCATCTTC |
| | | CCGCCATCTGATGAGCAGTTGAAATCTGGAACTGCCTCTGTTGTGTGC |
| | | CTGCTGAATAACTTCTATCCCAGAGAGGCCAAAGTACAGTGGAAGGT |
| | | GGATAACGCCCTCCAATCGGGTAACTCCCAGGAGAGTGTCACAGAGC |
| | | AGGACAGCAAGGACAGCACCTACAGCCTCAGCAGCACCCTGACGCTG |
| | | AGCAAAGCAGACTACGAGAAACACAAAGTCTACGCCTGCGAAGTCAC |
| | | CCATCAGGGCCTGAGCTCGCCCGTCACAAAGAGCTTCAACAGGGGAG |
| | | AGTGT |
| 68 | 6.147-AbL-Ab23 LC AA | SYVLTQPPSVSVAPGQTARITCGGNNIGSKSVHWYQQKPGQAPVLVVYD DSDRPSEIPERFSGSNSGNTATLTISRVEAGDEADYYCQVWDSSSDHVVF GGGTRLTVLGQPKAAPSVTLFPPDIQMTQSPSSLSASVGDRVTITCRASQD ISSYLNWYQQKPGKAPKLLIYSTSRLNSGVPSRFSGSGSGTDFTLTISSLQP EDFATYYCQQDIKHPTFGQGTKVEIKR*TVAAPSVFIFPPSDEQLKSGTAS* *VVCLLNNFYPREAKVQWKVDNALQSGNSQESVTEQDSKDSTYSLSSTLTL* *SKADYEKHKVYACEVTHQGLSSPVTKSFNRGEC* |
| 69 | Ab5-AbS-6.147 G2 NA | GAGGTGCAGCTCGTGCAGTCCGGAGCCGAGGTGAAGAAGCCTGGGGC ATCCGTCAAAGTCTCGTGCAAGGCGTCAGGGTACACATTCACCGACTA TAACATGCATTGGGTCCGGCAGGCTCCCGGTCAGGGGCTGGAGTGGA TGGGGGAAATCAATCCGAACTCCGGAGGGGCAGGATACAATCAAAAG TTTAAGGGACGCGTAACGATGACCACTGACACGTCAACCTCCACGGC GTATATGGAGCTCAGAAGCCTCCGAAGCGACGACACTGCTGTCTATTA CTGTGCGAGACTGGGATATGATGATATCTACGACGATTGGTACTTCGA TGTATGGGGACAAGGGACGACGGTCACGGTCTCCTCAGCGTCAACGA AAGGACCGCAGGTGCAGCTTGTCGAGAGCGGTGGAGGGGTGGTACAA CCCGGAAGATCACTCCGGCTTTCATGCGCAGCATCCGGTTTTACATTTT CGCGGTATGACATGCACTGGGTGAGACAGGCACCAGGAAAGGGCTG GAGTGGGTGGCCATCATCTTCTATGATGGGTCCAATAAGTACTACGCC GACCCGGTAAAAGGGAGGTTCACTATTAGCCGCGACAACTCGAAGAA TACGCTGTACCTGCAGATGAACTCGTTGCGAGCCGAAGATACCGCGGT CTACTATTGTGCGACGCTCGCGGCTGCGTTAGATTACTGGGGCCAAGG AACATTGGTCACCGTCTCTAGTGCCTCCACCAAGGGCCCATCGGTCTT CCCCCTGGCGCCCTGCTCCAGGAGCACCTCCGAGAGCACAGCGGCCCT |

TABLE 1-continued

| SEQ ID NO: | DESCRIPTION | SEQUENCE |
|---|---|---|
| | | GGGCTGCCTGGTCAAGGACTACTTCCCCGAACCGGTGACGGTGTCGTG |
| | | GAACTCAGGCGCTCTGACCAGCGGCGTGCACACCTTCCCAGCTGTCTT |
| | | ACAGTCCTCAGGACTCTACTCCCTCAGCAGCGTGGTGACCGTGCCCTC |
| | | CAGCAACTTCGGCACCCAGACCTACACCTGCAACGTAGATCACAAGC |
| | | CCAGCAACACCAAGGTGGACAAGACAGTTGAGCGCAAATGTTGTGTC |
| | | GAGTGCCCACCGTGCCCAGCACCACCTGTGGCAGGACCGTCAGTCTTC |
| | | CTCTTCCCCCCAAAACCCAAGGACACCCTCATGATCTCCCGGACCCCT |
| | | GAGGTCACGTGCGTGGTGGTGGACGTGAGCCACGAAGACCCCGAGGT |
| | | CCAGTTCAACTGGTACGTGGACGGCGTGGAGGTGCATAATGCCAAGA |
| | | CAAAGCCACGGGAGGAGCAGTTCAACAGCACGTTCCGTGTGGTCAGC |
| | | GTCCTCACCGTTGTGCACCAGGACTGGCTGAACGGCAAGGAGTACAA |
| | | GTGCAAGGTCTCCAACAAAGGCCTCCCAGCCCCCATCGAGAAAACCA |
| | | TCTCCAAAACCAAAGGGCAGCCCCGAGAACCACAGGTGTACACCCTG |
| | | CCCCCATCCCGGGAGGAGATGACCAAGAACCAGGTCAGCCTGACCTG |
| | | CCTGGTCAAAGGCTTCTACCCCAGCGACATCGCCGTGGAGTGGGAGA |
| | | GCAATGGGCAGCCGGAGAACAACTACAAGACCACACCTCCCATGCTG |
| | | GACTCCGACGGCTCCTTCTTCCTCTACAGCAAGCTCACCGTGGACAAG |
| | | AGCAGGTGGCAGCAGGGGAACGTCTTCTCATGCTCCGTGATGCATGA |
| | | GGCTCTGCACAACCACTACACGCAGAAGAGCCTCTCCCTGTCTCCGGG |
| | | TAAA |
| 70 | Ab5-AbS-6.147 G2 AA | EVQLVQSGAEVKKPGASVKVSCKASGYTFTDYNMHWVRQAPGQGLEW MGEINPNSGGAGYNQKFKGRVTMTTDTSTSTAYMELRSLRSDDTAVYY CARLGYDDIYDDWYFDVWGQGTTVTVSS*ASTKGP*QVQLVESGGGVVQP GRSLRLSCAASGFTFSRYDMHWVRQAPGKGLEWVAIIFYDGSNKYYAD PVKGRFTISRDNSKNTLYLQMNSLRAEDTAVYYCATLAAFDYWGQGT LVTVSS*ASTKGPSVFPLAPCSRSTSESTAALGCLVKDYFPEPVTVSWNSGA LTSGVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVVDV SHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDK SRWQQGNVFSCSVMHEALHNHYTQKSLSLSPGK* |
| 71 | Ab5-AbS-6.147 LC NA | GACATTCAGATGACTCAGTCGCCTTCGTCATTGAGCGCGTCGGTGGGA GATCGGGTCACGATTACTTGTCGGGCATCGCAAGACATCTCGAACTAT TTGAATTGGTACCAGCAAAAGCCTGGTAAAGCGCCCAAACTTCTTATC TACTATACGTCCCGCCTCCTCTCGGGCGTCCCGTCAAGGTTTAGCGGA TCGGGAAGCGGGACGGATTTCACACTGACGATTTCATCACTTCAGCCC GAAGATTTCGCCACCTATTACTGTCAGCAAGGAGACACCCTGCCATAC |

| SEQ ID NO: | DESCRIPTION | SEQUENCE |
|---|---|---|
| | | ACTTTTGGCGGTGGGACAAAGGTCGAAATCAAGCGCACAGTGGCTGC |
| | | TCCATCATACGTGCTCACTCAGCCGCCCAGCGTATCGGTGGCTCCCGG |
| | | ACAGACGGCGCGAATCACGTGCGGTGGGAACAATATCGGCTCCAAGT |
| | | CAGTCCATTGGTATCAACAGAAACCTGGTCAGGCACCAGTCCTGGTGG |
| | | TATACGATGACTCGGACAGGCCCTCGGAGATTCCGGAACGCTTCTCCG |
| | | GATCGAATTCGGGGAACACAGCGACCTTGACGATCAGCAGAGTGGAG |
| | | GCCGGAGATGAAGCCGACTACTATTGTCAGGTGTGGGATTCCAGCTCC |
| | | GACCACGTCGTATTTGGAGGTGGGACACGGCTTACCGTCCTAGGTCAG |
| | | CCCAAGGCCAACCCCACTGTCACTCTGTTCCCGCCCTCCTCTGAGGAG |
| | | CTCCAAGCCAACAAGGCCACACTAGTGTGTCTGATCAGTGACTTCTAC |
| | | CCGGGAGCTGTGACAGTGGCCTGGAAGGCAGATGGCAGCCCCGTCAA |
| | | GGCGGGAGTGGAGACCACCAAACCCTCCAAACAGAGCAACAACAAGT |
| | | ACGCGGCCAGCAGCTACCTGAGCCTGACGCCCGAGCAGTGGAAGTCC |
| | | CACAGAAGCTACAGCTGCCAGGTCACGCATGAAGGGAGCACCGTGGA |
| | | GAAGACAGTGGCCCCTACAGAATGTTCA |
| 72 | Ab5-AbS-6.147 LC AA | DIQMTQSPSSLSASVGDRVTITCRASQDISNYLNWYQQKPGKAPKLLIYY TSRLLSGVPSRFSGSGSGTDFTLTISSLQPEDFATYYCQQGDTLPYTFGG GTKVEIKR<u>TVAAP</u>SYVLTQPPSVSVAPGQTARITCGGNNIGSKSVHWYQ QKPGQAPVLVVYDDSDRPSEIPERFSGSNSGNTATLTISRVEAGDEADYY CQVWDSSSDHVVFGGGTRLTVLG*QPKANPTVTLFPPSSEELQANKATLV CLISDFYPGAVTVAWKADGSPVKAGVETTPSKQSNNKYAASSYLSLTPE QWKSHRSYSCQVTHEGSTVEKTVAPTECS* |
| 73 | Ab5-AbL-6.147 G2 NA | GAGGTGCAGCTCGTGCAGTCCGGAGCCGAGGTGAAGAAGCCTGGGGC ATCCGTCAAAGTCTCGTGCAAGGCGTCAGGGTACACATTCACCGACTA TAACATGCATTGGGTCCGGCAGGCTCCCGGTCAGGGGCTGGAGTGGA TGGGGGAAATCAATCCGAACTCCGGAGGGGCAGGATACAATCAAAAG TTTAAGGGACGCGTAACGATGACCACTGACACGTCAACCTCCACGGC GTATATGGAGCTCAGAAGCCTCCGAAGCGACGACACTGCTGTCTATTA CTGTGCGAGACTGGGATATGATGATATCTACGACGATTGGTACTTCGA TGTATGGGGACAAGGGACGACGGTCACGGTCTCCTCAGCGTCAACGA AAGGACCGTCGGTGTTCCCCTTGGCCCCTCAGGTGCAGCTTGTCGAGA GCGGTGGAGGGGTGGTACAACCCGGAAGATCACTCCGGCTTTCATGC GCAGCATCCGGTTTTACATTTTCGCGGTATGACATGCACTGGGTGAGA CAGGCACCAGGAAAAGGGCTGGAGTGGGTGGCCATCATCTTCTATGA TGGGTCCAATAAGTACTACGCCGACCCGGTAAAAGGGAGGTTCACTA TTAGCCGCGACAACTCGAAGAATACGCTGTACCTGCAGATGAACTCGT TGCGAGCCGAAGATACCGCGGTCTACTATTGTGCGACGCTCGCGGCTG |

TABLE 1-continued

| SEQ ID NO: | DESCRIPTION | SEQUENCE |
|---|---|---|
| | | CGTTCGATTACTGGGGCCAAGGAACATTGGTCACCGTCTCTAGTGCCT |
| | | CCACCAAGGGCCCATCGGTCTTCCCCCTGGCGCCCTGCTCCAGGAGCA |
| | | CCTCCGAGAGCACAGCGGCCCTGGGCTGCCTGGTCAAGGACTACTTCC |
| | | CCGAACCGGTGACGGTGTCGTGGAACTCAGGCGCTCTGACCAGCGGC |
| | | GTGCACACCTTCCCAGCTGTCCTACAGTCCTCAGGACTCTACTCCCTC |
| | | AGCAGCGTGGTGACCGTGCCCTCCAGCAACTTCGGCACCCAGACCTAC |
| | | ACCTGCAACGTAGATCACAAGCCCAGCAACACCAAGGTGGACAAGAC |
| | | AGTTGAGCGCAAATGTTGTGTCGAGTGCCCACCGTGCCCAGCACCACC |
| | | TGTGGCAGGACCGTCAGTCTTCCTCTTCCCCCCAAAACCCAAGGACAC |
| | | CCTCATGATCTCCCGGACCCCTGAGGTCACGTGCGTGGTGGTGGACGT |
| | | GAGCCACGAAGACCCCGAGGTCCAGTTCAACTGGTACGTGGACGGCG |
| | | TGGAGGTGCATAATGCCAAGACAAAGCCACGGGAGGAGCAGTTCAAC |
| | | AGCACGTTCCGTGTGGTCAGCGTCCTCACCGTTGTGCACCAGGACTGG |
| | | CTGAACGGCAAGGAGTACAAGTGCAAGGTCTCCAACAAAGGCCTCCC |
| | | AGCCCCCATCGAGAAAACCATCTCCAAAACCAAAGGGCAGCCCCGAG |
| | | AACCACAGGTGTACACCCTGCCCCCATCCCGGGAGGAGATGACCAAG |
| | | AACCAGGTCAGCCTGACCTGCCTGGTCAAAGGCTTCTACCCCAGCGAC |
| | | ATCGCCGTGGAGTGGGAGAGCAATGGGCAGCCGGAGAACAACTACAA |
| | | GACCACACCTCCCATGCTGGACTCCGACGGCTCCTTCTTCCTCTACAG |
| | | CAAGCTCACCGTGGACAAGAGCAGGTGGCAGCAGGGGAACGTCTTCT |
| | | CATGCTCCGTGATGCATGAGGCTCTGCACAACCACTACACGCAGAAG |
| | | AGCCTCTCCCTGTCTCCGGGTAAA |
| 74 | Ab5-AbL-6.147 G2 AA | EVQLVQSGAEVKKPGASVKVSCKASGYTFTDYNMHWVRQAPGQGLEW MGEINPNSGGAGYNQKFKGRVTMTTDTSTSTAYMELRSLRSDDTAVYY CARLGYDDIYDDWYFDVWGQGTTVTVSSASTKGPSVFPLAPQVQLVES GGGVVQPGRSLRLSCAASGFTFSRYDMHWVRQAPGKGLEWVAIIFYDG SNKYYADPVKGRFTISRDNSKNTLYLQMNSLRAEDTAVYYCATLAAAF DYWGQGTLVTVSS*ASTKGPSVFPLAPCSRSTSESTAALGCLVKDYFPEPV TVSWNSGALTSGVHTFPAVLQSSGLYSLSSVVTVPSSNFGTQTYTCNVDH KPSNTKVDKTVERKCCVECPPCPAPPVAGPSVFLFPPKPKDTLMISRTPE VTCVVVDVSHEDPEVQFNWYVDGVEVHNAKTKPREEQFNSTFRVVSVLT VVDQDWLNGKEYKCKVSNKGLPAPIEKTISKTKGQPREPQVYTLPPSREE MTKNQVSLTCLVKGFYPSDIAVEWESNGQPENNYKTTPPMLDSDGSFFL YSKLTVDKSRWQQGNVFSCSVMHEALHNHYTQKSLSLSPGK* |
| 75 | Ab5-AbL-6.147 LC NA | GACATTCAGATGACTCAGTCGCCTTCGTCATTGAGCGCGTCGGTGGGA GATCGGGTCACGATTACTTGTCGGGCATCGCAAGACATCTCGAACTAT TTGAATTGGTACCAGCAAAAGCCTGGTAAAGCGCCCAAACTTCTTATC TACTATACGTCCCGCCTCCTCTCGGGCGTCCCGTCAAGGTTTAGCGGA |

TABLE 1-continued

| SEQ ID NO: | DESCRIPTION | SEQUENCE |
|---|---|---|
| | | TCGGGAAGCGGGACGGATTTCACACTGACGATTTCATCACTTCAGCCC |
| | | GAAGATTTCGCCACCTATTACTGTCAGCAAGGAGACACCCTGCCATAC |
| | | ACTTTTGGCGGTGGGACAAAGGTCGAAATCAAGCGCACAGTGGCTGC |
| | | TCCATCCGTCTTTATCTTCCCTCCATCATACGTGCTCACTCAGCCGCCC |
| | | AGCGTATCGGTGGCTCCCGGACAGACGGCGCGAATCACGTGCGGTGG |
| | | GAACAATATCGGCTCCAAGTCAGTCCATTGGTATCAACAGAAACCTGG |
| | | TCAGGCACCAGTCCTGGTGGTATACGATGACTCGGACAGGCCCTCGGA |
| | | GATTCCGGAACGCTTCTCCGGATCGAATTCGGGGAACACAGCGACCTT |
| | | GACGATCAGCAGAGTGGAGGCCGGAGATGAAGCCGACTACTATTGTC |
| | | AGGTGTGGGATTCCAGCTCCGACCACGTCGTATTTGGAGGTGGGACAC |
| | | GGCTTACCGTCCTAGGTCAGCCCAAGGCCAACCCCACTGTCACTCTGT |
| | | TCCCGCCCTCCTCTGAGGAGCTCCAAGCCAACAAGGCCACACTAGTGT |
| | | GTCTGATCAGTGACTTCTACCCGGGAGCTGTGACAGTGGCCTGGAAGG |
| | | CAGATGGCAGCCCCGTCAAGGCGGGAGTGGAGACCACCAAACCCTCC |
| | | AAACAGAGCAACAACAAGTACGCGGCCAGCAGCTACCTGAGCCTGAC |
| | | GCCCGAGCAGTGGAAGTCCCACAGAAGCTACAGCTGCCAGGTCACGC |
| | | ATGAAGGGAGCACCGTGGAGAAGACAGTGGCCCCTACAGAATGTTCA |
| 76 | Ab5-AbL-6.147 LC AA | DIQMTQSPSSLSASVGDRVTITCRASQDISNYLNWYQQKPGKAPKLLIYTTSRLLSGVPSRFSGSGSGTDFTLTISSLQPEDFATYYCQQGDTLPYTFGG GTKVEIKR*TVAAPSVFIFPPP*SYVLTQPPSVSVAPGQTARITCGGNNIGSKS VHWYQQKPGQAPVLVVYDDSDRPSEIPERFSGSNSGNTATLTISRVEAGD EADYYC*QVWDSSSDHVV*FGGGTRLTVLG*QPKANPTVTLFPPSSEELQAN* *KATLVCLISDFYPGAVTVAWKADGSPVKAGVETTKPSKQSNNKYAASSYL* *SLTPEQWKSHRSYSCQVTHEGSTVEKTVAPTECS* |
| 77 | Ab23-2x-6.37 G2 NA | GAGGTGCAGCTCGTACAGTCGGGTGCGGAAGTAAAGAAACCCGGCTC ATCCGTGAAAGTCTCGTGTAAAGCCTCCGGGTTCACCTTCACAGACTA CATTATGCACTGGGTGCGGCAGGCCCCTGGGCAGGGCCTTGAATGGAT GGGGTATATCAACCCCTACAATGATGACACGGAGTATAACGAAAAGT TTAAGGGAAGGGTGACAATCACGGCGGATAAGAGCACCAGCACTGCA TACATGGAGCTCTCGTCATTGCGCTCGGAGGACACTGCAGTCTACTAT TGCGCGAGATCCATCTACTATTACGATGCGCCGTTTGCTTATTGGGGA CAAGGAACGCTGGTCACAGTGAGCTCAGGCGGTGGAGGCTCGGGAGG TGGTGGATCCCAGGTACAACTGGTCGAGTCAGGTGGAGGCGTGGTCC AGCCCGGACGGTCGCTCAGGCTCAGCTGTGCTGCGTCAGGGTTCACCT TTTCGGGGTATGGGATGCACTGGGTGCGCCAAGCACCGGGAAAAGGG CTTGAATGGGTCGCGGTCATTTCCTACGACGGGAACGACAAATACTAC GCGGACTCCGTAAAGGGAAGGTTCACAATCAGCCGGGATAACGCCAA |

TABLE 1-continued

| SEQ ID NO: | DESCRIPTION | SEQUENCE |
|---|---|---|
| | | GAATACGTTGTATCTCCAGATGAATTCGTTGCGAGCAGAAGATACGGC |
| | | CGTGTACTATTGCGCGAGAGAGCTTCGCGTGTTGTGGGGACAGGGTAC |
| | | TCTGGTGACCGTCTCTAGTGCCTCCACCAAGGGCCCATCGGTCTTCCC |
| | | CCTGGCGCCCTGCTCCAGGAGCACCTCCGAGAGCACAGCGGCCCTGG |
| | | GCTGCCTGGTCAAGGACTACTTCCCCGAACCGGTGACGGTGTCGTGGA |
| | | ACTCAGGCGCTCTGACCAGCGGCGTGCACACCTTCCCAGCTGTCCTAC |
| | | AGTCCTCAGGACTCTACTCCCTCAGCAGCGTGGTGACCGTGCCCTCCA |
| | | GCAACTTCGGCACCCAGACCTACACCTGCAACGTAGATCACAAGCCC |
| | | AGCAACACCAAGGTGGACAAGACAGTTGAGCGCAAATGTTGTGTCGA |
| | | GTGCCCACCGTGCCCAGCACCACCTGTGGCAGGACCGTCAGTCTTCCT |
| | | CTTCCCCCCAAAACCCAAGGACACCCTCATGATCTCCCGGACCCCTGA |
| | | GGTCACGTGCGTGGTGGTGGACGTGAGCCACGAAGACCCCGAGGTCC |
| | | AGTTCAACTGGTACGTGGACGGCGTGGAGGTGCATAATGCCAAGACA |
| | | AAGCCACGGGAGGAGCAGTTCAACAGCACGTTCCGTGTGGTCAGCGT |
| | | CCTCACCGTTGTGCACCAGGACTGGCTGAACGGCAAGGAGTACAAGT |
| | | GCAAGGTCTCCAACAAAGGCCTCCCAGCCCCCATCGAGAAAACCATC |
| | | TCCAAAACCAAAGGGCAGCCCCGAGAACCACAGGTGTACACCCTGCC |
| | | CCCATCCCGGGAGGAGATGACCAAGAACCAGGTCAGCCTGACCTGCC |
| | | TGGTCAAAGGCTTCTACCCCAGCGACATCGCCGTGGAGTGGGAGAGC |
| | | AATGGGCAGCCGGAGAACAACTACAAGACCACACCTCCCATGCTGGA |
| | | CTCCGACGGCTCCTTCTTCCTCTACAGCAAGCTCACCGTGGACAAGAG |
| | | CAGGTGGCAGCAGGGGAACGTCTTCTCATGCTCCGTGATGCATGAGGC |
| | | TCTGCACAACCACTACACGCAGAAGAGCCTCTCCCTGTCTCCGGGTAA |
| | | A |
| 78 | Ab23-2x-6.37 G2 AA | EVQLVQSGAEVKKPGSSVKVSCKASGFTFTDYIMHWVRQAPGQGLEWM |
| | | GYINPYNDDTEYNEKFKGRVTITADKSTSTAYMELSSLRSEDTAVYYCA |
| | | RSIYYYDAPFAYWGQGTLVTSSGGGGSGGGGSQVQLVESGGGVVQPG |
| | | RSLRLSCAASGFTFSGYGMHWVRQAPGKGLEWVAVISYDGNDKYYAD |
| | | SVKGRFTISRDNAKNTLYLQMNSLRAEDTAVYYCARELRVLWGQGTLV |
| | | TVSS*ASTKGPSVFPLAPCSRSTSESTAALGCLVKDYFPEPVTVSWNSGALT* |
| | | *SGVHTFPAVLQSSGLYSLSSVVTVPSSNFGTQTYTCNVDHKPSNTKVDKT* |
| | | *VERKCCVECPPCPAPPVAGPSVFLFPPKPKDTLMISRTPEVTCVVVDVSH* |
| | | *EDPEVQFNWYVDGVEVHNAKTKPREEQFNSTFRVVSVLTVVHQDWLNG* |
| | | *KEYKCKVSNKGLPAPIEKTISKTKGQPREPQVYTLPPSREEMTKNQVSLTC* |
| | | *LVKGFYPSDIAVEWESNGQPENNYKTTPPMLDSDGSFFLYSKLTVDKSR* |
| | | *WQQGNVFSCSVMHEALHNHYTQKSLSLSPGK* |

TABLE 1-continued

| SEQ ID NO: | DESCRIPTION | SEQUENCE |
|---|---|---|
| 79 | Ab23-2x-6.37 LC NA | GACATTCAAATGACACAGTCGCCCTCCTCGCTCTCGGCGTCAGTCGGG GATCGCGTGACAATCACGTGTCGGGCCAGCCAGGACATTTCGAGCTAC CTCAACTGGTATCAGCAGAAACCGGGGAAAGCGCCGAAGCTGCTTAT CTACTCCACCTCAAGGTTGAATTCCGGAGTACCCTCAAGATTTTCGGG TAGCGGATCAGGAACCGACTTCACACTTACGATCTCGTCGTTGCAGCC AGAAGATTTCGCAACGTACTATTGCCAGCAAGATATCAAGCACCCTAC GTTTGGTCAGGGCACTAAAGTGGAGATTAAGGGCGGTGGAGGCTCGG GAGGTGGTGGATCCGATATTGTGATGACCCAGACGCCGTTGTCACTGA GCGTCACACCCGGACAGCCCGCGTCGATTAGCTGCAAATCGGGACAA TCGCTTCTCCACTCGGACGGGAAAACGTATCTTTACTGGTATTTGCAA AAGCCAGGGCAGCCTCCCCAGTTTCTTATCTACGAAGTGTCGAACAGG TTTTCCAGAGTACCTGACCGATTCTCCGGATCAGGTAGCGGAACGGAC TTCACTCTGCGCATCTCACGGGTCGAAGCCGAGGATGTGGGCATCTAC TACTGTATGCAGTCAATTCAGCTCCCGTGGACATTCGGTCAGGGGACC CAAGTAGAGATCAAGCGTACGGTGGCTGCACCATCTGTCTTCATCTTC CCGCCATCTGATGAGCAGTTGAAATCTGGAACTGCCTCTGTTGTGTGC CTGCTGAATAACTTCTATCCCAGAGAGGCCAAAGTACAGTGGAAGGT GGATAACGCCCTCCAATCGGGTAACTCCCAGGAGAGTGTCACAGAGC AGGACAGCAAGGACAGCACCTACAGCCTCAGCAGCACCCTGACGCTG AGCAAAGCAGACTACGAGAAACACAAAGTCTACGCCTGCGAAGTCAC CCATCAGGGCCTGAGCTCGCCCGTCACAAAGAGCTTCAACAGGGGAG AGTGT |
| 80 | Ab23-2x-6.37 LC AA | DIQMTQSPSSLSASVGDRVTITCRASQDISSYLNWYQQKPGKAPKLLIYS TSRLNSGVPSRFSGSGSGTDFTLTISSLQPEDFATYYCQQDIKHPTFGQGT KVEIKGGGGSGGGGSDIVMTQTPLSLSVTPGQPASISCKSGQSLLHSDGK TYLYWYLQKPGQPPQFLIYEVSNRFSRVPDRFSGSGSGTDFTLRISRVEAE DVGIYYCMQSIQLPWTFGQGTQVEIKR*TVAAPSVFIFPPSDEQLKSGTAS VVCLLNNFYPREAKVQWKVDNALQSGNSQESVTEQDSKDSTYSLSSTLTL SKADYEKHKVYACEVTHQGLSSPVTKSFNRGEC* |
| 81 | Ab23-AbL-6.147 G2 NA | GAGGTGCAGCTCGTACAGTCGGGTGCGGAAGTAAAGAAACCCGGCTC ATCCGTGAAAGTCTCGTGTAAAGCCTCCGGGTTCACCTTCACAGACTA CATTATGCACTGGGTGCGGCAGGCCCCTGGGCAGGGCCTTGAATGGAT GGGGTATATCAACCCCTACAATGATGACACGGAGTATAACGAAAGT TTAAGGGAAGGGTGACAATCACGGCGGATAAGAGCACCAGCACTGCA TACATGGAGCTCTCGTCATTGCGCTCGGAGGACACTGCAGTCTACTAT TGCGCGAGATCCATCTACTATTACGATGCGCCGTTTGCTTATTGGGGA CAAGGAACGCTGGTCACGGTCTCCTCAGCGTCAACGAAAGGACCGTC GGTGTTCCCCTTGGCCCCTCAGGTGCAGCTTGTCGAGAGCGGTGGAGG |

TABLE 1-continued

| SEQ ID NO: | DESCRIPTION | SEQUENCE |
|---|---|---|
| | | GGTGGTACAACCCGGAAGATCACTCCGGCTTTCATGCGCAGCATCCGG |
| | | TTTTACATTTTCGCGGTATGACATGCACTGGGTGAGACAGGCACCAGG |
| | | AAAAGGGCTGGAGTGGGTGGCCATCATCTTCTATGATGGGTCCAATAA |
| | | GTACTACGCCGACCCGGTAAAAGGGAGGTTCACTATTAGCCGCGACA |
| | | ACTCGAAGAATACGCTGTACCTGCAGATGAACTCGTTGCGAGCCGAA |
| | | GATACCGCGGTCTACTATTGTGCGACGCTCGCGGCTGCGTTCGATTAC |
| | | TGGGGCCAAGGAACATTGGTCACCGTCTCTAGTGCCTCCACCAAGGGC |
| | | CCATCGGTCTTCCCCCTGGCGCCCTGCTCCAGGAGCACCTCCGAGAGC |
| | | ACAGCGGCCCTGGGCTGCCTGGTCAAGGACTACTTCCCCGAACCGGTG |
| | | ACGGTGTCGTGGAACTCAGGCGCTCTGACCAGCGGCGTGCACACCTTC |
| | | CCAGCTGTCCTACAGTCCTCAGGACTCTACTCCCTCAGCAGCGTGGTG |
| | | ACCGTGCCCTCCAGCAACTTCGGCACCCAGACCTACACCTGCAACGTA |
| | | GATCACAAGCCCAGCAACACCAAGGTGGACAAGACAGTTGAGCGCAA |
| | | ATGTTGTGTCGAGTGCCCACCGTGCCCAGCACCACCTGTGGCAGGACC |
| | | GTCAGTCTTCCTCTTCCCCCCAAAACCCAAGGACACCCTCATGATCTC |
| | | CCGGACCCCTGAGGTCACGTGCGTGGTGGTGGACGTGAGCCACGAAG |
| | | ACCCCGAGGTCCAGTTCAACTGGTACGTGGACGGCGTGGAGGTGCAT |
| | | AATGCCAAGACAAAGCCACGGGAGGAGCAGTTCAACAGCACGTTCCG |
| | | TGTGGTCAGCGTCCTCACCGTTGTGCACCAGGACTGGCTGAACGGCAA |
| | | GGAGTACAAGTGCAAGGTCTCCAACAAAGGCCTCCCAGCCCCCATCG |
| | | AGAAAACCATCTCCAAAACCAAAGGGCAGCCCCGAGAACCACAGGTG |
| | | TACACCCTGCCCCCATCCCGGGAGGAGATGACCAAGAACCAGGTCAG |
| | | CCTGACCTGCCTGGTCAAAGGCTTCTACCCCAGCGACATCGCCGTGGA |
| | | GTGGGAGAGCAATGGGCAGCCGGAGAACAACTACAAGACCACACCTC |
| | | CCATGCTGGACTCCGACGGCTCCTTCTTCCTCTACAGCAAGCTCACCG |
| | | TGGACAAGAGCAGGTGGCAGCAGGGGAACGTCTTCTCATGCTCCGTG |
| | | ATGCATGAGGCTCTGCACAACCACTACACGCAGAAGAGCCTCTCCCTG |
| | | TCTCCGGGTAAA |

TABLE 1-continued

| SEQ ID NO: | DESCRIPTION | SEQUENCE |
|---|---|---|
| 82 | Ab23-AbL-6.147 G2 AA | EVQLVQSGAEVKKPGSSVKVSCKASGFTFTDYIMHWVRQAPGQGLEWM GYINPYNDDTEYNEKFKGRVTITADKSTSTAYMELSSLRSEDTAVYYCA RSIYYYDAPFAYWGQGTLVTVSS*ASTKGPSVFPLAP*QVQLVESGGGVVQ PGRSLRLSCAASGFTFSRYDMHWVRQAPGKGLEWVAIIFYDGSNKYYA DPVKGRFTISRDNSKNTLYLQMNSLRAEDTAVYYCATLAAAFDYWGQG TLVTVSS*ASTKGPSVFPLAPCSRSTSESTAALGCLVKDYFPEPVTVSWNSG ALTSGVHTFPAVLQSSGLYSLSSVVTVPSSNFGTQTYTCNVDHKPSNTKV DKTVERKCCVECPPCPAPPVAGPSVFLFPPKPKDTLMISRTPEVTCVVVD VSHEDPEVQFNWYVDGVEVHNAKTKPREEQFNSTFRVVSVLTVVHQDW LNGKEYKCKVSNKGLPAPIEKTISKTKGQPREPQVYTLPPSREEMTKNQV SLTCLVKGFYPSDIAVEWESNGQPENNYKTTPPMLDSDGSFFLYSKLTVD KSRWQQGNVFSCSVMHEALHNHYTQKSLSLSPGK* |
| 83 | Ab23-AbL-6.147 LC NA | GACATTCAAATGACACAGTCGCCCTCCTCGCTCTCGGCGTCAGTCGGG GATCGCGTGACAATCACGTGTCGGGCCAGCCAGGACATTTCGAGCTAC CTCAACTGGTATCAGCAGAAACCGGGGAAAGCGCCGAAGCTGCTTAT CTACTCCACCTCAAGGTTGAATTCCGGAGTACCCTCAAGATTTTCGGG TAGCGGATCAGGAACCGACTTCACACTTACGATCTCGTCGTTGCAGCC AGAAGATTTCGCAACGTACTATTGCCAGCAAGATATCAAGCACCCTAC GTTTGGTCAGGGCACTAAAGTGGAGATTAAGCGCACAGTGGCTGCTCC ATCCGTCTTTATCTTCCCTCCATCATACGTGCTCACTCAGCCGCCCAGC GTATCGGTGGCTCCCGGACAGACGGCGCGAATCACGTGCGGTGGGAA CAATATCGGCTCCAAGTCAGTCCATTGGTATCAACAGAAACCTGGTCA GGCACCAGTCCTGGTGGTATACGATGACTCGGACAGGCCCTCGGAGA TTCCGGAACGCTTCTCCGGATCGAATTCGGGGAACACAGCGACCTTGA CGATCAGCAGAGTGGAGGCCGGAGATGAAGCCGACTACTATTGTCAG GTGTGGGATTCCAGCTCCGACCACGTCGTATTTGGAGGTGGGACACGG CTTACCGTCCTAGGTCAGCCCAAGGCCAACCCCACTGTCACTCTGTTC CCGCCCTCCTCTGAGGAGCTCCAAGCCAACAAGGCACACTAGTGTGT CTGATCAGTGACTTCTACCCGGGAGCTGTGACAGTGGCCTGGAAGGCA GATGGCAGCCCCGTCAAGGCGGGAGTGGAGACCACCAAACCCTCCAA ACAGAGCAACAACAAGTACGCGGCCAGCAGCTACCTGAGCCTGACGC CCGAGCAGTGGAAGTCCCACAGAAGCTACAGCTGCCAGGTCACGCAT GAAGGGAGCACCGTGGAGAAGACAGTGGCCCCTACAGAATGTTCA |

TABLE 1-continued

| SEQ ID NO: | DESCRIPTION | SEQUENCE |
|---|---|---|
| 84 | Ab23-AbL-6.147 LC AA | DIQMTQSPSSLSASVGDRVTITCRASQDISSYLNWYQQKPGKAPKLLIYSTSRLNSGVPSRFSGSGSGTDFTLTISSLQPEDFATYYCQQDIKHPTFGQGTKVEIKRTVAAPSVFIFPPSYVLTQPPSVSVAPGQTARITCGGNNIGSKSVHWYQQKPGQAPVLVVYDDSDRPSEIPERFSGSNSGNTATLTISRVEAGDEADYYCQVWDSSSDHVVFGGGTRLTVLG*QPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS* |
| 85 | 5.80-AbL-Ab23 G2 NA | GAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGACGGCCTCGGACACCGCCATGTATTACTGTGCGAGACAGGGAGAGAGCTTTGACTACTGGGGCCAGGGAACCCTGGTCACGGTCTCCTCAGCGTCAACGAAAGGACCGTCGGTGTTCCCCTTGGCCCCTGAGGTGCAGCTCGTACAGTCGGGTGCGGAAGTAAAGAAACCCGGCTCATCCGTGAAAGTCTCGTGTAAAGCCTCCGGGTTCACCTTCACAGACTACATTATGCACTGGGTGCGGCAGGCCCCTGGGCAGGGCCTTGAATGGATGGGGTATATCAACCCCTACAATGATGACACGGAGTATAACGAAAAGTTTAAGGGAAGGGTGACAATCACGGCGGATAAGAGCACCAGCACTGCATACATGGAGCTCTCGTCATTGCGCTCGGAGGACACTGCAGTCTACTATTGCGCGAGATCCATCTACTATTACGATGCGCCGTTTGCTTATTGGGGACAAGGAACGCTGGTCACCGTCTCTAGTGCCTCCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCCAGCTGTCCTACAGTCCTCAGGACTCTACTCCCTCAGCAGCGTGGTGACCGTGCCCTCCAGCAACTTCGGCACCCAGACCTACACCTGCAACGTAGATCACAAGCCCAGCAACACCAAGGTGGACAAGACAGTTGAGCGCAAATGTTGTGTCGAGTGCCCACCGTGCCCAGCACCACCTGTGGCAGGACCGTCAGTCTTCCTCTTCCCCCCAAAACCCAAGGACACCCTCATGATCTCCCGGACCCCTGAGGTCACGTGCGTGGTGGTGGACGTGAGCCACGAAGACCCCGAGGTCCAGTTCAACTGGTACGTGGACGGCGTGGAGGTGCATAATGCCAAGACAAAGCCACGGGAGGAGCAGTTCAACAGCACGTTCCGTGTGGTCAGCGTCCTCACCGTTGTGCACCAGGACTGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCACAGGT |

TABLE 1-continued

| SEQ ID NO: | DESCRIPTION | SEQUENCE |
|---|---|---|
| | | GTACACCCTGCCCCCATCCCGGGAGGAGATGACCAAGAACCAGGTCA |
| | | GCCTGACCTGCCTGGTCAAAGGCTTCTACCCCAGCGACATCGCCGTGG |
| | | AGTGGGAGAGCAATGGGCAGCCGGAGAACAACTACAAGACCACACCT |
| | | CCCATGCTGGACTCCGACGGCTCCTTCTTCCTCTACAGCAAGCTCACC |
| | | GTGGACAAGAGCAGGTGGCAGCAGGGGAACGTCTTCTCATGCTCCGT |
| | | GATGCATGAGGCTCTGCACAACCACTACACGCAGAAGAGCCTCTCCCT |
| | | GTCTCCGGGTAAA |
| 86 | 5.80-AbL-Ab23 G2 AA | EVQLVQSGAEVKKPGESLKISCKGSGYSFTSYWIGWVRQMPGKGLEWM GIIYPGDSDTRYSPSFQGQVTISADKSISTAYLQWSSLTASDTAMYYCAR QGESFDYWGQGTLVTVSS*ASTKGPSVFPLAP*EVQLVQSGAEVKKPGSSV KVSCKASGFTFTDYIMHWVRQAPGQGLEWMGYINPYNDDTEYNEKFK GRVTITADKSTSTAYMELSSLRSEDTAVYYCARSIYYYDAPFAYWGQGT LVTVSS*ASTKGPSVFPLAPCSRSTSESTAALGCLVKDYFPEPVTVSWNSGA LTSGVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVVDV SHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDK SRWQQGNVFSCSVMHEALHNHYTQKSLSLSPGK* |
| 87 | 5.80-AbL-Ab23 LC NA | CAGTCAGTGCTGACGCAGCCGCCCTCAGTGTCTGGGGCCCCAGGGCA GAGGGTCACCATCTCCTGCACTGGGAGCAGCTCCAACATCGGGGCAG ATTATGATGTACACTGGTACCAGCAGCTTCCAGGAACAGCCCCCAAAC TCCTCATCTATGATTACAGCAATCGGCCCTCAGGGGTCCCTGACCGAT TCTCTGGCTCCAAGTCTGGCACCTCAGCCTCCCTGGCCATCACTGGGC TCCAGGCTGAGGATGAGGCTGATTATTACTGCCAGTCCTATGACAACA GCCTGAGTGGTTATGTGGTATTCGGCGGAGGGACCAAGCTGACCGTCC TCGGGCAGCCCAAGGCTGCGCCATCGGTCACTCTGTTCCCACCTGACA TTCAAATGACACAGTCGCCCTCCTCGCTCTCGGCGTCAGTCGGGGATC GCGTGACAATCACGTGTCGGGCCAGCCAGGACATTTCGAGCTACCTCA ACTGGTATCAGCAGAAACCGGGGAAAGCGCCGAAGCTGCTTATCTAC TCCACCTCAAGGTTGAATTCCGGAGTACCCTCAAGATTTTCGGGTAGC GGATCAGGAACCGACTTCACACTTACGATCTCGTCGTTGCAGCCAGAA GATTTCGCAACGTACTATTGCCAGCAAGATATCAAGCACCCTACGTTT GGTCAGGGCACTAAAGTGGAGATTAAGCGTACGGTGGCTGCACCATC TGTCTTCATCTTCCCGCCATCTGATGAGCAGTTGAAATCTGGAACTGC CTCTGTTGTGTGCCTGCTGAATAACTTCTATCCCAGAGAGGCCAAAGT ACAGTGGAAGGTGGATAACGCCCTCCAATCGGGTAACTCCCAGGAGA GTGTCACAGAGCAGGACAGCAAGGACAGCACCTACAGCCTCAGCAGC |

TABLE 1-continued

| SEQ ID NO: | DESCRIPTION | SEQUENCE |
|---|---|---|
| | | ACCCTGACGCTGAGCAAAGCAGACTACGAGAAACACAAAGTCTACGC |
| | | CTGCGAAGTCACCCATCAGGGCCTGAGCTCGCCCGTCACAAAGAGCTT |
| | | CAACAGGGGAGAGTGT |
| 88 | 5.80-AbL-Ab23 LC AA | QSVLTQPPSVSGAPGQRVTISCTGSSSNIGADYDVHWYQQLPGTAPKLLIYDYSNRPSGVPDRFSGSKSGTSASLAITGLQAEDEADYYCQSYDNSLSGYVVFGGGTKLTVLGQPKAAPSVTLFPPDIQMTQSPSSLSASVGDRVTITCRASQDISSYLNWYQQKPGKAPKLLIYSTSRLNSGVPSRFSGSGSGTDFTLTISSLQPEDFATYYCQQDIKHPTFGQGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC* |
| 89 | Ab23-AbL-5.80 G2 NA | GAGGTGCAGCTCGTACAGTCGGGTGCGGAAGTAAAGAAACCCGGCTC |
| | | ATCCGTGAAAGTCTCGTGTAAAGCCTCCGGGTTCACCTTCACAGACTA |
| | | CATTATGCACTGGGTGCGGCAGGCCCCTGGGCAGGGCCTTGAATGGAT |
| | | GGGGTATATCAACCCCTACAATGATGACACGGAGTATAACGAAAAGT |
| | | TTAAGGGAAGGGTGACAATCACGGCGGATAAGAGCACCAGCACTGCA |
| | | TACATGGAGCTCTCGTCATTGCGCTCGGAGGACACTGCAGTCTACTAT |
| | | TGCGCGAGATCCATCTACTATTACGATGCGCCGTTTGCTTATTGGGGA |
| | | CAAGGAACGCTGGTCACGGTCTCCTCAGCGTCAACGAAAGGACCGTC |
| | | GGTGTTCCCCTTGGCCCCTGAGGTGCAGCTGGTGCAGTCTGGAGCAGA |
| | | GGTGAAAAAGCCCGGGGAGTCTCTGAAGATCTCCTGTAAGGGTTCTG |
| | | GATACAGCTTTACCAGCTACTGGATCGGCTGGGTGCGCCAGATGCCCG |
| | | GGAAAGGCCTGGAGTGGATGGGGATCATCTATCCTGGTGACTCTGATA |
| | | CCAGATACAGCCCGTCCTTCCAAGGCCAGGTCACCATCTCAGCCGACA |
| | | AGTCCATCAGCACCGCCTACCTGCAGTGGAGCAGCCTGACGGCCTCG |
| | | GACACCGCCATGTATTACTGTGCGAGACAGGGAGAGAGCTTTGACTA |
| | | CTGGGGCCAGGGAACCCTGGTCACCGTCTCTAGTGCCTCCACCAAGGG |
| | | CCCATCGGTCTTCCCCCTGGCGCCCTGCTCCAGGAGCACCTCCGAGAG |
| | | CACAGCGGCCCTGGGCTGCCTGGTCAAGGACTACTTCCCCGAACCGGT |
| | | GACGGTGTCGTGGAACTCAGGCGCTCTGACCAGCGGCGTGCACACCTT |
| | | CCCAGCTGTCCTACAGTCCTCAGGACTCTACTCCCTCAGCAGCGTGGT |
| | | GACCGTGCCCTCCAGCAACTTCGGCACCCAGACCTACACCTGCAACGT |
| | | AGATCACAAGCCCAGCAACACCAAGGTGGACAAGACAGTTGAGCGCA |
| | | AATGTTGTGTCGAGTGCCCACCGTGCCCAGCACCACCTGTGGCAGGAC |
| | | CGTCAGTCTTCCTCTTCCCCCCAAAACCCAAGGACACCCTCATGATCT |
| | | CCCGGACCCCTGAGGTCACGTGCGTGGTGGTGGACGTGAGCCACGAA |
| | | GACCCCGAGGTCCAGTTCAACTGGTACGTGGACGGCGTGGAGGTGCA |
| | | TAATGCCAAGACAAAGCCACGGGAGGAGCAGTTCAACAGCACGTTCC |

TABLE 1-continued

| SEQ ID NO: | DESCRIPTION | SEQUENCE |
|---|---|---|
| | | GTGTGGTCAGCGTCCTCACCGTTGTGCACCAGGACTGGCTGAACGGCA |
| | | AGGAGTACAAGTGCAAGGTCTCCAACAAAGGCCTCCCAGCCCCCATC |
| | | GAGAAAACCATCTCCAAAACCAAAGGGCAGCCCCGAGAACCACAGGT |
| | | GTACACCCTGCCCCCATCCCGGGAGGAGATGACCAAGAACCAGGTCA |
| | | GCCTGACCTGCCTGGTCAAAGGCTTCTACCCCAGCGACATCGCCGTGG |
| | | AGTGGGAGAGCAATGGGCAGCCGGAGAACAACTACAAGACCACACCT |
| | | CCCATGCTGGACTCCGACGGCTCCTTCTTCCTCTACAGCAAGCTCACC |
| | | GTGGACAAGAGCAGGTGGCAGCAGGGGAACGTCTTCTCATGCTCCGT |
| | | GATGCATGAGGCTCTGCACAACCACTACACGCAGAAGAGCCTCTCCCT |
| | | GTCTCCGGGTAAA |
| 90 | Ab23-AbL-5.80 G2 AA | EVQLVQSGAEVKKPGSSVKVSCKASGFTFTDYIMHWVRQAPGQGLEWM GYINPYNDDTEYNEKFKGRVTITADKSTSTAYMELSSLRSEDTAVYYCA RSIYYYDAPFAYWGQGTLVTVSSASTKGPSVFPLAPEVQLVQSGAEVKK PGESLKISCKGSGYSFTSYWIGWVRQMPGKGLEWMGIIYPGDSDTRYSP SFQGQVTISADKSISTAYLQWSSLTASDTAMYYCARQGESFDYWGQGTL VTVSS*ASTKGPSVFPLAPCSRSTSESTAALGCLVKDYFPEPVTVSWNSGAL TSGVHTFPAVLQSSGLYSLSSVVTVPSSNFGTQTYTCNVDHKPSNTKVDK TVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLT CLVKGFYPSDIAVEWESNGQPENNYKTTPPMLDSDGSFFLYSKLTVDKSR WQQGNVFSCSVMHEALHNHYTQKSLSLSPGK* |
| 91 | Ab23-AbL-5.80 LC NA | GACATTCAAATGACACAGTCGCCCTCCTCGCTCTCGGCGTCAGTCGGG GATCGCGTGACAATCACGTGTCGGGCCAGCCAGGACATTTCGAGCTAC CTCAACTGGTATCAGCAGAAACCGGGGAAAGCGCCGAAGCTGCTTAT CTACTCCACCTCAAGGTTGAATTCCGGAGTACCCTCAAGATTTTCGGG TAGCGGATCAGGAACCGACTTCACACTTACGATCTCGTCGTTGCAGCC AGAAGATTTCGCAACGTACTATTGCCAGCAAGATATCAAGCACCCTAC GTTTGGTCAGGGCACTAAAGTGGAGATTAAGCGCACAGTGGCTGCTCC ATCCGTCTTTATCTTCCCTCCACAGTCAGTGCTGACGCAGCCGCCCTCA GTGTCTGGGCCCCAGGGCAGAGGGTCACCATCTCCTGCACTGGGAG CAGCTCCAACATCGGGGCAGATTATGATGTACACTGGTACCAGCAGCT TCCAGGAACAGCCCCCAAACTCCTCATCTATGATTACAGCAATCGGCC CTCAGGGGTCCCTGACCGATTCTCTGGCTCCAAGTCTGGCACCTCAGC CTCCCTGGCCATCACTGGGCTCCAGGCTGAGGATGAGGCTGATTATTA CTGCCAGTCCTATGACAACAGCCTGAGTGGTTATGTGGTATTCGGCGG AGGGACCAAGCTGACCGTCCTAGGTCAGCCCAAGGCCAACCCCACTG TCACTCTGTTCCCGCCCTCCTCTGAGGAGCTCCAAGCCAACAAGGCCA |

TABLE 1-continued

| SEQ ID NO: | DESCRIPTION | SEQUENCE |
|---|---|---|
| | | CACTAGTGTGTCTGATCAGTGACTTCTACCCGGGAGCTGTGACAGTGG |
| | | CCTGGAAGGCAGATGGCAGCCCCGTCAAGGCGGGAGTGGAGACCACC |
| | | AAACCCTCCAAACAGAGCAACAACAAGTACGCGGCCAGCAGCTACCT |
| | | GAGCCTGACGCCCGAGCAGTGGAAGTCCCACAGAAGCTACAGCTGCC |
| | | AGGTCACGCATGAAGGGAGCACCGTGGAGAAGACAGTGGCCCCTACA |
| | | GAATGTTCA |
| 92 | Ab 23-AbL-5.80 LC AA | DIQMTQSPSSLSASVGDRVTITCRASQDISSYLNWYQQKPGKAPKLLIYS TSRLNSGVPSRFSGSGSGTDFTLTISSLQPEDFATYYCQQDIKHPTFGQGT KVEIKRTVAAPSVFIFPPQSVLTQPPSVSGAPGQRVTISCTGSSSNIGADYD VHWYQQLPGTAPKLLIYDYSNRPSGVPDRFSGSKSGTSASLAITGLQAED EADYYCQSYDNSLSGYVVFGGGTKLTVLG*QPKANPTVTLFPPSSEELQA* *NKATLVCLISDFYPGAVTVAWKADGSPVKAGVETTKPSKQSNNKYAASSY* *LSLTPEQWKSHRSYSCQVTHEGSTVEKTVAPTECS* |
| 93 | vK1 leader sequence | MDMRVPAQLLGLLLLWLRGARC |
| | Sclerostin mAbs AA sequences | |
| 94 | Ab5 and Ab5K VL | DIQMTQSPSSLSASVGDRVTITCRASQDISNYLNWYQQKPGKAPKLLIYY TSRLLSGVPSRFSGSGSGTDFTLTISSLQPEDFATYYCQQGDTLPYTFGGG TKVEIK |
| 95 | Ab5 VH | EVQLVQSGAEVKKPGASVKVSCKASGYTFTDYNMHWVRQAPGQGLEW MGEINPNSGGAGYNQKFKGRVTMTTDTSTSTAYMELRSLRSDDTAVYY CARLGYDDIYDDWYFDVWGQGTTVTVSS |
| 96 | Ab5K VH | EVQLVQSGAEVVQPGASVKVSCAASGYTFTDYNMHWVRQAPGQGLEW MGEINPNSGGAGYNQKFKGRVTMTTDTSTSTAYMELRSLRSDDTAVYY CARLGYDDIYDDWYFDVWGQGTTVTVSS |
| 97 | Ab5 and Ab5K VL CDR1 | RASQDISNYLN |
| 98 | Ab5 and Ab5K VL CDR2 | YTSRLLS |
| 99 | Ab5 and Ab5K VL CDR3 | QQGDTLPYT |
| 100 | Ab5 and Ab5K VH CDR1 | DYNMH |
| 101 | Ab5 and Ab5K VH CDR2 | EINPNSGGAGYNQKFKG |
| 102 | Ab5 and Ab5K VH CDR3 | LGYDDIYDDWYFDV |

TABLE 1-continued

| SEQ ID NO: | DESCRIPTION | SEQUENCE |
|---|---|---|
| 103 | Ab23 VL | DIQMTQSPSSLSASVGDRVTITCRASQDISSYLNWYQQKPGKAPKWYSTSRLNSGVPSRFSGSGSGTDFTLTISSLQPEDFATYYCQQDIKHPTFGQGTKVEIK |
| 104 | Ab23 VH | EVQLVQSGAEVKKPGSSVKVSCKASGFTFTDYIMHWVRQAPGQGLEWMGYINPYNDDTEYNEKFKGRVTITADKSTSTAYMELSSLRSEDTAVYYCARSIYYYDAPFAYWGQGTLVTVSS |
| 105 | Ab23VL CDR1 | RASQDISSYLN |
| 106 | Ab23VL CDR2 | STSRLNS |
| 107 | Ab23VL CDR3 | QQDIKHPT |
| 108 | Ab23VH CDR1 | DYIMH |
| 109 | Ab23VH CDR2 | YINPYNDDTEYNEKFKG |
| 110 | Ab23VH CDR3 | SIYYYDAPFAY |
| 111 | 13F3 VL | DIQMTQSPSSVSASVGDRVTITCRASQGISNWLAWYQQKPGTAPKLLIYAASSLQSGVPSRFSGSGSGTDFTLTISSLQPEDFATYYCQQANSFPFTFGPGTKVDIK |
| 112 | 13F3 VH | QVQLVQSGTEVKKPGASMKVSCKASGYTFTSYYMHWVRQAPGQGLEWMGIINPSGDSTSYAQKFQGRVTMTRDTSTNTVYMELSSLRSEDTAMYYCARDVEVRGISHFDYWGQGTLVTVSS |
| 113 | 13F3 VL CDR1 | RASQGISNWLA |
| 114 | 13F3 VL CDR2 | AASSLQS |
| 115 | 13F3 VL CDR3 | QQANSFPFT |
| 116 | 13F3 VH CDR1 | SYYMH |
| 117 | 13F3 VH CDR2 | IINPSGDSTSYAQKFQG |
| 118 | 13F3 VH CDR3 | DVEVRGISHFDY |
| 119 | 20C3.1 VL | QSALTQPASVSGSPGQSITISCTGTSSDVGGYNYVSWYQQHPGKAPKLMIYEVSYRPSGVSNRFSGSKSGSTASLTISGLQPEDEADYYCSSYAISSTLVFGGGTKMTVLG |
| 120 | 20C3.1 VH | QVQLQESGPGLVKPSETLSLTCTVSGGSISSYYWSWIRQPPGKGLEWIGYISDSGSTNYNPSLKSRIPISVDTSKNQFSLKLSSVTAADTAVYYCARWQLAHDAFDIWGQGTMVTVSS |
| 121 | 20C3.1 VL CDR1 | TGTSSDVGGYNYVS |
| 122 | 20C3.1 VL CDR2 | EVSYRPS |
| 123 | 20C3.1 VL CDR3 | SSYAISSTLV |
| 124 | 20C3.1 VH CDR1 | SYYWS |

TABLE 1-continued

| SEQ ID NO: | DESCRIPTION | SEQUENCE |
|---|---|---|
| 125 | 20C3.1 VH CDR2 | YISDSGSTNYNPSLKS |
| 126 | 20C3.1 VH CDR3 | WQLAHDAFDI |
| 127 | 38B12.1 VL | DIQMTQSPSSLSASVGDRVTITCRASQTISNYLNWYQQKPGKAPNLLIYAASGLQSGVPSRFSGSGSGTDFTLTISSLQPEDFGTYYCQQSFSTPITFGQGTRLEIK |
| 128 | 38B12.1 VH | QVQLVQSGAEVKKPGASVKVSCKASGYTFTNYYMYWVRQAPGQGLEWMGIINPSGGSTSYAQKFQGRVTMTRDTSTSTVYMELSSLRSEDTAVYYCAREDTAMAYFDYWGQGTLVTVSS |
| 129 | 38B12.1 VL CDR1 | RASQTISNYLN |
| 130 | 38B12.1 VL CDR2 | AASGLQS |
| 131 | 38B12.1 VL CDR3 | QQSFSTPIT |
| 132 | 38B12.1 VH CDR1 | NYYMY |
| 133 | 38B12.1 VH CDR2 | IINPSGGSTSYAQKFQG |
| 134 | 38B12.1 VH CDR3 | EDTAMAYFDY |
| 135 | 46H1 VL | DIQMTQSPASVSASVGDRVTITCRASQGISSWLAWYQQKPGKAPKLLIYNTFSLESGVPSRFSGSGSGTDFTLTISSLQPEDFATYYCQQANSFPFTFGPGTKVDMK |
| 136 | 46H1VH | QVQLQESGPGLVKPSETLSLTCTVSGGSISSYYWSWIRQPPGKGLEWIGYIYYSGSTSYNPSLKSRVTISIDTSKNQFSLKLSSVTAADTAVYYCARDLELEAFDIWGQGTMVTVSS |
| 137 | 46H1 VL CDR1 | RASQGISSWLA |
| 138 | 46H1 VL CDR2 | NTFSLES |
| 139 | 46H1 VL CDR3 | QQANSFPFT |
| 140 | 46H1 VH CDR1 | SYYWS |
| 141 | 46H1 VH CDR2 | YIYYSGSTSYNPSLKS |

TABLE 1-continued

| SEQ ID NO: | DESCRIPTION | SEQUENCE |
|---|---|---|
| 142 | 46H1 VH CDR3 | DLELEAFDI |
| 143 | 2B8.1 VL | NFMLTQPHSVSESPGKTVAISCTRNSGSIASNSVQWYQQRPGSSPTTVIFE DNQRPSGVPDRFSGSIDSSSNSASLTISGLKTEDEADYYCQSYDSNNWVF GGGTKLTVL |
| 144 | 2B8.1 VH | QVQLVESGGGVVQPGRSLRLSCAASGFTFSSYVMHWVRQAPGKGLEWV AVIWYDGSNKYYADSVKGRFTISRDNSKNTLYLQMNSLRAEDTAVYYC AREGYDYGEDYYYYGMDVWGQGTTVTVSS |
| 145 | 2B8.1 VL CDR1 | TRNSGSIASNSVQ |
| 146 | 2B8.1 VL CDR2 | EDNQRPS |
| 147 | 2B8.1 VL CDR3 | QSYDSNNWV |
| 148 | 2B8.1 VH CDR1 | SYVMH |
| 149 | 2B8.1 VH CDR2 | VIWYDGSNKYYADSVKG |
| 150 | 2B8.1 VH CDR3 | EGYDYGEDYYYYGMDV |
| 151 | 8G2.1 VL | DIQMTQSPSSVSASVGDRVTITCRASQDISNWLAWYQQKPGKVPKLLIYA ASYLQSGVPSRFSGSGSGTDFTLTISSLQPEDFATYSCQQANSFPFTFGPGT KVDIK |
| 152 | 8G2.1 VH | QVQLVQSGAEVKKPGASVKVSCKASGYTFTSYDINWVRQATGQGLEWM GWMNPNSGKTGYAQKFQGRVTMTRDTSISTAYMELSSLRSEDTAVYYC AREEEYYESGSLFYYYGLDVWGQGTTVTVSS |
| 153 | 8G2.1 VL CDR1 | RASQDISNWLA |
| 154 | 8G2.1 VL CDR2 | AASYLQS |
| 155 | 8G2.1 VL CDR3 | QQANSFPFT |
| 156 | 8G2.1 VH CDR1 | SYDIN |
| 157 | 8G2.1 VH CDR2 | WMNPNSGKTGYAQKFQG |
| 158 | 8G2.1 VH CDR3 | EEEYYESGSLFYYYGLDV |

TABLE 1-continued

| SEQ ID NO: | DESCRIPTION | SEQUENCE |
|---|---|---|
| 159 | 19D11.1 VL | SYVLTQPPSVSVAPGQTARITCGGDNIGSISVHWYQQKPGQAPVLVVYDD SDRPSGIPERFSGSNSGNTATLTISWVEAGDEADYYCQVWDSSIDHPVLF GGGTKLTVL |
| 160 | 19D11.1 VH | EVQLVESGGGLVQPGGSLRLSCAASGFTFSSYDMHWVRQATGKGLEWV SAIGTAGDTYYAGSVKGRFTISRENAKNSLYLQMNSLRVGDTAVYYCAR SWGEGNYYFYYGMDVWGQGTTVTVSS |
| 161 | 19D11.1 VL CDR1 | GGDNIGSISVH |
| 162 | 19D11.1 VL CDR2 | DDSDRPS |
| 163 | 19D11.1 VL CDR3 | QVWDSSIDHPVL |
| 164 | 19D11.1 VH CDR1 | SYDMH |
| 165 | 19D11.1 VH CDR2 | AIGTAGDTYYAGSVKG |
| 166 | 19D11.1 VH CDR3 | SWGEGNYYFYYGMDV |
| 167 | 34H3.1 VL | DIQMTQSPSSVSASVGDRVTITCRASQGINTWLAWYQQKPGKAPKLLIYV ASSLQSGVPSRFSGSGSGTDFTLTISSLQPEDFATYYCQQSDSFPWTFGPGT KVEIT |
| 168 | 34H3.1 VH | QVQLVQSGAEVKKPGASVKVSCKVSGYTLTELSMHWVRQAPGKGLEW MGGFDPEDGETIYVQKFQGRVTMTEDTSTDTAYMELSSLRSEDTAVYYC ATDLGYGSGNSYYYYSGMDVWGQGTTVTVSS |
| 169 | 34H3.1 VL CDR1 | RASQGINTWLA |
| 170 | 34H3.1 VL CDR2 | VASSLQS |
| 171 | 34H3.1 VL CDR3 | QQSDSFPWT |
| 172 | 34H3.1 VH CDR1 | ELSMH |
| 173 | 34H3.1 VH CDR2 | GFDPEDGETIYVQKFQG |
| 174 | 34H3.1 VH CDR3 | DLGYGSGNSYYYYSGMDV |
| 175 | 27H6.1 VL | DIVMTQTPLSLPVTPGEPASISCRSSQSLLNSVDGSTNLDWYLQKPGQSPQ LLIYTLSYRASGVPDRFSGSGSGTDFTLKISRVEAEDVGVYYCMQRIEFPL TFGGGTKVEIK |

TABLE 1-continued

| SEQ ID NO: | DESCRIPTION | SEQUENCE |
|---|---|---|
| 176 | 27H6.1 VH | EVQLVESGGGLVQPGGSLRLSCAASGFTFSSYSMNWVRQAPGKGLEWVSYISSSGSSIYYADSVKGRFTISRDNAKNSLYLQMNSLRDEDTAVYYCARERYYGDTPFDYWGQGTLVTVSS |
| 177 | 27H6.1 VL CDR1 | RSSQSLLNSVDGSTNLD |
| 178 | 27H6.1 VL CDR2 | TLSYRAS |
| 179 | 27H6.1 VL CDR3 | MQRIEFPLT |
| 180 | 27H6.1 VH CDR1 | SYSMN |
| 181 | 27H6.1 VH CDR2 | YISSSGSSIYYADSVKG |
| 182 | 27H6.1 VH CDR3 | ERYYGDTPFDY |
| 183 | 42F4HZ VL | DIQLTQSPSFLSASVGDRVTITCRASSSVTSSYLNWYQQKPGKAPKLLIYSTSNLASGVPSRFSGSGSGTEFTLTISSLQPEDFATYYCQQYDFFPSTFGGGTKVEIK |
| 184 | 42F4HZ VH | EVQLVQSGAEVKKPGASVKVSCKASGYTFTDYYMNWVRQAPGQRLEWMGDINPYNDDTTYNHKFKGRVTITRDTSASTAYMELSSLRSEDTAVYYCARETAVITTNAMDYWGQGTTVTVSS |
| 185 | 42F4HZ VL CDR1 | RASSSVTSSYLN |
| 186 | 42F4HZ VL CDR2 | STSNLAS |
| 187 | 42F4HZ VL CDR3 | QQYDFFPST |
| 188 | 42F4HZ VH CDR1 | DYYMN |
| 189 | 42F4HZ VH CDR2 | DINPYNDDTTYNHKFKG |
| 190 | 42F4HZ VH CDR3 | ETAVITTNAMDY |
| 191 | 42F4MU VL | QIVLTQSPAIMSASPGEKVTMTCRASSSVTSSYLNWYQQKPGSSPKLWIYSTSNLASGVPARFSGSGSGTSYSLTISSVEAEDAATYYCQQYDFFPSTFGGGTKLEIK |

TABLE 1-continued

| SEQ ID NO: | DESCRIPTION | SEQUENCE |
|---|---|---|
| 192 | 42F4MU VH | EVQLQQSGPELVKPGASVKMSCKASGYTFTDYYMNWVKQSHGESLEWI GDINPYNDDTTYNHKFKGKATLTVDKSSNTAYMQLNSLTSEDSAVYYCA RETAVITTNAMDYWGQGTSVTVSS |
| 193 | 42F4MU VL CDR1 | RASSSVTSSYLN |
| 194 | 42F4MU VL CDR2 | STSNLAS |
| 195 | 42F4MU VL CDR3 | QQYDFFPST |
| 196 | 42F4MU VH CDR1 | DYYMN |
| 197 | 42F4MU VH CDR2 | DINPYNDDTTYNHKFKG |
| 198 | 42F4MU VH CDR3 | ETAVITTNAMDY |
| 199 | 13C7MU VL | DIQMTQITSSLSASLGDRVSISCRASQDISNYLNWYQQKPDGTFKLLIFYTS RLLSGVPSRFSGSGSGTDYSLTIYNLEQEDFATYFCQQGDTLPYTFGGGTK LEIK |
| 200 | 13C7MU VH | EVQLQQSGPELMKPGASVKMSCKASGYTFTDYNMHWVKQNQGKTLEW IGEINPNSGGAGYNQKFKGKATLTVDKSSTTAYMELRSLTSEDSAVYYCA RLGYDDIYDDWYFDVWGAGTTVTVSS |
| 201 | 13C7MU VL CDR1 | RASQDISNYLN |
| 202 | 13C7MU VL CDR2 | YTSRLLS |
| 203 | 13C7MU VL CDR3 | QQGDTLPYT |
| 204 | 13C7MU VH CDR1 | DYNMH |
| 205 | 13C7MU VH CDR2 | EINPNSGGAGYNQKFKG |
| 206 | 13C7MU VH CDR3 | LGYDDIYDDWYFDV |
| 207 | 13C7Rat VL | DIQMTQSPSSLSASLGDRVTITCRASQDISNYLNWYQQKPDGTVKRLIYY TSRLLSGVPSRFSGSGSGTDYSLSISSLESEDFAMYYCQQGDTLPYTFGGG TKLELK |

TABLE 1-continued

| SEQ ID NO: | DESCRIPTION | SEQUENCE |
|---|---|---|
| 208 | 13C7Rat VH | EVQLQQSGPELQRPGASVKLSCKASGYTFTDYNMHWVKQSHGKSLEWIGEINPNSGGAGYNQKFKGKATLTADKSSNTAYMELSRLTSEDSAVYYCARLGYDDIYDDWYFDVWGQGTTVTVSS |
| 209 | 13C7Rat VL CDR1 | RASQDISNYLN |
| 210 | 13C7Rat VL CDR2 | YTSRLLS |
| 211 | 13C7Rat VL CDR3 | QQGDTLPYT |
| 212 | 13C7Rat VH CDR1 | DYNMH |
| 213 | 13C7Rat VH CDR2 | EINPNSGGAGYNQKFKG |
| 214 | 13C7Rat VH CDR3 | LGYDDIYDDWYFDV |
| 215 | 13C7Hu VL | DIQMTQSPSSLSASVGDRVTITCRASQDISNYLNWYQQKPGKAPKLLIYYTSRLLSGVPSRFSGSGSGTDFTLTISSLQPEDFATYYCQQGDTLPYTFGGGTKVEIK |
| 216 | 13C7Hu VH | EVQLVQSGAEVKKPGASVKVSCKASGYTFTDYNMHWVRQAPGQGLEWMGEINPNSGGAGYNQKFKGRVTMTTDTSTSTAYMELRSLRSDDTAVYYCARLGYDDIYDDWYFDVWGQGTTVTVSS |
| 217 | 13C7Hu VL CDR1 | RASQDISNYLN |
| 218 | 13C7Hu VL CDR2 | YTSRLLS |
| 219 | 13C7Hu VL CDR3 | QQGDTLPYT |
| 220 | 13C7Hu VH CDR1 | DYNMH |
| 221 | 13C7Hu VH CDR2 | EINPNSGGAGYNQKFKG |
| 222 | 13C7Hu VH CDR3 | LGYDDIYDDWYFDV |
| | DKK-1 mAbs AA Sequences | |
| 223 | 11H10Hu VL | EIVLTQSPATLSLSPGERATLSCRASQWVSSYLAWYQQKPGQAPRLLIYDASNRATGIPARFSGSGSGTDFTLTISSLEPEDFAVYYCAWQEFFGQGTKLEIK |

TABLE 1-continued

| SEQ ID NO: | DESCRIPTION | SEQUENCE |
|---|---|---|
| 224 | 11H10Hu VH | EVQLVQSGGGLVQPGGSLRLSCTASGFTFSNHWIHWVRQAPGKGLEWVS GINWNSGSRGYSDSVKGRFTISRDNAKNSLYLQMNSLRAEDTAVYYCAR ERPVATGAFDIWGQGTTVTVSS |
| 225 | 11H10Hu VL CDR1 | RASQWVSSYLA |
| 226 | 11H10Hu VL CDR2 | DASNRAT |
| 227 | 11H10Hu VL CDR3 | AWQEF |
| 228 | 11H10Hu VH CDR1 | NHWIH |
| 229 | 11H10Hu VH CDR2 | GINWNSGSRGYSDSVKG |
| 230 | 11H10Hu VH CDR3 | ERPVATGAFDI |
| 231 | 11H10Rat VL | DIRMTQSPASLSASLGETVNIECLASEDIYSDLAWYQQKPGKSPQLLIYNA NSLQNGVPSRFSGSGSGTQYSLKINSLQSEDVATYFCQQYNNYPPTEGGG TKLELK |
| 232 | 11H10Rat VH | EVQLVESGGGLVQPANSLKLSCAASGFTFSDYAMAWVRQSPKKGLEWV ATIIYDGSSTYYRDSVKGRETISRDNAKSTLYLQMDSLRSEDTATYYCAT GLGIATDYFDYWGQGVLVTVSS |
| 233 | 11H10Rat VL CDR1 | LASEDIYSDLA |
| 234 | 11H10Rat VL CDR2 | NANSLQN |
| 235 | 11H10Rat VL CDR3 | QQYNNYPPT |
| 236 | 11H10Rat VH CDR1 | DYAMA |
| 237 | 11H10Rat VH CDR2 | TIIYDGSSTYYRDSVKG |
| 238 | 11H10Rat VH CDR3 | GLGIATDYFDY |
| 239 | 2.4.1 VL | DIQMTQSPSSLSASVGDRVTITCRASQGIRDDLGWFQQKPGKAPKRLIYA ASSLQSGVPSRFSGSGSGTEFTLTISSLQPEDFATYYCLQHNSYPCSFGQGT KLEFK |

TABLE 1-continued

| SEQ ID NO: | DESCRIPTION | SEQUENCE |
|---|---|---|
| 240 | 2.4.1 VH | QVQLMQSGAEVKKPGASVKVSCKASGYTFTSYGISWVRQAPGQGLEWMGWISADNGHTNYAQKLQGRVTMTTDTSTSTAYMELRSLRSDDTAVYYCARDGELLNYYYYYGMDVWGQGTTVTVSS |
| 241 | 2.4.1 VL CDR1 | RASQGIRDDLG |
| 242 | 2.4.1 VL CDR2 | AASSLQS |
| 243 | 2.4.1 VL CDR3 | LQHNSYPCS |
| 244 | 2.4.1 VH CDR1 | SYGIS |
| 245 | 2.4.1 VH CDR2 | WISADNGHTNYAQKLQG |
| 246 | 2.4.1 VH CDR3 | DGELLNYYYYYGMDV |
| 247 | 2.20.1 VL | DIVMTQTPLSLSVIPGQPASISCKSSQSLLHSDGKTYLYWYLQRPGQPPQLLIYEVSNRFSGVPHRLSGSGSGTDFTLKISRVEAEDVGVYYCMQSIQVPWTFGQGTKVEIK |
| 248 | 2.20.1 VH | QVQLVESGGGVVQPGRSLRLSCAASGFTFSSYGMHWVRQAPGKGLEWVAVISYDGSDKYYADSVKGRFTISRDNSKNTLYLQMNSLRAEDTAVYYCARDQWGGSPAGPWGQGTLVTVSS |
| 249 | 2.20.1 VL CDR1 | KSSQSLLHSDGKTYLY |
| 250 | 2.20.1 VL CDR2 | EVSNRFS |
| 251 | 2.20.1 VL CDR3 | MQSIQVPWT |
| 252 | 2.20.1 VH CDR1 | SYGMH |
| 253 | 2.20.1 VH CDR2 | VISYDGSDKYYADSVKG |
| 254 | 2.20.1 VH CDR3 | DQWGGSPAGP |
| 255 | 2.37.1 VL | EIVLTQSPGTLSLSPGERATLSCRASQSVSSNYLAWYQQKPGQAPRLLIYGASSRATGIPDRFSGSGSGTDFTLTISRLEPEDFAVYYCQQYGSSPITEGQGTRLEIK |
| 256 | 2.37.1 VH | QVQLVESGGGVVQPGRSLRLSCAASGFTFSSYGMHWVRQAPGKGLEWVAVISYDGSDKYYADSVKGRFTFSRDNSKNTLYLQMNSLRAEDTAVYYCARELGIAASFDYWGQGTLVTVSS |
| 257 | 2.37.1 VL CDR1 | RASQSVSSNYLA |
| 258 | 2.37.1 VL CDR2 | GASSRAT |

TABLE 1-continued

| SEQ ID NO: | DESCRIPTION | SEQUENCE |
|---|---|---|
| 259 | 2.37.1 VL CDR3 | QQYGSSPIT |
| 260 | 2.37.1 VH CDR1 | SYGMH |
| 261 | 2.37.1 VH CDR2 | VISYDGSDKYYADSVKG |
| 262 | 2.37.1 VH CDR3 | ELGIAASFDY |
| 263 | 2.40.1 VL | DIVMTQSPLSLSVTPGQPASISCKSSQSLLHSDGKTYLYWYLQKPGQPPQLLIYEVSNRFSGVPDRFSGSGSGTDFTLKISRVEAEDVGVYYCMQSIQVPWTFGQGTKVEIK |
| 264 | 2.40.1 VH | QVQLVESGGGVVQPGRSLRLSCAASGFTFSSYGMHWVRQAPGKGLWVAVISYDGSDKYYADSVKGRFTISRDNSKNTLYLQMNSLRAEDTAVYYCARDLVDTAMPWGQGTTVTVSS |
| 265 | 2.40.1 VL CDR1 | KSSQSLLHSDGKTYLY |
| 266 | 2.40.1 VL CDR2 | EVSNRFS |
| 267 | 2.40.1 VL CDR3 | MQSIQVPWT |
| 268 | 2.40.1 VH CDR1 | SYGMH |
| 269 | 2.40.1 VH CDR2 | VISYDGSDKYYADSVKG |
| 270 | 2.40.1 VH CDR3 | DLVDTAMP |
| 271 | 2.41.1 VL | DIVMTQTPLSLSVTPGQPASISCKSSQSLLHSDGKTYLYWYLQKPGQPPQLLIYEVSNRFSGVPDRFSGSGSGTDFTLKISRVEAEDVGVYYCMQSKQLPFTFGPGTKVDIK |
| 272 | 2.41.1 VH | QVQLVESGGGVVQPGRSLRLSCAASGFTFSSYGMHWVRQAPGKGLEWVAVISYDGSDKYYADSVKGRFTISRDNSKNTLYLQMNSLRAEDTAVYYCARAGYSLYYYYGMDVWGQGTTVTVSS |
| 273 | 2.41.1 VL CDR1 | KSSQSLLHSDGKTYLY |
| 274 | 2.41.1 VL CDR2 | EVSNRFS |
| 275 | 2.41.1 VL CDR3 | MQSKQLPFT |

TABLE 1-continued

| SEQ ID NO: | DESCRIPTION | SEQUENCE |
|---|---|---|
| 276 | 2.41.1 VH CDR1 | SYGMH |
| 277 | 2.41.1 VH CDR2 | VISYDGSDKYYADSVKG |
| 278 | 2.41.1 VH CDR3 | AGYSLYYYYGMDV |
| 279 | 2.47.1 VL | DIVMTQTPLSLPVTPGEPASISCRSSQSLLDSDDGDTYLDWYLQKPGQSPQ LLIYTLSYRASGVPDRFSGSGSGTDFTLKISRVEAEDVGVYYCMQRIEFPF TFGPGTKVDIK |
| 280 | 2.47.1 VH | QVQLQESGPGLVKPSQTLSLTCTVSGGSISSGGYYWSWIRQHPGKGLEWI GDIYYSGSTYYNPSLKSRVTISVDTSKNQFSLKLSSVTAADTAVYYCARD RAYGDYGGDYYYGMDVWGQGTTVTVSS |
| 281 | 2.47.1 VL CDR1 | RSSQSLLDSDDGDTYLD |
| 282 | 2.47.1 VL CDR2 | TLSYRAS |
| 283 | 2.47.1 VL CDR3 | MQRIEFPMQRIEFP |
| 284 | 2.47.1 VH CDR1 | SGGYYWS |
| 285 | 2.47.1 VH CDR2 | DIYYSGSTYYNPSLKS |
| 286 | 2.47.1 VH CDR3 | DRAYGDYGGDYYYGMDV |
| 287 | 5.17.1 VL | DIQMTQSPSSLSASVGDRVTITCQASQDINNYLNWYQQKPGKAPNLLIYD ASNLETGVPSRFSGSGSGTDFTFTISSLQPADIATYYCQQYDDFPLTFGGG TKVEIK |
| 288 | 5.17.1 VH | QVQLQESGPGLVKPSETLSLTCTVSGGSISSYYWSWIRQPPGKGLEWIGYI YYSGNTNYNPSLKSRVTISVDTSKNQFSLKLRSVTAADTAVYYCARYNW NNDLFDYWGQGTLVTVSS |
| 289 | 5.17.1 VL CDR1 | QASQDINNYLN |
| 290 | 5.17.1 VL CDR2 | DASNLET |
| 291 | 5.17.1 VL CDR3 | QQYDDFPLT |
| 292 | 5.17.1 VH CDR1 | SYYWS |

TABLE 1-continued

| SEQ ID NO: | DESCRIPTION | SEQUENCE |
|---|---|---|
| 293 | 5.17.1 VH CDR2 | YIYYSGNTNYNPSLKS |
| 294 | 5.17.1 VH CDR3 | YNWNNDLFDY |
| 295 | 5.23.1 VL | DIQMTQSPSSLSASVGDRVTITCQASQDISNYLNWYQQKPGKAPKLLIYDASNLETGVPSRFSGSGSGTDFTFTISSLQPEDIATYYCQQYDNLPLTEGGGTKVEIK |
| 296 | 5.23.1 VH | QVQLVESGGGVVQPGRSLRLSCAASGFTFSSYGMHWVRQAPGKGLEWVAVIWCDGSNKYYADSVKGRFTISRDSSKNTLYLQMNSLRAEDTAVYYCARGGYGSGSYEDYYYGMDVWGQGTTVTVSS |
| 297 | 5.23.1 VL CDR1 | QASQDISNYLN |
| 298 | 5.23.1 VL CDR2 | DASNLET |
| 299 | 5.23.1 VL CDR3 | QQYDNLPLT |
| 300 | 5.23.1 VH CDR1 | SYGMH |
| 301 | 5.23.1 VH CDR2 | VIWCDGSNKYYADSVKG |
| 302 | 5.23.1 VH CDR3 | GGYGSGSYEDYYYGMDV |
| 303 | 5.25.1 VL | DIQMTQSPSSLSASVGDRVTITCQASQDISKDLNWYQQKPGKAPRLLIYDASNLETGVPSRFSGSGSGTDFTFTISSLQPEDIATFYCQQYDHLPIAFGQGTRLEIK |
| 304 | 5.25.1 VH | QVQLVQSGAEVKKPGASVKVSCKASGYTFTSYDINWVRQATGQGLEWMGWMDPNSGNTGYAQKFQGRVTMTRNTSISTAFMELSSLRSEDTAVYYCARTDYFYFGMDVWGQGTTVTVSS |
| 305 | 5.25.1 VL CDR1 | QASQDISKDLN |
| 306 | 5.25.1 VL CDR2 | DASNLET |
| 307 | 5.25.1 VL CDR3 | QQYDNLPLT |
| 308 | 5.25.1 VH CDR1 | SYGMH |
| 309 | 5.25.1 VH CDR2 | WMDPNSGNTGYAQKFQG |

TABLE 1-continued

| SEQ ID NO: | DESCRIPTION | SEQUENCE |
|---|---|---|
| 310 | VH CDR3 | TDYFYFGMDV |
| 311 | 5.31.1 VL | DIQVTQSPSSLSASVGDRVTITCQASQDISNYLNWYQQKPGKAPKFLIYDASNLEAGVPSRFSGSGSGTDFTFTISSLQPEDIATYYCQQYDNLPLTEGGGTKVEIK |
| 312 | 5.31.1 VH | QVQLVESGGGVVQPGRSLRLSCAASGFTFSSYGMHWVRQAPGKGLEWVAVIWYDGRNKYYADSVKGRFTISRDNSKNTLYLQMNSLRAEDTAVYYCARGGGAVADYNYYYGMDVWGQGTTVTVSS |
| 313 | 5.31.1 VL CDR1 | QASQDISNYLN |
| 314 | 5.31.1 VL CDR2 | DASNLEA |
| 315 | 5.31.1 VL CDR3 | QQYDNLPLT |
| 316 | 5.31.1 VH CDR1 | SYGMH |
| 317 | 5.31.1 VH CDR2 | VIWYDGRNKYYADSVKG |
| 318 | 5.31.1 VH CDR3 | GGGAVADYNYYYGMDV |
| 319 | 5.32.1 VL | DIQMTQSPSSLSASVGDRVTITCQASQDISKDLNWYQQKPGKAPKLLIYDASNLETGVPSRFSGSGSGTDFTFTISSLQPEDIATYYCQQYDDLPITFGQGTRLEIK |
| 320 | 5.32.1 VH | QVQLVQSGAEVKKPGASVKVSCKASGFTFTSYDISWVRQATGLGLEWMGWMNPSSGYTGYAQNFQGRVTMTWNTSISTVYMELSSLRSEDTAVYYCARTDYYYYGMDVWGRGTTVTVSS |
| 321 | 5.32.1 VL CDR1 | QASQDISKDLN |
| 322 | 5.32.1 VL CDR2 | DASNLET |
| 323 | 5.32.1 VL CDR3 | QQYDDLPIT |
| 324 | 5.32.1 VH CDR1 | SYDIS |
| 325 | 5.32.1 VH CDR2 | WMNPSSGYTGYAQNFQG |
| 326 | 5.32.1 VH CDR3 | TDYYYYGMDV |

TABLE 1-continued

| SEQ ID NO: | DESCRIPTION | SEQUENCE |
|---|---|---|
| 327 | 5.40.1 VL | DIRLTQSPSSLSASVGDRVTITCQASQDISNYLNWYQQEPGKAPKLLIYDASNLETGVPSRFSGSGSGTDFTFTISSLQPEDIATYYCQQYDNFPLTFGGGTKVEIK |
| 328 | 5.40.1 VH | QVLLQESGPGLVKPSETLSLTCTVSGGSISSYYWSWIRQTPGKGLEWIGYVYYSGSTSYNPSLKSRVTISMYTSKTEFSLKLSSVTAADTAVYYCARYNWNNDLFDYWGQGTLVTVSS |
| 329 | 5.40.1 VL CDR1 | QASQDISNYLN |
| 330 | 5.40.1 VL CDR2 | DASNLET |
| 331 | 5.40.1 VL CDR3 | QQYDNFPLT |
| 332 | 5.40.1 VH CDR1 | SYYWS |
| 333 | 5.40.1 VH CDR2 | YVYYSGSTSYNPSLKS |
| 334 | 5.40.1 VH CDR3 | YNWNNDLFDY |
| 335 | 5.65.1 VL | SYVLTQPPSVSVAPGQTARITCGGNNIGSKSVHWYQQKPGQAPVLVVYDDSDRPSGIPERFSGSNSGNTATLTISRVEAGDEADYYCQVLDSSSDHVIFGGGTKLTVL |
| 336 | 5.65.1 VH | EVQLLESGGGLVQPGGSLRLSCAASGFTSGNYAMSWVRQAPGKGLEWVSAISGGGGTTYYADSVEGRFTISRDNSKNTLYLQLNSLRAEDTAVYYCAKEFGELEPRFDYWGQGTLVTVSS |
| 337 | 5.65.1 VL CDR1 | GGNNIGSKSVH |
| 338 | 5.65.1 VL CDR2 | DDSDRPS |
| 339 | 5.65.1 VL CDR3 | QVLDSSSDHVI |
| 340 | 5.65.1 VH CDR1 | NYAMS |
| 341 | 5.65.1 VH CDR2 | AISGGGGTTYYADSVEG |
| 342 | 5.65.1 VH CDR3 | EFGELEPRFDY |

TABLE 1-continued

| SEQ ID NO: | DESCRIPTION | SEQUENCE |
|---|---|---|
| 343 | 5.76.1 VL | SYVLTQPPSVSVAPGQTARITCGGNNIGSESVHWYQQKPGQAPVLVVYD DSDRPSGIPERFSGSNSGNTATLTISRVEAGDEADYYCQVWDSSNDHVVF GGGTKLTVL |
| 344 | 5.76.1 VH | QLQLQESGPGLVKPSETLSLTCTVSGGSISSSNYYWGWIRQPPGKGLEWIG TIYYSGSTYYTPSLKSRVTISVDTSKNQFSLKLSSVTAADTAVYYCARERA IAVAAIVFFDYWGQGTLVTVSS |
| 345 | 5.76.1 VL CDR1 | GGNNIGSESVH |
| 346 | 5.76.1 VL CDR2 | DDSDRPS |
| 347 | 5.76.1 VL CDR3 | QVWDSSNDHVV |
| 348 | 5.76.1 VH CDR1 | SSNYYWG |
| 349 | 5.76.1 VH CDR2 | TIYYSGSTYYTPSLKS |
| 350 | 5.76.1 VH CDR3 | ERAIAVAAIVFFDY |
| 351 | 5.77.1 VL | QSPSVSVAPGQTARITCGGNNIGSKSVHWYQQKPGQAPVLVVYDDSDRP SGIPERFSGSNSGNTATLTISRVEAGDEADYYCQVWDSSSDHWVFGGGT KLTVL |
| 352 | 5.77.1 VH | QVQLVQSGAEVKKPGASVKVSCKASGYTFTSYDINWVRQATGQGLEWM GWMNLNSDNTGYAQKFQGRVTMTRNTSISTAYMELSSLRSEDTAVYYC ASIAARRDYNYYGMDVWGQGTKVTVSS |
| 353 | 5.77.1 VL CDR1 | GGNNIGSKSVH |
| 354 | 5.77.1 VL CDR2 | DDSDRPS |
| 355 | 5.77.1 VL CDR3 | QVWDSSSDHWV |
| 356 | 5.77.1 VH CDR1 | SYDIN |
| 357 | 5.77.1 VH CDR2 | WMNLNSDNTGYAQKFQG |
| 358 | 5.77.1 VH CDR3 | IAARRDYNYYGMDV |

TABLE 1-continued

| SEQ ID NO: | DESCRIPTION | SEQUENCE |
|---|---|---|
| 359 | 5.78.1 VL | EIVLTQSPGTLSVSPGERATLSCRASQSVSSSYLAWYQQKPGQAPRLLIYGASGRATGIPDRFSGSGSGTDFILTISRLEPEDFAVYYCQQYGSSFTEGGGTKVEIK |
| 360 | 5.78.1 VH | QVQLVESGGGVVQPGRSLRLSCAASGFTFSSYGMHWVRQAPGKGLEWVAVILYDGSDNYYADSVKGRFTISRDNSKNTLYLQMNSLRAEDTAVYYCAREGIAVAGDYYYYGMDVWGQGTTVTVSS |
| 361 | 5.78.1 VL CDR1 | RASQSVSSSYLA |
| 362 | 5.78.1 VL CDR2 | GASGRAT |
| 363 | 5.78.1 VL CDR3 | QQYGSSFT |
| 364 | 5.78.1 VH CDR1 | SYGMH |
| 365 | 5.78.1 VH CDR2 | VILYDGSDNYYADSVKG |
| 366 | 5.78.1 VH CDR3 | EGIAVAGDYYYYGMDV |
| 367 | 5.80.1 VL | QSVLTQPPSVSGAPGQRVTISCTGSSSNIGADYDVHWYQQLPGTAPKLLIYDYSNRPSGVPDRFSGSKSGTSASLAITGLQAEDEADYYCQSYDNSLSGYVVFGGGTKLTVL |
| 368 | 5.80.1 VH | EVQLVQSGAEVKKPGESLKISCKGSGYSFTSYWIGWVRQMPGKGLEWMGIIYPGDSDTRYSPSFQGQVTISADKSISTAYLQWSSLTASDTAMYYCARQGESFDYWGQGTLVTVSS |
| 369 | 5.80.1 VL CDR1 | TGSSSNIGADYDVH |
| 370 | 5.80.1 VL CDR2 | DYSNRPS |
| 371 | 5.80.1 VL CDR3 | QSYDNSLSGYVV |
| 372 | 5.80.1 VH CDR1 | SYWIG |
| 373 | 5.80.1 VH CDR2 | IIYPGDSDTRYSPSFQG |
| 374 | 5.80.1 VH CDR3 | QGESFDY |

TABLE 1-continued

| SEQ ID NO: | DESCRIPTION | SEQUENCE |
|---|---|---|
| 375 | 5.85.1 VL | QSVLTQPPSVSGAPGQRVTISCTGSSSNIGAGYDVHWYQQLPRTAPKLLIY GNSNRPSGVPDRFSDSKSGTSASLAITGLQAEDEADYYCQSYDSSLSVIFG GGTKLTVL |
| 376 | 5.85.1 VH | EVQLVQSGAEVKKPGESLKISCKVSGYSFTTYWIGWVRQMPGKGLDWM GIIYPGDSDTRYSPSFQGQVTISADKSISTAYLQWSSLKASDTAMYYCARQ GIAFDYWGQGTLVTVSS |
| 377 | 5.85.1 VL CDR1 | TGSSSNIGAGYDVH |
| 378 | 5.85.1 VL CDR2 | GNSNRPS |
| 379 | 5.85.1 VL CDR3 | QSYDSSLSVI |
| 380 | 5.85.1 VH CDR1 | TYWIG |
| 381 | 5.85.1 VH CDR2 | IIYPGDSDTRYSPSFQG |
| 382 | 5.85.1 VH CDR3 | QGIAFDY |
| 383 | 6.37.5 VL | DIVMTQTPLSLSVTPGQPASISCKSGQSLLHSDGKTYLYWYLQKPGQPPQ FLIYEVSNRFSRVPDRFSGSGSGTDFTLRISRVEAEDVGIYYCMQSIQLPW TFGQGTQVEIK |
| 384 | 6.37.5 VH | QVQLVESGGGVVQPGRSLRLSCAASGFTFSGYGMHWVRQAPGKGLEWV AVISYDGNDKYYADSVKGRFTISRDNAKNTLYLQMNSLRAEDTAVYYC ARELRVLWGQGTLVTVSS |
| 385 | 6.37.5 VL CDR1 | KSGQSLLHSDGKTYLY |
| 386 | 6.37.5 VL CDR2 | EVSNRFS |
| 387 | 6.37.5 VL CDR3 | MQSIQLPWT |
| 388 | 6.37.5 VH CDR1 | GYGMH |
| 389 | 6.37.5 VH CDR2 | VISYDGNDKYYADSVKG |
| 390 | 6.37.5 VH CDR3 | ELRVL |

TABLE 1-continued

| SEQ ID NO: | DESCRIPTION | SEQUENCE |
|---|---|---|
| 391 | 6.116.6 VL | DIVMTQTPLSLSVTPGQPASISCKSGQSLLHNDGKTYLYWYLQKPGQPPQFLIYEVSNRFSRVPDRFSGSGSGTDFTLKISRVEAEDVGIYYCMQSIQLPWTFGQGTQVEIK |
| 392 | 6.116.6 VH | QVQLVESGGGVVQPGRSLRLSCAASGFTFSGYGMHWVRQAPGKGLEWVAVISYDGNDKYYADSVKGRFTISRDNAKNTLYLQMNSLRAEDTAVYYCARELRVLWGQGTLVTVSS |
| 393 | 6.116.6 VL CDR1 | KSGQSLLHNDGKTYLY |
| 394 | 6.116.6 VL CDR2 | EVSNRFS |
| 395 | 6.116.6 VL CDR3 | MQSIQLPWT |
| 396 | 6.116.6 VH CDR1 | GYGMH |
| 397 | 6.116.6 VH CDR2 | VISYDGNDKYYADSVKG |
| 398 | 6.116.6 VH CDR3 | ELRVL |
| 399 | 6.139.5 VL | DIVMTQTPLSLSVTPRQPASISCKSSQSLLHSDGKTYLYWYLQKPGQPPQFLIYEVSNRFSGVPDRFSGSGSGTDFTLKISRVEAEDVGVYYCMQSIQLPWTFGQGTKVEIK |
| 400 | 6.139.5 VH | QVQLVESGGGVVQPGRSLRLSCAASGFTFSSYGMHWVRQAPGKGLEWVAVISYDGGDQYYADSVKGRFTISRDNSKNTLYLQMNSLRTEDTAEYYCARELRVLWGQGTLVTVSS |
| 401 | 6.139.5 VL CDR1 | AASGFTFSRYDMH |
| 402 | 6.139.5 VL CDR2 | IFYDGSNKYYAD |
| 403 | 6.139.5 VL CDR3 | ATLAAAFDY |
| 404 | 6.139.5 VH CDR1 | SYGMH |
| 405 | 6.139.5 VH CDR2 | VISYDGGDQYYADSVKG |
| 406 | 6.139.5 VH CDR3 | ELRVL |

TABLE 1-continued

| SEQ ID NO: | DESCRIPTION | SEQUENCE |
|---|---|---|
| 407 | 6.147.4 VL | YVLTQPPSVSVAPGQTARITCGGNNIGSKSVHWYQQKPGQAPVLVVYDDSDRPSEIPERFSGSNSGNTATLTISRVEAGDEADYYCQVWDSSSDHVVFGGGTRLTVL |
| 408 | 6.147.4 VH | QVQLVESGGGVVQPGRSLRLSCAASGFTFSRYDMHWVRQAPGKGLEWVAIIFYDGSNKYYADPVKGRFTISRDNSKNTLYLQMNSLRAEDTAVYYCATLAAAFDYWGQGTLVTVSS |
| 409 | 6.147.4 VL CDR1 | GGNNIGSKSVH |
| 410 | 6.147.4 VL CDR2 | DDSDRPS |
| 411 | 6.147.4 VL CDR3 | QVWDSSSDHVV |
| 412 | 6.147.4 VH CDR1 | RYDMH |
| 413 | 6.147.4 VH CDR2 | IIFYDGSNKYYADPVKG |
| 414 | 6.147.4 VH CDR3 | LAAAFDY |
| Linkers | | |
| 415 | linker | AKTTPKLEEGEFSEAR |
| 416 | linker | AKTTPKLEEGEFSEARV |
| 417 | linker | AKTTPKLGG |
| 418 | linker | SAKTTPKLGG |
| 419 | linker | SAKTTP |
| 420 | linker | RADAAP |
| 421 | linker | RADAAPTVS |
| 422 | linker | RADAAAAGGPGS |
| 423 | linker | RADAAAA($G_4S$)$_4$ |
| 424 | linker | SAKTTPKLEEGEFSEARV |
| 425 | linker | ADAAP |
| 426 | linker | ADAAPTVSIFPP |
| 427 | linker | TVAA |
| 428 | linker | TVAAP |
| 429 | linker | TVAAPSVFIFP |
| 430 | linker | TVAAPSVFIFPP |
| 431 | linker | QPKAAP (lambda "AbS") |
| 432 | linker | QPKAAPSVTLFPP (lambda "AbL") |
| 433 | linker | AKTTPP |
| 434 | linker | AKTTPPSVTPLAP |

TABLE 1-continued

| SEQ ID NO: | DESCRIPTION | SEQUENCE |
|---|---|---|
| 435 | linker | AKTTAP |
| 436 | linker | AKTTAPSVYPLAP |
| 437 | linker | ASTKGP (gamma "AbS") |
| 438 | linker | ASTKGPSVFPLAP (gamma "AbL") |
| 439 | linker | GGGGS ("1x") |
| 440 | linker | GGGGSGGGGS ("2X") |
| 441 | linker | GGGGSGGGGSGGGGS ("3X") |
| 442 | linker | GENKVEYAPALMALS |
| 443 | linker | GPAKELTPLKEAKVS |
| 444 | linker | GHEAAAVMQVQYPAS |
| 445 | linker | GGGGGGGP |
| 446 | linker | GGGGGGGGP |
| 447 | linker | PAPNLLGGP |
| 448 | linker | PNLLGGP |
| 449 | linker | GGGGGGP |
| 450 | linker | PAPELLGGP |
| 451 | linker | PTISPAPNLLGGP |
| 452 | linker | TVAADDDDKSVFIVPP |
| 453 | linker | TVDDDDKAAP |
| 454 | linker | LVPRGSAAP |
| 455 | linker | ASDDDDKGGP |
| 456 | linker | ALVPRGSGP |
| 457 | linker | ASTDDDDKSVFPLAP |
| 458 | linker | TVALVPRGSVFIFPP |
| 459 | linker | ASTLVPRGSVFPLAP |
| 460 | linker | TVAADDDKSVFIVPP |
| 461 | linker | ASTDDDKSVFPLAP |
| 462 | linker | LEVLFQGP |
| 463 | linker | TVAALEVLFQGPAP |
| 464 | linker | ASTLEVLFQGPLAP |
| 465 | linker | PAPLEVLFQGP |
| 466 | linker | TAENLYFQGAP |
| 467 | linker | AENLYFQGA |
| 468 | linker | PGPFGRSAGGP |
| 469 | linker | PGPFGRSAGG |
| 470 | linker | PQRGRSAG |
| 471 | linker | PHYGRSGG |
| 472 | linker | GPFGRSAGP |

TABLE 1-continued

| SEQ ID NO: | DESCRIPTION | SEQUENCE |
|---|---|---|
| 473 | linker | GDDDDKGGP |
| 474 | linker | AGDDDDKGGP |
| 475 | linker | GGDDDDKGGP |
| 476 | linker | AS |
| 477 | linker | TVA |
| 478 | linker | ASTK |
| 479 | linker | ASTKGPSV |
| 480 | linker | ASTKGPSVFP |
| 481 | linker | TVAAPSV |
| 482 | linker | TVAAPSVFI |
| 483 | linker | RTVAAP (kappa "AbS") |
| 484 | linker | RTVAAPSVFIFPP (kappa "AbL") |
| Additional DVD-Ig Sequences | | |
| 485 | 6.147-AbL-Ab5 G2 NA | ATGGACATGAGGGTGCCCGCTCAGCTCCTGGGGCTCCTGCTGCTGTGGCTGAGA GGTGCGCGCTGTCAGGTGCAGCTTGTCGAGAGCGGTGGAGGGGTGGTACAACCC GGAAGATCACTCCGGCTTTCATGCGCAGCATCCGGTTTTACATTTTCGCGGTAT GACATGCACTGGGTGAGACAGGCACCAGGAAAAGGGCTGGAGTGGGTGGCCATC ATCTTCTATGATGGGTCCAATAAGTACTACGCCGACCCGGTAAAAGGGAGGTTC ACTATTAGCCGCGACAACTCGAAGAATACGCTGTACCTGCAGATGAACTCGTTG CGAGCCGAAGATACCGCGGTCTACTATTGTGCGACGCTCGCGGCTGCGTTCGAT TACTGGGGCCAAGGAACATTGGTCACGGTCTCCTCAGCGTCAACGAAAGGACCG TCGGTGTTCCCCTTGGCCCCTGAGGTGCAGCTCGTGCAGTCCGGAGCCGAGGTG AAGAAGCCTGGGGCATCCGTCAAAGTCTCGTGCAAGGCGTCAGGGTACACATTC ACCGACTATAACATGCATTGGGTCCGGCAGGCTCCCGGTCAGGGGCTGGAGTGG ATGGGGGAAATCAATCCGAACTCCGGAGGGGCAGGATACAATCAAAAGTTTAAG GGACGCGTAACGATGACCACTGACACGTCAACCTCCACGGCGTATATGGAGCTC AGAAGCCTCCGAAGCGACGACACTGCTGTCTATTACTGTGCGAGACTGGGATAT GATGATATCTACGACGATTGGTACTTCGATGTATGGGGACAAGGGACGACGGTC ACCGTCTCTAGTGCCTCCACCAAGGGCCCATCGGTCTTCCCCCTGGCGCCCTGC TCCAGGAGCACCTCCGAGAGCACAGCGGCCCTGGGCTGCCTGGTCAAGGACTAC TTCCCCGAACCGGTGACGGTGTCGTGGAACTCAGGCGCTCTGACCAGCGGCGTG CACACCTTCCCAGCTGTCCTACAGTCCTCAGGACTCTACTCCCTCAGCAGCGTG GTGACCGTGCCCTCCAGCAACTTCGGCACCCAGACCTACACCTGCAACGTAGAT CACAAGCCCAGCAACACCAAGGTGGACAAGACAGTTGAGCGCAAATGTTGTGTC GAGTGCCCACCGTGCCCAGCACCACCTGTGGCAGGACCGTCAGTCTTCCTCTTC CCCCCAAAACCCAAGGACACCCTCATGATCTCCCGGACCCCTGAGGTCACGTGC GTGGTGGTGGACGTGAGCCACGAAGACCCCGAGGTCCAGTTCAACTGGTACGTG GACGGCGTGGAGGTGCATAATGCCAAGACAAAGCCACGGGAGGAGCAGTTCAAC AGCACGTTCCGTGTGGTCAGCGTCCTCACCGTTGTGCACCAGGACTGGCTGAAC |

| SEQ ID NO: | DESCRIPTION | SEQUENCE |
|---|---|---|
| | | GGCAAGGAGTACAAGTGCAAGGTCTCCAACAAAGGCCTCCCAGCCCCCATCGAG |
| | | AAAACCATCTCCAAAACCAAAGGGCAGCCCCGAGAACCACAGGTGTACACCCTG |
| | | CCCCCATCCCGGGAGGAGATGACCAAGAACCAGGTCAGCCTGACCTGCCTGGTC |
| | | AAAGGCTTCTACCCCAGCGACATCGCCGTGGAGTGGGAGAGCAATGGGCAGCCG |
| | | GAGAACAACTACAAGACCACACCTCCCATGCTGGACTCCGACGGCTCCTTCTTC |
| | | CTCTACAGCAAGCTCACCGTGGACAAGAGCAGGTGGCAGCAGGGGAACGTCTTC |
| | | TCATGCTCCGTGATGCATGAGGCTCTGCACAACCACTACACGCAGAAGAGCCTC |
| | | TCCCTGTCTCCGGGTAAA |
| 486 | 6.147-AbL-Ab5 G2 AA | QVQLVESGGGVVQPGRSLRLSCAASGFTFSRYDMHWVRQAPGKGLEWVAIIFYD GSNKYYADPVKGRFTISRDNSKNTLYLQMNSLRAEDTAVYYCATLAAAFDYWGQ GTLVTVSSASTKGPSVFPLAPEVQLVQSGAEVKKPGASVKVSCKASGYTFTDYN MHWVRQAPGQGLEWMGEINPNSGGAGYNQKFKGRVTMTTDTSTSTAYMELRSLR SDDTAVYYCARLGYDDIYDDWYFDVWGQGTTVTVSS*ASTKGPSVFPLAPCSRST SESTAALGCLVKDYFPEPVTVSWNSGALTSGVHTFPAVLQSSGLYSLSSVVTVP SSNFGTQTYTCNVDHKPSNTKVDKTVERKCCVECPPCPAPPVAGPSVFLFPPKP KDTLMISRTPEVTCVVVDVSHEDPEVQFNWYVDGVEVHNAKTKPREEQFNSTFR VVSVLTVVHQDWLNGKEYKCKVSNKGLPAPIEKTISKTKGQPREPQVYTLPPSR EEMTKNQVSLTCLVKGFYPSDIAVEWESNGQPENNYKTTPPMLDSDGSFFLYSK LTVDKSRWQQGNVFSCSVMHEALHNHYTQKSLSLSPGK* |
| 487 | 6.147-AbL-Ab5 LC NA | ATGGACATGAGGGTGCCCGCTCAGCTCCTGGGGCTCCTGCTGCTGTGGCTGAGA GGTGCGCGCTGTTCATACGTGCTCACTCAGCCGCCCAGCGTATCGGTGGCTCCC GGACAGACGGCGCGAATCACGTGCGGTGGGAACAATATCGGCTCCAAGTCAGTC CATTGGTATCAACAGAAACCTGGTCAGGCACCAGTCCTGGTGGTATACGATGAC TCGGACAGGCCCTCGGAGATTCCGGAACGCTTCTCCGGATCGAATTCGGGGAAC ACAGCGACCTTGACGATCAGCAGAGTGGAGGCCGGAGATGAAGCCGACTACTAT TGTCAGGTGTGGGATTCCAGCTCCGACCACGTCGTATTTGGAGGTGGGACACGG CTTACCGTCCTCGGGCAGCCCAAGGCTGCGCCATCGGTCACTCTGTTCCCACCT GACATTCAGATGACTCAGTCGCCTTCGTCATTGAGCGCGTCGGTGGGAGATCGG GTCACGATTACTTGTCGGGCATCGCAAGACATCTCGAACTATTTGAATTGGTAC CAGCAAAAGCCTGGTAAAGCGCCCAAACTTCTTATCTACTATACGTCCCGCCTC CTCTCGGGCGTCCCGTCAAGGTTTAGCGGATCGGGAAGCGGGACGGATTTCACA CTGACGATTTCATCACTTCAGCCCGAAGATTTCGCCACCTATTACTGTCAGCAA GGAGACACCCTGCCATACACTTTTGGCGGTGGGACAAAGGTCGAAATCAAGCGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG |

TABLE 1-continued

| SEQ ID NO: | DESCRIPTION | SEQUENCE |
|---|---|---|
| | | CTGAGCAAAGCAGACTACGAGAAACACAAAGTCTACGCCTGCGAAGTCACCCAT |
| | | CAGGGCCTGAGCTCGCCCGTCACAAAGAGCTTCAACAGGGGAGAGTGT |
| 488 | 6.147-AbL-Ab5 LC AA | SYVLTQPPSVSVAPGQTARITCGGNNIGSKSVHWYQQKPGQAPVLVVYDDSDRP |
| | | SEIPERFSGSNSGNTATLTISRVEAGDEADYYCQVWDSSSDHVVFGGGTRLTVL |
| | | GQPKAAPSVTLFPPDIQMTQSPSSLSASVGDRVTITCRASQDISNYLNWYQQKP |
| | | GKAPKLLIYYTSRLLSGVPSRFSGSGSGTDFTLTISSLQPEDFATYYCQQGDTL |
| | | PYTFGGGTKVEIKR*TVAAPSVFIFPPSDEQLKSGTASVVCLLNNFYPREAKVQW* |
| | | *KVDNALQSGNSQESVTEQDSKDSTYSLSSTLTLSKADYEKHKVYACEVTHQGLS* |
| | | *SPVTKSFNRGEC* |
| 489 | 6.147-3x-Ab5 G2 NA | ATGGACATGAGGGTGCCCGCTCAGCTCCTGGGGCTCCTGCTGCTGTGGCTGAGA |
| | | GGTGCGCGCTGTCAGGTGCAGCTTGTCGAGAGCGGTGGAGGGGTGGTACAACCC |
| | | GGAAGATCACTCCGGCTTTCATGCGCAGCATCCGGTTTTACATTTTCGCGGTAT |
| | | GACATGCACTGGGTGAGACAGGCACCAGGAAAAGGGCTGGAGTGGGTGGCCATC |
| | | ATCTTCTATGATGGGTCCAATAAGTACTACGCCGACCCGGTAAAAGGGAGGTTC |
| | | ACTATTAGCCGCGACAACTCGAAGAATACGCTGTACCTGCAGATGAACTCGTTG |
| | | CGAGCCGAAGATACCGCGGTCTACTATTGTGCGACGCTCGCGGCTGCGTTCGAT |
| | | TACTGGGGCCAAGGAACATTGGTCACAGTGAGCTCAGGGGGTGGCGGTTCGGGC |
| | | GGTGGAGGCTCGGGAGGTGGTGGATCCGAGGTGCAGCTCGTGCAGTCCGGAGCC |
| | | GAGGTGAAGAAGCCTGGGGCATCCGTCAAAGTCTCGTGCAAGGCGTCAGGGTAC |
| | | ACATTCACCGACTATAACATGCATTGGGTCCGGCAGGCTCCCGGTCAGGGGCTG |
| | | GAGTGGATGGGGAAATCAATCCGAACTCCGGAGGGGCAGGATACAATCAAAAG |
| | | TTTAAGGGACGCGTAACGATGACCACTGACACGTCAACCTCCACGGCGTATATG |
| | | GAGCTCAGAAGCCTCCGAAGCGACGACACTGCTGTCTATTACTGTGCGAGACTG |
| | | GGATATGATGATATCTACGACGATTGGTACTTCGATGTATGGGGACAAGGGACG |
| | | ACGGTCACCGTCTCTAGTGCCTCCACCAAGGGCCCATCGGTCTTCCCCCTGGCG |
| | | CCCTGCTCCAGGAGCACCTCCGAGAGCACAGCGGCCCTGGGCTGCCTGGTCAAG |
| | | GACTACTTCCCCGAACCGGTGACGGTGTCGTGGAACTCAGGCGCTCTGACCAGC |
| | | GGCGTGCACACCTTCCCAGCTGTCCTACAGTCCTCAGGACTCTACTCCCTCAGC |
| | | AGCGTGGTGACCGTGCCCTCCAGCAACTTCGGCACCCAGACCTACACCTGCAAC |
| | | GTAGATCACAAGCCCAGCAACACCAAGGTGGACAAGACAGTTGAGCGCAAATGT |
| | | TGTGTCGAGTGCCCACCGTGCCCAGCACCACCTGTGGCAGGACCGTCAGTCTTC |
| | | CTCTTCCCCCCAAAACCCAAGGACACCCTCATGATCTCCCGGACCCCTGAGGTC |
| | | ACGTGCGTGGTGGTGGACGTGAGCCACGAAGACCCCGAGGTCCAGTTCAACTGG |
| | | TACGTGGACGGCGTGGAGGTGCATAATGCCAAGACAAAGCCACGGGAGGAGCAG |
| | | TTCAACAGCACGTTCCGTGTGGTCAGCGTCCTCACCGTTGTGCACCAGGACTGG |
| | | CTGAACGGCAAGGAGTACAAGTGCAAGGTCTCCAACAAAGGCCTCCCAGCCCCC |
| | | ATCGAGAAAACCATCTCCAAAACCAAAGGGCAGCCCCGAGAACCACAGGTGTAC |
| | | ACCCTGCCCCCATCCCGGGAGGAGATGACCAAGAACCAGGTCAGCCTGACCTGC |

TABLE 1-continued

| SEQ ID NO: | DESCRIPTION | SEQUENCE |
|---|---|---|
| | | CTGGTCAAAGGCTTCTACCCCAGCGACATCGCCGTGGAGTGGGAGAGCAATGGG |
| | | CAGCCGGAGAACAACTACAAGACCACACCTCCCATGCTGGACTCCGACGGCTCC |
| | | TTCTTCCTCTACAGCAAGCTCACCGTGGACAAGAGCAGGTGGCAGCAGGGGAAC |
| | | GTCTTCTCATGCTCCGTGATGCATGAGGCTCTGCACAACCACTACACGCAGAAG |
| | | AGCCTCTCCCTGTCTCCGGGTAAA |
| 490 | 6.147-3x-Ab5 G2 AA | QVQLVESGGGVVQPGRSLRLSCAASGFTFSRYDMHWVRQAPGKGLEWVAIIFYD GSNKYYADPVKGRFTISRDNSKNTLYLQMNSLRAEDTAVYYCATLAAAFDYWGQ GTLVTVSSGGGGSGGGGSGGGGSEVQLVQSGAEVKKPGASVKVSCKASGYTFTD YNMHWVRQAPGQGLEWMGEINPNSGGAGYNQKFKGRVTMTTDTSTSTAYMELRS LRSDDTAVYYCARLGYDDIYDDWYFDVWGQGTTVTVSS*ASTKGPSVFPLAPCSR STSESTAALGCLVKDYFPEPVTVSWNSGALTSGVHTFPAVLQSSGLYSLSSVVT VPSSNFGTQTYTCNVDHKPSNTKVDKTVERKCCVECPPCPAPPVAGPSVFLFPP KPKDTLMISRTPEVTCVVVDVSHEDPEVQFNWYVDGVEVHNAKTKPREEQFNST FRVVSVLTVVHQDWLNGKEYKCKVSNKGLPAPIEKTISKTKGQPREPQVYTLPP SREEMTKNQVSLTCLVKGFYPSDIAVEWESNGQPENNYKTTPPMLDSDGSFFLY SKLTVDKSRWQQGNVFSCSVMHEALHNHYTQKSLSLSPGK* |
| 491 | 6.147-3x-Ab5 LC NA | ATGGACATGAGGGTGCCCGCTCAGCTCCTGGGGCTCCTGCTGCTGTGGCTGAGA GGTGCGCGCTGTTCATACGTGCTCACTCAGCCGCCCAGCGTATCGGTGGCTCCC GGACAGACGGCGCGAATCACGTGCGGTGGGAACAATATCGGCTCCAAGTCAGTC CATTGGTATCAACAGAAACCTGGTCAGGCACCAGTCCTGGTGGTATACGATGAC TCGGACAGGCCCTCGGAGATTCCGGAACGCTTCTCCGGATCGAATTCGGGGAAC ACAGCGACCTTGACGATCAGCAGAGTGGAGGCCGGAGATGAAGCCGACTACTAT TGTCAGGTGTGGGATTCCAGCTCCGACCACGTCGTATTTGGAGGTGGGACACGG CTTGGGGGTGGCGGTTCGGCGGTGGAGGCTCGGAGGTGGTGGATCCGACATT CAGATGACTCAGTCGCCTTCGTCATTGAGCGCGTCGGTGGGAGATCGGGTCACG ATTACTTGTCGGGCATCGCAAGACATCTCGAACTATTTGAATTGGTACCAGCAA AAGCCTGGTAAAGCGCCCAAACTTCTTATCTACTATACGTCCCGCCTCCTCTCG GGCGTCCCGTCAAGGTTTAGCGGATCGGGAAGCGGGACGGATTTCACACTGACG ATTTCATCACTTCAGCCCGAAGATTTCGCCACCTATTACTGTCAGCAAGGAGAC ACCCTGCCATACACTTTTGGCGGTGGGACAAAGGTCGAAATCAAGCGTACGGTG GCTGCACCATCTGTCTTCATCTTCCCGCCATCTGATGAGCAGTTGAAATCTGGA ACTGCCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGTCACA GAGCAGGACAGCAAGGACAGCACCTACAGCCTCAGCAGCACCCTGACGCTGAGC AAAGCAGACTACGAGAAACACAAAGTCTACGCCTGCGAAGTCACCCATCAGGGC CTGAGCTCGCCCGTCACAAAGAGCTTCAACAGGGGAGAGTGT |

TABLE 1-continued

| SEQ ID NO: | DESCRIPTION | SEQUENCE |
|---|---|---|
| 492 | 6.147-3x-Ab5 LC AA | SYVLTQPPSVSVAPGQTARITCGGNNIGSKSVHWYQQKPGQAPVLVVYDDSDRP SEIPERFSGSNSGNTATLTISRVEAGDEADYYCQVWDSSSDHVVFGGGTRLGGG GSGGGGSGGGGSDIQMTQSPSSLSASVGDRVTITCRASQDISNYLNWYQQKPGK APKLLIYYTSRLLSGVPSRFSGSGSGTDFTLTISSLQPEDFATYYCQQGDTLPY TFGGGTKVEIKR*TVAAPSVFIFPPSDEQLKSGTASVVCLLNNFYPREAKVQWKV DNALQSGNSQESVTEQDSKDSTYSLSSTLTLSKADYEKHKVYACEVTHQGLSSP VTKSFNRGEC* |
| 493 | 11H10-AbL-Ab23 G2 NA | ATGGACATGAGGGTGCCCGCTCAGCTCCTGGGGCTCCTGCTGCTGTGGCTGAGA GGTGCGCGCTGTGAAGTGCAGTTGGTACAGTCGGGTGGGGACTGGTGCAGCCA GGGGGTTCGCTTAGGTTGTCGTGCACAGCGTCGGGGTTTACATTCTCAAACCAC TGGATTCACTGGGTGAGACAAGCCCCTGGTAAAGGGCTGGAATGGGTCAGCGGG ATCAATTGGAATTCAGGCAGCCGGGGATATTCGGATTCCGTAAAAGGAAGGTTC ACTATCTCGAGGGATAACGCAAAGAACTCCCTCTATTTGCAGATGAACAGCCTT CGGGCGGAGGACACGGCAGTCTACTACTGTGCCCGAGAAAGACCCGTGGCCACA GGCGCGTTTGACATTTGGGGTCAGGGCACGACAGTAACGGTCTCCTCAGCGTCA ACGAAAGGACCGTCGGTGTTCCCCTTGGCCCCTGAGGTGCAGCTCGTACAGTCG GGTGCGGAAGTAAAGAAACCCGGCTCATCCGTGAAAGTCTCGTGTAAAGCCTCC GGGTTCACCTTCACAGACTACATTATGCACTGGGTGCGGCAGGCCCCTGGGCAG GGCCTTGAATGGATGGGTATATCAACCCCTACAATGATGACACGGAGTATAAC GAAAAGTTTAAGGGAAGGGTGACAATCACGGCGGATAAGAGCACCAGCACTGCA TACATGGAGCTCTCGTCATTGCGCTCGGAGGACACTGCAGTCTACTATTGCGCG AGATCCATCTACTATTACGATGCGCCGTTTGCTTATTGGGGACAAGGAACGCTG GTCACCGTCTCTAGTGCCTCCACCAAGGGCCCATCGGTCTTCCCCCTGGCGCCC TGCTCCAGGAGCACCTCCGAGAGCACAGCGGCCCTGGGCTGCCTGGTCAAGGAC TACTTCCCCGAACCGGTGACGGTGTCGTGGAACTCAGGCGCTCTGACCAGCGGC GTGCACACCTTCCCAGCTGTCCTACAGTCCTCAGGACTCTACTCCCTCAGCAGC GTGGTGACCGTGCCCTCCAGCAACTTCGGCACCCAGACCTACACCTGCAACGTA GATCACAAGCCCAGCAACACCAAGGTGGACAAGACAGTTGAGCGCAAATGTTGT GTCGAGTGCCCACCGTGCCCAGCACCACCTGTGGCAGGACCGTCAGTCTTCCTC TTCCCCCCAAAACCCAAGGACACCCTCATGATCTCCCGGACCCCTGAGGTCACG TGCGTGGTGGTGGACGTGAGCCACGAAGACCCCGAGGTCCAGTTCAACTGGTAC GTGGACGGCGTGGAGGTGCATAATGCCAAGACAAAGCCACGGGAGGAGCAGTTC AACAGCACGTTCCGTGTGGTCAGCGTCCTCACCGTTGTGCACCAGGACTGGCTG AACGGCAAGGAGTACAAGTGCAAGGTCTCCAACAAAGGCCTCCCAGCCCCCATC GAGAAAACCATCTCCAAAACCAAAGGGCAGCCCCGAGAACCACAGGTGTACACC CTGCCCCCATCCCGGGAGGAGATGACCAAGAACCAGGTCAGCCTGACCTGCCTG GTCAAAGGCTTCTACCCCAGCGACATCGCCGTGGAGTGGGAGAGCAATGGGCAG CCGGAGAACAACTACAAGACCACACCTCCCATGCTGGACTCCGACGGCTCCTTC |

TABLE 1-continued

| SEQ ID NO: | DESCRIPTION | SEQUENCE |
|---|---|---|
| | | TTCCTCTACAGCAAGCTCACCGTGGACAAGAGCAGGTGGCAGCAGGGGAACGTC |
| | | TTCTCATGCTCCGTGATGCATGAGGCTCTGCACAACCACTACACGCAGAAGAGC |
| | | CTC TCCCTGTCTCCGGGTAAA |
| 494 | 11H10-AbL-Ab23 G2 AA | EVQLVQSGGGLVQPGGSLRLSCTASGFTFSNHWIHWVRQAPGKGLEWVSGINWN SGSRGYSDSVKGRFTISRDNAKNSLYLQMNSLRAEDTAVYYCARERPVATGAFD IWGQGTTVTVSSASTKGPSVFPLAPEVQLVQSGAEVKKPGSSVKVSCKASGFTF TDYIMHWVRQAPGQGLEWMGYINPYNDDTEYNEKFKGRVTITADKSTSTAYMEL SSLRSEDTAVYYCARSIYYYDAPFAYWGQGTLVTVSS*ASTKGPSVFPLAPCSRS TSESTAALGCLVKDYFPEPVTVSWNSGALTSGVHTFPAVLQSSGLYSLSSVVTV PSSNFGTQTYTCNVDHKPSNTKVDKTVERKCCVECPPCPAPPVAGPSVFLFPPK PKDTLMISRTPEVTCVVVDVSHEDPEVQFNWYVDGVEVHNAKTKPREEQFNSTF RVVSVLTVVHQDWLNGKEYKCKVSNKGLPAPIEKTISKTKGQPREPQVYTLPPS REEMTKNQVSLTCLVKGFYPSDIAVEWESNGQPENNYKTTPPMLDSDGSFFLYS KLTVDKSRWQQGNVFSCSVMHEALHNHYTQKSLSLSPGK* |
| 495 | 11H10-AbL-Ab23 LC NA | ATGGACATGAGGGTGCCCGCTCAGCTCCTGGGGCTCCTGCTGCTGTGGCTGAGA GGTGCGCGCTGTGAGATTGTATTGACTCAGTCACCGGCCACGCTCTCGCTGTCA CCCGGCGAAAGAGCAACACTGAGCTGTCGGGCGTCGCAGTGGGTGTCGTCGTAT TTGGCCTGGTATCAACAAAAGCCTGGACAGGCGCCCAGGCTGCTCATCTACGAC GCGTCCAACCGCGCCACCGGTATCCCGGCACGATTCTCCGGTTCGGGGTCGGGA ACAGACTTCACGTTGACGATTAGCTCCCTTGAGCCAGAAGATTTTGCGGTCTAC TACTGCGCTTGGCAGGAGTTCTTTGGGCAGGGGACCAAGCTTGAAATCAAACGC ACAGTGGCTGCTCCATCCGTCTTTATCTTCCCTCCAGACATTCAAATGACACAG TCGCCCTCCTCGCTCTCGGCGTCAGTCGGGGATCGCGTGACAATCACGTGTCGG GCCAGCCAGGACATTTCGAGCTACCTCAACTGGTATCAGCAGAAACCGGGGAAA GCGCCGAAGCTGCTTATCTACTCCACCTCAAGGTTGAATTCCGGAGTACCCTCA AGATTTTCGGGTAGCGGATCAGGAACCGACTTCACACTTACGATCTCGTCGTTG CAGCCAGAAGATTTCGCAACGTACTATTGCCAGCAAGATATCAAGCACCCTACG TTTGGTCAGGGCACTAAAGTGGAGATTAAGCGTACGGTGGCTGCACCATCTGTC TTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGAT AACGCCCTCCAATCGGGTAACTCCCAGGAGAGTGTCACAGAGCAGGACAGCAAG GACAGCACCTACAGCCTCAGCAGCACCCTGACGCTGAGCAAAGCAGACTACGAG AAACACAAAGTCTACGCCTGCGAAGTCACCCATCAGGGCCTGAGCTCGCCCGTC ACAAAGAGCTTCAACAGGGGAGAGTGT |

TABLE 1-continued

| SEQ ID NO: | DESCRIPTION | SEQUENCE |
|---|---|---|
| 496 | 11H10-AbL-Ab23 LCAA | EIVLTQSPATLSLSPGERATLSCRASQWVSSYLAWYQQKPGQAPRLLIYDASNR ATGIPARFSGSGSGTDFTLTISSLEPEDFAVYYCAWQEPFGQGTKLEIKR*TVAA PSVFIFPPDIQMTQSPSSLSASVGDRVTITC*RASQDISSYLNWYQQKPGKAPKL LIYSTSRLNSGVPSRFSGSGSGTDFTLTISSLQPEDFATYYCQQDIKHPTFGQG TKVEIKR*TVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSF NRGEC* |

\*Note that the CDRs are bold/highlighted and the heavy chain constant region is bold/italic for SEQ ID NOs 17-92 and 485-496.

EXAMPLES

Example 1

Engineering of Bi-Specific Dual Variable Domain Ig Molecules: Anti-Sclerostin and Anti-DKK1

Antibodies directed against human Sclerostin and DKK1 were used for construction of several sets of dual variable domain (DVD) Ig molecules. The DNAs for light chain and heavy chain genes were obtained from mouse, rat or xenomouse hybridomas. To construct the dual domain light chain light, the VL domain of anti-human sclerostin antibody was fused in tandem by a linker (the first 12 amino acids of the CL1 domain of light chains) to the N-terminus of the variable domain of anti-hu DKK1 antibody light chain followed by CL to form the full length DVD-Ig light chain.

Similarly, the variable domain of heavy chain (VH) of anti-hu sclerostin antibody was fused in tandem by a linker (the first 13 or 12 amino acids of CH1 on heavy chain) to N-terminus of VH of anti-hu DKK1 antibody followed by full constant region of heavy chain. The other version of DVD is VH/VL of anti-DKK1 on the N-terminus of heavy/light chain of anti-Sclerostin with respective linkers.

The linker between two variable domains of light chain was derived from CL1 region while the linker between two variable domains of heavy chain was derived from CH1 region of constant region of heavy chain. All DNA constructs were cloned into pTT5 vector through unique restriction sites.

One example of the DVD-Ig molecules generated is the rat chimeric DVD AB-4-11H10 where VL/VH of a mouse anti-hu Sclerostin antibody AB-4 were joined to the N-terminus of the light/heavy chain of rat anti-hu DKK1 11H10 antibody and contains rat IgG2a constant region. DVD's with reversed orientation of variable domains were also made, where the variable domains (VL/VH) of rat anti-hu DKK1 11H10 were fused to the N-terminus of the light/heavy chain of mouse anti-SclerostinAB-4.

Rat constant domain derived linkers were selected to provide structural stability as well as make the construct more rat like. This type of ratized bispecific antibody should have less risk of potential immunogenicity when used in short and long term rat models.

Example 2

Expression of Sclerostin-DKK1 DVD-Ig

Large scale production of the sclerostin-DKK1 DVD-Ig was performed in a Wave bioreactor (25 L) as follows: 3 L flasks were inoculated with 1 L each of 293-6E cells at 3E5 viable cells per ml (VC/ml). F17 expression medium was used and supplemented with 1.1 mg/ml Pluronic, 6 mM L-Glutamine and 25 ug/ml Geneticin. After 48 hrs, cell counts were performed and viability ranging between 99.1% to 99.9% was observed. A 1:2 dilution of the culture was obtained by mixing 11.25 liters of 293-6E culture in a 50 L Wave bag with 11.25 liters of fresh F17 medium. Another cell count was performed 24 hrs later and 98.5% viability was determined. A 1:10 dilution in F17 media was then carried out and 0.5 mg of total plasmid DNA/L of culture (or 12.5 mg) was added with 3 ml PEI Max/mg DNA. Equal amounts of DNA for each of the antibody chains was added (6.25 mg). Twenty four hours post transfection, 625 mls (25 ml/L of culture) of feed (consisting of 20% Tryptone N1 in F17 with 0.1% Pluronic) were added to the culture followed by a five day incubation. Subsequently, cell counts were performed and 82.9% cell viability was observed. The conditioned media (CM) was then harvested by centrifugation at 4000 rpm for 45 minutes and the CM was filtered with a 0.2 um filter. An aliquot of the antibody was analyzed by SDS-PAGE under reducing and non-reducing conditions.

Example 3

Purification and Formulation of Sclerostin-DKK1 DVD-Ig for In Vivo Studies

Sclerostin-DKK1 DVD-Ig was purified from transient cell culture. The purification scheme used affinity chromatography followed by hydrophobic interaction chromatography (HIC).

Cell Culture Fluid Concentration

Concentration of the cell culture fluid was performed at 4° C. using a TFF (tangential flow filtration) device. PES 10 kD MWCO (5×1 sq. ft.) membranes were used to concentrate the product approximately ten-fold. Cross flow was 0.7 L/sq. ft/min, and the TMP was 25-30 psi.

Protein G Chromatography

Protein G chromatography was performed at room temperature, although the cell culture fluid remained cold during loading. The flow rate remained constant at 0.2 column volumes per minute.

20 liters of clarified cell culture fluid was concentrated ten-fold, diluted with a half volume of 1.2 M sodium citrate, 75 mM Tris pH 9, and then loaded onto a 230 mL Protein G Sepharose Fast Flow column (XK50, 19.6 cm2×12.5 cm) equilibrated in 0.4 M sodium citrate, 25 mM Tris, pH 9. After loading the cell culture fluid, the column was washed with 0.4 M sodium citrate, 25 mM Tris, pH 9 until the absorbance at 280 nm returned to baseline. Following the wash, the antibody was eluted from the column with 0.1 M acetic acid pH 3 and the entire elution peak was collected. The elution pool contained 2.197 grams of product. Following elution the Protein G pool was immediately adjusted to pH 7 with 1M Tris Base.

Phenyl HP Chromatography

Phenyl HP chromatography was performed at room temperature, binding at approximately 7 mg of protein per mL of resin. The flow rate remained constant at 0.2 column volumes per minute.

The Protein G pool was conditioned for binding onto Phenyl HP by adding 20 mM sodium phosphate, 3M ammonium sulfate pH 7 to a final concentration of 0.6 M ammonium sulfate. 115 mL (245 mg) of the conditioned Protein G pool was loaded onto a 35 mL Phenyl HP column (XK 26, 5.3 cm2×6.6 cm) equilibrated in 20 mM sodium phosphate, 0.6 M ammonium sulfate pH 7. After loading, the column was washed with 20 mM sodium phosphate, 0.6 M ammonium sulfate pH 7 until the absorbance at 280 nm of the flow-through returned to baseline. A 20 column volume linear gradient of decreasing ammonium sulfate (0.6-0M) in 20 mM sodium phosphate at pH 7 was used to elute the product from the Phenyl HP column. 0.5 column volume fractions were collected and assayed by size exclusion HPLC to determine purity. Fractions were pooled based on % main peak to form a product pool. 86% of the product was recovered, yielding 210 mg.

Formulation: Buffer Exchange and Concentration

Buffer exchange was performed at 4° C. using regenerated cellulose 10 kD MWCO dialysis cassettes. Concentration was performed at 4° C. using a PES 10 kD MWCO centrifugal device. Recovery was 85%.

80 mL (80 mg) of Phenyl HP pool was buffer exchanged into 10 mM Tris, 250 mM L-Proline pH 7.5. Dialysis was performed by dialyzing three times against 3 liters of 10 mM Tris, 250 mM L-Proline pH 7.5. The volume of the post-dialysis product pool was 113 mL at a protein concentration of 0.674 mg/mL. Following dialysis the product pool was concentrated down to 18.5 mL using a centrifugal concentration device. The product pool was then sterile filtered (0.22 micron). The concentration of the filtered pure bulk measured 3.65 mg/mL. Overall recovery was 73%, or 67.6 mg. The endotoxin level of the filtered pure bulk measured less than 0.07 EU/mg. The filtered pure bulk product was stored at 4° C.

Example 4

Sclerostin and DKK1 ELISA

Figure 2:
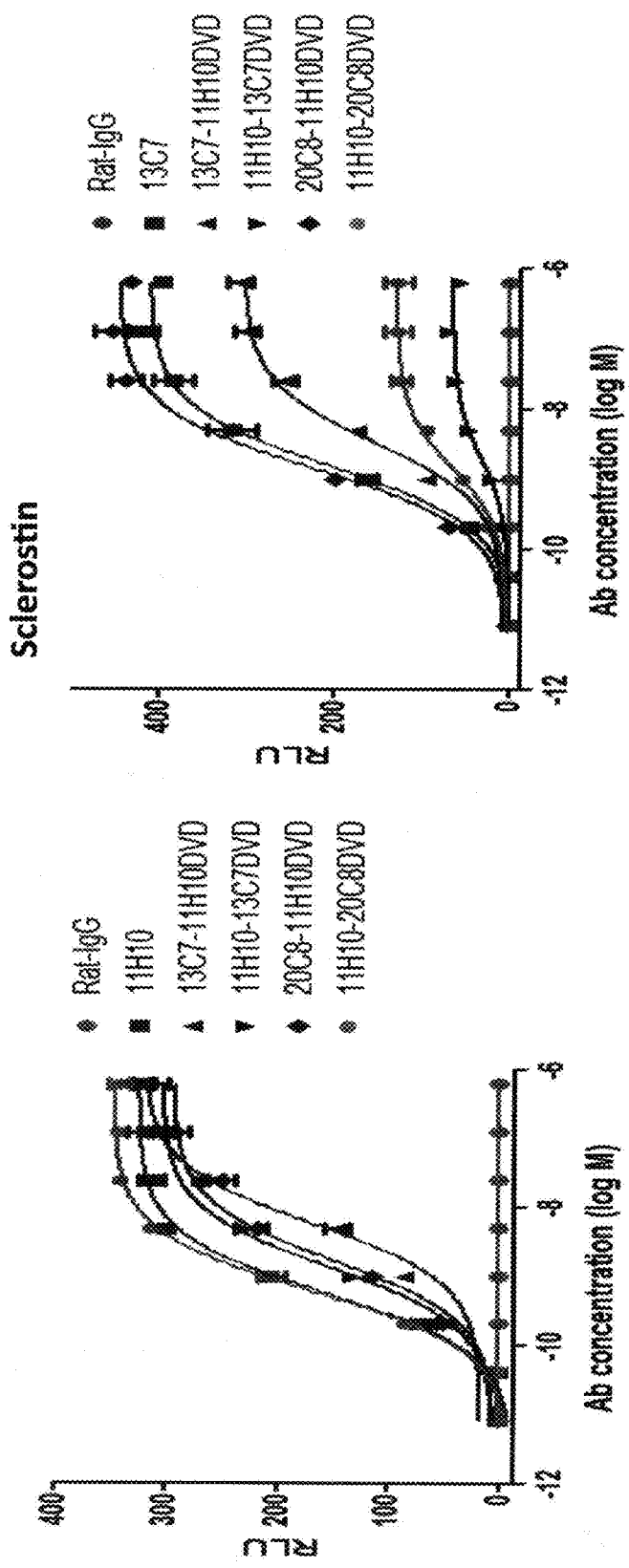
FIG. 2 summarizes ELISA analysis of bispecific Rat-Abs binding to huDKK1 or huScl.
Figure 3:
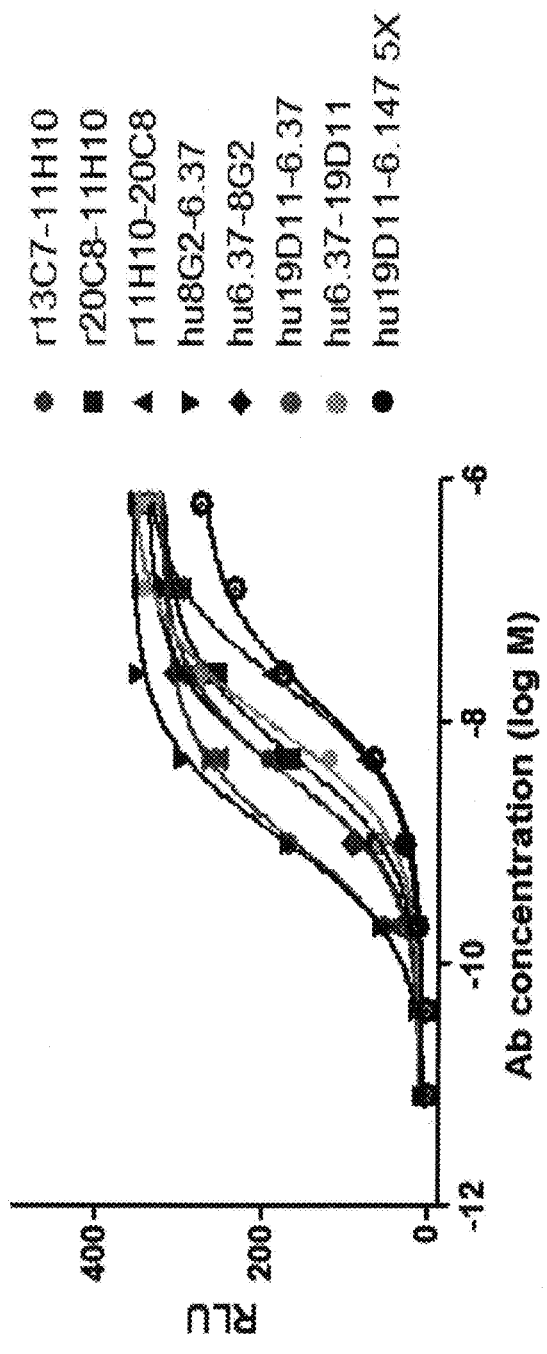
FIG. 3 summarizes ELISA analysis of bispecific Abs binding to huDKK1 and huScl at the same time.

The ability of various bispecific antibodies to specifically bind Sclerostin and Dkk1 simultaneously was determined by an ELISA capture assay. Plates were coated with 20 ml/well of 1 mg/ml of mouse anti-huScl MAb 56H2 in coating buffer (0.015M Na2CO3, 0.035M NaHCO3, pH9.6) in 96-well half-area plate (Costar, cat#3694) and incubated at RT for one hour or 4° C. overnight. The plates were washed once with 100 ml/well of washing solution (PBS containing 0.2% Tween20, BIO-RAD) and subsequently 100 ml/well of blocking solution (PBS containing 1% BSA, 1% goat serum and 0.5% Tween20) was added for one hour at RT. Human Sclerostin protein was added (20 ml/well of a 10 ng/ml stock solution diluted in blocking solution) and incubated at room temperature for one hour followed by washing as described above. 20 ml/well of various diluted bispecific Abs (0, 0.008, 0.04, 0.2, 1, 5, 25, 125, 625 nM), parental Abs (positive control) and non-DKK1/Scl related IgG (human or rat IgG, negative control) were added in blocking solution and plates were incubated at room temperature for one hour. Following incubation in washing solution, 20 ml/well of huDKK1-biotin (10 ng/ml) diluted in blocking solution was added to the plates for 1 hour at room temperature and then in washing solution. Neutravidin-HRP dilution (Pierce, cat#31001) diluted in blocking solution was added at a 1:50,000 dilution to the wells (20 ml/well), followed by incubation at RT for one hour and subsequent washing three times with 100 ml/well of washing solution. As a final step 20 ml/well of a SuperSignal ELISA Femto (Thermo, cat#37074) working solution was added to the plates and the signal was read using a luminometer at 425 nm. The data, as summarized in FIGS. 1-3, indicate that all bispecifics tested are capable of binding both targets simultaneously and hence the linker sequences joining the variable regions of the antibodies nor the binding of each variable domain to one ligand pose significant steric constraints on binding of the second ligand.

Example 5

Sclerostin and DKK1 Biacore Assay

To further demonstrate that the bispecific antibodies can bind both targets, tetravalent dual specific binding activity was assessed by Biacore analysis. Briefly, goat anti-huIgG, Fc fragment specific antibody was immobilized to all four flowcells of a CM5 chip at a high surface density (>3,500 RU immobilized). The bispecific antibodies were diluted to 20 nM in 25 mM Tris, pH 8.5, 250 mM NaCl, 0.005% P-20, 0.1 mg/mL BSA and captured on individual flowcells. Ligands (human Dkk-1 and human Sclerostin) were diluted to 100 nM in the same buffer and were injected sequentially over the captured bispecific Ig.

The sensograms show that when the bispecific antibody was saturated with the first antigen (either human Dkk1 or human Sclerostin) and the second antigen was injected, a second binding signal was observed. This observation was similar when the antigen injection sequence was reversed. The observation of two separate binding events indicate that the bispecific antibody can bind both ligands simultaneously.

Example 6

Osteoblast Wnt Activation Bioassay

Engineered bispecific antibodies are capable of neutralizing the ability of both targets to block canonical Wnt signaling as demonstrated in an osteoblast Wnt activation assay. MC3T3-E1 cells were transfected with a Super-TOPFlash reporter construct, and the stable cell lines were selected and evaluated. Clone C10 was identified as the best clone and it has been well characterized under various conditions and shown to have decreased reporter activity following incubation with either purified Sclerostin or Dkk1 proteins due to inhibition of Wnt pathway activation. Cells were cultured in Expansion Medium (Alpha-MEM medium containing 10% FBS, 1×Pen-Strep-Glu and 1.0 ug/ml of puromycin). When the cells reached 80% confluence, the medium was switched to Differentiation Medium (Expansion Medium, 50 ug/ml ascorbic acid and 10 mM beta-glycerophosphate) for 4 days. Following differentiation, this cell line produces an endogenous protein (s) that triggers canonical Wnt activation in an autocrine manner. Media was aspirated and 100uLs of fresh DM containing various concentrations of monospecific or bispecific antibodies (preincubated for 4 hrs with Dkk1 and/or Sclerostin for 45-60 min at 37 C) was added to the wells for 24 hrs. Luciferase activity was measured following manufacturer's instructions (Promega's Luciferase Assay System, Cat No: E4530).

Various rat and human bispecific antibodies tested were capable of dose-dependently activating the osteoblast canonical Wnt pathway in the presence of both Sclerostin and Dkk1 further demonstrating that the antibodies can simultaneously neutralize the Wnt inhibitory function of both soluble proteins.

Example 7

Wnt Induced Luciferase Bioassay

Figure 4:
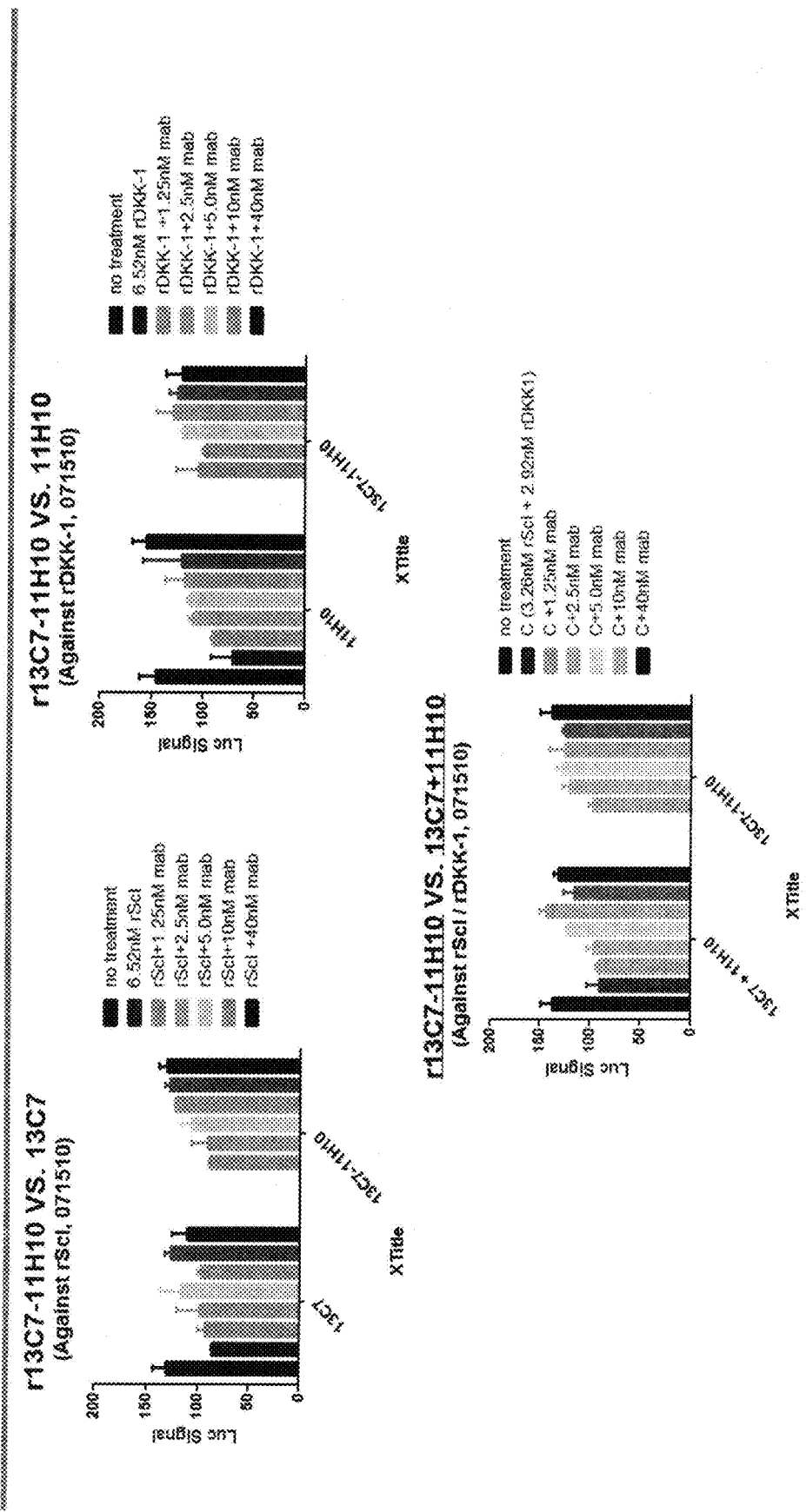
FIG. 4 summarizes in vitro bioassay results showing that rAB-4-11H10 has similar neutralizing activity to control Mabs when same molar ratio is used.
Figure 18:
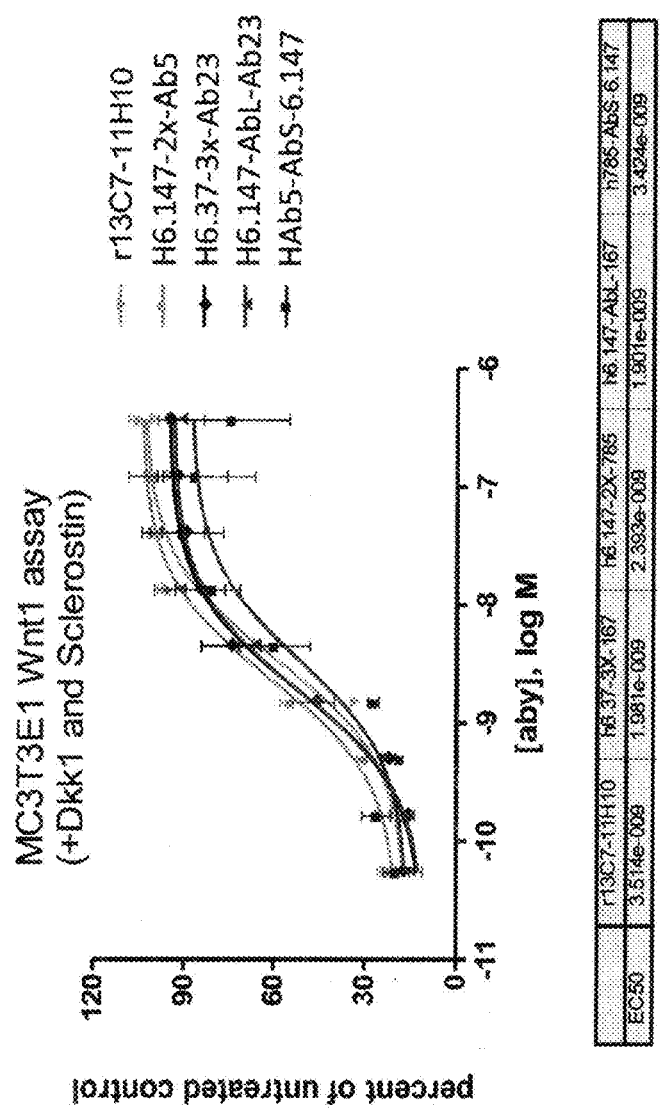
FIG. 18 summarizes the results of an osteoblast supertopflash competition assay showing rat and human DVD-Igs have potent neutralizing activity against both sclerostin and Dkk1 in osteoblast MC3T3E1STF cells treated with Wnt1 protein.

The engineered bispecific antibodies were capable of neutralizing Dkk1 and blocking Wnt1 induced TCF/LEF luciferase activity as determined in an osteoblast cell based assay. The osteoblast MC3T3E1/TetON-Wnt1/STF-Luc#5 cell line was engineered by lentiviral transduction with a T-Cell Factor (TCF)-responsive luciferase construct, a Tet repressor construct and a doxycycline inducible Wnt1 construct. In this assay, addition of doxycycline (10 ng/ml) to the culture medium for 22-26 hr induced expression of Wnt1 and signal transduction via the binding of Wnt1 to cell surface LRP5/6 and Frizzled receptors, resulting in the expression of the luciferase reporter gene. MC3T3E1/TetON-Wnt1/STF-luc#5 cells were incubated in the presence of Sclerostin and/or Dkk1 and Wnt signaling was inhibited due to competitive binding of Sclerostin and Dkk1 to LRP5/6. Human Dkk1 protein (0.1 ug/ml) or human Sclerostin proten (1 g/ml) were premixed with control PBS or a serial dilution of the bispecific antibodies. 24 hrs later the luciferase signal was determined as described above and the data were plotted by using PRISM software. As summarized in FIGS. 4 and 18, the bispecific antibodies dose-dependently inhibited Sclerostin and Dkk1 and restored Wnt signaling induced by Wnt1.

Example 8

Screening Method for Binders of Sclerostin and/or DKK1

Figure 19:
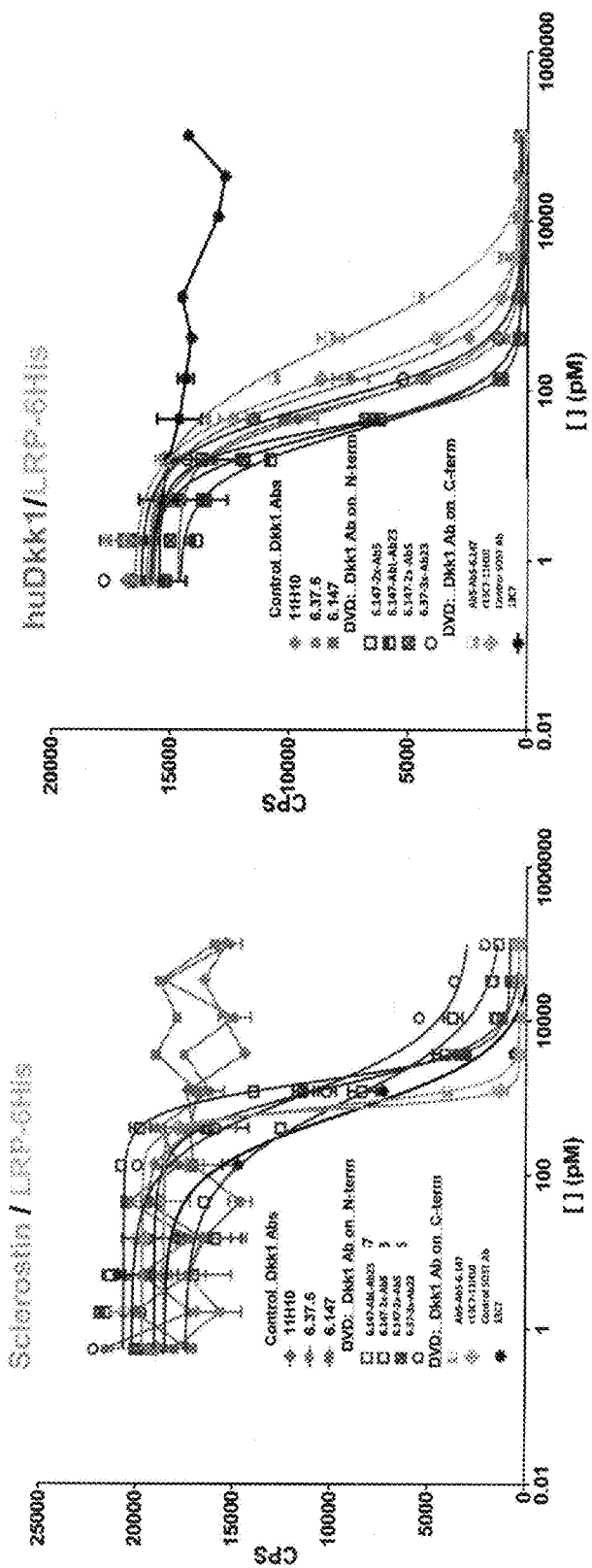
FIG. 19 summarizes the results of an Alphascreen competition assay showing inhibition of Lrp6 binding to sclerostin or Dkk1 by DVD-Igs.
Figure 20:
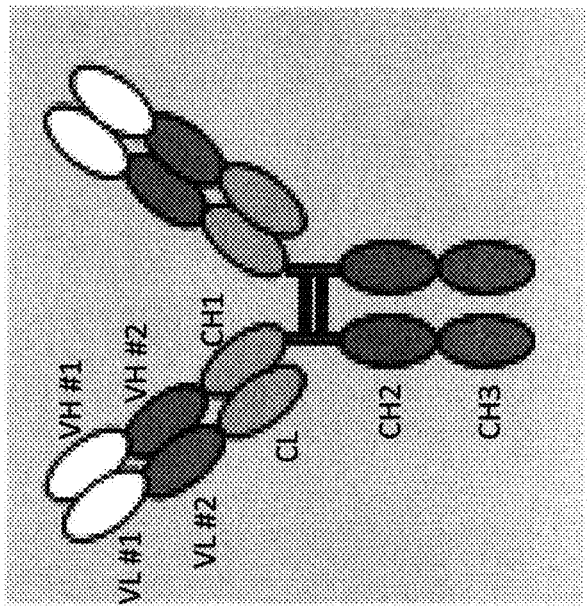
FIG. 20 is a schematic of a representative bispecific binding molecule known as a DVD-Ig.

A method for screening the ability of bispecific abs, peptibodies and avimers to block Sclerostin or Dkk1 binding to Lrp6 was established using purified biotin-labeled Dkk1 and Sclerostin proteins and purified His-tagged Lrp6 or Lrp5. The ability of the bispecifics/peptides/avimers to block Scl or Dkk1 binding to Lrp6/Lrp5 was determined using an AlphaScreen assay. 5 µl of biotin-Scl (or biotin-Dkk1) and 5 µl of Lrp6-His were incubated for 1 hour at room temperature first, and then 5 µl of bispecific agent was added for additional 1 hour followed by addition of 10 ul of a donor/acceptor beads mixture. The reaction was incubated for 1 more hour before the AlphaScreen signal was read on an EnVision apparatus at 520-620 nM. The loss of signal in the bispecific agent treated wells indicated that the bispecifics block the binding of Dkk1 and Sclerostin to Lrp5/Lrp6 and may thereby allow canonical signaling to be triggered by various Wnt proteins. FIG. 19 summarizes data from one such screening experiment.

Example 9

In Vivo Mouse Bone Mass and Bone Strength Model

Figure 5:
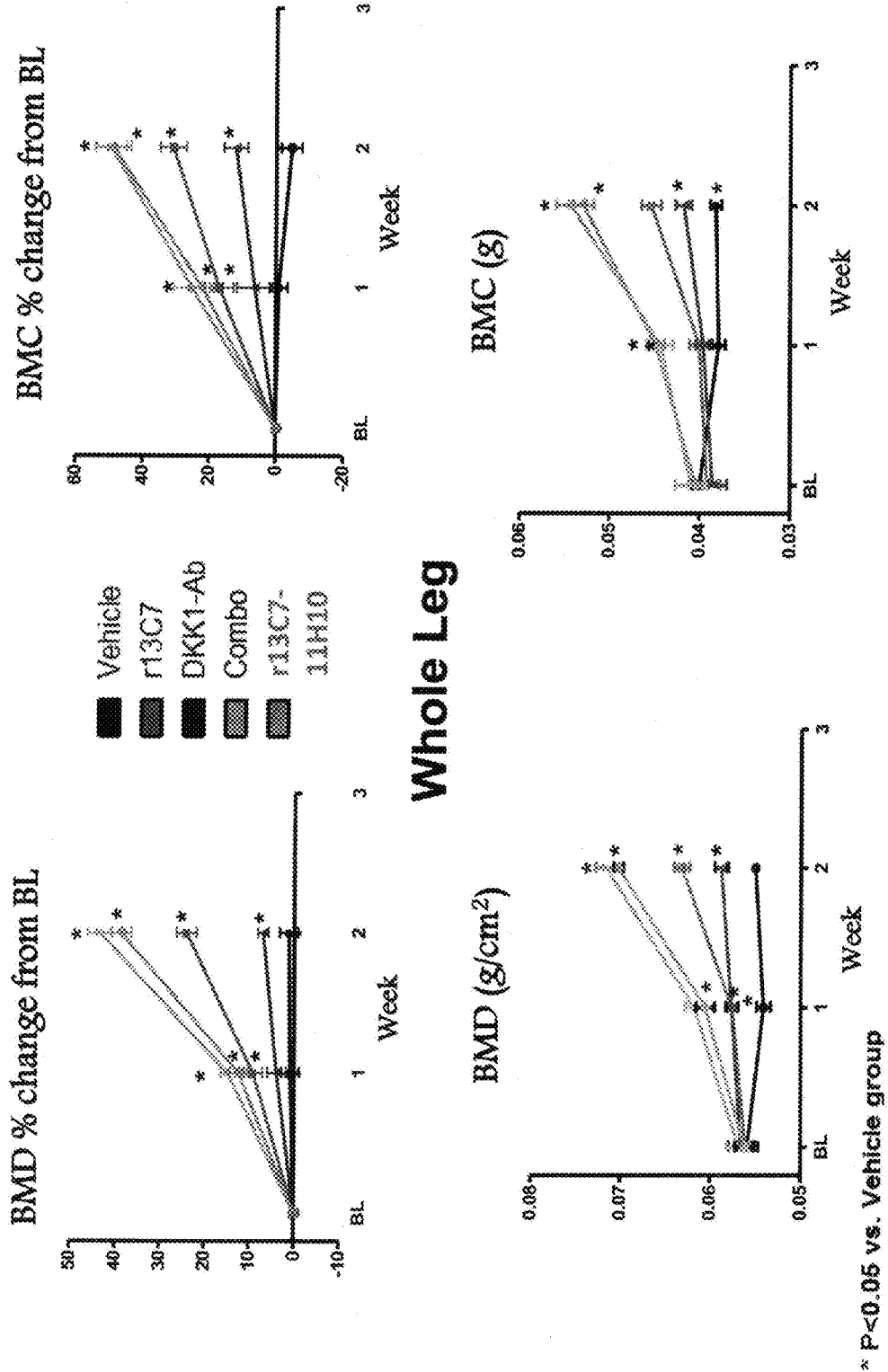
FIG. 5 summarizes the percent change in bone mass density (BMD) and bone mineral content (BMC) in lumbar vertebrae and whole leg data from an in vivo study using mice treated with vehicle, anti-sclerostin mAb, anti-DKK1 mAb, a combination of anti-sclerostin mAb and DKK1 mAb, and 13C7-11H10 bispecific.

These studies and results are summarized in FIG. 5. Study Design: Total of 45 male 10 weeks old B6D2F1 mice were used in this study. At the beginning of the study, animals were divided into 5 groups (n=9/group), balancing by both body weight and BMD at the femur-tibia region by in vivo DXA. Mice were subcutaneously injected with either vehicle (proline) or sclerostin-Ab (Scl-Ab), or DKK1-Ab or combination of Scl-Ab and DKK1-Ab (Combination) or bispecific antibody (Bisp-Ab) twice per week for 3 weeks. Due to the differences in molecular weight, the antibodies were dosed at equal molarity ($1.82 \times 10$-5M), with 18.2 mg/kg Scl-Ab, 18.07 mg/kg DKK1-Ab, 18.2 mg/kg Scl-Ab+18.07 mg/kg DKK1-Ab in the Combination group, and 25 mg/kg Bisp-Ab. Animals were scanned weekly by in vivo DXA to monitor the bone anabolic effects of the drug treatments at lumbar vertebral and femur-tibia regions; then euthanized at the end of study. Femurs were collected for ex vivo densitometry by µCT and bone strength analysis.

In vivo densitometry: animals were scanned by DXA (GE Lunar PIXImus II) at the regions of tibia-fibula junction to femur neck (femur-tibia) and lumbar vertebrae (LV1-5) to determine areal BMD at these sites.

Ex vivo densitometry: femurs were scanned using a desktop micro-CT system (eXplore Locus SP, GE Healthcare, London, Ontario, Canada) and reconstructed to a resolution of 13 µm. The regions spanning 10% of the femur height at the cortical midshaft (threshold 800 mg/cc) for cortical bone and 10% of the trabecular distal femur (threshold 500 mg/cc for vehicle and DKK1-Ab; 550 mg/cc for Scl-Ab, and 600 mg/cc for Combination and Bisp-Ab) were examined. Cortical bone area (Ct.Ar) and cross-sectional moment of inertia (CSMI) were measured at the midshaft region. Cancellous bone volume fraction (BV/TV), trabecular number (Tb.N), trabecular thickness (Tb.Th), and trabecular BMD (Tb.BMD) were assessed at the distal femur.

Biomechanics: Femurs were tested in 3-point bending to failure at the midshaft, and bone strength parameters maximum load and stiffness were assessed (MTS 858 Mini Bionix II; span length=6 mm; displacement rate=6 mm/min).

Statistical analyses: GraphPad Prism (v. 5.01) was used to perform the statistical analyses. The comparison was conducted using the one way Anova, with a Tukey Kramer post-hoc test. Data reported as Mean+SEM, and $p<0.05$ considered as significance.

Results:

In vivo BMD: Significant increases in BMC and BMD were noted at both lumbar vertebrae (LV1-5) and femur-tibia regions for the Combination and Bisp-Ab groups as early as one week after treatment, and the response continued to increase at the level greater than Scl-Ab and DKK1-Ab alone over the treatment period. The data shown in FIG. X represent the percent change in BMC from baseline at tibia-femur at the end of the study (3-weeks). All treatments resulted in significantly increased BMC compared to the vehicle treated group, which decreased only −3.5% compared to baseline. Animals treated with Scl-Ab increased BMC by 27%, Dkk1-Ab increased BMC by 13%, Combination increased BMC by 51% and Bisp-Ab increased BMC by 48% compared to baseline. The increases in BMC and BMD at both the lumbar vertebrae and femur-tibia induced by Combination or Bisp-Ab treatments were significantly greater than either Scl-Ab or Dkk1-Ab alone.

Bone Mass and Bone Strength: DKK1-Ab significantly increased distal femur BV/TV (+47%), Tb.N (+30%), and Tb.vBMD (+23%), but not Tb.Th (+13%) compared to vehicle. DKK1-Ab did not significantly affect diaphyseal Ct.Ar (+3%) and CSMI (+1%) compared to vehicle. Femoral shaft bending strength was not affected by DKK1-Ab treatment.

Scl-Ab significantly increased distal femur BV/TV (+76%), Tb.N (+21%), Tb.Th (+71%), and Tb.vBMD (+47%) compared with vehicle. Scl-Ab significantly increased diaphyseal Ct.Ar (+24%) but not CSMI (+22%) compared to vehicle. Scl-Ab significantly increased femur shaft maximum load (+29%) and stiffness (+24%) compared to vehicle.

Combination significantly increased distal femur BV/TV (+278%), Tb.N (+64%), Tb.Th (+175%), and Tb.vBMD (+149%) compared to vehicle. Combination significantly increased diaphyseal Ct.Ar (+37%) and CSMI (+44%) compared to vehicle. Combination significantly increased femur shaft maximum load (+47%) and stiffness (+46%) compared to vehicle. The mean values of all of these parameters in Combination were significantly greater than those observed for the Scl-Ab (except for CSMI) and DKK1-Ab alone groups.

Similar to Combination, Bisp-Ab significantly increased distal femur BV/TV (+228%), Tb.N (+57%), Tb.Th (+152%), and Tb.vBMD (129%) compared to vehicle. Bisp-Ab significantly increased diaphyseal Ct.Ar (+35%) and CSMI (+39%) compared with vehicle. Bisp-Ab significantly increased femur shaft maximum load (+45%) and stiffness (+44%) compared to vehicle. The mean values of all of these parameters in Bisp-Ab were significantly greater than those observed for the Scl-Ab (except for CSMI) and DKK1-Ab alone groups.

Summary: Both Combination and Bisp-Ab treatments resulted in greater increases in bone mass and bone strength compared to the either monotherapy. These results clearly indicated both Combination and Bisp-Ab treatments have an unexpected synergistic effect on enhancing bone mass and bone strength in this mouse model.

Conclusion: Bispecific-Ab, a molecule containing inhibitory effects towards both sclerostin and Dkk1 appears to have stronger therapeutic activity than Scl-Ab or DKK1-Ab alone in conditions associated with low bone mass and bone repair.

Example 10

Sost-Ab and Dkk1-Ab Combination Therapy Increase PTHR1 expression

To better understand the molecular mechanism underlying the synergistic impact of Sost- and Dkk1-antibody combination treatment on bone formation the expression of bone anabolic pathway members was studied. Male 7-9 month old Sprague Dawley rats were treated with vehicle (Veh), Dkk1-Ab (10 mg/kg 2×/wk), Sost-Ab (10 mg/kg 2×/wk), combination (combo 5 mg/kg or 10 mg/kg 2×/wk) for two-weeks. Animals were sacrificed at day 14 and the rat femur was removed and cleaned of all muscle. The epiphyses and cartilage were removed and the femur was flushed with ice-cold PBS to remove the bone marrow. The bone was then flash frozen in liquid nitrogen and pulverized. Bone RNA was purified using PureLink™ Pro 96 total RNA Purification Kit (Invitrogen; Carlsbad, Calif.). Gene expression was analyzed with the Affymetrix QuantiGene-Plex 2.0 Panel 331140 (Affymetrix; Santa Clara, Calif.).

Figure 6:
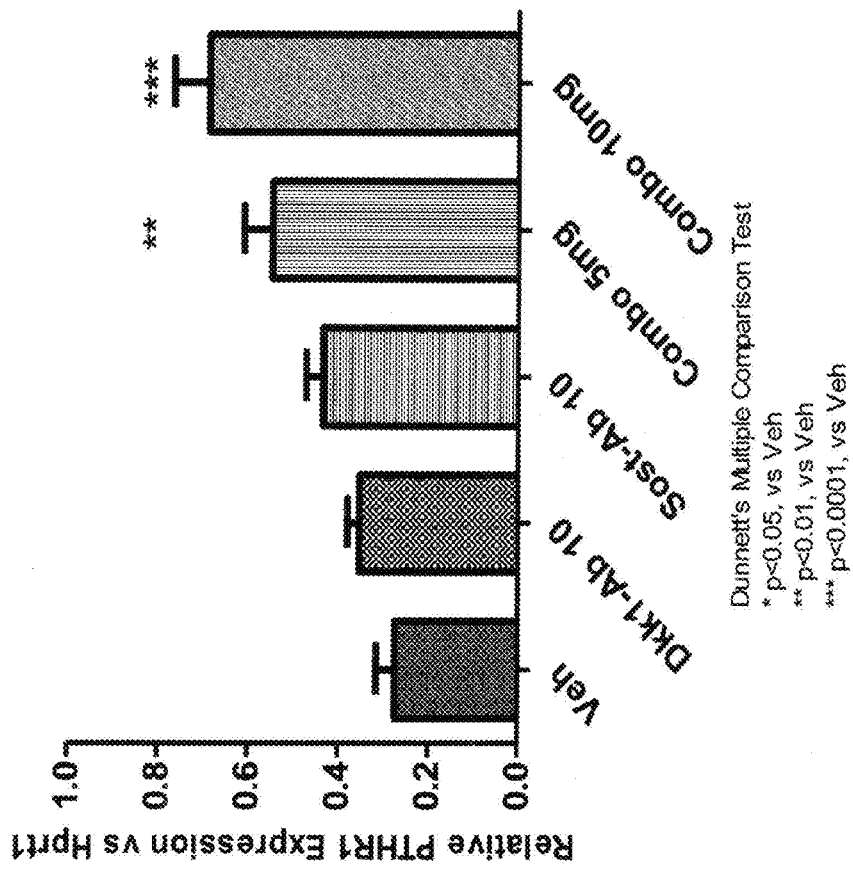
FIG. 6 summarizes the analysis of gene expression data after treatment with combination anti-sclerostin/anti-DKK-1 therapy.
Figure 7:
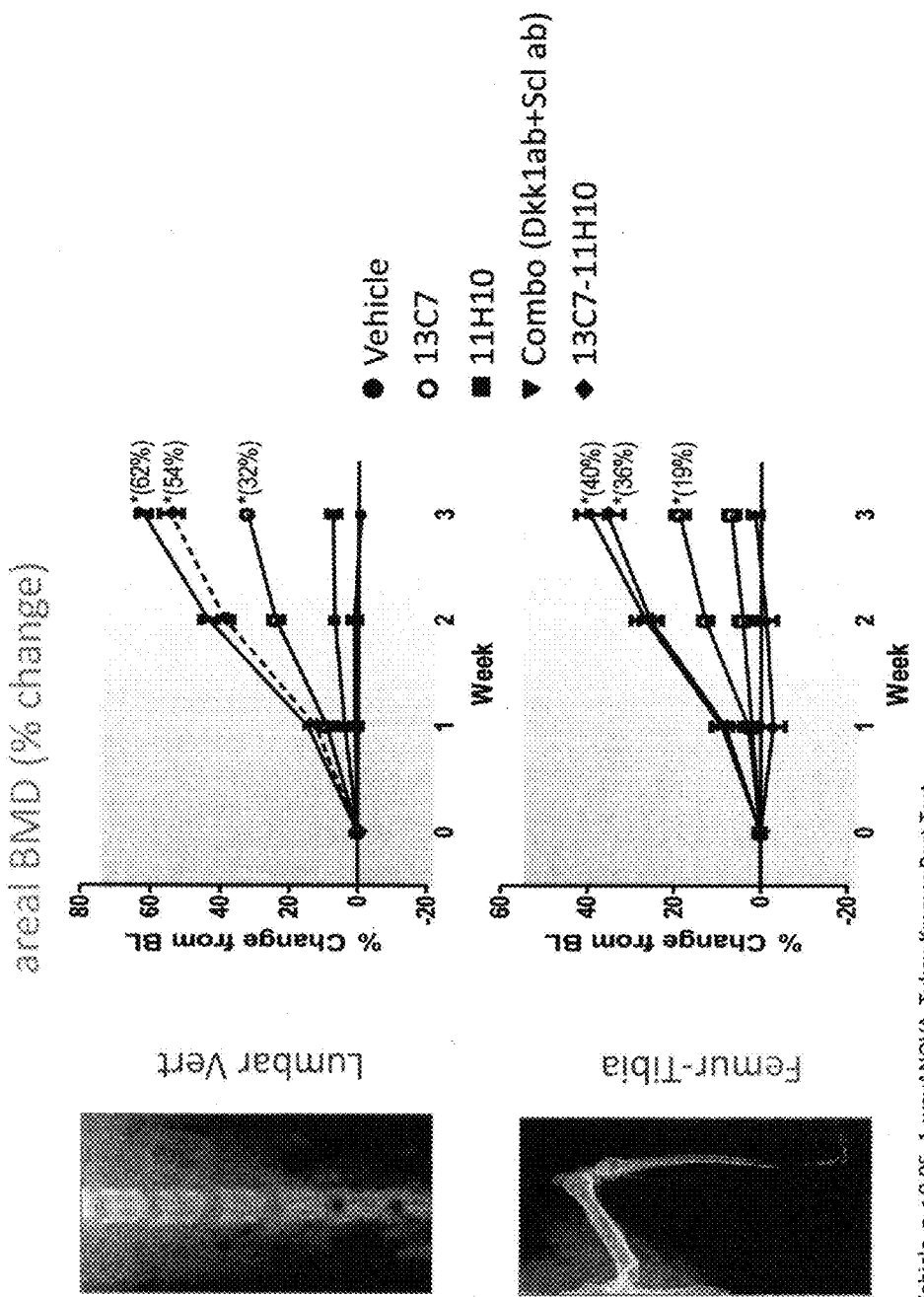
FIGS. 7 and 8 summarize the BMD percent change of the lumbar vertebrae and the femur-tibia in mice treated with vehicle, anti-sclerostin mAb, anti-DKK1 mAb, a combination of anti-sclerostin mAb and DKK1 mAb, and 13C7-11H10 bispecific.
Figure 8:
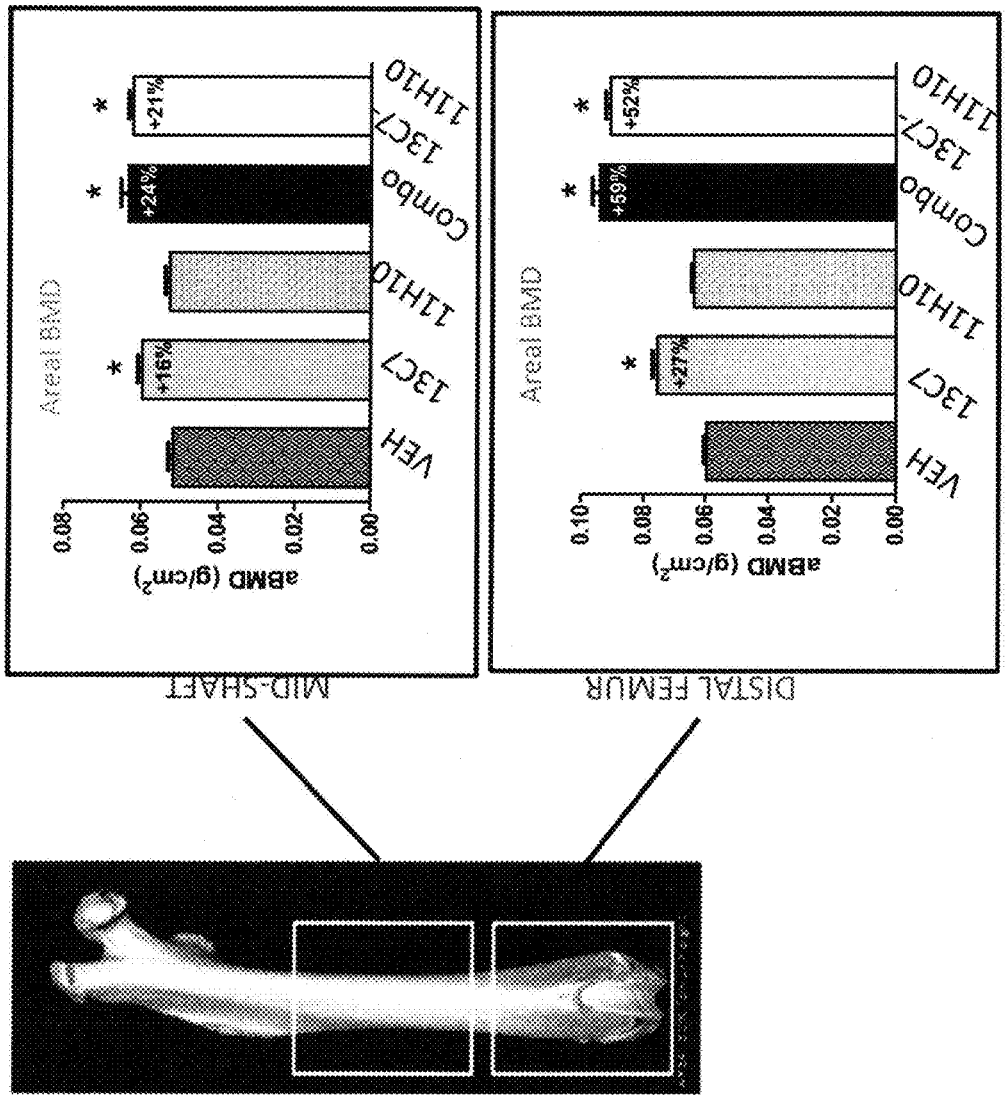
Figure 9:
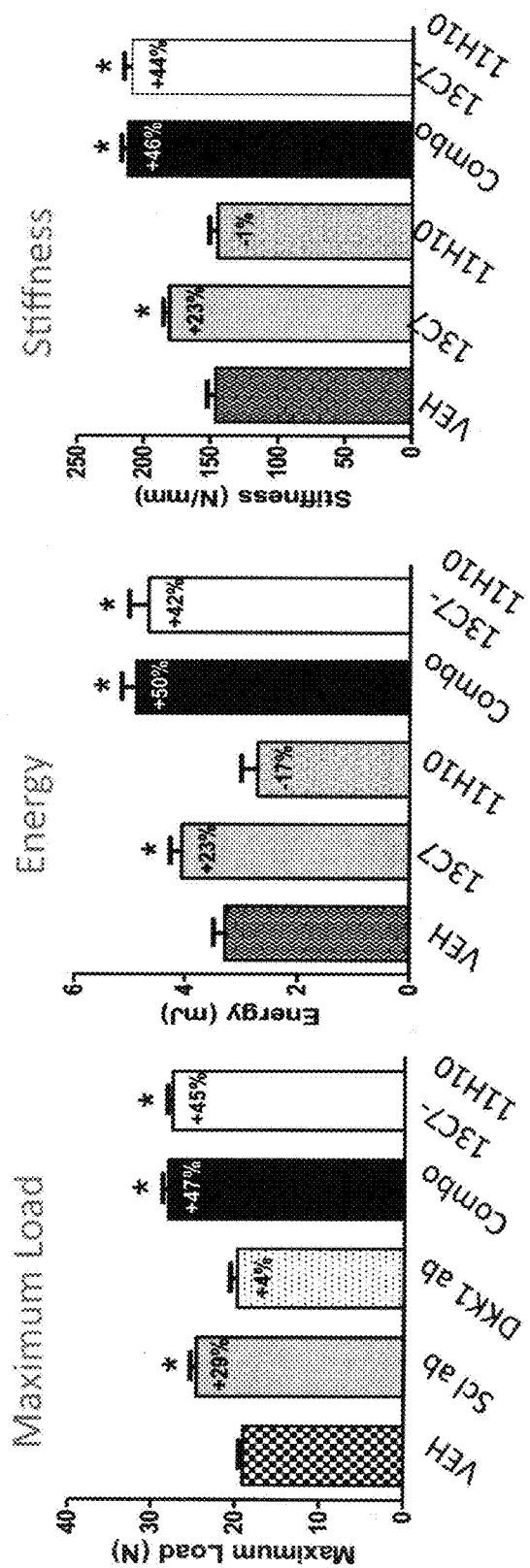
FIGS. 9 and 10 summarize the percent change in bone strength from mice treated with vehicle, anti-sclerostin mAb, anti-DKK1 mAb, a combination of anti-sclerostin mAb and DKK1 mAb, and 13C7-11H10 bispecific.
Figure 10:
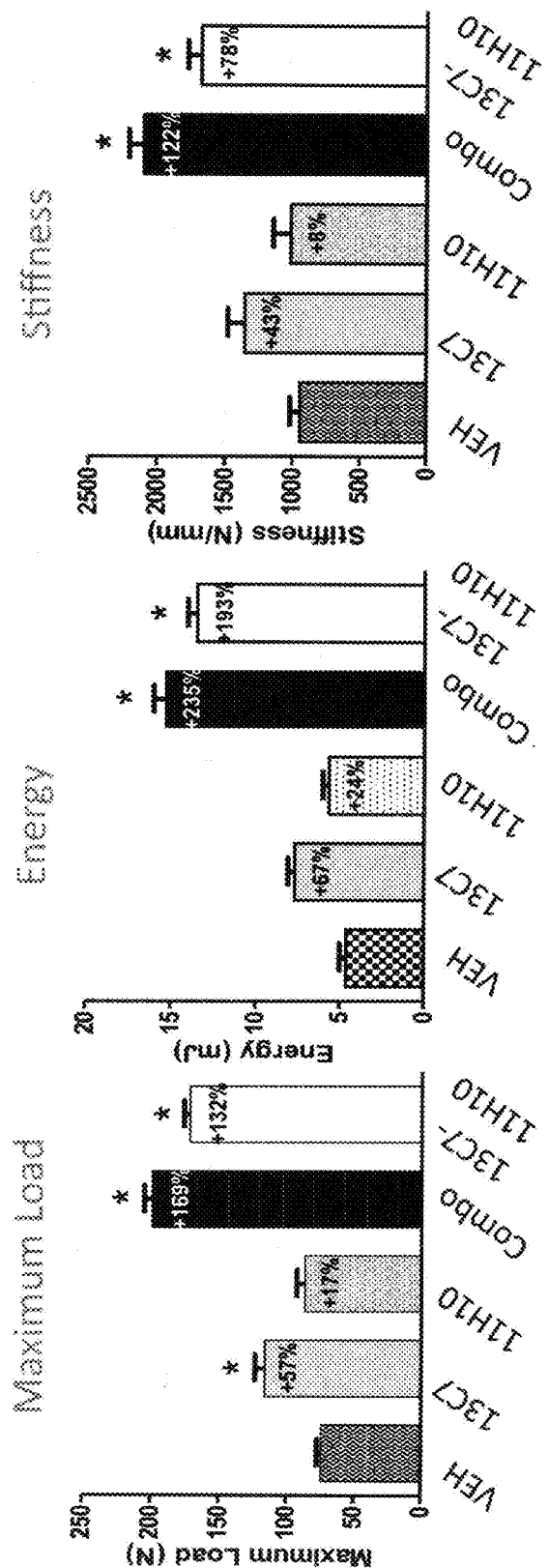
Figure 11:
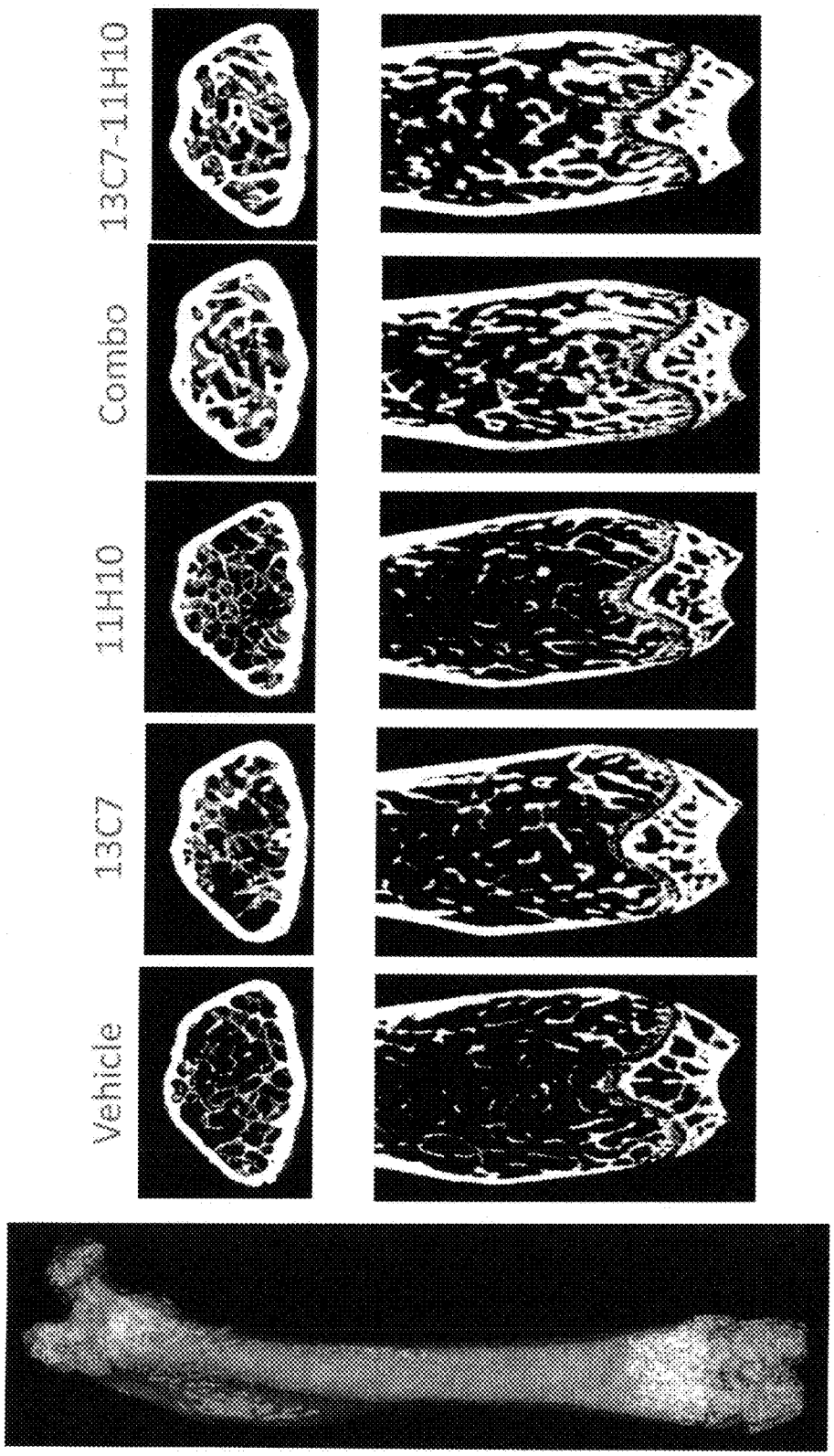
FIG. 11 contains cross section images of mouse femurs from mice treated with vehicle, anti-sclerostin mAb, anti-DKK1 mAb, a combination of anti-sclerostin mAb and DKK1 mAb, and 13C7-11H10 bispecific.
Figure 12:
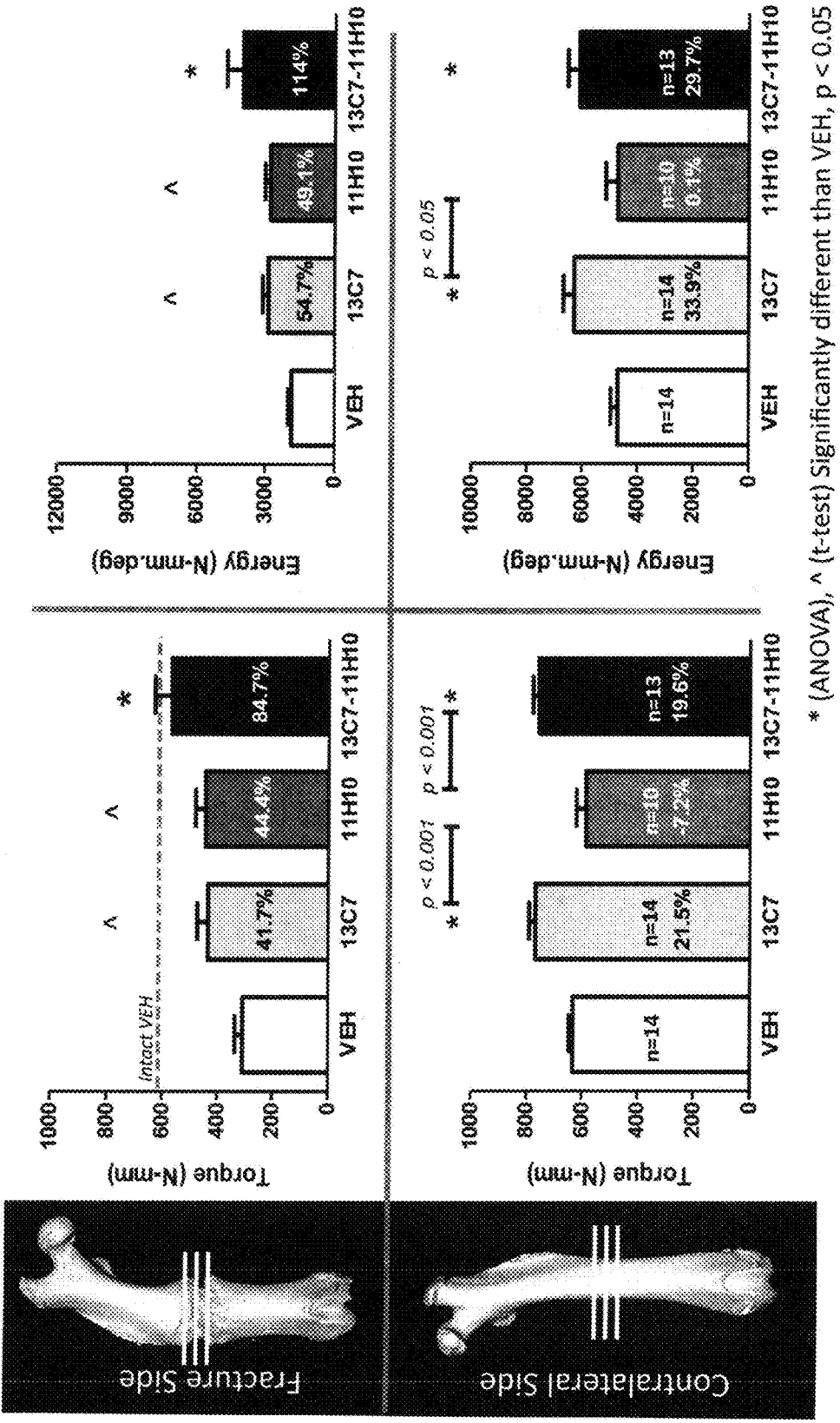
FIG. 12 summarizes percent change in bone strength in a torsional model from rats treated with vehicle, anti-sclerostin mAb, anti-DKK1 mAb, and DKK1 mAb, and 13C7-11H10 bispecific.
Figure 15:
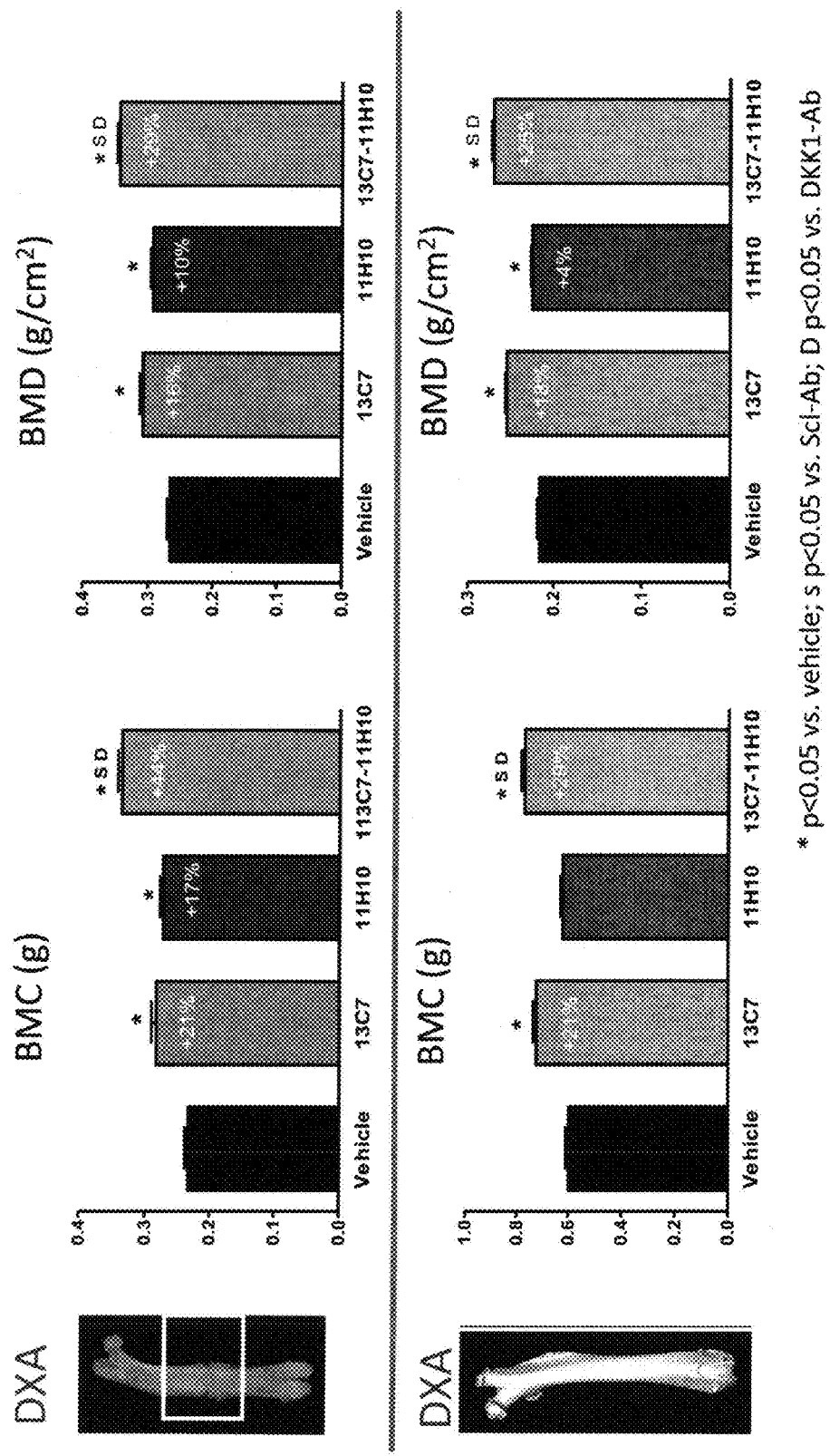
FIGS. 15-16 summarize the percent change in bone strength from mice treated with vehicle, anti-sclerostin mAb, anti-DKK1 mAb, and 13C7-11H10 bispecific.
Figure 16:
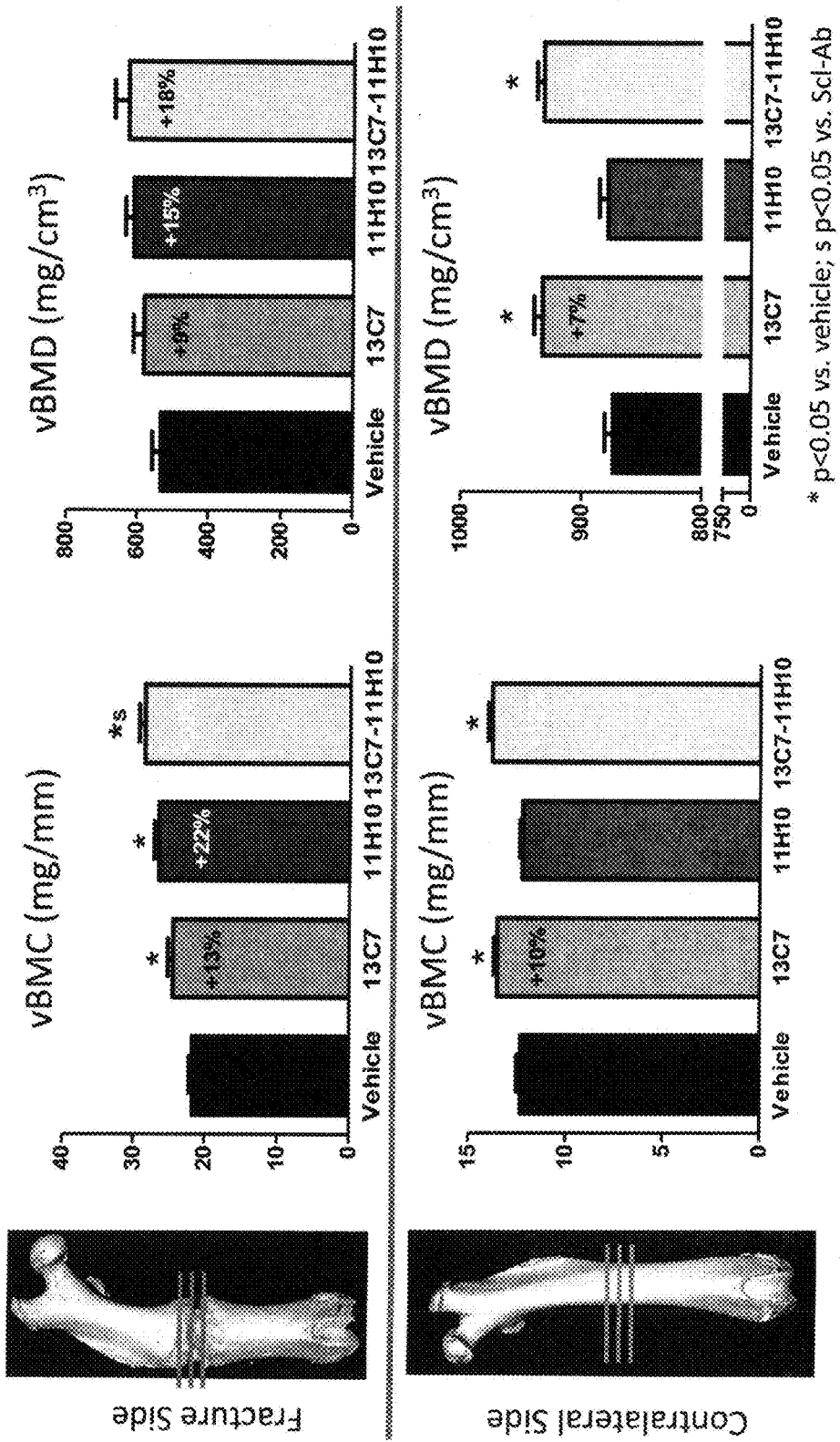
Figure 17:
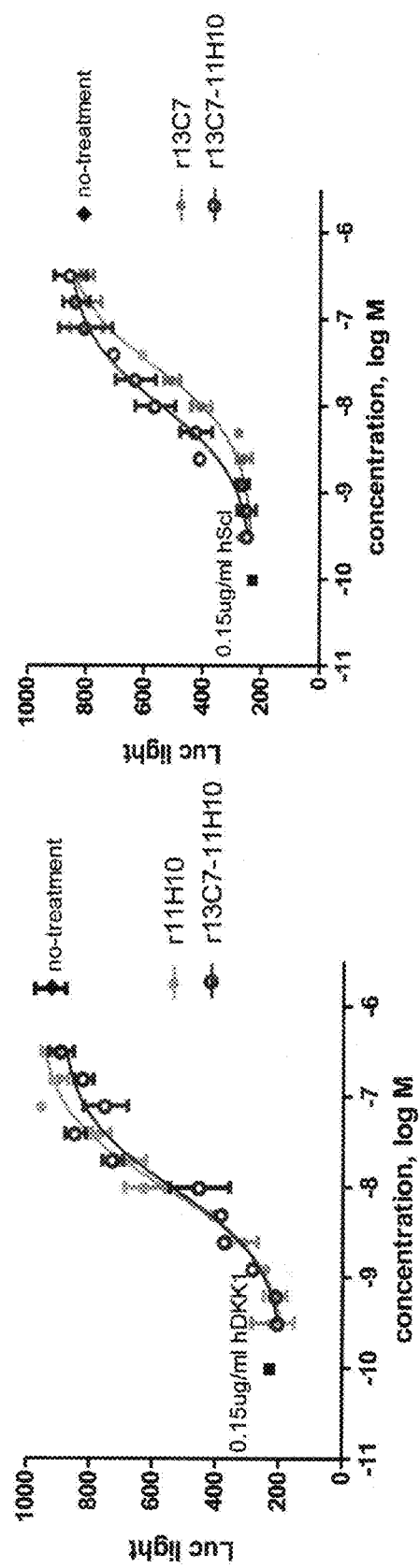
FIG. 17 summarizes the results of an osteoblast supertopflash competition assay showing rat 13C7-11H10 retains the neutralizing activity of parental antibodies in osteoblast MC3T3E1 cells treated with Wnt proteins.

Treatment with combination therapy increased the expression of a large number of genes associated with bone anabolism to a much greater extent than either therapy alone. These genes included markers of osteocyte (DMP1), canonical Wnt-signaling pathway (Axing), osteogenic (Col1A1) and osteoblast transcription (Osterix) biology. Unexpectedly, a synergistic increase in the parathyroid hormone (PTH) signaling pathway component PTH receptor 1 (PTHR1) was also observed (FIG. XX below). These data, as summarized in FIG. 6, suggest that the synergistic action of Sost-Ab and Dkk1-Ab combination treatment on bone anabolism may in part be due to an unexpected increase in PTH signaling arising from combination treatment.

Example 11

High Throughput (HT) expression of binding molecules
Sclerostin/DKK1 pairings of the following were generated:

| Sclerostin | DKK1 |
|---|---|
| 13F3 | 6.37.5 |
| 13F3 | 6.147 |
| 20C3 | 6.37.5 |
| 20C3 | 6.147 |
| 46H1 | 6.37.5 |
| 46H1 | 6.147 |
| 38B12 | 6.3755 |
| 38B12 | 6.147 |
| 13C7 | 6.37.5 |
| 13C7 | 6.147 |
| Ab23 | 6.37.5 |
| Ab23 | 6.147 |
| Ab23 | PD17 |
| 13F3 | PD17 |
| 20C3 | PD17 |
| 46H1 | PD17 |
| 38B12 | PD17 |
| 13C7 | PD17 |
| 19D11 | 6.37.5 |

Two different orientations and 5 different linkers (GGGS, GGGGSGGGGS, GGGGSGGGGSGGGGS, $1^{st}$ 6 amino acids of CL/CH1, $1^{st}$ 13 amino acids of CL/CH1) per orientation were tested for each pair. Binding molecules were transiently expressed in adherence-adapted 293 6E cells in 96-well plates. Adherent 293 6E cells were seeded in Poly-D-Lysine coated 96-well tissue culture plates at 5E4 cells per well in Freestyle 293 Expression medium (Gibco #12338) supplemented with 0.01% Pluronic F68, G418 at 25 µg/ml, and 5% FBS 24 hours prior to the transfection and incubated overnight at 37° C. in 5% CO2.

On the day of transfection, 100 ng (40 ng/µl) each of the corresponding HC and LC DNA of the binding molecules were mixed together. 25 µl/well of premixed Freestyle Media: FugeneHD (Roche, cat#04-709-713-001) (24:1) was added to the DNA mixtures. After incubation at room temperature for 15-30 min, the entire transfection mixtures were added to the culture plates seeded the day before and mixed with gentle rocking motions. The culture plates were put back into the 37° C., 5% CO2 incubator overnight. The next day media and transfection mixtures were aspirated out and replaced with 130 µl of serum free media containing 0.5% Tryptone. The plates were incubated for another 6 days. Conditioned media (CM) were harvested on day 7 after transfection. The plates were spun at 1000 rpm for 5 min to pellet any cell debris. Supernatants were carefully transferred into sterile polypropylene blocks.

Concentrations of binding molecules in the CM were measured on ForteBio QK using Protein A biosensors (ForteBio, Cat#18-5010). Protein A biosensors were soaked for 10 min in Sample buffer before the run. At the start of the run, the prewet biosensors were dipped in two-fold diluted CM samples for 2 min and captured molecules were recorded. Sample Concentrations were calculated with Data Analysis 6.3 software using the preloaded IgG1 concentration standard curve.

ELISA screening was performed as described in Example 4 herein. The WNT assays were performed as described in Example 6 and 7 herein.

Conclusion: The HT screen led to identification of several fully human DVD-Ig candidates with potent dual neutralizing activity against Sclerostin and Dkk1. Of the 157 candidates screened 35% showed good transient expression in the HT expression screen, with several candidates yielding expression levels of greater than 10 ug/ml.

Example 12

Stimulating bone formation and increasing bone strength in intact young growing mouse model.

Study Design: Total of 45 male 10 weeks old B6D2F1 mice were used in this study. At the beginning of the study, animals were divided into 5 groups (n=9/group), balancing by both body weight and BMD at the femur-tibia region by in vivo DXA. Mice were subcutaneously injected with either vehicle (proline) or sclerostin-Ab (Scl-Ab), or DKK1-Ab or combination of Scl-Ab and DKK1-Ab (Combination) or 13C7-11H10 twice per week for 3 weeks. Due to the differences in molecular weight, the antibodies were dosed at equal molarity ($1.82 \times 10^{-5}$M), with 18.2 mg/kg Scl-Ab, 18.07 mg/kg DKK1-Ab, 18.2 mg/kg Scl-Ab+18.07 mg/kg DKK1-Ab in the Combination group, and 25 mg/kg 13C7-11H10. Animals were scanned weekly by in vivo DXA to monitor the bone anabolic effects of the drug treatments at lumbar vertebral and femur-tibia regions; then euthanized at the end of study. Femurs were collected for ex vivo densitometry by μCT and bone strength analysis.

In vivo densitometry: animals were scanned by DXA (GE Lunar PIXImus II) at the regions of tibia-fibula junction to femur neck (femur-tibia) and lumbar vertebrae (LV1-5) to determine areal BMD at these sites.

Ex vivo densitometry: femurs were scanned using a desktop micro-CT system (eXplore Locus SP, GE Healthcare, London, Ontario, Canada) and reconstructed to a resolution of 13 μm. The regions spanning 10% of the femur height at the cortical midshaft (threshold 800 mg/cc) for cortical bone and 10% of the trabecular distal femur (threshold 500 mg/cc for vehicle and DKK1-Ab; 550 mg/cc for Scl-Ab, and 600 mg/cc for Combination and Bisp-Ab) were examined. Cortical bone area (Ct.Ar) and cross-sectional moment of inertia (CSMI) were measured at the midshaft region. Cancellous bone volume fraction (BV/TV), trabecular number (Tb.N), trabecular thickness (Tb.Th), and trabecular BMD (Tb.BMD) were assessed at the distal femur.

Biomechanics: Femurs were tested in 3-point bending to failure at the midshaft, and bone strength parameters maximum load and stiffness were assessed (MTS 858 Mini Bionix II; span length=6 mm; displacement rate=6 mm/min).

Statistical analyses: GraphPad Prism (v. 5.01) was used to perform the statistical analyses. The comparison was conducted using the one way Anova, with a Tukey Kramer post-hoc test. Data reported as Mean+SEM, and $p<0.05$ considered as significance.

Results:

In vivo BMD: Significant increases in BMC and BMD were noted at both lumbar vertebrae (LV1-5) and femur-tibia regions for the Combination and 13C7-11H10 groups as early as one week after treatment, and the response continued to increase at the level greater than Scl-Ab and DKK1-Ab alone over the treatment period. The data shown represents the percent change in BMC from baseline at tibia-femur at the end of the study (3-weeks). All treatments resulted in significantly increased BMC compared to the vehicle treated group, which decreased only −3.5% compared to baseline. Animals treated with Scl-Ab increased BMC by 27%, Dkk1-Ab increased BMC by 13%, Combination increased BMC by 51% and 13C7-11H10 increased BMC by 48% compared to baseline. The increases in BMC and BMD at both the lumbar vertebrae and femur-tibia induced by Combination or Bisp-Ab treatments were significantly greater than either Scl-Ab or Dkk1-Ab alone.

Bone Mass and Bone Strength:

DKK1-Ab significantly increased distal femur BV/TV (+47%), Tb.N (+30%), and Tb.vBMD (+23%), but not Tb.Th (+13%) compared to vehicle. DKK1-Ab did not significantly affect diaphyseal Ct.Ar (+3%) and CSMI (+1%) compared to vehicle. Femoral shaft bending strength was not affected by DKK1-Ab treatment.

Scl-Ab significantly increased distal femur BV/TV (+76%), Tb.N (+21%), Tb.Th (+71%), and Tb.vBMD (+47%) compared with vehicle. Scl-Ab significantly increased diaphyseal Ct.Ar (+24%) but not CSMI (+22%) compared to vehicle. Scl-Ab significantly increased femur shaft maximum load (+29%) and stiffness (+24%) compared to vehicle.

Combination significantly increased distal femur BV/TV (+278%), Tb.N (+64%), Tb.Th (+175%), and Tb.vBMD (+149%) compared to vehicle. Combination significantly increased diaphyseal Ct.Ar (+37%) and CSMI (+44%) compared to vehicle. Combination significantly increased femur shaft maximum load (+47%) and stiffness (+46%) compared to vehicle. The mean values of all of these parameters in Combination were significantly greater than those observed for the Scl-Ab (except for CSMI) and DKK1-Ab alone groups.

Similar to Combination, 13C7-11H10 significantly increased distal femur BV/TV (+228%), Tb.N (+57%), Tb.Th (+152%), and Tb.vBMD (129%) compared to vehicle. 13C7-11H10 significantly increased diaphyseal Ct.Ar (+35%) and CSMI (+39%) compared with vehicle. 13C7-11H10 significantly increased femur shaft maximum load (+45%) and stiffness (+44%) compared to vehicle. The mean values of all of these parameters in 13C7-11H10 were significantly greater than those observed for the Scl-Ab (except for CSMI) and DKK1-Ab alone groups.

The results from this Example are summarized in FIGS. 7-11. Both Combination and 13C7-11H10 treatments resulted in greater increases in bone mass and bone strength compared to the either monotherapy. These results clearly indicated both Combination and 13C7-11H10 treatments have a synergistic effect on enhancing bone mass and bone strength in an intact mouse model.

Example 13

Stimulating bone formation and increasing bone strength of the fractured femur in a rat closed femoral fracture model.

Study Design: 12-week old male Sprague-Dawley (SD) rats (mean body weight 428 g) underwent unilateral closed femoral mid-diaphyseal fracture as reported previously (Bonnarens F, et al. J Orthop Res 1984; 2: 97-101). Briefly, an 18 gauge syringe needle was inserted into the medullary canal through the femoral condyles, and served as an internal fixation. The femur then underwent transverse fracture via blunt impact loading at the anterior (lateral) aspect of the thigh. One day after fracture, animals (n=18/group) were subcutaneously injected with either saline vehicle, Scl-Ab (25 mg/kg), DKK1-Ab (25 mg/kg), or the DVD-Igs 13C7-11H10, 6.147-2x-Ab5, 6.37-AbL-Ab23, Ab5K-AbS-6.147, 6.147-AbL-27H6 or 8G2-AbL-6.37.5 (indicated on each Figure) (34.37 mg/kg) twice per week. At 5 weeks post-fracture, animals were euthanized; the fractured and non-fractured contralateral (CL) femurs were collected for densitometry and biomechanics. This study was approved by Amgen's Institution Animal Care and Use Committee.

Densitometry by DXA: The intramedullary pins were removed from the fractured femurs prior to the densitometric analysis. Femurs were scanned ex vivo by dual energy x-ray absorptiometry (DXA; GE Lunar PIXImus II); analyses were performed at the central 30% of the fractured femur or the entire contralateral intact femur to determine areal bone mineral content (BMC).

Densitometry by pQCT: Both femurs were also scanned by peripheral quantitative computed tomography (pQCT; Stratec XCT research SA+; Germany), at a resolution of 100 μm. Analyses were performed for three 0.5-mm slices at the center of the fractured femur callus and the mid-point of contralateral femur (BMC).

Biomechanics: The proximal and distal ends of each femur were embedded in Slow Set Lab Plaster (Heraeus-Kulzer) to isolate a 14-16 mm long central region. These fractured and CL femurs were tested in torsion to failure at an angular displacement rate of 2.0 deg/sec (MTS 858 Mini Bionix II, MTS Corp., Mineapolis, USA). Bone strength parameters including maximum torque (N-mm), energy to failure (N-mm·deg) and torsional stiffness (N/mm) were assessed.

Statistical analyses: GraphPad Prism (v. 5.01) was used to determine statistical differences between groups by unpaired 2-sided t-tests, with $p<0.05$ considered significant.

RESULTS: Fractured femurs: Both Scl-Ab and DKK1-Ab showed similar improvements in bone mass and bone strength at the fractured callus, as demonstrated by significant increases in BMC by DXA (+17 to 21%) and by pQCT (+13 to 22%) compared with vehicle controls. These increases in bone mass were associated with 42-44% greater maximum torque in the fractured femur, compared with vehicle controls.

The DVD-Igs greatly enhanced bone mass and bone strength at the fractured callus to levels greater than either Scl-Ab or DKK1-Ab alone. Compared with vehicle, fracture callus BMC was 44% greater by DXA and 32% greater by pQCT in the DVD-Ig group. This enhancement of bone mass was associated with an 85% increase in maximum torque in the DVD-Ig group as compared with vehicle. In addition, DXA BMC was significantly higher in the DVD-Ig group compared with Scl-Ab alone or DKK1-Ab alone groups.

Non-fractured contralateral femurs: DKK1-Ab did not significantly affect diaphyseal bone mass and bone strength in non-fractured contralateral femurs. However, Scl-Ab significantly increased mid-diaphyseal cortical thickness and maximum torque by 13% and 22% respectively, compared with vehicle. The DVD-Igs significantly increased contralateral femoral cortical bone thickness and maximum torque by 13% and 20% respectively, compared with vehicle, changes which were similar to those in the Scl-Ab group. Data expressed as Mean±SE, *$p<0.05$ vs. vehicle.

The results from this Example are summarized in FIGS. 12-16.

Example 14

Lrp6/Sclerostin and Lrp6/Dkk1 alpha screen assays

The AlphaScreen competition assay was performed essentially as described in Silverman et. al 2005 Nature Biotech 23(12):1556-1561. Dose-response curves were generated by serially diluting parental and DVD-Ig proteins in assay buffer (40 mM HEPES pH 7.5, 100 mM NaCl, 1 mM CaCl2, 0.1% BSA, 0.05% Tween-20) in a 384-well Greiner microtiter plate. A tracer amount of in-house purified and chemically biotinylated recombinant human or rat Sclerostin (up to 1.5 nM) was added to the microtiter plate followed by the addition of a mixture containing either mouse LRP6-his or rhLRP6-Fc (R&D Systems) (up to 6-12 nM) and AlphaScreen 'donor' streptavidin and 'acceptor' protein A beads (10 mg/ml each) (PerkinElmer). The microtiter plate was then sealed and incubated overnight at room temperature. Inhibition of complex formation was measured as a reduction in chemiluminescent signal as measured on the Fusion Plate Reader (PerkinElmer) using excitation at 680 nm and emission at 520-620 nm. The results are summarized in FIG. 19.

What is claimed is:

1. A binding molecule that specifically binds sclerostin and DKK-1 and comprises first and second polypeptide chains, wherein said first polypeptide chain comprises VH1-(X1)n-VH2-C-(X2)n, wherein VH1 comprises the amino acid sequence of SEQ ID NO: 95; wherein VH2 comprises the amino acid sequence of SEQ ID NO: 4086; C is a heavy chain constant domain; (X1)n is a linker set forth in SEQ ID NO: 440 or SEQ ID NO: 441, and (X2)n is an Fc region and wherein said second polypeptide chain comprises a VL1-(X1)n-VL2-C, wherein VL1 comprises the amino acid sequence of SEQ ID NO: 94; wherein VL2 comprises the amino acid sequence of SEQ ID NO: 407; and wherein C is a light chain constant domain.

2. The binding molecule of claim 1, wherein the binding molecule comprises two first polypeptide chains and two second polypeptide chains.

3. The binding molecule of claim 1, wherein the Fc region is selected from the group consisting of a native sequence Fc region and a variant sequence Fc region.

4. The binding molecule of claim 1, wherein the Fc region is selected from the group consisting of an Fc region from an IgG1, IgG2, IgG3, IgG4, IgA, IgM, IgE, and IgD.

5. The binding molecule of claim 1, wherein said binding molecule possesses at least one antibody parameter exhibited by said first parent antibody, or antigen binding portion thereof, or said second parent antibody, or antigen binding portion thereof, wherein said antibody parameter is selected from the group consisting of antigen specificity, affinity to antigen, potency, biological function, epitope recognition, stability, solubility, production efficiency, immunogenicity, pharmacokinetics, bioavailability, tissue cross reactivity, and orthologous antigen binding.

6. A binding molecule that binds both sclerostin and DKK-1 comprising four polypeptide chains, wherein first and third polypeptide chains comprise the amino acid sequence set forth in SEQ ID NO: 62 and wherein second and fourth polypeptide chains comprise the amino acid sequence set forth in SEQ ID NO: 64.

7. A binding molecule that binds both sclerostin and DKK-1 comprising four polypeptide chains, wherein first and third polypeptide chains comprise the amino acid sequence set forth in SEQ ID NO: 490 and wherein second and fourth polypeptide chains comprise the amino acid sequence set forth in SEQ ID NO: 492.

8. The binding molecule of claim 1, wherein said (X1)n of the VL1-(X1)n-VL2-C is SEQ ID NO: 440.

9. The binding molecule of claim 1, wherein said (X1)n of the VL1-(X1)n-VL2-C is SEQ ID NO: 441.

10. A method for generating a binding molecule that binds sclerostin and DKK-1 comprising the steps of: expressing said first, second, third and fourth polypeptide chains of claim 6 such that a binding molecule that binds sclerostin and DKK-1 is generated.

11. A pharmaceutical composition comprising the binding molecule of claim 6.

12. The binding molecule of claim 6 in combination with one or more of a pharmaceutically acceptable excipient, diluent or carrier.

13. A method of treating a bone disorder comprising administering to a patient in need thereof the binding molecule of claim 1.

14. A method of accelerating bone fracture repair comprising administering to a patient in need thereof the binding molecule of claim 1.

15. A method of increasing bone density comprising administering to a patient in need thereof the binding molecule of claim 1.

16. A method of increasing bone strength comprising administering to a patient in need thereof the binding molecule of claim 1.

* * * * *

SEQUENCE LISTING

```
<160> NUMBER OF SEQ ID NOS: 496

<210> SEQ ID NO 1
<211> LENGTH: 798
<212> TYPE: DNA
<213> ORGANISM: Homo sapiens

<400> SEQUENCE: 1
atgatggctc tgggcgcagc gggagctacc cgggtctttg tcgcgatggt agcggcggct      60
ctcggcggcc accctctgct gggagtgagc gccaccttga actcggttct caattccaac     120
gctatcaaga acctgccccc accgctgggc ggcgctgcgg ggcacccagg ctctgcagtc     180
agcgccgcgc cgggaatcct gtacccgggc gggaataagt accagaccat tgacaactac     240
cagccgtacc cgtgcgcaga ggacgaggag tcggcactga tgagtactg cgctagtccc     300 acccgcggag gggacgcagg cgtgcaaatc tgtctcgcct gcaggaagcg ccgaaaacgc     360
tgcatgcgtc acgctatgtg ctgccccggg aattactgca aaaatggaat atgtgtgtct     420
tctgatcaaa atcatttccg aggagaaatt gaggaaacca tcactgaaag ctttggtaat     480
gatcatagca ccttggatgg gtattccaga agaaccacct tgtcttcaaa aatgtatcac     540
accaaaggac aagaaggttc tgtttgtctc aggtcatcag actgtgcctc aggattgtgt     600
```
tgtgatagac acttctggtc caagatctgt aaacctgtcc tgaaagaagg tcaagtgtgt     660
accaagcata ggagaaaagg ctctcatgga ctagaaatat tccagcgttg ttactgtgga     720
gaaggtctgt cttgccggat acagaaagat caccatcaag ccagtaattc ttctaggctt    780
cacacttgtc agagacac                                                   798

<210> SEQ ID NO 2
<211> LENGTH: 266
<212> TYPE: PRT
<213> ORGANISM: Homo sapiens

<400> SEQUENCE: 2

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Asp Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 3
<211> LENGTH: 816
<212> TYPE: DNA
<213> ORGANISM: Mus musculus

<400> SEQUENCE: 3
atgatggttg tgtgtgcagc ggcagctgtc cggttcttgg ccgtgtttac aatgatggct     60
ctctgcagcc tccctctgct aggagccagt gccaccttga actcagttct catcaattcc    120

```
aacgcgatca agaacctgcc cccaccgctg ggtggtgctg gggggcagcc gggctctgct      180
gtcagtgtgg cgccgggagt tctctatgag ggcgggaaca agtaccagac tcttgacaac      240
taccagccct acccttgcgc tgaagatgag gagtgcggct ctgacgagta ctgctccagc      300
cccagccgcg gggcagccgg cgtcggaggt gtacagatct gtctggcttg ccgaaagcgc      360
aggaagcgct gcatgaggca cgctatgtgc tgccccggga actactgcaa aaatggaata      420
tgcatgccct ctgaccacag ccattttcct cgaggggaga ttgaggaaag catcattgaa      480
aaccttggta atgaccacaa cgccgccgcg ggggatggat atcccagaag aaccacactg      540
acttcaaaaa tatatcacac caaaggacaa gaaggctccg tctgcctccg atcatcagac      600
tgtgccgcag gctgtgttg tgcaagacac ttctggtcca agatctgtaa acctgtcctt      660
aaagaaggtc agtgtgcac caagcacaaa cggaaaggct cccacgggct ggagatattc      720
cagcgctgtt actgcgggga aggcctggct tgcaggatac agaaagatca ccatcaagcc      780
agcaattctt ctaggctcca cacctgccag agacac                                816
```

<210> SEQ ID NO 4
<211> LENGTH: 272
<212> TYPE: PRT
<213> ORGANISM: Mus musculus

<400> SEQUENCE: 4

```
Met Met Val Val Cys Ala Ala Ala Val Arg Phe Leu Ala Val Phe
1               5                   10                  15

Thr Met Met Ala Leu Cys Ser Leu Pro Leu Leu Gly Ala Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95

Tyr Cys Ser Ser Pro Ser Arg Gly Ala Ala Gly Val Gly Gly Val Gln
            100                 105                 110

Ile Cys Leu Ala Cys Arg Lys Arg Arg Lys Arg Cys Met Arg His Ala
        115                 120                 125

Met Cys Cys Pro Gly Asn Tyr Cys Lys Asn Gly Ile Cys Met Pro Ser
    130                 135                 140

Asp His Ser His Phe Pro Arg Gly Glu Ile Glu Glu Ser Ile Ile Glu
145                 150                 155                 160

Asn Leu Gly Asn Asp His Asn Ala Ala Ala Gly Asp Gly Tyr Pro Arg
                165                 170                 175

Arg Thr Thr Leu Thr Ser Lys Ile Tyr His Thr Lys Gly Gln Glu Gly
            180                 185                 190

Ser Val Cys Leu Arg Ser Ser Asp Cys Ala Ala Gly Leu Cys Cys Ala
        195                 200                 205

Arg His Phe Trp Ser Lys Ile Cys Lys Pro Val Leu Lys Glu Gly Gln
    210                 215                 220

Val Cys Thr Lys His Lys Arg Lys Gly Ser His Gly Leu Glu Ile Phe
225                 230                 235                 240

Gln Arg Cys Tyr Cys Gly Glu Gly Leu Ala Cys Arg Ile Gln Lys Asp
```

His His Gln Ala Ser Asn Ser Ser Arg Leu His Thr Cys Gln Arg His
            245                 250                 255
            260                 265                 270

<210> SEQ ID NO 5
<211> LENGTH: 810
<212> TYPE: DNA
<213> ORGANISM: Rattus rattus

<400> SEQUENCE: 5
atgacggttg tgcgtgcagt ggcagctgtc cggttcttgg tcgtgcttac aacgatggct      60
ctctgcagcc tccctccgct cggagtcagc gccactttga actcagttct catcaattcc    120
aacgcgatca agaacctgcc cccaccgctg gtggtgctg gggggcagcc gggctctgct     180
gtcagcgtgg cgcccggagt cctctatgag gcgggaaca agtaccagac tcttgacaac    240
taccagccct acccttgcgc ggaggatgag gagtgcggca ctgacgagta ctgctccagt    300
cccagccgcg gggcagccgg cgtgggaggt gtacaaatct gcctggcttg ccgaaagcgc    360
aggaaacgct gcatgaggca cgctatgtgc tgccccggga attactgcaa aaacggaata    420
tgcatgccct ctgaccacag ccatttacct cgaggggaaa tcgaggaagg catcattgaa    480
aaccttggca atgaccacgg tgccggggat ggatatccca agaaccac actgacttca    540 aaatatatc acaccaaagg caagaaggc tctgtctgcc tccgatcatc agactgcgcc    600
acagggctgt gttgtgcaag acatttctgg tccaagatct gtaaacctgt ccttaaagaa    660
ggtcaggtat gcaccaagca cagaaggaaa ggctcccacg ggctggagat attccagcgc    720
tgttactgtg gggaaggtct ggcttgcagg atacagaaag atcaccatca aaccagcaat    780
tcttccaggc tccacacctg ccagagacac                                      810

<210> SEQ ID NO 6
<211> LENGTH: 270
<212> TYPE: PRT
<213> ORGANISM: Rattus rattus

<400> SEQUENCE: 6

Met Thr Val Val Arg Ala Val Ala Ala Val Arg Phe Leu Val Val Leu
1               5                   10                  15

Thr Thr Met Ala Leu Cys Ser Leu Pro Pro Leu Gly Val Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Thr Asp Glu
                85                  90                  95

Tyr Cys Ser Ser Pro Ser Arg Gly Ala Ala Gly Val Gly Gly Val Gln
            100                 105                 110

Ile Cys Leu Ala Cys Arg Lys Arg Arg Lys Arg Cys Met Arg His Ala
        115                 120                 125

Met Cys Cys Pro Gly Asn Tyr Cys Lys Asn Gly Ile Cys Met Pro Ser
    130                 135                 140

Asp His Ser His Leu Pro Arg Gly Glu Ile Glu Glu Gly Ile Ile Glu
145                 150                 155                 160

| | | | | | | | | | | | | |
|---|---|---|---|---|---|---|---|---|---|---|---|---|
| Asn | Leu | Gly | Asn | Asp | His | Gly | Ala | Gly | Asp | Gly | Tyr | Pro | Arg | Arg | Thr |
| | | | | 165 | | | | 170 | | | | 175 | |

Thr Leu Thr Ser Lys Ile Tyr His Thr Lys Gly Gln Glu Gly Ser Val
    180                 185                 190

Cys Leu Arg Ser Ser Asp Cys Ala Thr Gly Leu Cys Cys Ala Arg His
        195                 200                 205

Phe Trp Ser Lys Ile Cys Lys Pro Val Leu Lys Glu Gly Gln Val Cys
    210                 215                 220

Thr Lys His Arg Arg Lys Gly Ser His Gly Leu Glu Ile Phe Gln Arg
225                 230                 235                 240

Cys Tyr Cys Gly Glu Gly Leu Ala Cys Arg Ile Gln Lys Asp His His
                245                 250                 255

Gln Thr Ser Asn Ser Ser Arg Leu His Thr Cys Gln Arg His
            260                 265                 270

<210> SEQ ID NO 7
<211> LENGTH: 798
<212> TYPE: DNA
<213> ORGANISM: ARTIFICIAL SEQUENCE
<220> FEATURE:
<223> OTHER INFORMATION: Cyno DKK-1
<220> FEATURE:
<221> NAME/KEY: CDS
<222> LOCATION: (1)..(798)

<400> SEQUENCE: 7

```
atg atg gct ctg ggc gca gca gga gct gcc cgg gtc ttg gtc gcg ctg    48
Met Met Ala Leu Gly Ala Ala Gly Ala Ala Arg Val Leu Val Ala Leu
1               5                  10                  15 gta gcg gcg gct ctt ggc ggc cac cct ctg ctg gga gtg agc gcc acc    96
Val Ala Ala Ala Leu Gly Gly His Pro Leu Leu Gly Val Ser Ala Thr
                20                  25                  30 ttg aac tcg gtt ctc aat tcc aac gcg atc aag aac ctg ccc cca ccg   144
Leu Asn Ser Val Leu Asn Ser Asn Ala Ile Lys Asn Leu Pro Pro Pro
            35                  40                  45 ctg ggc ggc gct gcg ggg cac cca ggc tct gca gtc agc gcc gcg cca   192
Leu Gly Gly Ala Ala Gly His Pro Gly Ser Ala Val Ser Ala Ala Pro
        50                  55                  60 gga att ctg tac ccg ggc ggg aat aag tac cag acc att gac aac tac   240
Gly Ile Leu Tyr Pro Gly Gly Asn Lys Tyr Gln Thr Ile Asp Asn Tyr
65                  70                  75                  80 cag ccg tac cct tgc gca gag gat gag gag tgc ggc act gat gag tac   288
Gln Pro Tyr Pro Cys Ala Glu Asp Glu Glu Cys Gly Thr Asp Glu Tyr
                85                  90                  95 tgc gct agt ccc acc cgc gga ggg gac gcg ggc gtg caa atc tgt ctc   336
Cys Ala Ser Pro Thr Arg Gly Gly Asp Ala Gly Val Gln Ile Cys Leu
                100                 105                 110 gcc tgc agg aag cgc cga aaa cgc tgc atg cgt cac gct atg tgc tgc   384
Ala Cys Arg Lys Arg Arg Lys Arg Cys Met Arg His Ala Met Cys Cys
            115                 120                 125 ccc ggg aat tac tgc aaa aat gga ata tgt gtg tct tct gat caa aat   432
Pro Gly Asn Tyr Cys Lys Asn Gly Ile Cys Val Ser Ser Asp Gln Asn
        130                 135                 140 aat ttc cga ggg gaa att gag gaa acc att act gaa agc ttt ggt aat   480
Asn Phe Arg Gly Glu Ile Glu Glu Thr Ile Thr Glu Ser Phe Gly Asn
145                 150                 155                 160 gat cat agc act ttg gat ggg tat tcc aga aga aca aca ttg tct tca   528
Asp His Ser Thr Leu Asp Gly Tyr Ser Arg Arg Thr Thr Leu Ser Ser
                165                 170                 175 aaa atg tat cac agc aaa gga caa gaa ggt tct gtg tgt ctc cgg tca   576
Lys Met Tyr His Ser Lys Gly Gln Glu Gly Ser Val Cys Leu Arg Ser
```

```
Lys Met Tyr His Ser Lys Gly Gln Glu Gly Ser Val Cys Leu Arg Ser
            180                 185                 190 tca gac tgt gcc aca gga ctg tgt tgt gct aga cac ttc tgg tcc aag    624
Ser Asp Cys Ala Thr Gly Leu Cys Cys Ala Arg His Phe Trp Ser Lys
        195                 200                 205 atc tgt aaa cct gtc ctc aaa gaa ggt caa gtg tgt acc aag cat aga    672
Ile Cys Lys Pro Val Leu Lys Glu Gly Gln Val Cys Thr Lys His Arg
210                 215                 220 aga aaa ggc tct cat ggg cta gaa ata ttc cag cgt tgt tac tgc gga    720
Arg Lys Gly Ser His Gly Leu Glu Ile Phe Gln Arg Cys Tyr Cys Gly
225                 230                 235                 240 gaa ggt ctg tct tgc cgg ata cag aaa gat cac cat caa gcc agt aat    768
Glu Gly Leu Ser Cys Arg Ile Gln Lys Asp His His Gln Ala Ser Asn
            245                 250                 255 tct tct agg ctt cac act tgt cag aga cac                             798
Ser Ser Arg Leu His Thr Cys Gln Arg His
            260                 265

<210> SEQ ID NO 8
<211> LENGTH: 266
<212> TYPE: PRT
<213> ORGANISM: ARTIFICIAL SEQUENCE
<220> FEATURE:
<223> OTHER INFORMATION: Synthetic Construct

<400> SEQUENCE: 8

Met Met Ala Leu Gly Ala Ala Gly Ala Ala Arg Val Leu Val Ala Leu
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

Asn Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Ser Lys Gly Gln Glu Gly Ser Val Cys Leu Arg Ser
            180                 185                 190

Ser Asp Cys Ala Thr Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
```

Ser Ser Arg Leu His Thr Cys Gln Arg His
        245                 250                 255
                260                 265

<210> SEQ ID NO 9
<211> LENGTH: 642
<212> TYPE: DNA
<213> ORGANISM: Homo sapiens
<220> FEATURE:
<221> NAME/KEY: CDS
<222> LOCATION: (1)..(642)
<220> FEATURE:
<221> NAME/KEY: sig_peptide
<222> LOCATION: (1)..(23)

<400> SEQUENCE: 9

| | | |
|---|---|---|
| atg cag ctc cca ctg gcc ctg tgt ctc gtc tgc ctg ctg gta cac aca<br>Met Gln Leu Pro Leu Ala Leu Cys Leu Val Cys Leu Leu Val His Thr<br>1               5                   10                  15 | 48 |
| gcc ttc cgt gta gtg gag ggc cag ggg tgg cag gcg ttc aag aat gat<br>Ala Phe Arg Val Val Glu Gly Gln Gly Trp Gln Ala Phe Lys Asn Asp<br>            20                  25                  30 | 96 |
| gcc acg gaa atc atc ccc gag ctc gga gag tac ccc gag cct cca ccg<br>Ala Thr Glu Ile Ile Pro Glu Leu Gly Glu Tyr Pro Glu Pro Pro Pro<br>        35                  40                  45 | 144 |
| gag ctg gag aac aac aag acc atg aac cgg gcg gag aac gga ggg cgg<br>Glu Leu Glu Asn Asn Lys Thr Met Asn Arg Ala Glu Asn Gly Gly Arg<br>    50                  55                  60 | 192 |
| cct ccc cac cac ccc ttt gag acc aaa gac gtg tcc gag tac agc tgc<br>Pro Pro His His Pro Phe Glu Thr Lys Asp Val Ser Glu Tyr Ser Cys<br>65                  70                  75                  80 | 240 |
| cgc gag ctg cac ttc acc cgc tac gtg acc gat ggg ccg tgc cgc agc<br>Arg Glu Leu His Phe Thr Arg Tyr Val Thr Asp Gly Pro Cys Arg Ser<br>                85                  90                  95 | 288 |
| gcc aag ccg gtc acc gag ctg gtg tgc tcc ggc cag tgc ggc ccg gcg<br>Ala Lys Pro Val Thr Glu Leu Val Cys Ser Gly Gln Cys Gly Pro Ala<br>            100                 105                 110 | 336 |
| cgc ctg ctg ccc aac gcc atc ggc cgc ggc aag tgg tgg cga cct agt<br>Arg Leu Leu Pro Asn Ala Ile Gly Arg Gly Lys Trp Trp Arg Pro Ser<br>        115                 120                 125 | 384 |
| ggg ccc gac ttc cgc tgc atc ccc gac cgc tac cgc gcg cag cgc gtg<br>Gly Pro Asp Phe Arg Cys Ile Pro Asp Arg Tyr Arg Ala Gln Arg Val<br>    130                 135                 140 | 432 |
| cag ctg ctg tgt ccc ggt ggt gag gcg ccg cgc gcg cgc aag gtg cgc<br>Gln Leu Leu Cys Pro Gly Gly Glu Ala Pro Arg Ala Arg Lys Val Arg<br>145                 150                 155                 160 | 480 |
| ctg gtg gcc tcg tgc aag tgc aag cgc ctc acc cgc ttc cac aac cag<br>Leu Val Ala Ser Cys Lys Cys Lys Arg Leu Thr Arg Phe His Asn Gln<br>                165                 170                 175 | 528 |
| tcg gag ctc aag gac ttc ggg acc gag gcc gct cgg ccg cag aag ggc<br>Ser Glu Leu Lys Asp Phe Gly Thr Glu Ala Ala Arg Pro Gln Lys Gly<br>            180                 185                 190 | 576 |
| cgg aag ccg cgg ccc cgc gcc cgg agc gcc aaa gcc aac cag gcc gag<br>Arg Lys Pro Arg Pro Arg Ala Arg Ser Ala Lys Ala Asn Gln Ala Glu<br>        195                 200                 205 | 624 |
| ctg gag aac gcc tac tag<br>Leu Glu Asn Ala Tyr<br>    210 | 642 |

<210> SEQ ID NO 10
<211> LENGTH: 213
<212> TYPE: PRT

<213> ORGANISM: Homo sapiens

<400> SEQUENCE: 10

```
Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

<210> SEQ ID NO 11
<211> LENGTH: 636
<212> TYPE: DNA
<213> ORGANISM: Mus musculus
<220> FEATURE:
<221> NAME/KEY: CDS
<222> LOCATION: (1)..(636)
<220> FEATURE:
<221> NAME/KEY: sig_peptide
<222> LOCATION: (1)..(23)

<400> SEQUENCE: 11

```
atg cag ccc tca cta gcc ccg tgc ctc atc tgc cta ctt gtg cac gct    48
Met Gln Pro Ser Leu Ala Pro Cys Leu Ile Cys Leu Leu Val His Ala
1               5                   10                  15 gcc ttc tgt gct gtg gag ggc cag ggg tgg caa gcc ttc agg aat gat    96
Ala Phe Cys Ala Val Glu Gly Gln Gly Trp Gln Ala Phe Arg Asn Asp
            20                  25                  30 gcc aca gag gtc atc cca ggg ctt gga gag tac ccc gag cct cct cct   144
Ala Thr Glu Val Ile Pro Gly Leu Gly Glu Tyr Pro Glu Pro Pro Pro
        35                  40                  45 gag aac aac cag acc atg aac cgg gcg gag aat gga ggc aga cct ccc   192
Glu Asn Asn Gln Thr Met Asn Arg Ala Glu Asn Gly Gly Arg Pro Pro
    50                  55                  60 cac cat ccc tat gac gcc aaa gat gtg tcc gag tac agc tgc cgc gag   240
His His Pro Tyr Asp Ala Lys Asp Val Ser Glu Tyr Ser Cys Arg Glu
65                  70                  75                  80
```

```
ctg cac tac acc cgc ttc ctg aca gac ggc cca tgc cgc agc gcc aag          288
Leu His Tyr Thr Arg Phe Leu Thr Asp Gly Pro Cys Arg Ser Ala Lys
            85                  90                  95 ccg gtc acc gag ttg gtg tgc tcc ggc cag tgc ggc ccc gcg cgg ctg          336
Pro Val Thr Glu Leu Val Cys Ser Gly Gln Cys Gly Pro Ala Arg Leu
        100                 105                 110 ctg ccc aac gcc atc ggg cgc gtg aag tgg tgg cgc ccg aac gga ccg          384
Leu Pro Asn Ala Ile Gly Arg Val Lys Trp Trp Arg Pro Asn Gly Pro
        115                 120                 125 gat ttc cgc tgc atc ccg gat cgc tac cgc gcg cag cgg gtg cag ctg          432
Asp Phe Arg Cys Ile Pro Asp Arg Tyr Arg Ala Gln Arg Val Gln Leu
        130                 135                 140 ctg tgc ccc ggg ggc gcg gcg ccg cgc tcg cgc aag gtg cgt ctg gtg          480
Leu Cys Pro Gly Gly Ala Ala Pro Arg Ser Arg Lys Val Arg Leu Val
145                 150                 155                 160 gcc tcg tgc aag tgc aag cgc ctc acc cgc ttc cac aac cag tcg gag          528
Ala Ser Cys Lys Cys Lys Arg Leu Thr Arg Phe His Asn Gln Ser Glu
                165                 170                 175 ctc aag gac ttc ggg ccg gag acc gcg cgg ccg cag aag ggt cgc aag          576
Leu Lys Asp Phe Gly Pro Glu Thr Ala Arg Pro Gln Lys Gly Arg Lys
            180                 185                 190 ccg cgg ccc ggc gcc cgg gga gcc aaa gcc aac cag gcg gag ctg gag          624
Pro Arg Pro Gly Ala Arg Gly Ala Lys Ala Asn Gln Ala Glu Leu Glu
        195                 200                 205 aac gcc tac tag                                                          636
Asn Ala Tyr
        210

<210> SEQ ID NO 12
<211> LENGTH: 211
<212> TYPE: PRT
<213> ORGANISM: Mus musculus

<400> SEQUENCE: 12

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
```

```
                        180                 185                 190
Pro Arg Pro Gly Ala Arg Gly Ala Lys Ala Asn Gln Ala Glu Leu Glu
            195                 200                 205

Asn Ala Tyr
    210

<210> SEQ ID NO 13
<211> LENGTH: 642
<212> TYPE: DNA
<213> ORGANISM: Rattus rattus
<220> FEATURE:
<221> NAME/KEY: CDS
<222> LOCATION: (1)..(642)
<220> FEATURE:
<221> NAME/KEY: sig_peptide
<222> LOCATION: (1)..(23)

<400> SEQUENCE: 13 atg cag ctc tca cta gcc cct tgc ctt gcc tgc ctg ctt gta cat gca      48
Met Gln Leu Ser Leu Ala Pro Cys Leu Ala Cys Leu Leu Val His Ala
1               5                   10                  15 gcc ttc gtt gct gtg gag agc cag ggg tgg caa gcc ttc aag aat gat      96
Ala Phe Val Ala Val Glu Ser Gln Gly Trp Gln Ala Phe Lys Asn Asp
                20                  25                  30 gcc aca gaa atc atc ccg gga ctc aga gag tac cca gag cct cct cag     144
Ala Thr Glu Ile Ile Pro Gly Leu Arg Glu Tyr Pro Glu Pro Pro Gln
            35                  40                  45 gaa cta gag aac aac cag acc atg aac cgg gcc gag aac gga ggc aga     192
Glu Leu Glu Asn Asn Gln Thr Met Asn Arg Ala Glu Asn Gly Gly Arg
        50                  55                  60 ccc ccc cac cat cct tat gac acc aaa gac gtg tcc gag tac agc tgc     240
Pro Pro His His Pro Tyr Asp Thr Lys Asp Val Ser Glu Tyr Ser Cys
65                  70                  75                  80 cgc gag ctg cac tac acc cgc ttc gtg acc gac ggc ccg tgc cgc agt     288
Arg Glu Leu His Tyr Thr Arg Phe Val Thr Asp Gly Pro Cys Arg Ser
                85                  90                  95 gcc aag ccg gtc acc gag ttg gtg tgc tcg ggc cag tgc ggc ccc gcg     336
Ala Lys Pro Val Thr Glu Leu Val Cys Ser Gly Gln Cys Gly Pro Ala
            100                 105                 110 cgg ctg ctg ccc aac gcc atc ggg cgc gtg aag tgg tgg cgc ccg aac     384
Arg Leu Leu Pro Asn Ala Ile Gly Arg Val Lys Trp Trp Arg Pro Asn
        115                 120                 125 gga ccc gac ttc cgc tgc atc ccg gat cgc tac cgc gcg cag cgg gtg     432
Gly Pro Asp Phe Arg Cys Ile Pro Asp Arg Tyr Arg Ala Gln Arg Val
130                 135                 140 cag ctg ctg tgc ccc ggc ggc gcg gcg ccg cgc tcg cgc aag gtg cgt     480
Gln Leu Leu Cys Pro Gly Gly Ala Ala Pro Arg Ser Arg Lys Val Arg
145                 150                 155                 160 ctg gtg gcc tcg tgc aag tgc aag cgc ctc acc cgc ttc cac aac cag     528
Leu Val Ala Ser Cys Lys Cys Lys Arg Leu Thr Arg Phe His Asn Gln
                165                 170                 175 tcg gag ctc aag gac ttc gga cct gag acc gcg cgg ccg cag aag ggt     576
Ser Glu Leu Lys Asp Phe Gly Pro Glu Thr Ala Arg Pro Gln Lys Gly
            180                 185                 190 cgc aag ccg cgg ccc cgc gcc cgg gga gcc aaa gcc aac cag gcg gag     624
Arg Lys Pro Arg Pro Arg Ala Arg Gly Ala Lys Ala Asn Gln Ala Glu
        195                 200                 205 ctg gag aac gcc tac tag                                             642
Leu Glu Asn Ala Tyr
    210
```

```
<210> SEQ ID NO 14
<211> LENGTH: 213
<212> TYPE: PRT
<213> ORGANISM: Rattus rattus

<400> SEQUENCE: 14

Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210

<210> SEQ ID NO 15
<211> LENGTH: 642
<212> TYPE: DNA
<213> ORGANISM: Macaca Cynomolgous
<220> FEATURE:
<221> NAME/KEY: CDS
<222> LOCATION: (1)..(642)
<220> FEATURE:
<221> NAME/KEY: sig_peptide
<222> LOCATION: (1)..(23)

<400> SEQUENCE: 15 atg cag ctc cca cta gcc ctg tgt ctt gtc tgc ctg ctg gta cac gca     48
Met Gln Leu Pro Leu Ala Leu Cys Leu Val Cys Leu Leu Val His Ala
1               5                   10                  15 gcc ttc cgt gta gtg gag ggc cag ggg tgg cag gcc ttc aag aat gat     96
Ala Phe Arg Val Val Glu Gly Gln Gly Trp Gln Ala Phe Lys Asn Asp
            20                  25                  30 gcc acg gaa atc atc ccc gag ctc gga gag tac ccc gag cct cca ccg    144
Ala Thr Glu Ile Ile Pro Glu Leu Gly Glu Tyr Pro Glu Pro Pro Pro
        35                  40                  45 gag ctg gag aac aac aag acc atg aac cgg gcg gag aac gga ggg cgg    192
Glu Leu Glu Asn Asn Lys Thr Met Asn Arg Ala Glu Asn Gly Gly Arg
    50                  55                  60
```

```
cct ccc cac cac ccc ttt gag acc aaa gac gtg tcc gag tac agc tgc     240
Pro Pro His His Pro Phe Glu Thr Lys Asp Val Ser Glu Tyr Ser Cys
 65                  70                  75                  80 cga gag ctg cac ttc acc cgc tac gtg acc gac ggg cag tgc cgc agc     288
Arg Glu Leu His Phe Thr Arg Tyr Val Thr Asp Gly Gln Cys Arg Ser
                 85                  90                  95 gcc aag cca gtc acc gag ttg gtg tgc tcc ggc cag tgc ggc ccg gca     336
Ala Lys Pro Val Thr Glu Leu Val Cys Ser Gly Gln Cys Gly Pro Ala
            100                 105                 110 cgc ctg ctg ccc aac gcc atc ggc cgc ggc aag tgg tgg cgc ccg agt     384
Arg Leu Leu Pro Asn Ala Ile Gly Arg Gly Lys Trp Trp Arg Pro Ser
        115                 120                 125 ggg ccc gac ttt cgc tgc atc ccc gac cgc tac cgc gcg cag cgt gtg     432
Gly Pro Asp Phe Arg Cys Ile Pro Asp Arg Tyr Arg Ala Gln Arg Val
    130                 135                 140 cag ctg ctg tgt ccc ggt ggt gcc gcg ccg cgc gcg cgc aag gtg cgc     480
Gln Leu Leu Cys Pro Gly Gly Ala Ala Pro Arg Ala Arg Lys Val Arg
145                 150                 155                 160 ctg gtg gcc tcg tgc aag tgc aag cgc ctc acc cgc ttc cac aac cag     528
Leu Val Ala Ser Cys Lys Cys Lys Arg Leu Thr Arg Phe His Asn Gln
                165                 170                 175 tcg gag ctc aag gac ttc ggt ccc gag gcc gct cgg ccg cag aag ggc     576
Ser Glu Leu Lys Asp Phe Gly Pro Glu Ala Ala Arg Pro Gln Lys Gly
            180                 185                 190 cgg aag ccg cgg ccc cgc gcc cgg ggg gcc aaa gcc aat cag gct gag     624
Arg Lys Pro Arg Pro Arg Ala Arg Gly Ala Lys Ala Asn Gln Ala Glu
        195                 200                 205 ctg gag aac gcc tac tag                                             642
Leu Glu Asn Ala Tyr
    210

<210> SEQ ID NO 16
<211> LENGTH: 213
<212> TYPE: PRT
<213> ORGANISM: Macaca Cynomolgous
<220> FEATURE:
<223> OTHER INFORMATION: Cyno Sclerostin

<400> SEQUENCE: 16

Met Gln Leu Pro Leu Ala Leu Cys Leu Val Cys Leu Leu Val His Ala
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Gln Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ala Arg Lys Val Arg
145                 150                 155                 160
```

```
                Leu Val Ala Ser Cys Lys Cys Lys Arg Leu Thr Arg Phe His Asn Gln
                            165                 170                 175

Ser Glu Leu Lys Asp Phe Gly Pro Glu Ala Ala Arg Pro Gln Lys Gly
                            180                 185                 190

Arg Lys Pro Arg Pro Arg Ala Arg Gly Ala Lys Ala Asn Gln Ala Glu
                            195                 200                 205

Leu Glu Asn Ala Tyr
                            210

<210> SEQ ID NO 17
<211> LENGTH: 1794
<212> TYPE: DNA
<213> ORGANISM: ARTIFICIAL SEQUENCE
<220> FEATURE:
<223> OTHER INFORMATION: 19D11-6.37 G2

<400> SEQUENCE: 17
```

| | | | | | |
|---|---|---|---|---|---|
| atggacatga | gggtgcccgc | tcagctcctg | gggctcctgc | tgctgtggct | gagaggtgcg | 60 |
| cgctgtgagg | tgcagctggt | ggagtctggg | ggaggcttgg | tacagcctgg | ggggtccctg | 120 |
| agactctcct | gtgcagcctc | tggattcacc | ttcagtagct | acgacatgca | ctgggtccgc | 180 |
| caagctacag | gaaaaggtct | ggagtgggtc | tcagctattg | gtactgctgg | tgacacatac | 240 |
| tatgcaggct | ccgtgaaggg | ccgattcacc | atctccagag | aaaatgccaa | gaactccttg | 300 |
| tatcttcaaa | tgaacagcct | gagagtcggg | gacacggctg | tgtattactg | tgcaaggtcc | 360 |
| tggggagagg | ggaattacta | cttctactac | ggtatggacg | tctggggcca | agggaccacg | 420 |
| gtcaccgtct | ctagtgcctc | caccaagggc | ccatcggtct | tccccctggc | gccccaggtg | 480 |
| cagctggtgg | agtctggggg | aggcgtggtc | cagcctggga | ggtccctgag | actctcctgt | 540 |
| gcagcctctg | gattcacctt | cagtggctat | ggcatgcact | gggtccgcca | ggctccaggc | 600 |
| aaggggctgg | agtgggtggc | agttatatca | tatgatggaa | atgataaata | ctatgcagac | 660 |
| tccgtgaagg | gccgattcac | catctccaga | gacaatgcca | agaacacgct | gtatctgcaa | 720 |
| atgaacagcc | tgagagctga | ggacacggct | gtgtattact | gtgcgagaga | gctacgggtc | 780 |
| ctctggggcc | agggaaccct | ggtcaccgtc | tctagtgcct | ccaccaaggg | cccatcggtc | 840 |
| ttccccctgg | cgccctgctc | caggagcacc | tccgagagca | cagcggccct | gggctgcctg | 900 |
| gtcaaggact | acttccccga | accggtgacg | gtgtcgtgga | actcaggcgc | tctgaccagc | 960 |
| ggcgtgcaca | ccttcccagc | tgtcctacag | tcctcaggac | tctactccct | cagcagcgtg | 1020 |
| gtgaccgtgc | cctccagcaa | cttcggcacc | cagacctaca | cctgcaacgt | agatcacaag | 1080 |
| cccagcaaca | ccaaggtgga | caagacagtt | gagcgcaaat | gttgtgtcga | gtgcccaccg | 1140 |
| tgcccagcac | cacctgtggc | aggaccgtca | gtcttcctct | tccccccaaa | acccaaggac | 1200 |
| accctcatga | tctcccggac | ccctgaggtc | acgtgcgtgg | tggtggacgt | gagccacgaa | 1260 |
| gaccccgagg | tccagttcaa | ctggtacgtg | gacggcgtgg | aggtgcataa | tgccaagaca | 1320 |
| aagccacggg | aggagcagtt | caacagcacg | ttccgtgtgg | tcagcgtcct | caccgttgtg | 1380 |
| caccaggact | ggctgaacgg | caaggagtac | aagtgcaagg | tctccaacaa | aggcctccca | 1440 |
| gcccccatcg | agaaaaccat | ctccaaaacc | aaagggcagc | ccgagaacc | acaggtgtac | 1500 |
| accctgcccc | catcccggga | ggagatgacc | aagaaccagg | tcagcctgac | ctgcctggtc | 1560 |
| aaaggcttct | accccagcga | catcgccgtg | gagtgggaga | gcaatgggca | gccggagaac | 1620 |
| aactacaaga | ccacacctcc | catgctggac | tccgacggct | ccttcttcct | ctacagcaag | 1680 |

```
ctcaccgtgg acaagagcag gtggcagcag gggaacgtct tctcatgctc cgtgatgcat    1740
gaggctctgc acaaccacta cacgcagaag agcctctccc tgtctccggg taaa          1794
```

<210> SEQ ID NO 18
<211> LENGTH: 576
<212> TYPE: PRT
<213> ORGANISM: ARTIFICIAL SEQUENCE
<220> FEATURE:
<223> OTHER INFORMATION: 19D11-6.37 G2

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Ala Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Ser Trp Gly Glu Gly Asn Tyr Tyr Phe Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Gln Val Gln Leu Val Glu Ser Gly
    130                 135                 140

Gly Gly Val Val Gln Pro Gly Arg Ser Leu Arg Leu Ser Cys Ala Ala
145                 150                 155                 160

Ser Gly Phe Thr Phe Ser Gly Tyr Gly Met His Trp Val Arg Gln Ala
                165                 170                 175

Pro Gly Lys Gly Leu Glu Trp Val Ala Val Ile Ser Tyr Asp Gly Asn
            180                 185                 190

Asp Lys Tyr Tyr Ala Asp Ser Val Lys Gly Arg Phe Thr Ile Ser Arg
        195                 200                 205

Asp Asn Ala Lys Asn Thr Leu Tyr Leu Gln Met Asn Ser Leu Arg Ala
    210                 215                 220

Glu Asp Thr Ala Val Tyr Tyr Cys Ala Arg Glu Leu Arg Val Leu Trp
225                 230                 235                 240

Gly Gln Gly Thr Leu Val Thr Val Ser Ser Ala Ser Thr Lys Gly Pro
                245                 250                 255

Ser Val Phe Pro Leu Ala Pro Cys Ser Arg Ser Thr Ser Glu Ser Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Asn Phe Gly Thr Gln Thr Tyr Thr Cys Asn Val Asp
                325                 330                 335

His Lys Pro Ser Asn Thr Lys Val Asp Lys Thr Val Glu Arg Lys Cys
            340                 345                 350
```

Cys Val Glu Cys Pro Pro Cys Pro Ala Pro Pro Val Ala Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Gln Phe Asn Trp Tyr Val Asp Gly Val Glu Val His Asn Ala
                405                 410                 415

Lys Thr Lys Pro Arg Glu Glu Gln Phe Asn Ser Thr Phe Arg Val Val
                420                 425                 430

Ser Val Leu Thr Val Val His Gln Asp Trp Leu Asn Gly Lys Glu Tyr
            435                 440                 445

Lys Cys Lys Val Ser Asn Lys Gly Leu Pro Ala Pro Ile Glu Lys Thr
        450                 455                 460

Ile Ser Lys Thr Lys Gly Gln Pro Arg Glu Pro Gln Val Tyr Thr Leu
465                 470                 475                 480

Pro Pro Ser Arg Glu Glu Met Thr Lys Asn Gln Val Ser Leu Thr Cys
                485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Lys Thr Thr Pro Pro Met Leu Asp
        515                 520                 525

Ser Asp Gly Ser Phe Phe Leu Tyr Ser Lys Leu Thr Val Asp Lys Ser
    530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
                565                 570                 575

<210> SEQ ID NO 19
<211> LENGTH: 1086
<212> TYPE: DNA
<213> ORGANISM: ARTIFICIAL SEQUENCE
<220> FEATURE:
<223> OTHER INFORMATION: 19D11-6.37 LC

<400> SEQUENCE: 19
atggacatga gggtgcccgc tcagctcctg gggctcctgc tgctgtggct gagaggtgcg    60
cgctgttcct atgtgctgac tcagccaccc tcggtgtcag tggccccagg acagacggcc   120
aggattacct gtgggggaga caacattgga agtataagtg tgcattggta ccagcagaag   180
ccaggccagg cccctgtgct ggtcgtctat gatgatagcg accggccctc agggatccct   240
gagcgattct ctggctccaa ctctgggaac acgccacccc tgaccatcag ctgggtcgaa   300
gccggggatg aggccgacta ttactgtcag gtgtgggata gtagtattga tcatcctgtg   360
ttattcggcg gagggaccaa gctgaccgtc ctaggtcagc ccaaggctgc ccctcggtc    420 actctgttcg atattgtgat gacccagact ccactctctc tgtccgtcac ccctggacag   480
ccggcctcca tctcctgcaa gtctggtcag agcctcctgc atagtgatgg aaagacctat   540
ttgtattggt acctgcagaa gccaggccag cctccacagt tcctgatcta tgaagtttcc   600
aaccggttct ctagagtgcc agataggttc agtggcagcg gtcagggaca gatttcaca    660 ctgagaatca gccgggtgga ggctgaggat gttggaattt attactgcat gcaaagtata   720
cagcttccgt ggacgttcgg ccaagggacc caggtggaaa tcaaacgaac tgtggctgca   780

```
ccatctgtct tcatcttccc gccatctgat gagcagttga aatctggaac tgcctctgtt    840
gtgtgcctgc tgaataactt ctatcccaga gaggccaaag tacagtggaa ggtggataac    900
gccctccaat cgggtaactc ccaggagagt gtcacagagc aggacagcaa ggacagcacc    960
tacagcctca gcagcaccct gacgctgagc aaagcagact acgagaaaca caaagtctac   1020
gcctgcgaag tcacccatca gggcctgagc tcgcccgtca caaagagctt caacagggga   1080
gagtgt                                                              1086

<210> SEQ ID NO 20
<211> LENGTH: 340
<212> TYPE: PRT
<213> ORGANISM: ARTIFICIAL SEQUENCE
<220> FEATURE:
<223> OTHER INFORMATION: 19D11-6.37 LC

<400> SEQUENCE: 20
```

Ser Tyr Val Leu Thr Gln Pro Pro Ser Val Ala Pro Gly Gln
1               5                   10                  15

Thr Ala Arg Ile Thr Cys Gly Gly Asp Asn Ile Gly Ser Ile Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Trp Val Glu Ala Gly
65                  70                  75                  80

Asp Glu Ala Asp Tyr Tyr Cys Gln Val Trp Asp Ser Ser Ile Asp His
                85                  90                  95

Pro Val Leu Phe Gly Gly Gly Thr Lys Leu Thr Val Leu Gly Gln Pro
            100                 105                 110

Lys Ala Ala Pro Ser Val Thr Leu Phe Asp Ile Val Met Thr Gln Thr
        115                 120                 125

Pro Leu Ser Leu Ser Val Thr Pro Gly Gln Pro Ala Ser Ile Ser Cys
    130                 135                 140

Lys Ser Gly Gln Ser Leu Leu His Ser Asp Gly Lys Thr Tyr Leu Tyr
145                 150                 155                 160

Trp Tyr Leu Gln Lys Pro Gly Gln Pro Pro Gln Phe Leu Ile Tyr Glu
                165                 170                 175

Val Ser Asn Arg Phe Ser Arg Val Pro Asp Arg Phe Ser Gly Ser Gly
            180                 185                 190

Ser Gly Thr Asp Phe Thr Leu Arg Ile Ser Arg Val Glu Ala Glu Asp
        195                 200                 205

Val Gly Ile Tyr Tyr Cys Met Gln Ser Ile Gln Leu Pro Trp Thr Phe
    210                 215                 220

Gly Gln Gly Thr Gln Val Glu Ile Lys Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

```
Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
            325                 330                 335

Arg Gly Glu Cys
            340

<210> SEQ ID NO 21
<211> LENGTH: 1794
<212> TYPE: DNA
<213> ORGANISM: ARTIFICIAL SEQUENCE
<220> FEATURE:
<223> OTHER INFORMATION: 6.37.5-19D11 G2

<400> SEQUENCE: 21
atggacatga gggtgcccgc tcagctcctg gggctcctgc tgctgtggct gagaggtgcg      60
cgctgtcagg tgcagctggt ggagtctggg ggaggcgtgg tccagcctgg aggtccctg     120 agactctcct gtgcagcctc tggattcacc ttcagtggct atggcatgca ctgggtccgc    180
caggctccag gcaaggggct ggagtgggtg gcagttatat catatgatgg aaatgataaa    240
tactatgcag actccgtgaa gggccgattc accatctcca gagacaatgc caagaacacg    300
ctgtatctgc aaatgaacag cctgagagct gaggacacgg ctgtgtatta ctgtgcgaga    360
gagctacggg tcctctgggg ccagggaacc ctggtcaccg tctctagtgc ctccaccaag    420
ggcccatcgg tcttccccct ggcgcccgag gtgcagctgg tggagtctgg gggaggcttg    480
gtacagcctg gggggtccct gagactctcc tgtgcagcct ctggattcac cttcagtagc    540
tacgacatgc actgggtccg ccaagctaca ggaaaaggtc tggagtgggt ctcagctatt    600
ggtactgctg gtgacacata ctatgcaggc tccgtgaagg gccgattcac catctcccaga   660 gaaaatgcca agaactcctt gtatcttcaa atgaacagc tgagagtcgg ggacacggct    720
gtgtattact gtgcaaggtc ctggggagag ggaattact acttctacta cggtatggac    780
gtctggggcc aagggaccac ggtcaccgtc tctagtgcct ccaccaaggg cccatcggtc    840
ttccccctgg cgccctgctc caggagcacc tccgagagca gcggccct gggctgcctg      900 gtcaaggact acttccccga accggtgacg gtgtcgtgga actcaggcgc tctgaccagc    960
ggcgtgcaca ccttcccagc tgtcctacag tcctcaggac tctactccct cagcagcgtg   1020
gtgaccgtgc cctccagcaa cttcggcacc cagacctaca cctgcaacgt agatcacaag   1080
cccagcaaca ccaaggtgga caagacagtt gagcgcaaat gttgtgtcga gtgcccaccg   1140
tgcccagcac cacctgtggc aggaccgtca gtcttcctct tccccccaaa acccaaggac   1200
accctcatga tctcccggac ccctgaggtc acgtgcgtgg tggtggacgt gagccacgaa   1260
gaccccgagg tccagttcaa ctggtacgtg acggcgtgg aggtgcataa tgccaagaca     1320
aagccacggg aggagcagtt caacagcacg ttccgtgtgg tcagcgtcct caccgttgtg   1380
caccaggact ggctgaacgg caaggagtac aagtgcaagg tctccaacaa aggcctccca   1440 gccccatcg agaaaaccat ctccaaaacc aaagggcagc ccgagaacc acaggtgtac    1500 accctgcccc catcccggga ggagatgacc aagaaccagg tcagcctgac ctgcctggtc   1560
aaaggcttct accccagcga catcgccgtg gagtgggaga gcaatgggca gccggagaac   1620
aactacaaga ccacacctcc catgctggac tccgacggct ccttcttcct ctacagcaag   1680
ctcaccgtgg acaagagcag gtggcagcag gggaacgtct tctcatgctc cgtgatgcat   1740
gaggctctgc acaaccacta cacgcagaag agcctctccc tgtctccggg taaa         1794
```

<210> SEQ ID NO 22
<211> LENGTH: 576
<212> TYPE: PRT
<213> ORGANISM: ARTIFICIAL SEQUENCE
<220> FEATURE:
<223> OTHER INFORMATION: 6.37.5-19D11 G2

<400> SEQUENCE: 22

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser Ala Ser Thr Lys Gly Pro Ser Val Phe Pro Leu Ala Pro Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Ser Tyr Asp
145                 150                 155                 160

Met His Trp Val Arg Gln Ala Thr Gly Lys Gly Leu Glu Trp Val Ser
                165                 170                 175

Ala Ile Gly Thr Ala Gly Asp Thr Tyr Tyr Ala Gly Ser Val Lys Gly
            180                 185                 190

Arg Phe Thr Ile Ser Arg Glu Asn Ala Lys Asn Ser Leu Tyr Leu Gln
        195                 200                 205

Met Asn Ser Leu Arg Val Gly Asp Thr Ala Val Tyr Tyr Cys Ala Arg
    210                 215                 220

Ser Trp Gly Glu Gly Asn Tyr Tyr Phe Tyr Tyr Gly Met Asp Val Trp
225                 230                 235                 240

Gly Gln Gly Thr Thr Val Thr Val Ser Ser Ala Ser Thr Lys Gly Pro
                245                 250                 255

Ser Val Phe Pro Leu Ala Pro Cys Ser Arg Ser Thr Ser Glu Ser Thr
            260                 265                 270

Ala Ala Leu Gly Cys Leu Val Lys Asp Tyr Phe Pro Glu Pro Val Thr
        275                 280                 285

Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Asn Phe Gly Thr Gln Thr Tyr Thr Cys Asn Val Asp
                325                 330                 335

His Lys Pro Ser Asn Thr Lys Val Asp Lys Thr Val Glu Arg Lys Cys
            340                 345                 350

Cys Val Glu Cys Pro Pro Cys Pro Ala Pro Pro Val Ala Gly Pro Ser
        355                 360                 365
```

```
Val Phe Leu Phe Pro Pro Lys Pro Lys Asp Thr Leu Met Ile Ser Arg
    370                 375                 380
Thr Pro Glu Val Thr Cys Val Val Val Asp Val Ser His Glu Asp Pro
385                 390                 395                 400
Glu Val Gln Phe Asn Trp Tyr Val Asp Gly Val Glu Val His Asn Ala
                405                 410                 415
Lys Thr Lys Pro Arg Glu Glu Gln Phe Asn Ser Thr Phe Arg Val Val
                420                 425                 430
Ser Val Leu Thr Val Val His Gln Asp Trp Leu Asn Gly Lys Glu Tyr
                435                 440                 445
Lys Cys Lys Val Ser Asn Lys Gly Leu Pro Ala Pro Ile Glu Lys Thr
450                 455                 460
Ile Ser Lys Thr Lys Gly Gln Pro Arg Glu Pro Gln Val Tyr Thr Leu
465                 470                 475                 480
Pro Pro Ser Arg Glu Glu Met Thr Lys Asn Gln Val Ser Leu Thr Cys
                485                 490                 495
Leu Val Lys Gly Phe Tyr Pro Ser Asp Ile Ala Val Glu Trp Glu Ser
                500                 505                 510
Asn Gly Gln Pro Glu Asn Asn Tyr Lys Thr Thr Pro Pro Met Leu Asp
                515                 520                 525
Ser Asp Gly Ser Phe Phe Leu Tyr Ser Lys Leu Thr Val Asp Lys Ser
530                 535                 540
Arg Trp Gln Gln Gly Asn Val Phe Ser Cys Ser Val Met His Glu Ala
545                 550                 555                 560
Leu His Asn His Tyr Thr Gln Lys Ser Leu Ser Leu Ser Pro Gly Lys
                565                 570                 575

<210> SEQ ID NO 23
<211> LENGTH: 1083
<212> TYPE: DNA
<213> ORGANISM: ARTIFICIAL SEQUENCE
<220> FEATURE:
<223> OTHER INFORMATION: 6.37.5-19D11 LC

<400> SEQUENCE: 23
atggacatga gggtgcccgc tcagctcctg gggctcctgc tgctgtggct gagaggtgcg     60
cgctgtgata ttgtgatgac ccagactcca ctctctctgt ccgtcacccc tggacagccg    120
gcctccatct cctgcaagtc tggtcagagc ctcctgcata gtgatggaaa gacctatttg    180
tattggtacc tgcagaagcc aggccagcct ccacagttcc tgatctatga gtttccaac    240 cggttctcta gagtgccaga taggttcagt ggcagcgggt cagggacaga tttcacactg    300
agaatcagcc gggtggaggc tgaggatgtt ggaatttatt actgcatgca agtatacag    360 cttccgtgga cgttcggcca agggaccag gtggaaatca aacgaacggt ggctgcacca    420
tctgtcttca tcttcccgtc ctatgtgctg actcagccac cctcggtgtc agtggcccca    480
ggacagacgg ccaggattac ctgtggggga gacaacattg gaagtataag tgtgcattgg    540
taccagcaga agccaggcca ggcccctgtg ctggtcgtct atgatgatag cgaccggccc    600
tcagggatcc ctgagcgatt ctctggctcc aactctggga cacggccac cctgaccatc    660 agctgggtcg aagccgggga tgaggccgac tattactgtc aggtgtggga tagtagtatt    720
gatcatcctg tgttattcgg cggagggacc aagctgaccg tcctaggtca gcccaaggcc    780
aaccccactg tcactctgtt cccgccctcc tctgaggagc tcaagccaa caaggccaca    840 ctagtgtgtc tgatcagtga cttctacccg ggagctgtga cagtggcctg gaaggcagat    900
```

```
ggcagccccg tcaaggcggg agtggagacc accaaaccct ccaaacagag caacaacaag    960
tacgcggcca gcagctacct gagcctgacg cccgagcagt ggaagtccca cagaagctac   1020
agctgccagg tcacgcatga agggagcacc gtggagaaga cagtggcccc tacagaatgt   1080
tca                                                                 1083
```

<210> SEQ ID NO 24
<211> LENGTH: 339
<212> TYPE: PRT
<213> ORGANISM: ARTIFICIAL SEQUENCE
<220> FEATURE:
<223> OTHER INFORMATION: 6.37.5-19D11 LC

<400> SEQUENCE: 24

```
Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

Arg Thr Val Ala Ala Pro Ser Val Phe Ile Phe Pro Ser Tyr Val Leu
        115                 120                 125

Thr Gln Pro Pro Ser Val Ser Val Ala Pro Gly Gln Thr Ala Arg Ile
    130                 135                 140

Thr Cys Gly Gly Asp Asn Ile Gly Ser Ile Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ser Gly Ile Pro Glu Arg Phe Ser Gly Ser Asn Ser Gly Asn
            180                 185                 190

Thr Ala Thr Leu Thr Ile Ser Trp Val Glu Ala Gly Asp Glu Ala Asp
        195                 200                 205

Tyr Tyr Cys Gln Val Trp Asp Ser Ser Ile Asp His Pro Val Leu Phe
    210                 215                 220

Gly Gly Gly Thr Lys Leu Thr Val Leu Gly Gln Pro Lys Ala Asn Pro
225                 230                 235                 240

Thr Val Thr Leu Phe Pro Pro Ser Ser Glu Glu Leu Gln Ala Asn Lys
                245                 250                 255

Ala Thr Leu Val Cys Leu Ile Ser Asp Phe Tyr Pro Gly Ala Val Thr
            260                 265                 270

Val Ala Trp Lys Ala Asp Gly Ser Pro Val Lys Ala Gly Val Glu Thr
        275                 280                 285

Thr Lys Pro Ser Lys Gln Ser Asn Asn Lys Tyr Ala Ala Ser Ser Tyr
    290                 295                 300

Leu Ser Leu Thr Pro Glu Gln Trp Lys Ser His Arg Ser Tyr Ser Cys
305                 310                 315                 320

Gln Val Thr His Glu Gly Ser Thr Val Glu Lys Thr Val Ala Pro Thr
```

Glu Cys Ser

<210> SEQ ID NO 25
<211> LENGTH: 1806
<212> TYPE: DNA
<213> ORGANISM: ARTIFICIAL SEQUENCE
<220> FEATURE:
<223> OTHER INFORMATION: 8G2-6.37 G2

<400> SEQUENCE: 25

```
atggacatga gggtgcccgc tcagctcctg gggctcctgc tgctgtggct gagaggtgcg      60
cgctgtcagg tgcagctggt gcagtctggg gctgaggtga agaagcctgg ggcctcagtg     120
aaggtctcct gcaaggcttc tggatacacc ttcaccagtt atgatatcaa ctgggtgcga     180
caggccactg gacaagggct tgagtggatg ggatggatga cccctaacag tggtaaaaca     240
gggtatgcac agaagttcca gggcagagtc accatgacca ggacacctc cataagcaca     300
gcctacatgg agctgagcag cctgagatct gaggacacgg ccgtgtatta ctgtgcgaga     360
gaggaggaat actatgaatc ggggagcctc ttctactact acggtttgga cgtctggggc     420
caagggacca cggtcaccgt ctctagtgcc tccaccaagg gcccatcggt cttcccctg      480
gcgccccagg tgcagctggt ggagtctggg ggaggcgtgg tccagcctgg aggtccctg      540
agactctcct gtgcagcctc tggattcacc ttcagtggct atggcatgca ctgggtccgc     600
caggctccag gcaaggggct ggagtgggtg gcagttatat catatgatgg aaatgataaa     660
tactatgcag actccgtgaa gggccgattc accatctcca gagacaatgc caagaacacg     720
ctgtatctgc aaatgaacag cctgagagct gaggacacgg ctgtgtatta ctgtgcgaga     780
gagctacggg tcctctgggg ccagggaacc ctggtcaccg tctctagtgc ctccaccaag     840
ggcccatcgg tcttccccct ggcgccctgc tccaggagca cctccgagag cacagcggcc     900
ctgggctgcc tggtcaagga ctacttcccc gaaccggtga cggtgtcgtg gaactcaggc     960
gctctgacca gcggcgtgca caccttccca gctgtcctac agtcctcagg actctactcc    1020
ctcagcagcg tggtgaccgt gccctccagc aacttcggca cccagaccta cacctgcaac    1080
gtagatcaca agcccagcaa caccaaggtg gacaagacag ttgagcgcaa atgttgtgtc    1140
gagtgcccac cgtgcccagc accacctgtg caggaccgt cagtcttcct cttcccccca    1200
aaacccaagg acaccctcat gatctcccgg acccctgagg tcacgtgcgt ggtggtggac    1260
gtgagccacg aagaccccga ggtccagttc aactggtacg tggacggcgt ggaggtgcat    1320
aatgccaaga caaagccacg ggaggagcag ttcaacagca cgttccgtgt ggtcagcgtc    1380
ctcaccgttg tgcaccagga ctggctgaac ggcaaggagt acaagtgcaa ggtctccaac    1440
aaaggcctcc cagcccccat cgagaaaacc atctccaaaa ccaaagggca gccccgagaa    1500
ccacaggtgt acaccctgcc cccatcccgg gaggagatga ccaagaacca ggtcagcctg    1560
acctgcctgg tcaaaggctt ctaccccagc gacatcgccg tggagtggga gagcaatggg    1620
cagccggaga acaactacaa gaccacacct cccatgctgg actccgacgg ctccttcttc    1680
ctctacagca agctcaccgt ggacaagagc aggtggcagc aggggaacgt cttctcatgc    1740
tccgtgatgc atgaggctct gcacaaccac tacacgcaga agagcctctc cctgtctccg    1800
ggtaaa                                                              1806
```

<210> SEQ ID NO 26
<211> LENGTH: 580

```
<212> TYPE: PRT
<213> ORGANISM: ARTIFICIAL SEQUENCE
<220> FEATURE:
<223> OTHER INFORMATION: 8G2-6.37 G2

<400> SEQUENCE: 26
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ala|
|1| | | |5| | | | |10| | | | |15|

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Pro Asn Ser Gly Lys Thr Gly Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Glu Tyr Tyr Glu Ser Gly Ser Leu Phe Tyr Tyr Tyr
                100                 105                 110

Gly Leu Asp Val Trp Gly Gln Gly Thr Thr Val Thr Val Ser Ser Ala
                115                 120                 125

Ser Thr Lys Gly Pro Ser Val Phe Pro Leu Ala Pro Gln Val Gln Leu
130                 135                 140

Val Glu Ser Gly Gly Gly Val Val Gln Pro Gly Arg Ser Leu Arg Leu
145                 150                 155                 160

Ser Cys Ala Ala Ser Gly Phe Thr Phe Ser Gly Tyr Gly Met His Trp
                165                 170                 175

Val Arg Gln Ala Pro Gly Lys Gly Leu Glu Trp Val Ala Val Ile Ser
                180                 185                 190

Tyr Asp Gly Asn Asp Lys Tyr Tyr Ala Asp Ser Val Lys Gly Arg Phe
                195                 200                 205

Thr Ile Ser Arg Asp Asn Ala Lys Asn Thr Leu Tyr Leu Gln Met Asn
210                 215                 220

Ser Leu Arg Ala Glu Asp Thr Ala Val Tyr Tyr Cys Ala Arg Glu Leu
225                 230                 235                 240

Arg Val Leu Trp Gly Gln Gly Thr Leu Val Thr Val Ser Ser Ala Ser
                245                 250                 255

Thr Lys Gly Pro Ser Val Phe Pro Leu Ala Pro Cys Ser Arg Ser Thr
                260                 265                 270

Ser Glu Ser Thr Ala Ala Leu Gly Cys Leu Val Lys Asp Tyr Phe Pro
                275                 280                 285

Glu Pro Val Thr Val Ser Trp Asn Ser Gly Ala Leu Thr Ser Gly Val
                290                 295                 300

His Thr Phe Pro Ala Val Leu Gln Ser Ser Gly Leu Tyr Ser Leu Ser
305                 310                 315                 320

Ser Val Val Thr Val Pro Ser Ser Asn Phe Gly Thr Gln Thr Tyr Thr
                325                 330                 335

Cys Asn Val Asp His Lys Pro Ser Asn Thr Lys Val Asp Lys Thr Val
                340                 345                 350

Glu Arg Lys Cys Cys Val Glu Cys Pro Pro Cys Pro Ala Pro Pro Val
                355                 360                 365

Ala Gly Pro Ser Val Phe Leu Phe Pro Pro Lys Pro Lys Asp Thr Leu
                370                 375                 380

-continued

```
Met Ile Ser Arg Thr Pro Glu Val Thr Cys Val Val Asp Val Ser
385                 390                 395                 400

His Glu Asp Pro Glu Val Gln Phe Asn Trp Tyr Val Asp Gly Val Glu
                405                 410                 415

Val His Asn Ala Lys Thr Lys Pro Arg Glu Glu Gln Phe Asn Ser Thr
            420                 425                 430

Phe Arg Val Val Ser Val Leu Thr Val Val His Gln Asp Trp Leu Asn
        435                 440                 445

Gly Lys Glu Tyr Lys Cys Lys Val Ser Asn Lys Gly Leu Pro Ala Pro
    450                 455                 460

Ile Glu Lys Thr Ile Ser Lys Thr Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525

Pro Met Leu Asp Ser Asp Gly Ser Phe Phe Leu Tyr Ser Lys Leu Thr
    530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580
```

<210> SEQ ID NO 27
<211> LENGTH: 1083
<212> TYPE: DNA
<213> ORGANISM: ARTIFICIAL SEQUENCE
<220> FEATURE:
<223> OTHER INFORMATION: 8G2-6.37 LC

<400> SEQUENCE: 27

```
atggacatga gggtgcccgc tcagctcctg gggctcctgc tgctgtggct gagaggtgcg      60
cgctgtgaca tccagatgac ccagtctcca tcttccgtgt ctgcgtctgt aggagacaga     120
gtcaccatca cttgtcgggc gagtcaggat attagcaact ggttagcctg gtatcagcag     180
aaaccaggga agtccccaa gctcctgatc tatgctgcgt cctatttaca aagtggggtc      240
ccatcaaggt tcagcggcag tggatctggg acagatttca ctctcaccat cagcagcctg     300
cagcctgaag attttgcaac ttactcttgt caacaggcta acagtttccc attcactttc     360
ggccctggga ccaaagtgga tatcaaacgt actgtggctg caccatctgt cttcatcttc     420
ccgccagata ttgtgatgac ccagactcca ctctctctgt ccgtcacccc tggacagccg     480
gcctccatct cctgcaagtc tggtcagagc tcctgcata gtgatggaaa gacctatttg      540
tattggtacc tgcagaagcc aggccagcct ccacagttcc tgatctatga gtttccaac      600 cggttctcta gagtgccaga taggttcagt ggcagcgggt cagggacaga tttcacactg     660
agaatcagcc gggtggaggc tgaggatgtt ggaatttatt actgcatgca agtatacag      720 cttccgtgga cgttcggcca agggacccag gtggaaatca aacgaactgt ggctgcacca     780
tctgtcttca tcttcccgcc atctgatgag cagttgaaat ctggaactgc ctctgttgtg     840
tgcctgctga ataacttcta tcccagagag gccaaagtac agtggaaggt ggataacgcc     900
```

```
ctccaatcgg gtaactccca ggagagtgtc acagagcagg acagcaagga cagcacctac    960
agcctcagca gcaccctgac gctgagcaaa gcagactacg agaaacacaa agtctacgcc   1020
tgcgaagtca cccatcaggg cctgagctcg cccgtcacaa agagcttcaa caggggagag   1080
tgt                                                                 1083
```

<210> SEQ ID NO 28
<211> LENGTH: 339
<212> TYPE: PRT
<213> ORGANISM: ARTIFICIAL SEQUENCE
<220> FEATURE:
<223> OTHER INFORMATION: 8G2-6.37 LC

<400> SEQUENCE: 28

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Val Pro Lys Leu Leu Ile
        35                  40                  45

Tyr Ala Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ala Asn Ser Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Asp Ile Val Met Thr Gln Thr Pro
        115                 120                 125

Leu Ser Leu Ser Val Thr Pro Gly Gln Pro Ala Ser Ile Ser Cys Lys
130                 135                 140

Ser Gly Gln Ser Leu Leu His Ser Asp Gly Lys Thr Tyr Leu Tyr Trp
145                 150                 155                 160

Tyr Leu Gln Lys Pro Gly Gln Pro Pro Gln Phe Leu Ile Tyr Glu Val
                165                 170                 175

Ser Asn Arg Phe Ser Arg Val Pro Asp Arg Phe Ser Gly Ser Gly Ser
            180                 185                 190

Gly Thr Asp Phe Thr Leu Arg Ile Ser Arg Val Glu Ala Glu Asp Val
        195                 200                 205

Gly Ile Tyr Tyr Cys Met Gln Ser Ile Gln Leu Pro Trp Thr Phe Gly
    210                 215                 220

Gln Gly Thr Gln Val Glu Ile Lys Arg Thr Val Ala Ala Pro Ser Val
225                 230                 235                 240

Phe Ile Phe Pro Pro Ser Asp Glu Gln Leu Lys Ser Gly Thr Ala Ser
                245                 250                 255

Val Val Cys Leu Leu Asn Asn Phe Tyr Pro Arg Glu Ala Lys Val Gln
            260                 265                 270

Trp Lys Val Asp Asn Ala Leu Gln Ser Gly Asn Ser Gln Glu Ser Val
        275                 280                 285

Thr Glu Gln Asp Ser Lys Asp Ser Thr Tyr Ser Ser Ser Thr Leu
    290                 295                 300

Thr Leu Ser Lys Ala Asp Tyr Glu Lys His Lys Val Tyr Ala Cys Glu
305                 310                 315                 320

Val Thr His Gln Gly Leu Ser Ser Pro Val Thr Lys Ser Phe Asn Arg
```

Gly Glu Cys

<210> SEQ ID NO 29
<211> LENGTH: 1806
<212> TYPE: DNA
<213> ORGANISM: ARTIFICIAL SEQUENCE
<220> FEATURE:
<223> OTHER INFORMATION: 6.37-8G2 G2

<400> SEQUENCE: 29

```
atggacatga gggtgcccgc tcagctcctg gggctcctgc tgctgtggct gagaggtgcg      60
cgctgtcagg tgcagctggt ggagtctggg ggaggcgtgg tccagcctgg gaggtccctg     120
agactctcct gtgcagcctc tggattcacc ttcagtggct atggcatgca ctgggtccgc     180
caggctccag gcaaggggct ggagtgggtg gcagttatat catatgatgg aaatgataaa     240
tactatgcag actccgtgaa gggccgattc accatctcca gagacaatgc caagaacacg     300
ctgtatctgc aaatgaacag cctgagagct gaggacacgc tgtgtatta ctgtgcgaga     360
gagctacggg tcctctgggg ccagggaacc ctggtcaccg tctctagtgc ctccaccaag     420
ggcccatcgg tcttcccct ggcgccccag gtgcagctgg tgcagtctgg ggctgaggtg     480
aagaagcctg ggcctcagt gaaggtctcc tgcaaggctt ctggatacac cttcaccagt     540
tatgatatca ctgggtgcg acaggccact ggacaagggc ttgagtggat gggatggatg     600
aaccctaaca gtggtaaaac agggtatgca cagaagttcc agggcagagt caccatgacc     660
agggacacct ccataagcac agcctacatg gagctgagca gcctgagatc tgaggacacg     720
gccgtgtatt actgtgcgag agaggaggaa tactatgaat cggggagcct cttctactac     780
tacggtttgg acgtctgggg ccaagggacc acggtcaccg tctctagtgc ctccaccaag     840
ggcccatcgg tcttcccct ggcgccctgc tccaggagca cctccgagag cacagcggcc     900
ctgggctgcc tggtcaagga ctacttcccc gaaccggtga cggtgtcgtg aactcaggc     960
gctctgacca gcggcgtgca caccttccca gctgtcctac agtcctcagg actctactcc    1020
ctcagcagcg tggtgaccgt gccctccagc aacttcggca cccagaccta cacctgcaac    1080
gtagatcaca agcccagcaa caccaaggtg gacaagacag ttgagcgcaa atgttgtgtc    1140
gagtgcccac cgtgcccagc accacctgtg gcaggaccgt cagtcttcct cttccccca    1200
aaacccaagg acaccctcat gatctcccgg acccctgagg tcacgtgcgt ggtggtggac    1260
gtgagccacg aagaccccga ggtccagttc aactggtacg tggacggcgt ggaggtgcat    1320
aatgccaaga caaagccacg ggaggagcag ttcaacagca cgttccgtgt ggtcagcgtc    1380
ctcaccgttg tgcaccagga ctggctgaac ggcaaggagt acaagtgcaa ggtctccaac    1440
aaaggcctcc cagcccccat cgagaaaacc atctccaaaa ccaaagggca gccccgagaa    1500
ccacaggtgt acaccctgcc cccatcccgg gaggagatga ccaagaacca ggtcagcctg    1560
acctgcctgg tcaaaggctt ctaccccagc gacatcgccg tggagtggga gagcaatggg    1620
cagccggaga acaactacaa gaccacacct cccatgctgg actccgacgg ctccttcttc    1680
ctctacagca agctcaccgt ggacaagagc aggtggcagc aggggaacgt cttctcatgc    1740
tccgtgatgc atgaggctct gcacaaccac tacacgcaga agagcctctc cctgtctccg    1800
ggtaaa                                                                1806
```

<210> SEQ ID NO 30
<211> LENGTH: 580

```
<212> TYPE: PRT
<213> ORGANISM: ARTIFICIAL SEQUENCE
<220> FEATURE:
<223> OTHER INFORMATION: 6.37-8G2 G2

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser Ala Ser Thr Lys Gly Pro Ser Val Phe Pro Leu Ala Pro Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Asp
145                 150                 155                 160

Ile Asn Trp Val Arg Gln Ala Thr Gly Gln Gly Leu Glu Trp Met Gly
                165                 170                 175

Trp Met Asn Pro Asn Ser Gly Lys Thr Gly Tyr Ala Gln Lys Phe Gln
            180                 185                 190

Gly Arg Val Thr Met Thr Arg Asp Thr Ser Ile Ser Thr Ala Tyr Met
        195                 200                 205

Glu Leu Ser Ser Leu Arg Ser Glu Asp Thr Ala Val Tyr Tyr Cys Ala
    210                 215                 220

Arg Glu Glu Glu Tyr Tyr Glu Ser Gly Ser Leu Phe Tyr Tyr Tyr Gly
225                 230                 235                 240

Leu Asp Val Trp Gly Gln Gly Thr Thr Val Thr Val Ser Ser Ala Ser
                245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Asn Phe Gly Thr Gln Thr Tyr Thr
                325                 330                 335

Cys Asn Val Asp His Lys Pro Ser Asn Thr Lys Val Asp Lys Thr Val
            340                 345                 350

Glu Arg Lys Cys Cys Val Glu Cys Pro Pro Cys Pro Ala Pro Pro Val
        355                 360                 365

Ala Gly Pro Ser Val Phe Leu Phe Pro Pro Lys Pro Lys Asp Thr Leu
    370                 375                 380
```

```
Met Ile Ser Arg Thr Pro Glu Val Thr Cys Val Val Asp Val Ser
385                 390                 395                 400

His Glu Asp Pro Glu Val Gln Phe Asn Trp Tyr Val Asp Gly Val Glu
                405                 410                 415

Val His Asn Ala Lys Thr Lys Pro Arg Glu Glu Gln Phe Asn Ser Thr
            420                 425                 430

Phe Arg Val Val Ser Val Leu Thr Val Val His Gln Asp Trp Leu Asn
        435                 440                 445

Gly Lys Glu Tyr Lys Cys Lys Val Ser Asn Lys Gly Leu Pro Ala Pro
450                 455                 460

Ile Glu Lys Thr Ile Ser Lys Thr Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525

Pro Met Leu Asp Ser Asp Gly Ser Phe Phe Leu Tyr Ser Lys Leu Thr
530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 31
<211> LENGTH: 1080
<212> TYPE: DNA
<213> ORGANISM: ARTIFICIAL SEQUENCE
<220> FEATURE:
<223> OTHER INFORMATION: 6.37-8G2 LC

<400> SEQUENCE: 31
atggacatga gggtgcccgc tcagctcctg gggctcctgc tgctgtggct gagaggtgcg      60
cgctgtgata ttgtgatgac ccagactcca ctctctctgt ccgtcacccc tggacagccg     120
gcctccatct cctgcaagtc tggtcagagc ctcctgcata gtgatggaaa gacctatttg     180
tattggtacc tgcagaagcc aggccagcct ccacagttcc tgatctatga gtttccaac     240 cggttctcta gagtgccaga taggttcagt ggcagcgggt cagggacaga tttcacactg     300
agaatcagcc gggtggaggc tgaggatgtt ggaatttatt actgcatgca agtatacag     360 cttccgtgga cgttcggcca agggaccag gtggaaatca aacgaacggt ggctgcacca     420
tctgtcttca tcttcccgga catccagatg acccagtctc catcttccgt gtctgcgtct     480
gtaggagaca gagtcaccat cacttgtcgg gcgagtcagg atattagcaa ctggttagcc     540
tggtatcagc agaaaccagg gaaagtcccc aagctcctga tctatgctgc gtcctattta     600
caaagtgggg tcccatcaag gttcagcggc agtggatctg ggacagattt cactctcacc     660
atcagcagcc tgcagcctga agattttgca acttactctt gtcaacaggc taacagtttc     720
ccattcactt tcggccctgg gaccaaagtg gatatcaaac gtacggtggc tgcaccatct     780
gtcttcatct tcccgccatc tgatgagcag ttgaaatctg gaactgcctc tgttgtgtgc     840
ctgctgaata cttctatccc agagaggcc aaagtacagt ggaaggtgga taacgccctc     900
```

```
caatcgggta actcccagga gagtgtcaca gagcaggaca gcaaggacag cacctacagc    960
ctcagcagca ccctgacgct gagcaaagca gactacgaga aacacaaagt ctacgcctgc   1020
gaagtcaccc atcagggcct gagctcgccc gtcacaaaga gcttcaacag gggagagtgt   1080
```

<210> SEQ ID NO 32
<211> LENGTH: 338
<212> TYPE: PRT
<213> ORGANISM: ARTIFICIAL SEQUENCE
<220> FEATURE:
<223> OTHER INFORMATION: 6.37-8G2 LC

<400> SEQUENCE: 32

```
Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

Arg Thr Val Ala Ala Pro Ser Val Phe Ile Phe Pro Asp Ile Gln Met
        115                 120                 125

Thr Gln Ser Pro Ser Ser Val Ser Ala Ser Val Gly Asp Arg Val Thr
    130                 135                 140

Ile Thr Cys Arg Ala Ser Gln Asp Ile Ser Asn Trp Leu Ala Trp Tyr
145                 150                 155                 160

Gln Gln Lys Pro Gly Lys Val Pro Lys Leu Leu Ile Tyr Ala Ala Ser
                165                 170                 175

Tyr Leu Gln Ser Gly Val Pro Ser Arg Phe Ser Gly Ser Gly Ser Gly
            180                 185                 190

Thr Asp Phe Thr Leu Thr Ile Ser Ser Leu Gln Pro Glu Asp Phe Ala
        195                 200                 205

Thr Tyr Ser Cys Gln Gln Ala Asn Ser Phe Pro Phe Thr Phe Gly Pro
    210                 215                 220

Gly Thr Lys Val Asp Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335
```

Glu Cys

<210> SEQ ID NO 33
<211> LENGTH: 1719
<212> TYPE: DNA
<213> ORGANISM: ARTIFICIAL SEQUENCE
<220> FEATURE:
<223> OTHER INFORMATION: 6.147-AbL-20C3.1 G2

<400> SEQUENCE: 33

| | | | | | |
|---|---|---|---|---|---|
| caggtgcagc | ttgtcgagag | cggtggaggg | gtggtacaac | ccggaagatc | actccggctt | 60 |
| tcatgcgcag | catccggttt | tacatttcg | cggtatgaca | tgcactgggt | gagacaggca | 120 |
| ccaggaaaag | ggctggagtg | ggtggccatc | atcttctatg | atgggtccaa | taagtactac | 180 |
| gccgacccgg | taaagggag | gttcactatt | agccgcgaca | actcgaagaa | tacgctgtac | 240 |
| ctgcagatga | actcgttgcg | agccgaagat | accgcggtct | actattgtgc | gacgctcgcg | 300 |
| gctgcgttcg | attactgggg | ccaaggaaca | ttggtcacgg | tctcctcagc | gtcaacgaaa | 360 |
| ggaccgtcgg | tgttcccctt | ggcccctcag | gtccaactgc | aagagtcagg | accccggcctt | 420 |
| gtgaaacctt | cggaaactct | tagcttgacg | tgtactgtgt | cgggaggatc | aatctcgtca | 480 |
| tactattggt | cgtggattcg | gcagccgcct | ggtaaaggct | tggagtggat | tgggtatatc | 540 |
| tccgactccg | ggtccacgaa | ttacaacccc | tccctcaagt | cgagaattcc | gatcagcgtg | 600 |
| gatacctcga | agaaccagtt | tagcctcaag | ctgtcgtcag | tgacagcggc | cgacaccgcc | 660 |
| gtctattact | gcgcacgctg | gcagctcgct | cacgatgcgt | tcgacatctg | gggtcagggg | 720 |
| acaatggtaa | ccgtctctag | tgcctccacc | aagggcccat | cggtcttccc | cctggcgccc | 780 |
| tgctccagga | gcacctccga | gagcacagcg | gccctgggct | gcctggtcaa | ggactacttc | 840 |
| cccgaaccgg | tgacggtgtc | gtggaactca | ggcgctctga | ccagcggcgt | gcacaccttc | 900 |
| ccagctgtcc | tacagtcctc | aggactctac | tccctcagca | gcgtggtgac | cgtgccctcc | 960 |
| agcaacttcg | gcacccagac | ctacacctgc | aacgtagatc | acaagcccag | caacaccaag | 1020 |
| gtggacaaga | cagttgagcg | caaatgttgt | gtcgagtgcc | caccgtgccc | agcaccacct | 1080 |
| gtggcaggac | cgtcagtctt | cctcttcccc | caaaaccca | aggacaccct | catgatctcc | 1140 |
| cggacccctg | aggtcacgtg | cgtggtggtg | gacgtgagcc | acgaagaccc | cgaggtccag | 1200 |
| ttcaactggt | acgtggacgg | cgtggaggtg | cataatgcca | agacaaagcc | acgggaggag | 1260 |
| cagttcaaca | gcacgttccg | tgtggtcagc | gtcctcaccg | ttgtgcacca | ggactggctg | 1320 |
| aacggcaagg | agtacaagtg | caaggtctcc | aacaaaggcc | tcccagcccc | catcgagaaa | 1380 |
| accatctcca | aaaccaaagg | gcagccccga | gaaccacagg | tgtacaccct | gcccccatcc | 1440 |
| cgggaggaga | tgaccaagaa | ccaggtcagc | ctgacctgcc | tggtcaaagg | cttctacccc | 1500 |
| agcgacatcg | ccgtggagtg | ggagagcaat | gggcagccgg | agaacaacta | caagaccaca | 1560 |
| cctcccatgc | tggactccga | cggctccttc | ttcctctaca | gcaagctcac | cgtggacaag | 1620 |
| agcaggtggc | agcaggggaa | cgtcttctca | tgctccgtga | tgcatgaggc | tctgcacaac | 1680 |
| cactacacgc | agaagagcct | ctccctgtct | ccgggtaaa | | | 1719 |

<210> SEQ ID NO 34
<211> LENGTH: 573
<212> TYPE: PRT
<213> ORGANISM: ARTIFICIAL SEQUENCE
<220> FEATURE:
<223> OTHER INFORMATION: 6.147-AbL-20C3.1 G2

<400> SEQUENCE: 34

-continued

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Gln Val Gln Leu Gln Glu Ser Gly Pro Gly Leu Val Lys Pro Ser
    130                 135                 140

Glu Thr Leu Ser Leu Thr Cys Thr Val Ser Gly Gly Ser Ile Ser Ser
145                 150                 155                 160

Tyr Tyr Trp Ser Trp Ile Arg Gln Pro Pro Gly Lys Gly Leu Glu Trp
                165                 170                 175

Ile Gly Tyr Ile Ser Asp Ser Gly Ser Thr Asn Tyr Asn Pro Ser Leu
            180                 185                 190

Lys Ser Arg Ile Pro Ile Ser Val Asp Thr Ser Lys Asn Gln Phe Ser
        195                 200                 205

Leu Lys Leu Ser Ser Val Thr Ala Ala Asp Thr Ala Val Tyr Tyr Cys
    210                 215                 220

Ala Arg Trp Gln Leu Ala His Asp Ala Phe Asp Ile Trp Gly Gln Gly
225                 230                 235                 240

Thr Met Val Thr Val Ser Ser Ala Ser Thr Lys Gly Pro Ser Val Phe
                245                 250                 255

Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Asn Phe Gly Thr Gln Thr Tyr Thr Cys Asn Val Asp His Lys Pro
                325                 330                 335

Ser Asn Thr Lys Val Asp Lys Thr Val Glu Arg Lys Cys Cys Val Glu
            340                 345                 350

Cys Pro Pro Cys Pro Ala Pro Pro Val Ala Gly Pro Ser Val Phe Leu
        355                 360                 365

Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Gln
385                 390                 395                 400

Phe Asn Trp Tyr Val Asp Gly Val Glu Val His Asn Ala Lys Thr Lys
                405                 410                 415
```

```
Pro Arg Glu Glu Gln Phe Asn Ser Thr Phe Arg Val Val Ser Val Leu
            420                 425                 430

Thr Val Val His Gln Asp Trp Leu Asn Gly Lys Glu Tyr Lys Cys Lys
        435                 440                 445

Val Ser Asn Lys Gly Leu Pro Ala Pro Ile Glu Lys Thr Ile Ser Lys
    450                 455                 460

Thr Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Met Leu Asp Ser Asp Gly
        515                 520                 525

Ser Phe Phe Leu Tyr Ser Lys Leu Thr Val Asp Lys Ser Arg Trp Gln
    530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 35
<211> LENGTH: 1014
<212> TYPE: DNA
<213> ORGANISM: ARTIFICIAL SEQUENCE
<220> FEATURE:
<223> OTHER INFORMATION: 6.147-AbL-20C3.1 LC

<400> SEQUENCE: 35
tcatacgtgc tcactcagcc gcccagcgta tcggtggctc ccggacagac ggcgcgaatc      60
acgtgcggtg gaacaatat cggctccaag tcagtccatt ggtatcaaca gaaacctggt     120
caggcaccag tcctggtggt atacgatgac tcggacaggc cctcggagat ccggaacgc     180 ttctccggat cgaattcggg aacacagcg accttgacga tcagcagagt ggaggccgga     240
gatgaagccg actactattg tcaggtgtgg gattccagct ccgaccacgt cgtatttgga     300
ggtgggacac ggcttaccgt cctcgggcag cccaaggctg cgccatcggt cactctgttc     360
ccacctcaga gcgccctgac caaccggcg tccgtgtcgg gttcaccagg ccagtcaatc     420
actatttcat gtacgggac gtcgtccgac gtgggagggt acaactacgt atcatggtat     480
caacagcacc ccgtaaagc gccgaagctg atgatctacg aggtcagcta taggccttcc     540
ggagtgtcaa atcggttctc cgggtcgaaa tcgggttcga cggcatcgtt gacaatcagc     600
gggctccagc cgaagatga ggccgactac tattgctcct cgtatgcgat tccagcact      660 cttgtctttg gcggaggaac aaagatgacc gtcctaggtc agcccaaggc caacccact      720 gtcactctgt tcccgccctc ctctgaggag ctccaagcca caaggccac actagtgtgt     780 ctgatcagtg acttctaccc gggagctgtg acagtggcct ggaaggcaga tggcagcccc     840
gtcaaggcgg gagtggagac caccaaaccc tccaaacaga gcaacaacaa gtacgcggcc     900
agcagctacc tgagcctgac gcccgagcag tggaagtccc acagaagcta cagctgccag     960
gtcacgcatg aagggagcac cgtggagaag acagtggccc ctacagaatg ttca          1014

<210> SEQ ID NO 36
<211> LENGTH: 1014
<212> TYPE: PRT
<213> ORGANISM: ARTIFICIAL SEQUENCE
```

<220> FEATURE:
<223> OTHER INFORMATION: 6.147-AbL-20C3.1 LC

<400> SEQUENCE: 36

Thr Cys Ala Thr Ala Cys Gly Thr Gly Cys Thr Cys Ala Cys Thr Cys
1               5                   10                  15

Ala Gly Cys Cys Gly Cys Cys Ala Gly Cys Gly Thr Ala Thr Cys
            20                  25                  30

Gly Gly Thr Gly Gly Cys Thr Cys Cys Gly Gly Ala Cys Ala Gly
            35                  40                  45

Ala Cys Gly Gly Cys Gly Cys Gly Ala Ala Thr Cys Ala Cys Gly Thr
    50                  55                  60

Gly Cys Gly Gly Thr Gly Gly Ala Ala Cys Ala Ala Thr Ala Thr
65                  70                  75                  80

Cys Gly Gly Cys Thr Cys Cys Ala Ala Gly Thr Cys Ala Gly Thr Cys
                85                  90                  95

Cys Ala Thr Thr Gly Gly Thr Ala Thr Cys Ala Ala Cys Ala Gly Ala
                100                 105                 110

Ala Ala Cys Cys Thr Gly Gly Thr Cys Ala Gly Gly Cys Ala Cys Cys
            115                 120                 125

Ala Gly Thr Cys Cys Thr Gly Gly Thr Gly Gly Thr Ala Thr Ala Cys
            130                 135                 140

Gly Ala Thr Gly Ala Cys Thr Cys Gly Gly Ala Cys Ala Gly Gly Cys
145                 150                 155                 160

Cys Cys Thr Cys Gly Gly Ala Gly Ala Thr Thr Cys Gly Gly Ala
                165                 170                 175

Ala Cys Gly Cys Thr Thr Cys Thr Cys Gly Gly Ala Thr Cys Gly
            180                 185                 190

Ala Ala Thr Thr Cys Gly Gly Gly Ala Ala Cys Ala Cys Ala Gly
            195                 200                 205

Cys Gly Ala Cys Cys Thr Thr Gly Ala Cys Gly Ala Thr Cys Ala Gly
            210                 215                 220

Cys Ala Gly Ala Gly Thr Gly Gly Ala Gly Gly Cys Cys Gly Gly Ala
225                 230                 235                 240

Gly Ala Thr Gly Ala Ala Gly Cys Cys Gly Ala Cys Thr Ala Cys Thr
                245                 250                 255

Ala Thr Thr Gly Thr Cys Ala Gly Gly Thr Gly Thr Gly Gly Ala
            260                 265                 270

Thr Thr Cys Cys Ala Gly Cys Thr Cys Cys Gly Ala Cys Cys Ala Cys
            275                 280                 285

Gly Thr Cys Gly Thr Ala Thr Thr Thr Gly Gly Ala Gly Gly Thr Gly
            290                 295                 300

Gly Gly Ala Cys Ala Gly Gly Cys Thr Thr Ala Cys Cys Gly Thr
305                 310                 315                 320

Cys Cys Thr Cys Gly Gly Gly Cys Ala Gly Cys Cys Ala Ala Gly
                325                 330                 335

Gly Cys Thr Gly Cys Gly Cys Cys Ala Thr Cys Gly Gly Thr Cys Ala
            340                 345                 350

Cys Thr Cys Thr Gly Thr Thr Cys Cys Cys Ala Cys Cys Thr Cys Ala
            355                 360                 365

Gly Ala Gly Cys Gly Cys Cys Thr Gly Ala Cys Cys Ala Ala
            370                 375                 380

Cys Cys Gly Gly Cys Gly Thr Cys Cys Gly Thr Gly Thr Cys Gly Gly
385                 390                 395                 400

```
Gly Thr Thr Cys Ala Cys Cys Ala Gly Gly Cys Cys Ala Gly Thr Cys
                405                 410                 415

Ala Ala Thr Cys Ala Cys Thr Ala Thr Thr Thr Cys Ala Thr Gly Thr
            420                 425                 430

Ala Cys Gly Gly Gly Gly Ala Cys Gly Thr Cys Gly Thr Cys Cys Gly
        435                 440                 445

Ala Cys Gly Thr Gly Gly Gly Ala Gly Gly Gly Thr Ala Cys Ala Ala
    450                 455                 460

Cys Thr Ala Cys Gly Thr Ala Thr Cys Ala Thr Gly Gly Thr Ala Thr
465                 470                 475                 480
Cys Ala Ala Cys Ala Gly Cys Ala Cys Cys Cys Gly Gly Thr Ala
                485                 490                 495
Ala Ala Gly Cys Gly Cys Cys Gly Ala Ala Gly Cys Thr Gly Ala Thr
            500                 505                 510

Gly Ala Thr Cys Thr Ala Cys Gly Ala Gly Gly Thr Cys Ala Gly Cys
        515                 520                 525

Thr Ala Thr Ala Gly Gly Cys Cys Thr Thr Cys Cys Gly Gly Ala Gly
    530                 535                 540

Thr Gly Thr Cys Ala Ala Ala Thr Cys Gly Gly Thr Thr Cys Thr Cys
545                 550                 555                 560

Cys Gly Gly Gly Thr Cys Gly Ala Ala Ala Thr Cys Gly Gly Gly Thr
                565                 570                 575

Thr Cys Gly Ala Cys Gly Gly Cys Ala Thr Cys Gly Thr Thr Gly Ala
            580                 585                 590

Cys Ala Ala Thr Cys Ala Gly Cys Gly Gly Gly Cys Thr Cys Cys Ala
        595                 600                 605

Gly Cys Cys Cys Gly Ala Ala Gly Ala Thr Gly Ala Gly Gly Cys Cys
    610                 615                 620

Gly Ala Cys Thr Ala Cys Thr Ala Thr Thr Gly Cys Thr Cys Cys Thr
625                 630                 635                 640

Cys Gly Thr Ala Thr Gly Cys Gly Ala Thr Thr Thr Cys Cys Ala Gly
                645                 650                 655

Cys Ala Cys Thr Cys Thr Thr Gly Thr Cys Thr Thr Thr Gly Gly Cys
            660                 665                 670

Gly Gly Ala Gly Gly Ala Ala Cys Ala Ala Ala Gly Ala Thr Gly Ala
        675                 680                 685

Cys Cys Gly Thr Cys Cys Thr Ala Gly Gly Thr Cys Ala Gly Cys Cys
    690                 695                 700

Cys Ala Ala Gly Gly Cys Cys Ala Ala Cys Cys Cys Cys Ala Cys Thr
705                 710                 715                 720

Gly Thr Cys Ala Cys Thr Cys Thr Gly Thr Thr Cys Cys Cys Gly Cys
                725                 730                 735

Cys Cys Thr Cys Cys Thr Cys Thr Gly Ala Gly Gly Ala Gly Cys Thr
            740                 745                 750

Cys Cys Ala Ala Gly Cys Cys Ala Ala Cys Ala Ala Gly Gly Cys Cys
        755                 760                 765

Ala Cys Ala Cys Thr Ala Gly Thr Gly Thr Gly Thr Cys Thr Gly Ala
    770                 775                 780

Thr Cys Ala Gly Thr Gly Ala Cys Thr Thr Cys Thr Ala Cys Cys Cys
785                 790                 795                 800

Gly Gly Gly Ala Gly Cys Thr Gly Thr Gly Ala Cys Ala Gly Thr Gly
                805                 810                 815
```

Gly Cys Cys Thr Gly Ala Ala Gly Cys Ala Gly Thr Gly
                820                 825                 830

Gly Cys Ala Gly Cys Cys Cys Gly Thr Cys Ala Ala Gly Gly Cys
                835                 840                 845

Gly Gly Gly Ala Gly Thr Gly Gly Ala Gly Ala Cys Cys Ala Cys Cys
                850                 855                 860

Ala Ala Ala Cys Cys Cys Thr Cys Cys Ala Ala Cys Ala Gly Ala
865                 870                 875                 880

Gly Cys Ala Ala Cys Ala Ala Cys Ala Ala Gly Thr Ala Cys Gly Cys
                885                 890                 895

Gly Gly Cys Cys Ala Gly Cys Ala Gly Cys Thr Ala Cys Cys Thr Gly
                900                 905                 910

Ala Gly Cys Cys Thr Gly Ala Cys Gly Cys Cys Cys Gly Ala Gly Cys
                915                 920                 925

Ala Gly Thr Gly Gly Ala Ala Gly Thr Cys Cys Cys Ala Cys Ala Gly
                930                 935                 940

Ala Ala Gly Cys Thr Ala Cys Ala Gly Cys Thr Gly Cys Cys Ala Gly
945                 950                 955                 960

Gly Thr Cys Ala Cys Gly Cys Ala Thr Gly Ala Ala Gly Gly Gly Ala
                965                 970                 975

Gly Cys Ala Cys Cys Gly Thr Gly Gly Ala Gly Ala Ala Gly Ala Cys
                980                 985                 990

Ala Gly Thr Gly Gly Cys Cys Cys Thr Ala Cys Ala Gly Ala Ala
                995                 1000                1005

Thr Gly  Thr Thr Cys Ala
     1010

<210> SEQ ID NO 37
<211> LENGTH: 1725
<212> TYPE: DNA
<213> ORGANISM: ARTIFICIAL SEQUENCE
<220> FEATURE:
<223> OTHER INFORMATION: 6.147-AbL-27H6 G2

<400> SEQUENCE: 37
caggtgcagc ttgtcgagag cggtggaggg gtggtacaac ccggaagatc actccggctt      60
tcatgcgcag catccggttt tacattttcg cggtatgaca tgcactgggt gagacaggca     120
ccaggaaaag ggctggagtg ggtggccatc atcttctatg atgggtccaa taagtactac     180
gccgacccgg taaagggag gttcactatt agccgcgaca actcgaagaa tacgctgtac     240
ctgcagatga actcgttgcg agccgaagat accgcggtct actattgtgc gacgctcgcg     300
gctgcgttcg attactgggg ccaaggaaca ttggtcacgg tctcctcagc gtcaacgaaa     360
ggaccgtcgg tgttcccctt ggcccctgag gtgcagctcg tcgaaagcgg aggaggcctg     420
gtccaacctg gtggttccct ccgactgtca tgtgccgcat ccggtttcac gttttcatcg     480
tactcgatga actgggtccg ccaggcaccg gggaaaggt tggaatgggt atcctacatt     540
tcgtccagcg ggtcaagcat ctactatgcg gatagcgtaa agggccggtt cacgatctcg     600
agagacaacg cgaagaattc gttgtatctt cagatgaatt cgctcaggga tgaggacaca     660
gcggtgtatt actgcgctcg cgaaagatac tatgagaca ccccctttga ttactgggga     720
cagggaactc ttgtgaccgt ctctagtgcc tccaccaagg gcccatcggt cttcccctg     780 gcgccctgct ccaggagcac ctccgagagc acagcggccc tgggctgcct ggtcaaggac     840
tacttccccg aaccggtgac ggtgtcgtgg aactcaggcg ctctgaccag cggcgtgcac     900

```
accttcccag ctgtcctaca gtcctcagga ctctactccc tcagcagcgt ggtgaccgtg    960
ccctccagca acttcggcac ccagacctac acctgcaacg tagatcacaa gcccagcaac   1020
accaaggtgg acaagacagt tgagcgcaaa tgttgtgtcg agtgcccacc gtgcccagca   1080
ccacctgtgg caggaccgtc agtcttcctc ttccccccaa aacccaagga caccctcatg   1140
atctcccgga cccctgaggt cacgtgcgtg gtggtggacg tgagccacga agaccccgag   1200
gtccagttca actggtacgt ggacggcgtg gaggtgcata atgccaagac aaagccacgg   1260
gaggagcagt tcaacagcac gttccgtgtg gtcagcgtcc tcaccgttgt gcaccaggac   1320
tggctgaacg gcaaggagta caagtgcaag gtctccaaca aaggcctccc agcccccatc   1380
gagaaaacca tctccaaaac caaagggcag ccccgagaac acaggtgta caccctgccc   1440 ccatcccggg aggagatgac caagaaccag gtcagcctga cctgcctggt caaaggcttc   1500
taccccagcg acatcgccgt ggagtgggag agcaatgggc agccggagaa caactacaag   1560
accacacctc ccatgctgga ctccgacggc tccttcttcc tctacagcaa gctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaa                   1725
```

<210> SEQ ID NO 38
<211> LENGTH: 575
<212> TYPE: PRT
<213> ORGANISM: ARTIFICIAL SEQUENCE
<220> FEATURE:
<223> OTHER INFORMATION: 6.147-AbL-27H6 G2

<400> SEQUENCE: 38

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

Tyr Ser Met Asn Trp Val Arg Gln Ala Pro Gly Lys Gly Leu Glu Trp
                165                 170                 175

Val Ser Tyr Ile Ser Ser Gly Ser Ser Ile Tyr Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Asp Glu Asp Thr Ala Val Tyr Tyr
    210                 215                 220
```

Cys Ala Arg Glu Arg Tyr Tyr Gly Asp Thr Pro Phe Asp Tyr Trp Gly
225                 230                 235                 240

Gln Gly Thr Leu Val Thr Val Ser Ser Ala Ser Thr Lys Gly Pro Ser
            245                 250                 255

Val Phe Pro Leu Ala Pro Cys Ser Arg Ser Thr Ser Glu Ser Thr Ala
        260                 265                 270

Ala Leu Gly Cys Leu Val Lys Asp Tyr Phe Pro Glu Pro Val Thr Val
    275                 280                 285

Ser Trp Asn Ser Gly Ala Leu Thr Ser Gly Val His Thr Phe Pro Ala
290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
                325                 330                 335

Lys Pro Ser Asn Thr Lys Val Asp Lys Thr Val Glu Arg Lys Cys Cys
            340                 345                 350

Val Glu Cys Pro Pro Cys Pro Ala Pro Pro Val Ala Gly Pro Ser Val
        355                 360                 365

Phe Leu Phe Pro Pro Lys Pro Lys Asp Thr Leu Met Ile Ser Arg Thr
370                 375                 380

Pro Glu Val Thr Cys Val Val Val Asp Val Ser His Glu Asp Pro Glu
385                 390                 395                 400

Val Gln Phe Asn Trp Tyr Val Asp Gly Val Glu Val His Asn Ala Lys
                405                 410                 415

Thr Lys Pro Arg Glu Glu Gln Phe Asn Ser Thr Phe Arg Val Val Ser
            420                 425                 430

Val Leu Thr Val Val His Gln Asp Trp Leu Asn Gly Lys Glu Tyr Lys
        435                 440                 445

Cys Lys Val Ser Asn Lys Gly Leu Pro Ala Pro Ile Glu Lys Thr Ile
450                 455                 460

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Met Leu Asp Ser
        515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 39
<211> LENGTH: 1026
<212> TYPE: DNA
<213> ORGANISM: ARTIFICIAL SEQUENCE
<220> FEATURE:
<223> OTHER INFORMATION: 6.147-AbL-27H6 LC

<400> SEQUENCE: 39
tcatacgtgc tcactcagcc gcccagcgta tcggtggctc ccggacagac ggcgcgaatc    60

```
acgtgcggtg ggaacaatat cggctccaag tcagtccatt ggtatcaaca gaaacctggt    120
caggcaccag tcctggtggt atacgatgac tcggacaggc cctcggagat tccggaacgc    180
ttctccggat cgaattcggg gaacacagcg accttgacga tcagcagagt ggaggccgga    240
gatgaagccg actactattg tcaggtgtgg gattccagct ccgaccacgt cgtatttgga    300
ggtgggacac ggcttaccgt cctcgggcag cccaaggctg cgccatcggt cactctgttc    360
ccacctgata tcgtaatgac acagacaccc ctctccctcc ccgtgacccc aggggagcct    420
gcatcaatct cctgccgctc atcgcagtcg cttctgaatt cggtggacgg atcgactaac    480
cttgactggt atttgcaaaa accgggacag tcacctcaac tcctgatcta cactctgagc    540
tatcgggcgt caggcgtccc cgacaggttt agcggttccg ggtccggcac ggatttcacg    600
cttaagattt cgcgagtcga ggccgaagat gtgggtgtat actactgtat gcagagaatc    660
gaattcccgt tgacatttgg gggagggacc aaagtggaga ttaagcgtac ggtggctgca    720
ccatctgtct tcatcttccc gccatctgat gagcagttga atctggaact gcctctgtt    780 gtgtgcctgc tgaataactt ctatcccaga gaggccaaag tacagtggaa ggtggataac    840
gccctccaat cgggtaactc ccaggagagt gtcacagagc aggacagcaa ggacagcacc    900
tacagcctca gcagcaccct gacgctgagc aaagcagact acgagaaaca caaagtctac    960
gcctgcgaag tcacccatca gggcctgagc tcgcccgtca caaagagctt caacagggga   1020
gagtgt                                                              1026
```

<210> SEQ ID NO 40
<211> LENGTH: 342
<212> TYPE: PRT
<213> ORGANISM: ARTIFICIAL SEQUENCE
<220> FEATURE:
<223> OTHER INFORMATION: 6.147-AbL-27H6 LC

<400> SEQUENCE: 40

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Arg Leu Thr Val Leu Gly Gln Pro Lys
            100                 105                 110

Ala Ala Pro Ser Val Thr Leu Phe Pro Pro Asp Ile Val Met Thr Gln
        115                 120                 125

Thr Pro Leu Ser Leu Pro Val Thr Pro Gly Glu Pro Ala Ser Ile Ser
    130                 135                 140

Cys Arg Ser Ser Gln Ser Leu Leu Asn Ser Val Asp Gly Ser Thr Asn
145                 150                 155                 160

Leu Asp Trp Tyr Leu Gln Lys Pro Gly Gln Ser Pro Gln Leu Leu Ile
                165                 170                 175

Tyr Thr Leu Ser Tyr Arg Ala Ser Gly Val Pro Asp Arg Phe Ser Gly
            180                 185                 190
```

```
Ser Gly Ser Gly Thr Asp Phe Thr Leu Lys Ile Ser Arg Val Glu Ala
        195                 200                 205

Glu Asp Val Gly Val Tyr Tyr Cys Met Gln Arg Ile Glu Phe Pro Leu
    210                 215                 220

Thr Phe Gly Gly Gly Thr Lys Val Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340
```

<210> SEQ ID NO 41
<211> LENGTH: 1734
<212> TYPE: DNA
<213> ORGANISM: ARTIFICIAL SEQUENCE
<220> FEATURE:
<223> OTHER INFORMATION: 6.147-AbL-785K G2

<400> SEQUENCE: 41

```
caggtgcagc ttgtcgagag cggtggaggg gtggtacaac ccggaagatc actccggctt    60
tcatgcgcag catccggttt tacattttcg cggtatgaca tgcactgggt gagacaggca   120
ccaggaaaag ggctggagtg ggtggccatc atcttctatg atgggtccaa taagtactac   180
gccgacccgg taaagggag gttcactatt agccgcgaca actcgaagaa tacgctgtac   240
ctgcagatga actcgttgcg agccgaagat accgcggtct actattgtgc gacgctcgcg   300
gctgcgttcg attactgggg ccaaggaaca ttggtcacgg tctcctcagc gtcaacgaaa   360
ggaccgtcgg tgttcccctt ggcccctgag gtgcagctcg tgcagtccgg agccgaggtg   420
gtgcagcctg ggcatccgt caaagtctcg tgcgccgcgt cagggtacac attcaccgac   480
tataacatgc attgggtccg gcaggctccc ggtcaggggc tggagtggat ggggaaatc    540
aatccgaact ccggagggggc aggatacaat caaaagttta agggacgcgt aacgatgacc   600
actgacacgt caacctccac ggcgtatatg gagctcagaa gcctccgaag cgacgacact   660
gctgtctatt actgtgcgag actgggatat gatgatatct acgacgattg gtacttcgat   720
gtatggggac aagggacgac ggtcaccgtc tctagtgcct ccaccaaggg cccatcggtc   780
ttccccctgg cgccctgctc caggagcacc tccgagagca gcggccct   gggctgcctg   840
gtcaaggact acttccccga accggtgacg gtgtcgtgga actcaggcgc tctgaccagc   900
ggcgtgcaca ccttcccagc tgtcctacag tcctcaggac tctactccct cagcagcgtg   960
gtgaccgtgc cctccagcaa cttcggcacc cagacctaca cctgcaacgt agatcacaag  1020
cccagcaaca ccaaggtgga caagacagtt gagcgcaaat gttgtgtcga gtgcccaccg  1080
tgcccagcac cacctgtggc aggaccgtca gtcttcctct tcccccccaaa acccaaggac  1140
```

```
accctcatga tctcccggac ccctgaggtc acgtgcgtgg tggtggacgt gagccacgaa    1200
gaccccgagg tccagttcaa ctggtacgtg gacggcgtgg aggtgcataa tgccaagaca    1260
aagccacggg aggagcagtt caacagcacg ttccgtgtgg tcagcgtcct caccgttgtg    1320
caccaggact ggctgaacgg caaggagtac aagtgcaagg tctccaacaa aggcctccca    1380
gcccccatcg agaaaaccat ctccaaaacc aaagggcagc ccgagaacc acaggtgtac     1440 accctgcccc catcccggga ggagatgacc aagaaccagg tcagcctgac ctgcctggtc    1500
aaaggcttct accccagcga catcgccgtg gagtgggaga gcaatgggca gccggagaac    1560
aactacaaga ccacacctcc catgctggac tccgacggct ccttcttcct ctacagcaag    1620
ctcaccgtgg acaagagcag gtggcagcag gggaacgtct tctcatgctc cgtgatgcat    1680
gaggctctgc acaaccacta cacgcagaag agcctctccc tgtctccggg taaa          1734
```

<210> SEQ ID NO 42
<211> LENGTH: 578
<212> TYPE: PRT
<213> ORGANISM: ARTIFICIAL SEQUENCE
<220> FEATURE:
<223> OTHER INFORMATION: 6.147-AbL-785K G2

<400> SEQUENCE: 42

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Glu Val Gln Leu Val Gln Ser Gly Ala Glu Val Val Gln Pro Gly
    130                 135                 140

Ala Ser Val Lys Val Ser Cys Ala Ala Ser Gly Tyr Thr Phe Thr Asp
145                 150                 155                 160

Tyr Asn Met His Trp Val Arg Gln Ala Pro Gly Gln Gly Leu Glu Trp
                165                 170                 175

Met Gly Glu Ile Asn Pro Asn Ser Gly Gly Ala Gly Tyr Asn Gln Lys
            180                 185                 190

Phe Lys Gly Arg Val Thr Met Thr Thr Asp Thr Ser Thr Ser Thr Ala
        195                 200                 205

Tyr Met Glu Leu Arg Ser Leu Arg Ser Asp Asp Thr Ala Val Tyr Tyr
    210                 215                 220

Cys Ala Arg Leu Gly Tyr Asp Asp Ile Tyr Asp Asp Trp Tyr Phe Asp
225                 230                 235                 240

Val Trp Gly Gln Gly Thr Thr Val Thr Val Ser Ser Ala Ser Thr Lys
                245                 250                 255

Gly Pro Ser Val Phe Pro Leu Ala Pro Cys Ser Arg Ser Thr Ser Glu
```

|   |     |     |     |     | 260 |     |     |     |     | 265 |     |     |     |     | 270 |     |     |     |
|---|-----|-----|-----|-----|-----|-----|-----|-----|-----|-----|-----|-----|-----|-----|-----|-----|-----|-----|
|   | Ser | Thr | Ala | Ala | Leu | Gly | Cys | Leu | Val | Lys | Asp | Tyr | Phe | Pro | Glu | Pro |     |     |
|   |     |     | 275 |     |     |     |     | 280 |     |     |     |     | 285 |     |     |     |     |     |

Ser Thr Ala Ala Leu Gly Cys Leu Val Lys Asp Tyr Phe Pro Glu Pro
                275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Asn Phe Gly Thr Gln Thr Tyr Thr Cys Asn
                325                 330                 335

Val Asp His Lys Pro Ser Asn Thr Lys Val Asp Lys Thr Val Glu Arg
                340                 345                 350

Lys Cys Cys Val Glu Cys Pro Pro Cys Pro Ala Pro Pro Val Ala Gly
                355                 360                 365

Pro Ser Val Phe Leu Phe Pro Pro Lys Pro Lys Asp Thr Leu Met Ile
                370                 375                 380

Ser Arg Thr Pro Glu Val Thr Cys Val Val Val Asp Val Ser His Glu
385                 390                 395                 400

Asp Pro Glu Val Gln Phe Asn Trp Tyr Val Asp Gly Val Glu Val His
                405                 410                 415

Asn Ala Lys Thr Lys Pro Arg Glu Glu Gln Phe Asn Ser Thr Phe Arg
                420                 425                 430

Val Val Ser Val Leu Thr Val Val His Gln Asp Trp Leu Asn Gly Lys
                435                 440                 445

Glu Tyr Lys Cys Lys Val Ser Asn Lys Gly Leu Pro Ala Pro Ile Glu
                450                 455                 460

Lys Thr Ile Ser Lys Thr Lys Gly Gln Pro Arg Glu Pro Gln Val Tyr
465                 470                 475                 480

Thr Leu Pro Pro Ser Arg Glu Glu Met Thr Lys Asn Gln Val Ser Leu
                485                 490                 495

Thr Cys Leu Val Lys Gly Phe Tyr Pro Ser Asp Ile Ala Val Glu Trp
                500                 505                 510

Glu Ser Asn Gly Gln Pro Glu Asn Asn Tyr Lys Thr Thr Pro Pro Met
                515                 520                 525

Leu Asp Ser Asp Gly Ser Phe Phe Leu Tyr Ser Lys Leu Thr Val Asp
                530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 43
<211> LENGTH: 1008
<212> TYPE: DNA
<213> ORGANISM: ARTIFICIAL SEQUENCE
<220> FEATURE:
<223> OTHER INFORMATION: 6.147-AbL-785 LC

<400> SEQUENCE: 43
tcatacgtgc tcactcagcc gcccagcgta tcggtggctc ccggacagac ggcgcgaatc    60
acgtgcggtg gaacaatat cggctccaag tcagtccatt ggtatcaaca gaaacctggt   120
caggcaccag tcctggtggt atacgatgac tcggacaggc cctcggagat tccggaacgc   180
ttctccggat cgaattcggg gaacacagcg accttgacga tcagcagagt ggaggccgga   240

```
gatgaagccg actactattg tcaggtgtgg gattccagct ccgaccacgt cgtatttgga    300
ggtgggacac ggcttaccgt cctcgggcag cccaaggctg cgccatcggt cactctgttc    360
ccacctgaca ttcagatgac tcagtcgcct tcgtcattga gcgcgtcggt gggagatcgg    420
gtcacgatta cttgtcgggc atcgcaagac atctcgaact atttgaattg gtaccagcaa    480
aagcctggta aagcgcccaa acttcttatc tactatacgt cccgcctcct ctcgggcgtc    540
ccgtcaaggt ttagcggatc gggaagcggg acggatttca cactgacgat ttcatcactt    600
cagcccgaag atttcgccac ctattactgt cagcaaggag acaccctgcc atacactttt    660
ggcggtggga caaggtcgaa atcaagcgt acggtggctg caccatctgt cttcatcttc    720
ccgccatctg atgagcagtt gaaatctgga actgcctctg ttgtgtgcct gctgaataac    780
ttctatccca gagaggccaa agtacagtgg aaggtggata cgccctcca atcgggtaac    840
tcccaggaga gtgtcacaga gcaggacagc aaggacagcc cctacagcct cagcagcacc    900
ctgacgctga gcaaagcaga ctacgagaaa cacaaagtct acgcctgcga agtcacccat    960
cagggcctga gctcgcccgt cacaaagagc ttcaacaggg gagagtgt                1008
```

<210> SEQ ID NO 44
<211> LENGTH: 336
<212> TYPE: PRT
<213> ORGANISM: ARTIFICIAL SEQUENCE
<220> FEATURE:
<223> OTHER INFORMATION: 6.147-AbL-785 LC

<400> SEQUENCE: 44

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Arg Leu Thr Val Leu Gly Gln Pro Lys
            100                 105                 110

Ala Ala Pro Ser Val Thr Leu Phe Pro Pro Asp Ile Gln Met Thr Gln
        115                 120                 125

Ser Pro Ser Ser Leu Ser Ala Ser Val Gly Asp Arg Val Thr Ile Thr
130                 135                 140

Cys Arg Ala Ser Gln Asp Ile Ser Asn Tyr Leu Asn Trp Tyr Gln Gln
145                 150                 155                 160

Lys Pro Gly Lys Ala Pro Lys Leu Leu Ile Tyr Tyr Thr Ser Arg Leu
                165                 170                 175

Leu Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Gly Asp Thr Leu Pro Tyr Thr Phe Gly Gly Gly Thr
210                 215                 220

Lys Val Glu Ile Lys Arg Thr Val Ala Ala Pro Ser Val Phe Ile Phe
```

| | 225 | | | 230 | | | 235 | | | 240 | |
|---|---|---|---|---|---|---|---|---|---|---|---|
Pro Pro Ser Asp Glu Gln Leu Lys Ser Gly Thr Ala Ser Val Val Cys
                        245                        250                        255

Leu Leu Asn Asn Phe Tyr Pro Arg Glu Ala Lys Val Gln Trp Lys Val
              260                        265                        270

Asp Asn Ala Leu Gln Ser Gly Asn Ser Gln Glu Ser Val Thr Glu Gln
          275                        280                        285

Asp Ser Lys Asp Ser Thr Tyr Ser Leu Ser Ser Thr Leu Thr Leu Ser
 290                       295                        300

Lys Ala Asp Tyr Glu Lys His Lys Val Tyr Ala Cys Glu Val Thr His
305                     310                        315                    320

Gln Gly Leu Ser Ser Pro Val Thr Lys Ser Phe Asn Arg Gly Glu Cys
                   325                        330                    335

<210> SEQ ID NO 45
<211> LENGTH: 1713
<212> TYPE: DNA
<213> ORGANISM: ARTIFICIAL SEQUENCE
<220> FEATURE:
<223> OTHER INFORMATION: 6.147-AbS-785K G2

<400> SEQUENCE: 45

| | |
|---|---|
| caggtgcagc ttgtcgagag cggtggaggg gtggtacaac ccggaagatc actccggctt | 60 |
| tcatgcgcag catccggttt tacatttccg cggtatgaca tgcactgggt gagacaggca | 120 |
| ccaggaaaag ggctggagtg ggtggccatc atcttctatg atgggtccaa taagtactac | 180 |
| gccgacccgg taaagggag gttcactatt agccgcgaca ctcgaagaa tacgctgtac | 240 |
| ctgcagatga actcgttgcg agccgaagat accgcggtct actattgtgc gacgctcgcg | 300 |
| gctgcgttcg attactgggg ccaaggaaca ttggtcacgg tctcctcagc gtcaacgaaa | 360 |
| ggaccggagg tgcagctcgt gcagtccgga gccgaggtgg tgcagcctgg ggcatccgtc | 420 |
| aaagtctcgt gcgccgcgtc agggtacaca ttcaccgact ataacatgca ttgggtccgg | 480 |
| caggctcccg gtcaggggct ggagtggatg ggggaaatca atccgaactc cggaggggca | 540 |
| ggatacaatc aaaagtttaa gggacgcgta acgatgacca ctgacacgtc aacctccacg | 600 |
| gcgtatatgg agctcagaag cctccgaagc gacgacactg ctgtctatta ctgtgcgaga | 660 |
| ctggatatg atgatatcta cgacgattgg tacttcgatg tatggggaca agggacgacg | 720 |
| gtcaccgtct ctagtgcctc caccaagggc ccatcggtct tccccctggc gccctgctcc | 780 |
| aggagcacct ccgagagcac agcggccctg ggctgcctgg tcaaggacta cttccccgaa | 840 |
| ccggtgacgg tgtcgtggaa ctcaggcgct ctgaccagcg gcgtgcacac cttcccagct | 900 |
| gtcctacagt cctcaggact ctactccctc agcagcgtgg tgaccgtgcc ctccagcaac | 960 |
| ttcggcaccc agacctacac ctgcaacgta gatcacaagc ccagcaacac caaggtggac | 1020 |
| aagacagttg agcgcaaatg ttgtgtcgag tgcccaccgt gcccagcacc acctgtggca | 1080 |
| ggaccgtcag tcttcctctt ccccccaaaa cccaaggaca cctcatgat ctcccggacc | 1140 |
| cctgaggtca cgtgcgtggt ggtggacgtg agccacgaag accccgaggt ccagttcaac | 1200 |
| tggtacgtgg acggcgtgga ggtgcataat gccaagacaa agccacggga ggagcagttc | 1260 |
| aacagcacgt tccgtgtggt cagcgtcctc accgttgtgc accaggactg gctgaacggc | 1320 |
| aaggagtaca agtgcaaggt ctccaacaaa ggcctcccag cccccatcga gaaaaccatc | 1380 |
| tccaaaacca aagggcagcc ccgagaacca caggtgtaca ccctgccccc atccggggag | 1440 |
| gagatgacca agaaccaggt cagcctgacc tgcctggtca aaggcttcta ccccagcgac | 1500 |

-continued

```
atcgccgtgg agtgggagag caatgggcag ccggagaaca actacaagac cacacctccc    1560
atgctggact ccgacggctc cttcttcctc tacagcaagc tcaccgtgga caagagcagg    1620
tggcagcagg ggaacgtctt ctcatgctcc gtgatgcatg aggctctgca caaccactac    1680
acgcagaaga gcctctccct gtctccgggt aaa                                  1713
```

<210> SEQ ID NO 46
<211> LENGTH: 571
<212> TYPE: PRT
<213> ORGANISM: ARTIFICIAL SEQUENCE
<220> FEATURE:
<223> OTHER INFORMATION: 6.147-AbS-785K G2

<400> SEQUENCE: 46

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Glu Val Gln Leu Val Gln
        115                 120                 125

Ser Gly Ala Glu Val Val Gln Pro Gly Ala Ser Val Lys Val Ser Cys
130                 135                 140

Ala Ala Ser Gly Tyr Thr Phe Thr Asp Tyr Asn Met His Trp Val Arg
145                 150                 155                 160

Gln Ala Pro Gly Gln Gly Leu Glu Trp Met Gly Glu Ile Asn Pro Asn
                165                 170                 175

Ser Gly Gly Ala Gly Tyr Asn Gln Lys Phe Lys Gly Arg Val Thr Met
            180                 185                 190

Thr Thr Asp Thr Ser Thr Ser Thr Ala Tyr Met Glu Leu Arg Ser Leu
        195                 200                 205

Arg Ser Asp Asp Thr Ala Val Tyr Tyr Cys Ala Arg Leu Gly Tyr Asp
    210                 215                 220

Asp Ile Tyr Asp Asp Trp Tyr Phe Asp Val Trp Gly Gln Gly Thr Thr
225                 230                 235                 240

Val Thr Val Ser Ser Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Asn
305                 310                 315                 320
```

Phe Gly Thr Gln Thr Tyr Thr Cys Asn Val Asp His Lys Pro Ser Asn
                325                 330                 335

Thr Lys Val Asp Lys Thr Val Glu Arg Lys Cys Cys Val Glu Cys Pro
            340                 345                 350

Pro Cys Pro Ala Pro Pro Val Ala Gly Pro Ser Val Phe Leu Phe Pro
        355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Phe Arg Val Val Ser Val Leu Thr Val
            420                 425                 430

Val His Gln Asp Trp Leu Asn Gly Lys Glu Tyr Lys Cys Lys Val Ser
        435                 440                 445

Asn Lys Gly Leu Pro Ala Pro Ile Glu Lys Thr Ile Ser Lys Thr Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Met Leu Asp Ser Asp Gly Ser Phe
        515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 47
<211> LENGTH: 987
<212> TYPE: DNA
<213> ORGANISM: ARTIFICIAL SEQUENCE
<220> FEATURE:
<223> OTHER INFORMATION: 6.147-AbS-785 LC

<400> SEQUENCE: 47
tcatacgtgc tcactcagcc gcccagcgta tcggtggctc ccggacagac ggcgcgaatc      60
acgtgcggtg ggaacaatat cggctccaag tcagtccatt ggtatcaaca gaaacctggt     120
caggcaccag tcctggtggt atacgatgac tcggacaggc cctcggagat tccggaacgc     180
ttctccggat cgaattcggg gaacacagcg accttgacga tcagcagagt ggaggccgga     240
gatgaagccg actactattg tcaggtgtgg gattccagct ccgaccacgt cgtatttgga     300
ggtgggacac ggcttaccgt cctcgggcag cccaaggctg cgccagacat tcagatgact     360
cagtcgcctt cgtcattgag cgcgtcggtg ggagatcggg tcacgattac ttgtcgggca     420
tcgcaagaca tctcgaacta tttgaattgg taccagcaaa agcctggtaa agcgcccaaa     480
cttcttatct actatacgtc ccgcctcctc tcgggcgtcc cgtcaaggtt tagcggatcg     540
ggaagcggga cggattcac actgacgatt tcatcacttc agcccgaaga tttcgccacc     600
tattactgtc agcaaggaga caccctgcca tacacttttg gcggtgggac aaaggtcgaa     660

-continued

```
atcaagcgta cggtggctgc accatctgtc ttcatcttcc cgccatctga tgagcagttg    720
aaatctggaa ctgcctctgt tgtgtgcctg ctgaataact tctatcccag agaggccaaa    780
gtacagtgga aggtggataa cgccctccaa tcgggtaact cccaggagag tgtcacagag    840
caggacagca aggacagcac ctacagcctc agcagcaccc tgacgctgag caaagcagac    900
tacgagaaac acaaagtcta cgcctgcgaa gtcacccatc agggcctgag ctcgcccgtc    960
acaaagagct tcaacagggg agagtgt                                        987
```

<210> SEQ ID NO 48
<211> LENGTH: 329
<212> TYPE: PRT
<213> ORGANISM: ARTIFICIAL SEQUENCE
<220> FEATURE:
<223> OTHER INFORMATION: 6.147-AbS-785 LC

<400> SEQUENCE: 48

```
Ser Tyr Val Leu Thr Gln Pro Pro Ser Val Ser Val Ala Pro Gly Gln
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Glu Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Arg Leu Thr Val Leu Gly Gln Pro Lys
            100                 105                 110

Ala Ala Pro Asp Ile Gln Met Thr Gln Ser Pro Ser Ser Leu Ser Ala
        115                 120                 125

Ser Val Gly Asp Arg Val Thr Ile Thr Cys Arg Ala Ser Gln Asp Ile
130                 135                 140

Ser Asn Tyr Leu Asn Trp Tyr Gln Gln Lys Pro Gly Lys Ala Pro Lys
145                 150                 155                 160

Leu Leu Ile Tyr Tyr Thr Ser Arg Leu Leu Ser Gly Val Pro Ser Arg
                165                 170                 175

Phe Ser Gly Ser Gly Ser Gly Thr Asp Phe Thr Leu Thr Ile Ser Ser
            180                 185                 190

Leu Gln Pro Glu Asp Phe Ala Thr Tyr Tyr Cys Gln Gln Gly Asp Thr
        195                 200                 205

Leu Pro Tyr Thr Phe Gly Gly Gly Thr Lys Val Glu Ile Lys Arg Thr
    210                 215                 220

Val Ala Ala Pro Ser Val Phe Ile Phe Pro Pro Ser Asp Glu Gln Leu
225                 230                 235                 240

Lys Ser Gly Thr Ala Ser Val Val Cys Leu Leu Asn Asn Phe Tyr Pro
                245                 250                 255

Arg Glu Ala Lys Val Gln Trp Lys Val Asp Asn Ala Leu Gln Ser Gly
            260                 265                 270

Asn Ser Gln Glu Ser Val Thr Glu Gln Asp Ser Lys Asp Ser Thr Tyr
        275                 280                 285

Ser Leu Ser Ser Thr Leu Thr Leu Ser Lys Ala Asp Tyr Glu Lys His
    290                 295                 300
```

Lys Val Tyr Ala Cys Glu Val Thr His Gln Gly Leu Ser Ser Pro Val
305                 310                 315                 320

Thr Lys Ser Phe Asn Arg Gly Glu Cys
            325

<210> SEQ ID NO 49
<211> LENGTH: 1719
<212> TYPE: DNA
<213> ORGANISM: ARTIFICIAL SEQUENCE
<220> FEATURE:
<223> OTHER INFORMATION: 6.37-AbL-167 G2

<400> SEQUENCE: 49

```
caggtacaac tggtcgagtc aggtggaggc gtggtccagc ccggacggtc gctcaggctc      60
agctgtgctg cgtcagggtt cacctttcg gggtatggga tgcactgggt gcgccaagca     120
ccgggaaaag ggcttgaatg ggtcgcggtc atttcctacg acgggaacga caaatactac    180
gcggactccg taaagggaag gttcacaatc agccgggata cgccaagaa tacgttgtat     240
ctccagatga attcgttgcg agcagaagat acggccgtgt actattgcgc gagagagctt    300
cgcgtgttgt ggggacaggg tactctggtg acggtctcct cagcgtcaac gaaaggaccg    360
tcggtgttcc ccttggcccc tgaggtgcag ctcgtacagt cgggtgcgga agtaaagaaa    420
cccggctcat ccgtgaaagt ctcgtgtaaa gcctccgggt tcaccttcac agactacatt    480
atgcactggg tgcggcaggc ccctgggcag ggccttgaat ggatggggta tatcaacccc    540
tacaatgatg acacggagta taacgaaaag tttaagggaa gggtgacaat cacggcggat    600
aagagcacca gcactgcata catggagctc tcgtcattgc gctcggagga cactgcagtc    660
tactattgcg cgagatccat ctactattac gatgcgccgt ttgcttattg gggacaagga    720
acgctggtca ccgtctctag tgcctccacc aagggcccat cggtcttccc cctggcgccc    780
tgctccagga gcacctccga gagcacagcg gccctgggct gcctggtcaa ggactacttc    840
cccgaaccgg tgacggtgtc gtggaactca ggcgctctga ccagcggcgt gcacaccttc    900
ccagctgtcc tacagtcctc aggactctac tccctcagca gcgtggtgac cgtgccctcc    960
agcaacttcg gcacccagac ctacacctgc aacgtagatc acaagcccag caacaccaag   1020
gtggacaaga cagttgagcg caaatgttgt gtcgagtgcc caccgtgccc agcaccacct   1080
gtggcaggac cgtcagtctt cctcttcccc ccaaaaccca aggacaccct catgatctcc   1140
cggacccctg aggtcacgtg cgtggtggtg gacgtgagcc acgaagaccc cgaggtccag   1200
ttcaactggt acgtggacgg cgtggaggtg cataatgcca agacaaagcc acgggaggag   1260
cagttcaaca gcacgttccg tgtggtcagc gtcctcaccg ttgtgcacca ggactggctg   1320
aacggcaagg agtacaagtg caaggtctcc aacaaaggcc tcccagcccc catcgagaaa   1380
accatctcca aaccaaagg gcagccccga gaaccacagg tgtacaccct gcccccatcc   1440
cgggaggaga tgaccaagaa ccaggtcagc ctgacctgcc tggtcaaagg cttctacccc   1500
agcgacatcg ccgtggagtg ggagagcaat gggcagccgg agaacaacta caagaccaca   1560
cctcccatgc tggactccga cggctccttc ttcctctaca gcaagctcac cgtggacaag   1620
agcaggtggc agcaggggaa cgtcttctca tgctccgtga tgcatgaggc tctgcacaac   1680
cactacacgc agaagagcct ctccctgtct ccgggtaaa                          1719
```

<210> SEQ ID NO 50
<211> LENGTH: 573
<212> TYPE: PRT

<213> ORGANISM: ARTIFICIAL SEQUENCE
<220> FEATURE:
<223> OTHER INFORMATION: 6.37-AbL-167 G2

<400> SEQUENCE: 50

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser Ala Ser Thr Lys Gly Pro Ser Val Phe Pro Leu Ala Pro Glu
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Phe Thr Phe Thr Asp Tyr Ile
145                 150                 155                 160

Met His Trp Val Arg Gln Ala Pro Gly Gln Gly Leu Glu Trp Met Gly
                165                 170                 175

Tyr Ile Asn Pro Tyr Asn Asp Asp Thr Glu Tyr Asn Glu Lys Phe Lys
            180                 185                 190

Gly Arg Val Thr Ile Thr Ala Asp Lys Ser Thr Ser Thr Ala Tyr Met
        195                 200                 205

Glu Leu Ser Ser Leu Arg Ser Glu Asp Thr Ala Val Tyr Tyr Cys Ala
    210                 215                 220

Arg Ser Ile Tyr Tyr Asp Ala Pro Phe Ala Tyr Trp Gly Gln Gly
225                 230                 235                 240

Thr Leu Val Thr Val Ser Ser Ala Ser Thr Lys Gly Pro Ser Val Phe
            245                 250                 255

Pro Leu Ala Pro Cys Ser Arg Ser Thr Ser Glu Ser Thr Ala Ala Leu
        260                 265                 270

Gly Cys Leu Val Lys Asp Tyr Phe Pro Glu Pro Val Thr Val Ser Trp
    275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Asn Phe Gly Thr Gln Thr Tyr Thr Cys Asn Val Asp His Lys Pro
                325                 330                 335

Ser Asn Thr Lys Val Asp Lys Thr Val Glu Arg Lys Cys Cys Val Glu
            340                 345                 350

Cys Pro Pro Cys Pro Ala Pro Pro Val Ala Gly Pro Ser Val Phe Leu
        355                 360                 365

Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Gln
```

```
               385                 390                 395                 400
Phe Asn Trp Tyr Val Asp Gly Val Glu Val His Asn Ala Lys Thr Lys
                405                 410                 415

Pro Arg Glu Glu Gln Phe Asn Ser Thr Phe Arg Val Val Ser Val Leu
            420                 425                 430

Thr Val His Gln Asp Trp Leu Asn Gly Lys Glu Tyr Lys Cys Lys
        435                 440                 445

Val Ser Asn Lys Gly Leu Pro Ala Pro Ile Glu Lys Thr Ile Ser Lys
    450                 455                 460

Thr Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
                500                 505                 510

Pro Glu Asn Asn Tyr Lys Thr Thr Pro Pro Met Leu Asp Ser Asp Gly
            515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570
```

<210> SEQ ID NO 51
<211> LENGTH: 1014
<212> TYPE: DNA
<213> ORGANISM: ARTIFICIAL SEQUENCE
<220> FEATURE:
<223> OTHER INFORMATION: 6.37-AbL-167 LC

<400> SEQUENCE: 51

```
gatattgtga tgacccagac gccgttgtca ctgagcgtca cacccggaca gcccgcgtcg      60
attagctgca aatcgggaca atcgcttctc cactcggacg ggaaaacgta tctttactgg     120
tatttgcaaa agccagggca gcctccccag tttcttatct acgaagtgtc gaacaggttt     180
tccagagtac ctgaccgatt ctccggatca ggtagcggaa cggacttcac tctgcgcatc     240
tcacgggtcg aagccgagga tgtgggcatc tactactgta tgcagtcaat tcagctcccg     300
tggacattcg gtcaggggac ccaagtagag atcaagcgca cagtggctgc tccatccgtc     360
tttatcttcc ctccagacat tcaaatgaca cagtcgccct cctcgctctc ggcgtcagtc     420
ggggatcgcg tgacaatcac gtgtcgggcc agccaggaca tttcgagcta cctcaactgg     480
tatcagcaga aaccggggaa agcgccgaag ctgcttatct actccacctc aaggttgaat     540
tccggagtac cctcaagatt ttcgggtagc ggatcaggaa ccgacttcac acttacgatc     600
tcgtcgttgc agccagaaga tttcgcaacg tactattgcc agcaagatat caagcaccct     660
acgtttggtc agggcactaa agtggagatt aagcgtacgg tggctgcacc atctgtcttc     720
atcttcccgc catctgatga gcagttgaaa tctggaactg cctctgttgt gtgcctgctg     780
aataacttct atcccagaga ggccaaagta cagtggaagg tggataacgc cctccaatcg     840
ggtaactccc aggagagtgt cacagagcag gacagcaagg acagcaccta cagcctcagc     900
agcaccctga cgctgagcaa agcagactac gagaaacaca agtctacgc ctgcgaagtc     960
acccatcagg gcctgagctc gcccgtcaca aagagcttca caggggaga gtgt           1014
```

<210> SEQ ID NO 52
<211> LENGTH: 338
<212> TYPE: PRT
<213> ORGANISM: ARTIFICIAL SEQUENCE
<220> FEATURE:
<223> OTHER INFORMATION: 6.37-AbL-167 LC

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

Arg Thr Val Ala Ala Pro Ser Val Phe Ile Phe Pro Pro Asp Ile Gln
        115                 120                 125

Met Thr Gln Ser Pro Ser Ser Leu Ser Ala Ser Val Gly Asp Arg Val
    130                 135                 140

Thr Ile Thr Cys Arg Ala Ser Gln Asp Ile Ser Ser Tyr Leu Asn Trp
145                 150                 155                 160

Tyr Gln Gln Lys Pro Gly Lys Ala Pro Lys Leu Leu Ile Tyr Ser Thr
                165                 170                 175

Ser Arg Leu Asn Ser Gly Val Pro Ser Arg Phe Ser Gly Ser Gly Ser
            180                 185                 190

Gly Thr Asp Phe Thr Leu Thr Ile Ser Ser Leu Gln Pro Glu Asp Phe
        195                 200                 205

Ala Thr Tyr Tyr Cys Gln Gln Asp Ile Lys His Pro Thr Phe Gly Gln
    210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 53
<211> LENGTH: 1734
<212> TYPE: DNA

<213> ORGANISM: ARTIFICIAL SEQUENCE
<220> FEATURE:
<223> OTHER INFORMATION: 785K-AbL-6.147 G2

<400> SEQUENCE: 53

```
gaggtgcagc tcgtgcagtc cggagccgag gtggtgcagc ctggggcatc cgtcaaagtc    60
tcgtgcgccg cgtcagggta cacattcacc gactataaca tgcattgggt ccggcaggct   120
cccggtcagg ggctggagtg gatgggggaa atcaatccga actccggagg ggcaggatac   180
aatcaaaagt ttaagggacg cgtaacgatg accactgaca cgtcaacctc cacggcgtat   240
atggagctca gaagcctccg aagcgacgac actgctgtct attactgtgc gagactggga   300
tatgatgata tctacgacga ttggtacttc gatgtatggg gacaagggac gacggtcacg   360
gtctcctcag cgtcaacgaa aggaccgtcg gtgttcccct ggcccctca ggtgcagctt   420
gtcgagagcg gtggaggggt ggtacaaccc ggaagatcac tccggctttc atgcgcagca   480
tccggtttta cattttcgcg gtatgacatg cactgggtga gacaggcacc aggaaaaggg   540
ctggagtggg tggccatcat cttctatgat gggtccaata agtactacgc cgacccggta   600
aaagggaggt tcactattag ccgcgacaac tcgaagaata cgctgtacct gcagatgaac   660
tcgttgcgag ccgaagatac cgcggtctac tattgtgcga cgctcgcggc tgcgttcgat   720
tactggggcc aaggaacatt ggtcaccgtc tctagtgcct ccaccaaggg cccatcggtc   780
ttccccctgg cgccctgctc caggagcacc tccgagagca gcggccct gggctgcctg   840
gtcaaggact acttccccga accggtgacg gtgtcgtgga actcaggcgc tctgaccagc   900
ggcgtgcaca ccttcccagc tgtcctacag tcctcaggac tctactccct cagcagcgtg   960
gtgaccgtgc cctccagcaa cttcggcacc cagacctaca cctgcaacgt agatcacaag  1020
cccagcaaca ccaaggtgga caagacagtt gagcgcaaat gttgtgtcga gtgcccaccg  1080
tgcccagcac cacctgtggc aggaccgtca gtcttcctct tccccccaaa acccaaggac  1140
accctcatga tctcccggac ccctgaggtc acgtgcgtgg tggtggacgt gagccacgaa  1200
gaccccgagg tccagttcaa ctggtacgtg gacggcgtgg aggtgcataa tgccaagaca  1260
aagccacggg aggagcagtt caacagcacg ttccgtgtgg tcagcgtcct caccgttgtg  1320
caccaggact ggctgaacgg caaggagtac aagtgcaagg tctccaacaa aggcctccca  1380
gccccatcg agaaaccat ctccaaaacc aaagggcagc cccgagaacc acaggtgtac  1440
accctgcccc catcccggga ggagatgacc aagaaccagg tcagcctgac ctgcctggtc  1500
aaaggcttct accccagcga catcgccgtg gagtgggaga gcaatgggca gccggagaac  1560
aactacaaga ccacacctcc catgctggac tccgacggct ccttcttcct ctacagcaag  1620
ctcaccgtgg acaagagcag gtggcagcag gggaacgtct tctcatgctc cgtgatgcat  1680
gaggctctgc acaaccacta cacgcagaag agcctctccc tgtctccggg taaa         1734
```

<210> SEQ ID NO 54
<211> LENGTH: 578
<212> TYPE: PRT
<213> ORGANISM: ARTIFICIAL SEQUENCE
<220> FEATURE:
<223> OTHER INFORMATION: 785K-AbL-6.147 G2

<400> SEQUENCE: 54

```
Glu Val Gln Leu Val Gln Ser Gly Ala Glu Val Val Gln Pro Gly Ala
1               5                   10                  15

Ser Val Lys Val Ser Cys Ala Ala Ser Gly Tyr Thr Phe Thr Asp Tyr
            20                  25                  30
```

```
Asn Met His Trp Val Arg Gln Ala Pro Gly Gln Gly Leu Glu Trp Met
         35                  40                  45
Gly Glu Ile Asn Pro Asn Ser Gly Gly Ala Gly Tyr Asn Gln Lys Phe
 50                  55                  60
Lys Gly Arg Val Thr Met Thr Thr Asp Thr Ser Thr Ser Thr Ala Tyr
 65                  70                  75                  80
Met Glu Leu Arg Ser Leu Arg Ser Asp Thr Ala Val Tyr Tyr Cys
             85                  90                  95
Ala Arg Leu Gly Tyr Asp Asp Ile Tyr Asp Asp Trp Tyr Phe Asp Val
             100                 105                 110
Trp Gly Gln Gly Thr Thr Val Thr Val Ser Ser Ala Ser Thr Lys Gly
             115                 120                 125
Pro Ser Val Phe Pro Leu Ala Pro Gln Val Gln Leu Val Glu Ser Gly
             130                 135                 140
Gly Gly Val Val Gln Pro Gly Arg Ser Leu Arg Leu Ser Cys Ala Ala
145                 150                 155                 160
Ser Gly Phe Thr Phe Ser Arg Tyr Asp Met His Trp Val Arg Gln Ala
                 165                 170                 175
Pro Gly Lys Gly Leu Glu Trp Val Ala Ile Ile Phe Tyr Asp Gly Ser
             180                 185                 190
Asn Lys Tyr Tyr Ala Asp Pro Val Lys Gly Arg Phe Thr Ile Ser Arg
             195                 200                 205
Asp Asn Ser Lys Asn Thr Leu Tyr Leu Gln Met Asn Ser Leu Arg Ala
 210                 215                 220
Glu Asp Thr Ala Val Tyr Tyr Cys Ala Thr Leu Ala Ala Ala Phe Asp
225                 230                 235                 240
Tyr Trp Gly Gln Gly Thr Leu Val Thr Val Ser Ser Ala Ser Thr Lys
                 245                 250                 255
Gly Pro Ser Val Phe Pro Leu Ala Pro Cys Ser Arg Ser Thr Ser Glu
             260                 265                 270
Ser Thr Ala Ala Leu Gly Cys Leu Val Lys Asp Tyr Phe Pro Glu Pro
         275                 280                 285
Val Thr Val Ser Trp Asn Ser Gly Ala Leu Thr Ser Gly Val His Thr
 290                 295                 300
Phe Pro Ala Val Leu Gln Ser Ser Gly Leu Tyr Ser Leu Ser Ser Val
305                 310                 315                 320
Val Thr Val Pro Ser Ser Asn Phe Gly Thr Gln Thr Tyr Thr Cys Asn
                 325                 330                 335
Val Asp His Lys Pro Ser Asn Thr Lys Val Asp Lys Thr Val Glu Arg
             340                 345                 350
Lys Cys Cys Val Glu Cys Pro Pro Cys Pro Ala Pro Pro Val Ala Gly
             355                 360                 365
Pro Ser Val Phe Leu Phe Pro Pro Lys Pro Lys Asp Thr Leu Met Ile
         370                 375                 380
Ser Arg Thr Pro Glu Val Thr Cys Val Val Val Asp Val Ser His Glu
385                 390                 395                 400
Asp Pro Glu Val Gln Phe Asn Trp Tyr Val Asp Gly Val Glu Val His
                 405                 410                 415
Asn Ala Lys Thr Lys Pro Arg Glu Glu Gln Phe Asn Ser Thr Phe Arg
             420                 425                 430
Val Val Ser Val Leu Thr Val Val His Gln Asp Trp Leu Asn Gly Lys
         435                 440                 445
```

Glu Tyr Lys Cys Lys Val Ser Asn Lys Gly Leu Pro Ala Pro Ile Glu
450                 455                 460

Lys Thr Ile Ser Lys Thr Lys Gly Gln Pro Arg Glu Pro Gln Val Tyr
465                 470                 475                 480

Thr Leu Pro Pro Ser Arg Glu Glu Met Thr Lys Asn Gln Val Ser Leu
            485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Met
            515                 520                 525

Leu Asp Ser Asp Gly Ser Phe Phe Leu Tyr Ser Lys Leu Thr Val Asp
530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
            565                 570                 575

Gly Lys

<210> SEQ ID NO 55
<211> LENGTH: 1713
<212> TYPE: DNA
<213> ORGANISM: ARTIFICIAL SEQUENCE
<220> FEATURE:
<223> OTHER INFORMATION: 785K-AbS-6.147 G2

<400> SEQUENCE: 55

```
gaggtgcagc tcgtgcagtc cggagccgag gtggtgcagc tggggcatc cgtcaaagtc      60
tcgtgcgccg cgtcagggta cacattcacc gactataaca tgcattgggt ccggcaggct    120
cccggtcagg gctggagtg gatgggggaa atcaatccga actccggagg ggcaggatac    180
aatcaaaagt ttaagggacg cgtaacgatg accactgaca cgtcaacctc cacggcgtat    240
atggagctca aagcctccg aagcgacgac actgctgtct attactgtgc gagactggga    300
tatgatgata tctacgacga ttggtacttc gatgtatggg gacaagggac gacggtcacg    360
gtctcctcag cgtcaacgaa aggaccgcag gtgcagcttg tcgagagcgg tggaggggtg    420
gtacaacccg gaagatcact ccggctttca tgcgcagcat ccggttttac attttcgcgg    480
tatgacatgc actgggtgag acaggcacca ggaaaagggc tggagtgggt ggccatcatc    540
ttctatgatg ggtccaataa gtactacgcc gacccggtaa agggaggtt cactattagc    600
cgcgacaact cgaagaatac gctgtacctg cagatgaact cgttgcgagc cgaagatacc    660
gcggtctact attgtgcgac gctcgcggct gcgttcgatt actgggccaa ggaacattgg    720
gtcaccgtct ctagtgcctc caccaagggc ccatcggtct tccccctggc gccctgctcc    780
aggagcacct ccgagagcac agcggccctg ggctgcctgg tcaaggacta cttccccgaa    840
ccggtgacgg tgtcgtggaa ctcaggcgct ctgaccagcg gcgtgcacac cttcccagct    900
gtcttacagt cctcaggact ctactccctc agcagcgtgg tgaccgtgcc ctccagcaac    960
ttcggcaccc agacctacac ctgcaacgta gatcacaagc ccagcaacac caaggtggac   1020
aagacagttg agcgcaaatg ttgtgtcgag tgcccaccgt gcccagcacc acctgtggca   1080
ggaccgtcag tcttcctctt ccccccaaaa cccaaggaca ccctcatgat ctcccggacc   1140
cctgaggtca cgtgcgtggt ggtggacgtg agccacgaag accccgaggt ccagttcaac   1200
tggtacgtgg acggcgtgga ggtgcataat gccaagacaa agccacggga ggagcagttc   1260
aacagcacgt tccgtgtggt cagcgtcctc accgttgtgc accaggactg gctgaacggc   1320
```

-continued

```
aaggagtaca agtgcaaggt ctccaacaaa ggcctcccag cccccatcga gaaaaccatc    1380
tccaaaacca aagggcagcc ccgagaacca caggtgtaca ccctgccccc atcccgggag    1440
gagatgacca agaaccaggt cagcctgacc tgcctggtca aaggcttcta ccccagcgac    1500
atcgccgtgg agtgggagag caatgggcag ccggagaaca actacaagac cacacctccc    1560
atgctggact ccgacggctc cttcttcctc tacagcaagc tcaccgtgga caagagcagg    1620
tggcagcagg ggaacgtctt tcatgctcc gtgatgcatg aggctctgca caaccactac    1680
acgcagaaga gcctctccct gtctccgggt aaa                                 1713
```

<210> SEQ ID NO 56
<211> LENGTH: 571
<212> TYPE: PRT
<213> ORGANISM: ARTIFICIAL SEQUENCE
<220> FEATURE:
<223> OTHER INFORMATION: 785K-AbS-6.147 G2

<400> SEQUENCE: 56

```
Glu Val Gln Leu Val Gln Ser Gly Ala Glu Val Val Gln Pro Gly Ala
1               5                   10                  15

Ser Val Lys Val Ser Cys Ala Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Gln Val Gln Leu Val Glu Ser Gly Gly Val Val Gln Pro Gly
    130                 135                 140

Arg Ser Leu Arg Leu Ser Cys Ala Ala Ser Gly Phe Thr Phe Ser Arg
145                 150                 155                 160

Tyr Asp Met His Trp Val Arg Gln Ala Pro Gly Lys Gly Leu Glu Trp
                165                 170                 175

Val Ala Ile Ile Phe Tyr Asp Gly Ser Asn Lys Tyr Tyr Ala Asp Pro
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Thr Leu Ala Ala Ala Phe Asp Tyr Trp Gly Gln Gly Thr Leu
225                 230                 235                 240

Val Thr Val Ser Ser Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270

Leu Val Lys Asp Tyr Phe Pro Glu Pro Val Thr Val Ser Trp Asn Ser
        275                 280                 285
```

Gly Ala Leu Thr Ser Gly Val His Thr Phe Pro Ala Val Leu Gln Ser
            290                 295                 300

Ser Gly Leu Tyr Ser Leu Ser Ser Val Val Thr Val Pro Ser Ser Asn
305                 310                 315                 320

Phe Gly Thr Gln Thr Tyr Thr Cys Asn Val Asp His Lys Pro Ser Asn
                325                 330                 335

Thr Lys Val Asp Lys Thr Val Glu Arg Lys Cys Cys Val Glu Cys Pro
            340                 345                 350

Pro Cys Pro Ala Pro Pro Val Ala Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Phe Arg Val Val Ser Val Leu Thr Val
            420                 425                 430

Val His Gln Asp Trp Leu Asn Gly Lys Glu Tyr Lys Cys Lys Val Ser
        435                 440                 445

Asn Lys Gly Leu Pro Ala Pro Ile Glu Lys Thr Ile Ser Lys Thr Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Met Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 57
<211> LENGTH: 1725
<212> TYPE: DNA
<213> ORGANISM: ARTIFICIAL SEQUENCE
<220> FEATURE:
<223> OTHER INFORMATION: 6.37-3x-167 G2

<400> SEQUENCE: 57
caggtacaac tggtcgagtc aggtggaggc gtggtccagc ccggacggtc gctcaggctc      60
agctgtgctg cgtcagggtt caccttttcg gggtatggga tgcactgggt gcgccaagca     120
ccgggaaaag ggcttgaatg ggtcgcggtc atttcctacg acgggaacga caaatactac     180
gcggactccg taaagggaag gttcacaatc agccgggata cgccaagaa tacgttgtat      240 ctccagatga attcgttgcg agcagaagat acggccgtgt actattgcgc gagagagctt     300
cgcgtgttgt ggggacaggg tactctggtg acagtgagct caggggtgg cggttcgggc     360 ggtgaggct cggaggtgg tggatccgag gtgcagctcg tacagtcggg tgcggaagta      420 aagaaaccg gctcatccgt gaaagtctcg tgtaaagcct ccgggttcac cttcacagac     480

```
tacattatgc actgggtgcg gcaggcccct gggcagggcc ttgaatggat ggggtatatc    540 aaccctaca atgatgacac ggagtataac gaaaagttta agggaagggt gacaatcacg    600
gcggataaga gcaccagcac tgcatacatg gagctctcgt cattgcgctc ggaggacact    660
gcagtctact attgcgcgag atccatctac tattacgatg cgccgtttgc ttattgggga    720
caaggaacgc tggtcaccgt ctctagtgcc tccaccaagg gcccatcggt cttccccctg    780
gcgccctgct ccaggagcac ctccgagagc acagcggccc tgggctgcct ggtcaaggac    840
tacttccccg aaccggtgac ggtgtcgtgg aactcaggcg ctctgaccag cggcgtgcac    900
accttcccag ctgtcctaca gtcctcagga ctctactccc tcagcagcgt ggtgaccgtg    960
ccctccagca acttcggcac ccagacctac acctgcaacg tagatcacaa gcccagcaac   1020
accaaggtgg acaagacagt tgagcgcaaa tgttgtgtcg agtgcccacc gtgcccagca   1080
ccacctgtgg caggaccgtc agtcttcctc ttccccccaa aacccaagga caccctcatg   1140
atctcccgga cccctgaggt cacgtgcgtg gtggtggacg tgagccacga agaccccgag   1200
gtccagttca actggtacgt ggacggcgtg gaggtgcata atgccaagac aaagccacgg   1260
gaggagcagt tcaacagcac gttccgtgtg gtcagcgtcc tcaccgttgt gcaccaggac   1320
tggctgaacg gcaaggagta caagtgcaag gtctccaaca aaggcctccc agcccccatc   1380
gagaaaacca tctccaaaac caagggcagc cccgagaac cacaggtgta cccctgccc    1440 ccatcccggg aggagatgac caagaaccag gtcagcctga cctgcctggt caaaggcttc   1500
taccccagcg acatcgccgt ggagtgggag agcaatgggc agccggagaa caactacaag   1560
accacacctc ccatgctgga ctccgacggc tccttcttcc tctacagcaa gctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaa               1725
```

<210> SEQ ID NO 58
<211> LENGTH: 575
<212> TYPE: PRT
<213> ORGANISM: ARTIFICIAL SEQUENCE
<220> FEATURE:
<223> OTHER INFORMATION: 6.37-3x-167 G2

<400> SEQUENCE: 58

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Glu Val Gln Leu Val Gln Ser Gly Ala Glu Val Lys Lys Pro Gly
    130                 135                 140
```

-continued

```
Ser Ser Val Lys Val Ser Cys Lys Ala Ser Gly Phe Thr Phe Thr Asp
145                 150                 155                 160

Tyr Ile Met His Trp Val Arg Gln Ala Pro Gly Gln Gly Leu Glu Trp
                165                 170                 175

Met Gly Tyr Ile Asn Pro Tyr Asn Asp Asp Thr Glu Tyr Asn Glu Lys
            180                 185                 190

Phe Lys Gly Arg Val Thr Ile Thr Ala Asp Lys Ser Thr Ser Thr Ala
        195                 200                 205

Tyr Met Glu Leu Ser Ser Leu Arg Ser Glu Asp Thr Ala Val Tyr Tyr
210                 215                 220

Cys Ala Arg Ser Ile Tyr Tyr Asp Ala Pro Phe Ala Tyr Trp Gly
225                 230                 235                 240

Gln Gly Thr Leu Val Thr Val Ser Ser Ala Ser Thr Lys Gly Pro Ser
                245                 250                 255

Val Phe Pro Leu Ala Pro Cys Ser Arg Ser Thr Ser Glu Ser Thr Ala
            260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
                325                 330                 335

Lys Pro Ser Asn Thr Lys Val Asp Lys Thr Val Glu Arg Lys Cys Cys
            340                 345                 350

Val Glu Cys Pro Pro Cys Pro Ala Pro Pro Val Ala Gly Pro Ser Val
        355                 360                 365

Phe Leu Phe Pro Pro Lys Pro Lys Asp Thr Leu Met Ile Ser Arg Thr
370                 375                 380

Pro Glu Val Thr Cys Val Val Val Asp Val Ser His Glu Asp Pro Glu
385                 390                 395                 400

Val Gln Phe Asn Trp Tyr Val Asp Gly Val Glu Val His Asn Ala Lys
                405                 410                 415

Thr Lys Pro Arg Glu Glu Gln Phe Asn Ser Thr Phe Arg Val Val Ser
            420                 425                 430

Val Leu Thr Val Val His Gln Asp Trp Leu Asn Gly Lys Glu Tyr Lys
        435                 440                 445

Cys Lys Val Ser Asn Lys Gly Leu Pro Ala Pro Ile Glu Lys Thr Ile
450                 455                 460

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Met Leu Asp Ser
        515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560
```

His Asn His Tyr Thr Gln Lys Ser Leu Ser Leu Ser Pro Gly Lys
            565                 570                 575

<210> SEQ ID NO 59
<211> LENGTH: 1020
<212> TYPE: DNA
<213> ORGANISM: ARTIFICIAL SEQUENCE
<220> FEATURE:
<223> OTHER INFORMATION: 6.37-3x-167 LC

<400> SEQUENCE: 59

```
gatattgtga tgacccagac gccgttgtca ctgagcgtca cacccggaca gcccgcgtcg      60
attagctgca atcgggaca atcgcttctc cactcggacg ggaaaacgta tctttactgg     120
tatttgcaaa agccagggca gcctccccag tttcttatct acgaagtgtc gaacaggttt    180
tccagagtac ctgaccgatt ctccggatca ggtagcggaa cggacttcac tctgcgcatc    240
tcacgggtcg aagccgagga tgtgggcatc tactactgta tgcagtcaat tcagctcccg    300
tggacattcg gtcaggggac ccaagtagag atcaaggggg gtggcggttc gggcggtgga    360
ggctcgggag gtggtggatc cgacattcaa atgacacagt cgccctcctc gctctcggcg    420
tcagtcgggg atcgcgtgac aatcacgtgt cgggccagcc aggacatttc gagctacctc    480
aactggtatc agcagaaacc ggggaaagcg ccgaagctgc ttatctactc cacctcaagg    540
ttgaattccg gagtaccctc aagatttcg ggtagcggat caggaaccga cttcacactt    600
acgatctcgt cgttgcagcc agaagatttc gcaacgtact attgccagca agatatcaag    660
caccctacgt ttggtcaggg cactaaagtg gagattaagc gtacggtggc tgcaccatct    720
gtcttcatct tcccgccatc tgatgagcag ttgaaatctg gaactgcctc tgttgtgtgc    780
ctgctgaata acttctatcc cagagaggcc aaagtacagt ggaaggtgga taacgccctc    840
caatcgggta actcccagga gagtgtcaca gagcaggaca gcaaggacag cacctacagc    900
ctcagcagca ccctgacgct gagcaaagca gactacgaga aacacaaagt ctacgcctgc    960
gaagtcaccc atcagggcct gagctcgccc gtcacaaaga gcttcaacag gggagagtgt   1020
```

<210> SEQ ID NO 60
<211> LENGTH: 340
<212> TYPE: PRT
<213> ORGANISM: ARTIFICIAL SEQUENCE
<220> FEATURE:
<223> OTHER INFORMATION: 6.37-3x-167 LC

<400> SEQUENCE: 60

Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

Gly Gly Gly Gly Ser Gly Gly Gly Gly Ser Gly Gly Gly Gly Ser Asp

```
                115                 120                 125
Ile Gln Met Thr Gln Ser Pro Ser Ser Leu Ser Ala Ser Val Gly Asp
130                 135                 140

Arg Val Thr Ile Thr Cys Arg Ala Ser Gln Asp Ile Ser Ser Tyr Leu
145                 150                 155                 160

Asn Trp Tyr Gln Gln Lys Pro Gly Lys Ala Pro Lys Leu Leu Ile Tyr
                165                 170                 175

Ser Thr Ser Arg Leu Asn Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Gln Gln Asp Ile Lys His Pro Thr Phe
    210                 215                 220

Gly Gln Gly Thr Lys Val Glu Ile Lys Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys
            340

<210> SEQ ID NO 61
<211> LENGTH: 1725
<212> TYPE: DNA
<213> ORGANISM: ARTIFICIAL SEQUENCE
<220> FEATURE:
<223> OTHER INFORMATION: 6.147-2x-785 G2 NA

<400> SEQUENCE: 61
caggtgcagc ttgtcgagag cggtggaggg gtggtacaac ccggaagatc actccggctt      60
tcatgcgcag catccggttt tacattttcg cggtatgaca tgcactgggt gagacaggca     120
ccaggaaaag ggctggagtg ggtggccatc atcttctatg atgggtccaa taagtactac     180
gccgacccgg taaagggag gttcactatt agccgcgaca actcgaagaa tacgctgtac     240
ctgcagatga actcgttgcg agccgaagat accgcggtct actattgtgc gacgctcgcg     300
gctgcgttcg attactgggg ccaaggaaca ttggtcacag tgagctcagg cggtggaggc     360
tcgggaggtg gtggatccga ggtgcagctc gtcagtccg agccgaggt gaagaagcct     420
ggggcatccg tcaaagtctc gtgcaaggcg tcagggtaca cattcaccga ctataacatg     480
cattgggtcc ggcaggctcc cggtcagggg ctggagtgga tggggaaat caatccgaac     540
tccggagggg caggatacaa tcaaaagttt aaggacgcg taacgatgac cactgacacg     600
tcaacctcca cggcgtatat ggagctcaga agcctccgaa gcgacgacac tgctgtctat     660
tactgtgcga gactgggata tgatgatatc tacgacgatt ggtacttcga tgtatgggga     720
caagggacga cggtcaccgt ctctagtgcc tccaccaagg gcccatcggt cttccccctg     780
```

-continued

```
gcgccctgct ccaggagcac ctccgagagc acagcggccc tgggctgcct ggtcaaggac    840
tacttccccg aaccggtgac ggtgtcgtgg aactcaggcg ctctgaccag cggcgtgcac    900
accttcccag ctgtcctaca gtcctcagga ctctactccc tcagcagcgt ggtgaccgtg    960
ccctccagca acttcggcac ccagacctac acctgcaacg tagatcacaa gcccagcaac   1020
accaaggtgg acaagacagt tgagcgcaaa tgttgtgtcg agtgcccacc gtgcccagca   1080
ccacctgtgg caggaccgtc agtcttcctc ttccccccaa acccaaggac acccctcatg   1140
atctcccgga cccctgaggt cacgtgcgtg gtggtggacg tgagccacga agaccccgag   1200
gtccagttca actggtacgt ggacggcgtg gaggtgcata atgccaagac aaagccacgg   1260
gaggagcagt tcaacagcac gttccgtgtg gtcagcgtcc tcaccgttgt gcaccaggac   1320
tggctgaacg gcaaggagta caagtgcaag gtctccaaca aaggcctccc agcccccatc   1380
gagaaaacca tctccaaaac caaagggcag ccccgagaac cacaggtgta caccctgccc   1440
ccatcccggg aggagatgac caagaaccag gtcagcctga cctgcctggt caaaggcttc   1500
taccccagcg acatcgccgt ggagtgggag agcaatgggc agccggagaa caactacaag   1560
accacacctc ccatgctgga ctccgacggc tccttcttcc tctacagcaa gctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaa                   1725
```

```
<210> SEQ ID NO 62
<211> LENGTH: 575
<212> TYPE: PRT
<213> ORGANISM: ARTIFICIAL SEQUENCE
<220> FEATURE:
<223> OTHER INFORMATION: 6.147-2x-785 G2

<400> SEQUENCE: 62

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Gly Gly Gly Gly Ser Gly Gly Gly Gly Ser Glu Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Asp Tyr Asn Met
145                 150                 155                 160

His Trp Val Arg Gln Ala Pro Gly Gln Gly Leu Glu Trp Met Gly Glu
                165                 170                 175

Ile Asn Pro Asn Ser Gly Gly Ala Gly Tyr Asn Gln Lys Phe Lys Gly
            180                 185                 190
```

```
Arg Val Thr Met Thr Thr Asp Thr Ser Thr Ser Thr Ala Tyr Met Glu
            195                 200                 205
Leu Arg Ser Leu Arg Ser Asp Asp Thr Ala Val Tyr Tyr Cys Ala Arg
        210                 215                 220
Leu Gly Tyr Asp Asp Ile Tyr Asp Asp Trp Tyr Phe Asp Val Trp Gly
225                 230                 235                 240
Gln Gly Thr Thr Val Thr Val Ser Ser Ala Ser Thr Lys Gly Pro Ser
                245                 250                 255
Val Phe Pro Leu Ala Pro Cys Ser Arg Ser Thr Ser Glu Ser Thr Ala
            260                 265                 270
Ala Leu Gly Cys Leu Val Lys Asp Tyr Phe Pro Glu Pro Val Thr Val
        275                 280                 285
Ser Trp Asn Ser Gly Ala Leu Thr Ser Gly Val His Thr Phe Pro Ala
    290                 295                 300
Val Leu Gln Ser Ser Gly Leu Tyr Ser Leu Ser Ser Val Val Thr Val
305                 310                 315                 320
Pro Ser Ser Asn Phe Gly Thr Gln Thr Tyr Thr Cys Asn Val Asp His
                325                 330                 335
Lys Pro Ser Asn Thr Lys Val Asp Lys Thr Val Glu Arg Lys Cys Cys
            340                 345                 350
Val Glu Cys Pro Pro Cys Pro Ala Pro Pro Val Ala Gly Pro Ser Val
        355                 360                 365
Phe Leu Phe Pro Pro Lys Pro Lys Asp Thr Leu Met Ile Ser Arg Thr
370                 375                 380
Pro Glu Val Thr Cys Val Val Val Asp Val Ser His Glu Asp Pro Glu
385                 390                 395                 400
Val Gln Phe Asn Trp Tyr Val Asp Gly Val Glu Val His Asn Ala Lys
            405                 410                 415
Thr Lys Pro Arg Glu Glu Gln Phe Asn Ser Thr Phe Arg Val Val Ser
        420                 425                 430
Val Leu Thr Val Val His Gln Asp Trp Leu Asn Gly Lys Glu Tyr Lys
    435                 440                 445
Cys Lys Val Ser Asn Lys Gly Leu Pro Ala Pro Ile Glu Lys Thr Ile
450                 455                 460
Ser Lys Thr Lys Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
            485                 490                 495
Val Lys Gly Phe Tyr Pro Ser Asp Ile Ala Val Glu Trp Glu Ser Asn
        500                 505                 510
Gly Gln Pro Glu Asn Asn Tyr Lys Thr Thr Pro Pro Met Leu Asp Ser
    515                 520                 525
Asp Gly Ser Phe Phe Leu Tyr Ser Lys Leu Thr Val Asp Lys Ser Arg
530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Lys
            565                 570                 575

<210> SEQ ID NO 63
<211> LENGTH: 996
<212> TYPE: DNA
<213> ORGANISM: ARTIFICIAL SEQUENCE
<220> FEATURE:
<223> OTHER INFORMATION: 6.147-2x-785 LC
```

<400> SEQUENCE: 63

```
tcatacgtgc tcactcagcc gcccagcgta tcggtggctc ccggacagac ggcgcgaatc    60
acgtgcggtg ggaacaatat cggctccaag tcagtccatt ggtatcaaca gaaacctggt   120
caggcaccag tcctggtggt atacgatgac tcggacaggc cctcggagat tccggaacgc   180
ttctccggat cgaattcggg gaacacagcg accttgacga tcagcagagt ggaggccgga   240
gatgaagccg actactattg tcaggtgtgg gattccagct ccgaccacgt cgtatttgga   300
ggtgggacac ggcttaccgt cttgggcggt ggaggctcgg aggtggtgga atccgacatt   360
cagatgactc agtcgccttc gtcattgagc gcgtcggtgg gagatcgggt cacgattact   420
tgtcgggcat cgcaagacat ctcgaactat ttgaattggt accagcaaaa gcctggtaaa   480
gcgcccaaac ttcttatcta ctatacgtcc cgcctcctct cgggcgtccc gtcaaggttt   540
agcggatcgg gaagcgggac ggatttcaca ctgacgattt catcacttca gcccgaagat   600
ttcgccacct attactgtca gcaaggagac accctgccat acacttttgg cggtgggaca   660
aaggtcgaaa tcaagcgtac ggtggctgca ccatctgtct tcatcttccc gccatctgat   720
gagcagttga atctggaaac tgcctctgtt gtgtgcctgc tgaataactt ctatcccaga   780
gaggccaaag tacagtggaa ggtggataac gccctccaat cgggtaactc ccaggagagt   840
gtcacagagc aggacagcaa ggacagcacc tacagcctca gcagcaccct gacgctgagc   900
aaagcagact acgagaaaca caaagtctac gcctgcgaag tcacccatca gggcctgagc   960
tcgcccgtca caaagagctt caacagggga gagtgt                             996
```

<210> SEQ ID NO 64
<211> LENGTH: 332
<212> TYPE: PRT
<213> ORGANISM: ARTIFICIAL SEQUENCE
<220> FEATURE:
<223> OTHER INFORMATION: 6.147-2x-785 LC

<400> SEQUENCE: 64

```
Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Arg Leu Thr Val Leu Gly Gly Gly Gly
            100                 105                 110

Ser Gly Gly Gly Gly Ser Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Asp Ile Ser Asn Tyr Leu Asn Trp Tyr Gln Gln Lys Pro Gly Lys
145                 150                 155                 160

Ala Pro Lys Leu Leu Ile Tyr Tyr Thr Ser Arg Leu Leu Ser Gly Val
                165                 170                 175
```

```
Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

Gly Asp Thr Leu Pro Tyr Thr Phe Gly Gly Gly Thr Lys Val Glu Ile
    210                 215                 220

Lys Arg Thr Val Ala Ala Pro Ser Val Phe Ile Phe Pro Pro Ser Asp
225                 230                 235                 240

Glu Gln Leu Lys Ser Gly Thr Ala Ser Val Val Cys Leu Leu Asn Asn
                245                 250                 255

Phe Tyr Pro Arg Glu Ala Lys Val Gln Trp Lys Val Asp Asn Ala Leu
            260                 265                 270

Gln Ser Gly Asn Ser Gln Glu Ser Val Thr Glu Gln Asp Ser Lys Asp
        275                 280                 285

Ser Thr Tyr Ser Leu Ser Ser Thr Leu Thr Leu Ser Lys Ala Asp Tyr
    290                 295                 300

Glu Lys His Lys Val Tyr Ala Cys Glu Val Thr His Gln Gly Leu Ser
305                 310                 315                 320

Ser Pro Val Thr Lys Ser Phe Asn Arg Gly Glu Cys
                325                 330

<210> SEQ ID NO 65
<211> LENGTH: 1725
<212> TYPE: DNA
<213> ORGANISM: ARTIFICIAL SEQUENCE
<220> FEATURE:
<223> OTHER INFORMATION: 6.147-AbL-167 G2

<400> SEQUENCE: 65
caggtgcagc ttgtcgagag cggtggaggg gtggtacaac ccggaagatc actccggctt      60
tcatgcgcag catccggttt acatttttcg cggtatgaca tgcactgggt gagacaggca     120
ccaggaaaag ggctggagtg ggtggccatc atcttctatg atgggtccaa taagtactac     180
gccgacccgg taaagggag gttcactatt agccgcgaca actcgaagaa tacgctgtac     240
ctgcagatga actcgttgcg agccgaagat accgcggtct actattgtgc gacgctcgcg     300
gctgcgttcg attactgggg ccaaggaaca ttggtcacgg tctcctcagc gtcaacgaaa     360
ggaccgtcgg tgttcccctt ggcccctgag gtgcagctcg tacagtcggg tgcggaagta     420
aagaaacccg gctcatccgt gaaagtctcg tgtaaagcct ccgggttcac cttcacagac     480
tacattatgc actgggtgcg gcaggcccct gggcagggcc ttgaatggat ggggtatatc     540
aacccctaca atgatgacac ggagtataac gaaaagtttta agggaagggt gacaatcacg     600
gcggataaga gcaccagcac tgcatacatg gagctctcgt cattgcgctc ggaggacact     660
gcagtctact attgcgcgag atccatctac tattacgatg cgccgtttgc ttattgggga     720
caaggaacgc tggtcaccgt ctctagtgcc tccaccaagg gcccatcggt cttccccctg     780
gcgccctgct ccaggagcac ctccgagagc acagcggccc tgggctgcct ggtcaaggac     840
tacttccccg aaccggtgac ggtgtcgtgg aactcaggcg ctctgaccag cggcgtgcac     900
accttcccag ctgtcctaca gtcctcagga ctctactccc tcagcagcgt ggtgaccgtg     960
ccctccagca acttcggcac ccagacctac acctgcaacg tagatcacaa gcccagcaac    1020
accaaggtgg acaagacagt tgagcgcaaa tgttgtgtcg agtgcccacc gtgcccagca    1080
ccacctgtgg caggaccgtc agtcttcctc ttccccccaa aacccaagga caccctcatg    1140
```

```
atctcccgga cccctgaggt cacgtgcgtg gtggtggacg tgagccacga agaccccgag    1200
gtccagttca actggtacgt ggacggcgtg gaggtgcata atgccaagac aaagccacgg    1260
gaggagcagt tcaacagcac gttccgtgtg gtcagcgtcc tcaccgttgt gcaccaggac    1320
tggctgaacg gcaaggagta caagtgcaag gtctccaaca aaggcctccc agcccccatc    1380
gagaaaacca tctccaaaac caagggcagc cccgagaac acaggtgta cccctgccc      1440 ccatcccggg aggagatgac caagaaccag gtcagcctga cctgcctggt caaaggcttc    1500
taccccagcg acatcgccgt ggagtgggag agcaatgggc agccggagaa caactacaag    1560
accacacctc ccatgctgga ctccgacggc tccttcttcc tctacagcaa gctcaccgtg    1620
gacaagagca ggtggcagca ggggaacgtc ttctcatgct ccgtgatgca tgaggctctg    1680
cacaaccact acacgcagaa gagcctctcc ctgtctccgg gtaaa                   1725
```

<210> SEQ ID NO 66
<211> LENGTH: 575
<212> TYPE: PRT
<213> ORGANISM: ARTIFICIAL SEQUENCE
<220> FEATURE:
<223> OTHER INFORMATION: 6.147-AbL-167 G2

<400> SEQUENCE: 66

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Glu Val Gln Leu Val Gln Ser Gly Ala Glu Val Lys Lys Pro Gly
    130                 135                 140

Ser Ser Val Lys Val Ser Cys Lys Ala Ser Gly Phe Thr Phe Thr Asp
145                 150                 155                 160

Tyr Ile Met His Trp Val Arg Gln Ala Pro Gly Gln Gly Leu Glu Trp
                165                 170                 175

Met Gly Tyr Ile Asn Pro Tyr Asn Asp Asp Thr Glu Tyr Asn Glu Lys
            180                 185                 190

Phe Lys Gly Arg Val Thr Ile Thr Ala Asp Lys Ser Thr Ser Thr Ala
        195                 200                 205

Tyr Met Glu Leu Ser Ser Leu Arg Ser Glu Asp Thr Ala Val Tyr Tyr
    210                 215                 220

Cys Ala Arg Ser Ile Tyr Tyr Tyr Asp Ala Pro Phe Ala Tyr Trp Gly
225                 230                 235                 240

Gln Gly Thr Leu Val Thr Val Ser Ser Ala Ser Thr Lys Gly Pro Ser
                245                 250                 255

Val Phe Pro Leu Ala Pro Cys Ser Arg Ser Thr Ser Glu Ser Thr Ala
```

260                 265                 270
Ala Leu Gly Cys Leu Val Lys Asp Tyr Phe Pro Glu Pro Val Thr Val
            275                 280                 285

Ser Trp Asn Ser Gly Ala Leu Thr Ser Gly Val His Thr Phe Pro Ala
        290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
                325                 330                 335

Lys Pro Ser Asn Thr Lys Val Asp Lys Thr Val Glu Arg Lys Cys Cys
            340                 345                 350

Val Glu Cys Pro Pro Cys Pro Ala Pro Pro Val Ala Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser His Glu Asp Pro Glu
385                 390                 395                 400

Val Gln Phe Asn Trp Tyr Val Asp Gly Val Glu Val His Asn Ala Lys
                405                 410                 415

Thr Lys Pro Arg Glu Glu Gln Phe Asn Ser Thr Phe Arg Val Val Ser
            420                 425                 430

Val Leu Thr Val Val His Gln Asp Trp Leu Asn Gly Lys Glu Tyr Lys
        435                 440                 445

Cys Lys Val Ser Asn Lys Gly Leu Pro Ala Pro Ile Glu Lys Thr Ile
    450                 455                 460

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Met Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 67
<211> LENGTH: 1005
<212> TYPE: DNA
<213> ORGANISM: ARTIFICIAL SEQUENCE
<220> FEATURE:
<223> OTHER INFORMATION: 6.147-AbL-167 LC

<400> SEQUENCE: 67
tcatacgtgc tcactcagcc gcccagcgta tcggtggctc ccggacagac ggcgcgaatc    60
acgtgcggtg ggaacaatat cggctccaag tcagtccatt ggtatcaaca gaaacctggt   120
caggcaccag tcctggtggt atacgatgac tcggacaggc cctcggagat tccggaacgc   180
ttctccggat cgaattcggg gaacacagcg accttgacga tcagcagagt ggaggccgga   240
gatgaagccg actactattg tcaggtgtgg gattccagct ccgaccacgt cgtatttgga   300

-continued

```
ggtgggacac ggcttaccgt cctcgggcag cccaaggctg cgccatcggt cactctgttc    360
ccacctgaca ttcaaatgac acagtcgccc tcctcgctct cggcgtcagt cggggatcgc    420
gtgacaatca cgtgtcgggc cagccaggac atttcgagct acctcaactg gtatcagcag    480
aaaccgggga agcgccgaa gctgcttatc tactccacct caaggttgaa ttccggagta    540
ccctcaagat tttcgggtag cggatcagga accgacttca cacttacgat ctcgtcgttg    600
cagccagaag atttcgcaac gtactattgc cagcaagata tcaagcaccc tacgtttggt    660
cagggcacta aagtggagat taagcgtacg gtggctgcac catctgtctt catcttcccg    720
ccatctgatg agcagttgaa atctggaact gcctctgttg tgtgcctgct gaataacttc    780
tatcccagag aggccaaagt acagtggaag gtggataacg ccctccaatc gggtaactcc    840
caggagagtg tcacagagca ggacagcaag gacagcacct acagcctcag cagcaccctg    900
acgctgagca aagcagacta cgagaaacac aaagtctacg cctgcgaagt cacccatcag    960
ggcctgagct cgcccgtcac aaagagcttc aacaggggag agtgt               1005
```

<210> SEQ ID NO 68
<211> LENGTH: 335
<212> TYPE: PRT
<213> ORGANISM: ARTIFICIAL SEQUENCE
<220> FEATURE:
<223> OTHER INFORMATION: 6.147-AbL-167 LC

<400> SEQUENCE: 68

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Arg Leu Thr Val Leu Gly Gln Pro Lys
            100                 105                 110

Ala Ala Pro Ser Val Thr Leu Phe Pro Pro Asp Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Asp Ile Ser Ser Tyr Leu Asn Trp Tyr Gln Gln
145                 150                 155                 160

Lys Pro Gly Lys Ala Pro Lys Leu Leu Ile Tyr Ser Thr Ser Arg Leu
                165                 170                 175

Asn Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Asp Ile Lys His Pro Thr Phe Gly Gln Gly Thr Lys
    210                 215                 220

Val Glu Ile Lys Arg Thr Val Ala Ala Pro Ser Val Phe Ile Phe Pro
225                 230                 235                 240
```

```
Pro Ser Asp Glu Gln Leu Lys Ser Gly Thr Ala Ser Val Val Cys Leu
            245                 250                 255

Leu Asn Asn Phe Tyr Pro Arg Glu Ala Lys Val Gln Trp Lys Val Asp
        260                 265                 270

Asn Ala Leu Gln Ser Gly Asn Ser Gln Glu Ser Val Thr Glu Gln Asp
        275                 280                 285

Ser Lys Asp Ser Thr Tyr Ser Leu Ser Ser Thr Leu Thr Leu Ser Lys
    290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 69
<211> LENGTH: 1713
<212> TYPE: DNA
<213> ORGANISM: ARTIFICIAL SEQUENCE
<220> FEATURE:
<223> OTHER INFORMATION: 785-AbS-6.147 G2

<400> SEQUENCE: 69
gaggtgcagc tcgtgcagtc cggagccgag gtgaagaagc tggggcatc cgtcaaagtc      60 tcgtgcaagg cgtcagggta cacattcacc gactataaca tgcattgggt ccggcaggct    120
cccggtcagg ggctggagtg gatggggaa tcaatccga actccggagg ggcaggatac      180
aatcaaaagt ttaagggacg cgtaacgatg accactgaca cgtcaacctc acggcgtat    240 atggagctca aagcctccg aagcgacgac actgctgtct attactgtgc gagactggga    300
tatgatgata tctacgacga ttggtacttc gatgtatggg acaagggac gacggtcacg    360 gtctcctcag cgtcaacgaa aggaccgcag gtgcagcttg tcgagagcgg tggaggggtg    420
gtacaacccg gaagatcact ccggctttca tgcgcagcat ccggttttac attttcgcgg   480
tatgacatgc actgggtgag acaggcacca ggaaaagggc tggagtgggt ggccatcatc   540
ttctatgatg ggtccaataa gtactacgcc gacccggtaa agggaggtt cactattagc    600 cgcgacaact cgaagaatac gctgtacctg cagatgaact cgttgcgagc cgaagatacc   660
gcggtctact attgtgcgac gctcgcggct gcgttagatt actggggcca aggaacattg   720
gtcaccgtct ctagtgcctc caccaagggc ccatcggtct tccccctggc gccctgctcc    780
aggagcacct ccgagagcac agcggccctg gcctgcctgg tcaaggacta cttccccgaa   840
ccggtgacgg tgtcgtggaa ctcaggcgct ctgaccagcg gcgtgcacac cttcccagct    900
gtcttacagt cctcaggact ctactcctc agcagcgtgg tgaccgtgcc ctccagcaac    960
ttcggcaccc agacctacac ctgcaacgta gatcacaagc ccagcaacac caaggtggac   1020
aagacagttg agcgcaaatg ttgtgtcgag tgcccaccgt gcccagcacc acctgtggca   1080
ggaccgtcag tcttcctctt cccccaaaa cccaaggaca ccctcatgat ctcccggacc    1140
cctgaggtca cgtgcgtggt ggtggacgtg agccacgaag accccgaggt ccagttcaac   1200
tggtacgtgg acggcgtgga ggtgcataat gccaagacaa agccacggga ggagcagttc   1260
aacagcacgt tccgtgtggt cagcgtcctc accgttgtgc accaggactg gctgaacggc   1320
aaggagtaca agtgcaaggt ctccaacaaa ggcctcccag cccccatcga gaaaaccatc   1380
tccaaaacca agggcagcc cgagaacca caggtgtaca ccctgccccc atcccgggag    1440
gagatgacca gaaccaggt cagcctgacc tgcctggtca aaggcttcta ccccagcgac    1500
atcgccgtgg agtgggagag caatgggcag ccggagaaca actacaagac cacacctccc   1560
```

```
atgctggact ccgacggctc cttcttcctc tacagcaagc tcaccgtgga caagagcagg   1620
tggcagcagg ggaacgtctt ctcatgctcc gtgatgcatg aggctctgca caaccactac   1680
acgcagaaga gcctctccct gtctccgggt aaa                                1713
```

<210> SEQ ID NO 70
<211> LENGTH: 571
<212> TYPE: PRT
<213> ORGANISM: ARTIFICIAL SEQUENCE
<220> FEATURE:
<223> OTHER INFORMATION: 785-AbS-6.147 G2

<400> SEQUENCE: 70

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Gln Val Gln Leu Val Glu Ser Gly Gly Val Val Gln Pro Gly
    130                 135                 140

Arg Ser Leu Arg Leu Ser Cys Ala Ala Ser Gly Phe Thr Phe Ser Arg
145                 150                 155                 160

Tyr Asp Met His Trp Val Arg Gln Ala Pro Gly Lys Gly Leu Glu Trp
                165                 170                 175

Val Ala Ile Ile Phe Tyr Asp Gly Ser Asn Lys Tyr Tyr Ala Asp Pro
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Thr Leu Ala Ala Ala Phe Asp Tyr Trp Gly Gln Gly Thr Leu
225                 230                 235                 240

Val Thr Val Ser Ser Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Asn
305                 310                 315                 320

Phe Gly Thr Gln Thr Tyr Thr Cys Asn Val Asp His Lys Pro Ser Asn
                325                 330                 335
```

Thr Lys Val Asp Lys Thr Val Glu Arg Lys Cys Cys Val Glu Cys Pro
            340                 345                 350

Pro Cys Pro Ala Pro Pro Val Ala Gly Pro Ser Val Phe Leu Phe Pro
            355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Gln Phe Asn
385                 390                 395                 400

Trp Tyr Val Asp Gly Val Glu Val His Asn Ala Lys Thr Lys Pro Arg
            405                 410                 415

Glu Glu Gln Phe Asn Ser Thr Phe Arg Val Val Ser Val Leu Thr Val
            420                 425                 430

Val His Gln Asp Trp Leu Asn Gly Lys Glu Tyr Lys Cys Lys Val Ser
            435                 440                 445

Asn Lys Gly Leu Pro Ala Pro Ile Glu Lys Thr Ile Ser Lys Thr Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Met Leu Asp Ser Asp Gly Ser Phe
            515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 71
<211> LENGTH: 981
<212> TYPE: DNA
<213> ORGANISM: ARTIFICIAL SEQUENCE
<220> FEATURE:
<223> OTHER INFORMATION: 785-AbS-6.147 LC

<400> SEQUENCE: 71

| gacattcaga tgactcagtc gccttcgtca ttgagcgcgt cggtgggaga tcgggtcacg | 60 |
| attacttgtc gggcatcgca agacatctcg aactatttga attggtacca gcaaaagcct | 120 |
| ggtaaagcgc ccaaacttct tatctactat acgtcccgcc tcctctcggg cgtcccgtca | 180 |
| aggtttagcg gatcgggaag cgggacggat ttcacactga cgatttcatc acttcagccc | 240 |
| gaagatttcg ccacctatta ctgtcagcaa ggagacaccc tgccatacac ttttggcggt | 300 |
| gggacaaagg tcgaaatcaa gcgcacagtg gctgctccat catacgtgct cactcagccc | 360 |
| cccagcgtat cggtggctcc cggacagacg gcgcgaatca cgtgcggtgg gaacaatatc | 420 |
| ggctccaagt cagtccattg gtatcaacag aaacctggtc aggcaccagt cctggtggta | 480 |
| tacgatgact cggacaggcc ctcggagatt ccggaacgct ctccggatc gaattcgggg | 540 |
| aacacagcga ccttgacgat cagcagagtg gaggccggag atgaagccga ctactattgt | 600 |
| caggtgtggg attccagctc cgaccacgtc gtatttggag gtgggacacg gcttaccgtc | 660 |
| ctaggtcagc ccaaggccaa ccccactgtc actctgttcc cgccctcctc tgaggagctc | 720 |

```
caagccaaca aggccacact agtgtgtctg atcagtgact tctacccggg agctgtgaca    780
gtggcctgga aggcagatgg cagccccgtc aaggcgggag tggagaccac caaaccctcc    840
aaacagagca acaacaagta cgcggccagc agctacctga gcctgacgcc cgagcagtgg    900
aagtcccaca aagctacag ctgccaggtc acgcatgaag ggagcaccgt ggagaagaca    960
gtggccccta cagaatgttc a    981
```

<210> SEQ ID NO 72
<211> LENGTH: 327
<212> TYPE: PRT
<213> ORGANISM: ARTIFICIAL SEQUENCE
<220> FEATURE:
<223> OTHER INFORMATION: 785-AbS-6.147 LC

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Leu Thr Gln Pro Pro Ser Val Ser Val Ala Pro Gly
        115                 120                 125

Gln Thr Ala Arg Ile Thr Cys Gly Gly Asn Asn Ile Gly Ser Lys Ser
    130                 135                 140

Val His Trp Tyr Gln Gln Lys Pro Gly Gln Ala Pro Val Leu Val Val
145                 150                 155                 160

Tyr Asp Asp Ser Asp Arg Pro Ser Glu Ile Pro Glu Arg Phe Ser Gly
                165                 170                 175

Ser Asn Ser Gly Asn Thr Ala Thr Leu Thr Ile Ser Arg Val Glu Ala
            180                 185                 190

Gly Asp Glu Ala Asp Tyr Tyr Cys Gln Val Trp Asp Ser Ser Ser Asp
        195                 200                 205

His Val Val Phe Gly Gly Gly Thr Arg Leu Thr Val Leu Gly Gln Pro
    210                 215                 220

Lys Ala Asn Pro Thr Val Thr Leu Phe Pro Pro Ser Ser Glu Glu Leu
225                 230                 235                 240

Gln Ala Asn Lys Ala Thr Leu Val Cys Leu Ile Ser Asp Phe Tyr Pro
                245                 250                 255

Gly Ala Val Thr Val Ala Trp Lys Ala Asp Gly Ser Pro Val Lys Ala
            260                 265                 270

Gly Val Glu Thr Thr Lys Pro Ser Lys Gln Ser Asn Asn Lys Tyr Ala
        275                 280                 285

Ala Ser Ser Tyr Leu Ser Leu Thr Pro Glu Gln Trp Lys Ser His Arg
    290                 295                 300

Ser Tyr Ser Cys Gln Val Thr His Glu Gly Ser Thr Val Glu Lys Thr
```

```
                305                 310                 315                 320
Val Ala Pro Thr Glu Cys Ser
                325

<210> SEQ ID NO 73
<211> LENGTH: 1734
<212> TYPE: DNA
<213> ORGANISM: ARTIFICIAL SEQUENCE
<220> FEATURE:
<223> OTHER INFORMATION: 785-AbL-6.147 G2

<400> SEQUENCE: 73
gaggtgcagc tcgtgcagtc cggagccgag gtgaagaagc tggggcatc  cgtcaaagtc      60 tcgtgcaagg cgtcagggta cacattcacc gactataaca tgcattgggt ccggcaggct     120
cccggtcagg ggctggagtg gatgggggaa atcaatccga actccggagg ggcaggatac     180
aatcaaaagt ttaagggacg cgtaacgatg accactgaca cgtcaacctc cacggcgtat     240
atggagctca aagcctccg  aagcgacgac actgctgtct attactgtgc gagactggga     300
tatgatgata tctacgacga ttggtacttc gatgtatggg gacaagggac gacggtcacg     360
gtctcctcag cgtcaacgaa aggaccgtcg gtgttcccct ggcccctca  ggtgcagctt     420 gtcgagagcg gtggagggt  ggtacaaccc ggaagatcac tccggctttc atgcgcagca     480
tccggtttta cattttcgcg gtatgacatg cactgggtga caggcacc  aggaaaaggg     540 ctggagtggg tggccatcat cttctatgat gggtccaata agtactacgc cgacccggta     600
aaagggaggt tcactattag ccgcgacaac tcgaagaata cgctgtacct gcagatgaac     660
tcgttgcgag ccgaagatac cgcggtctac tattgtgcga cgctcgcggc tgcgttcgat     720
tactggggcc aaggaacatt ggtcaccgtc tctagtgcct ccaccaaggg cccatcggtc     780
ttccccctgg cgccctgctc caggagcacc tccgagagca gcggccct  gggctgcctg     840 gtcaaggact acttccccga accggtgacg gtgtcgtgga actcaggcgc tctgaccagc     900
ggcgtgcaca ccttcccagc tgtcctacag tcctcaggac tctactccct cagcagcgtg     960
gtgaccgtgc cctccagcaa cttcggcacc cagacctaca cctgcaacgt agatcacaag    1020
cccagcaaca ccaaggtgga caagacagtt gagcgcaaat gttgtgtcga gtgcccaccg    1080
tgcccagcac cacctgtggc aggaccgtca gtcttcctct tccccccaaa acccaaggac    1140
accctcatga tctcccggac ccctgaggtc acgtgcgtgg tggtggacgt gagccacgaa    1200
gaccccgagg tccagttcaa ctggtacgtg gacggcgtgg aggtgcataa tgccaagaca    1260
aagccacggg aggagcagtt caacagcacg ttccgtgtgg tcagcgtcct caccgttgtg    1320
caccaggact ggctgaacgg caaggagtac aagtgcaagg tctccaacaa aggcctccca    1380
gcccccatcg agaaaccat  ctccaaaacc aaagggcagc ccgagaacc  acaggtgtac    1440 accctgcccc catcccggga ggagatgacc aagaaccagg tcagcctgac ctgcctggtc    1500
aaaggcttct accccagcga catcgccgtg gagtgggaga gcaatgggca gccggagaac    1560
aactacaaga ccacacctcc catgctggac tccgacggct ccttcttcct ctacagcaag    1620
ctcaccgtgg acaagagcag gtggcagcag gggaacgtct tctcatgctc cgtgatgcat    1680
gaggctctgc acaaccacta cacgcagaag agcctctccc tgtctccggg taaa          1734

<210> SEQ ID NO 74
<211> LENGTH: 578
<212> TYPE: PRT
<213> ORGANISM: ARTIFICIAL SEQUENCE
<220> FEATURE:
```

<223> OTHER INFORMATION: 785-AbL-6.147 G2

<400> SEQUENCE: 74

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Gln Val Gln Leu Val Glu Ser Gly
    130                 135                 140

Gly Gly Val Val Gln Pro Gly Arg Ser Leu Arg Leu Ser Cys Ala Ala
145                 150                 155                 160

Ser Gly Phe Thr Phe Ser Arg Tyr Asp Met His Trp Val Arg Gln Ala
                165                 170                 175

Pro Gly Lys Gly Leu Glu Trp Val Ala Ile Ile Phe Tyr Asp Gly Ser
            180                 185                 190

Asn Lys Tyr Tyr Ala Asp Pro Val Lys Gly Arg Phe Thr Ile Ser Arg
        195                 200                 205

Asp Asn Ser Lys Asn Thr Leu Tyr Leu Gln Met Asn Ser Leu Arg Ala
    210                 215                 220

Glu Asp Thr Ala Val Tyr Tyr Cys Ala Thr Leu Ala Ala Ala Phe Asp
225                 230                 235                 240

Tyr Trp Gly Gln Gly Thr Leu Val Thr Val Ser Ser Ala Ser Thr Lys
                245                 250                 255

Gly Pro Ser Val Phe Pro Leu Ala Pro Cys Ser Arg Ser Thr Ser Glu
            260                 265                 270

Ser Thr Ala Ala Leu Gly Cys Leu Val Lys Asp Tyr Phe Pro Glu Pro
        275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Asn Phe Gly Thr Gln Thr Tyr Thr Cys Asn
                325                 330                 335

Val Asp His Lys Pro Ser Asn Thr Lys Val Asp Lys Thr Val Glu Arg
            340                 345                 350

Lys Cys Cys Val Glu Cys Pro Pro Cys Pro Ala Pro Pro Val Ala Gly
        355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400
```

```
Asp Pro Glu Val Gln Phe Asn Trp Tyr Val Asp Gly Val Glu Val His
                405                 410                 415
Asn Ala Lys Thr Lys Pro Arg Glu Glu Gln Phe Asn Ser Thr Phe Arg
            420                 425                 430
Val Val Ser Val Leu Thr Val Val His Gln Asp Trp Leu Asn Gly Lys
        435                 440                 445
Glu Tyr Lys Cys Lys Val Ser Asn Lys Gly Leu Pro Ala Pro Ile Glu
    450                 455                 460
Lys Thr Ile Ser Lys Thr Lys Gly Gln Pro Arg Glu Pro Gln Val Tyr
465                 470                 475                 480
Thr Leu Pro Pro Ser Arg Glu Glu Met Thr Lys Asn Gln Val Ser Leu
                485                 490                 495
Thr Cys Leu Val Lys Gly Phe Tyr Pro Ser Asp Ile Ala Val Glu Trp
            500                 505                 510
Glu Ser Asn Gly Gln Pro Glu Asn Asn Tyr Lys Thr Thr Pro Pro Met
        515                 520                 525
Leu Asp Ser Asp Gly Ser Phe Phe Leu Tyr Ser Lys Leu Thr Val Asp
    530                 535                 540
Lys Ser Arg Trp Gln Gln Gly Asn Val Phe Ser Cys Ser Val Met His
545                 550                 555                 560
Glu Ala Leu His Asn His Tyr Thr Gln Lys Ser Leu Ser Leu Ser Pro
                565                 570                 575
Gly Lys

<210> SEQ ID NO 75
<211> LENGTH: 1002
<212> TYPE: DNA
<213> ORGANISM: ARTIFICIAL SEQUENCE
<220> FEATURE:
<223> OTHER INFORMATION: 785-AbL-6.147 LC

<400> SEQUENCE: 75
gacattcaga tgactcagtc gccttcgtca ttgagcgcgt cggtgggaga tcgggtcacg      60
attacttgtc gggcatcgca agacatctcg aactatttga attggtacca gcaaaagcct    120
ggtaaagcgc ccaaacttct tatctactat acgtcccgcc tcctctcggg cgtcccgtca    180
aggtttagcg gatcgggaag cgggacggat ttcacactga cgatttcatc acttcagccc    240
gaagatttcg ccacctatta ctgtcagcaa ggagacaccc tgccatacac ttttggcggt    300
gggacaaagg tcgaaatcaa gcgcacagtg gctgctccat ccgtctttat cttccctcca    360
tcatacgtgc tcactcagcc gcccagcgta tcggtggctc ccggacagac ggcgcgaatc    420
acgtgcggtg ggaacaatat cggctccaag tcagtccatt ggtatcaaca gaaacctggt    480
caggcaccag tcctggtggt atacgatgac tcggacaggc cctcggagat tccggaacgc    540
ttctccggat cgaattcggg gaacacagcg accttgacga tcagcagagt ggaggccgga    600
gatgaagccg actactattg tcaggtgtgg gattccagct ccgaccacgt cgtatttgga    660
ggtgggacac ggcttaccgt cctaggtcag cccaaggcca accccactgt cactctgttc    720
ccgcccctcct ctgaggagct ccaagccaac aaggccacac tagtgtgtct gatcagtgac    780
ttctacccgg gagctgtgac agtggcctgg aaggcagatg cagcccccgt caaggcggga    840
gtggagacca ccaaaccctc caaacagagc aacaacaagt acgcggccag cagctacctg    900
agcctgacgc ccgagcagtg gaagtccac agaagctaca gctgccaggt cacgcatgaa    960
gggagcaccg tggagaagac agtggcccct acagaatgtt ca                      1002
```

<210> SEQ ID NO 76
<211> LENGTH: 334
<212> TYPE: PRT
<213> ORGANISM: ARTIFICIAL SEQUENCE
<220> FEATURE:
<223> OTHER INFORMATION: 785-AbL-6.147 LC

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Tyr Val Leu Thr Gln Pro Pro
        115                 120                 125

Ser Val Ser Val Ala Pro Gly Gln Thr Ala Arg Ile Thr Cys Gly Gly
    130                 135                 140

Asn Asn Ile Gly Ser Lys Ser Val His Trp Tyr Gln Gln Lys Pro Gly
145                 150                 155                 160

Gln Ala Pro Val Leu Val Val Tyr Asp Asp Ser Asp Arg Pro Ser Glu
                165                 170                 175

Ile Pro Glu Arg Phe Ser Gly Ser Asn Ser Gly Asn Thr Ala Thr Leu
            180                 185                 190

Thr Ile Ser Arg Val Glu Ala Gly Asp Glu Ala Asp Tyr Tyr Cys Gln
        195                 200                 205

Val Trp Asp Ser Ser Asp His Val Val Phe Gly Gly Gly Thr Arg
    210                 215                 220

Leu Thr Val Leu Gly Gln Pro Lys Ala Asn Pro Thr Val Thr Leu Phe
225                 230                 235                 240

Pro Pro Ser Ser Glu Glu Leu Gln Ala Asn Lys Ala Thr Leu Val Cys
                245                 250                 255

Leu Ile Ser Asp Phe Tyr Pro Gly Ala Val Thr Val Ala Trp Lys Ala
            260                 265                 270

Asp Gly Ser Pro Val Lys Ala Gly Val Glu Thr Thr Lys Pro Ser Lys
        275                 280                 285

Gln Ser Asn Asn Lys Tyr Ala Ala Ser Ser Tyr Leu Ser Leu Thr Pro
    290                 295                 300

Glu Gln Trp Lys Ser His Arg Ser Tyr Ser Cys Gln Val Thr His Glu
305                 310                 315                 320

Gly Ser Thr Val Glu Lys Thr Val Ala Pro Thr Glu Cys Ser
                325                 330
```

<210> SEQ ID NO 77
<211> LENGTH: 1710
<212> TYPE: DNA
<213> ORGANISM: ARTIFICIAL SEQUENCE
<220> FEATURE:

<223> OTHER INFORMATION: 167-2x-6.37 G2

<400> SEQUENCE: 77

```
gaggtgcagc tcgtacagtc gggtgcggaa gtaaagaaac ccggctcatc cgtgaaagtc      60
tcgtgtaaag cctccgggtt caccttcaca gactacatta tgcactgggt gcggcaggcc     120
cctgggcagg gccttgaatg gatggggtat atcaacccct acaatgatga cacggagtat     180
aacgaaaagt ttaagggaag ggtgacaatc acggcggata agagcaccag cactgcatac     240
atggagctct cgtcattgcg ctcggaggac actgcagtct actattgcgc gagatccatc     300
tactattacg atgcgccgtt tgcttattgg ggacaaggaa cgctggtcac agtgagctca     360
ggcggtggag gctcggagg tggtggatcc caggtacaac tggtcgagtc aggtggaggc      420
gtggtccagc ccgacggtc gctcaggctc agctgtgctg cgtcagggtt cacctttcg       480
gggtatggga tgcactgggt gcgccaagca ccgggaaaag ggcttgaatg ggtcgcggtc     540
atttcctacg acgggaacga caaatactac gcggactccg taagggaag gttcacaatc      600
agccgggata cgccaagaa tacgttgtat ctccagatga attcgttgcg agcagaagat      660
acggccgtgt actattgcgc gagagagctt cgcgtgttgt ggggacaggg tactctggtg     720
accgtctcta gtgcctccac caagggccca tcggtcttcc cctggcgcc ctgctccagg      780
agcacctccg agagcacagc ggccctgggc tgcctggtca aggactactt ccccgaaccg     840
gtgacggtgt cgtggaactc aggcgctctg accagcggcg tgcacacctt cccagctgtc     900
ctacagtcct caggactcta ctccctcagc agcgtggtga ccgtgccctc cagcaacttc     960
ggcacccaga cctacacctg caacgtagat cacaagccca gcaacaccaa ggtggacaag    1020
acagttgagc gcaaatgttg tgtcgagtgc ccaccgtgcc cagcaccacc tgtggcagga    1080
ccgtcagtct tcctcttccc cccaaaaccc aaggacaccc tcatgatctc ccggacccct    1140
gaggtcacgt gcgtggtggt ggacgtgagc cacgaagacc ccgaggtcca gttcaactgg    1200
tacgtggacg gcgtggaggt gcataatgcc aagacaaagc cacgggagga gcagttcaac    1260
agcacgttcc gtgtggtcag cgtcctcacc gttgtgcacc aggactggct gaacggcaag    1320
gagtacaagt gcaaggtctc caacaaaggc ctcccagccc ccatcgagaa aaccatctcc    1380
aaaaccaaag ggcagccccg agaaccacag gtgtacaccc tgcccccatc ccgggaggag    1440
atgaccaaga accaggtcag cctgacctgc ctggtcaaag gcttctaccc cagcgacatc    1500
gccgtggagt gggagagcaa tgggcagccg gagaacaact acaagaccac acctcccatg    1560
ctggactccg acggctcctt cttcctctac agcaagctca ccgtggacaa gagcaggtgg    1620
cagcagggga acgtcttctc atgctccgtg atgcatgagg ctctgcacaa ccactacacg    1680
cagaagagcc tctccctgtc tccgggtaaa                                     1710
```

<210> SEQ ID NO 78
<211> LENGTH: 570
<212> TYPE: PRT
<213> ORGANISM: ARTIFICIAL SEQUENCE
<220> FEATURE:
<223> OTHER INFORMATION: 167-2x-6.37 G2

<400> SEQUENCE: 78

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
```

```
                35                  40                  45
Gly Tyr Ile Asn Pro Tyr Asn Asp Asp Thr Glu Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Asp Ala Pro Phe Ala Tyr Trp Gly Gln
                100                 105                 110

Gly Thr Leu Val Thr Val Ser Ser Gly Gly Gly Gly Ser Gly Gly Gly
                115                 120                 125

Gly Ser Gln Val Gln Leu Val Glu Ser Gly Gly Val Val Gln Pro
                130                 135                 140

Gly Arg Ser Leu Arg Leu Ser Cys Ala Ala Ser Gly Phe Thr Phe Ser
145                 150                 155                 160

Gly Tyr Gly Met His Trp Val Arg Gln Ala Pro Gly Lys Gly Leu Glu
                165                 170                 175

Trp Val Ala Val Ile Ser Tyr Asp Gly Asn Asp Lys Tyr Tyr Ala Asp
                180                 185                 190

Ser Val Lys Gly Arg Phe Thr Ile Ser Arg Asp Asn Ala Lys Asn Thr
                195                 200                 205

Leu Tyr Leu Gln Met Asn Ser Leu Arg Ala Glu Asp Thr Ala Val Tyr
210                 215                 220

Tyr Cys Ala Arg Glu Leu Arg Val Leu Trp Gly Gln Gly Thr Leu Val
225                 230                 235                 240

Thr Val Ser Ser Ala Ser Thr Lys Gly Pro Ser Val Phe Pro Leu Ala
                245                 250                 255

Pro Cys Ser Arg Ser Thr Ser Glu Ser Thr Ala Ala Leu Gly Cys Leu
                260                 265                 270

Val Lys Asp Tyr Phe Pro Glu Pro Val Thr Val Ser Trp Asn Ser Gly
                275                 280                 285

Ala Leu Thr Ser Gly Val His Thr Phe Pro Ala Val Leu Gln Ser Ser
                290                 295                 300

Gly Leu Tyr Ser Leu Ser Ser Val Val Thr Val Pro Ser Ser Asn Phe
305                 310                 315                 320

Gly Thr Gln Thr Tyr Thr Cys Asn Val Asp His Lys Pro Ser Asn Thr
                325                 330                 335

Lys Val Asp Lys Thr Val Glu Arg Lys Cys Cys Val Glu Cys Pro Pro
                340                 345                 350

Cys Pro Ala Pro Pro Val Ala Gly Pro Ser Val Phe Leu Phe Pro Pro
                355                 360                 365

Lys Pro Lys Asp Thr Leu Met Ile Ser Arg Thr Pro Glu Val Thr Cys
                370                 375                 380

Val Val Val Asp Val Ser His Glu Asp Pro Glu Val Gln Phe Asn Trp
385                 390                 395                 400

Tyr Val Asp Gly Val Glu Val His Asn Ala Lys Thr Lys Pro Arg Glu
                405                 410                 415

Glu Gln Phe Asn Ser Thr Phe Arg Val Val Ser Val Leu Thr Val Val
                420                 425                 430

His Gln Asp Trp Leu Asn Gly Lys Glu Tyr Lys Cys Lys Val Ser Asn
                435                 440                 445

Lys Gly Leu Pro Ala Pro Ile Glu Lys Thr Ile Ser Lys Thr Lys Gly
                450                 455                 460
```

Gln Pro Arg Glu Pro Gln Val Tyr Thr Leu Pro Pro Ser Arg Glu Glu
465                 470                 475                 480

Met Thr Lys Asn Gln Val Ser Leu Thr Cys Leu Val Lys Gly Phe Tyr
            485                 490                 495

Pro Ser Asp Ile Ala Val Glu Trp Glu Ser Asn Gly Gln Pro Glu Asn
        500                 505                 510

Asn Tyr Lys Thr Thr Pro Pro Met Leu Asp Ser Asp Gly Ser Phe Phe
            515                 520                 525

Leu Tyr Ser Lys Leu Thr Val Asp Lys Ser Arg Trp Gln Gln Gly Asn
        530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
            565                 570

<210> SEQ ID NO 79
<211> LENGTH: 1005
<212> TYPE: DNA
<213> ORGANISM: ARTIFICIAL SEQUENCE
<220> FEATURE:
<223> OTHER INFORMATION: 167-2x-6.37 LC

<400> SEQUENCE: 79
gacattcaaa tgacacagtc gccctcctcg ctctcggcgt cagtcgggga tcgcgtgaca      60
atcacgtgtc gggccagcca ggacatttcg agctacctca actggtatca gcagaaaccg     120
gggaaagcgc cgaagctgct tatctactcc acctcaaggt tgaattccgg agtaccctca     180
agattttcgg gtagcggatc aggaaccgac ttcacactta cgatctcgtc gttgcagcca     240
gaagatttcg caacgtacta ttgccagcaa gatatcaagc accctacgtt tggtcagggc     300
actaaagtgg agattaaggg cggtggaggc tcggaggtg gtggatccga tattgtgatg      360
acccagacgc cgttgtcact gagcgtcaca cccggacagc ccgcgtcgat tagctgcaaa     420
tcgggacaat cgcttctcca ctcggacggg aaaacgtatc tttactggta tttgcaaaag     480
ccagggcagc ctccccagtt tcttatctac gaagtgtcga acaggttttc cagagtacct     540
gaccgattct ccggatcagg tagcggaacg gacttcactc tgcgcatctc acgggtcgaa     600
gccgaggatg tgggcatcta ctactgtatg cagtcaattc agctcccgtg gacattcggt     660
caggggaccc aagtagagat caagcgtacg gtggctgcac catctgtctt catcttcccg     720
ccatctgatg agcagttgaa atctggaact gcctctgttg tgtgcctgct gaataacttc     780
tatcccagag aggccaaagt acagtggaag gtggataacg ccctccaatc gggtaactcc     840
caggagagtg tcacagagca ggacagcaag gacagcacct acagcctcag cagcaccctg     900
acgctgagca agcagactac gagaaacac aaagtctacg cctgcgaagt cacccatcag     960
ggcctgagct cgcccgtcac aaagagcttc aacaggggag agtgt                    1005

<210> SEQ ID NO 80
<211> LENGTH: 335
<212> TYPE: PRT
<213> ORGANISM: ARTIFICIAL SEQUENCE
<220> FEATURE:
<223> OTHER INFORMATION: 167-2x-6.37 LC

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys Gly Gly Gly Gly Ser Gly
            100                 105                 110

Gly Gly Gly Ser Asp Ile Val Met Thr Gln Thr Pro Leu Ser Leu Ser
        115                 120                 125

Val Thr Pro Gly Gln Pro Ala Ser Ile Ser Cys Lys Ser Gly Gln Ser
    130                 135                 140

Leu Leu His Ser Asp Gly Lys Thr Tyr Leu Tyr Trp Tyr Leu Gln Lys
145                 150                 155                 160

Pro Gly Gln Pro Pro Gln Phe Leu Ile Tyr Glu Val Ser Asn Arg Phe
                165                 170                 175

Ser Arg Val Pro Asp Arg Phe Ser Gly Ser Gly Ser Gly Thr Asp Phe
            180                 185                 190

Thr Leu Arg Ile Ser Arg Val Glu Ala Glu Asp Val Gly Ile Tyr Tyr
        195                 200                 205

Cys Met Gln Ser Ile Gln Leu Pro Trp Thr Phe Gly Gln Gly Thr Gln
210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
        275                 280                 285

Ser Lys Asp Ser Thr Tyr Ser Leu Ser Ser Thr Leu Thr Leu Ser Lys
290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 81
<211> LENGTH: 1725
<212> TYPE: DNA
<213> ORGANISM: ARTIFICIAL SEQUENCE
<220> FEATURE:
<223> OTHER INFORMATION: 167-AbL-6.147 G2

<400> SEQUENCE: 81
gaggtgcagc tcgtacagtc gggtgcggaa gtaaagaaac ccggctcatc cgtgaaagtc     60
tcgtgtaaag cctccggggtt caccttcaca gactacatta tgcactgggt gcggcaggcc    120
cctgggcagg gccttgaatg gatggggtat atcaacccct acaatgatga cacggagtat    180
aacgaaaagt ttaagggaag ggtgacaatc acggcggata agagccacag cactgcatac    240
atggagctct cgtcattgcg ctcggaggac actgcagtct actattgcgc gagatccatc    300

```
tactattacg atgcgccgtt tgcttattgg ggacaaggaa cgctggtcac ggtctcctca    360
gcgtcaacga aggaccgtc ggtgttcccc ttggcccctc aggtgcagct tgtcgagagc    420
ggtggagggg tggtacaacc cggaagatca ctccggcttt catgcgcagc atccggtttt    480
acattttcgc ggtatgacat gcactgggtg agacaggcac caggaaaagg gctggagtgg    540
gtggccatca tcttctatga tgggtccaat aagtactacg ccgacccggt aaagggagg    600
ttcactatta gccgcgacaa ctcgaagaat acgctgtacc tgcagatgaa ctcgttgcga    660
gccgaagata ccgcggtcta ctattgtgcg acgctcgcgg ctgcgttcga ttactggggc    720
caaggaacat tggtcaccgt ctctagtgcc tccaccaagg gcccatcggt cttccccctg    780
gcgccctgct ccaggagcac ctccgagagc acagcggccc tgggctgcct ggtcaaggac    840
tacttccccg aaccggtgac ggtgtcgtgg aactcaggcg ctctgaccag cggcgtgcac    900
accttcccag ctgtcctaca gtcctcagga ctctactccc tcagcagcgt ggtgaccgtg    960
ccctccagca cttcggcac ccagacctac acctgcaacg tagatcacaa gcccagcaac   1020
accaaggtgg acaagacagt tgagcgcaaa tgttgtgtcg agtgcccacc gtgcccagca   1080
ccacctgtgg caggaccgtc agtcttcctc ttccccccaa acccaaggac acccctcatg   1140
atctcccgga ccctgaggt cacgtgcgtg gtggtggacg tgagccacga agaccccgag   1200
gtccagttca actggtacgt ggacggcgtg gaggtgcata atgccaagac aaagccacgg   1260
gaggagcagt tcaacagcac gttccgtgtg gtcagcgtcc tcaccgttgt gcaccaggac   1320
tggctgaacg gcaaggagta caagtgcaag gtctccaaca aaggcctccc agcccccatc   1380
gagaaaacca tctccaaaac caaagggcag ccccgagaac acaggtgta caccctgccc   1440
ccatcccggg aggagatgac caagaaccag gtcagcctga cctgcctggt caaaggcttc   1500
taccccagcg acatcgccgt ggagtgggag agcaatgggc agccggagaa caactacaag   1560
accacacctc ccatgctgga ctccgacggc tccttcttcc tctacagcaa gctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaa                   1725
```

<210> SEQ ID NO 82
<211> LENGTH: 575
<212> TYPE: PRT
<213> ORGANISM: ARTIFICIAL SEQUENCE
<220> FEATURE:
<223> OTHER INFORMATION: 167-AbL-6.147 G2

<400> SEQUENCE: 82

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Gln Val Gln Leu Val Glu Ser Gly Gly Gly Val
130                 135                 140

Val Gln Pro Gly Arg Ser Leu Arg Leu Ser Cys Ala Ala Ser Gly Phe
145                 150                 155                 160

Thr Phe Ser Arg Tyr Asp Met His Trp Val Arg Gln Ala Pro Gly Lys
            165                 170                 175

Gly Leu Glu Trp Val Ala Ile Ile Phe Tyr Asp Gly Ser Asn Lys Tyr
            180                 185                 190

Tyr Ala Asp Pro Val Lys Gly Arg Phe Thr Ile Ser Arg Asp Asn Ser
195                 200                 205

Lys Asn Thr Leu Tyr Leu Gln Met Asn Ser Leu Arg Ala Glu Asp Thr
210                 215                 220

Ala Val Tyr Tyr Cys Ala Thr Leu Ala Ala Phe Asp Tyr Trp Gly
225                 230                 235                 240

Gln Gly Thr Leu Val Thr Val Ser Ser Ala Ser Thr Lys Gly Pro Ser
            245                 250                 255

Val Phe Pro Leu Ala Pro Cys Ser Arg Ser Thr Ser Glu Ser Thr Ala
            260                 265                 270

Ala Leu Gly Cys Leu Val Lys Asp Tyr Phe Pro Glu Pro Val Thr Val
            275                 280                 285

Ser Trp Asn Ser Gly Ala Leu Thr Ser Gly Val His Thr Phe Pro Ala
            290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
            325                 330                 335

Lys Pro Ser Asn Thr Lys Val Asp Lys Thr Val Glu Arg Lys Cys Cys
            340                 345                 350

Val Glu Cys Pro Pro Cys Pro Ala Pro Pro Val Ala Gly Pro Ser Val
            355                 360                 365

Phe Leu Phe Pro Pro Lys Pro Lys Asp Thr Leu Met Ile Ser Arg Thr
            370                 375                 380

Pro Glu Val Thr Cys Val Val Val Asp Val Ser His Glu Asp Pro Glu
385                 390                 395                 400

Val Gln Phe Asn Trp Tyr Val Asp Gly Val Glu Val His Asn Ala Lys
            405                 410                 415

Thr Lys Pro Arg Glu Glu Gln Phe Asn Ser Thr Phe Arg Val Val Ser
            420                 425                 430

Val Leu Thr Val Val His Gln Asp Trp Leu Asn Gly Lys Glu Tyr Lys
            435                 440                 445

Cys Lys Val Ser Asn Lys Gly Leu Pro Ala Pro Ile Glu Lys Thr Ile
450                 455                 460

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
            485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Met Leu Asp Ser
            515                 520                 525
```

Asp Gly Ser Phe Phe Leu Tyr Ser Lys Leu Thr Val Asp Lys Ser Arg
            530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 83
<211> LENGTH: 999
<212> TYPE: DNA
<213> ORGANISM: ARTIFICIAL SEQUENCE
<220> FEATURE:
<223> OTHER INFORMATION: 167-AbL-6.147 LC

<400> SEQUENCE: 83

```
gacattcaaa tgacacagtc gccctcctcg ctctcggcgt cagtcgggga tcgcgtgaca      60
atcacgtgtc gggccagcca ggacatttcg agctacctca actggtatca gcagaaaccg     120
gggaaagcgc cgaagctgct tatctactcc acctcaaggt tgaattccgg agtaccctca     180
agatttcgg gtagcggatc aggaaccgac ttcacactta cgatctcgtc gttgcagcca     240
gaagatttcg caacgtacta ttgccagcaa gatatcaagc accctacgtt tggtcagggc     300
actaaagtgg agattaagcg cacagtggct gctccatccg tctttatctt ccctccatca     360
tacgtgctca ctcagccgcc cagcgtatcg gtggctcccg acagacggc gcgaatcacg      420
tgcggtggga caatatcgg ctccaagtca gtccattggt atcaacagaa acctggtcag      480
gcaccagtcc tggtggtata cgatgactcg gacaggccct cggagattcc ggaacgcttc     540
tccggatcga attcggggaa cacagcgacc ttgacgatca gcagagtgga ggccggagat     600
gaagccgact actattgtca ggtgtgggat tccagctccg accacgtcgt atttggaggt     660
gggacacggc ttaccgtcct aggtcagccc aaggccaacc ccactgtcac tctgttcccg     720
ccctcctctg aggagctcca agccaacaag gccacactag tgtgtctgat cagtgacttc     780
tacccgggag ctgtgacagt ggcctggaag gcagatggca gccccgtcaa ggcgggagtg     840
gagaccacca acccctccaa acagagcaac aacaagtacg cggccagcag ctacctgagc     900
ctgacgcccg agcagtggaa gtcccacaga agctacagct gccaggtcac gcatgaaggg     960
agcaccgtgg agaagacagt ggcccctaca gaatgttca                            999
```

<210> SEQ ID NO 84
<211> LENGTH: 333
<212> TYPE: PRT
<213> ORGANISM: ARTIFICIAL SEQUENCE
<220> FEATURE:
<223> OTHER INFORMATION: 167-AbL-6.147 LC

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr 85                  90                  95
Phe Gly Gln Gly Thr Lys Val Glu Ile Lys Arg Thr Val Ala Ala Pro
                100                 105                 110

Ser Val Phe Ile Phe Pro Pro Ser Tyr Val Leu Thr Gln Pro Pro Ser
            115                 120                 125

Val Ser Val Ala Pro Gly Gln Thr Ala Arg Ile Thr Cys Gly Gly Asn
        130                 135                 140

Asn Ile Gly Ser Lys Ser Val His Trp Tyr Gln Gln Lys Pro Gly Gln
145                 150                 155                 160

Ala Pro Val Leu Val Val Tyr Asp Asp Ser Asp Arg Pro Ser Glu Ile
                165                 170                 175

Pro Glu Arg Phe Ser Gly Ser Asn Ser Gly Asn Thr Ala Thr Leu Thr
            180                 185                 190

Ile Ser Arg Val Glu Ala Gly Asp Glu Ala Asp Tyr Tyr Cys Gln Val
        195                 200                 205

Trp Asp Ser Ser Ser Asp His Val Val Phe Gly Gly Gly Thr Arg Leu
210                 215                 220

Thr Val Leu Gly Gln Pro Lys Ala Asn Pro Thr Val Thr Leu Phe Pro
225                 230                 235                 240

Pro Ser Ser Glu Glu Leu Gln Ala Asn Lys Ala Thr Leu Val Cys Leu
                245                 250                 255

Ile Ser Asp Phe Tyr Pro Gly Ala Val Thr Val Ala Trp Lys Ala Asp
            260                 265                 270

Gly Ser Pro Val Lys Ala Gly Val Glu Thr Thr Lys Pro Ser Lys Gln
        275                 280                 285

Ser Asn Asn Lys Tyr Ala Ala Ser Ser Tyr Leu Ser Leu Thr Pro Glu
290                 295                 300

Gln Trp Lys Ser His Arg Ser Tyr Ser Cys Gln Val Thr His Glu Gly
305                 310                 315                 320

Ser Thr Val Glu Lys Thr Val Ala Pro Thr Glu Cys Ser
                325                 330

<210> SEQ ID NO 85
<211> LENGTH: 1725
<212> TYPE: DNA
<213> ORGANISM: ARTIFICIAL SEQUENCE
<220> FEATURE:
<223> OTHER INFORMATION: 5.80-AbL-167 G2

<400> SEQUENCE: 85
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac     240 ctgcagtgga gcagcctgac ggcctcggac accgccatgt attactgtgc gagacaggga     300
gagagctttg actactgggg ccagggaacc ctggtcacgg tctcctcagc gtcaacgaaa     360
ggaccgtcgg tgttcccctt ggcccctgag gtgcagctcg tacagtcggg tgcggaagta     420
aagaaacccg gctcatccgt gaaagtctcg tgtaaagcct ccgggttcac cttcacagac     480
tacattatgc actgggtgcg gcaggcccct gggcagggcc ttgaatggat gggtatatc     540 aaccctaca atgatgacac ggagtataac gaaaagttta agggaagggt gacaatcacg     600
gcggataaga gcaccagcac tgcatacatg gagctctcgt cattgcgctc ggaggacact     660

-continued

```
gcagtctact attgcgcgag atccatctac tattacgatg cgccgtttgc ttattgggga    720
caaggaacgc tggtcaccgt ctctagtgcc tccaccaagg gcccatcggt cttccccctg    780
gcgccctgct ccaggagcac ctccgagagc acagcggccc tgggctgcct ggtcaaggac    840
tacttccccg aaccggtgac ggtgtcgtgg aactcaggcg ctctgaccag cggcgtgcac    900
accttcccag ctgtcctaca gtcctcagga ctctactccc tcagcagcgt ggtgaccgtg    960
ccctccagca acttcggcac ccagacctac acctgcaacg tagatcacaa gcccagcaac   1020
accaaggtgg acaagacagt tgagcgcaaa tgttgtgtcg agtgcccacc gtgcccagca   1080
ccacctgtgg caggaccgtc agtcttcctc ttccccccaa acccaaggga caccctcatg   1140
atctcccgga cccctgaggt cacgtgcgtg gtggtggacg tgagccacga agaccccgag   1200
gtccagttca actggtacgt ggacggcgtg gaggtgcata atgccaagac aaagccacgg   1260
gaggagcagt tcaacagcac gttccgtgtg gtcagcgtcc tcaccgttgt gcaccaggac   1320
tggctgaacg gcaaggagta caagtgcaag gtctccaaca aaggcctccc agcccccatc   1380
gagaaaacca tctccaaaac caagggcagc cccgagaac cacaggtgta caccctgccc   1440
ccatcccggg aggagatgac caagaaccag gtcagcctga cctgcctggt caaaggcttc   1500
taccccagcg acatcgccgt ggagtgggag agcaatgggc agccggagaa caactacaag   1560
accacacctc ccatgctgga ctccgacggc tccttcttcc tctacagcaa gctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaa               1725
```

<210> SEQ ID NO 86
<211> LENGTH: 575
<212> TYPE: PRT
<213> ORGANISM: ARTIFICIAL SEQUENCE
<220> FEATURE:
<223> OTHER INFORMATION: 5.80-AbL-167 G2

<400> SEQUENCE: 86

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Thr Ala Ser Asp Thr Ala Met Tyr Tyr Cys
                85                  90                  95

Ala Arg Gln Gly Glu Ser Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Glu Val Gln Leu Val Gln Ser Gly Ala Glu Val Lys Lys Pro Gly
    130                 135                 140

Ser Ser Val Lys Val Ser Cys Lys Ala Ser Gly Phe Thr Phe Thr Asp
145                 150                 155                 160

Tyr Ile Met His Trp Val Arg Gln Ala Pro Gly Gln Gly Leu Glu Trp
                165                 170                 175
```

-continued

```
Met Gly Tyr Ile Asn Pro Tyr Asn Asp Asp Thr Glu Tyr Asn Glu Lys
                180                 185                 190

Phe Lys Gly Arg Val Thr Ile Thr Ala Asp Lys Ser Thr Ser Thr Ala
        195                 200                 205

Tyr Met Glu Leu Ser Ser Leu Arg Ser Glu Asp Thr Ala Val Tyr Tyr
    210                 215                 220

Cys Ala Arg Ser Ile Tyr Tyr Asp Ala Pro Phe Ala Tyr Trp Gly
225                 230                 235                 240

Gln Gly Thr Leu Val Thr Val Ser Ser Ala Ser Thr Lys Gly Pro Ser
                245                 250                 255

Val Phe Pro Leu Ala Pro Cys Ser Arg Ser Thr Ser Glu Ser Thr Ala
            260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
    290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
                325                 330                 335

Lys Pro Ser Asn Thr Lys Val Asp Lys Thr Val Glu Arg Lys Cys Cys
            340                 345                 350

Val Glu Cys Pro Pro Cys Pro Ala Pro Pro Val Ala Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Asp Val Ser His Glu Asp Pro Glu
385                 390                 395                 400

Val Gln Phe Asn Trp Tyr Val Asp Gly Val Glu Val His Asn Ala Lys
                405                 410                 415

Thr Lys Pro Arg Glu Glu Gln Phe Asn Ser Thr Phe Arg Val Val Ser
            420                 425                 430

Val Leu Thr Val Val His Gln Asp Trp Leu Asn Gly Lys Glu Tyr Lys
        435                 440                 445

Cys Lys Val Ser Asn Lys Gly Leu Pro Ala Pro Ile Glu Lys Thr Ile
    450                 455                 460

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Met Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 87
<211> LENGTH: 1017
<212> TYPE: DNA
```

<213> ORGANISM: ARTIFICIAL SEQUENCE
<220> FEATURE:
<223> OTHER INFORMATION: 5.80-AbL-167 LC

<400> SEQUENCE: 87

```
cagtcagtgc tgacgcagcc gccctcagtg tctggggccc cagggcagag ggtcaccatc      60
tcctgcactg ggagcagctc aacatcgggg gcagattatg atgtacactg gtaccagcag     120
cttccaggaa cagcccccaa actcctcatc tatgattaca gcaatcggcc ctcaggggtc     180
cctgaccgat tctctggctc caagtctggc acctcagcct ccctggccat cactgggctc     240
caggctgagg atgaggctga ttattactgc cagtcctatg acaacagcct gagtggttat     300
gtggtattcg gcggagggac caagctgacc gtcctcgggc agcccaaggc tgcgccatcg     360
gtcactctgt tcccacctga cattcaaatg acacagtcgc cctcctcgct ctcggcgtca     420
gtcggggatc gcgtgacaat cacgtgtcgg gccagccagg acatttcgag ctacctcaac     480
tggtatcagc agaaaccggg gaaagcgccg aagctgctta tctactccac ctcaaggttg     540
aattccggag taccctcaag atttcggggt agcggatcag gaaccgactt cacacttacg     600
atctcgtcgt tgcagccaga agatttcgca acgtactatt gccagcaaga tatcaagcac     660
cctacgtttg gtcagggcac taaagtggag attaagcgta cggtggctgc accatctgtc     720
ttcatcttcc cgccatctga tgagcagttg aaatctggaa ctgcctctgt tgtgtgcctg     780
ctgaataact tctatcccag agaggccaaa gtacagtgga aggtggataa cgccctccaa     840
tcgggtaact cccaggagag tgtcacagag caggacagca aggacagcac ctacagcctc     900
agcagcaccc tgacgctgag caaagcagac tacgagaaac acaaagtcta cgcctgcgaa     960
gtcacccatc agggcctgag ctcgcccgtc acaaagagct tcaacagggg agagtgt      1017
```

<210> SEQ ID NO 88
<211> LENGTH: 339
<212> TYPE: PRT
<213> ORGANISM: ARTIFICIAL SEQUENCE
<220> FEATURE:
<223> OTHER INFORMATION: 5.80-AbL-167 LC

<400> SEQUENCE: 88

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr Asp Val His Trp Tyr Gln Gln Leu Pro Gly Thr Ala Pro Lys Leu
        35                  40                  45

Leu Ile Tyr Asp Tyr Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Val Phe Gly Gly Gly Thr Lys Leu Thr Val Leu
            100                 105                 110

Gly Gln Pro Lys Ala Ala Pro Ser Val Thr Leu Phe Pro Pro Asp Ile
        115                 120                 125

Gln Met Thr Gln Ser Pro Ser Ser Leu Ser Ala Ser Val Gly Asp Arg
    130                 135                 140

Val Thr Ile Thr Cys Arg Ala Ser Gln Asp Ile Ser Ser Tyr Leu Asn
145                 150                 155                 160
```

```
Trp Tyr Gln Gln Lys Pro Gly Lys Ala Pro Lys Leu Leu Ile Tyr Ser
                165                 170                 175

Thr Ser Arg Leu Asn Ser Gly Val Pro Ser Arg Phe Ser Gly Ser Gly
            180                 185                 190

Ser Gly Thr Asp Phe Thr Leu Thr Ile Ser Ser Leu Gln Pro Glu Asp
        195                 200                 205

Phe Ala Thr Tyr Tyr Cys Gln Gln Asp Ile Lys His Pro Thr Phe Gly
    210                 215                 220

Gln Gly Thr Lys Val Glu Ile Lys Arg Thr Val Ala Ala Pro Ser Val
225                 230                 235                 240

Phe Ile Phe Pro Pro Ser Asp Glu Gln Leu Lys Ser Gly Thr Ala Ser
                245                 250                 255

Val Val Cys Leu Leu Asn Asn Phe Tyr Pro Arg Glu Ala Lys Val Gln
            260                 265                 270

Trp Lys Val Asp Asn Ala Leu Gln Ser Gly Asn Ser Gln Glu Ser Val
        275                 280                 285

Thr Glu Gln Asp Ser Lys Asp Ser Thr Tyr Ser Leu Ser Ser Thr Leu
    290                 295                 300

Thr Leu Ser Lys Ala Asp Tyr Glu Lys His Lys Val Tyr Ala Cys Glu
305                 310                 315                 320

Val Thr His Gln Gly Leu Ser Ser Pro Val Thr Lys Ser Phe Asn Arg
                325                 330                 335

Gly Glu Cys

<210> SEQ ID NO 89
<211> LENGTH: 1725
<212> TYPE: PRT
<213> ORGANISM: ARTIFICIAL SEQUENCE
<220> FEATURE:
<223> OTHER INFORMATION: 167-AbL-5.80 G2

<400> SEQUENCE: 89

Gly Ala Gly Gly Thr Gly Cys Ala Gly Cys Thr Cys Gly Thr Ala Cys
1               5                   10                  15

Ala Gly Thr Cys Gly Gly Thr Gly Cys Gly Ala Ala Gly Thr
        20                  25                  30

Ala Ala Ala Gly Ala Ala Ala Cys Cys Cys Gly Gly Cys Thr Cys Ala
        35                  40                  45

Thr Cys Cys Gly Thr Gly Ala Ala Gly Thr Cys Thr Gly Thr
    50                  55                  60

Gly Thr Ala Ala Ala Gly Cys Cys Thr Cys Cys Gly Gly Thr Thr
65                  70                  75                  80

Cys Ala Cys Cys Thr Thr Cys Ala Cys Gly Ala Cys Thr Ala Cys
                85                  90                  95

Ala Thr Thr Ala Thr Gly Cys Ala Cys Thr Gly Gly Gly Thr Gly Cys
            100                 105                 110

Gly Gly Cys Ala Gly Gly Cys Cys Cys Thr Gly Gly Cys Ala
        115                 120                 125

Gly Gly Gly Cys Cys Thr Thr Gly Ala Ala Thr Gly Ala Thr Gly
        130                 135                 140

Gly Gly Gly Thr Ala Thr Ala Thr Cys Ala Ala Cys Cys Cys Thr
145                 150                 155                 160

Ala Cys Ala Ala Thr Gly Ala Thr Gly Ala Cys Ala Cys Gly Gly Ala
                165                 170                 175
```

```
Gly Thr Ala Thr Ala Ala Cys Gly Ala Ala Ala Ala Gly Thr Thr Thr
            180                 185                 190

Ala Ala Gly Gly Gly Ala Ala Gly Gly Gly Thr Gly Ala Cys Ala Ala
        195                 200                 205

Thr Cys Ala Cys Gly Gly Cys Gly Gly Ala Thr Ala Ala Gly Ala Gly
    210                 215                 220

Cys Ala Cys Cys Ala Gly Cys Ala Cys Thr Gly Cys Ala Thr Ala Cys
225                 230                 235                 240

Ala Thr Gly Gly Ala Gly Cys Thr Cys Thr Cys Gly Thr Cys Ala Thr
                245                 250                 255

Thr Gly Cys Gly Cys Thr Cys Gly Gly Ala Gly Gly Ala Cys Ala Cys
            260                 265                 270

Thr Gly Cys Ala Gly Thr Cys Thr Ala Cys Thr Ala Thr Thr Gly Cys
        275                 280                 285

Gly Cys Gly Ala Gly Ala Thr Cys Cys Ala Thr Cys Thr Ala Cys Thr
    290                 295                 300

Ala Thr Thr Ala Cys Gly Ala Thr Gly Cys Gly Cys Cys Gly Thr Thr
305                 310                 315                 320

Thr Gly Cys Thr Thr Ala Thr Thr Gly Gly Gly Gly Ala Cys Ala Ala
                325                 330                 335

Gly Gly Ala Ala Cys Gly Cys Thr Gly Gly Thr Cys Ala Cys Gly Gly
            340                 345                 350

Thr Cys Thr Cys Cys Thr Cys Ala Gly Cys Gly Thr Cys Ala Ala Cys
        355                 360                 365

Gly Ala Ala Ala Gly Gly Ala Cys Cys Gly Thr Cys Gly Gly Thr Gly
    370                 375                 380

Thr Thr Cys Cys Cys Cys Thr Thr Gly Gly Cys Cys Cys Cys Thr Gly
385                 390                 395                 400

Ala Gly Gly Thr Gly Cys Ala Gly Cys Thr Gly Gly Thr Gly Cys Ala
                405                 410                 415

Gly Thr Cys Thr Gly Gly Ala Gly Cys Ala Gly Ala Gly Gly Thr Gly
            420                 425                 430

Ala Ala Ala Ala Ala Gly Cys Cys Cys Gly Gly Gly Gly Ala Gly Thr
        435                 440                 445

Cys Thr Cys Thr Gly Ala Ala Gly Ala Thr Cys Thr Cys Cys Thr Gly
    450                 455                 460

Thr Ala Ala Gly Gly Gly Thr Thr Cys Thr Gly Gly Ala Thr Ala Cys
465                 470                 475                 480

Ala Gly Cys Thr Thr Thr Ala Cys Cys Ala Gly Cys Thr Ala Cys Thr
                485                 490                 495

Gly Gly Ala Thr Cys Gly Gly Cys Thr Gly Gly Gly Thr Gly Cys Gly
            500                 505                 510

Cys Cys Ala Gly Ala Thr Gly Cys Cys Cys Gly Gly Gly Ala Ala Ala
        515                 520                 525

Gly Gly Cys Cys Thr Gly Gly Ala Gly Thr Gly Gly Ala Thr Gly Gly
    530                 535                 540

Gly Gly Ala Thr Cys Ala Thr Cys Thr Ala Thr Cys Cys Thr Gly Gly
545                 550                 555                 560

Thr Gly Ala Cys Thr Cys Thr Gly Ala Thr Ala Cys Cys Ala Gly Ala
                565                 570                 575

Thr Ala Cys Ala Gly Cys Cys Cys Gly Thr Cys Cys Thr Thr Cys Cys
            580                 585                 590

Ala Ala Gly Gly Cys Cys Ala Gly Gly Thr Cys Ala Cys Cys Ala Thr
```

```
                595                 600                 605
Cys Thr Cys Ala Gly Cys Cys Gly Ala Cys Ala Ala Gly Thr Cys Cys
        610                 615                 620
Ala Thr Cys Ala Gly Cys Ala Cys Cys Gly Cys Cys Thr Ala Cys Cys
625                 630                 635                 640
Thr Gly Cys Ala Gly Thr Gly Gly Ala Gly Cys Ala Gly Cys Cys Thr
                645                 650                 655
Gly Ala Cys Gly Gly Cys Cys Thr Cys Gly Gly Ala Cys Ala Cys Cys
            660                 665                 670
Gly Cys Cys Ala Thr Gly Thr Ala Thr Thr Ala Cys Thr Gly Thr Gly
            675                 680                 685
Cys Gly Ala Gly Ala Cys Ala Gly Gly Gly Ala Gly Ala Gly Ala Gly
            690                 695                 700
Cys Thr Thr Thr Gly Ala Cys Thr Ala Cys Thr Gly Gly Gly Gly Cys
705                 710                 715                 720
Cys Ala Gly Gly Gly Ala Ala Cys Cys Cys Thr Gly Gly Thr Cys Ala
                725                 730                 735
Cys Cys Gly Thr Cys Thr Cys Thr Cys Ala Gly Thr Gly Cys Cys Thr
            740                 745                 750
Cys Ala Cys Cys Ala Ala Gly Gly Gly Cys Cys Cys Ala Thr Cys Gly
        755                 760                 765
Gly Thr Cys Thr Thr Cys Cys Cys Cys Cys Thr Gly Gly Cys Gly Cys
770                 775                 780
Cys Cys Thr Gly Cys Thr Cys Cys Ala Gly Gly Ala Gly Cys Ala Cys
785                 790                 795                 800
Cys Thr Cys Cys Gly Ala Gly Ala Gly Cys Ala Cys Ala Gly Cys Gly
                805                 810                 815
Gly Cys Cys Cys Thr Gly Gly Gly Cys Thr Gly Cys Cys Thr Gly Gly
            820                 825                 830
Thr Cys Ala Ala Gly Gly Ala Cys Thr Ala Cys Thr Thr Cys Cys Cys
        835                 840                 845
Cys Gly Ala Ala Cys Cys Gly Gly Thr Gly Ala Cys Gly Gly Thr Gly
850                 855                 860
Thr Cys Gly Thr Gly Gly Ala Ala Cys Thr Cys Ala Gly Gly Cys Gly
865                 870                 875                 880
Cys Thr Cys Thr Gly Ala Cys Cys Ala Gly Cys Gly Gly Cys Gly Thr
                885                 890                 895
Gly Cys Ala Cys Ala Cys Cys Thr Thr Cys Cys Cys Ala Gly Cys Thr
            900                 905                 910
Gly Thr Cys Cys Thr Ala Cys Ala Gly Thr Cys Cys Thr Cys Ala Gly
        915                 920                 925
Gly Ala Cys Thr Cys Thr Ala Cys Thr Cys Cys Cys Thr Cys Ala Gly
            930                 935                 940
Cys Ala Gly Cys Gly Thr Gly Gly Thr Gly Ala Cys Cys Gly Thr Gly
945                 950                 955                 960
Cys Cys Cys Thr Cys Cys Ala Gly Cys Ala Ala Cys Thr Thr Cys Gly
                965                 970                 975
Gly Cys Ala Cys Cys Cys Ala Gly Ala Cys Cys Thr Ala Cys Ala Cys
            980                 985                 990
Cys Thr Gly Cys Ala Ala Cys Gly Thr Ala Gly Ala Thr Cys Ala Cys
        995                 1000                1005
Ala Ala Gly Cys Cys Cys Ala Gly Cys Ala Ala Cys Ala Cys Cys
    1010                1

```
Ala Ala Gly Gly Thr Gly Gly Ala Cys Ala Ala Gly Ala Cys Ala
    1025                1030                1035

Gly Thr Thr Gly Ala Gly Cys Gly Cys Ala Ala Ala Thr Gly Thr
    1040                1045                1050

Thr Gly Thr Gly Thr Cys Gly Ala Gly Thr Gly Cys Cys Cys Ala
    1055                1060                1065

Cys Cys Gly Thr Gly Cys Cys Ala Gly Cys Ala Cys Cys Ala
    1070                1075                1080

Cys Cys Thr Gly Thr Gly Gly Cys Ala Gly Gly Ala Cys Cys Gly
    1085                1090                1095

Thr Cys Ala Gly Thr Cys Thr Thr Cys Cys Thr Cys Thr Thr Cys
    1100                1105                1110

Cys Cys Cys Cys Cys Ala Ala Ala Ala Cys Cys Ala Ala Gly
    1115                1120                1125

Gly Ala Cys Ala Cys Cys Thr Cys Ala Thr Gly Ala Thr Cys
    1130                1135                1140

Thr Cys Cys Cys Gly Gly Ala Cys Cys Cys Cys Thr Gly Ala Gly
    1145                1150                1155

Gly Thr Cys Ala Cys Gly Thr Gly Cys Gly Thr Gly Gly Thr Gly
    1160                1165                1170

Gly Thr Gly Gly Ala Cys Gly Thr Gly Ala Gly Cys Cys Ala Cys
    1175                1180                1185

Gly Ala Ala Gly Ala Cys Cys Cys Gly Ala Gly Gly Thr Cys
    1190                1195                1200

Cys Ala Gly Thr Thr Cys Ala Ala Cys Thr Gly Gly Thr Ala Cys
    1205                1210                1215

Gly Thr Gly Gly Ala Cys Gly Gly Cys Gly Thr Gly Gly Ala Gly
    1220                1225                1230

Gly Thr Gly Cys Ala Thr Ala Ala Thr Gly Cys Cys Ala Ala Gly
    1235                1240                1245

Ala Cys Ala Ala Ala Gly Cys Cys Ala Cys Gly Gly Gly Ala Gly
    1250                1255                1260

Gly Ala Gly Cys Ala Gly Thr Thr Cys Ala Ala Cys Ala Gly Cys
    1265                1270                1275

Ala Cys Gly Thr Thr Cys Cys Gly Thr Gly Thr Gly Gly Thr Cys
    1280                1285                1290

Ala Gly Cys Gly Thr Cys Cys Thr Cys Ala Cys Cys Gly Thr Thr
    1295                1300                1305

Gly Thr Gly Cys Ala Cys Cys Ala Gly Gly Ala Cys Thr Gly Gly
    1310                1315                1320

Cys Thr Gly Ala Ala Cys Gly Gly Cys Ala Ala Gly Gly Ala Gly
    1325                1330                1335

Thr Ala Cys Ala Ala Gly Thr Gly Cys Ala Ala Gly Gly Thr Cys
    1340                1345                1350

Thr Cys Cys Ala Ala Cys Ala Ala Gly Gly Cys Cys Thr Cys
    1355                1360                1365

Cys Cys Ala Gly Cys Cys Cys Cys Cys Ala Thr Cys Gly Ala Gly
    1370                1375                1380

Ala Ala Ala Ala Cys Cys Ala Thr Cys Thr Cys Cys Ala Ala Ala
    1385                1390                1395

Ala Cys Cys Ala Ala Ala Gly Gly Gly Cys Ala Gly Cys Cys Cys
    1400                1405                1410
```

Cys Gly Ala Gly Ala Ala Cys Ala Cys Ala Gly Gly Thr Gly
    1415                1420                1425

Thr Ala Cys Ala Cys Cys Thr Gly Cys Cys Cys Cys Cys Ala
    1430                1435                1440

Thr Cys Cys Cys Gly Gly Ala Gly Gly Ala Gly Ala Thr Gly
    1445                1450                1455

Ala Cys Cys Ala Ala Gly Ala Ala Cys Cys Ala Gly Gly Thr Cys
    1460                1465                1470

Ala Gly Cys Cys Thr Gly Ala Cys Cys Thr Gly Cys Cys Thr Gly
    1475                1480                1485

Gly Thr Cys Ala Ala Ala Gly Gly Cys Thr Thr Cys Thr Ala Cys
    1490                1495                1500

Cys Cys Cys Ala Gly Cys Gly Ala Cys Ala Thr Cys Gly Cys Cys
    1505                1510                1515

Gly Thr Gly Gly Ala Gly Thr Gly Gly Ala Gly Ala Gly Cys
    1520                1525                1530

Ala Ala Thr Gly Gly Gly Cys Ala Gly Cys Cys Gly Gly Ala Gly
    1535                1540                1545

Ala Ala Cys Ala Ala Cys Thr Ala Cys Ala Ala Gly Ala Cys Cys
    1550                1555                1560

Ala Cys Ala Cys Cys Thr Cys Cys Cys Ala Thr Gly Cys Thr Gly
    1565                1570                1575

Gly Ala Cys Thr Cys Cys Gly Ala Cys Gly Gly Cys Thr Cys Cys
    1580                1585                1590

Thr Thr Cys Thr Thr Cys Cys Thr Cys Thr Ala Cys Ala Gly Cys
    1595                1600                1605

Ala Ala Gly Cys Thr Cys Ala Cys Cys Gly Thr Gly Gly Ala Cys
    1610                1615                1620

Ala Ala Gly Ala Gly Cys Ala Gly Gly Thr Gly Gly Cys Ala Gly
    1625                1630                1635

Cys Ala Gly Gly Gly Gly Ala Ala Cys Gly Thr Cys Thr Thr Cys
    1640                1645                1650

Thr Cys Ala Thr Gly Cys Thr Cys Cys Gly Thr Gly Ala Thr Gly
    1655                1660                1665

Cys Ala Thr Gly Ala Gly Gly Cys Thr Cys Thr Gly Cys Ala Cys
    1670                1675                1680

Ala Ala Cys Cys Ala Cys Thr Ala Cys Ala Cys Gly Cys Ala Gly
    1685                1690                1695

Ala Ala Gly Ala Gly Cys Cys Thr Cys Thr Cys Cys Cys Thr Gly
    1700                1705                1710

Thr Cys Thr Cys Cys Gly Gly Gly Thr Ala Ala Ala
    1715                1720                1725

<210> SEQ ID NO 90
<211> LENGTH: 575
<212> TYPE: PRT
<213> ORGANISM: ARTIFICIAL SEQUENCE
<220> FEATURE:
<223> OTHER INFORMATION: 167-AbL-5.80 G2

<400> SEQUENCE: 90

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

```
Ile Met His Trp Val Arg Gln Ala Pro Gly Gln Gly Leu Glu Trp Met
         35                  40                  45
Gly Tyr Ile Asn Pro Tyr Asn Asp Thr Glu Tyr Asn Glu Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Ile Tyr Tyr Asp Ala Pro Phe Ala Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Glu Val Gln Leu Val Gln Ser Gly Ala Glu Val
        130                 135                 140
Lys Lys Pro Gly Glu Ser Leu Lys Ile Ser Cys Lys Gly Ser Gly Tyr
145                 150                 155                 160
Ser Phe Thr Ser Tyr Trp Ile Gly Trp Val Arg Gln Met Pro Gly Lys
                165                 170                 175
Gly Leu Glu Trp Met Gly Ile Ile Tyr Pro Gly Asp Ser Asp Thr Arg
            180                 185                 190
Tyr Ser Pro Ser Phe Gln Gly Gln Val Thr Ile Ser Ala Asp Lys Ser
        195                 200                 205
Ile Ser Thr Ala Tyr Leu Gln Trp Ser Ser Leu Thr Ala Ser Asp Thr
    210                 215                 220
Ala Met Tyr Tyr Cys Ala Arg Gln Gly Glu Ser Phe Asp Tyr Trp Gly
225                 230                 235                 240
Gln Gly Thr Leu Val Thr Val Ser Ser Ala Ser Thr Lys Gly Pro Ser
                245                 250                 255
Val Phe Pro Leu Ala Pro Cys Ser Arg Ser Thr Ser Glu Ser Thr Ala
            260                 265                 270
Ala Leu Gly Cys Leu Val Lys Asp Tyr Phe Pro Glu Pro Val Thr Val
        275                 280                 285
Ser Trp Asn Ser Gly Ala Leu Thr Ser Gly Val His Thr Phe Pro Ala
    290                 295                 300
Val Leu Gln Ser Ser Gly Leu Tyr Ser Leu Ser Ser Val Val Thr Val
305                 310                 315                 320
Pro Ser Ser Asn Phe Gly Thr Gln Thr Tyr Thr Cys Asn Val Asp His
                325                 330                 335
Lys Pro Ser Asn Thr Lys Val Asp Lys Thr Val Glu Arg Lys Cys Cys
            340                 345                 350
Val Glu Cys Pro Pro Cys Pro Ala Pro Pro Val Ala Gly Pro Ser Val
        355                 360                 365
Phe Leu Phe Pro Pro Lys Pro Lys Asp Thr Leu Met Ile Ser Arg Thr
    370                 375                 380
Pro Glu Val Thr Cys Val Val Val Asp Val Ser His Glu Asp Pro Glu
385                 390                 395                 400
Val Gln Phe Asn Trp Tyr Val Asp Gly Val Glu Val His Asn Ala Lys
                405                 410                 415
Thr Lys Pro Arg Glu Glu Gln Phe Asn Ser Thr Phe Arg Val Val Ser
            420                 425                 430
Val Leu Thr Val Val His Gln Asp Trp Leu Asn Gly Lys Glu Tyr Lys
        435                 440                 445
Cys Lys Val Ser Asn Lys Gly Leu Pro Ala Pro Ile Glu Lys Thr Ile
```

Ser Lys Thr Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Met Leu Asp Ser
            515                 520                 525

Asp Gly Ser Phe Phe Leu Tyr Ser Lys Leu Thr Val Asp Lys Ser Arg
        530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 91
<211> LENGTH: 1011
<212> TYPE: DNA
<213> ORGANISM: ARTIFICIAL SEQUENCE
<220> FEATURE:
<223> OTHER INFORMATION: 167-AbL-5.80 LC

<400> SEQUENCE: 91

```
gacattcaaa tgacacagtc gccctcctcg ctctcggcgt cagtcgggga tcgcgtgaca      60
atcacgtgtc gggccagcca ggacatttcg agctacctca actggtatca gcagaaaccg     120
gggaaagcgc cgaagctgct tatctactcc acctcaaggt tgaattccgg agtaccctca     180
agattttcgg gtagcggatc aggaaccgac ttcacactta cgatctcgtc gttgcagcca     240
gaagatttcg caacgtacta ttgccagcaa gatatcaagc ccctacgttt ggtcagggc     300
actaaagtgg agattaagcg cacagtggct gctccatccg tctttatctt ccctccacag     360
tcagtgctga cgcagccgcc ctcagtgtct ggggccccag gcagagggt caccatctcc     420
tgcactggga gcagctccaa catcggggca gattatgatg tacactggta ccagcagctt     480
ccaggaacag ccccaaact cctcatctat gattacagca atcggccctc aggggtccct     540
gaccgattct ctggctccaa gtctggcacc tcagcctccc tggccatcac tgggctccag     600
gctgaggatg aggctgatta ttactgccag tcctatgaca cagcctgag tggttatgtg     660
gtattcggcg agggaccaa gctgaccgtc ctaggtcagc ccaaggccaa ccccactgtc     720
actctgttcc cgccctcctc tgaggagctc aagccaaca aggccacact agtgtgtctg     780
atcagtgact tctacccggg agctgtgaca gtggcctgga aggcagatgg cagccccgtc     840
aaggcgggag tggagaccac caaaccctcc aaacagagca caacaagta cgcggccagc     900
agctacctga gcctgacgcc cgagcagtgg aagtcccaca gaagctacag ctgccaggtc     960
acgcatgaag ggagcaccgt ggagaagaca gtggccccta cagaatgttc a            1011
```

<210> SEQ ID NO 92
<211> LENGTH: 337
<212> TYPE: PRT
<213> ORGANISM: ARTIFICIAL SEQUENCE
<220> FEATURE:
<223> OTHER INFORMATION: 167-AbL-5.80 LC

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Gln Ser Val Leu Thr Gln Pro Pro Ser
        115                 120                 125

Val Ser Gly Ala Pro Gly Gln Arg Val Thr Ile Ser Cys Thr Gly Ser
    130                 135                 140

Ser Ser Asn Ile Gly Ala Asp Tyr Asp Val His Trp Tyr Gln Gln Leu
145                 150                 155                 160

Pro Gly Thr Ala Pro Lys Leu Leu Ile Tyr Asp Tyr Ser Asn Arg Pro
                165                 170                 175

Ser Gly Val Pro Asp Arg Phe Ser Gly Ser Lys Ser Gly Thr Ser Ala
            180                 185                 190

Ser Leu Ala Ile Thr Gly Leu Gln Ala Glu Asp Glu Ala Asp Tyr Tyr
        195                 200                 205

Cys Gln Ser Tyr Asp Asn Ser Leu Ser Gly Tyr Val Val Phe Gly Gly
    210                 215                 220

Gly Thr Lys Leu Thr Val Leu Gly Gln Pro Lys Ala Asn Pro Thr Val
225                 230                 235                 240

Thr Leu Phe Pro Pro Ser Ser Glu Glu Leu Gln Ala Asn Lys Ala Thr
                245                 250                 255

Leu Val Cys Leu Ile Ser Asp Phe Tyr Pro Gly Ala Val Thr Val Ala
            260                 265                 270

Trp Lys Ala Asp Gly Ser Pro Val Lys Ala Gly Val Glu Thr Thr Lys
        275                 280                 285

Pro Ser Lys Gln Ser Asn Asn Lys Tyr Ala Ala Ser Ser Tyr Leu Ser
    290                 295                 300

Leu Thr Pro Glu Gln Trp Lys Ser His Arg Ser Tyr Ser Cys Gln Val
305                 310                 315                 320

Thr His Glu Gly Ser Thr Val Glu Lys Thr Val Ala Pro Thr Glu Cys
                325                 330                 335

Ser

<210> SEQ ID NO 93
<211> LENGTH: 22
<212> TYPE: PRT
<213> ORGANISM: Homo sapiens
<220> FEATURE:
<221> NAME/KEY: MISC_FEATURE
<223> OTHER INFORMATION: vK1 leader sequence

<400> SEQUENCE: 93

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 94
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs / 785 and 785K VL

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105

<210> SEQ ID NO 95
<211> LENGTH: 123
<212> TYPE: PRT
<213> ORGANISM: Homo sapiens
<220> FEATURE:
<221> NAME/KEY: MISC_FEATURE
<223> OTHER INFORMATION: Sclerostin mAbs 785 VH

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120

<210> SEQ ID NO 96
<211> LENGTH: 123
<212> TYPE: PRT
<213> ORGANISM: Homo sapiens
<220> FEATURE:
<221> NAME/KEY: MISC_FEATURE
<223> OTHER INFORMATION: Sclerostin mAbs 785K VH

<400> SEQUENCE: 96

```
Glu Val Gln Leu Val Gln Ser Gly Ala Glu Val Val Gln Pro Gly Ala
1               5                   10                  15

Ser Val Lys Val Ser Cys Ala Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
            115                 120
```

```
<210> SEQ ID NO 97
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 785 and 785K VL CDR1

<400> SEQUENCE: 97

Arg Ala Ser Gln Asp Ile Ser Asn Tyr Leu Asn
1               5                   10

<210> SEQ ID NO 98
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 785 and 785K VL CDR2

<400> SEQUENCE: 98

Tyr Thr Ser Arg Leu Leu Ser
1               5

<210> SEQ ID NO 99
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 785 and 785K VL CDR3

<400> SEQUENCE: 99

Gln Gln Gly Asp Thr Leu Pro Tyr Thr
1               5

<210> SEQ ID NO 100
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 785 and 785K VH CDR1

<400> SEQUENCE: 100

Asp Tyr Asn Met His
1               5
```

```
<210> SEQ ID NO 101
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 785 and 785K VH CDR2

<400> SEQUENCE: 101

Glu Ile Asn Pro Asn Ser Gly Gly Ala Gly Tyr Asn Gln Lys Phe Lys
 1               5                  10                  15
Gly

<210> SEQ ID NO 102
<211> LENGTH: 14
<212> TYPE: PRT
<213> ORGANISM: Homo sapiens
<220> FEATURE:
<221> NAME/KEY: misc_feature
<223> OTHER INFORMATION: Sclerostin mAbs 785 and 785K VH CDR3

<400> SEQUENCE: 102

Leu Gly Tyr Asp Asp Ile Tyr Asp Asp Trp Tyr Phe Asp Val
 1               5                  10

<210> SEQ ID NO 103
<211> LENGTH: 106
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23 VL

<400> SEQUENCE: 103

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Ser Thr Ser Arg Leu Asn Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Ile Lys His Pro Thr
                 85                  90                  95

Phe Gly Gln Gly Thr Lys Val Glu Ile Lys
            100                 105

<210> SEQ ID NO 104
<211> LENGTH: 120
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23 VH

<400> SEQUENCE: 104

Glu Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Tyr
             20                  25                  30
```

```
Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
            115                 120

<210> SEQ ID NO 105
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23VL CDR1

<400> SEQUENCE: 105

Arg Ala Ser Gln Asp Ile Ser Ser Tyr Leu Asn
1               5                   10

<210> SEQ ID NO 106
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23VL CDR2

<400> SEQUENCE: 106

Ser Thr Ser Arg Leu Asn Ser
1               5

<210> SEQ ID NO 107
<211> LENGTH: 8
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23VL CDR3

<400> SEQUENCE: 107

Gln Gln Asp Ile Lys His Pro Thr
1               5

<210> SEQ ID NO 108
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23VH CDR1

<400> SEQUENCE: 108

Asp Tyr Ile Met His
1               5

<210> SEQ ID NO 109
<211> LENGTH: 17
<212> TYPE: PRT
```

```
<213> ORGANISM: Homo sapiens
<220> FEATURE:
<221> NAME/KEY: MISC_FEATURE
<223> OTHER INFORMATION: Sclerostin mAbs Ab23VH CDR2

<400> SEQUENCE: 109

Tyr Ile Asn Pro Tyr Asn Asp Asp Thr Glu Tyr Asn Glu Lys Phe Lys
1               5                   10                  15
Gly

<210> SEQ ID NO 110
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs Ab23VH CDR3

<400> SEQUENCE: 110

Ser Ile Tyr Tyr Tyr Asp Ala Pro Phe Ala Tyr
1               5                   10

<210> SEQ ID NO 111
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs N13F3 VL

<400> SEQUENCE: 111

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Thr Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 112
<211> LENGTH: 121
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VH

<400> SEQUENCE: 112

Gln Val Gln Leu Val Gln Ser Gly Thr Glu Val Lys Lys Pro Gly Ala
1               5                   10                  15

Ser Met Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Asp Ser Thr Ser Tyr Ala Gln Lys Phe
```

```
                50                  55                  60
Gln Gly Arg Val Thr Met Thr Arg Asp Thr Ser Thr Asn Thr Val Tyr
 65                  70                  75                  80

Met Glu Leu Ser Ser Leu Arg Ser Glu Asp Thr Ala Met Tyr Tyr Cys
                 85                  90                  95

Ala Arg Asp Val Glu Val Arg Gly Ile Ser His Phe Asp Tyr Trp Gly
                100                 105                 110

Gln Gly Thr Leu Val Thr Val Ser Ser
        115                 120

<210> SEQ ID NO 113
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VL CDR1

<400> SEQUENCE: 113

Arg Ala Ser Gln Gly Ile Ser Asn Trp Leu Ala
 1               5                  10

<210> SEQ ID NO 114
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VL CDR2

<400> SEQUENCE: 114

Ala Ala Ser Ser Leu Gln Ser
 1               5

<210> SEQ ID NO 115
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VL CDR3

<400> SEQUENCE: 115

Gln Gln Ala Asn Ser Phe Pro Phe Thr
 1               5

<210> SEQ ID NO 116
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VH CDR1

<400> SEQUENCE: 116

Ser Tyr Tyr Met His
 1               5

<210> SEQ ID NO 117
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VH CDR2
```

<400> SEQUENCE: 117

Ile Ile Asn Pro Ser Gly Asp Ser Thr Ser Tyr Ala Gln Lys Phe Gln
1               5                   10                  15

Gly

<210> SEQ ID NO 118
<211> LENGTH: 12
<212> TYPE: PRT
<213> ORGANISM: Homo sapiens
<220> FEATURE:
<221> NAME/KEY: MISC_FEATURE
<223> OTHER INFORMATION: Sclerostin mAbs 13F3 VH CDR3

<400> SEQUENCE: 118

Asp Val Glu Val Arg Gly Ile Ser His Phe Asp Tyr
1               5                   10

<210> SEQ ID NO 119
<211> LENGTH: 111
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VL

<400> SEQUENCE: 119

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Tyr Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Pro Glu Asp Glu Ala Asp Tyr Tyr Cys Ser Ser Tyr Ala Ile Ser
                85                  90                  95

Ser Thr Leu Val Phe Gly Gly Gly Thr Lys Met Thr Val Leu Gly
            100                 105                 110

<210> SEQ ID NO 120
<211> LENGTH: 118
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VH

<400> SEQUENCE: 120

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Ser Asp Ser Gly Ser Thr Asn Tyr Asn Pro Ser Leu Lys
    50                  55                  60

Ser Arg Ile Pro Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
            85                  90                  95

Arg Trp Gln Leu Ala His Asp Ala Phe Asp Ile Trp Gly Gln Gly Thr
        100                 105                 110

Met Val Thr Val Ser Ser
        115

<210> SEQ ID NO 121
<211> LENGTH: 14
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VL CDR1

<400> SEQUENCE: 121

Thr Gly Thr Ser Ser Asp Val Gly Gly Tyr Asn Tyr Val Ser
1               5                   10

<210> SEQ ID NO 122
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VL CDR2

<400> SEQUENCE: 122

Glu Val Ser Tyr Arg Pro Ser
1               5

<210> SEQ ID NO 123
<211> LENGTH: 10
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VL CDR3

<400> SEQUENCE: 123

Ser Ser Tyr Ala Ile Ser Ser Thr Leu Val
1               5                   10

<210> SEQ ID NO 124
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VH CDR1

<400> SEQUENCE: 124

Ser Tyr Tyr Trp Ser
1               5

<210> SEQ ID NO 125
<211> LENGTH: 16
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VH CDR2

<400> SEQUENCE: 125

Tyr Ile Ser Asp Ser Gly Ser Thr Asn Tyr Asn Pro Ser Leu Lys Ser
1               5                   10                  15
```

<210> SEQ ID NO 126
<211> LENGTH: 10
<212> TYPE: PRT
<213> ORGANISM: Homo sapiens
<220> FEATURE:
<221> NAME/KEY: MISC_FEATURE
<223> OTHER INFORMATION: Sclerostin mAbs 20C3.1 VH CDR3

<400> SEQUENCE: 126

Trp Gln Leu Ala His Asp Ala Phe Asp Ile
1               5                   10

<210> SEQ ID NO 127
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VL

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Tyr
            20                  25                  30

Leu Asn Trp Tyr Gln Gln Lys Pro Gly Lys Ala Pro Asn Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ser Phe Ser Thr Pro Ile
                85                  90                  95

Thr Phe Gly Gln Gly Thr Arg Leu Glu Ile Lys
            100                 105

<210> SEQ ID NO 128
<211> LENGTH: 119
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VH

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asp Thr Ala Met Ala Tyr Phe Asp Tyr Trp Gly Gln Gly
            100                 105                 110

Thr Leu Val Thr Val Ser Ser

```
               115

<210> SEQ ID NO 129
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VL CDR1

<400> SEQUENCE: 129

Arg Ala Ser Gln Thr Ile Ser Asn Tyr Leu Asn
1               5                   10

<210> SEQ ID NO 130
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VL CDR2

<400> SEQUENCE: 130

Ala Ala Ser Gly Leu Gln Ser
1               5

<210> SEQ ID NO 131
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VL CDR3

<400> SEQUENCE: 131

Gln Gln Ser Phe Ser Thr Pro Ile Thr
1               5

<210> SEQ ID NO 132
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 38B12.1 VH CDR1

<400> SEQUENCE: 132

Asn Tyr Tyr Met Tyr
1               5

<210> SEQ ID NO 133
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mABs 38B12.1 VH CDR2

<400> SEQUENCE: 133

Ile Ile Asn Pro Ser Gly Gly Ser Thr Ser Tyr Ala Gln Lys Phe Gln
1               5                   10                  15

Gly

<210> SEQ ID NO 134
<211> LENGTH: 10
<212> TYPE: PRT
<213> ORGANISM: Homo sapiens
```

<220> FEATURE:
<221> NAME/KEY: MISC_FEATURE
<223> OTHER INFORMATION: Sclerostin mAbs 38B12.1 VH CDR3

<400> SEQUENCE: 134

Glu Asp Thr Ala Met Ala Tyr Phe Asp Tyr
1               5                   10

<210> SEQ ID NO 135
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VL

<400> SEQUENCE: 135

Asp Ile Gln Met Thr Gln Ser Pro Ala Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asn Thr Phe Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Met Lys
            100                 105

<210> SEQ ID NO 136
<211> LENGTH: 117
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1VH

<400> SEQUENCE: 136

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Ser Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Glu Leu Glu Ala Phe Asp Ile Trp Gly Gln Gly Thr Met
            100                 105                 110

Val Thr Val Ser Ser
            115

<210> SEQ ID NO 137
<211> LENGTH: 11

```
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VL CDR1

<400> SEQUENCE: 137

Arg Ala Ser Gln Gly Ile Ser Ser Trp Leu Ala
1               5                   10

<210> SEQ ID NO 138
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VL CDR2

<400> SEQUENCE: 138

Asn Thr Phe Ser Leu Glu Ser
1               5

<210> SEQ ID NO 139
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VL CDR3

<400> SEQUENCE: 139

Gln Gln Ala Asn Ser Phe Pro Phe Thr
1               5

<210> SEQ ID NO 140
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VH CDR1

<400> SEQUENCE: 140

Ser Tyr Tyr Trp Ser
1               5

<210> SEQ ID NO 141
<211> LENGTH: 16
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VH CDR2

<400> SEQUENCE: 141

Tyr Ile Tyr Tyr Ser Gly Ser Thr Ser Tyr Asn Pro Ser Leu Lys Ser
1               5                   10                  15

<210> SEQ ID NO 142
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 46H1 VH CDR3

<400> SEQUENCE: 142

Asp Leu Glu Leu Glu Ala Phe Asp Ile
```

<210> SEQ ID NO 143
<211> LENGTH: 110
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VL

<400> SEQUENCE: 143

```
Asn Phe Met Leu Thr Gln Pro His Ser Val Ser Glu Ser Pro Gly Lys
 1               5                  10                  15

Thr Val Ala Ile Ser Cys Thr Arg Asn Ser Gly Ser Ile Ala Ser Asn
            20                  25                  30

Ser Val Gln Trp Tyr Gln Gln Arg Pro Gly Ser Pro Thr Thr Val
        35                  40                  45

Ile Phe Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Asn Asn Trp Val Phe Gly Gly Gly Thr Lys Leu Thr Val Leu
            100                 105                 110
```

<210> SEQ ID NO 144
<211> LENGTH: 125
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VH

<400> SEQUENCE: 144

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Tyr Asp Tyr Gly Glu Asp Tyr Tyr Tyr Gly Met
            100                 105                 110

Asp Val Trp Gly Gln Gly Thr Thr Val Thr Val Ser Ser
            115                 120                 125
```

<210> SEQ ID NO 145
<211> LENGTH: 13
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VL CDR1

<400> SEQUENCE: 145

Thr Arg Asn Ser Gly Ser Ile Ala Ser Asn Ser Val Gln
1               5                   10

<210> SEQ ID NO 146
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VL CDR2

<400> SEQUENCE: 146

Glu Asp Asn Gln Arg Pro Ser
1               5

<210> SEQ ID NO 147
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VL CDR3

<400> SEQUENCE: 147

Gln Ser Tyr Asp Ser Asn Asn Trp Val
1               5

<210> SEQ ID NO 148
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VH CDR1

<400> SEQUENCE: 148

Ser Tyr Val Met His
1               5

<210> SEQ ID NO 149
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VH CDR2

<400> SEQUENCE: 149

Val Ile Trp Tyr Asp Gly Ser Asn Lys Tyr Tyr Ala Asp Ser Val Lys
1               5                   10                  15
Gly

<210> SEQ ID NO 150
<211> LENGTH: 16
<212> TYPE: PRT
<213> ORGANISM: Homo sapiens
<220> FEATURE:
<221> NAME/KEY: MISC_FEATURE
<223> OTHER INFORMATION: Sclerostin mAbs 2B8.1 VH CDR3

<400> SEQUENCE: 150

Glu Gly Tyr Asp Tyr Gly Glu Asp Tyr Tyr Tyr Gly Met Asp Val
1               5                   10                  15

<210> SEQ ID NO 151
<211> LENGTH: 107

```
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VL

<400> SEQUENCE: 151

Asp Ile Gln Met Thr Gln Ser Pro Ser Ser Val Ala Ser Val Gly
1               5                   10                  15

Asp Arg Val Thr Ile Thr Cys Arg Ala Ser Gln Asp Ile Ser Asn
            20                  25                  30

Leu Ala Trp Tyr Gln Gln Lys Pro Gly Lys Val Pro Lys Leu Leu Ile
        35                  40                  45

Tyr Ala Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ala Asn Ser Phe Pro Phe
                85                  90                  95

Thr Phe Gly Pro Gly Thr Lys Val Asp Ile Lys
            100                 105

<210> SEQ ID NO 152
<211> LENGTH: 127
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VH

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Lys Thr Gly Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Tyr Tyr Glu Ser Gly Ser Leu Phe Tyr Tyr Tyr
            100                 105                 110

Gly Leu Asp Val Trp Gly Gln Gly Thr Thr Val Thr Val Ser Ser
        115                 120                 125

<210> SEQ ID NO 153
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VL CDR1

<400> SEQUENCE: 153

Arg Ala Ser Gln Asp Ile Ser Asn Trp Leu Ala
1               5                   10
```

```
<210> SEQ ID NO 154
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VL CDR2

<400> SEQUENCE: 154

Ala Ala Ser Tyr Leu Gln Ser
1               5

<210> SEQ ID NO 155
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VL CDR3

<400> SEQUENCE: 155

Gln Gln Ala Asn Ser Phe Pro Phe Thr
1               5

<210> SEQ ID NO 156
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VH CDR1

<400> SEQUENCE: 156

Ser Tyr Asp Ile Asn
1               5

<210> SEQ ID NO 157
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VH CDR2

<400> SEQUENCE: 157

Trp Met Asn Pro Asn Ser Gly Lys Thr Gly Tyr Ala Gln Lys Phe Gln
1               5                   10                  15

Gly

<210> SEQ ID NO 158
<211> LENGTH: 18
<212> TYPE: PRT
<213> ORGANISM: Homo sapiens
<220> FEATURE:
<221> NAME/KEY: MISC_FEATURE
<223> OTHER INFORMATION: Sclerostin mAbs 8G2.1 VH CDR3

<400> SEQUENCE: 158

Glu Glu Glu Tyr Tyr Glu Ser Gly Ser Leu Phe Tyr Tyr Tyr Gly Leu
1               5                   10                  15

Asp Val

<210> SEQ ID NO 159
<211> LENGTH: 109
<212> TYPE: PRT
<213> ORGANISM: Homo sapiens
<220> FEATURE:
```

<221> NAME/KEY: MISC_FEATURE
<223> OTHER INFORMATION: Sclerostin mAbs 19D11.1 VL

<400> SEQUENCE: 159

Ser Tyr Val Leu Thr Gln Pro Pro Ser Val Ser Val Ala Pro Gly Gln
1               5                   10                  15

Thr Ala Arg Ile Thr Cys Gly Gly Asp Asn Ile Gly Ser Ile Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Trp Val Glu Ala Gly
65                  70                  75                  80

Asp Glu Ala Asp Tyr Tyr Cys Gln Val Trp Asp Ser Ser Ile Asp His
                85                  90                  95

Pro Val Leu Phe Gly Gly Gly Thr Lys Leu Thr Val Leu
            100                 105

<210> SEQ ID NO 160
<211> LENGTH: 123
<212> TYPE: PRT
<213> ORGANISM: Homo sapiens
<220> FEATURE:
<221> NAME/KEY: MISC_FEATURE
<223> OTHER INFORMATION: Sclerostin mABs 19D11.1 VH

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Ala Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Ser Trp Gly Glu Gly Asn Tyr Tyr Phe Tyr Tyr Gly Met Asp Val
            100                 105                 110

Trp Gly Gln Gly Thr Thr Val Thr Val Ser Ser
        115                 120

<210> SEQ ID NO 161
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 19D11.1 VL CDR1

<400> SEQUENCE: 161

Gly Gly Asp Asn Ile Gly Ser Ile Ser Val His
1               5                   10

<210> SEQ ID NO 162
<211> LENGTH: 7
<212> TYPE: PRT

```
<213> ORGANISM: Homo sapiens
<220> FEATURE:
<221> NAME/KEY: MISC_FEATURE
<223> OTHER INFORMATION: Sclerostin mAbs 19D11.1 VL CDR2

<400> SEQUENCE: 162

Asp Asp Ser Asp Arg Pro Ser
1               5

<210> SEQ ID NO 163
<211> LENGTH: 12
<212> TYPE: PRT
<213> ORGANISM: Homo sapiens
<220> FEATURE:
<221> NAME/KEY: MISC_FEATURE
<223> OTHER INFORMATION: Sclerostin mAbs 19D11.1 VL CDR3

<400> SEQUENCE: 163

Gln Val Trp Asp Ser Ser Ile Asp His Pro Val Leu
1               5                   10

<210> SEQ ID NO 164
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 19D11.1 VH CDR1

<400> SEQUENCE: 164

Ser Tyr Asp Met His
1               5

<210> SEQ ID NO 165
<211> LENGTH: 16
<212> TYPE: PRT
<213> ORGANISM: Homo sapiens
<220> FEATURE:
<221> NAME/KEY: MISC_FEATURE
<223> OTHER INFORMATION: Sclerostin mAbs 19D11.1 VH CDR2

<400> SEQUENCE: 165

Ala Ile Gly Thr Ala Gly Asp Thr Tyr Tyr Ala Gly Ser Val Lys Gly
1               5                   10                  15

<210> SEQ ID NO 166
<211> LENGTH: 15
<212> TYPE: PRT
<213> ORGANISM: Homo sapiens
<220> FEATURE:
<221> NAME/KEY: MISC_FEATURE
<223> OTHER INFORMATION: Sclerostin mAbs 19D11.1 VH CDR3

<400> SEQUENCE: 166

Ser Trp Gly Glu Gly Asn Tyr Tyr Phe Tyr Tyr Gly Met Asp Val
1               5                   10                  15

<210> SEQ ID NO 167
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VL

<400> SEQUENCE: 167

Asp Ile Gln Met Thr Gln Ser Pro Ser Ser Val Ser Ala Ser Val Gly
1               5                   10                  15
```

Asp Arg Val Thr Ile Thr Cys Arg Ala Ser Gln Gly Ile Asn Thr Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Phe Pro Trp
                85                  90                  95

Thr Phe Gly Pro Gly Thr Lys Val Glu Ile Thr
            100                 105

<210> SEQ ID NO 168
<211> LENGTH: 127
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VH

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Val Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Gly Tyr Gly Ser Gly Asn Ser Tyr Tyr Tyr Tyr Ser
            100                 105                 110

Gly Met Asp Val Trp Gly Gln Gly Thr Thr Val Thr Val Ser Ser
        115                 120                 125

<210> SEQ ID NO 169
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VL CDR1

<400> SEQUENCE: 169

Arg Ala Ser Gln Gly Ile Asn Thr Trp Leu Ala
1               5                   10

<210> SEQ ID NO 170
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VL CDR2

<400> SEQUENCE: 170

```
Val Ala Ser Ser Leu Gln Ser
1               5

<210> SEQ ID NO 171
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VL CDR3

<400> SEQUENCE: 171

Gln Gln Ser Asp Ser Phe Pro Trp Thr
1               5

<210> SEQ ID NO 172
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VH CDR1

<400> SEQUENCE: 172

Glu Leu Ser Met His
1               5

<210> SEQ ID NO 173
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VH CDR2

<400> SEQUENCE: 173

Gly Phe Asp Pro Glu Asp Gly Glu Thr Ile Tyr Val Gln Lys Phe Gln
1               5                   10                  15

Gly

<210> SEQ ID NO 174
<211> LENGTH: 18
<212> TYPE: PRT
<213> ORGANISM: Homo sapiens
<220> FEATURE:
<221> NAME/KEY: MISC_FEATURE
<223> OTHER INFORMATION: Sclerostin mAbs 34H3.1 VH CDR3

<400> SEQUENCE: 174

Asp Leu Gly Tyr Gly Ser Gly Asn Ser Tyr Tyr Tyr Tyr Ser Gly Met
1               5                   10                  15

Asp Val

<210> SEQ ID NO 175
<211> LENGTH: 113
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VL

<400> SEQUENCE: 175

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30
```

```
Val Asp Gly Ser Thr Asn Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
                100                 105                 110

Lys

<210> SEQ ID NO 176
<211> LENGTH: 120
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VH

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Gly Ser Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Arg Tyr Tyr Gly Asp Thr Pro Phe Asp Tyr Trp Gly Gln
                100                 105                 110

Gly Thr Leu Val Thr Val Ser Ser
            115                 120

<210> SEQ ID NO 177
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VL CDR1

<400> SEQUENCE: 177

Arg Ser Ser Gln Ser Leu Leu Asn Ser Val Asp Gly Ser Thr Asn Leu
1               5                   10                  15

Asp

<210> SEQ ID NO 178
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VL CDR2

<400> SEQUENCE: 178
```

Thr Leu Ser Tyr Arg Ala Ser
1               5

<210> SEQ ID NO 179
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VL CDR3

<400> SEQUENCE: 179

Met Gln Arg Ile Glu Phe Pro Leu Thr
1               5

<210> SEQ ID NO 180
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VH CDR1

<400> SEQUENCE: 180

Ser Tyr Ser Met Asn
1               5

<210> SEQ ID NO 181
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VH CDR2

<400> SEQUENCE: 181

Tyr Ile Ser Ser Ser Gly Ser Ser Ile Tyr Tyr Ala Asp Ser Val Lys
1               5                   10                  15

Gly

<210> SEQ ID NO 182
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 27H6.1 VH CDR3

<400> SEQUENCE: 182

Glu Arg Tyr Tyr Gly Asp Thr Pro Phe Asp Tyr
1               5                   10

<210> SEQ ID NO 183
<211> LENGTH: 108
<212> TYPE: PRT
<213> ORGANISM: ARTIFICIAL SEQUENCE
<220> FEATURE:
<223> OTHER INFORMATION: Sclerostin mAbs 42F4HZ VL

<400> SEQUENCE: 183

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu

```
                35                  40                  45
Ile Tyr Ser Thr Ser Asn Leu Ala Ser Gly Val Pro Ser Arg Phe Ser
         50                  55                  60
Gly Ser Gly Ser Gly Thr Glu Phe Thr Leu Thr Ile Ser Ser Leu Gln
 65                  70                  75                  80
Pro Glu Asp Phe Ala Thr Tyr Tyr Cys Gln Gln Tyr Asp Phe Phe Pro
                 85                  90                  95
Ser Thr Phe Gly Gly Gly Thr Lys Val Glu Ile Lys
            100                 105

<210> SEQ ID NO 184
<211> LENGTH: 121
<212> TYPE: PRT
<213> ORGANISM: ARTIFICIAL SEQUENCE
<220> FEATURE:
<223> OTHER INFORMATION: Sclerostin mAbs 42F4HZ VH

<400> SEQUENCE: 184

Glu Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Tyr Met Asn Trp Val Arg Gln Ala Pro Gly Gln Arg Leu Glu Trp Met
         35                  40                  45
Gly Asp Ile Asn Pro Tyr Asn Asp Asp Thr Thr Tyr Asn His Lys Phe
     50                  55                  60
Lys Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Thr Ala Val Ile Thr Thr Asn Ala Met Asp Tyr Trp Gly
            100                 105                 110
Gln Gly Thr Thr Val Thr Val Ser Ser
        115                 120

<210> SEQ ID NO 185
<211> LENGTH: 12
<212> TYPE: PRT
<213> ORGANISM: ARTIFICIAL SEQUENCE
<220> FEATURE:
<223> OTHER INFORMATION: Sclerostin mAbs 42F4HZ VL CDR1

<400> SEQUENCE: 185

Arg Ala Ser Ser Ser Val Thr Ser Ser Tyr Leu Asn
 1               5                  10

<210> SEQ ID NO 186
<211> LENGTH: 7
<212> TYPE: PRT
<213> ORGANISM: ARTIFICIAL SEQUENCE
<220> FEATURE:
<223> OTHER INFORMATION: Sclerostin mAbs 42F4HZ VL CDR2

<400> SEQUENCE: 186

Ser Thr Ser Asn Leu Ala Ser
 1               5

<210> SEQ ID NO 187
<211> LENGTH: 9
<212> TYPE: PRT
<213> ORGANISM: ARTIFICIAL SEQUENCE
```

```
<220> FEATURE:
<223> OTHER INFORMATION: Sclerostin mAbs 42F4HZ VL CDR3

<400> SEQUENCE: 187

Gln Gln Tyr Asp Phe Phe Pro Ser Thr
1               5

<210> SEQ ID NO 188
<211> LENGTH: 5
<212> TYPE: PRT
<213> ORGANISM: ARTIFICIAL SEQUENCE
<220> FEATURE:
<223> OTHER INFORMATION: Sclerostin mAbs 42F4HZ VH CDR1

<400> SEQUENCE: 188

Asp Tyr Tyr Met Asn
1               5

<210> SEQ ID NO 189
<211> LENGTH: 17
<212> TYPE: PRT
<213> ORGANISM: ARTIFICIAL SEQUENCE
<220> FEATURE:
<223> OTHER INFORMATION: Sclerostin mAbs 42F4HZ VH CDR2

<400> SEQUENCE: 189

Asp Ile Asn Pro Tyr Asn Asp Asp Thr Thr Tyr Asn His Lys Phe Lys
1               5                   10                  15

Gly

<210> SEQ ID NO 190
<211> LENGTH: 12
<212> TYPE: PRT
<213> ORGANISM: ARTIFICIAL SEQUENCE
<220> FEATURE:
<223> OTHER INFORMATION: Sclerostin mAbs 42F4HZ VH CDR3

<400> SEQUENCE: 190

Glu Thr Ala Val Ile Thr Thr Asn Ala Met Asp Tyr
1               5                   10

<210> SEQ ID NO 191
<211> LENGTH: 108
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VL

<400> SEQUENCE: 191

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Thr Ser Ser
                20                  25                  30

Tyr Leu Asn Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Phe Phe Pro
                85                  90                  95

Ser Thr Phe Gly Gly Gly Thr Lys Leu Glu Ile Lys
```

<210> SEQ ID NO 192
<211> LENGTH: 121
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VH

<400> SEQUENCE: 192

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Glu Ser Leu Glu Trp Ile
        35                  40                  45

Gly Asp Ile Asn Pro Tyr Asn Asp Asp Thr Thr Tyr Asn His Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Ser Val Thr Val Ser Ser
        115                 120

<210> SEQ ID NO 193
<211> LENGTH: 12
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VL CDR1

<400> SEQUENCE: 193

Arg Ala Ser Ser Ser Val Thr Ser Ser Tyr Leu Asn
1               5                   10

<210> SEQ ID NO 194
<211> LENGTH: 7
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VL CDR2

<400> SEQUENCE: 194

Ser Thr Ser Asn Leu Ala Ser
1               5

<210> SEQ ID NO 195
<211> LENGTH: 9
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VL CDR3

<400> SEQUENCE: 195

Gln Gln Tyr Asp Phe Phe Pro Ser Thr
1               5

<210> SEQ ID NO 196
<211> LENGTH: 5
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VH CDR1

<400> SEQUENCE: 196

Asp Tyr Tyr Met Asn
1               5

<210> SEQ ID NO 197
<211> LENGTH: 17
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VH CDR2

<400> SEQUENCE: 197

Asp Ile Asn Pro Tyr Asn Asp Asp Thr Thr Tyr Asn His Lys Phe Lys
1               5                   10                  15

Gly

<210> SEQ ID NO 198
<211> LENGTH: 12
<212> TYPE: PRT
<213> ORGANISM: Mus musculus
<220> FEATURE:
<221> NAME/KEY: MISC_FEATURE
<223> OTHER INFORMATION: Sclerostin mAbs 42F4MU VH CDR3

<400> SEQUENCE: 198

Glu Thr Ala Val Ile Thr Thr Asn Ala Met Asp Tyr
1               5                   10

<210> SEQ ID NO 199
<211> LENGTH: 107
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VL

<400> SEQUENCE: 199

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys
            100                 105

<210> SEQ ID NO 200
<211> LENGTH: 123

```
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VH

<400> SEQUENCE: 200

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Thr Leu Glu Trp Ile
        35                  40                  45

Gly Glu Ile Asn Pro Asn Ser Gly Ala Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser
            115                 120

<210> SEQ ID NO 201
<211> LENGTH: 11
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VL CDR1

<400> SEQUENCE: 201

Arg Ala Ser Gln Asp Ile Ser Asn Tyr Leu Asn
1               5                   10

<210> SEQ ID NO 202
<211> LENGTH: 7
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VL CDR2

<400> SEQUENCE: 202

Tyr Thr Ser Arg Leu Leu Ser
1               5

<210> SEQ ID NO 203
<211> LENGTH: 9
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VL CDR3

<400> SEQUENCE: 203

Gln Gln Gly Asp Thr Leu Pro Tyr Thr
1               5

<210> SEQ ID NO 204
<211> LENGTH: 5
<212> TYPE: PRT
<213> ORGANISM: Mus musculus
```

```
<220> FEATURE:
<221> NAME/KEY: MISC_FEATURE
<223> OTHER INFORMATION: Sclerostin mAbs 13C7MU VH CDR1

<400> SEQUENCE: 204

Asp Tyr Asn Met His
1               5

<210> SEQ ID NO 205
<211> LENGTH: 17
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VH CDR2

<400> SEQUENCE: 205

Glu Ile Asn Pro Asn Ser Gly Gly Ala Gly Tyr Asn Gln Lys Phe Lys
1               5                   10                  15

Gly

<210> SEQ ID NO 206
<211> LENGTH: 14
<212> TYPE: PRT
<213> ORGANISM: Mus musculus
<220> FEATURE:
<221> NAME/KEY: MISC_FEATURE
<223> OTHER INFORMATION: Sclerostin mAbs 13C7MU VH CDR3

<400> SEQUENCE: 206

Leu Gly Tyr Asp Asp Ile Tyr Asp Asp Trp Tyr Phe Asp Val
1               5                   10

<210> SEQ ID NO 207
<211> LENGTH: 107
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VL

<400> SEQUENCE: 207

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Arg Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Glu Asp Phe Ala Met Tyr Tyr Cys Gln Gln Gly Asp Thr Leu Pro Tyr
                85                  90                  95

Thr Phe Gly Gly Gly Thr Lys Leu Glu Leu Lys
            100                 105

<210> SEQ ID NO 208
<211> LENGTH: 123
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VH
```

<400> SEQUENCE: 208

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Glu Leu Ser Arg Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120

<210> SEQ ID NO 209
<211> LENGTH: 11
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VL CDR1

<400> SEQUENCE: 209

Arg Ala Ser Gln Asp Ile Ser Asn Tyr Leu Asn
1               5                   10

<210> SEQ ID NO 210
<211> LENGTH: 7
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VL CDR2

<400> SEQUENCE: 210

Tyr Thr Ser Arg Leu Leu Ser
1               5

<210> SEQ ID NO 211
<211> LENGTH: 9
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VL CDR3

<400> SEQUENCE: 211

Gln Gln Gly Asp Thr Leu Pro Tyr Thr
1               5

<210> SEQ ID NO 212
<211> LENGTH: 5
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VH CDR1

<400> SEQUENCE: 212

```
Asp Tyr Asn Met His
1               5

<210> SEQ ID NO 213
<211> LENGTH: 17
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VH CDR2

<400> SEQUENCE: 213

Glu Ile Asn Pro Asn Ser Gly Gly Ala Gly Tyr Asn Gln Lys Phe Lys
1               5                   10                  15

Gly

<210> SEQ ID NO 214
<211> LENGTH: 14
<212> TYPE: PRT
<213> ORGANISM: Rattus norvegicus
<220> FEATURE:
<221> NAME/KEY: MISC_FEATURE
<223> OTHER INFORMATION: Sclerostin mAbs 13C7Rat VH CDR3

<400> SEQUENCE: 214

Leu Gly Tyr Asp Asp Ile Tyr Asp Asp Trp Tyr Phe Asp Val
1               5                   10

<210> SEQ ID NO 215
<211> LENGTH: 107
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VL

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105

<210> SEQ ID NO 216
<211> LENGTH: 123
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VH

<400> SEQUENCE: 216

Glu Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
         20                  25                  30

Asn Met His Trp Val Arg Gln Ala Pro Gly Gln Gly Leu Glu Trp Met
         35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
             85                  90                  95

Ala Arg Leu Gly Tyr Asp Ile Tyr Asp Asp Trp Tyr Phe Asp Val
            100                 105                 110

Trp Gly Gln Gly Thr Thr Val Thr Val Ser Ser
        115                 120

<210> SEQ ID NO 217
<211> LENGTH: 11
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VL CDR1

<400> SEQUENCE: 217

Arg Ala Ser Gln Asp Ile Ser Asn Tyr Leu Asn
1               5                   10

<210> SEQ ID NO 218
<211> LENGTH: 7
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VL CDR2

<400> SEQUENCE: 218

Tyr Thr Ser Arg Leu Leu Ser
1               5

<210> SEQ ID NO 219
<211> LENGTH: 9
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VL CDR3

<400> SEQUENCE: 219

Gln Gln Gly Asp Thr Leu Pro Tyr Thr
1               5

<210> SEQ ID NO 220
<211> LENGTH: 5
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VH CDR1

<400> SEQUENCE: 220

Asp Tyr Asn Met His
1               5
```

```
<210> SEQ ID NO 221
<211> LENGTH: 17
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VH CDR2

<400> SEQUENCE: 221

Glu Ile Asn Pro Asn Ser Gly Gly Ala Gly Tyr Asn Gln Lys Phe Lys
1               5                   10                  15

Gly

<210> SEQ ID NO 222
<211> LENGTH: 14
<212> TYPE: PRT
<213> ORGANISM: Homo sapiens
<220> FEATURE:
<221> NAME/KEY: MISC_FEATURE
<223> OTHER INFORMATION: Sclerostin mAbs 13C7Hu VH CDR3

<400> SEQUENCE: 222

Leu Gly Tyr Asp Asp Ile Tyr Asp Asp Trp Tyr Phe Asp Val
1               5                   10

<210> SEQ ID NO 223
<211> LENGTH: 103
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VL

<400> SEQUENCE: 223

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Trp Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ala Trp Gln Glu Phe Phe Gly Gln
                85                  90                  95

Gly Thr Lys Leu Glu Ile Lys
            100

<210> SEQ ID NO 224
<211> LENGTH: 120
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VH

<400> SEQUENCE: 224

Glu Val Gln Leu Val Gln Ser Gly Gly Gly Leu Val Gln Pro Gly Gly
1               5                   10                  15

Ser Leu Arg Leu Ser Cys Thr Ala Ser Gly Phe Thr Phe Ser Asn His
                20                  25                  30

Trp Ile His Trp Val Arg Gln Ala Pro Gly Lys Gly Leu Glu Trp Val
```

```
                35                  40                  45
Ser Gly Ile Asn Trp Asn Ser Gly Arg Gly Tyr Ser Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Pro Val Ala Thr Gly Ala Phe Asp Ile Trp Gly Gln
            100                 105                 110

Gly Thr Thr Val Thr Val Ser Ser
        115                 120

<210> SEQ ID NO 225
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VL CDR1

<400> SEQUENCE: 225

Arg Ala Ser Gln Trp Val Ser Ser Tyr Leu Ala
 1               5                  10

<210> SEQ ID NO 226
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VL CDR2

<400> SEQUENCE: 226

Asp Ala Ser Asn Arg Ala Thr
 1               5

<210> SEQ ID NO 227
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VL CDR3

<400> SEQUENCE: 227

Ala Trp Gln Glu Phe
 1               5

<210> SEQ ID NO 228
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VH CDR1

<400> SEQUENCE: 228

Asn His Trp Ile His
 1               5

<210> SEQ ID NO 229
<211> LENGTH: 17
<212> TYPE: PRT
<213> ORGANISM: Homo sapiens
<220> FEATURE:
```

```
<221> NAME/KEY: MISC_FEATURE
<223> OTHER INFORMATION: DKK-1 mAbs 11H10Hu VH CDR2

<400> SEQUENCE: 229

Gly Ile Asn Trp Asn Ser Gly Ser Arg Gly Tyr Ser Asp Ser Val Lys
1               5                   10                  15
Gly

<210> SEQ ID NO 230
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 11H10Hu VH CDR3

<400> SEQUENCE: 230

Glu Arg Pro Val Ala Thr Gly Ala Phe Asp Ile
1               5                   10

<210> SEQ ID NO 231
<211> LENGTH: 107
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VL

<400> SEQUENCE: 231

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Tyr Ser Asp
                20                  25                  30

Leu Ala Trp Tyr Gln Gln Lys Pro Gly Lys Ser Pro Gln Leu Leu Ile
            35                  40                  45

Tyr Asn Ala Asn Ser Leu Gln Asn Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Tyr Asn Asn Tyr Pro Pro
                85                  90                  95

Thr Phe Gly Gly Gly Thr Lys Leu Glu Leu Lys
            100                 105

<210> SEQ ID NO 232
<211> LENGTH: 120
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VH

<400> SEQUENCE: 232

Glu Val Gln Leu Val Glu Ser Gly Gly Gly Leu Val Gln Pro Ala Asn
1               5                   10                  15

Ser Leu Lys Leu Ser Cys Ala Ala Ser Gly Phe Thr Phe Ser Asp Tyr
                20                  25                  30

Ala Met Ala Trp Val Arg Gln Ser Pro Lys Lys Gly Leu Glu Trp Val
            35                  40                  45

Ala Thr Ile Ile Tyr Asp Gly Ser Ser Thr Tyr Tyr Arg Asp Ser Val
        50                  55                  60
```

```
Lys Gly Arg Phe Thr Ile Ser Arg Asp Asn Ala Lys Ser Thr Leu Tyr
 65                  70                  75                  80

Leu Gln Met Asp Ser Leu Arg Ser Glu Asp Thr Ala Thr Tyr Tyr Cys
                 85                  90                  95

Ala Thr Gly Leu Gly Ile Ala Thr Asp Tyr Phe Asp Tyr Trp Gly Gln
            100                 105                 110

Gly Val Leu Val Thr Val Ser Ser
        115                 120

<210> SEQ ID NO 233
<211> LENGTH: 11
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VL CDR1

<400> SEQUENCE: 233

Leu Ala Ser Glu Asp Ile Tyr Ser Asp Leu Ala
1               5                   10

<210> SEQ ID NO 234
<211> LENGTH: 7
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VL CDR2

<400> SEQUENCE: 234

Asn Ala Asn Ser Leu Gln Asn
1               5

<210> SEQ ID NO 235
<211> LENGTH: 9
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VL CDR3

<400> SEQUENCE: 235

Gln Gln Tyr Asn Asn Tyr Pro Pro Thr
1               5

<210> SEQ ID NO 236
<211> LENGTH: 5
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VH CDR1

<400> SEQUENCE: 236

Asp Tyr Ala Met Ala
1               5

<210> SEQ ID NO 237
<211> LENGTH: 17
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VH CDR2

<400> SEQUENCE: 237
```

```
Thr Ile Ile Tyr Asp Gly Ser Ser Thr Tyr Tyr Arg Asp Ser Val Lys
1               5                   10                  15

Gly
```

<210> SEQ ID NO 238
<211> LENGTH: 11
<212> TYPE: PRT
<213> ORGANISM: Rattus norvegicus
<220> FEATURE:
<221> NAME/KEY: MISC_FEATURE
<223> OTHER INFORMATION: DKK-1 mAbs 11H10Rat VH CDR3

<400> SEQUENCE: 238

```
Gly Leu Gly Ile Ala Thr Asp Tyr Phe Asp Tyr
1               5                   10
```

<210> SEQ ID NO 239
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VL

<400> SEQUENCE: 239

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Phe Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Phe Lys
            100                 105
```

<210> SEQ ID NO 240
<211> LENGTH: 124
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VH

<400> SEQUENCE: 240

```
Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Asp Asn Gly His Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Asp Gly Glu Leu Leu Asn Tyr Tyr Tyr Tyr Gly Met Asp
            100                 105                 110
Val Trp Gly Gln Gly Thr Thr Val Thr Val Ser Ser
            115                 120
```

<210> SEQ ID NO 241
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VL CDR1

<400> SEQUENCE: 241

```
Arg Ala Ser Gln Gly Ile Arg Asp Asp Leu Gly
1               5                   10
```

<210> SEQ ID NO 242
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VL CDR2

<400> SEQUENCE: 242

```
Ala Ala Ser Ser Leu Gln Ser
1               5
```

<210> SEQ ID NO 243
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VL CDR3

<400> SEQUENCE: 243

```
Leu Gln His Asn Ser Tyr Pro Cys Ser
1               5
```

<210> SEQ ID NO 244
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VH CDR1

<400> SEQUENCE: 244

```
Ser Tyr Gly Ile Ser
1               5
```

<210> SEQ ID NO 245
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VH CDR2

<400> SEQUENCE: 245

```
Trp Ile Ser Ala Asp Asn Gly His Thr Asn Tyr Ala Gln Lys Leu Gln
1               5                   10                  15
Gly
```

```
<210> SEQ ID NO 246
<211> LENGTH: 15
<212> TYPE: PRT
<213> ORGANISM: Homo sapiens
<220> FEATURE:
<221> NAME/KEY: MISC_FEATURE
<223> OTHER INFORMATION: DKK-1 mAbs 2.4.1 VH CDR3

<400> SEQUENCE: 246

Asp Gly Glu Leu Leu Asn Tyr Tyr Tyr Tyr Tyr Gly Met Asp Val
1               5                   10                  15

<210> SEQ ID NO 247
<211> LENGTH: 112
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VL

<400> SEQUENCE: 247

Asp Ile Val Met Thr Gln Thr Pro Leu Ser Leu Ser Val Ile Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Arg Pro Gly Gln Pro
        35                  40                  45

Pro Gln Leu Leu Ile Tyr Glu Val Ser Asn Arg Phe Ser Gly Val Pro
    50                  55                  60

His Arg Leu Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Val Pro Trp Thr Phe Gly Gln Gly Thr Lys Val Glu Ile Lys
            100                 105                 110

<210> SEQ ID NO 248
<211> LENGTH: 119
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VH

<400> SEQUENCE: 248

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Trp Gly Gly Ser Pro Ala Gly Pro Trp Gly Gln Gly
            100                 105                 110

Thr Leu Val Thr Val Ser Ser
```

<210> SEQ ID NO 249
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VL CDR1

<400> SEQUENCE: 249

Lys Ser Ser Gln Ser Leu Leu His Ser Asp Gly Lys Thr Tyr Leu Tyr
1               5                   10                  15

<210> SEQ ID NO 250
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VL CDR2

<400> SEQUENCE: 250

Glu Val Ser Asn Arg Phe Ser
1               5

<210> SEQ ID NO 251
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VL CDR3

<400> SEQUENCE: 251

Met Gln Ser Ile Gln Val Pro Trp Thr
1               5

<210> SEQ ID NO 252
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VH CDR1

<400> SEQUENCE: 252

Ser Tyr Gly Met His
1               5

<210> SEQ ID NO 253
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.20.1 VH CDR2

<400> SEQUENCE: 253

Val Ile Ser Tyr Asp Gly Ser Asp Lys Tyr Tyr Ala Asp Ser Val Lys
1               5                   10                  15

Gly

<210> SEQ ID NO 254
<211> LENGTH: 10
<212> TYPE: PRT
<213> ORGANISM: Homo sapiens

```
<220> FEATURE:
<221> NAME/KEY: MISC_FEATURE
<223> OTHER INFORMATION: DKK-1 mAbs 2.20.1 VH CDR3

<400> SEQUENCE: 254

Asp Gln Trp Gly Gly Ser Pro Ala Gly Pro
1               5                   10

<210> SEQ ID NO 255
<211> LENGTH: 108
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VL

<400> SEQUENCE: 255

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 256
<211> LENGTH: 119
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VH

<400> SEQUENCE: 256

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Phe Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Gly Ile Ala Ala Ser Phe Asp Tyr Trp Gly Gln Gly
            100                 105                 110

Thr Leu Val Thr Val Ser Ser
        115

<210> SEQ ID NO 257
<211> LENGTH: 12
```

```
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VL CDR1

<400> SEQUENCE: 257

Arg Ala Ser Gln Ser Val Ser Ser Asn Tyr Leu Ala
1               5                   10

<210> SEQ ID NO 258
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VL CDR2

<400> SEQUENCE: 258

Gly Ala Ser Ser Arg Ala Thr
1               5

<210> SEQ ID NO 259
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VL CDR3

<400> SEQUENCE: 259

Gln Gln Tyr Gly Ser Ser Pro Ile Thr
1               5

<210> SEQ ID NO 260
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VH CDR1

<400> SEQUENCE: 260

Ser Tyr Gly Met His
1               5

<210> SEQ ID NO 261
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VH CDR2

<400> SEQUENCE: 261

Val Ile Ser Tyr Asp Gly Ser Asp Lys Tyr Tyr Ala Asp Ser Val Lys
1               5                   10                  15

Gly

<210> SEQ ID NO 262
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs 2.37.1 VH CDR3

<400> SEQUENCE: 262
```

```
Glu Leu Gly Ile Ala Ala Ser Phe Asp Tyr
1               5                   10
```

<210> SEQ ID NO 263
<211> LENGTH: 112
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VL

<400> SEQUENCE: 263

```
Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Val Pro Trp Thr Phe Gly Gln Gly Thr Lys Val Glu Ile Lys
            100                 105                 110
```

<210> SEQ ID NO 264
<211> LENGTH: 117
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VH

<400> SEQUENCE: 264

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Gly Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Val Asp Thr Ala Met Pro Trp Gly Gln Gly Thr Thr
            100                 105                 110

Val Thr Val Ser Ser
        115
```

<210> SEQ ID NO 265
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VL CDR1

-continued

```
<400> SEQUENCE: 265

Lys Ser Ser Gln Ser Leu Leu His Ser Asp Gly Lys Thr Tyr Leu Tyr
1               5                   10                  15

<210> SEQ ID NO 266
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VL CDR2

<400> SEQUENCE: 266

Glu Val Ser Asn Arg Phe Ser
1               5

<210> SEQ ID NO 267
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VL CDR3

<400> SEQUENCE: 267

Met Gln Ser Ile Gln Val Pro Trp Thr
1               5

<210> SEQ ID NO 268
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VH CDR1

<400> SEQUENCE: 268

Ser Tyr Gly Met His
1               5

<210> SEQ ID NO 269
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VH CDR2

<400> SEQUENCE: 269

Val Ile Ser Tyr Asp Gly Ser Asp Lys Tyr Tyr Ala Asp Ser Val Lys
1               5                   10                  15

Gly

<210> SEQ ID NO 270
<211> LENGTH: 8
<212> TYPE: PRT
<213> ORGANISM: Homo sapiens
<220> FEATURE:
<221> NAME/KEY: MISC_FEATURE
<223> OTHER INFORMATION: DKK-1 mAbs 2.40.1 VH CDR3

<400> SEQUENCE: 270

Asp Leu Val Asp Thr Ala Met Pro
1               5
```

```
<210> SEQ ID NO 271
<211> LENGTH: 112
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VL

<400> SEQUENCE: 271

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Lys Gln Leu Pro Phe Thr Phe Gly Pro Gly Thr Lys Val Asp Ile Lys
            100                 105                 110

<210> SEQ ID NO 272
<211> LENGTH: 122
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VH

<400> SEQUENCE: 272

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Tyr Ser Leu Tyr Tyr Tyr Tyr Gly Met Asp Val Trp
            100                 105                 110

Gly Gln Gly Thr Thr Val Thr Val Ser Ser
        115                 120

<210> SEQ ID NO 273
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VL CDR1

<400> SEQUENCE: 273

Lys Ser Ser Gln Ser Leu Leu His Ser Asp Gly Lys Thr Tyr Leu Tyr
 1               5                  10                  15
```

<210> SEQ ID NO 274
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VL CDR2

<400> SEQUENCE: 274

Glu Val Ser Asn Arg Phe Ser
1               5

<210> SEQ ID NO 275
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VL CDR3

<400> SEQUENCE: 275

Met Gln Ser Lys Gln Leu Pro Phe Thr
1               5

<210> SEQ ID NO 276
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VH CDR1

<400> SEQUENCE: 276

Ser Tyr Gly Met His
1               5

<210> SEQ ID NO 277
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VH CDR2

<400> SEQUENCE: 277

Val Ile Ser Tyr Asp Gly Ser Asp Lys Tyr Tyr Ala Asp Ser Val Lys
1               5                   10                  15

Gly

<210> SEQ ID NO 278
<211> LENGTH: 13
<212> TYPE: PRT
<213> ORGANISM: Homo sapiens
<220> FEATURE:
<221> NAME/KEY: MISC_FEATURE
<223> OTHER INFORMATION: DKK-1 mAbs 2.41.1 VH CDR3

<400> SEQUENCE: 278

Ala Gly Tyr Ser Leu Tyr Tyr Tyr Tyr Gly Met Asp Val
1               5                   10

<210> SEQ ID NO 279
<211> LENGTH: 113
<212> TYPE: PRT
<213> ORGANISM: Homo sapiens
<220> FEATURE:

<221> NAME/KEY: MISC_FEATURE
<223> OTHER INFORMATION: DKK-1 mAbs 2.47.1 VL

<400> SEQUENCE: 279

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys

<210> SEQ ID NO 280
<211> LENGTH: 127
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VH

<400> SEQUENCE: 280

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asp Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Ala Tyr Gly Asp Tyr Gly Gly Asp Tyr Tyr Tyr
            100                 105                 110

Gly Met Asp Val Trp Gly Gln Gly Thr Thr Val Thr Val Ser Ser
        115                 120                 125

<210> SEQ ID NO 281
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VL CDR1

<400> SEQUENCE: 281

Arg Ser Ser Gln Ser Leu Leu Asp Ser Asp Asp Gly Asp Thr Tyr Leu
1               5                   10                  15

Asp

```
<210> SEQ ID NO 282
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VL CDR2

<400> SEQUENCE: 282

Thr Leu Ser Tyr Arg Ala Ser
1               5

<210> SEQ ID NO 283
<211> LENGTH: 14
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VL CDR3

<400> SEQUENCE: 283

Met Gln Arg Ile Glu Phe Pro Met Gln Arg Ile Glu Phe Pro
1               5                   10

<210> SEQ ID NO 284
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VH CDR1

<400> SEQUENCE: 284

Ser Gly Gly Tyr Tyr Trp Ser
1               5

<210> SEQ ID NO 285
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VH CDR2

<400> SEQUENCE: 285

Asp Ile Tyr Tyr Ser Gly Ser Thr Tyr Tyr Asn Pro Ser Leu Lys Ser
1               5                   10                  15

<210> SEQ ID NO 286
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 2.47.1 VH CDR3

<400> SEQUENCE: 286

Asp Arg Ala Tyr Gly Asp Tyr Gly Gly Asp Tyr Tyr Tyr Gly Met Asp
1               5                   10                  15

Val

<210> SEQ ID NO 287
<211> LENGTH: 107
<212> TYPE: PRT
<213> ORGANISM: Homo sapiens
<220> FEATURE:
<221> NAME/KEY: MISC_FEATURE
```

<223> OTHER INFORMATION: DKK-1 mAbs 5.17.1 VL

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Asn Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Ala Asp Ile Ala Thr Tyr Tyr Cys Gln Gln Tyr Asp Asp Phe Pro Leu
                85                  90                  95

Thr Phe Gly Gly Gly Thr Lys Val Glu Ile Lys
            100                 105

<210> SEQ ID NO 288
<211> LENGTH: 118
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VH

<400> SEQUENCE: 288

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Tyr Asn Trp Asn Asn Asp Leu Phe Asp Tyr Trp Gly Gln Gly Thr
            100                 105                 110

Leu Val Thr Val Ser Ser
        115

<210> SEQ ID NO 289
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VL CDR1

<400> SEQUENCE: 289

Gln Ala Ser Gln Asp Ile Asn Asn Tyr Leu Asn
1               5                   10

<210> SEQ ID NO 290
<211> LENGTH: 7
<212> TYPE: PRT
<213> ORGANISM: Homo sapiens

```
<220> FEATURE:
<221> NAME/KEY: MISC_FEATURE
<223> OTHER INFORMATION: DKK-1 mAbs 5.17.1 VL CDR2

<400> SEQUENCE: 290

Asp Ala Ser Asn Leu Glu Thr
1               5

<210> SEQ ID NO 291
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VL CDR3

<400> SEQUENCE: 291

Gln Gln Tyr Asp Asp Phe Pro Leu Thr
1               5

<210> SEQ ID NO 292
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VH CDR1

<400> SEQUENCE: 292

Ser Tyr Tyr Trp Ser
1               5

<210> SEQ ID NO 293
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VH CDR2

<400> SEQUENCE: 293

Tyr Ile Tyr Tyr Ser Gly Asn Thr Asn Tyr Asn Pro Ser Leu Lys Ser
1               5                   10                  15

<210> SEQ ID NO 294
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs 5.17.1 VH CDR3

<400> SEQUENCE: 294

Tyr Asn Trp Asn Asn Asp Leu Phe Asp Tyr
1               5                   10

<210> SEQ ID NO 295
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VL

<400> SEQUENCE: 295

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

<210> SEQ ID NO 296
<211> LENGTH: 126
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VH

<400> SEQUENCE: 296

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Cys Asp Gly Ser Asn Lys Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Ser Gly Ser Tyr Glu Asp Tyr Tyr Tyr Gly
            100                 105                 110

Met Asp Val Trp Gly Gln Gly Thr Thr Val Thr Val Ser Ser
        115                 120                 125
```

<210> SEQ ID NO 297
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VL CDR1

<400> SEQUENCE: 297

```
Gln Ala Ser Gln Asp Ile Ser Asn Tyr Leu Asn
1               5                   10
```

<210> SEQ ID NO 298
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VL CDR2

<400> SEQUENCE: 298

Asp Ala Ser Asn Leu Glu Thr

-continued

```
1               5

<210> SEQ ID NO 299
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VL CDR3

<400> SEQUENCE: 299

Gln Gln Tyr Asp Asn Leu Pro Leu Thr
1               5

<210> SEQ ID NO 300
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VH CDR1

<400> SEQUENCE: 300

Ser Tyr Gly Met His
1               5

<210> SEQ ID NO 301
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VH CDR2

<400> SEQUENCE: 301

Val Ile Trp Cys Asp Gly Ser Asn Lys Tyr Tyr Ala Asp Ser Val Lys
1               5                   10                  15

Gly

<210> SEQ ID NO 302
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.23.1 VH CDR3

<400> SEQUENCE: 302

Gly Gly Tyr Gly Ser Gly Ser Tyr Glu Asp Tyr Tyr Tyr Gly Met Asp
1               5                   10                  15

Val

<210> SEQ ID NO 303
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VL

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Asp
            20                  25                  30
```

```
Leu Asn Trp Tyr Gln Gln Lys Pro Gly Lys Ala Pro Arg Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Phe Tyr Cys Gln Gln Tyr Asp His Leu Pro Ile
                    85                  90                  95

Ala Phe Gly Gln Gly Thr Arg Leu Glu Ile Lys
                100                 105

<210> SEQ ID NO 304
<211> LENGTH: 119
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VH

<400> SEQUENCE: 304

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asp Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Phe
 65                  70                  75                  80

Met Glu Leu Ser Ser Leu Arg Ser Glu Asp Thr Ala Val Tyr Tyr Cys
                    85                  90                  95

Ala Arg Thr Asp Tyr Phe Tyr Phe Gly Met Asp Val Trp Gly Gln Gly
                100                 105                 110

Thr Thr Val Thr Val Ser Ser
        115

<210> SEQ ID NO 305
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAps 5.25.1 VL CDR1

<400> SEQUENCE: 305

Gln Ala Ser Gln Asp Ile Ser Lys Asp Leu Asn
 1               5                  10

<210> SEQ ID NO 306
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VL CDR2

<400> SEQUENCE: 306

Asp Ala Ser Asn Leu Glu Thr
 1               5
```

```
<210> SEQ ID NO 307
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VL CDR3

<400> SEQUENCE: 307

Gln Gln Tyr Asp Asn Leu Pro Leu Thr
1               5

<210> SEQ ID NO 308
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VH CDR1

<400> SEQUENCE: 308

Ser Tyr Gly Met His
1               5

<210> SEQ ID NO 309
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.25.1 VH CDR2

<400> SEQUENCE: 309

Trp Met Asp Pro Asn Ser Gly Asn Thr Gly Tyr Ala Gln Lys Phe Gln
1               5                   10                  15

Gly

<210> SEQ ID NO 310
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs VH CDR3

<400> SEQUENCE: 310

Thr Asp Tyr Phe Tyr Phe Gly Met Asp Val
1               5                   10

<210> SEQ ID NO 311
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VL

<400> SEQUENCE: 311

Asp Ile Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Glu Ala Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Leu
                 85                  90                  95

Thr Phe Gly Gly Gly Thr Lys Val Glu Ile Lys
            100                 105

<210> SEQ ID NO 312
<211> LENGTH: 125
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VH

<400> SEQUENCE: 312

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Arg Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gly Ala Val Ala Asp Tyr Asn Tyr Tyr Tyr Gly Met
            100                 105                 110

Asp Val Trp Gly Gln Gly Thr Thr Val Thr Val Ser Ser
            115                 120                 125

<210> SEQ ID NO 313
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VL CDR1

<400> SEQUENCE: 313

Gln Ala Ser Gln Asp Ile Ser Asn Tyr Leu Asn
  1               5                  10

<210> SEQ ID NO 314
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VL CDR2

<400> SEQUENCE: 314

Asp Ala Ser Asn Leu Glu Ala
  1               5

<210> SEQ ID NO 315
<211> LENGTH: 9
<212> TYPE: PRT
<213> ORGANISM: Homo sapiens
<220> FEATURE:
```

```
<221> NAME/KEY: MISC_FEATURE
<223> OTHER INFORMATION: DKK-1 mAbs 5.31.1 VL CDR3

<400> SEQUENCE: 315

Gln Gln Tyr Asp Asn Leu Pro Leu Thr
1               5

<210> SEQ ID NO 316
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VH CDR1

<400> SEQUENCE: 316

Ser Tyr Gly Met His
1               5

<210> SEQ ID NO 317
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VH CDR2

<400> SEQUENCE: 317

Val Ile Trp Tyr Asp Gly Arg Asn Lys Tyr Tyr Ala Asp Ser Val Lys
1               5                   10                  15

Gly

<210> SEQ ID NO 318
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 5.31.1 VH CDR3

<400> SEQUENCE: 318

Gly Gly Gly Ala Val Ala Asp Tyr Asn Tyr Tyr Gly Met Asp Val
1               5                   10                  15

<210> SEQ ID NO 319
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VL

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Ile
```

```
                    85                  90                  95

Thr Phe Gly Gln Gly Thr Arg Leu Glu Ile Lys
                100                 105

<210> SEQ ID NO 320
<211> LENGTH: 119
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VH

<400> SEQUENCE: 320

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Ser Trp Val Arg Gln Ala Thr Gly Leu Gly Leu Glu Trp Met
        35                  40                  45

Gly Trp Met Asn Pro Ser Ser Gly Tyr Thr Gly Tyr Ala Gln Asn Phe
    50                  55                  60

Gln Gly Arg Val Thr Met Thr Trp Asn Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Asp Tyr Tyr Tyr Gly Met Asp Val Trp Gly Arg Gly
                100                 105                 110

Thr Thr Val Thr Val Ser Ser
        115

<210> SEQ ID NO 321
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VL CDR1

<400> SEQUENCE: 321

Gln Ala Ser Gln Asp Ile Ser Lys Asp Leu Asn
1               5                   10

<210> SEQ ID NO 322
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VL CDR2

<400> SEQUENCE: 322

Asp Ala Ser Asn Leu Glu Thr
1               5

<210> SEQ ID NO 323
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VL CDR3

<400> SEQUENCE: 323
```

-continued

```
Gln Gln Tyr Asp Asp Leu Pro Ile Thr
1               5

<210> SEQ ID NO 324
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VH CDR1

<400> SEQUENCE: 324

Ser Tyr Asp Ile Ser
1               5

<210> SEQ ID NO 325
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VH CDR2

<400> SEQUENCE: 325

Trp Met Asn Pro Ser Ser Gly Tyr Thr Gly Tyr Ala Gln Asn Phe Gln
1               5                   10                  15

Gly

<210> SEQ ID NO 326
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs 5.32.1 VH CDR3

<400> SEQUENCE: 326

Thr Asp Tyr Tyr Tyr Tyr Gly Met Asp Val
1               5                   10

<210> SEQ ID NO 327
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VL

<400> SEQUENCE: 327

Asp Ile Arg Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Glu Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Leu
                85                  90                  95

Thr Phe Gly Gly Gly Thr Lys Val Glu Ile Lys
            100                 105
```

```
<210> SEQ ID NO 328
<211> LENGTH: 118
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VH

<400> SEQUENCE: 328
```

Gln Val Leu Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Thr Pro Gly Lys Gly Leu Glu Trp Ile
        35                  40                  45

Gly Tyr Val Tyr Tyr Ser Gly Ser Thr Tyr Asn Pro Ser Leu Lys
    50                  55                  60

Ser Arg Val Thr Ile Ser Met Tyr Thr Ser Lys Thr Glu Phe Ser Leu
65                  70                  75                  80

Lys Leu Ser Ser Val Thr Ala Ala Asp Thr Ala Val Tyr Tyr Cys Ala
                85                  90                  95

Arg Tyr Asn Trp Asn Asn Asp Leu Phe Asp Tyr Trp Gly Gln Gly Thr
            100                 105                 110

Leu Val Thr Val Ser Ser
        115

```
<210> SEQ ID NO 329
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VL CDR1

<400> SEQUENCE: 329
```

Gln Ala Ser Gln Asp Ile Ser Asn Tyr Leu Asn
1               5                   10

```
<210> SEQ ID NO 330
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VL CDR2

<400> SEQUENCE: 330
```

Asp Ala Ser Asn Leu Glu Thr
1               5

```
<210> SEQ ID NO 331
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VL CDR3

<400> SEQUENCE: 331
```

Gln Gln Tyr Asp Asn Phe Pro Leu Thr
1               5

```
<210> SEQ ID NO 332
```

```
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VH CDR1

<400> SEQUENCE: 332

Ser Tyr Tyr Trp Ser
1               5

<210> SEQ ID NO 333
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VH CDR2

<400> SEQUENCE: 333

Tyr Val Tyr Tyr Ser Gly Ser Thr Ser Tyr Asn Pro Ser Leu Lys Ser
1               5                   10                  15

<210> SEQ ID NO 334
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs 5.40.1 VH CDR3

<400> SEQUENCE: 334

Tyr Asn Trp Asn Asn Asp Leu Phe Asp Tyr
1               5                   10

<210> SEQ ID NO 335
<211> LENGTH: 108
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VL

<400> SEQUENCE: 335

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Leu Ser Ser Ser Asp His
                85                  90                  95

Val Ile Phe Gly Gly Gly Thr Lys Leu Thr Val Leu
            100                 105

<210> SEQ ID NO 336
<211> LENGTH: 120
<212> TYPE: PRT
<213> ORGANISM: Homo sapiens
<220> FEATURE:
<221> NAME/KEY: MISC_FEATURE
```

<223> OTHER INFORMATION: DKK-1 mAbs 5.65.1 VH

<400> SEQUENCE: 336

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Gly Asn Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Thr Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Glu Phe Gly Glu Leu Glu Pro Arg Phe Asp Tyr Trp Gly Gln
            100                 105                 110

Gly Thr Leu Val Thr Val Ser Ser
        115                 120

<210> SEQ ID NO 337
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VL CDR1

<400> SEQUENCE: 337

Gly Gly Asn Asn Ile Gly Ser Lys Ser Val His
1               5                   10

<210> SEQ ID NO 338
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VL CDR2

<400> SEQUENCE: 338

Asp Asp Ser Asp Arg Pro Ser
1               5

<210> SEQ ID NO 339
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VL CDR3

<400> SEQUENCE: 339

Gln Val Leu Asp Ser Ser Ser Asp His Val Ile
1               5                   10

<210> SEQ ID NO 340
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VH CDR1

```
<400> SEQUENCE: 340

Asn Tyr Ala Met Ser
1               5

<210> SEQ ID NO 341
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VH CDR2

<400> SEQUENCE: 341

Ala Ile Ser Gly Gly Gly Gly Thr Thr Tyr Tyr Ala Asp Ser Val Glu
1               5                   10                  15

Gly

<210> SEQ ID NO 342
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.65.1 VH CDR3

<400> SEQUENCE: 342

Glu Phe Gly Glu Leu Glu Pro Arg Phe Asp Tyr
1               5                   10

<210> SEQ ID NO 343
<211> LENGTH: 108
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VL

<400> SEQUENCE: 343

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asn Asp His
                85                  90                  95

Val Val Phe Gly Gly Gly Thr Lys Leu Thr Val Leu
            100                 105

<210> SEQ ID NO 344
<211> LENGTH: 124
<212> TYPE: PRT
<213> ORGANISM: Homo sapiens
<220> FEATURE:
<221> NAME/KEY: MISC_FEATURE
<223> OTHER INFORMATION: DKK-1 mABs 5.76.1 VH

<400> SEQUENCE: 344

Gln Leu Gln Leu Gln Glu Ser Gly Pro Gly Leu Val Lys Pro Ser Glu
```

```
                1               5                  10                 15
            Thr Leu Ser Leu Thr Cys Thr Val Ser Gly Gly Ser Ile Ser Ser Ser
                            20                  25                 30

Asn Tyr Tyr Trp Gly Trp Ile Arg Gln Pro Pro Gly Lys Gly Leu Glu
                        35                  40                 45

Trp Ile Gly Thr Ile Tyr Tyr Ser Gly Ser Thr Tyr Tyr Thr Pro Ser
                    50                  55                 60

Leu Lys Ser Arg Val Thr Ile Ser Val Asp Thr Ser Lys Asn Gln Phe
             65                  70                  75                 80

Ser Leu Lys Leu Ser Ser Val Thr Ala Ala Asp Thr Ala Val Tyr Tyr
                            85                  90                 95

Cys Ala Arg Glu Arg Ala Ile Ala Val Ala Ala Ile Val Phe Phe Asp
                            100                 105            110

Tyr Trp Gly Gln Gly Thr Leu Val Thr Val Ser Ser
                        115                 120
```

<210> SEQ ID NO 345
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VL CDR1

<400> SEQUENCE: 345

```
Gly Gly Asn Asn Ile Gly Ser Glu Ser Val His
 1               5                  10
```

<210> SEQ ID NO 346
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VL CDR2

<400> SEQUENCE: 346

```
Asp Asp Ser Asp Arg Pro Ser
 1               5
```

<210> SEQ ID NO 347
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VL CDR3

<400> SEQUENCE: 347

```
Gln Val Trp Asp Ser Ser Asn Asp His Val Val
 1               5                  10
```

<210> SEQ ID NO 348
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VH CDR1

<400> SEQUENCE: 348

```
Ser Ser Asn Tyr Tyr Trp Gly
 1               5
```

<210> SEQ ID NO 349
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VH CDR2

<400> SEQUENCE: 349

Thr Ile Tyr Tyr Ser Gly Ser Thr Tyr Tyr Thr Pro Ser Leu Lys Ser
1               5                   10                  15

<210> SEQ ID NO 350
<211> LENGTH: 14
<212> TYPE: PRT
<213> ORGANISM: Homo sapiens
<220> FEATURE:
<221> NAME/KEY: MISC_FEATURE
<223> OTHER INFORMATION: DKK-1 mAbs 5.76.1 VH CDR3

<400> SEQUENCE: 350

Glu Arg Ala Ile Ala Val Ala Ala Ile Val Phe Phe Asp Tyr
1               5                   10

<210> SEQ ID NO 351
<211> LENGTH: 103
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VL

<400> SEQUENCE: 351

Gln Ser Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
                20                  25                  30

Lys Pro Gly Gln Ala Pro Val Leu Val Val Tyr Asp Asp Ser Asp Arg
            35                  40                  45

Pro Ser Gly Ile Pro Glu Arg Phe Ser Gly Ser Asn Ser Gly Asn Thr
        50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Ser Asp His Trp Val Phe Gly Gly
                85                  90                  95

Gly Thr Lys Leu Thr Val Leu
            100

<210> SEQ ID NO 352
<211> LENGTH: 123
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VH

<400> SEQUENCE: 352

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

```
Gly Trp Met Asn Leu Asn Ser Asp Asn Thr Gly Tyr Ala Gln Lys Phe
        50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ile Ala Ala Arg Arg Asp Tyr Asn Tyr Gly Met Asp Val
            100                 105                 110

Trp Gly Gln Gly Thr Lys Val Thr Val Ser Ser
            115                 120
```

<210> SEQ ID NO 353
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VL CDR1

<400> SEQUENCE: 353

```
Gly Gly Asn Asn Ile Gly Ser Lys Ser Val His
 1               5                  10
```

<210> SEQ ID NO 354
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VL CDR2

<400> SEQUENCE: 354

```
Asp Asp Ser Asp Arg Pro Ser
 1               5
```

<210> SEQ ID NO 355
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs  5.77.1 VL CDR3

<400> SEQUENCE: 355

```
Gln Val Trp Asp Ser Ser Ser Asp His Trp Val
 1               5                  10
```

<210> SEQ ID NO 356
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VH CDR1

<400> SEQUENCE: 356

```
Ser Tyr Asp Ile Asn
 1               5
```

<210> SEQ ID NO 357
<211> LENGTH: 17
<212> TYPE: PRT
<213> ORGANISM: Homo sapiens
<220> FEATURE:
<221> NAME/KEY: MISC_FEATURE

```
<223> OTHER INFORMATION: DKK-1 mAbs 5.77.1 VH CDR2

<400> SEQUENCE: 357

Trp Met Asn Leu Asn Ser Asp Asn Thr Gly Tyr Ala Gln Lys Phe Gln
1               5                   10                  15
Gly

<210> SEQ ID NO 358
<211> LENGTH: 14
<212> TYPE: PRT
<213> ORGANISM: Homo sapiens
<220> FEATURE:
<221> NAME/KEY: MISC_FEATURE
<223> OTHER INFORMATION: DKK-1 mAbs 5.77.1 VH CDR3

<400> SEQUENCE: 358

Ile Ala Ala Arg Arg Asp Tyr Asn Tyr Tyr Gly Met Asp Val
1               5                   10

<210> SEQ ID NO 359
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VL

<400> SEQUENCE: 359

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Gly Arg Ala Thr Gly Ile Pro Asp Arg Phe Ser
    50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Gly Gly Thr Lys Val Glu Ile Lys
            100                 105

<210> SEQ ID NO 360
<211> LENGTH: 125
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VH

<400> SEQUENCE: 360

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asp Asn Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95
Ala Arg Glu Gly Ile Ala Val Ala Gly Asp Tyr Tyr Tyr Gly Met
                100                 105                 110
Asp Val Trp Gly Gln Gly Thr Thr Val Thr Val Ser Ser
        115                 120                 125
```

<210> SEQ ID NO 361
<211> LENGTH: 12
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VL CDR1

<400> SEQUENCE: 361

```
Arg Ala Ser Gln Ser Val Ser Ser Ser Tyr Leu Ala
1               5                   10
```

<210> SEQ ID NO 362
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VL CDR2

<400> SEQUENCE: 362

```
Gly Ala Ser Gly Arg Ala Thr
1               5
```

<210> SEQ ID NO 363
<211> LENGTH: 8
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VL CDR3

<400> SEQUENCE: 363

```
Gln Gln Tyr Gly Ser Ser Phe Thr
1               5
```

<210> SEQ ID NO 364
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VH CDR1

<400> SEQUENCE: 364

```
Ser Tyr Gly Met His
1               5
```

<210> SEQ ID NO 365
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VH CDR2

<400> SEQUENCE: 365

```
Val Ile Leu Tyr Asp Gly Ser Asp Asn Tyr Tyr Ala Asp Ser Val Lys
```

Gly

<210> SEQ ID NO 366
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 5.78.1 VH CDR3

<400> SEQUENCE: 366

Glu Gly Ile Ala Val Ala Gly Asp Tyr Tyr Tyr Gly Met Asp Val
1               5                   10                  15

<210> SEQ ID NO 367
<211> LENGTH: 112
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VL

<400> SEQUENCE: 367

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr Asp Val His Trp Tyr Gln Gln Leu Pro Gly Thr Ala Pro Lys Leu
        35                  40                  45

Leu Ile Tyr Asp Tyr Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Val Phe Gly Gly Gly Thr Lys Leu Thr Val Leu
            100                 105                 110

<210> SEQ ID NO 368
<211> LENGTH: 116
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VH

<400> SEQUENCE: 368

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Thr Ala Ser Asp Thr Ala Met Tyr Tyr Cys
                85                  90                  95

```
Ala Arg Gln Gly Glu Ser Phe Asp Tyr Trp Gly Gln Gly Thr Leu Val
            100                 105                 110
Thr Val Ser Ser
        115

<210> SEQ ID NO 369
<211> LENGTH: 14
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VL CDR1

<400> SEQUENCE: 369

Thr Gly Ser Ser Ser Asn Ile Gly Ala Asp Tyr Asp Val His
1               5                   10

<210> SEQ ID NO 370
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VL CDR2

<400> SEQUENCE: 370

Asp Tyr Ser Asn Arg Pro Ser
1               5

<210> SEQ ID NO 371
<211> LENGTH: 12
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VL CDR3

<400> SEQUENCE: 371

Gln Ser Tyr Asp Asn Ser Leu Ser Gly Tyr Val Val
1               5                   10

<210> SEQ ID NO 372
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VH CDR1

<400> SEQUENCE: 372

Ser Tyr Trp Ile Gly
1               5

<210> SEQ ID NO 373
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VH CDR2

<400> SEQUENCE: 373

Ile Ile Tyr Pro Gly Asp Ser Asp Thr Arg Tyr Ser Pro Ser Phe Gln
1               5                   10                  15
Gly
```

```
<210> SEQ ID NO 374
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.80.1 VH CDR3

<400> SEQUENCE: 374

Gln Gly Glu Ser Phe Asp Tyr
1               5

<210> SEQ ID NO 375
<211> LENGTH: 110
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VL

<400> SEQUENCE: 375

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Arg Thr Ala Pro Lys Leu
        35                  40                  45

Leu Ile Tyr Gly Asn Ser Asn Arg Pro Ser Gly Val Pro Asp Arg Phe
    50                  55                  60

Ser Asp Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Ile Phe Gly Gly Gly Thr Lys Leu Thr Val Leu
            100                 105                 110

<210> SEQ ID NO 376
<211> LENGTH: 116
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VH

<400> SEQUENCE: 376

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Thr Tyr
            20                  25                  30

Trp Ile Gly Trp Val Arg Gln Met Pro Gly Lys Gly Leu Asp Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Ile Ala Phe Asp Tyr Trp Gly Gln Gly Thr Leu Val
            100                 105                 110

Thr Val Ser Ser
            115
```

<210> SEQ ID NO 377
<211> LENGTH: 14
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VL CDR1

<400> SEQUENCE: 377

Thr Gly Ser Ser Ser Asn Ile Gly Ala Gly Tyr Asp Val His
1               5                   10

<210> SEQ ID NO 378
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VL CDR2

<400> SEQUENCE: 378

Gly Asn Ser Asn Arg Pro Ser
1               5

<210> SEQ ID NO 379
<211> LENGTH: 10
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VL CDR3

<400> SEQUENCE: 379

Gln Ser Tyr Asp Ser Ser Leu Ser Val Ile
1               5                   10

<210> SEQ ID NO 380
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VH CDR1

<400> SEQUENCE: 380

Thr Tyr Trp Ile Gly
1               5

<210> SEQ ID NO 381
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 5.85.1 VH CDR2

<400> SEQUENCE: 381

Ile Ile Tyr Pro Gly Asp Ser Asp Thr Arg Tyr Ser Pro Ser Phe Gln
1               5                   10                  15
Gly

<210> SEQ ID NO 382
<211> LENGTH: 7
<212> TYPE: PRT
<213> ORGANISM: Homo sapiens
<220> FEATURE:

```
<221> NAME/KEY: MISC_FEATURE
<223> OTHER INFORMATION: DKK-1 mAbs 5.85.1 VH CDR3

<400> SEQUENCE: 382

Gln Gly Ile Ala Phe Asp Tyr
1               5

<210> SEQ ID NO 383
<211> LENGTH: 112
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VL

<400> SEQUENCE: 383

Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

<210> SEQ ID NO 384
<211> LENGTH: 114
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VH

<400> SEQUENCE: 384

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser

<210> SEQ ID NO 385
<211> LENGTH: 16
<212> TYPE: PRT
<213> ORGANISM: Homo sapiens
```

```
<220> FEATURE:
<221> NAME/KEY: MISC_FEATURE
<223> OTHER INFORMATION: DKK-1 mAbs 6.37.5 VL CDR1

<400> SEQUENCE: 385

Lys Ser Gly Gln Ser Leu Leu His Ser Asp Gly Lys Thr Tyr Leu Tyr
1               5                   10                  15

<210> SEQ ID NO 386
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VL CDR2

<400> SEQUENCE: 386

Glu Val Ser Asn Arg Phe Ser
1               5

<210> SEQ ID NO 387
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VL CDR3

<400> SEQUENCE: 387

Met Gln Ser Ile Gln Leu Pro Trp Thr
1               5

<210> SEQ ID NO 388
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VH CDR1

<400> SEQUENCE: 388

Gly Tyr Gly Met His
1               5

<210> SEQ ID NO 389
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 6.37.5 VH CDR2

<400> SEQUENCE: 389

Val Ile Ser Tyr Asp Gly Asn Asp Lys Tyr Tyr Ala Asp Ser Val Lys
1               5                   10                  15
Gly

<210> SEQ ID NO 390
<211> LENGTH: 5
<212> TYPE: PRT
<213> ORGANISM: Homo sapiens
<220> FEATURE:
<221> NAME/KEY: MISC_FEATURE
<223> OTHER INFORMATION: DDK-1 mAbs 6.37.5 VH CDR3

<400> SEQUENCE: 390

Glu Leu Arg Val Leu
```

<210> SEQ ID NO 391
<211> LENGTH: 112
<212> TYPE: PRT
<213> ORGANISM: Homo sapiens
<220> FEATURE:
<221> NAME/KEY: MISC_FEATURE
<223> OTHER INFORMATION: DDK-1 mAbs 6.116.6 VL

<400> SEQUENCE: 391

Asp Ile Val Met Thr Gln Thr Pro Leu Ser Leu Ser Val Thr Pro Gly
1               5                   10                  15

Gln Pro Ala Ser Ile Ser Cys Lys Ser Gly Gln Ser Leu Leu His Asn
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Arg Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Ile Gln Leu Pro Trp Thr Phe Gly Gln Gly Thr Gln Val Glu Ile Lys
            100                 105                 110

<210> SEQ ID NO 392
<211> LENGTH: 114
<212> TYPE: PRT
<213> ORGANISM: Homo sapiens
<220> FEATURE:
<221> NAME/KEY: MISC_FEATURE
<223> OTHER INFORMATION: DDK-1 mAbs 6.116.6 VH

<400> SEQUENCE: 392

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Val Leu Trp Gly Gln Gly Thr Leu Val Thr Val
            100                 105                 110

Ser Ser

<210> SEQ ID NO 393
<211> LENGTH: 16
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VL CDR1

<400> SEQUENCE: 393

```
Lys Ser Gly Gln Ser Leu Leu His Asn Asp Gly Lys Thr Tyr Leu Tyr
1               5                   10                  15

<210> SEQ ID NO 394
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VL CDR2

<400> SEQUENCE: 394

Glu Val Ser Asn Arg Phe Ser
1               5

<210> SEQ ID NO 395
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VL CDR3

<400> SEQUENCE: 395

Met Gln Ser Ile Gln Leu Pro Trp Thr
1               5

<210> SEQ ID NO 396
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VH CDR1

<400> SEQUENCE: 396

Gly Tyr Gly Met His
1               5

<210> SEQ ID NO 397
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VH CDR2

<400> SEQUENCE: 397

Val Ile Ser Tyr Asp Gly Asn Asp Lys Tyr Tyr Ala Asp Ser Val Lys
1               5                   10                  15

Gly

<210> SEQ ID NO 398
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.116.6 VH CDR3

<400> SEQUENCE: 398

Glu Leu Arg Val Leu
1               5

<210> SEQ ID NO 399
<211> LENGTH: 112
<212> TYPE: PRT
```

<213> ORGANISM: Homo sapiens
<220> FEATURE:
<221> NAME/KEY: MISC_FEATURE
<223> OTHER INFORMATION: DKK-1 mAbs 6.139.5 VL

<400> SEQUENCE: 399

Asp Ile Val Met Thr Gln Thr Pro Leu Ser Leu Ser Val Thr Pro Arg
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Phe Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Trp Thr Phe Gly Gln Gly Thr Lys Val Glu Ile Lys
            100                 105                 110

<210> SEQ ID NO 400
<211> LENGTH: 114
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VH

<400> SEQUENCE: 400

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Gly Asp Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Glu Tyr Tyr Cys
                85                  90                  95

Ala Arg Glu Leu Arg Val Leu Trp Gly Gln Gly Thr Leu Val Thr Val
            100                 105                 110

Ser Ser

<210> SEQ ID NO 401
<211> LENGTH: 13
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VL CDR1

<400> SEQUENCE: 401

Ala Ala Ser Gly Phe Thr Phe Ser Arg Tyr Asp Met His
1               5                   10

<210> SEQ ID NO 402
<211> LENGTH: 12

```
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VL CDR2

<400> SEQUENCE: 402

Ile Phe Tyr Asp Gly Ser Asn Lys Tyr Tyr Ala Asp
1               5                   10

<210> SEQ ID NO 403
<211> LENGTH: 9
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VL CDR3

<400> SEQUENCE: 403

Ala Thr Leu Ala Ala Ala Phe Asp Tyr
1               5

<210> SEQ ID NO 404
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VH CDR1

<400> SEQUENCE: 404

Ser Tyr Gly Met His
1               5

<210> SEQ ID NO 405
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VH CDR2

<400> SEQUENCE: 405

Val Ile Ser Tyr Asp Gly Gly Asp Gln Tyr Tyr Ala Asp Ser Val Lys
1               5                   10                  15

Gly

<210> SEQ ID NO 406
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.139.5 VH CDR3

<400> SEQUENCE: 406

Glu Leu Arg Val Leu
1               5

<210> SEQ ID NO 407
<211> LENGTH: 107
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VL

<400> SEQUENCE: 407
```

-continued

Tyr Val Leu Thr Gln Pro Pro Ser Val Ser Val Ala Pro Gly Gln Thr
1               5                   10                  15

Ala Arg Ile Thr Cys Gly Gly Asn Asn Ile Gly Ser Lys Ser Val His
            20                  25                  30

Trp Tyr Gln Gln Lys Pro Gly Gln Ala Pro Val Leu Val Val Tyr Asp
        35                  40                  45

Asp Ser Asp Arg Pro Ser Glu Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Ser Asp His Val
                85                  90                  95

Val Phe Gly Gly Gly Thr Arg Leu Thr Val Leu
            100                 105

<210> SEQ ID NO 408
<211> LENGTH: 116
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VH

<400> SEQUENCE: 408

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser
        115

<210> SEQ ID NO 409
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VL CDR1

<400> SEQUENCE: 409

Gly Gly Asn Asn Ile Gly Ser Lys Ser Val His
1               5                   10

<210> SEQ ID NO 410
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VL CDR2

```
<400> SEQUENCE: 410

Asp Asp Ser Asp Arg Pro Ser
1               5

<210> SEQ ID NO 411
<211> LENGTH: 11
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VL CDR3

<400> SEQUENCE: 411

Gln Val Trp Asp Ser Ser Ser Asp His Val Val
1               5                   10

<210> SEQ ID NO 412
<211> LENGTH: 5
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VH CDR1

<400> SEQUENCE: 412

Arg Tyr Asp Met His
1               5

<210> SEQ ID NO 413
<211> LENGTH: 17
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VH CDR2

<400> SEQUENCE: 413

Ile Ile Phe Tyr Asp Gly Ser Asn Lys Tyr Tyr Ala Asp Pro Val Lys
1               5                   10                  15

Gly

<210> SEQ ID NO 414
<211> LENGTH: 7
<212> TYPE: PRT
<213> ORGANISM: Homo sapiens
<220> FEATURE:
<221> NAME/KEY: MISC_FEATURE
<223> OTHER INFORMATION: DKK-1 mAbs 6.147.4 VH CDR3

<400> SEQUENCE: 414

Leu Ala Ala Ala Phe Asp Tyr
1               5

<210> SEQ ID NO 415
<211> LENGTH: 16
<212> TYPE: PRT
<213> ORGANISM: ARTIFICIAL SEQUENCE
<220> FEATURE:
<223> OTHER INFORMATION: Linker Sequence

<400> SEQUENCE: 415

Ala Lys Thr Thr Pro Lys Leu Glu Glu Gly Glu Phe Ser Glu Ala Arg
1               5                   10                  15

<210> SEQ ID NO 416
```

```
<211> LENGTH: 17
<212> TYPE: PRT
<213> ORGANISM: ARTIFICIAL SEQUENCE
<220> FEATURE:
<223> OTHER INFORMATION: Linker Sequence

<400> SEQUENCE: 416

Ala Lys Thr Thr Pro Lys Leu Glu Glu Gly Glu Phe Ser Glu Ala Arg
1               5                   10                  15

Val

<210> SEQ ID NO 417
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 417

Ala Lys Thr Thr Pro Lys Leu Gly Gly
1               5

<210> SEQ ID NO 418
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 418

Ser Ala Lys Thr Thr Pro Lys Leu Gly Gly
1               5                   10

<210> SEQ ID NO 419
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 419

Ser Ala Lys Thr Thr Pro
1               5

<210> SEQ ID NO 420
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 420

Arg Ala Asp Ala Ala Pro
1               5

<210> SEQ ID NO 421
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 421

Arg Ala Asp Ala Ala Pro Thr Val Ser
1               5
```

```
<210> SEQ ID NO 422
<211> LENGTH: 12
<212> TYPE: PRT
<213> ORGANISM: ARTIFICIAL SEQUENCE
<220> FEATURE:
<223> OTHER INFORMATION: Linker Sequence

<400> SEQUENCE: 422

Arg Ala Asp Ala Ala Ala Ala Gly Gly Pro Gly Ser
1               5                   10

<210> SEQ ID NO 423
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 423

Arg Ala Asp Ala Ala Ala Ala Gly Ser
1               5

<210> SEQ ID NO 424
<211> LENGTH: 18
<212> TYPE: PRT
<213> ORGANISM: ARTIFICIAL SEQUENCE
<220> FEATURE:
<223> OTHER INFORMATION: Linker Sequence

<400> SEQUENCE: 424

Ser Ala Lys Thr Thr Pro Lys Leu Glu Glu Gly Glu Phe Ser Glu Ala
1               5                   10                  15

Arg Val

<210> SEQ ID NO 425
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 425

Ala Asp Ala Ala Pro
1               5

<210> SEQ ID NO 426
<211> LENGTH: 12
<212> TYPE: PRT
<213> ORGANISM: ARTIFICIAL SEQUENCE
<220> FEATURE:
<223> OTHER INFORMATION: Linker Sequence

<400> SEQUENCE: 426

Ala Asp Ala Ala Pro Thr Val Ser Ile Phe Pro Pro
1               5                   10

<210> SEQ ID NO 427
<211> LENGTH: 4
<212> TYPE: PRT
<213> ORGANISM: ARTIFICIAL SEQUENCE
<220> FEATURE:
<223> OTHER INFORMATION: Linker Sequence

<400> SEQUENCE: 427

Thr Val Ala Ala
1
```

```
<210> SEQ ID NO 428
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 428

Thr Val Ala Ala Pro
1               5

<210> SEQ ID NO 429
<211> LENGTH: 11
<212> TYPE: PRT
<213> ORGANISM: ARTIFICIAL SEQUENCE
<220> FEATURE:
<223> OTHER INFORMATION: Linker Sequence

<400> SEQUENCE: 429

Thr Val Ala Ala Pro Ser Val Phe Ile Phe Pro
1               5                   10

<210> SEQ ID NO 430
<211> LENGTH: 12
<212> TYPE: PRT
<213> ORGANISM: ARTIFICIAL SEQUENCE
<220> FEATURE:
<223> OTHER INFORMATION: Linker Sequence

<400> SEQUENCE: 430

Thr Val Ala Ala Pro Ser Val Phe Ile Phe Pro Pro
1               5                   10

<210> SEQ ID NO 431
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 431

Gln Pro Lys Ala Ala Pro
1               5

<210> SEQ ID NO 432
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 432

Gln Pro Lys Ala Ala Pro Ser Val Thr Leu Phe Pro Pro
1               5                   10

<210> SEQ ID NO 433
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 433

Ala Lys Thr Thr Pro Pro
1               5
```

```
<210> SEQ ID NO 434
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 434

Ala Lys Thr Thr Pro Pro Ser Val Thr Pro Leu Ala Pro
1               5                   10

<210> SEQ ID NO 435
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 435

Ala Lys Thr Thr Ala Pro
1               5

<210> SEQ ID NO 436
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 436

Ala Lys Thr Thr Ala Pro Ser Val Tyr Pro Leu Ala Pro
1               5                   10

<210> SEQ ID NO 437
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 437

Ala Ser Thr Lys Gly Pro
1               5

<210> SEQ ID NO 438
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 438

Ala Ser Thr Lys Gly Pro Ser Val Phe Pro Leu Ala Pro
1               5                   10

<210> SEQ ID NO 439
<211> LENGTH: 5
<212> TYPE: PRT
<213> ORGANISM: ARTIFICIAL SEQUENCE
<220> FEATURE:
<223> OTHER INFORMATION: Linker Sequence

<400> SEQUENCE: 439

Gly Gly Gly Gly Ser
1               5

<210> SEQ ID NO 440
```

```
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 440

Gly Gly Gly Gly Ser Gly Gly Gly Gly Ser
1               5                   10

<210> SEQ ID NO 441
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 441

Gly Gly Gly Gly Ser Gly Gly Gly Ser Gly Gly Gly Gly Ser
1               5                   10                  15

<210> SEQ ID NO 442
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 442

Gly Glu Asn Lys Val Glu Tyr Ala Pro Ala Leu Met Ala Leu Ser
1               5                   10                  15

<210> SEQ ID NO 443
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 443

Gly Pro Ala Lys Glu Leu Thr Pro Leu Lys Glu Ala Lys Val Ser
1               5                   10                  15

<210> SEQ ID NO 444
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 444

Gly His Glu Ala Ala Ala Val Met Gln Val Gln Tyr Pro Ala Ser
1               5                   10                  15

<210> SEQ ID NO 445
<211> LENGTH: 8
<212> TYPE: PRT
<213> ORGANISM: ARTIFICIAL SEQUENCE
<220> FEATURE:
<223> OTHER INFORMATION: Linker Sequence

<400> SEQUENCE: 445

Gly Gly Gly Gly Gly Gly Gly Pro
1               5

<210> SEQ ID NO 446
<211> LENGTH: 9
```

-continued

```
<212> TYPE: PRT
<213> ORGANISM: ARTIFICIAL SEQUENCE
<220> FEATURE:
<223> OTHER INFORMATION: Linker Sequence

<400> SEQUENCE: 446

Gly Gly Gly Gly Gly Gly Gly Pro
1               5

<210> SEQ ID NO 447
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 447

Pro Ala Pro Asn Leu Leu Gly Gly Pro
1               5

<210> SEQ ID NO 448
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 448

Pro Asn Leu Leu Gly Gly Pro
1               5

<210> SEQ ID NO 449
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 449

Gly Gly Gly Gly Gly Gly Pro
1               5

<210> SEQ ID NO 450
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 450

Pro Ala Pro Glu Leu Leu Gly Gly Pro
1               5

<210> SEQ ID NO 451
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 451

Pro Thr Ile Ser Pro Ala Pro Asn Leu Leu Gly Gly Pro
1               5                   10

<210> SEQ ID NO 452
<211> LENGTH: 16
<212> TYPE: PRT
```

```
<213> ORGANISM: ARTIFICIAL SEQUENCE
<220> FEATURE:
<223> OTHER INFORMATION: Linker Sequence

<400> SEQUENCE: 452

Thr Val Ala Ala Asp Asp Asp Lys Ser Val Phe Ile Val Pro Pro
1               5                   10                  15

<210> SEQ ID NO 453
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 453

Thr Val Asp Asp Asp Asp Lys Ala Ala Pro
1               5                   10

<210> SEQ ID NO 454
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 454

Leu Val Pro Arg Gly Ser Ala Ala Pro
1               5

<210> SEQ ID NO 455
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 455

Ala Ser Asp Asp Asp Asp Lys Gly Gly Pro
1               5                   10

<210> SEQ ID NO 456
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 456

Ala Leu Val Pro Arg Gly Ser Gly Pro
1               5

<210> SEQ ID NO 457
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 457

Ala Ser Thr Asp Asp Asp Asp Lys Ser Val Phe Pro Leu Ala Pro
1               5                   10                  15

<210> SEQ ID NO 458
<211> LENGTH: 15
<212> TYPE: PRT
<213> ORGANISM: ARTIFICIAL SEQUENCE
```

```
<220> FEATURE:
<223> OTHER INFORMATION: Linker Sequence

<400> SEQUENCE: 458

Thr Val Ala Leu Val Pro Arg Gly Ser Val Phe Ile Phe Pro Pro
1               5                   10                  15

<210> SEQ ID NO 459
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 459

Ala Ser Thr Leu Val Pro Arg Gly Ser Val Phe Pro Leu Ala Pro
1               5                   10                  15

<210> SEQ ID NO 460
<211> LENGTH: 15
<212> TYPE: PRT
<213> ORGANISM: ARTIFICIAL SEQUENCE
<220> FEATURE:
<223> OTHER INFORMATION: Linker Sequence

<400> SEQUENCE: 460

Thr Val Ala Ala Asp Asp Asp Lys Ser Val Phe Ile Val Pro Pro
1               5                   10                  15

<210> SEQ ID NO 461
<211> LENGTH: 14
<212> TYPE: PRT
<213> ORGANISM: ARTIFICIAL SEQUENCE
<220> FEATURE:
<223> OTHER INFORMATION: Linker Sequence

<400> SEQUENCE: 461

Ala Ser Thr Asp Asp Asp Lys Ser Val Phe Pro Leu Ala Pro
1               5                   10

<210> SEQ ID NO 462
<211> LENGTH: 8
<212> TYPE: PRT
<213> ORGANISM: ARTIFICIAL SEQUENCE
<220> FEATURE:
<223> OTHER INFORMATION: Linker Sequence

<400> SEQUENCE: 462

Leu Glu Val Leu Phe Gln Gly Pro
1               5

<210> SEQ ID NO 463
<211> LENGTH: 14
<212> TYPE: PRT
<213> ORGANISM: ARTIFICIAL SEQUENCE
<220> FEATURE:
<223> OTHER INFORMATION: Linker Sequence

<400> SEQUENCE: 463

Thr Val Ala Ala Leu Glu Val Leu Phe Gln Gly Pro Ala Pro
1               5                   10

<210> SEQ ID NO 464
<211> LENGTH: 14
<212> TYPE: PRT
<213> ORGANISM: ARTIFICIAL SEQUENCE
<220> FEATURE:
```

<223> OTHER INFORMATION: Linker Sequence

<400> SEQUENCE: 464

Ala Ser Thr Leu Glu Val Leu Phe Gln Gly Pro Leu Ala Pro
1               5                   10

<210> SEQ ID NO 465
<211> LENGTH: 11
<212> TYPE: PRT
<213> ORGANISM: ARTIFICIAL SEQUENCE
<220> FEATURE:
<223> OTHER INFORMATION: Linker Sequence

<400> SEQUENCE: 465

Pro Ala Pro Leu Glu Val Leu Phe Gln Gly Pro
1               5                   10

<210> SEQ ID NO 466
<211> LENGTH: 11
<212> TYPE: PRT
<213> ORGANISM: ARTIFICIAL SEQUENCE
<220> FEATURE:
<223> OTHER INFORMATION: Linker Sequence

<400> SEQUENCE: 466

Thr Ala Glu Asn Leu Tyr Phe Gln Gly Ala Pro
1               5                   10

<210> SEQ ID NO 467
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 467

Ala Glu Asn Leu Tyr Phe Gln Gly Ala
1               5

<210> SEQ ID NO 468
<211> LENGTH: 11
<212> TYPE: PRT
<213> ORGANISM: ARTIFICIAL SEQUENCE
<220> FEATURE:
<223> OTHER INFORMATION: Linker Sequence

<400> SEQUENCE: 468

Pro Gly Pro Phe Gly Arg Ser Ala Gly Gly Pro
1               5                   10

<210> SEQ ID NO 469
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 469

Pro Gly Pro Phe Gly Arg Ser Ala Gly Gly
1               5                   10

<210> SEQ ID NO 470
<211> LENGTH: 8
<212> TYPE: PRT
<213> ORGANISM: ARTIFICIAL SEQUENCE
<220> FEATURE:
<223> OTHER INFORMATION: Linker Sequence

```
<400> SEQUENCE: 470

Pro Gln Arg Gly Arg Ser Ala Gly
1               5

<210> SEQ ID NO 471
<211> LENGTH: 8
<212> TYPE: PRT
<213> ORGANISM: ARTIFICIAL SEQUENCE
<220> FEATURE:
<223> OTHER INFORMATION: Linker Sequence

<400> SEQUENCE: 471

Pro His Tyr Gly Arg Ser Gly Gly
1               5

<210> SEQ ID NO 472
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 472

Gly Pro Phe Gly Arg Ser Ala Gly Pro
1               5

<210> SEQ ID NO 473
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 473

Gly Asp Asp Asp Asp Lys Gly Gly Pro
1               5

<210> SEQ ID NO 474
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 474

Ala Gly Asp Asp Asp Asp Lys Gly Gly Pro
1               5                   10

<210> SEQ ID NO 475
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 475

Gly Gly Asp Asp Asp Asp Lys Gly Gly Pro
1               5                   10

<210> SEQ ID NO 476
<211> LENGTH: 2
<212> TYPE: PRT
<213> ORGANISM: ARTIFICIAL SEQUENCE
<220> FEATURE:
<223> OTHER INFORMATION: Linker Sequence
```

```
<400> SEQUENCE: 476

Ala Ser
1

<210> SEQ ID NO 477
<211> LENGTH: 3
<212> TYPE: PRT
<213> ORGANISM: ARTIFICIAL SEQUENCE
<220> FEATURE:
<223> OTHER INFORMATION: Linker Sequence

<400> SEQUENCE: 477

Thr Val Ala
1

<210> SEQ ID NO 478
<211> LENGTH: 4
<212> TYPE: PRT
<213> ORGANISM: ARTIFICIAL SEQUENCE
<220> FEATURE:
<223> OTHER INFORMATION: Linker Sequence

<400> SEQUENCE: 478

Ala Ser Thr Lys
1

<210> SEQ ID NO 479
<211> LENGTH: 8
<212> TYPE: PRT
<213> ORGANISM: ARTIFICIAL SEQUENCE
<220> FEATURE:
<223> OTHER INFORMATION: Linker Sequence

<400> SEQUENCE: 479

Ala Ser Thr Lys Gly Pro Ser Val
1               5

<210> SEQ ID NO 480
<211> LENGTH: 10
<212> TYPE: PRT
<213> ORGANISM: ARTIFICIAL SEQUENCE
<220> FEATURE:
<223> OTHER INFORMATION: Linker Sequence

<400> SEQUENCE: 480

Ala Ser Thr Lys Gly Pro Ser Val Phe Pro
1               5                   10

<210> SEQ ID NO 481
<211> LENGTH: 7
<212> TYPE: PRT
<213> ORGANISM: ARTIFICIAL SEQUENCE
<220> FEATURE:
<223> OTHER INFORMATION: Linker Sequence

<400> SEQUENCE: 481

Thr Val Ala Ala Pro Ser Val
1               5

<210> SEQ ID NO 482
<211> LENGTH: 9
<212> TYPE: PRT
<213> ORGANISM: ARTIFICIAL SEQUENCE
<220> FEATURE:
<223> OTHER INFORMATION: Linker Sequence

<400> SEQUENCE: 482
```

Thr Val Ala Ala Pro Ser Val Phe Ile
1               5

<210> SEQ ID NO 483
<211> LENGTH: 6
<212> TYPE: PRT
<213> ORGANISM: ARTIFICIAL SEQUENCE
<220> FEATURE:
<223> OTHER INFORMATION: Linker Sequence

<400> SEQUENCE: 483

Arg Thr Val Ala Ala Pro
1               5

<210> SEQ ID NO 484
<211> LENGTH: 13
<212> TYPE: PRT
<213> ORGANISM: ARTIFICIAL SEQUENCE
<220> FEATURE:
<223> OTHER INFORMATION: Linker Sequence

<400> SEQUENCE: 484

Arg Thr Val Ala Ala Pro Ser Val Phe Ile Phe Pro Pro
1               5                   10

<210> SEQ ID NO 485
<211> LENGTH: 1800
<212> TYPE: DNA
<213> ORGANISM: ARTIFICIAL SEQUENCE
<220> FEATURE:
<223> OTHER INFORMATION: Additional DVD-Ig Seq / 6.147-AbL-Ab5 G2

<400> SEQUENCE: 485

```
atggacatga gggtgcccgc tcagctcctg gggctcctgc tgctgtggct gagaggtgcg    60
cgctgtcagg tgcagcttgt cgagagcggt ggaggggtgg tacaacccgg aagatcactc   120
cggctttcat cgcagcatc cggttttaca ttttcgcggt atgacatgca ctgggtgaga   180
caggcaccag gaaaagggct ggagtgggtg ccatcatct ctatgatgg gtccaataag   240
tactacgccg acccggtaaa agggaggttc actattagcc gcgacaactc gaagaatacg   300
ctgtacctgc agatgaactc gttgcgagcc gaagataccg cggtctacta ttgtgcgacg   360
ctcgcggctg cgttcgatta ctggggccaa ggaacattgg tcacggtctc ctcagcgtca   420
acgaaaggac cgtcggtgtt ccccttggcc cctgaggtgc agctcgtgca gtccggagcc   480
gaggtgaaga gcctggggc atccgtcaaa gtctcgtgca aggcgtcagg gtacacattc   540
accgactata acatgcattg ggtccggcag gctcccggtc aggggctgga gtggatgggg   600
gaaatcaatc cgaactccgg aggggcagga tacaatcaaa agtttaaggg acgcgtaacg   660
atgaccactg acacgtcaac ctccacggcg tatatggagc tcagaagcct ccgaagcgac   720
gacactgctg tctattactg tgcgagactg gatatgatg atatctacga cgattggtac   780
ttcgatgtat ggggacaagg gacgacggtc accgtctcta gtgcctccac caagggccca   840
tcggtcttcc ccctggcgcc ctgctccagg agcacctccg agagcacagc ggccctgggc   900
tgcctggtca aggactactt ccccgaaccg gtgacggtgt cgtggaactc aggcgctctg   960
accagcggcg tgcacacctt cccagctgtc ctacagtcct caggactcta ctccctcagc  1020
agcgtggtga ccgtgccctc agcaacttcg gcacccagag cctacacctg caacgtagat  1080
cacaagccca gcaacaccaa ggtggacaag acagttgagc gcaaatgttg tgtcgagtgc  1140
ccaccgtgcc cagcaccacc tgtggcagga ccgtcagtct tcctcttccc cccaaaaccc  1200
```

```
aaggacaccc tcatgatctc ccggacccct gaggtcacgt gcgtggtggt ggacgtgagc    1260
cacgaagacc ccgaggtcca gttcaactgg tacgtggacg gcgtggaggt gcataatgcc    1320
aagacaaagc cacgggagga gcagttcaac agcacgttcc gtgtggtcag cgtcctcacc    1380
gttgtgcacc aggactggct gaacggcaag gagtacaagt gcaaggtctc caacaaaggc    1440
ctcccagccc ccatcgagaa aaccatctcc aaaaccaaag ggcagccccg agaaccacag    1500
gtgtacaccc tgcccccatc ccgggaggag atgaccaaga accaggtcag cctgacctgc    1560
ctggtcaaag gcttctaccc cagcgacatc gccgtggagt gggagagcaa tgggcagccg    1620
gagaacaact acaagaccac acctcccatg ctggactccg acggctcctt cttcctctac    1680
agcaagctca ccgtggacaa gagcaggtgg cagcagggga acgtcttctc atgctccgtg    1740
atgcatgagg ctctgcacaa ccactacacg cagaagagcc tctccctgtc tccgggtaaa    1800

<210> SEQ ID NO 486
<211> LENGTH: 578
<212> TYPE: PRT
<213> ORGANISM: ARTIFICIAL SEQUENCE
<220> FEATURE:
<223> OTHER INFORMATION: Additional DVD-Ig Seq / 6.147-AbL-Ab5 G2

<400> SEQUENCE: 486

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Glu Val Gln Leu Val Gln Ser Gly Ala Glu Val Lys Lys Pro Gly
    130                 135                 140

Ala Ser Val Lys Val Ser Cys Lys Ala Ser Gly Tyr Thr Phe Thr Asp
145                 150                 155                 160

Tyr Asn Met His Trp Val Arg Gln Ala Pro Gly Gln Gly Leu Glu Trp
                165                 170                 175

Met Gly Glu Ile Asn Pro Asn Ser Gly Gly Ala Gly Tyr Asn Gln Lys
            180                 185                 190

Phe Lys Gly Arg Val Thr Met Thr Thr Asp Thr Ser Thr Ser Thr Ala
        195                 200                 205

Tyr Met Glu Leu Arg Ser Leu Arg Ser Asp Asp Thr Ala Val Tyr Tyr
    210                 215                 220

Cys Ala Arg Leu Gly Tyr Asp Asp Ile Tyr Asp Asp Trp Tyr Phe Asp
225                 230                 235                 240

Val Trp Gly Gln Gly Thr Thr Val Thr Val Ser Ser Ala Ser Thr Lys
                245                 250                 255
```

```
Gly Pro Ser Val Phe Pro Leu Ala Pro Cys Ser Arg Ser Thr Ser Glu
            260                 265                 270

Ser Thr Ala Ala Leu Gly Cys Leu Val Lys Asp Tyr Phe Pro Glu Pro
        275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Asn Phe Gly Thr Gln Thr Tyr Thr Cys Asn
                325                 330                 335

Val Asp His Lys Pro Ser Asn Thr Lys Val Asp Lys Thr Val Glu Arg
            340                 345                 350

Lys Cys Cys Val Glu Cys Pro Pro Cys Pro Ala Pro Pro Val Ala Gly
        355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400

Asp Pro Glu Val Gln Phe Asn Trp Tyr Val Asp Gly Val Glu Val His
                405                 410                 415

Asn Ala Lys Thr Lys Pro Arg Glu Glu Gln Phe Asn Ser Thr Phe Arg
            420                 425                 430

Val Val Ser Val Leu Thr Val His Gln Asp Trp Leu Asn Gly Lys
        435                 440                 445

Glu Tyr Lys Cys Lys Val Ser Asn Lys Gly Leu Pro Ala Pro Ile Glu
    450                 455                 460

Lys Thr Ile Ser Lys Thr Lys Gly Gln Pro Arg Glu Pro Gln Val Tyr
465                 470                 475                 480

Thr Leu Pro Pro Ser Arg Glu Glu Met Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Met
        515                 520                 525

Leu Asp Ser Asp Gly Ser Phe Phe Leu Tyr Ser Lys Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 487
<211> LENGTH: 1074
<212> TYPE: DNA
<213> ORGANISM: ARTIFICIAL SEQUENCE
<220> FEATURE:
<223> OTHER INFORMATION: Additional DVD-Ig Seq / 6.147-AbL-Ab5 LC

<400> SEQUENCE: 487
atggacatga gggtgcccgc tcagctcctg gggctcctgc tgctgtggct gagaggtgcg      60
cgctgttcat acgtgctcac tcagccgccc agcgtatcgg tggctcccgg acagacggcg     120
cgaatcacgt gcgtgggaa caatatcggc tccaagtcag tccattggta tcaacagaaa     180
cctggtcagg caccagtcct ggtggtatac gatgactcgg acaggccctc ggagattccg     240
```

```
gaacgcttct ccggatcgaa ttcggggaac acagcgacct tgacgatcag cagagtggag      300
gccggagatg aagccgacta ctattgtcag gtgtgggatt ccagctccga ccacgtcgta      360
tttggaggtg ggacacggct taccgtcctc gggcagccca aggctgcgcc atcggtcact      420
ctgttcccac ctgacattca gatgactcag tcgccttcgt cattgagcgc gtcggtggga      480
gatcgggtca cgattacttg tcgggcatcg caagacatct cgaactattt gaattggtac      540
cagcaaaagc ctggtaaagc gcccaaactt cttatctact atacgtcccg cctcctctcg      600
ggcgtcccgt caaggtttag cggatcggga agcgggacgg atttcacact gacgatttca      660
tcacttcagc ccgaagattt cgccacctat tactgtcagc aaggagacac cctgccatac      720
acttttggcg gtgggacaaa ggtcgaaatc aagcgtacgg tggctgcacc atctgtcttc      780
atcttcccgc catctgatga gcagttgaaa tctggaactg cctctgttgt gtgcctgctg      840
aataacttct atcccagaga ggccaaagta cagtggaagg tggataacgc cctccaatcg      900
ggtaactccc aggagagtgt cacagagcag gacagcaagg acagcaccta cagcctcagc      960
agcaccctga cgctgagcaa agcagactac gagaaacaca aagtctacgc ctgcgaagtc      1020
acccatcagg gcctgagctc gcccgtcaca aagagcttca caggggaga gtgt             1074
```

<210> SEQ ID NO 488
<211> LENGTH: 336
<212> TYPE: PRT
<213> ORGANISM: ARTIFICIAL SEQUENCE
<220> FEATURE:
<223> OTHER INFORMATION: Additional DVD-Ig Seq / 6.147-AbL-Ab5 LC

<400> SEQUENCE: 488

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Arg Leu Thr Val Leu Gly Gln Pro Lys
            100                 105                 110

Ala Ala Pro Ser Val Thr Leu Phe Pro Pro Asp Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Asp Ile Ser Asn Tyr Leu Asn Trp Tyr Gln Gln
145                 150                 155                 160

Lys Pro Gly Lys Ala Pro Lys Leu Leu Ile Tyr Tyr Thr Ser Arg Leu
                165                 170                 175

Leu Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Gly Asp Thr Leu Pro Tyr Thr Phe Gly Gly Gly Thr
```

```
               210                 215                 220
Lys Val Glu Ile Lys Arg Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
                260                 265                 270

Asp Asn Ala Leu Gln Ser Gly Asn Ser Gln Glu Ser Val Thr Glu Gln
                275                 280                 285

Asp Ser Lys Asp Ser Thr Tyr Ser Leu Ser Ser Thr Leu Thr Leu Ser
        290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335
```

<210> SEQ ID NO 489
<211> LENGTH: 1806
<212> TYPE: DNA
<213> ORGANISM: ARTIFICIAL SEQUENCE
<220> FEATURE:
<223> OTHER INFORMATION: Additional DVD-Ig Seq / 6.147-3x-Ab5 G2

<400> SEQUENCE: 489

```
atggacatga gggtgcccgc tcagctcctg gggctcctgc tgctgtggct gagaggtgcg      60
cgctgtcagg tgcagcttgt cgagagcggg ggaggggtgg tacaacccgg aagatcactc     120
cggctttcat gcgcagcatc cggttttaca ttttcgcggt atgacatgca ctgggtgaga     180
caggcaccag aaaagggct ggagtgggtg gccatcatct ctatgatgg gtccaataag      240
tactacgccg acccggtaaa agggaggttc actattagcc gcgacaactc gaagaatacg     300
ctgtacctgc agatgaactc gttgcgagcc gaagataccg cggtctacta ttgtgcgacg     360
ctcgcggctg cgttcgatta ctggggccaa ggaacattgg tcacagtgag ctcagggggt     420
ggcggttcgg gcggtggagg ctcgggaggt ggtggatccg aggtgcagct cgtgcagtcc     480
ggagccgagg tgaagaagcc tggggcatcc gtcaaagtct cgtgcaaggc gtcagggtac     540
acattcaccg actataacat gcattgggtc cggcaggctc ccggtcaggg gctggagtgg     600
atgggggaaa tcaatccgaa ctccggaggg gcaggataca atcaaaagtt taagggacgc     660
gtaacgatga ccactgacac gtcaacctcc acggcgtata tggagctcag aagcctccga     720
agcgacgaca ctgctgtcta ttactgtgcg agactgggat atgatgatat ctacgacgat     780
tggtacttcg atgtatgggg acaagggacg acggtcaccg tctctagtgc ctccaccaag     840
ggcccatcgg tcttccccct ggcgccctgc tccaggagca cctccgagag cacagcggcc     900
ctgggctgcc tggtcaagga ctacttcccc gaaccggtga cggtgtcgtg gaactcaggc     960
gctctgacca gcggcgtgca caccttccca gctgtcctac agtcctcagg actctactcc    1020
ctcagcagcg tggtgaccgt gccctccagc aacttcggca cccagaccta cacctgcaac    1080
gtagatcaca agcccagcaa caccaaggtg gacaagacag ttgagcgcaa atgttgtgtc    1140
gagtgcccac cgtgcccagc accacctgtg gcaggaccgt cagtcttcct cttccccca    1200
aaacccaagg acaccctcat gatctcccgg acccctgagg tcacgtgcgt ggtggtggac    1260
gtgagccaca agaccccga ggtccagttc aactggtacg tggacggcgt ggaggtgcat    1320
aatgccaaga caaagccacg ggaggagcag ttcaacagca cgttccgtgt ggtcagcgtc    1380
```

```
ctcaccgttg tgcaccagga ctggctgaac ggcaaggagt acaagtgcaa ggtctccaac    1440
aaaggcctcc cagccccat cgagaaaacc atctccaaaa ccaaagggca gccccgagaa     1500
ccacaggtgt acaccctgcc cccatcccgg gaggagatga ccaagaacca ggtcagcctg    1560
acctgcctgg tcaaaggctt ctaccccagc gacatcgccg tggagtggga gagcaatggg    1620
cagccggaga acaactacaa gaccacacct cccatgctgg actccgacgg ctccttcttc    1680
ctctacagca agctcaccgt ggacaagagc aggtggcagc aggggaacgt cttctcatgc    1740
tccgtgatgc atgaggctct gcacaaccac tacacgcaga agagcctctc cctgtctccg    1800
ggtaaa                                                              1806
```

<210> SEQ ID NO 490
<211> LENGTH: 580
<212> TYPE: PRT
<213> ORGANISM: ARTIFICIAL SEQUENCE
<220> FEATURE:
<223> OTHER INFORMATION: Additional DVD-Ig Seq / 6.147-3x-Ab5 G2

<400> SEQUENCE: 490

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Ala Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Asp Tyr Asn Met His Trp Val Arg Gln Ala Pro Gly Gln Gly Leu
                165                 170                 175

Glu Trp Met Gly Glu Ile Asn Pro Asn Ser Gly Gly Ala Gly Tyr Asn
            180                 185                 190

Gln Lys Phe Lys Gly Arg Val Thr Met Thr Thr Asp Thr Ser Thr Ser
        195                 200                 205

Thr Ala Tyr Met Glu Leu Arg Ser Leu Arg Ser Asp Asp Thr Ala Val
    210                 215                 220

Tyr Tyr Cys Ala Arg Leu Gly Tyr Asp Asp Ile Tyr Asp Asp Trp Tyr
225                 230                 235                 240

Phe Asp Val Trp Gly Gln Gly Thr Thr Val Thr Val Ser Ser Ala Ser
                245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
        275                 280                 285
```

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Asn Phe Gly Thr Gln Thr Tyr Thr
                325                 330                 335

Cys Asn Val Asp His Lys Pro Ser Asn Thr Lys Val Asp Lys Thr Val
                340                 345                 350

Glu Arg Lys Cys Cys Val Glu Cys Pro Pro Cys Pro Ala Pro Pro Val
            355                 360                 365

Ala Gly Pro Ser Val Phe Leu Phe Pro Pro Lys Pro Lys Asp Thr Leu
    370                 375                 380

Met Ile Ser Arg Thr Pro Glu Val Thr Cys Val Val Val Asp Val Ser
385                 390                 395                 400

His Glu Asp Pro Glu Val Gln Phe Asn Trp Tyr Val Asp Gly Val Glu
                405                 410                 415

Val His Asn Ala Lys Thr Lys Pro Arg Glu Glu Gln Phe Asn Ser Thr
                420                 425                 430

Phe Arg Val Val Ser Val Leu Thr Val Val His Gln Asp Trp Leu Asn
            435                 440                 445

Gly Lys Glu Tyr Lys Cys Lys Val Ser Asn Lys Gly Leu Pro Ala Pro
    450                 455                 460

Ile Glu Lys Thr Ile Ser Lys Thr Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
    515                 520                 525

Pro Met Leu Asp Ser Asp Gly Ser Phe Phe Leu Tyr Ser Lys Leu Thr
530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 491
<211> LENGTH: 1068
<212> TYPE: DNA
<213> ORGANISM: ARTIFICIAL SEQUENCE
<220> FEATURE:
<223> OTHER INFORMATION: Additional DVD-Ig Seq / 6.147-3x-Ab5 LC

<400> SEQUENCE: 491
atggacatga gggtgcccgc tcagctcctg ggctcctgc tgctgtggct gagaggtgcg      60
cgctgttcat acgtgctcac tcagccgccc agcgtatcgg tggctcccgg acagacggcg     120
cgaatcacgt gcggtgggaa caatatcggc tccaagtcag tccattggta tcaacagaaa     180
cctggtcagg caccagtcct ggtggtatac gatgactcgg acaggccctc ggagattccg     240
gaacgcttct ccggatcgaa ttcggggaac acagcgacct tgacgatcag cagagtggag     300
gccggagatg aagccgacta ctattgtcag gtgtgggatt ccagctccga ccacgtcgta     360

```
tttggaggtg ggacacggct tgggggtggc ggttcgggcg gtggaggctc gggaggtggt      420
ggatccgaca ttcagatgac tcagtcgcct tcgtcattga gcgcgtcggt gggagatcgg      480
gtcacgatta cttgtcgggc atcgcaagac atctcgaact atttgaattg gtaccagcaa      540
aagcctggta aagcgcccaa acttcttatc tactatacgt cccgcctcct ctcgggcgtc      600
ccgtcaaggt ttagcggatc gggaagcggg acggatttca cactgacgat ttcatcactt      660
cagcccgaag atttcgccac ctattactgt cagcaaggag acaccctgcc atacactttt      720
ggcggtggga caaggtcga atcaagcgt acggtggctg caccatctgt cttcatcttc       780
ccgccatctg atgagcagtt gaaatctgga actgcctctg ttgtgtgcct gctgaataac      840
ttctatccca gagaggccaa agtacagtgg aaggtggata acgccctcca atcgggtaac      900
tcccaggaga gtgtcacaga gcaggacagc aaggacagca cctacagcct cagcagcacc      960
ctgacgctga gcaaagcaga ctacgagaaa cacaaagtct acgcctgcga agtcacccat     1020
cagggcctga gctcgcccgt cacaaagagc ttcaacaggg gagagtgt                  1068
```

<210> SEQ ID NO 492
<211> LENGTH: 334
<212> TYPE: PRT
<213> ORGANISM: ARTIFICIAL SEQUENCE
<220> FEATURE:
<223> OTHER INFORMATION: Additional DVD-Ig Seq / 6.147-3x-Ab5 LC

<400> SEQUENCE: 492

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Glu Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Arg Leu Gly Gly Gly Ser Gly Gly
                100                 105                 110

Gly Gly Ser Gly Gly Gly Gly Ser Asp Ile Gln Met Thr Gln Ser Pro
            115                 120                 125

Ser Ser Leu Ser Ala Ser Val Gly Asp Arg Val Thr Ile Thr Cys Arg
130                 135                 140

Ala Ser Gln Asp Ile Ser Asn Tyr Leu Asn Trp Tyr Gln Gln Lys Pro
145                 150                 155                 160

Gly Lys Ala Pro Lys Leu Leu Ile Tyr Tyr Thr Ser Arg Leu Leu Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Gly Asp Thr Leu Pro Tyr Thr Phe Gly Gly Gly Thr Lys Val
    210                 215                 220

Glu Ile Lys Arg Thr Val Ala Ala Pro Ser Val Phe Ile Phe Pro Pro
225                 230                 235                 240
```

```
Ser Asp Glu Gln Leu Lys Ser Gly Thr Ala Ser Val Val Cys Leu Leu
            245                 250                 255

Asn Asn Phe Tyr Pro Arg Glu Ala Lys Val Gln Trp Lys Val Asp Asn
        260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
        290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330
```

<210> SEQ ID NO 493
<211> LENGTH: 1803
<212> TYPE: DNA
<213> ORGANISM: ARTIFICIAL SEQUENCE
<220> FEATURE:
<223> OTHER INFORMATION: Additional DVD-Ig Seq / 11H10-AbL-Ab23 G2

<400> SEQUENCE: 493

```
atggacatga gggtgcccgc tcagctcctg ggctcctgc tgctgtggct gagaggtgcg      60
cgctgtgaag tgcagttggt acagtcgggt ggggactgg tgcagccagg ggttcgctt     120
aggttgtcgt gcacagcgtc gggtttaca ttctcaaacc actggattca ctgggtgaga    180
caagccctg gtaaagggct ggaatgggtc agcgggatca attggaattc aggcagccgg    240
ggatattcgg attccgtaaa aggaaggttc actatctcga gggataacgc aaagaactcc   300
ctctatttgc agatgaacag ccttcgggcg gaggacacgg cagtctacta ctgtgcccga   360
gaaagacccg tggccacagg cgcgtttgac atttggggtc agggcacgac agtaacggtc   420
tcctcagcgt caacgaaagg accgtcggtg ttcccttgg ccctgaggt gcagctcgta     480
cagtcgggtg cggaagtaaa gaaacccggc tcatccgtga agtctcgtg taaagcctcc    540
gggttcacct tcacagacta cattatgcac tgggtgcggc aggcccctgg cagggcctt    600
gaatggatgg gtatatcaa ccctacaat gatgacacg agtataacga aaagtttaag      660
ggaagggtga caatcacggc ggataagagc accagcactg catacatgga gctctcgtca  720
ttgcgctcgg aggacactgc agtctactat tgcgcgagat ccatctacta ttacgatgcg   780
ccgtttgctt attggggaca aggaacgctg gtcaccgtct ctagtgcctc caccaagggc   840
ccatcggtct tccccctggc gcctgctcc aggagcacct ccgagagcac agcggccctg   900
ggctgcctgg tcaaggacta cttccccgaa ccggtgacgg tgtcgtggaa ctcaggcgct   960
ctgaccagcg gcgtgcacac cttcccagct gtcctacagt cctcaggact ctactccctc  1020
agcagcgtgg tgaccgtgcc ctccagcaac ttcggcaccc agacctacac ctgcaacgta  1080
gatcacaagc ccagcaacac caaggtggac aagacagttg agcgcaaatg ttgtgtcgag  1140
tgcccaccgt gcccagcacc acctgtggca ggaccgtcag tcttcctctt ccccccaaaa  1200
cccaaggaca ccctcatgat ctcccggacc cctgaggtca cgtgcgtggt ggtggacgtg  1260
agccacgaag acccccgaggt ccagttcaac tggtacgtgg acggcgtgga ggtgcataat  1320
gccaagacaa agccacggga ggagcagttc aacagcacgt tccgtgtggt cagcgtcctc  1380
accgttgtgc accaggactg gctgaacggc aaggagtaca agtgcaaggt ctccaacaaa  1440
ggcctcccag cccccatcga gaaaaccatc tccaaaacca agggcagcc ccgagaacca   1500
```

-continued

```
caggtgtaca ccctgccccc atcccgggag gagatgacca agaaccaggt cagcctgacc    1560
tgcctggtca aaggcttcta ccccagcgac atcgccgtgg agtgggagag caatgggcag    1620
ccggagaaca actacaagac cacacctccc atgctggact ccgacggctc cttcttcctc    1680
tacagcaagc tcaccgtgga caagagcagg tggcagcagg ggaacgtctt ctcatgctcc    1740
gtgatgcatg aggctctgca caaccactac acgcagaaga gcctctccct gtctccgggt    1800
aaa                                                                  1803
```

<210> SEQ ID NO 494
<211> LENGTH: 579
<212> TYPE: PRT
<213> ORGANISM: ARTIFICIAL SEQUENCE
<220> FEATURE:
<223> OTHER INFORMATION: Additonal DVD-Ig Seq / 11H10-AbL-Ab23 G2

<400> SEQUENCE: 494

```
Glu Val Gln Leu Val Gln Ser Gly Gly Gly Leu Val Gln Pro Gly Gly
1               5                   10                  15

Ser Leu Arg Leu Ser Cys Thr Ala Ser Gly Phe Thr Phe Ser Asn His
            20                  25                  30

Trp Ile His Trp Val Arg Gln Ala Pro Gly Lys Gly Leu Glu Trp Val
        35                  40                  45

Ser Gly Ile Asn Trp Asn Ser Gly Ser Arg Gly Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Pro Val Ala Thr Gly Ala Phe Asp Ile Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Glu Val Gln Leu Val Gln Ser Gly Ala Glu Val
    130                 135                 140

Lys Lys Pro Gly Ser Ser Val Lys Val Ser Cys Lys Ala Ser Gly Phe
145                 150                 155                 160

Thr Phe Thr Asp Tyr Ile Met His Trp Val Arg Gln Ala Pro Gly Gln
                165                 170                 175

Gly Leu Glu Trp Met Gly Tyr Ile Asn Pro Tyr Asn Asp Asp Thr Glu
            180                 185                 190

Tyr Asn Glu Lys Phe Lys Gly Arg Val Thr Ile Thr Ala Asp Lys Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Ser Ile Tyr Tyr Asp Ala Pro Phe
225                 230                 235                 240

Ala Tyr Trp Gly Gln Gly Thr Leu Val Thr Val Ser Ser Ala Ser Thr
                245                 250                 255

Lys Gly Pro Ser Val Phe Pro Leu Ala Pro Cys Ser Arg Ser Thr Ser
            260                 265                 270

Glu Ser Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300
```

```
Thr Phe Pro Ala Val Leu Gln Ser Ser Gly Leu Tyr Ser Leu Ser Ser
305                 310                 315                 320
Val Val Thr Val Pro Ser Ser Asn Phe Gly Thr Gln Thr Tyr Thr Cys
                325                 330                 335
Asn Val Asp His Lys Pro Ser Asn Thr Lys Val Asp Lys Thr Val Glu
            340                 345                 350
Arg Lys Cys Cys Val Glu Cys Pro Pro Cys Pro Ala Pro Pro Val Ala
        355                 360                 365
Gly Pro Ser Val Phe Leu Phe Pro Pro Lys Pro Lys Asp Thr Leu Met
    370                 375                 380
Ile Ser Arg Thr Pro Glu Val Thr Cys Val Val Val Asp Val Ser His
385                 390                 395                 400
Glu Asp Pro Glu Val Gln Phe Asn Trp Tyr Val Asp Gly Val Glu Val
                405                 410                 415
His Asn Ala Lys Thr Lys Pro Arg Glu Glu Gln Phe Asn Ser Thr Phe
            420                 425                 430
Arg Val Val Ser Val Leu Thr Val Val His Gln Asp Trp Leu Asn Gly
        435                 440                 445
Lys Glu Tyr Lys Cys Lys Val Ser Asn Lys Gly Leu Pro Ala Pro Ile
    450                 455                 460
Glu Lys Thr Ile Ser Lys Thr Lys Gly Gln Pro Arg Glu Pro Gln Val
465                 470                 475                 480
Tyr Thr Leu Pro Pro Ser Arg Glu Glu Met Thr Lys Asn Gln Val Ser
                485                 490                 495
Leu Thr Cys Leu Val Lys Gly Phe Tyr Pro Ser Asp Ile Ala Val Glu
            500                 505                 510
Trp Glu Ser Asn Gly Gln Pro Glu Asn Asn Tyr Lys Thr Thr Pro Pro
        515                 520                 525
Met Leu Asp Ser Asp Gly Ser Phe Phe Leu Tyr Ser Lys Leu Thr Val
    530                 535                 540
Asp Lys Ser Arg Trp Gln Gln Gly Asn Val Phe Ser Cys Ser Val Met
545                 550                 555                 560
His Glu Ala Leu His Asn His Tyr Thr Gln Lys Ser Leu Ser Leu Ser
                565                 570                 575
Pro Gly Lys

<210> SEQ ID NO 495
<211> LENGTH: 1053
<212> TYPE: DNA
<213> ORGANISM: ARTIFICIAL SEQUENCE
<220> FEATURE:
<223> OTHER INFORMATION: Additional DVD-Ig Seq/ 11H10-AbL-Ab23 LC

<400> SEQUENCE: 495
atggacatga gggtgcccgc tcagctcctg ggctcctgc  tgctgtggct gagaggtgcg      60
cgctgtgaga ttgtattgac tcagtcaccg gccacgctct cgctgtcacc cggcgaaaga     120
gcaacactga gctgtcgggc gtcgcagtgg gtgtcgtcgt atttggcctg gtatcaacaa     180
aagcctggac aggcgcccag gctgctcatc tacgacgcgt ccaaccgcgc caccggtatc     240
ccggcacgat tctccggttc ggggtcggga acagacttca cgttgacgat tagctccctt     300
gagccagaag atttttgcggt ctactactgc gcttggcagg agttctttgg gcaggggacc     360
aagcttgaaa tcaaacgcac agtggctgct ccatccgtct ttatcttccc tccagacatt     420
caaatgacac agtcgccctc ctcgctctcg gcgtcagtcg gggatcgcgt gacaatcacg     480
```

```
tgtcgggcca gccaggacat ttcgagctac ctcaactggt atcagcagaa accgggaaa      540
gcgccgaagc tgcttatcta ctccacctca aggttgaatt ccggagtacc ctcaagattt     600
tcgggtagcg gatcaggaac cgacttcaca cttacgatct cgtcgttgca gccagaagat    660
ttcgcaacgt actattgcca gcaagatatc aagcaccccta cgtttggtca gggcactaaa  720
gtggagatta agcgtacggt ggctgcacca tctgtcttca tcttcccgcc atctgatgag    780
cagttgaaat ctggaactgc ctctgttgtg tgcctgctga ataacttcta tcccagagag    840
gccaaagtac agtggaaggt ggataacgcc ctccaatcgg gtaactccca ggagagtgtc    900
acagagcagg acagcaagga cagcacctac agcctcagca gcaccctgac gctgagcaaa     960
gcagactacg agaaacacaa agtctacgcc tgcgaagtca cccatcaggg cctgagctcg    1020
cccgtcacaa agagcttcaa caggggagag tgt                                  1053
```

<210> SEQ ID NO 496
<211> LENGTH: 329
<212> TYPE: PRT
<213> ORGANISM: ARTIFICIAL SEQUENCE
<220> FEATURE:
<223> OTHER INFORMATION: Additional DVD-Ig Seq / 11H10-AbL-Ab23 LC

<400> SEQUENCE: 496

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Trp Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ala Trp Gln Glu Phe Phe Gly Gln
                85                  90                  95

Gly Thr Lys Leu Glu Ile Lys Arg Thr Val Ala Ala Pro Ser Val Phe
            100                 105                 110

Ile Phe Pro Pro Asp Ile Gln Met Thr Gln Ser Pro Ser Ser Leu Ser
        115                 120                 125

Ala Ser Val Gly Asp Arg Val Thr Ile Thr Cys Arg Ala Ser Gln Asp
    130                 135                 140

Ile Ser Ser Tyr Leu Asn Trp Tyr Gln Gln Lys Pro Gly Lys Ala Pro
145                 150                 155                 160

Lys Leu Leu Ile Tyr Ser Thr Ser Arg Leu Asn Ser Gly Val Pro Ser
                165                 170                 175

Arg Phe Ser Gly Ser Gly Ser Gly Thr Asp Phe Thr Leu Thr Ile Ser
            180                 185                 190

Ser Leu Gln Pro Glu Asp Phe Ala Thr Tyr Tyr Cys Gln Gln Asp Ile
        195                 200                 205

Lys His Pro Thr Phe Gly Gln Gly Thr Lys Val Glu Ile Lys Arg Thr
    210                 215                 220

Val Ala Ala Pro Ser Val Phe Ile Phe Pro Pro Ser Asp Glu Gln Leu
225                 230                 235                 240

Lys Ser Gly Thr Ala Ser Val Val Cys Leu Leu Asn Asn Phe Tyr Pro
                245                 250                 255

Arg Glu Ala Lys Val Gln Trp Lys Val Asp Asn Ala Leu Gln Ser Gly
```

```
                    260                 265                 270
Asn Ser Gln Glu Ser Val Thr Glu Gln Asp Ser Lys Asp Ser Thr Tyr
            275                 280                 285

Ser Leu Ser Ser Thr Leu Thr Leu Ser Lys Ala Asp Tyr Glu Lys His
            290                 295                 300

Lys Val Tyr Ala Cys Glu Val Thr His Gln Gly Leu Ser Ser Pro Val
305                 310                 315                 320

Thr Lys Ser Phe Asn Arg Gly Glu Cys
                325
```